US012006342B2

(12) United States Patent
Møller et al.

(10) Patent No.: US 12,006,342 B2
(45) Date of Patent: Jun. 11, 2024

(54) PROTEINS AND NUCLEIC ACIDS USEFUL IN VACCINES TARGETING *PSEUDOMONAS AERUGINOSA*

(71) Applicant: Evaxion Biotech A/S, Hørsholm (DK)

(72) Inventors: Niels Iversen Møller, Hørsholm (DK); Andreas Holm Mattsson, Hørsholm (DK)

(73) Assignee: Evaxion Biotech A/S, Hørsholm (DK)

( * ) Notice: Subject to any disclaimer, the term of this patent is extended or adjusted under 35 U.S.C. 154(b) by 0 days.

(21) Appl. No.: 17/532,034

(22) Filed: Nov. 22, 2021

(65) Prior Publication Data

US 2022/0073570 A1   Mar. 10, 2022

Related U.S. Application Data

(62) Division of application No. 15/741,881, filed as application No. PCT/EP2016/065647 on Jul. 4, 2016, now abandoned.

(30) Foreign Application Priority Data

Jul. 4, 2015   (EP) .................................. 15175365

(51) Int. Cl.
   *C07K 14/21*   (2006.01)
   *A61K 39/00*   (2006.01)
   *A61K 39/104*  (2006.01)
   *A61K 47/64*   (2017.01)
   *A61P 31/04*   (2006.01)
   *C07K 16/12*   (2006.01)

(52) U.S. Cl.
   CPC ............ *C07K 14/21* (2013.01); *A61K 39/104* (2013.01); *A61K 47/6415* (2017.08); *A61K 47/643* (2017.08); *A61K 47/646* (2017.08); *A61P 31/04* (2018.01); *C07K 16/1214* (2013.01); *A61K 2039/545* (2013.01); *A61K 2039/55505* (2013.01); *A61K 2039/575* (2013.01)

(58) Field of Classification Search
   CPC .. C07K 14/21; C07K 16/1214; A61K 47/943; A61K 47/646; A61K 47/6415; A61K 39/104; A61K 2039/545; A61K 2039/55505; A61K 2039/575; A61P 31/04
   See application file for complete search history.

(56) References Cited

U.S. PATENT DOCUMENTS

| 4,683,195 | A | 7/1987  | Mullis et al.     |
|-----------|---|---------|-------------------|
| 4,683,202 | A | 7/1987  | Mullis            |
| 4,684,611 | A | 8/1987  | Schilperoort et al.|
| 4,800,159 | A | 1/1989  | Mullis et al.     |
| 4,879,236 | A | 11/1989 | Smith et al.      |
| 4,952,500 | A | 8/1990  | Finnerty et al.   |
| 5,302,523 | A | 4/1994  | Coffee et al.     |
| 5,322,783 | A | 6/1994  | Tomes et al.      |
| 5,384,253 | A | 1/1995  | Krzyzek et al.    |
| 5,464,765 | A | 11/1995 | Coffee et al.     |
| 5,538,877 | A | 7/1996  | Lundquist et al.  |
| 5,538,880 | A | 7/1996  | Lundquist et al.  |
| 5,550,318 | A | 8/1996  | Adams et al.      |
| 5,563,055 | A | 10/1996 | Townsend et al.   |
| 5,580,859 | A | 12/1996 | Felgner et al.    |
| 5,589,466 | A | 12/1996 | Felgner et al.    |
| 5,591,616 | A | 1/1997  | Hiei et al.       |
| 5,610,042 | A | 3/1997  | Chang et al.      |
| 5,656,610 | A | 8/1997  | Shuler et al.     |
| 5,702,932 | A | 12/1997 | Hoy et al.        |
| 5,736,524 | A | 4/1998  | Content et al.    |
| 5,780,448 | A | 7/1998  | Davis             |
| 5,789,215 | A | 8/1998  | Berns et al.      |
| 5,843,650 | A | 12/1998 | Segev             |
| 5,846,709 | A | 12/1998 | Segev             |
| 5,846,783 | A | 12/1998 | Wu et al.         |
| 5,849,497 | A | 12/1998 | Steinman          |
| 5,849,546 | A | 12/1998 | Sousa et al.      |
| 5,849,547 | A | 12/1998 | Cleuziat et al.   |
| 5,858,652 | A | 1/1999  | Laffler et al.    |
| 5,866,366 | A | 2/1999  | Kallender         |
| 5,871,986 | A | 2/1999  | Boyce             |
| 5,916,776 | A | 6/1999  | Kumar             |
| 5,922,574 | A | 7/1999  | Minter            |
| 5,925,565 | A | 7/1999  | Berloiz et al.    |
| 5,928,905 | A | 7/1999  | Stemmer et al.    |
| 5,928,906 | A | 7/1999  | Koster et al.     |

(Continued)

FOREIGN PATENT DOCUMENTS

| EP | 0717106 | 6/1996 |
|----|---------|--------|
| EP | 1946768 | 7/2008 |

(Continued)

OTHER PUBLICATIONS

Parra, M. et al, "The mycobacterial heparin-binding hemagglutinin is a protective antigen in the mouse aerosol challenge model of tuberculosis", Infection and Immunity, Amer. Soc. Micro., vol. 72:12, pp. 6799-6805, XP002551760, (Dec. 1, 2004).

(Continued)

*Primary Examiner* — Robert A Zeman

(74) *Attorney, Agent, or Firm* — McHale & Slavin, P.A.

(57) ABSTRACT

Disclosed are immunogenic proteins from *Pseudomonas aeruginosa* as well as nucleic acids, vectors and transformed cells useful for expression of the proteins. Also disclosed are methods for prophylaxis of infection with *Pseudomonas aeruginosa* using the proteins, nucleic acids, vectors or transformed cells.

18 Claims, 6 Drawing Sheets

Figure 1:
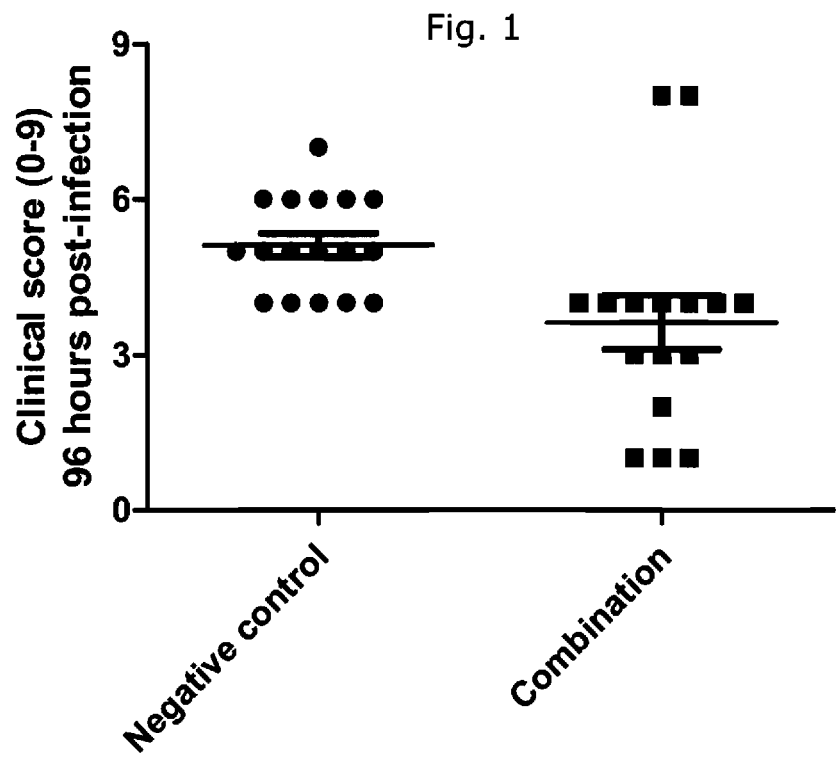

Specification includes a Sequence Listing.

(56) References Cited

U.S. PATENT DOCUMENTS

| | | | |
|---|---|---|---|
| 5,932,451 | A | 8/1999 | Wang et al. |
| 5,935,819 | A | 8/1999 | Eichner et al. |
| 5,935,825 | A | 8/1999 | Nishimura et al. |
| 5,939,291 | A | 8/1999 | Loewy et al. |
| 5,942,391 | A | 8/1999 | Zhang et al. |
| 5,945,100 | A | 8/1999 | Fick |
| 5,981,274 | A | 11/1999 | Tyrrell et al. |
| 5,994,624 | A | 11/1999 | Trolinder et al. |
| 6,551,795 | B1 * | 4/2003 | Rubenfield ............ C07K 14/21 435/6.15 |
| 2007/0020624 | A1 | 1/2007 | Rubenfield et al. |

FOREIGN PATENT DOCUMENTS

| | | |
|---|---|---|
| EP | 2011867 | 1/2009 |
| EP | 2135876 | 12/2009 |
| GB | 2202328 | 9/1988 |
| WO | WO8909284 | 10/1989 |
| WO | WO9014837 | 12/1990 |
| WO | WO9409699 | 5/1994 |
| WO | WO9506128 | 3/1995 |
| WO | WO9820734 | 5/1998 |
| WO | WO02083843 | 10/2002 |
| WO | WO03006672 | 1/2003 |
| WO | WO2012049662 | 4/2012 |
| WO | WO2013040142 | 3/2013 |
| WO | WO2014083060 | 6/2014 |

OTHER PUBLICATIONS

Stover, C. et al, "Complete genome sequence of pseudomonas aeruginosa, an opportunistic pathogen", UniProtKB/TrEMBL, XP002761138, (Mar. 1, 2001).

Rubenfield, M. et al, "Nucleic acid and amino acid sequences relating to pseudomonas aeruginosa for diagnostics and therapeutics", XP002761137, (Apr. 29, 2009).

Winsor, G. et al, "Hemagglutinin [pseudomonas aeruginosa PAO1]", XP002761139, (Jun. 5, 2015).

Donnelly, J. et al, "DNA vaccines: progress and challenges", J. Immunol., vol. 175, pp. 633-639, (2005).

Robinson, H. et al, "DNA vaccines", Seminars in Immunology, vol. 9:5, pp. 271-283, (Oct. 1997).

Kohler, J. et al, "Pillars article: continuous cultures of fused cells secreting antibody of predefined specificity", Nature, vol. 256:5517, pp. 495-497, (2005).

Innis, M. et al, "DNA sequencing with Thermus aquaticus DNA polymerase and direct sequencing of polymerase chain reaction-amplified DNA", Proc. Natl. Acad. Sci., USA, vol. 85, pp. 9436-9440, (Dec. 1988).

Levenson, V. et al, "Internal ribosomal entry site-containing retroviral vectors with green fluorescent protein and drug resistance markers", Hum. Gene her., vol. 9(8), pp. 1233-1236, (May 20, 1998).

Carbonelli, D. et al, "A plasmid vector for isolation of strong promoters in *Escherichia coli*", FEMS Microbiology Letters, vol. 177, pp. 75-82, (1999).

Cocea, L., "Stable DNA-binding yeast vector allowing high-bait expression for use in the two-hybrid system", Biotechniques, vol. 23, pp. 816-820, (Nov. 1997).

Skolnick, J. et al, "From genes to protein structure and function: novel applications of computational approaches in the genomic era", Trends in Biotechnology, vol. 18, pp. 34-39, (2000).

Boslego, J. et al, "Gonorrhea vaccines", Vaccines and Immunotherapy, Ch. 17, (1991).

Colman, P., "Effects of amino acids sequence changes on antibody-antigen interactions", Res. Immunology, vol. 145, pp. 33-36 (Jan. 1994).

Ellis, R., "New technologies for making vaccines", Vaccines, Plotkin & Mortimer, W.B. Saunders Co., Ch. 29, pp. 568-575, (1988).

Stover, C et al., "Ferric enterobactin receptor PirA; Pseudomonas aeruginosa (strain ATCC 15692 / PA01 / 1C / PRS 101 / LMG", Uniprot, database accesion No. Q91527, XP055982141, (May 2015).

Sharifi-Yyazdi, M et al., (ISR Cited as KAZEM), "Evaluation of outer membrane proteins of Pseudomonas aeruginosa as a protective agent in mice model", Pakistan Journal of Biological Sciences, vol. 10(24), pp. 4515-4518, XP055982220, (Dec. 2007).

* cited by examiner

SEQUENCE LISTING

<160> NUMBER OF SEQ ID NOS: 90

<210> SEQ ID NO 1
<211> LENGTH: 66
<212> TYPE: PRT
<213> ORGANISM: Pseudomonas aeruginosa

<400> SEQUENCE: 1

Met Ser Gln Glu Pro His Val His Gly Pro Asn Cys Asn His Asp His
1               5                   10                  15

Asp His His His Asp His Gly His Gly His Val His Gly Pro His Cys
                20                  25                  30

Asn His Ser His Glu Pro Val Arg Asn Pro Leu Lys Ala Val Gly Arg
            35                  40                  45

Asn Asp Pro Cys Pro Cys Gly Ser Glu Lys Lys Phe Lys Lys Cys His
        50                  55                  60

Gly Ala
65

<210> SEQ ID NO 2
<211> LENGTH: 78
<212> TYPE: PRT
<213> ORGANISM: Pseudomonas aeruginosa

<400> SEQUENCE: 2

Met Lys Lys Thr Val Thr Leu Ala Leu Leu Leu Ala Ala Ser Leu Gly
1               5                   10                  15

Leu Ala Ala Cys Asp Lys Lys Glu Glu Asp Lys Ala Ala Ala Pro Ala
                20                  25                  30

Ala Pro Ala Thr Glu Thr Gln Pro Ser Ala Pro Ala Thr Pro Pro Ala
            35                  40                  45

Glu Pro Ser Ala Pro Ala Pro Ser Ser Asp Thr Pro Ala Thr Pro Gln
        50                  55                  60

Thr Pro Ala Pro Thr Pro Glu Gln Pro Gln Gln Asn Gln Gln
65                  70                  75

<210> SEQ ID NO 3
<211> LENGTH: 104
<212> TYPE: PRT
<213> ORGANISM: Pseudomonas aeruginosa

<400> SEQUENCE: 3

Met Lys Lys Ile Ser Leu Ala Ser Ser Val Val Gly Ala Ala Leu Leu
1               5                   10                  15

Gly Val Ala Ser Val Gly Ala His Ala Ala Gln Asn Pro Phe Ala Val
                20                  25                  30

```
Gln Glu Leu Ser Ser Gly Tyr Ser Val Ala Ala Glu Lys Ala Lys
            35                  40                  45

Glu Gly Ser Cys Gly Glu Ala Lys Cys Gly Ala Asp Lys Gly Lys Arg
 50                  55                  60

Glu Ala Ser Lys Ala Gly His Glu Gly Ser Cys Gly Ala Asp Arg Lys
 65                  70                  75                  80

Ala Lys Glu Gly Ser Cys Gly Gly Lys Lys Ala Gly Glu Gly Asn
            85                  90                  95

Cys Gly Ala Asp Lys Lys Lys Ser
           100
```

<210> SEQ ID NO 4
<211> LENGTH: 155
<212> TYPE: PRT
<213> ORGANISM: Pseudomonas aeruginosa

<400> SEQUENCE: 4

```
Met Ser Val Phe Asp Ser Arg Gln Lys Thr Ser Ala Ser Leu Leu Gly
 1               5                  10                  15

Ala Val Leu Val Gly Gly Met Leu Leu Gly Gly Ser Ala Phe Ala Val
            20                  25                  30

Glu Pro Leu Gly Gln Gly Leu Gln Val Ala Ala Ala Ser Ala Gly Glu
            35                  40                  45

Gly Lys Cys Gly Glu Gly Lys Cys Gly Ser Gly Ser Ala Lys Thr
 50                  55                  60

Pro Ala Lys Ala Gly Ala Glu Gly Lys Cys Gly Glu Gly Lys Cys Gly
 65                  70                  75                  80

Asp Ala Ser Phe Ala Arg Thr Asp Thr Asp His Asp Gly Lys Val Ser
            85                  90                  95

Arg Ala Glu Phe Leu Ala Val Ala Lys Asp Arg Ala Gly Glu Phe Asp
           100                 105                 110

Ser Ile Asp Ser Asp His Asp Gly Phe Ile Ser Glu Ala Glu Ala Tyr
           115                 120                 125

Glu His Leu Arg Lys Thr Tyr Glu Ala Asn Gly Lys Pro Met Pro Ala
           130                 135                 140

Gly Leu Phe Ser Lys Leu Glu Gln Gly Gln His
145                 150                 155
```

<210> SEQ ID NO 5
<211> LENGTH: 179
<212> TYPE: PRT
<213> ORGANISM: Pseudomonas aeruginosa

<400> SEQUENCE: 5

```
Met Arg Ser Leu Ser Leu Leu Leu Leu Ser Leu Ala Ser Thr Cys
 1               5                  10                  15

Glu Ala Ala Ala Val Phe Arg Cys Glu Asp Ala Ser Gly His Val Ser
            20                  25                  30

Phe Thr Gln Leu Gly Cys Pro Ala Gly Gln Ala Gly Glu Thr Val Val
            35                  40                  45

Ala Asp Asn Pro Pro Gly Gly Arg Ser Val Thr Pro Met Ala Glu
 50                  55                  60

Thr Lys Thr Lys Lys Ala Ser Ile Gly Arg Lys Ser Val Pro Leu Ala
 65                  70                  75                  80

Val Ile Gly Glu Arg Glu Asp Arg Cys Gly Arg Leu Asp Glu Lys
            85                  90                  95
```

```
Glu Arg Arg Lys Ala Ile Val Glu Gln Arg Ile Met Ala Gly Met Thr
                100                 105                 110

Arg Ser Asp Val Glu Arg Ala Leu Gly Lys Pro Asp Arg Val Ser Gly
            115                 120                 125

Asn Asn Ala Glu Val Arg Tyr Gln Tyr Lys Ala Asp Lys Arg Arg Gly
        130                 135                 140

Ala Arg Ser Val Ser Phe Asp Gln Glu Gly Cys Val Lys Gly Arg Glu
145                 150                 155                 160

Gly Thr Gly Trp Ser Glu Ser Ile Pro Gly Ala Lys Ala Gly Pro Ser
                165                 170                 175

Ser Tyr Arg

<210> SEQ ID NO 6
<211> LENGTH: 304
<212> TYPE: PRT
<213> ORGANISM: Pseudomonas aeruginosa

<400> SEQUENCE: 6

Met Ser Gln Pro Ser Glu Asn Arg Leu Ile Thr Ser Ala Arg Tyr Ala
1               5                   10                  15

Leu Cys Leu Leu Thr Ala Ser Gly Val Leu Ser Gly Cys Ala Ser
                20                  25                  30

Ser Gly Val Gly Ser Val Ala Gln Thr Thr Arg Ala Glu Tyr Tyr Pro
            35                  40                  45

Ser Cys Tyr Glu Pro Val Ser His Leu Arg Ser Thr Asp Asn Ala Val
        50                  55                  60

Arg Asn Ser Ala Ile Thr Gly Ala Ile Thr Gly Leu Leu Gly Gly
65                  70                  75                  80

Leu Ala Gly Gly Leu Ala Ser Asp Glu Asn Arg Gly Arg Asn Ala Ala
                85                  90                  95

Leu Ala Ala Ala Gly Gly Ala Leu Ala Gly Gly Ala Ala Gly Tyr Tyr
                100                 105                 110

Met Glu Lys Gln Lys Gln Ile Ser Asp Asp Arg Ala Arg Ile Gly Ser
            115                 120                 125

Tyr Gly Thr Asp Val Asp Arg Ser Thr Val Glu Ile Asn Arg Ser Val
        130                 135                 140

Ala Tyr Ala Lys Ser Ala Gln Ser Cys Tyr Gln Ser Gln Phe Lys Ala
145                 150                 155                 160

Leu Leu Asp Gly Arg Lys Asn Lys Ser Ile Asn Glu Ala Glu Gly Arg
                165                 170                 175

Lys Arg Leu Ala Glu Ile Val Ser Gly Leu Gln Glu Thr Asn Ala Leu
            180                 185                 190

Leu Val Ala Ala Asn Gly Arg Ala Gly Glu Asn Ile Ser Asn Tyr Thr
        195                 200                 205

Gln Ala Tyr Glu Lys Asp Leu Gln Gln Val Gly Val Pro Arg Ala Glu
210                 215                 220

Val Thr Lys Val Ala Glu Ala Glu Asn Arg Ala Ser Thr Thr Lys Gly
225                 230                 235                 240

Gly Ser Lys Pro Lys Thr Gly Ser Asn Pro Lys Val Pro Lys Glu Ala
                245                 250                 255

Val Ala Thr Glu Gln Thr Ile Arg Lys Ala Gln Asp Ala Gln Ser Glu
            260                 265                 270

Gly Asn Lys Val Ala Ser Gln Gly Gln Gly Met Ile Arg Glu Val Cys
        275                 280                 285
```

```
Asn Ser Pro Asp Met Gly Asp Trp Ala Pro Pro Ser Cys Ala Lys Ala
    290                 295                 300
```

<210> SEQ ID NO 7
<211> LENGTH: 309
<212> TYPE: PRT
<213> ORGANISM: Pseudomonas aeruginosa

<400> SEQUENCE: 7

```
Met Ala Gly Lys Lys Ser Glu Lys Ser Ser Trp Ile Gly Glu
1               5                   10                  15

Ile Glu Lys Tyr Ser Arg Gln Ile Trp Leu Ala Gly Leu Gly Ala Tyr
            20                  25                  30

Ser Lys Val Ser Lys Asp Gly Ser Lys Leu Phe Glu Thr Leu Val Lys
            35                  40                  45

Asp Gly Glu Lys Ala Glu Lys Glu Ala Lys Ser Asp Val Asp Ala Gln
        50                  55                  60

Val Gly Ala Ala Lys Ala Ser Ala Arg Ser Ala Lys Ser Lys Val Asp
65                  70                  75                  80

Glu Val Arg Asp Arg Ala Leu Gly Lys Trp Ser Glu Leu Glu Glu Ala
                85                  90                  95

Phe Asp Lys Arg Leu Asn Ser Ala Ile Ser Arg Leu Gly Val Pro Ser
            100                 105                 110

Arg Asn Glu Val Lys Glu Leu His Ser Lys Val Asp Thr Leu Thr Lys
        115                 120                 125

Gln Ile Glu Lys Leu Thr Gly Val Ser Val Lys Pro Ala Ala Lys Ala
130                 135                 140

Ala Ala Lys Pro Ala Ala Lys Pro Ala Ala Lys Pro Ala Ala Lys Thr
145                 150                 155                 160

Ala Ala Ala Lys Pro Ala Ala Lys Pro Ala Ala Lys Ala Ala Ala Lys
                165                 170                 175

Pro Ala Ala Lys Pro Ala Ala Lys Lys Thr Ala Ala Lys Thr Ala Ala
            180                 185                 190

Ala Lys Pro Ala Ala Lys Pro Ala Ala Lys Pro Thr Ala Lys Ala Ala
        195                 200                 205

Ala Lys Pro Ala Thr Lys Pro Ala Lys Ala Ala Ala Lys Pro Ala
    210                 215                 220

Ala Lys Pro Ala Ala Ala Lys Pro Ala Lys Pro Ala Ala Lys Pro
225                 230                 235                 240

Ala Ala Ala Thr Ala Ala Lys Pro Ala Lys Pro Ala Ala Lys Pro
                245                 250                 255

Ala Ala Lys Lys Pro Ala Ala Lys Lys Pro Ala Ala Lys Pro Ala Ala
            260                 265                 270

Ala Lys Pro Ala Ala Pro Ala Ala Ser Ser Ser Ala Pro Ala Ala Pro
        275                 280                 285

Ala Ala Thr Pro Ala Ala Ser Ala Pro Ala Ala Asn Ala Pro Ala Thr
    290                 295                 300

Pro Ser Ser Gln Gly
305
```

<210> SEQ ID NO 8
<211> LENGTH: 340
<212> TYPE: PRT
<213> ORGANISM: Pseudomonas aeruginosa

<400> SEQUENCE: 8

Met Lys Ala Thr Met Val Leu Thr Pro Leu Ala Leu Ala Met Ala Ala
1               5                   10                  15

Val Leu Ser Val Ser Ala Tyr Ala Gly Asn Glu Gly Gly Trp His Pro
            20                  25                  30

Pro Lys Pro Asn Pro Gln Ser Asn Asn Lys Gly Gly Ala Thr Ala Leu
        35                  40                  45

Val Val Asp Thr Gln Gln Asn Tyr Asn Asn Lys Val Ser Asn Phe Gly
    50                  55                  60

Thr Leu Asn Asn Ala Ser Val Ser Gly Ser Ile Lys Asp Ala Ser Gly
65                  70                  75                  80

Asn Val Gly Val Asn Val Ala Ala Gly Asp Asn Asn Gln Gln Ala Asn
                85                  90                  95

Ala Ala Ala Leu Ala Ser Ala Asp Ala Ser Phe Val Phe Gly Thr Ala
            100                 105                 110

Thr Ala Ser Thr Ser Val Leu Gln Ser Gly Tyr Gly Asn Thr Leu Asn
        115                 120                 125

Asn Tyr Ser Asn Pro Asn Thr Ala Ser Leu Ser Asn Ser Ala Asn Asn
    130                 135                 140

Val Ser Gly Asn Leu Gly Val Asn Val Ala Ala Gly Asn Phe Asn Gln
145                 150                 155                 160

Gln Lys Asn Asp Leu Ala Ala Ala Val Ser Asn Gly Gln Tyr Ser Thr
                165                 170                 175

Ala Gly Ser Ala Ala Ser Gln Thr Ser Thr Gly Asn Thr Thr Val Asn
            180                 185                 190

Ser Ala Asn Tyr Ala Tyr Gly Gly Thr Tyr Val Ser Leu Lys Leu Asn
        195                 200                 205

Ala Asp Gly Ser Tyr Lys Gly Thr Ser Asp Gln Ile Gly Asp Val Tyr
    210                 215                 220

Leu Asp Thr Trp Glu Gly Gln Thr His Pro Gly Gly Ser Asn Thr Gly
225                 230                 235                 240

His Ile Asp Val Asp Ser Gln Ala Gln Gly Ala Lys Asp Leu Asn His
                245                 250                 255

Asp Gly Gly Ala Phe Ala Phe Lys Glu Lys Gly Asp Val Asp Leu Lys
            260                 265                 270

Gly Thr Val Ser Gly Phe Ile Pro Ala Ile Val Gly Phe Lys Thr Pro
        275                 280                 285

Val Thr Asn Asn Ala Ser Leu Ser Asn Ser Leu Gln Asn Val Ser Gly
    290                 295                 300

Asn Val Gly Val Asn Ile Ala Ala Gly Gly Asn Gln Gln Ser Asn
305                 310                 315                 320

Ser Leu Ser Ile Ala Ala Gly Cys Ser Ser Cys Pro Ala Gly Gly Glu
                325                 330                 335

Ser Leu Gly Phe
            340

<210> SEQ ID NO 9
<211> LENGTH: 347
<212> TYPE: PRT
<213> ORGANISM: Pseudomonas aeruginosa

<400> SEQUENCE: 9

Met Lys Gln Gln Phe Glu Arg Ser Pro Ser Glu Ser Tyr Phe Trp Pro
1               5                   10                  15

Val Val Leu Ala Val Val Leu His Val Leu Ile Phe Ala Met Leu Phe
            20                  25                  30

Val Ser Trp Ala Phe Ala Pro Glu Leu Pro Pro Ser Lys Pro Ile Val
        35                  40                  45

Gln Ala Thr Leu Tyr Gln Leu Lys Ser Lys Ser Gln Ala Thr Thr Gln
 50                  55                  60

Thr Asn Gln Lys Ile Ala Gly Glu Ala Lys Lys Thr Ala Ser Lys Gln
 65                  70                  75                  80

Tyr Glu Val Glu Gln Leu Glu Gln Lys Lys Leu Glu Gln Gln Lys Leu
                 85                  90                  95

Glu Gln Gln Lys Leu Glu Gln Gln Val Ala Ala Lys Ala Ala
            100                 105                 110

Glu Gln Lys Lys Ala Asp Glu Ala Arg Lys Ala Glu Ala Gln Lys Ala
            115                 120                 125

Ala Glu Ala Lys Lys Ala Asp Glu Ala Lys Lys Ala Ala Glu Ala Lys
130                 135                 140

Ala Ala Glu Gln Lys Lys Gln Ala Asp Ile Ala Lys Lys Arg Ala Glu
145                 150                 155                 160

Asp Glu Ala Lys Lys Ala Ala Glu Asp Ala Lys Lys Lys Ala Ala
                165                 170                 175

Glu Asp Ala Lys Lys Lys Ala Ala Glu Ala Lys Lys Lys Ala Ala
                180                 185                 190

Ala Glu Ala Ala Lys Lys Ala Ala Val Glu Ala Ala Lys Lys Lys
                195                 200                 205

Ala Ala Ala Ala Ala Ala Ala Arg Lys Ala Ala Glu Asp Lys Lys
            210                 215                 220

Ala Arg Ala Leu Ala Glu Leu Leu Ser Asp Thr Thr Glu Arg Gln Gln
225                 230                 235                 240

Ala Leu Ala Asp Glu Val Gly Ser Glu Val Thr Gly Ser Leu Asp Asp
                245                 250                 255

Leu Ile Val Asn Leu Val Ser Gln Gln Trp Arg Arg Pro Pro Ser Ala
                260                 265                 270

Arg Asn Gly Met Ser Val Glu Val Leu Ile Glu Met Leu Pro Asp Gly
            275                 280                 285

Thr Ile Thr Asn Ala Ser Val Ser Arg Ser Ser Gly Asp Lys Pro Phe
290                 295                 300

Asp Ser Ser Ala Val Ala Val Arg Asn Val Gly Arg Ile Pro Glu
305                 310                 315                 320

Met Gln Gln Leu Pro Arg Ala Thr Phe Asp Ser Leu Tyr Arg Gln Arg
                325                 330                 335

Arg Ile Ile Phe Lys Pro Glu Asp Leu Ser Leu
            340                 345

<210> SEQ ID NO 10
<211> LENGTH: 352
<212> TYPE: PRT
<213> ORGANISM: Pseudomonas aeruginosa

<400> SEQUENCE: 10

Met Ser Ala Asn Lys Lys Pro Val Thr Thr Pro Leu His Leu Leu Gln
1               5                   10                  15

Gln Leu Ser His Ser Leu Val Glu His Leu Glu Gly Ala Cys Lys Gln
                20                  25                  30

Ala Leu Val Asp Ser Glu Lys Leu Leu Ala Lys Leu Glu Lys Gln Arg
            35                  40                  45

Gly Lys Ala Gln Glu Lys Leu His Lys Ala Arg Thr Lys Leu Gln Asp

```
                 50                  55                  60
Ala Ala Lys Ala Gly Lys Thr Lys Ala Gln Ala Lys Ala Arg Glu Thr
 65                  70                  75                  80

Ile Ser Asp Leu Glu Glu Ala Leu Asp Thr Leu Lys Ala Arg Gln Ala
                     85                  90                  95

Asp Thr Arg Thr Tyr Ile Val Gly Leu Lys Arg Asp Val Gln Glu Ser
                100                 105                 110

Leu Lys Leu Ala Gln Gly Val Gly Lys Val Lys Glu Ala Ala Gly Lys
                115                 120                 125

Ala Leu Glu Ser Arg Lys Ala Lys Pro Ala Thr Lys Pro Ala Ala Lys
                130                 135                 140

Ala Ala Ala Lys Pro Ala Val Lys Thr Val Ala Ala Lys Pro Ala Ala
145                 150                 155                 160

Lys Pro Ala Ala Lys Pro Ala Ala Lys Pro Ala Ala Lys Pro Ala Ala
                165                 170                 175

Lys Thr Ala Ala Ala Lys Pro Ala Ala Lys Pro Thr Ala Lys Pro Ala
                180                 185                 190

Ala Lys Pro Ala Ala Lys Pro Ala Ala Lys Thr Ala Ala Ala Lys Pro
                195                 200                 205

Ala Ala Lys Pro Ala Ala Lys Pro Val Ala Lys Pro Ala Ala Lys Pro
210                 215                 220

Ala Ala Lys Thr Ala Ala Ala Lys Pro Ala Ala Lys Pro Ala Ala Lys
225                 230                 235                 240

Pro Val Ala Lys Pro Thr Ala Lys Pro Ala Ala Lys Thr Ala Ala Ala
                245                 250                 255

Lys Pro Ala Ala Lys Pro Ala Ala Lys Pro Ala Ala Lys Pro Ala Ala
                260                 265                 270

Lys Pro Val Ala Lys Ser Ala Ala Lys Pro Ala Ala Lys Pro Ala Ala
                275                 280                 285

Ala Lys Pro Ala Ala Lys Pro Ala Ala Lys Pro Ala Ala Lys Pro Val
                290                 295                 300

Ala Ala Lys Pro Ala Ala Thr Lys Pro Ala Thr Ala Pro Ala Ala Lys
305                 310                 315                 320

Pro Ala Ala Thr Pro Ser Ala Pro Ala Ala Ala Ser Ser Ala Ala Ser
                325                 330                 335

Ala Thr Pro Ala Ala Gly Ser Asn Gly Ala Ala Pro Thr Ser Ala Ser
                340                 345                 350

<210> SEQ ID NO 11
<211> LENGTH: 420
<212> TYPE: PRT
<213> ORGANISM: Pseudomonas aeruginosa

<400> SEQUENCE: 11

Met Trp Gly Leu Thr Met Lys Phe Ala Ser Leu Ile Leu Met Leu Leu
 1               5                  10                  15

Phe Ala Thr Val Ala Arg Ala Glu Asp Tyr Tyr Trp Lys Ile Gln Ser
                 20                  25                  30

Leu Pro Glu Arg Phe Ser Ser Pro Ser Ala Ala Cys Ala Ala Trp Ala
                 35                  40                  45

Lys Ala Thr Gly Arg Pro Gly Glu Phe Thr Phe Thr Gly Ser Met Lys
                 50                  55                  60

Ala Arg Asp Gln Thr Ser Phe Trp Cys Glu Phe Thr Asn Asn Glu Thr
 65                  70                  75                  80
```

```
Gly Lys Thr Ala Ala Gly Tyr Gly Pro Ala Gly Arg Tyr Gly Asp Ser
                85                  90                  95

Cys Pro Glu Gly Thr Glu Tyr Asp Lys Ala Thr Gly Val Cys Lys Ser
            100                 105                 110

Pro Pro Gln Glu Cys Lys Glu Gly Leu Phe Pro Ala Lys Gly Pro
        115                 120                 125

Asp Ser Pro Val Val Thr Ser Gly Arg Asn Tyr Val Gly Asp Gly
    130                 135                 140

Gly Ala Pro Thr Ala Cys Tyr Gln Ser Cys Glu Tyr Gly Gly Asn Pro
145                 150                 155                 160

Ser Pro Ala Ser Cys Tyr Leu Val Lys Gly Ser Thr Thr Gly Phe
                165                 170                 175

Cys Asn Tyr Ile Leu Lys Gly Thr Gly Gln Asn Cys Gly Ala Asp Ser
                180                 185                 190

Tyr Thr Phe Ser Gln Thr Gly Asp Ser Leu Asn Pro Asp Thr Pro
            195                 200                 205

Asn Thr Asp Pro Ser Asp Pro Asn Asp Pro Gly Cys Pro Pro Gly Trp
    210                 215                 220

Ser Trp Ser Gly Thr Thr Cys Val Lys Ala Pro Thr Asp Pro Thr Asp
225                 230                 235                 240

Pro Thr Asp Pro Thr Thr Pro Gly Ser Asp Gly Gly Asp Gly Asn
                245                 250                 255

Gly Gly Gly Asn Asn Asn Gly Gly Asn Asp Gly Gly Thr Gly Asn
            260                 265                 270

Gly Gly Asp Gly Ser Gly Gly Asp Gly Asn Gly Gly Asp Gly
        275                 280                 285

Ser Gly Asp Gly Asp Gly Ser Gly Thr Gly Gly Asp Gly Asn Gly Thr
    290                 295                 300

Cys Asp Pro Ala Lys Glu Asn Cys Ser Thr Gly Pro Glu Gly Pro Gly
305                 310                 315                 320

Gly Glu Leu Lys Glu Pro Thr Pro Gly Thr Trp Asp Asp Ala Ile Ala
                325                 330                 335

Thr Trp Glu Lys Lys Val Glu Asp Ala Lys Gln Glu Leu Lys Thr Lys
            340                 345                 350

Val Lys Ala Asn Val Asp Gln Met Lys Gly Ala Phe Asp Leu Asn Leu
        355                 360                 365

Ala Glu Gly Gly Gly Gln Leu Pro Cys Glu Ser Met Thr Ile Trp Gly
    370                 375                 380

Lys Ser Tyr Ser Leu Cys Ile Ser Asp Tyr Ala Gly Gln Leu Ser Ser
385                 390                 395                 400

Leu Arg Val Ala Leu Leu Leu Met Ala Ala Leu Ile Ala Ala Leu Ile
                405                 410                 415

Leu Leu Lys Asp
            420

<210> SEQ ID NO 12
<211> LENGTH: 427
<212> TYPE: PRT
<213> ORGANISM: Pseudomonas aeruginosa

<400> SEQUENCE: 12

Met Ala Val Ala Pro Gly Val Leu Leu Pro Pro Thr Pro Asp Val Lys
1               5                   10                  15

Pro Lys Ala Ala Ala Pro Lys Ser Gln Gln Lys Thr Pro Glu Pro Ser
            20                  25                  30
```

Asn Asp Lys Thr Ser Ser Phe Ser Asp Met Tyr Ala Lys Glu Thr Ala
         35                  40                  45

Lys Lys Pro Ala Glu Arg Ala Asp Gly Pro Ala Lys Gly Ser Arg Asp
     50                  55                  60

Lys Pro Arg Asp Ala Gly Lys Asp Ala Ala Glu Ala Gln Pro Thr Asp
 65                  70                  75                  80

Ala Val Arg Gln Pro Ala Val Ala Glu Asp Gly Lys Pro Leu Pro Ala
                 85                  90                  95

Asp Gly Gln Ala Lys Ala Asp Gly Glu Asp Lys Val Glu Thr Pro Val
             100                 105                 110

Asp Pro Leu Gln Leu Leu Gly Leu Gly Ala Val Pro Leu Leu Asp
             115                 120                 125

Glu Asn Thr Gln Ala Thr Leu Leu Pro Pro Ala Val Pro Thr Ala Ser
             130                 135                 140

Ser Ala Pro Ala Ser Leu Thr Glu Ala Ser Ser Asp Pro Thr Leu Val
145                 150                 155                 160

Lys Leu Asn Gly Val Pro Ala Val Asn Met Ala Leu Glu Gln Gly Ala
                 165                 170                 175

Gln Asp Ala Ala Gln Thr Ala Lys Gly Gly Pro Ala Lys Ser Ala Asp
             180                 185                 190

Pro Arg Gln Ala Asn Leu Gly Asp Ala Leu Ala Gly Leu Thr Ser Asp
             195                 200                 205

Ser Leu Thr Lys Ala Val Asp Gly Lys Ala Leu Glu Ala Gln Leu Gln
     210                 215                 220

Gln Thr Ala Glu Pro Ala Val Ala Ser Ala Ala Ser Glu Ser Leu Leu
225                 230                 235                 240

Glu Ser Lys Ala Glu Pro Arg Gly Glu Pro Phe Ala Ala Lys Leu Asn
                 245                 250                 255

Gly Leu Thr Gln Ala Met Ala Gln Gln Ala Leu Thr Asn Arg Pro Val
             260                 265                 270

Asn Gly Thr Val Pro Gly Gln Pro Val Ala Met Gln Gln Asn Gly Trp
         275                 280                 285

Ser Glu Ala Val Val Asp Arg Val Met Trp Met Ser Ser Gln Asn Leu
     290                 295                 300

Lys Ser Ala Glu Ile Gln Leu Asp Pro Ala Glu Leu Gly Arg Leu Asp
305                 310                 315                 320

Val Arg Ile His Met Thr Ala Asp Gln Thr Gln Val Thr Phe Ala Ser
                 325                 330                 335

Pro Asn Ala Gly Val Arg Asp Ala Leu Glu Ser Gln Met His Arg Leu
             340                 345                 350

Arg Asp Met Phe Ser Gln Gln Gly Met Asn Gln Leu Asp Val Asn Val
         355                 360                 365

Ser Asp Gln Ser Leu Ala Arg Gly Trp Gln Gly Gln Gln Gln Gly Glu
     370                 375                 380

Gly Gly Ser Ala Arg Gly Arg Gly Leu Ala Gly Glu Ala Ser Gly Asp
385                 390                 395                 400

Glu Glu Thr Leu Ala Gly Val Ser Glu Ile Arg Ser Arg Pro Gly Ala
                 405                 410                 415

Ser Ala Ala Arg Gly Leu Val Asp Tyr Tyr Ala
             420                 425

<210> SEQ ID NO 13
<211> LENGTH: 428

```
<212> TYPE: PRT
<213> ORGANISM: Pseudomonas aeruginosa

<400> SEQUENCE: 13

Met Leu Arg Leu Leu Pro Leu Leu Ser Leu Ala Cys Leu Ala Pro
1               5                   10                  15

Ala Phe Ala Asp Glu Arg Ala Asp Thr Gln Arg Gln Leu Glu Gln Thr
            20                  25                  30

Gln Lys Asp Ile Gly Glu Leu Lys Lys Leu Leu Asp Gly Ile Gln Gln
        35                  40                  45

Glu Lys Ser Gly Val Gln Lys Gln Leu Lys Ser Thr Glu Thr Glu Met
50                  55                  60

Gly Asp Leu Glu Lys Gln Ile Lys Ala Leu Gln Asp Glu Leu Asp Lys
65                  70                  75                  80

Ser Glu Ala Glu Leu Lys Arg Leu Asp Gly Lys Lys Lys Leu Gln
                85                  90                  95

Asp Ala Arg Ile Glu Gln Gln Arg Leu Leu Ala Ile Gln Ala Arg Ala
            100                 105                 110

Ala Tyr Gln Ser Gly Arg Glu Glu Tyr Leu Lys Leu Leu Leu Asn Gln
        115                 120                 125

Glu His Pro Glu Lys Phe Ser Arg Thr Leu Thr Tyr Tyr Asp Tyr Ile
130                 135                 140

Asn Lys Ala Arg Leu Glu Gln Leu Ala Ser Phe Asn Glu Thr Leu Arg
145                 150                 155                 160

Gln Leu Ala Asn Val Glu Gln Asp Ile Ser Ala Gln Lys Ala Glu Gln
                165                 170                 175

Leu Ser Lys Gln Gly Glu Leu Asp Ser Arg Arg Glu Ala Leu Ala Ala
            180                 185                 190

Thr Arg Lys Glu Arg Gln Gln Ala Leu Ala Lys Leu Asn Ser Asp Tyr
        195                 200                 205

Arg Glu Arg Asp Gln Lys Leu Lys Ser Arg Gln Asp Gln Ala Glu
210                 215                 220

Leu Ala Lys Val Leu Arg Thr Ile Glu Glu Thr Leu Ala Arg Gln Ala
225                 230                 235                 240

Arg Glu Ala Ala Ala Ala Glu Arg Glu Arg Gln Arg Ala Leu Ala
                245                 250                 255

Ala Glu Arg Glu Arg Ala Arg Gln Gln Gln Ala Ala Pro Gly Arg Val
            260                 265                 270

Thr Ser Pro Pro Arg Glu Pro Ala Pro Gly Pro Leu Val Ser Ser Thr
        275                 280                 285

Gly Ala Val Tyr Gly Gly Ala Phe Gly Ser Ala Arg Gly Lys Leu Pro
290                 295                 300

Trp Pro Val Asn Gly Arg Val Val Ala Arg Phe Gly Ser Gln Arg Gly
305                 310                 315                 320

Asp Asp Pro Arg Ala Lys Trp Asp Gly Val Leu Ile Ser Ala Ser Ala
                325                 330                 335

Gly Ser Thr Val Arg Ala Val His Gly Gly Arg Val Val Phe Ala Asp
            340                 345                 350

Trp Leu Arg Gly Ala Gly Leu Leu Val Ile Leu Asp His Gly Gly Gly
        355                 360                 365

Tyr Leu Ser Leu Tyr Gly His Asn Gln Ser Leu Leu Lys Asp Ala Gly
370                 375                 380

Asp Thr Val Lys Ala Gly Asp Pro Ile Ala Thr Val Gly Thr Ser Gly
385                 390                 395                 400
```

Gly Gln Ser Ser Pro Ala Val Tyr Phe Ala Ile Arg His Gln Gly Arg
                405                 410                 415

Pro Ala Asp Pro Thr Thr Trp Cys Arg Ala Gln Gly
            420                 425

<210> SEQ ID NO 14
<211> LENGTH: 568
<212> TYPE: PRT
<213> ORGANISM: Pseudomonas aeruginosa

<400> SEQUENCE: 14

Met Gln Arg Leu Ser Arg Ile Gly Arg Asn Thr Leu Ala Val Ser Val
1               5                   10                  15

Ser Thr Leu Leu Leu Ser Ala Cys Asn Gln Gly Asp Asp Ala Pro Lys
                20                  25                  30

Pro Ala Val Ala Pro Gln Pro Ala Ala Pro Ser Met Ala Ala Leu
            35                  40                  45

Ser Ile Pro Leu Cys Leu Asn Gly Gln Cys Ala Val Ile Asp Gln Asp
    50                  55                  60

Ala Lys Leu Leu Val Pro Phe Asp Asn Asp Tyr Asp Asn Ile Val Ala
65                  70                  75                  80

Ser Ala Tyr Gln Gly Thr Leu Met Ala Ala Arg Glu Glu Arg Trp Asn
                85                  90                  95

Leu Ile Gln Ala Lys Asp Gly Lys Val Leu Arg Asp Asp Ile Gly Glu
            100                 105                 110

Ala Leu Ser Leu Leu Thr Pro Asn Leu Tyr Gly Phe Val Arg Asp Gly
        115                 120                 125

Lys Tyr Gly Val Val Asp Gly Gln Gly Lys Glu Val Gln Ala Pro Arg
130                 135                 140

Phe Asp Asp Ile Tyr Pro Asn Ser Ala Asn Glu Phe Ile Ile Tyr Glu
145                 150                 155                 160

Ile Asp Gly Lys Arg Gly Ile Leu Asp Ala Lys Gly Lys Gln Leu Thr
                165                 170                 175

Glu Ala Leu Tyr Asp Thr Thr Leu Val Asn Gly Ser Val Ala Glu His
            180                 185                 190

Gly Gly Leu Ile Ser Ala Glu Arg Gly Glu Glu Lys Trp Ile Ile Asn
        195                 200                 205

Leu Ala Thr Gly Glu Gln Lys Ala Val Ala Tyr Glu Ser Leu Gly Asp
    210                 215                 220

Leu His Asp Gly Val Met Ser Ala Ser Val Ile Gly Lys Gly Ser Gln
225                 230                 235                 240

Leu Val Asp Ala Lys Gly Asp Val Val Gly Asp Gly Lys Ser Tyr Asp
                245                 250                 255

Tyr Leu Gly Thr Pro Ala Asn Gly Leu Val Ala Phe Arg Glu Lys Tyr
            260                 265                 270

Asp Ser Pro Cys Gly Tyr Leu Asp Tyr Gln Gly Lys Val Ala Ile Ala
        275                 280                 285

Ala Gln Phe Ala Gly Cys Gly Ala Phe Gly Lys Gln Gly Gly Leu Ala
    290                 295                 300

Gln Gln Arg Met Glu Asp Gly Ser Ser Gly Lys Tyr Gly Leu Ile Asp
305                 310                 315                 320

Arg Ser Gly Ala Trp Lys Val Gln Pro Gln Tyr Asp Ser Ala Asp Ser
                325                 330                 335

Ala Gly Leu Thr Ala Leu Gly Tyr Thr Val Asp Val Pro Gly Leu Ala

```
                340                 345                 350
Ala Val Gly Val Ser Thr Gly Leu Phe Ser Ala Asp Phe Gly Ile Phe
                355                 360                 365

Asn Leu Asp Glu Gly Ser Glu Trp Val Lys Pro Gly Tyr Ala Gln Ile
            370                 375                 380

Gly Ala Leu Gly Asn Asp Leu Phe Val Val Ala Lys Lys Gly Gly Pro
385                 390                 395                 400

Gln Lys Thr Val Ser Phe Met Gly Ser Glu Ser Gln Val Pro Val Val
                405                 410                 415

Gly Leu Met Asp Arg Ser Gly Lys Met Leu Leu Glu Pro Asp Glu Leu
            420                 425                 430

Ile Ser Ile Gln Ser Ala Tyr Asp Gly Arg Phe Leu Glu Gly Leu Asp
        435                 440                 445

Gly Met Asp Asn Ala Ala His Thr Val Leu Leu Asp Arg Gln Gly Arg
        450                 455                 460

Thr Leu Val Pro Ala Leu Trp Gln Lys Leu Glu Val Asn Pro Gln Gln
465                 470                 475                 480

Gly Tyr Ile Leu Gly Tyr Glu Val Ser Gly Thr Gly Asp Glu Ala Thr
                485                 490                 495

Glu Thr Leu Arg Ala Leu Tyr Asp Leu Asn Gly Lys Pro Arg Phe Thr
            500                 505                 510

Val Ala Thr Thr Asp Cys Gly Ala Glu Gln Leu Leu Asp Gly Asn Gly
            515                 520                 525

Lys Ala Ile Trp Pro Gln Asp Pro Thr Pro Tyr Cys Gln Ser Asp Asp
        530                 535                 540

Glu Gln Asp Asp Glu Gly Glu Pro Gln Glu Pro Ala Pro Val Glu
545                 550                 555                 560

Glu Ser Glu Glu Thr Ser Glu Ser
                565

<210> SEQ ID NO 15
<211> LENGTH: 579
<212> TYPE: PRT
<213> ORGANISM: Pseudomonas aeruginosa

<400> SEQUENCE: 15

Met Leu Arg Pro Ala Arg Ser Leu Ser Leu Cys Ser Ala Leu Val Ile
1               5                   10                  15

Leu Leu Ala Ala Cys Gly Glu Gly Glu Pro Leu Leu Pro Ala Asp Ala
            20                  25                  30

Arg Leu Pro Asp Gly Ala Arg Tyr Arg Gly Glu Leu Val Asp Gly Arg
        35                  40                  45

Leu Glu Gly Gln Gly Arg Leu Asp Tyr Asp Asn Gly Ala Trp Tyr Ala
    50                  55                  60

Gly Arg Phe Glu His Gly Leu Leu His Gly His Gly Thr Trp Gln Gly
65                  70                  75                  80

Ala Asp Gly Ser Arg Tyr Ser Gly Phe Ala Ala Gly Leu Phe Asp
                85                  90                  95

Gly Gln Gly Arg Leu Ala Met Ala Asp Gly Ser Val Tyr Gln Gly Gly
            100                 105                 110

Phe Arg Gln Gly Leu Phe Asp Gly Glu Gly Ser Leu Glu Gln Gln Gly
        115                 120                 125

Thr Arg Tyr Arg Gly Gly Phe Arg Lys Gly Leu Tyr Ser Gly Gln Gly
    130                 135                 140
```

```
Thr Leu Asp Gly Ser Asp Gly Ser Arg Tyr Gln Gly Ser Phe Arg Gln
145                 150                 155                 160

Gly Arg Leu Glu Gly Glu Gly Ser Phe Ser Asp Ser Gln Gly Asn Gln
            165                 170                 175

Tyr Ala Gly Thr Phe Arg Asp Gly Gln Leu Asn Gly Lys Gly Arg Trp
        180                 185                 190

Ser Gly Pro Asp Gly Asp Arg Tyr Val Gly Gln Phe Lys Asp Asn Gln
    195                 200                 205

Phe His Gly Gln Gly Arg Tyr Glu Ser Ala Ser Gly Asp Val Trp Ile
210                 215                 220

Gly Arg Phe Ser Glu Gly Ala Leu Asn Gly Pro Gly Glu Leu Leu Gly
225                 230                 235                 240

Ala Asp Gly Ser Arg Tyr Arg Gly Gly Phe Gln Phe Trp Arg Phe His
                245                 250                 255

Gly Gln Gly Leu Leu Glu Gln Leu Asp Gly Thr Arg Tyr Glu Gly Gly
            260                 265                 270

Phe Ala Ala Gly Ala Tyr Ala Gly Gln Gly Thr Leu Asp Arg Ala Asp
        275                 280                 285

Gly Ser Arg Glu Gln Gly Leu Trp Ala Asp Gly Lys Arg Ile Arg Asp
290                 295                 300

Ala Ala Gly Lys Ala Leu Pro Asp Thr Leu Glu Val Gly Leu Leu Ala
305                 310                 315                 320

Gln Gly Arg Leu Leu Asp Glu Glu Leu Arg Lys Ile Pro Ala Ser Thr
                325                 330                 335

Pro Ala Ser Glu Leu Tyr Ala Leu Ser Leu Gly Asp Gly Arg Gln
            340                 345                 350

Gly Val Phe Leu Arg Glu Ala Asp Tyr Ala Gly Asp Leu Leu Gly Gln
        355                 360                 365

Arg Phe Ala Ala Arg Gly Val Ile Arg Leu Val Asn His Arg Asp His
370                 375                 380

Phe Gly Asp Arg Pro Leu Ala Thr Arg Glu Ser Leu Ser Arg Ala Val
385                 390                 395                 400

Arg Thr Leu Ala Glu Arg Ser Gly Pro Glu Asp Leu Val Phe Ile Tyr
                405                 410                 415

Leu Thr Ser His Gly Ser Ser Asp His Gln Leu Ala Leu Asp Met Pro
            420                 425                 430

Gly Leu Asn Leu Gly Asp Leu Pro Ala Ala Glu Leu Ala Glu Leu Leu
        435                 440                 445

Ala Pro Leu Arg Gln Arg Asp Lys Val Leu Val Ser Ala Cys Tyr
450                 455                 460

Ser Gly Gly Phe Ile Pro Pro Leu Lys Asp Glu Arg Thr Leu Ile Leu
465                 470                 475                 480

Thr Ala Ala Arg Ala Asp Arg Val Ser Phe Gly Cys Ser Asp Ala
                485                 490                 495

Asp Phe Thr Tyr Phe Gly Arg Ala Leu Leu Ala Asn Ala Leu Asn Arg
            500                 505                 510

Thr Asp Asp Leu Ser Lys Ala Phe Glu Leu Ala Lys Glu Glu Val Arg
        515                 520                 525

Gln Arg Glu Lys Glu Glu Gly Phe Glu Ala Ser Glu Pro Gln Ala Trp
    530                 535                 540

Leu Pro Glu Arg Val Leu Ala His Trp Arg Thr Leu Arg Gly Gln Gln
545                 550                 555                 560

Ala Glu Arg Ala Leu Ala Ser Arg Glu Gly Lys Thr Gly Glu Gly Ala
```

Ala Gly Lys

<210> SEQ ID NO 16
<211> LENGTH: 621
<212> TYPE: PRT
<213> ORGANISM: Pseudomonas aeruginosa

<400> SEQUENCE: 16

Met Leu Gln Asn Ile Arg Asp Asn Ser Gln Gly Trp Ile Ala Lys Thr
1               5                   10                  15

Ile Ile Gly Val Ile Val Leu Leu Ser Leu Thr Gly Phe Asp Ala
            20                  25                  30

Ile Ile Arg Ala Thr Asp His Ser Asn Val Ala Ala Lys Val Asn Gly
        35                  40                  45

Asp Asp Ile Ser Leu Asn Glu Val Gln Gln Ala Val Asp Met Gln Arg
    50                  55                  60

Arg Gln Leu Leu Gln Arg Leu Gly Lys Asp Phe Asp Pro Ser Met Leu
65                  70                  75                  80

Asp Asp Lys Leu Leu Lys Glu Ala Ala Leu Lys Gly Leu Ile Glu Arg
                85                  90                  95

Thr Leu Leu Leu Gln Ala Ala Lys Asp Asp Lys Phe Ala Phe Ser Asp
            100                 105                 110

Gln Ala Leu Asp Gln Leu Ile Leu Gln Thr Pro Glu Phe Gln Val Asp
        115                 120                 125

Gly Lys Phe Asn Ala Asp Arg Phe Asp Gln Val Ile Arg Gln Met Asn
    130                 135                 140

Tyr Ser Arg Met Gln Phe Arg Gln Met Leu Gly Gln Glu Met Leu Ile
145                 150                 155                 160

Gly Gln Leu Arg Ala Gly Leu Ala Gly Thr Gly Phe Val Thr Asp Asn
                165                 170                 175

Glu Leu Gln Ser Phe Ala Arg Leu Glu Lys Gln Thr Arg Asp Phe Ala
            180                 185                 190

Thr Leu Ala Ile Lys Ala Asp Ala Ser Lys Ser Ser Val Ser Asp Asp
        195                 200                 205

Glu Val Lys Ala Phe Tyr Glu Gly His Lys Ser Glu Phe Met Thr Pro
    210                 215                 220

Glu Gln Val Val Val Glu Tyr Val Glu Leu Lys Lys Ser Ser Phe Phe
225                 230                 235                 240

Asp Gln Val Lys Val Lys Gln Glu Asp Leu Glu Ala Leu Tyr Gln Lys
                245                 250                 255

Glu Ile Ala Asn Leu Ser Glu Gln Arg Asp Ala Ala His Ile Leu Ile
            260                 265                 270

Glu Val Asn Asp Lys Val Gly Asp Glu Gln Ala Lys Ala Lys Ile Asp
        275                 280                 285

Glu Ile Lys Ala Arg Leu Ala Lys Gly Glu Asp Phe Ala Ala Leu Ala
    290                 295                 300

Lys Glu Phe Ser Gln Asp Ile Gly Ser Ala Ala Thr Gly Gly Asp Leu
305                 310                 315                 320

Gly Tyr Ala Gly Arg Gly Val Tyr Asp Pro Ala Phe Glu Glu Ala Leu
                325                 330                 335

Tyr Ala Leu Lys Gln Gly Glu Val Ser Ala Pro Val Lys Thr Pro Tyr
            340                 345                 350

Gly Tyr His Leu Ile Lys Leu Leu Gly Val Gln Ala Pro Glu Val Pro

```
            355                 360                 365
Ser Leu Glu Ser Leu Lys Pro Lys Leu Glu Asp Glu Leu Lys Lys Gln
    370                 375                 380

Met Val Glu Gln Arg Phe Val Glu Ala Thr Lys Asp Leu Glu Ser Ser
385                 390                 395                 400

Ala Tyr Glu Ala Ala Asp Leu Ser Gln Pro Ala Gln Glu Met Gly Leu
                405                 410                 415

Lys Val Gln Thr Ser Gln Pro Phe Gly Arg Ser Gly Gly Asp Gly Ile
            420                 425                 430

Ala Ala Asn Arg Gln Ile Val Gln Thr Ala Phe Ser Ala Glu Val Leu
        435                 440                 445

Glu Glu Ala Ala Asn Ser Gly Ala Ile Glu Leu Asp Pro Asp Thr Val
    450                 455                 460

Val Val Leu Arg Val Lys Glu His Asn Lys Pro Lys Glu Gln Pro Leu
465                 470                 475                 480

Glu Gln Val Ala Ala Asn Ile Arg Glu Arg Leu Ala Ala Glu Lys Ala
                485                 490                 495

Ala Glu Glu Ala Gln Lys Arg Gly Glu Ala Leu Ile Ala Glu Leu Arg
            500                 505                 510

Glu Gly Arg Thr Ser Ser Ala Ala Gly Glu Ser Trp Lys Val Val Glu
        515                 520                 525

Ala Ala Ser Arg Gly His Glu Gly Val Asp Pro Lys Leu Leu Gln Ala
    530                 535                 540

Val Phe Arg Met Gln Arg Pro Glu Ala Lys Asp Lys Pro Ser Phe Ser
545                 550                 555                 560

Gly Val Thr Leu Ala Asn Gly Asp Tyr Val Val Ile Arg Leu Asn Gly
                565                 570                 575

Val Ser Glu Pro Glu Glu Ala Ile Ser Asp Asp Glu Lys Ala Met Tyr
            580                 585                 590

Arg Arg Phe Leu Ala Ser Arg Ser Gly Gln Ala Asp Phe Ala Ala Phe
        595                 600                 605

Arg Arg Gln Leu Gln Asp Lys Ala Glu Val Glu Lys Tyr
    610                 615                 620

<210> SEQ ID NO 17
<211> LENGTH: 688
<212> TYPE: PRT
<213> ORGANISM: Pseudomonas aeruginosa

<400> SEQUENCE: 17

Met Asp Met Thr Ser Leu Met Pro Leu Leu Leu Gly Val Gly Leu Val
1               5                   10                  15

Val Leu Leu Val Val Gly Leu Leu Ala Leu Phe Lys Ala Phe Tyr Ile
            20                  25                  30

Lys Val Pro Gln Gly Thr Ala Leu Ile Val Asn Asp Met Ser Ser Thr
        35                  40                  45

Pro Lys Val His Phe Thr Gly Ala Leu Val Tyr Pro Val Ile His Leu
    50                  55                  60

Lys Glu Phe Met Arg Ile Ser Leu Ile Thr Leu Glu Val Asp Arg Arg
65                  70                  75                  80

Gly Lys Asp Gly Leu Ile Cys Arg Asp Asn Met Arg Ala Asp Ile Thr
                85                  90                  95

Val Ala Phe Tyr Leu Arg Val Asn Glu Thr Gln Asp Asp Val Leu Lys
            100                 105                 110
```

```
Val Ala Lys Ala Ile Gly Val Asp Arg Ala Ser Asp Arg Ser Ala Val
            115                 120                 125

Asn Glu Leu Phe Asn Ala Lys Phe Ser Glu Ala Leu Lys Thr Val Gly
        130                 135                 140

Lys Gln Phe Asp Phe Val Gln Leu Phe Glu Asn Arg Gln Asp Phe Arg
145                 150                 155                 160

Asp Arg Ile Ile Glu Val Ile Gly Asn Asp Leu Asn Gly Tyr Val Leu
                165                 170                 175

Glu Asp Val Ala Ile Asp Tyr Leu Glu Gln Thr Ala Lys Asn Ser Leu
            180                 185                 190

Asp Pro Ser Asn Ile Leu Asp Ala Glu Gly Ile Arg Lys Ile Thr Glu
        195                 200                 205

Leu Thr Ala Thr Gln Asn Val Ile Thr Asn Glu Leu Glu Arg Asn Glu
210                 215                 220

Glu Leu Ala Ile Lys Lys Lys Asn Val Glu Thr Arg Glu Ala Ala Leu
225                 230                 235                 240

Ala Leu Glu Arg Gln Gln Ala Asp Ala Glu Ala Arg Gln Lys Arg Glu
                245                 250                 255

Ile Glu Thr Ile Arg Ala Arg Glu Glu Ala Glu Thr Ala Arg Val Lys
            260                 265                 270

Glu Glu Glu Arg Leu Lys Ala Glu Gln Ala Arg Ile Gln Ala Gln Gln
        275                 280                 285

Glu Ile Asp Val Arg Thr Glu Asn His Gln Arg Glu Val Glu Val Ala
        290                 295                 300

Gln Gln Asn Arg Gln Arg Ala Val Val Ile Glu Val Glu Lys Val Thr
305                 310                 315                 320

Arg Ala Lys Asp Leu Glu Ile Val Ala Arg Glu Arg Glu Val Glu Leu
                325                 330                 335

Gln Lys Ile Glu Lys Glu Lys Ala Leu Glu Glu Gln Arg Lys Asn Ile
            340                 345                 350

Ala Asn Val Ile Arg Glu Arg Val Ala Val Glu Lys Thr Val Ala Gln
        355                 360                 365

Glu Glu Glu Arg Ile Lys Glu Val Arg Glu Val Ser Glu Ala Glu Arg
        370                 375                 380

Val Lys Gln Val Ile Leu Gln Ala Gln Ala Glu Ala Glu Gln Glu
385                 390                 395                 400

Leu Val Arg Gln Val Lys Gln Ala Glu Ala Asp Glu Ala Arg Ser Lys
                405                 410                 415

His Lys Ala Val Glu Ile Asn Thr Met Ala Gln Ala Glu Leu Glu Ala
            420                 425                 430

Ala Ser Lys Gln Ala Glu Ala Lys Lys Arg Leu Ala Glu Gly Ile Glu
        435                 440                 445

Ala Glu Arg Ala Ala Pro Gly Leu Ala Asp Ala Arg Val Leu Glu Val
    450                 455                 460

Thr Ala Ala Lys Glu Lys Asp Gly Leu Ala Ala Arg Val Arg
465                 470                 475                 480

Ala Glu Gln Leu Ile Ala Glu Ala Arg Gly Asp Glu Arg Gly Leu
                485                 490                 495

Ala Asp Ala Arg Val Leu Glu Ala Gln Ala Ala Lys Glu Lys Asp
            500                 505                 510

Gly Leu Ala Glu Ala Lys Val Leu Ala Glu Lys Leu Gly Ala Gln Ala
        515                 520                 525

Arg Gly Glu Glu Gln Leu Gly Ala Ala Lys Ala Lys Ala Thr Lys Asp
```

```
                530             535             540
Gln Gly Ser Ala Glu Ala Glu Val Leu Leu Gln Arg Leu Asn Ala Glu
545                 550                 555                 560

Ala Glu Gly Leu Gly Lys Lys Phe Gly Ala Leu Asp Ala Leu Ser Asp
                565                 570                 575

Ser Ala Arg Gln His Glu Gly Phe Arg Met Gln Leu Glu Lys Ser Phe
                580                 585                 590

Glu Glu Ala Met Ala Ala Ile Ala Ala Asn Lys Asp Ile Ala Lys Asp
                595                 600                 605

Gln Ala Glu Val Leu Ala Thr Ala Leu Gly Lys Ala Asn Ile Glu Ile
                610                 615                 620

Val Gly Gly Glu Gly Asp Phe Phe Asn Ser Phe Ala Lys Ser Leu Ser
625                 630                 635                 640

Val Gly Lys Ala Ile Glu Gly Val Val Gly Lys Ser Pro Val Val Gln
                645                 650                 655

Asp Val Leu Ala Arg Leu Leu Asn Gly Arg Gly Ala Ala Ala Ala Val
                660                 665                 670

Met Pro Glu Arg Lys Ser Gly His Glu Asn Glu Pro Ala Ala Glu Val
                675                 680                 685

<210> SEQ ID NO 18
<211> LENGTH: 742
<212> TYPE: PRT
<213> ORGANISM: Pseudomonas aeruginosa

<400> SEQUENCE: 18

Met Tyr Pro Gln Phe Arg Arg Gly His Leu Ala Ala Val Leu Phe
1               5                   10                  15

Ala Ser Ser Leu Leu Gly Gly Gln Ala Leu Ala Glu Asp Glu Arg
                20                  25                  30

Leu Glu Glu Leu Asp Glu Arg Ala Glu Ser Val Val Gln Leu Gly Asp
                35                  40                  45

Glu Val Val Leu Gly Thr Ala Glu Gln Glu Leu Lys Gln Ala Pro Gly
    50                  55                  60

Val Ser Ile Ile Thr Ala Glu Asp Ile Arg Lys Arg Pro Pro Val Asn
65                  70                  75                  80

Asp Leu Ser Glu Ile Ile Arg Thr Met Pro Gly Val Asn Leu Thr Gly
                85                  90                  95

Asn Ser Ser Ser Gly Gln Arg Gly Asn Asn Arg Gln Ile Asp Ile Arg
                100                 105                 110

Gly Met Gly Pro Glu Asn Thr Leu Ile Leu Val Asp Gly Lys Pro Val
                115                 120                 125

Ser Ser Arg Asn Ser Val Arg Tyr Gly Trp Arg Gly Glu Arg Asp Thr
    130                 135                 140

Arg Gly Asp Ser Asn Trp Val Pro Pro Glu Glu Val Glu Arg Ile Glu
145                 150                 155                 160

Val Leu Arg Gly Pro Ala Ala Arg Tyr Gly Ser Gly Ala Ala Gly
                165                 170                 175

Gly Val Val Asn Ile Ile Thr Lys Arg Pro Thr Asp Arg Leu Arg Gly
                180                 185                 190

Ser Met Thr Val Phe Thr Asn Ile Pro Glu Ser Ser Lys Asp Gly Ala
    195                 200                 205

Thr Arg Arg Ala Asn Phe Ser Leu Ser Gly Pro Leu Thr Glu Ala Leu
    210                 215                 220
```

```
Ser Phe Arg Ala Tyr Gly Ser Ala Asn Lys Thr Asp Ser Asp Asp Thr
225                 230                 235                 240

Asp Ile Asn Leu Gly His Thr Val Asn Pro Ser Arg Thr Val Ala Gly
            245                 250                 255

Arg Glu Gly Val Arg Asn Arg Asp Leu Ser Gly Met Leu Ser Trp Gln
        260                 265                 270

Val Thr Pro Asp Gln Val Val Asp Phe Glu Ala Gly Phe Ser Arg Gln
    275                 280                 285

Gly Asn Ile Tyr Ala Gly Asp Thr Gln Asn Asn Gly Thr Ala Asn
290                 295                 300

Thr Gln Gly Leu Ala Asp Asp Gly Ala Glu Thr Asn Arg Met Tyr Arg
305                 310                 315                 320

Glu Asn Tyr Ala Ile Thr His Asn Gly Thr Trp Ser Phe Gly Thr Ser
                325                 330                 335

Arg Phe Val Ala Gln Tyr Asp Ser Thr Arg Asn Asn Arg Leu Glu Glu
            340                 345                 350

Gly Leu Ala Gly Ser Val Glu Gly Gln Ile Gly Ala Asp Arg Ser Phe
        355                 360                 365

Ser Ala Ser Lys Leu Glu Asn Tyr Arg Leu Ser Gly Glu Leu Asn Leu
370                 375                 380

Pro Leu His Ala Leu Phe Glu Gln Val Leu Thr Val Gly Ala Glu Trp
385                 390                 395                 400

Asn Lys Glu Thr Leu Asn Asp Pro Ser Ser Leu Lys Gln Gly Phe Val
                405                 410                 415

Gly Ser Asp Ser Leu Pro Gly Thr Pro Ala Ala Gly Ser Arg Ser Pro
            420                 425                 430

Lys Ser Lys Ala Glu Ile Arg Ala Leu Tyr Val Glu Asp Asn Ile Glu
        435                 440                 445

Leu Arg Pro Gly Thr Met Leu Thr Pro Gly Leu Arg Leu Asp Asp His
450                 455                 460

Ser Asp Phe Gly Leu Asn Trp Ser Pro Ser Leu Asn Ala Ser Gln Thr
465                 470                 475                 480

Leu Gly Glu Tyr Phe Thr Val Lys Ala Gly Ile Ala Arg Ala Phe Lys
                485                 490                 495

Ala Pro Asn Leu Tyr Gln Ser Asn Pro Asn Tyr Leu Leu Tyr Thr Arg
            500                 505                 510

Gly Asn Gly Cys Pro Ile Gln Thr Ser Gly Gly Cys Tyr Leu Val
        515                 520                 525

Gly Asn Glu Asn Leu Asp Ala Glu Thr Ser Val Asn Lys Glu Leu Gly
530                 535                 540

Ile Glu Phe Arg Arg Asp Gly Trp Val Ala Gly Leu Thr Tyr Phe Arg
545                 550                 555                 560

Asn Asp Tyr Lys Asn Lys Ile Val Ala Pro Leu Asp Val Met Gly Gln
                565                 570                 575

Thr Gly Thr Gly Asn Asn Ile Leu Gln Trp Ser Asn Ala Lys Lys Ala
            580                 585                 590

Val Val Glu Gly Leu Glu Gly Asn Leu Val Pro Leu His Glu Asp
        595                 600                 605

Leu Ser Trp Ser Thr Asn Leu Thr Tyr Met Leu Gln Ser Lys Asp Lys
610                 615                 620

Asp Thr Gly Asn Pro Leu Ser Val Ile Pro Glu Tyr Thr Leu Asn Ser
625                 630                 635                 640

Thr Leu Asp Trp Gln Ala Ser Glu Arg Leu Ser Thr Gln Leu Thr Ser
```

-continued

```
                645                 650                 655
Thr Ile Tyr Gly Arg Gln Glu Pro Pro Lys His Gly Thr Ser Arg Asn
            660                 665                 670

Thr Pro Val Val Ser Arg Lys Glu Val Gly Thr Tyr Gly Ile Trp Gly
        675                 680                 685

Val Ser Ala Gly Tyr Thr Phe Ser Glu Asn Leu Ser Val Arg Gly Gly
    690                 695                 700

Val Ser Asn Leu Phe Asp Lys Arg Leu Tyr Arg Gln Gly Asn Ser Phe
705                 710                 715                 720

Asp Ala Gly Ala Ala Thr Tyr Asn Glu Pro Gly Arg Ala Tyr Tyr Val
                725                 730                 735

Ser Met Thr Thr Ser Phe
            740

<210> SEQ ID NO 19
<211> LENGTH: 746
<212> TYPE: PRT
<213> ORGANISM: Pseudomonas aeruginosa

<400> SEQUENCE: 19

Met Ser Ser Arg Ala Leu Pro Ala Val Pro Phe Leu Leu Leu Ser Ser
1               5                   10                  15

Cys Leu Leu Ala Asn Ala Val His Ala Ala Gly Gln Gly Asp Gly Ser
            20                  25                  30

Val Ile Glu Leu Gly Glu Gln Thr Val Ala Thr Ala Gln Glu Glu
        35                  40                  45

Thr Lys Gln Ala Pro Gly Val Ser Ile Ile Thr Ala Glu Asp Ile Ala
    50                  55                  60

Lys Arg Pro Pro Ser Asn Asp Leu Ser Gln Ile Ile Arg Thr Met Pro
65                  70                  75                  80

Gly Val Asn Leu Thr Gly Asn Ser Ser Ser Gly Gln Arg Gly Asn Asn
                85                  90                  95

Arg Gln Ile Asp Ile Arg Gly Met Gly Pro Glu Asn Thr Leu Ile Leu
            100                 105                 110

Val Asp Gly Lys Pro Val Ser Ser Arg Asn Ser Val Arg Tyr Gly Trp
        115                 120                 125

Arg Gly Glu Arg Asp Ser Arg Gly Asp Thr Asn Trp Val Pro Ala Asp
    130                 135                 140

Gln Val Glu Arg Ile Glu Val Ile Arg Gly Pro Ala Ala Arg Tyr
145                 150                 155                 160

Gly Asn Gly Ala Ala Gly Gly Val Val Asn Ile Ile Thr Lys Gln Ala
                165                 170                 175

Gly Ala Glu Thr His Gly Asn Leu Ser Val Tyr Ser Asn Phe Pro Gln
            180                 185                 190

His Lys Ala Glu Gly Ala Ser Glu Arg Met Ser Phe Gly Leu Asn Gly
        195                 200                 205

Pro Leu Thr Glu Asn Leu Ser Tyr Arg Val Tyr Gly Asn Ile Ala Lys
    210                 215                 220

Thr Asp Ser Asp Asp Trp Asp Ile Asn Ala Gly His Glu Ser Asn Arg
225                 230                 235                 240

Thr Gly Lys Gln Ala Gly Thr Leu Pro Ala Gly Arg Glu Gly Val Arg
                245                 250                 255

Asn Lys Asp Ile Asp Gly Leu Leu Ser Trp Arg Leu Thr Pro Glu Gln
            260                 265                 270
```

-continued

```
Thr Leu Glu Phe Glu Ala Gly Phe Ser Arg Gln Gly Asn Ile Tyr Thr
            275                 280                 285

Gly Asp Thr Gln Asn Thr Asn Ser Asn Asn Tyr Val Lys Gln Met Leu
    290                 295                 300

Gly His Glu Thr Asn Arg Met Tyr Arg Glu Thr Tyr Ser Val Thr His
305                 310                 315                 320

Arg Gly Glu Trp Asp Phe Gly Ser Ser Leu Ala Tyr Leu Gln Tyr Glu
                325                 330                 335

Lys Thr Arg Asn Ser Arg Ile Asn Glu Gly Leu Ala Gly Gly Thr Glu
                340                 345                 350

Gly Ile Phe Asp Pro Asn Asn Ala Gly Phe Tyr Thr Ala Thr Leu Arg
            355                 360                 365

Asp Leu Thr Ala His Gly Glu Val Asn Leu Pro Leu His Leu Gly Tyr
        370                 375                 380

Glu Gln Thr Leu Thr Leu Gly Ser Glu Trp Thr Glu Gln Lys Leu Asp
385                 390                 395                 400

Asp Pro Ser Ser Asn Thr Gln Asn Thr Glu Glu Gly Ser Ile Pro
                405                 410                 415

Gly Leu Ala Gly Lys Asn Arg Ser Ser Ser Ser Ala Arg Ile Phe
                420                 425                 430

Ser Leu Phe Ala Glu Asp Asn Ile Glu Leu Met Pro Gly Thr Met Leu
        435                 440                 445

Thr Pro Gly Leu Arg Trp Asp His His Asp Ile Val Gly Asp Asn Trp
        450                 455                 460

Ser Pro Ser Leu Asn Leu Ser His Ala Leu Thr Glu Arg Val Thr Leu
465                 470                 475                 480

Lys Ala Gly Ile Ala Arg Ala Tyr Lys Ala Pro Asn Leu Tyr Gln Leu
                485                 490                 495

Asn Pro Asp Tyr Leu Leu Tyr Ser Arg Gly Gln Gly Cys Tyr Gly Gln
                500                 505                 510

Ser Thr Ser Cys Tyr Leu Arg Gly Asn Asp Gly Leu Lys Ala Glu Thr
            515                 520                 525

Ser Val Asn Lys Glu Leu Gly Ile Glu Tyr Ser His Asp Gly Leu Val
    530                 535                 540

Ala Gly Leu Thr Tyr Phe Arg Asn Asp Tyr Lys Asn Lys Ile Glu Ser
545                 550                 555                 560

Gly Leu Ser Pro Val Asp His Ala Ser Gly Lys Gly Asp Tyr Ala
                565                 570                 575

Asn Ala Ala Ile Tyr Gln Trp Glu Asn Val Pro Lys Ala Val Val Glu
            580                 585                 590

Gly Leu Glu Gly Thr Leu Thr Leu Pro Leu Ala Asp Gly Leu Lys Trp
        595                 600                 605

Ser Asn Asn Leu Thr Tyr Met Leu Gln Ser Lys Asn Lys Glu Thr Gly
    610                 615                 620

Asp Val Leu Ser Val Thr Pro Arg Tyr Thr Leu Asn Ser Met Leu Asp
625                 630                 635                 640

Trp Gln Ala Thr Asp Asp Leu Ser Leu Gln Ala Thr Val Thr Trp Tyr
                645                 650                 655

Gly Lys Gln Lys Pro Lys Lys Tyr Asp Tyr His Gly Asp Arg Val Thr
                660                 665                 670

Gly Ser Ala Asn Asp Gln Leu Ser Pro Tyr Ala Ile Ala Gly Leu Gly
            675                 680                 685

Gly Thr Tyr Arg Leu Ser Lys Asn Leu Ser Leu Gly Ala Gly Val Asp
```

```
                690             695             700
Asn Leu Phe Asp Lys Arg Leu Phe Arg Ala Gly Asn Ala Gln Gly Val
705             710             715             720

Val Gly Ile Asp Gly Ala Gly Ala Ala Thr Tyr Asn Glu Pro Gly Arg
                725             730             735

Thr Phe Tyr Thr Ser Leu Thr Ala Ser Phe
                740             745

<210> SEQ ID NO 20
<211> LENGTH: 784
<212> TYPE: PRT
<213> ORGANISM: Pseudomonas aeruginosa

<400> SEQUENCE: 20

Met Ser Pro Ser Arg Ala Leu Ser Pro Leu Ser Arg Ala Leu Leu Leu
1               5                   10                  15

Ala Cys Leu Gly Gly Pro Val Leu Val Ser Ala Gly Ser Ala Cys Ala
                20                  25                  30

Ala Glu Ile Arg Thr Asp Ala Arg Gln Tyr Tyr Arg Leu Pro Ala Glu
            35                  40                  45

Pro Leu Glu Gln Ala Leu Asn His Leu Gly Arg Gln Ala Gly Val Leu
        50                  55                  60

Ile Ala Phe Ser Pro Glu Gln Thr Ala Ala Arg Arg Ser Gln Ala Leu
65                  70                  75                  80

Asp Gly Glu Tyr Thr Leu Glu Glu Ala Leu Ala Ala Leu Leu Val Gly
                85                  90                  95

Ser Gly Leu Glu Ala Arg Ala Arg Gly Asp Gly Ala Tyr Thr Leu Glu
                100                 105                 110

Ala Leu Pro Val Glu Asp Pro Ala Asn Leu Gln Ala Leu Thr Val Val
            115                 120                 125

Gly Asp Trp Leu Ala Asp Ala Ser Ala Ala Asp Val Phe Glu His Pro
130                 135                 140

Gly Ala Arg Asp Val Val Arg Arg Glu Gln Phe Gln Ala Gln Gly Ala
145                 150                 155                 160

Ala Ser Thr Arg Glu Val Leu Glu Arg Ile Pro Gly Val Ser Ala Pro
                165                 170                 175

Leu Asn Asn Gly Thr Gly Ser His Asp Leu Ala Leu Asn Phe Gly Ile
            180                 185                 190

Arg Gly Leu Asn Pro Arg Leu Ala Ser Arg Ser Thr Val Leu Met Asp
        195                 200                 205

Gly Ile Pro Val Pro Phe Ala Pro Tyr Gly Gln Pro Gln Leu Ser Leu
    210                 215                 220

Ala Pro Val Ser Ile Gly Asn Met Asp Ala Val Asp Val Val Arg Gly
225                 230                 235                 240

Gly Gly Ala Val Arg Tyr Gly Pro Gln Asn Val Gly Gly Ile Val Asn
                245                 250                 255

Phe Val Thr Arg Ala Ile Pro Glu Asp Phe Ala Thr Lys Leu Asp Val
            260                 265                 270

His Ser Glu Leu Ser Pro Ser Ser Gln Asp Gly Leu Lys Thr Thr
        275                 280                 285

His Asn Val Leu Ile Gly Gly Thr Gly Ala Asn Gly Leu Gly Gly Ala
    290                 295                 300

Leu Leu Tyr Ser Gly Thr Arg Gly Gly Asp Trp Arg Glu His Ser Asp
305                 310                 315                 320
```

```
Thr Arg Ile Asp Asp Leu Ile Leu Lys Gly Arg Phe Gln Pro Ser Asp
            325                 330                 335

Glu His Thr Phe Ser Ala Met Thr Gln Tyr Tyr Asp Gly Glu Ala Asp
            340                 345                 350

Met Pro Gly Gly Leu Gly Thr Ala Ala Tyr His Asp Pro Tyr Gln
            355                 360                 365

Ser Thr Arg Pro Tyr Asp Lys Phe Trp Gly Arg Thr Leu Ala Ser
    370                 375                 380

Ala Ser Tyr Glu Tyr Thr Pro Asn Ala Ser Gln Lys Leu Asn Val Thr
385                 390                 395                 400

Gly Phe Phe Thr Lys Thr Leu Arg Ser Gly Tyr Leu Asp Gln Gly Arg
                405                 410                 415

Asn Leu Thr Leu Ser Pro Arg Glu Tyr Trp Val Arg Gly Leu Glu Thr
            420                 425                 430

Arg Phe Ser Gln Gly Phe Glu Leu Gly Glu Ser Arg His Glu Val Gly
            435                 440                 445

Ile Gly His Arg Tyr Val Asn Glu Ala Ser His Glu Leu Arg Tyr Trp
            450                 455                 460

Thr Arg Ala Asp Ser Gly Gln Leu Pro Ser Thr Gly Ser Arg Asn Asp
465                 470                 475                 480

Arg Asp Thr Arg Gly Ser Thr Glu Ala Asn Ala Phe Tyr Ile Asp Asp
                485                 490                 495

Arg Ile Asp Ile Gly Asn Trp Thr Ile Thr Pro Gly Ile Arg Tyr Glu
            500                 505                 510

Lys Ile Asp Ser Glu Gln Lys Asn Leu Leu Lys Asn Ser Lys Asp Ser
            515                 520                 525

Gly Arg Tyr Asn Ala Ser Leu Pro Ala Leu Asn Val Ile Tyr His Leu
    530                 535                 540

Thr Pro Ser Trp Asn Leu Tyr Ala Asn Thr Glu Gly Ser Phe Gly Thr
545                 550                 555                 560

Val Gln Tyr Ser Gln Met Gly Lys Ala Val Arg Ser Gly Asp Ile Glu
                565                 570                 575

Pro Glu Lys Ala Arg Thr Trp Glu Leu Gly Ser Arg Tyr Asp Asp Gly
            580                 585                 590

Ile Leu Arg Ala Glu Leu Gly Ala Phe Leu Ile Asn Phe Asp Asn Gln
            595                 600                 605

Tyr Glu Ser Asn Gln Gln Thr Asp Ser Val Thr Ala Arg Gly Lys Thr
    610                 615                 620

Arg His Lys Gly Ile Glu Ala Ala Ile Ala Tyr Asp Leu Ala Asp Leu
625                 630                 635                 640

Asp Pro Leu Leu Ser Gly Phe Asp Val Tyr Ala Ser Tyr Ala Tyr Val
                645                 650                 655

Asp Ala Ser Ile Arg Glu Asp Gly Pro Asn Lys Gly Asn Gln Val Pro
            660                 665                 670

Phe Ser Ser Lys His Lys Gly Thr Leu Gly Ala Asn Tyr Arg Thr Gly
            675                 680                 685

Ala Trp Ser Tyr Asn Leu Asp Gly Ser Phe Gln Thr Ser Gln Tyr Ala
    690                 695                 700

Asp Asn Ala Asn Thr Glu Ser Glu Ser Ala Asp Gly Ser Thr Gly Arg
705                 710                 715                 720

Ile Ala Gly Trp Met Val Trp Ser Ala Arg Gly Thr Tyr Asp Phe Gly
                725                 730                 735

Pro Gln Leu Asn Asp Leu Lys Leu Gly Leu Gly Val Lys Asn Leu Phe
```

```
                    740                 745                 750
Asp Arg Arg Tyr Tyr Thr Arg Ser Phe Asp Asp Asn Asn Lys Gly Leu
                755                 760                 765

Tyr Val Gly Gln Pro Arg Thr Leu Tyr Val Gln Ala Ser Val Gly Phe
770                 775                 780

<210> SEQ ID NO 21
<211> LENGTH: 851
<212> TYPE: PRT
<213> ORGANISM: Pseudomonas aeruginosa

<400> SEQUENCE: 21

Met Thr Leu Pro Phe Thr Arg Ala Ala Trp Arg Pro Leu Cys Ser Ala
1               5                   10                  15

Ala Val Leu Gly Ala Ala Leu Trp Ala Ala Gly Ala Ser Ala Ala Glu
                20                  25                  30

Arg Arg Phe Asp Leu Pro Ala Gln Pro Leu Ala Ala Ser Leu Ser Arg
            35                  40                  45

Leu Ala Gln Gln Ala Gln Val Gln Val Leu Phe Asp Glu Ser Leu Leu
        50                  55                  60

Arg Gly Leu Arg Ala Pro Ala Leu Ser Gly Ser Tyr Gly Val Arg Glu
65                  70                  75                  80

Ala Leu Glu Arg Leu Leu Val Gly Ser Glu Leu Glu Leu Val Glu Ala
                85                  90                  95

Gly Gly Gly Tyr Val Val Arg Arg Gln Val Asp Ala Tyr Ser Asp
            100                 105                 110

Asn Ala Leu Gln Leu Asp Ala Gln Thr Ile Val Gly Asn Gly Arg Glu
            115                 120                 125

Val Asp Ala Ser Asn Val Gly Arg Ser Thr Leu Thr Arg Arg Asp Ile
130                 135                 140

Glu Arg Gln Gln Ala Asp Asn Ile Pro Ser Leu Leu Gln Thr Leu Pro
145                 150                 155                 160

Gly Val Thr Met Gly Gly Ser Pro Lys Pro Gly Gly Gln Thr Thr Asn
                165                 170                 175

Ile Trp Gly Leu Gly Asp Ala Glu Asp Val Pro Tyr Thr Leu Asp Gly
            180                 185                 190

Ala Gln Lys Ser Gly Phe Glu Arg Tyr Gln Gln Gly Thr Val Phe Ile
        195                 200                 205

Glu Pro Glu Met Ile Lys Arg Ile Glu Val Leu Lys Gly Pro His Ser
210                 215                 220

Val Phe Thr Gly Asn Gly Phe Gly Gly Thr Val His Met Glu Thr
225                 230                 235                 240

Lys Asp Ala Pro Asp Leu Leu Arg Glu Gly Arg Asp Val Gly Ala Met
                245                 250                 255

Leu Lys Tyr Gly Tyr His Ser Asn Asp Gln Gln Lys Ile Tyr Ser Gly
            260                 265                 270

Ala Val Phe Gly Arg Ser Glu Asp Arg Arg Val Asp Ala Leu Leu Tyr
        275                 280                 285

Leu Asn Gly Arg Asp Gly Arg Asp Met Lys Leu Ala Asp Asn Leu Pro
290                 295                 300

Leu Ser Pro Thr Asp Tyr Pro Ile Asn Pro Lys Arg Leu Pro Asn Ser
305                 310                 315                 320

Ala Gln Asp Glu Lys Thr Gly Leu Phe Lys Leu Asn Leu His Pro Thr
                325                 330                 335
```

```
Glu Glu His Asp Leu Gly Phe Thr Tyr Leu Arg Ser Lys Ser Ser Arg
            340                 345                 350

Trp Thr Pro Phe Ser Ala Ser Ser Tyr Pro Thr Pro Ser Gln Trp
    355                 360                 365

Thr Ile Asp Arg Tyr Gly Tyr Glu Leu Gly Leu Thr Arg Leu Leu Ala
    370                 375                 380

His Arg Asp Thr Thr Asp Thr Thr Trp Thr Gly Lys Tyr Asn Tyr His
385                 390                 395                 400

Pro Leu Asp Asn Pro Trp Ile Asp Leu Gln Leu Ser Tyr Ser Asp Ala
                405                 410                 415

Arg Thr Glu Gln Leu Asp Arg Arg Glu Asp Thr Ala Phe Tyr Gln Leu
            420                 425                 430

Ala Thr Gly Gly Lys Arg Met Arg Thr Glu Tyr Gln Asp Lys Val Leu
            435                 440                 445

Glu Leu Arg Asn Thr Ser Arg Phe Asp Thr Gly Ala Leu Gln His Glu
            450                 455                 460

Leu Thr Leu Gly Ala Ala Leu His Lys His Lys Arg Asp Ile Leu Met
465                 470                 475                 480

His Met Pro Gly Lys Thr Tyr Glu Thr Pro Arg Tyr Asn Tyr Gly Trp
                485                 490                 495

Leu Gln Pro Ala Phe Met Pro Ala Gly Lys Gln Asp Thr Gln Ser Phe
            500                 505                 510

Tyr Ile Gln Asp Ala Ile Thr Tyr Gly Ser Leu Thr Val Thr Pro Ser
            515                 520                 525

Met Arg Phe Asp Ser Val Arg Asn Asp Gly Gln Ala Asn Leu Ala Pro
            530                 535                 540

Ile Tyr Asp Asn Pro Lys Leu Gly His Asp Tyr Arg Ala Gln Thr Tyr
545                 550                 555                 560

Ser Gly Trp Ser Pro Arg Leu Ser Val Phe Trp Thr Ala Thr Pro Asn
                565                 570                 575

Leu Ala Phe Phe Ala Asp Tyr Thr Glu Thr Trp Arg Ala Pro Val Ile
            580                 585                 590

Asp Glu Gln Tyr Glu Val Gln Asn Ser Ser Thr Ile Gly Gly Ser Ser
            595                 600                 605

Arg Asp Leu Asp Ala Glu Arg Ile His Ala Ile Arg Gly Gly Ser Val
            610                 615                 620

Ile Asn Leu Pro Asp Leu Leu Val Ala Gly Asp Ser Leu Gln Ile Arg
625                 630                 635                 640

Thr Thr Leu Phe Gln Asn Arg Ile Lys Asp Glu Ile Phe Arg Thr Arg
                645                 650                 655

Ser Val Gly Cys Arg Gln Gln Ser Ile Asp Asn Gly Ser Ile Gly Gly
            660                 665                 670

Ser Cys Gly Asp Met Leu Pro Leu Ser Asn Tyr Arg Asn Leu Pro Gly
            675                 680                 685

Leu Thr Ile Lys Gly Phe Glu Ile Glu Ser Phe Tyr Asp Ser Gln Arg
            690                 695                 700

Leu Phe Gly Ser Leu Ser Tyr Ser Trp Met Thr Gly Lys His Asp Gly
705                 710                 715                 720

Ala Tyr Ser Asn Pro Trp Gly Pro Asn Val Trp Ala Arg Asp Ile Pro
                725                 730                 735

Pro Pro Lys Trp Val Ala Met Leu Gly Leu Lys Val Pro Glu Trp Asp
            740                 745                 750

Ala Lys Leu Gly Trp Gln Gly Glu Phe Val Arg Lys Thr Asp Arg Leu
```

```
              755                 760                 765
Pro Ser Asp Arg Tyr Ser Gly Gly Met Gly Thr Gly Ser Gly Asp Ile
        770                 775                 780

Tyr Trp Asp His Ala Ala Asn Asp Ser Tyr Asp Thr His Arg Leu Phe
785                 790                 795                 800

Ala Glu Trp Val Pro Ala Lys Leu Gly Leu Lys Asp Thr Arg Ile Asp
                    805                 810                 815

Phe Thr Val Asp Asn Leu Phe Asn Arg Ser Tyr Arg Gln Pro Leu Gly
                820                 825                 830

Gly Asp Leu Val Tyr Ser Gln Gly Arg Asn Ala Lys Ile Ser Val Thr
            835                 840                 845

Gln Phe Phe
        850

<210> SEQ ID NO 22
<211> LENGTH: 880
<212> TYPE: PRT
<213> ORGANISM: Pseudomonas aeruginosa

<400> SEQUENCE: 22

Met His Arg Ser Leu His Thr Asp Ala Pro Leu Gly Ala Ala Leu Leu
1               5                   10                  15

Leu Ala Leu Gln Leu Ala Pro Gly Ser Ala Ala Ala Ala Glu Glu Gln
            20                  25                  30

Ala Pro Val Asp Pro Pro Thr Val Gln Leu Gln Arg Ile Glu Val Thr
                35                  40                  45

Gly Ser Ala Ile Arg Arg Val Asp Ala Glu Thr Ala Val Pro Ile Ser
    50                  55                  60

Val Leu Arg Ala Glu Glu Leu Arg Gln Gln Gly Val Thr Ser Thr Glu
65                  70                  75                  80

Glu Leu Ile Gly Arg Leu Ser Gly Asn Gln Gly Val Tyr Asn Ser Ser
                85                  90                  95

Arg Ser Val Gly Ser Ala Thr Gly Gly Ala Ser Phe Ala Asp Leu Arg
            100                 105                 110

Gly Ile Gly Ala Asn Lys Thr Leu Val Leu Asn Gly Arg Arg Leu
                115                 120                 125

Ala Asn Asn Ala Ile Asp Gly Ser Ala Val Asp Leu Asn Thr Ile Pro
130                 135                 140

Phe Ala Ala Ile Asp Arg Val Glu Val Leu Arg Asp Gly Ala Ser Ala
145                 150                 155                 160

Leu Tyr Gly Thr Asp Ala Ile Gly Gly Val Ile Asn Phe Ile Thr Arg
                165                 170                 175

Lys Ser Leu Asn Glu Gly Arg Phe Asp Ser Gly Tyr Ala Ser Pro Thr
            180                 185                 190

His Asp Gly Gly Gly Asn Gln Arg Asn Val Ser Ala Ser Trp Gly Phe
        195                 200                 205

Gly Glu Leu Glu Glu Asp Arg Phe Asn Val Phe Ala Val Ala Asn Tyr
    210                 215                 220

Asp Lys Gln Glu Arg Leu Gly Ala Lys Asp Arg Gly Tyr Thr Tyr Asn
225                 230                 235                 240

Tyr Gln Pro Gly Arg Gly Leu Asp Tyr Ser Ser Gly Thr Ala Phe Pro
                245                 250                 255

Gly Asn Trp Ser Gln Gly Ala Asn Ala Ser Asn Pro Leu Ala Ala Gly
            260                 265                 270
```

```
Gly Cys Lys Gly Ala Asp Leu Ile Pro Arg Asn Gly Ile Cys Arg Gln
            275                 280                 285

Ser Leu Trp Arg Tyr Leu Asp Leu Val Pro Glu Thr Glu Lys Thr Ser
    290                 295                 300

Val Phe Ser Arg Ala Thr Gly Lys Leu Ala Asp Glu His Asn Val Ser
305                 310                 315                 320

Leu Glu Tyr Phe Trp Ser Arg Ser Asp Asn Ala Thr Gln Val Gly Pro
                325                 330                 335

Gly Thr Leu Thr Gly Leu Gln Ile Asp Pro Gly Thr Ala Phe Tyr Pro
            340                 345                 350

Gly Asn Gly Ile Thr Pro Gly Pro Gly Gly Phe Val Leu Asp Pro Ser
            355                 360                 365

Arg Pro Val Glu Val Asn Trp Arg Gln Ser Val Leu Gly Pro Arg Leu
370                 375                 380

Gln Ser Ser Gln Asn Thr Gly Gln Arg Leu Leu Leu Gly Phe Asp Gly
385                 390                 395                 400

Gln Phe Ala Gly Trp Asp Tyr Asp Ile Gly Ala Ser Tyr Asn Gln Asn
                405                 410                 415

Lys Val Val Asp His Ile His Ser Gly Tyr Val Asp Asp Arg Ala Ala
            420                 425                 430

Ala Leu Gly Ile Ala Asn Gly Thr Leu Asn Pro Phe Gly Pro Gln Thr
            435                 440                 445

Asp Ala Gly Leu Ala Tyr Leu Gly Ser His Ala Leu Ser Gly Asp Phe
    450                 455                 460

Arg Thr Ser Val Gly Arg Val Lys Gly Leu Asp Ala Arg Ala Ser Arg
465                 470                 475                 480

Glu Ile Gly Asp Trp Phe Gly Ala Gly Pro Ala Ala Leu Ala Leu Gly
                485                 490                 495

Gly Glu Phe Arg Lys Glu Ala Phe His Gln Asp Ile Gln Asp Phe Ala
            500                 505                 510

Gly Asn Val Gln Ser Leu Gly Val Asp Pro Ala Ala Thr Val Ser Gly
            515                 520                 525

Glu Arg Asn Leu Lys Ala Gln Tyr Ala Glu Leu Asn Val Pro Val Leu
530                 535                 540

Asp Ser Leu Glu Leu Ser Ala Ala Ile Arg His Asp Lys Tyr Ser Asp
545                 550                 555                 560

Phe Gly Ser Thr Ser Asn Pro Lys Tyr Ser Phe Arg Phe Gln Pro Phe
                565                 570                 575

Arg Gln Leu Val Leu Arg Gly Ala Tyr Ser Glu Gly Phe Arg Ala Pro
            580                 585                 590

Ser Leu Tyr Glu Leu Tyr Asn Pro Thr Phe Thr Thr Tyr Thr Ser Ala
            595                 600                 605

Asn Tyr Asp Asp Pro Arg Leu Cys Ala Gly Gln Pro Ser Gln Gly
610                 615                 620

Gly Ile Ala Asn Arg Asp Cys Ala Gln Gln Phe Tyr Asn Ala Thr Gly
625                 630                 635                 640

Gly Asn Thr Asp Leu Arg Pro Glu Thr Ala Arg Asn Val Thr Leu Gly
                645                 650                 655

Leu Val Tyr Gln Pro Leu Arg Asp Leu Ser Val Gly Leu Asp Phe Trp
            660                 665                 670

Trp Ile Arg Ile Ala Asn Gln Ile Ala Glu Phe Pro Glu Ala Ala Ile
            675                 680                 685

Phe Ala Asp Pro Gln Ala Tyr Ala Gly Arg Ile Val Arg Lys Ala Asp
```

```
            690                 695                 700
Gly Ser Ile Asp His Val Val Thr Gly Leu Ala Asn Leu Gly Lys Val
705                 710                 715                 720

Lys Thr Ser Gly Val Asp Leu Ser Leu Asp Tyr Arg Phe Pro Ala Ser
                725                 730                 735

Arg Tyr Gly Gln Phe Gly Leu Asp Leu Gln Gly Thr Tyr Val Ser Arg
                740                 745                 750

Tyr Asp Phe Gln Gln Gln Ile Gly Gly Gln Tyr Leu Asp Asn Val Gly
                755                 760                 765

Asp Phe Gln Gly Val Gly Val Ile Ala Arg Trp Lys His Val Ala Asn
                770                 775                 780

Ala Thr Trp Ser Arg Asp Ala Trp Gln Ala Thr Leu Ser Asn Arg Tyr
785                 790                 795                 800

Thr Ser Gly Tyr Asn Asp Tyr Asp Arg Ala Ser His Gly Lys Val Gly
                805                 810                 815

Ser Trp Asn Leu Trp Asp Leu Ala Gly Ser Tyr Arg Leu Ser His Ala
                820                 825                 830

Leu Gly Leu Thr Leu Gly Val Lys Asn Leu Phe Asp Arg Glu Pro Pro
                835                 840                 845

Phe Ser Asn Gln Thr Tyr Thr Phe Gln Ser Gly Tyr Asp Pro Arg Tyr
                850                 855                 860

Thr Asp Pro Tyr Gly Arg Ile Leu Phe Gly Arg Leu Ser Tyr Ser Phe
865                 870                 875                 880

<210> SEQ ID NO 23
<211> LENGTH: 919
<212> TYPE: PRT
<213> ORGANISM: Pseudomonas aeruginosa

<400> SEQUENCE: 23

Met Val Arg Leu Arg Thr Leu Val Arg Ala Ile Ala Ala Ala Ser Val
1               5                   10                  15

Leu Thr Ser Gly Met Ala His Gly Leu Gly Leu Gly Glu Ile Thr Leu
                20                  25                  30

Lys Ser Ala Leu Asn Gln Pro Leu Asp Ala Glu Ile Glu Leu Leu Glu
            35                  40                  45

Val Arg Asp Leu Gly Ser Gly Glu Val Ile Pro Ser Leu Ala Ser Pro
50                  55                  60

Glu Glu Phe Ser Lys Ala Gly Val Asp Arg Leu Tyr Tyr Leu Thr Asp
65                  70                  75                  80

Leu Lys Phe Thr Pro Val Val Lys Pro Asn Gly Lys Ser Val Ile Arg
                85                  90                  95

Val Thr Ser Ser Lys Pro Val Gln Glu Pro Tyr Leu Asn Phe Leu Val
                100                 105                 110

Gln Val Leu Trp Pro Asn Gly Arg Leu Leu Arg Glu Tyr Thr Val Leu
            115                 120                 125

Leu Asp Pro Pro Leu Tyr Ser Pro Gln Ala Ala Ser Ala Pro Gln
130                 135                 140

Ala Pro Val Ser Ala Pro Arg Ala Thr Gly Ala Pro Arg Ala Pro Gln
145                 150                 155                 160

Ala Pro Ala Pro Val Arg Thr Thr Ala Pro Ala Gly Ser Asp Thr Tyr
                165                 170                 175

Arg Thr Val Ser Asn Asp Thr Leu Trp Glu Ile Ala Gln Arg Asn Arg
            180                 185                 190
```

```
Thr Asp Arg Val Ser Val Pro Gln Ala Met Leu Ala Phe Gln Glu Leu
        195                 200                 205

Asn Pro Gly Ala Phe Val Asp Gly Asn Ile Asn Arg Leu Lys Ser Gly
        210                 215                 220

Gln Val Leu Arg Ile Pro Thr Glu Gln Met Leu Glu Arg Ser Pro
225                 230                 235                 240

Arg Glu Ala Leu Ser Gln Val Gln Ala Gln Asn Gln Ser Trp Arg Gly
            245                 250                 255

Ser Arg Asn Pro Ala Ala Gly Ser Gly Ala Arg Gln Leu Asp Ala
                260                 265                 270

Thr Gln Arg Asn Ala Ala Gly Ser Ala Pro Ser Lys Val Asp Ala Thr
        275                 280                 285

Asp Asn Leu Arg Leu Val Ser Gly Glu Gly Lys Ala Ser Lys Gly Ala
        290                 295                 300

Asp Lys Gly Gly Lys Gly Asp Ser Lys Ala Ile Ala Asp Thr Leu Ala
305                 310                 315                 320

Val Thr Lys Glu Ser Leu Asp Ser Thr Arg Arg Glu Asn Glu Glu Leu
            325                 330                 335

Gln Ser Arg Met Gln Asp Leu Gln Ser Gln Leu Asp Lys Leu Gln Lys
        340                 345                 350

Leu Ile Gln Leu Lys Asp Ala Gln Leu Ala Lys Leu Gln Gly Gln Leu
        355                 360                 365

Gly Ala Glu Gly Gln Gly Ala Ala Gln Pro Asn Ala Ala Leu Pro Asp
        370                 375                 380

Ala Ser Gln Pro Asn Ala Ala Gln Ala Pro Ala Gln Pro Gly Thr
385                 390                 395                 400

Pro Ala Ala Ala Ala Pro Thr Pro Ala Pro Ala Gly Glu Ala Pro Ala
                405                 410                 415

Ala Pro Ala Gln Pro Pro Val Ala Pro Pro Ala Pro Ala Ala Glu
        420                 425                 430

Lys Pro Pro Ala Pro Ala Val Pro Ala Pro Ala Pro Val Gln Ala Ala
        435                 440                 445

Glu Gln Pro Ala Pro Ser Phe Leu Asp Glu Leu Leu Ala Asn Pro Leu
        450                 455                 460

Trp Leu Ala Val Ile Gly Gly Ser Ala Leu Leu Ala Leu Leu Val Leu
465                 470                 475                 480

Leu Met Ile Leu Ser Arg Arg Asn Ala Gln Lys Glu Lys Glu Glu Ala
            485                 490                 495

Gln Ala Phe Ala Ala Asp Thr Gly Glu Glu Gln Glu Asp Ala Leu Asp
        500                 505                 510

Leu Gly Lys Asp Gly Phe Asp Asp Leu Thr Leu Asp Glu Pro Glu Pro
        515                 520                 525

Gln Val Ala Ala Val Ala Pro Gln Val Glu Lys Thr Thr Ala Gln Thr
        530                 535                 540

Ser Asp Ala Leu Gly Glu Ala Asp Ile Tyr Ile Ala Tyr Gly Arg Phe
545                 550                 555                 560

Asn Gln Ala Ala Glu Leu Leu Gln Asn Ala Ile Tyr Asp Glu Pro Gln
            565                 570                 575

Arg Thr Asp Leu Arg Leu Lys Leu Met Glu Val Tyr Ala Glu Met Gly
        580                 585                 590

Asp Arg Glu Gly Phe Ala Arg Gln Glu Asn Glu Leu Arg Glu Ile Gly
        595                 600                 605

Gly Ala Gln Pro Gln Val Glu Gln Leu Lys Ser Arg Tyr Pro Ala Met
```

```
                610             615             620
Val Ala Val Ala Val Ala Gly Leu Ala Gly Ala Lys Leu Ala Gln
625             630             635             640

Asp Glu Leu Asp Ser Phe Ser Leu Asp Asp Leu Ser Leu Asp Asp Ser
                645             650             655

Gly His Ala Ala Lys Pro Asp Ala Ala Gly Gln Asp Leu Asp Asp Ala
            660             665             670

Phe Asp Leu Ser Leu Asp Asp Leu Gly Gly Asp Val Gln Ala Asp
            675             680             685

Leu Lys Ser Asp Ser Gly Ala Leu Asp Asp Leu Thr Leu Asp Ser Asp
            690             695             700

Leu Asp Leu Ala Ala Ser Thr Pro Ala Asp Lys Pro Val Asp Asp Leu
705             710             715             720

Asp Phe Gly Leu Asp Phe Ala Glu Leu Ala Glu Thr Pro Ser Gln Pro
                725             730             735

Lys His Asp Asp Leu Gly Asp Phe Ser Leu Asp Leu Asp Ala Pro Glu
            740             745             750

Asp Lys Leu Ser Asp Asp Asp Phe Leu Leu Ser Leu Asn Asp Glu Val
            755             760             765

Pro Ala Ala Ala Pro Ala Asp Asn Glu Phe Thr Leu Asp Thr Glu Ala
770             775             780

Ala Glu Glu Pro Ala Leu Ser Leu Pro Asp Asp Phe Asp Leu Ser Leu
785             790             795             800

Ala Asp Glu Pro Thr Glu Pro Ala Ala Pro Glu Lys Gly Glu Asp Ser
                805             810             815

Phe Ala Ala Gln Leu Asp Glu Val Ser Ala Gln Leu Asp Glu Leu Ala
            820             825             830

Ser Asn Leu Asp Glu Pro Lys Ser Ala Thr Pro Ser Phe Ser Ala Glu
            835             840             845

Asp Ala Ala Val Ala Ser Ala Leu Asp Gly Asp Ala Asp Asp Asp Phe
850             855             860

Asp Phe Leu Ser Gly Ala Asp Glu Ala Ala Thr Lys Leu Asp Leu Ala
865             870             875             880

Arg Ala Tyr Ile Asp Met Gly Asp Ser Glu Gly Ala Arg Asp Ile Leu
                885             890             895

Asp Glu Val Leu Ala Glu Gly Asn Asp Ser Gln Gln Ala Glu Ala Arg
            900             905             910

Glu Leu Leu Glu Arg Leu Ala
            915

<210> SEQ ID NO 24
<211> LENGTH: 995
<212> TYPE: PRT
<213> ORGANISM: Pseudomonas aeruginosa

<400> SEQUENCE: 24

Met Thr Asp Asp His Ser Phe Arg Pro Arg Pro Thr Ser Leu Ser Ala
1               5               10              15

Ala Leu Leu Leu Gly Ala Trp Ile Ala Gln Pro Ala Thr Ala Ala Tyr
            20              25              30

Val Glu Ala Gly Arg Pro Gly Asp Pro Ala Ser Trp Arg Ser Ala Glu
        35              40              45

Tyr Gln Gln Asp Trp Gly Leu Glu Arg Met Arg Ala Asp Gln Ala Tyr
    50              55              60
```

-continued

```
Ala Ala Gly Ile Asp Gly Gln Gly Val Lys Ile Gly Glu Met Asp Ser
 65                  70                  75                  80

Gly Phe Asp Pro Ser His Pro Asp Thr Pro Ala Ser Arg Tyr Gln Pro
                 85                  90                  95

Val Thr Ala Ser Gly Thr Tyr Val Asp Gly Thr Pro Phe Ser Val Ser
            100                 105                 110

Gly Ala Met Asn Gly Asn Asn Asp Ser His Gly Thr His Val Gly Gly
        115                 120                 125

Thr Leu Gly Ala Ser Arg Asp Gly Val Gly Met His Gly Val Ala Tyr
    130                 135                 140

Ala Ala Gln Val Tyr Val Ala Asn Thr Asn Gln Asn Asp Ser Phe Leu
145                 150                 155                 160

Phe Gly Pro Thr Pro Asp Pro Asn Tyr Phe Lys Ala Ala Tyr Gln Ala
                165                 170                 175

Leu Ala Asp Ala Gly Val Arg Ala Ile Asn Asn Ser Trp Gly Ser Gln
                180                 185                 190

Pro Lys Asp Val Ser Tyr Glu Thr Leu Asp Gly Leu His Ala Ala Tyr
            195                 200                 205

Ala Gln His Tyr Gly Arg Ser Thr Trp Leu Asp Ala Ala Gly Val
210                 215                 220

Ser Arg Gln Gly Val Ile Asn Val Phe Ser Ala Gly Asn Ser Gly Tyr
225                 230                 235                 240

Ala Asn Ala Ser Val Arg Ser Ala Leu Pro Tyr Phe Gln Pro Asp Leu
                245                 250                 255

Glu Gly His Trp Leu Ala Val Ser Gly Leu Asp Gln Asn Gly Gln
                260                 265                 270

Arg Tyr Asn Arg Cys Gly Ile Ala Lys Tyr Trp Cys Ile Thr Thr Pro
            275                 280                 285

Gly Arg Leu Ile Asn Ser Thr Met Pro Gly Gly Tyr Ala Asn Lys
            290                 295                 300

Ser Gly Thr Ser Met Ala Ala Pro His Ala Thr Gly Ala Leu Ala Leu
305                 310                 315                 320

Val Met Gln Arg Tyr Pro Tyr Leu Asn Asn Glu Gln Ala Leu Gln Val
                325                 330                 335

Leu Leu Thr Thr Ala Thr Gln Leu Asp Gly Thr Pro Thr Gly Ala Pro
                340                 345                 350

Thr Asp Thr Val Gly Trp Gly Val Pro Asp Leu Gly Arg Ala Met His
            355                 360                 365

Gly Pro Gly Gln Leu Leu Gly Arg Phe Glu Ala Asn Leu Pro Ala Gly
    370                 375                 380

Leu Arg Asp Glu Trp Ser Asn Pro Ile Ser Asp Ser Ala Leu Leu Gln
385                 390                 395                 400

Arg Gln Ala Glu Asp Ala Ala Glu His Ala Ala Trp Gln Arg Thr Leu
                405                 410                 415

Lys Asp Lys Gly Trp Glu Asn Gly Leu Pro Ala Gly Ala Ser Gln Gln
                420                 425                 430

Glu Arg Thr Asp Tyr Ala Ile Gly Met Ala Arg Asp Gln Ala Ala Ala
            435                 440                 445

Gln Arg Gln Tyr Gln Gly Ser Leu Val Lys Ala Gly Ala Gly Ser Leu
            450                 455                 460

Val Leu Ser Gly Asp Ser Thr Tyr Arg Gly Pro Thr Leu Val Asp Gly
465                 470                 475                 480

Gly Leu Leu Ser Val Asp Gly Ser Leu Leu Ser Ala Val Glu Val Asn
```

485                 490                 495
Ala Gly Gly Thr Leu Gly Gly Ser Gly Arg Ile Gly Gly Leu Leu Ala
                    500                 505                 510

Arg Ser Gly Gly Thr Val Ala Ala Gly Asn Ser Ile Gly Thr Leu Glu
                515                 520                 525

Val Ala Gly Asp Leu Arg Phe Glu Ser Gly Ser Thr Tyr Ala Val Glu
            530                 535                 540

Leu Ser Glu Ser Ala Ser Asp Arg Ile Val Ala Ser Gly Lys Ala Ser
545                 550                 555                 560

Ile Ala Gly Gly Asn Val Thr Leu Ala Met Glu Asn Ser Pro Asp Leu
                565                 570                 575

Leu Ser Gln Ser Gln Val Glu Ser Leu Val Gly Arg Arg Tyr Asp Ile
            580                 585                 590

Leu Asp Ala Ala Gly Gly Ile Asp Gly Arg Phe Asp Ala Val Leu Pro
        595                 600                 605

Asn Tyr Leu Phe Leu Gly Gly Thr Leu Asp Tyr Ala Ala Asn Ala Ile
    610                 615                 620

Arg Leu Asp Ile Gly Arg Asn Gly Thr Thr Leu Ala Ser Val Ala Gln
625                 630                 635                 640

Thr Pro Asn Gln Ala Ala Val Ala Gly Ala Val Glu Thr Leu Gly Ala
                645                 650                 655

Gly Asn Pro Val Tyr Glu Ser Leu Leu Leu Ser Glu Asn Ala Ala Thr
            660                 665                 670

Ala Gln Arg Ala Phe Gln Gln Leu Ser Gly Glu Ile Tyr Pro Ala Leu
        675                 680                 685

Ala Gly Leu Leu Leu Asn Asp Ser Arg Tyr Leu Arg Asp Ser Val Gly
    690                 695                 700

Glu Arg Leu Arg Gln Thr Ser Asp Gly Glu Ala Gly Gly Glu Ala Pro
705                 710                 715                 720

Glu Gly Trp Phe Lys Ala Leu Gly Ser Trp Gly Lys Ser Ala Asp Gly
                725                 730                 735

Ser His Gly Ser Glu Gly Tyr Arg His Ser Val Gly Gly Phe Leu Leu
            740                 745                 750

Gly Val Asp Ser Gln Val Ala Ser Asp Thr Arg Leu Gly Leu Val Ala
        755                 760                 765

Gly Tyr Ser Asn Ser Ser Leu Asn Met Asp Ser Ser Leu Gln Ser Ser
    770                 775                 780

Ala Ser Ile Asp Ser Tyr His Leu Gly Ala Tyr Leu Gly Arg Gln Leu
785                 790                 795                 800

Gln Gln Trp Arg Leu Ser Leu Gly Ala Ala His Ala Trp His Arg Ala
                805                 810                 815

Glu Val Lys Arg Asp Leu Gln Tyr Gly Ala Val Ala Gly Lys Gln Lys
            820                 825                 830

Ala Lys Leu Asp Ala Gln Ser Ser Gln Leu Phe Ala Glu Ala Ala Tyr
        835                 840                 845

Ala Leu Gly Trp Arg Ser Leu Glu Leu Glu Pro Phe Ala Gly Leu Ala
    850                 855                 860

Tyr Val His Val Ala Ser Asp Phe Arg Glu Arg Gly Ser Ala Ala
865                 870                 875                 880

Ala Leu Glu Gly Gly Asp Asp Asn Leu Asp Ala Ala Phe Thr Thr Leu
                885                 890                 895

Gly Leu Arg Ala Lys Arg His Phe Glu Leu Asp Ala Gly Arg Arg Leu
            900                 905                 910

```
Ala Leu Ser Gly Thr Leu Gly Trp Arg His Asn Leu Ser Asp Thr Thr
        915                 920                 925

Pro Gln Arg His Leu Ala Phe Ala Ser Gly Ser Gln Pro Phe Ser Val
        930                 935                 940

Glu Ser Val Ala Leu Ser Arg Asp Ala Ala Leu Leu Gly Val Asp Ala
945                 950                 955                 960

Ser Leu Ala Val Asn Arg Glu Val Ser Val Arg Leu Gly Tyr Asn Gly
                965                 970                 975

Leu Leu Gly Ser Arg Glu Lys Asp His Gly Val Gly Leu Ala Val Asp
                980                 985                 990

Trp Arg Phe
        995

<210> SEQ ID NO 25
<211> LENGTH: 1057
<212> TYPE: PRT
<213> ORGANISM: Pseudomonas aeruginosa

<400> SEQUENCE: 25

Met Lys Arg Met Leu Ile Asn Ala Thr Gln Pro Glu Glu Leu Arg Val
1               5                   10                  15

Ala Leu Val Asp Gly Gln Arg Leu Phe Asp Leu Asp Ile Glu Ser Gly
                20                  25                  30

Ala Arg Glu Gln Lys Lys Ala Asn Ile Tyr Lys Gly Arg Ile Thr Arg
            35                  40                  45

Val Glu Pro Ser Leu Glu Ala Ala Phe Val Asp Phe Gly Ala Glu Arg
50                  55                  60

His Gly Phe Leu Pro Leu Lys Glu Ile Ser Arg Glu Tyr Phe Lys Lys
65                  70                  75                  80

Ser Pro Glu Gly Arg Ile Asn Ile Lys Glu Val Leu Ser Glu Gly Gln
                85                  90                  95

Glu Val Ile Val Gln Val Glu Lys Glu Arg Gly Asn Lys Gly Ala
            100                 105                 110

Ala Leu Thr Thr Phe Ile Ser Leu Ala Gly Arg Tyr Leu Val Leu Met
            115                 120                 125

Pro Asn Asn Pro Arg Ala Gly Gly Ile Ser Arg Arg Ile Glu Gly Glu
        130                 135                 140

Glu Arg Asn Glu Leu Arg Glu Ala Leu Asn Gly Leu Asn Ala Pro Ala
145                 150                 155                 160

Asp Met Gly Leu Ile Val Arg Thr Ala Gly Leu Gly Arg Ser Thr Glu
                165                 170                 175

Glu Leu Gln Trp Asp Leu Asp Tyr Leu Leu Gln Leu Trp Ser Ala Ile
            180                 185                 190

Lys Glu Ala Ser Gly Glu Arg Gly Ala Pro Phe Leu Ile Tyr Gln Glu
        195                 200                 205

Ser Asn Val Ile Ile Arg Ala Ile Arg Asp Tyr Leu Arg Gln Asp Ile
    210                 215                 220

Gly Glu Val Leu Ile Asp Ser Ile Asp Ala Gln Glu Glu Ala Leu Asn
225                 230                 235                 240

Phe Ile Arg Gln Val Met Pro Gln Tyr Ala Ser Lys Val Lys Leu Tyr
                245                 250                 255

Gln Asp Ser Val Pro Leu Phe Asn Arg Phe Gln Ile Glu Ser Gln Ile
            260                 265                 270

Glu Thr Ala Phe Gln Arg Glu Val Lys Leu Pro Ser Gly Gly Ser Ile
```

```
              275                 280                 285
Val Ile Asp Pro Thr Glu Ala Leu Val Ser Ile Asp Ile Asn Ser Ala
290                 295                 300
Arg Ala Thr Lys Gly Gly Asp Ile Glu Glu Thr Ala Leu Gln Thr Asn
305                 310                 315                 320
Leu Glu Ala Ala Glu Ile Ala Arg Gln Leu Arg Leu Arg Asp Ile
            325                 330                 335
Gly Gly Leu Ile Val Ile Asp Phe Ile Asp Met Thr Pro Ala Lys Asn
            340                 345                 350
Gln Arg Ala Val Glu Glu Arg Val Arg Glu Ala Leu Glu Ala Asp Arg
        355                 360                 365
Ala Arg Val Gln Val Gly Arg Ile Ser Arg Phe Gly Leu Leu Glu Met
    370                 375                 380
Ser Arg Gln Arg Leu Arg Pro Ser Leu Gly Thr Ser Gly Ile Val
385                 390                 395                 400
Cys Pro Arg Cys Asn Gly Gln Gly Ile Ile Arg Asp Val Glu Ser Leu
                405                 410                 415
Ser Leu Ala Ile Leu Arg Leu Ile Glu Glu Ala Leu Lys Asp Arg
            420                 425                 430
Thr Ala Glu Val Arg Ala Arg Val Pro Phe Gln Val Ala Ala Phe Leu
        435                 440                 445
Leu Asn Glu Lys Arg Asn Ala Ile Thr Lys Ile Glu Leu Arg Thr Arg
450                 455                 460
Ala Arg Ile Phe Ile Leu Pro Asp Asp His Leu Glu Thr Pro His Phe
465                 470                 475                 480
Glu Val Gln Arg Leu Arg Asp Asp Ser Pro Glu Leu Val Ala Gly Gln
                485                 490                 495
Thr Ser Tyr Glu Met Ala Thr Val Glu His Glu Ala Gln Pro Val
                500                 505                 510
Ser Ser Thr Arg Thr Leu Val Arg Gln Glu Ala Ala Val Lys Thr Val
            515                 520                 525
Ala Pro Gln Gln Pro Ala Pro Gln His Thr Glu Ala Pro Val Glu Pro
530                 535                 540
Ala Lys Pro Met Pro Glu Pro Ser Leu Phe Gln Gly Leu Val Lys Ser
545                 550                 555                 560
Leu Val Gly Leu Phe Ala Gly Lys Asp Gln Pro Ala Ala Lys Pro Ala
                565                 570                 575
Glu Thr Ser Lys Pro Ala Ala Glu Arg Gln Thr Arg Gln Asp Glu Arg
            580                 585                 590
Arg Asn Gly Arg Gln Gln Asn Arg Arg Asp Gly Arg Asp Gly Asn
        595                 600                 605
Arg Arg Asp Glu Glu Arg Lys Pro Arg Glu Glu Arg Ala Glu Arg Gln
    610                 615                 620
Pro Arg Glu Glu Arg Ala Glu Arg Pro Asn Arg Glu Glu Arg Ser Glu
625                 630                 635                 640
Arg Arg Arg Glu Glu Arg Ala Glu Arg Pro Ala Arg Glu Glu Arg Gln
                645                 650                 655
Pro Arg Glu Gly Arg Glu Glu Arg Ala Glu Arg Thr Pro Arg Glu Glu
                660                 665                 670
Arg Gln Pro Arg Glu Gly Arg Glu Gly Arg Glu Glu Arg Ser Glu Arg
            675                 680                 685
Arg Arg Glu Glu Arg Ala Glu Arg Pro Ala Arg Glu Glu Arg Gln Pro
        690                 695                 700
```

```
Arg Glu Gly Arg Glu Glu Arg Ala Glu Arg Pro Ala Arg Glu Arg
705                 710                 715                 720

Gln Pro Arg Glu Asp Arg Gln Ala Arg Asp Ala Ala Leu Glu Ala
            725                 730                 735

Glu Ala Leu Pro Asn Asp Glu Ser Leu Glu Gln Asp Glu Gln Asp
        740                 745                 750

Thr Asp Gly Glu Arg Pro Arg Arg Ser Arg Gly Gln Arg Arg Arg
    755                 760                 765

Ser Asn Arg Arg Glu Arg Gln Arg Glu Val Ser Gly Glu Leu Glu Gly
770                 775                 780

Ser Glu Ala Thr Asp Asn Ala Ala Pro Leu Asn Thr Val Ala Ala
785                 790                 795                 800

Ala Ala Ala Ala Gly Ile Ala Val Ala Ser Glu Ala Val Glu Ala Asn
                805                 810                 815

Val Glu Gln Ala Pro Ala Thr Thr Ser Glu Ala Ala Ser Glu Thr Thr
            820                 825                 830

Ala Ser Asp Glu Thr Asp Ala Ser Thr Ser Glu Ala Val Glu Thr Gln
        835                 840                 845

Gly Ala Asp Ser Glu Ala Asn Thr Gly Glu Thr Ala Asp Ile Glu Ala
    850                 855                 860

Pro Val Thr Val Ser Val Val Arg Asp Glu Ala Asp Gln Ser Thr Leu
865                 870                 875                 880

Leu Val Ala Gln Ala Thr Glu Ala Pro Phe Ala Ser Glu Ser Val
                885                 890                 895

Glu Ser Arg Glu Asp Ala Glu Ser Ala Val Gln Pro Ala Thr Glu Ala
            900                 905                 910

Ala Glu Glu Val Ala Ala Pro Val Pro Val Glu Val Ala Ala Pro Ser
        915                 920                 925

Glu Pro Ala Ala Thr Glu Glu Pro Thr Pro Ala Ile Ala Ala Val Pro
    930                 935                 940

Ala Asn Ala Thr Gly Arg Ala Leu Asn Asp Pro Arg Glu Lys Arg Arg
945                 950                 955                 960

Leu Gln Arg Glu Ala Glu Arg Leu Ala Arg Glu Ala Ala Ala Ala
                965                 970                 975

Glu Ala Ala Ala Gln Ala Pro Ala Val Glu Glu Ile Pro Ala Val
            980                 985                 990

Ala Ser Glu Glu Ala Ser Ala Gln Glu Glu Pro Ala Ala Pro Gln Ala
        995                 1000                1005

Glu Glu Ile Thr Gln Ala Asp Val Pro Ser Gln Ala Asp Glu Ala
    1010                1015                1020

Gln Glu Ala Val Gln Ala Glu Pro Glu Ala Ser Gly Glu Gly Ala
    1025                1030                1035

Ala Asp Thr Glu His Ala Lys Lys Thr Glu Glu Ser Glu Thr Ser
    1040                1045                1050

Arg Pro His Ala
    1055

<210> SEQ ID NO 26
<211> LENGTH: 1161
<212> TYPE: PRT
<213> ORGANISM: Pseudomonas aeruginosa

<400> SEQUENCE: 26

Met Lys Ser Val Leu His Gln Ile Gly Lys Thr Ser Leu Ala Ala Ala
```

```
1               5                  10                  15
Leu Ser Gly Ala Val Leu Leu Ser Ala Gln Thr Thr His Ala Ala Ala
                20                  25                  30
Leu Ser Val Ser Gln Gln Pro Leu Met Leu Ile Gln Gly Val Ala Pro
                35                  40                  45
Asn Met Leu Val Thr Leu Asp Asp Ser Gly Ser Met Ala Phe Ala Tyr
 50                  55                  60
Ala Pro Asp Ser Ile Ser Gly Tyr Gly Asn Tyr Thr Phe Phe Ala Ser
 65                  70                  75                  80
Asn Ser Phe Asn Pro Met Tyr Phe Asp Pro Asn Thr Gln Tyr Lys Leu
                85                  90                  95
Pro Lys Lys Leu Thr Leu Val Asn Gly Gln Val Gln Ile Gln Asp Tyr
                100                 105                 110
Pro Ala Pro Asn Phe Ser Ala Trp Arg Asn Gly Phe Thr Arg Ser
                115                 120                 125
Gly Ser Ile Asn Leu Ser Asn Ser Tyr Lys Val Thr Ile Glu Tyr Gly
         130                 135                 140
Arg Gly Tyr Asp Lys Glu Ser Thr Ile Lys Ala Asp Ala Ala Tyr Tyr
145                 150                 155                 160
Tyr Asp Phe Thr Gly Ser Ser Cys Asn Arg Thr Asn Gln Ala Cys
                165                 170                 175
Tyr Thr Arg Arg Tyr Val Ser Thr Glu Gln Arg Gln Asn Phe Ala Asn
                180                 185                 190
Trp Tyr Ser Phe Tyr Arg Thr Arg Ala Leu Ala Thr Gln Thr Ala Ala
                195                 200                 205
Asn Leu Ala Phe Tyr Ser Leu Pro Glu Asn Ala Arg Val Ser Trp Gln
         210                 215                 220
Leu Leu Asn Asp Ser Asn Cys Asn Gln Met Gly Ser Gly Ser Ser Ser
225                 230                 235                 240
Gly Asn Cys Phe Ser Asn Tyr Leu Arg Asp Phe Thr Gly Gln His Arg
                245                 250                 255
Val Asn Phe Phe Asn Trp Leu Glu Lys Leu Ser Val Asn Gly Gly Thr
                260                 265                 270
Pro Leu Arg Gln Ala Met Thr Arg Ala Gly Glu Phe Leu Lys Lys Thr
                275                 280                 285
Gly Val Asn Gly Pro Tyr Ala Tyr Arg Pro Gly Thr Gln Thr Ala Pro
                290                 295                 300
Glu Tyr Ser Cys Arg Gly Ser Tyr His Ile Leu Met Thr Asp Gly Leu
305                 310                 315                 320
Trp Asn Asn Asp Ser Ala Asn Val Gly Asn Ala Asp Ser Thr Ala Arg
                325                 330                 335
Asn Leu Pro Asp Gly Lys Ser Tyr Ser Ser Gln Thr Pro Tyr Arg Asp
                340                 345                 350
Gly Thr Phe Asp Thr Leu Ala Asp Gln Ala Phe His Tyr Trp Ala Thr
                355                 360                 365
Asp Ala Arg Pro Asp Ile Asp Asp Asn Ile Lys Pro Tyr Ile Pro Tyr
                370                 375                 380
Pro Asp Gln Ala Asn Pro Ser Ala Glu Tyr Trp Asn Pro Arg Asn Asp
385                 390                 395                 400
Pro Ala Thr Trp Gln His Met Val Thr Tyr Thr Leu Gly Leu Gly Leu
                405                 410                 415
Thr Thr Ser Leu Thr Ser Pro Arg Trp Glu Gly Ser Thr Phe Ser Gly
                420                 425                 430
```

```
Gly Tyr Asn Asp Ile Val Ala Gly Asn Leu Ser Trp Pro Arg Ala Ser
            435                 440                 445

Asn Asn Asp Ser Asn Asn Val Tyr Asp Leu Trp His Ala Ala Val Asn
450                 455                 460

Ser Arg Gly Glu Phe Phe Ser Ala Asp Ser Pro Asp Gln Leu Val Ala
465                 470                 475                 480

Ala Phe Gln Asp Ile Leu Asn Arg Ile Ser Gly Lys Asp Leu Pro Ala
                485                 490                 495

Ser Arg Pro Ala Ile Ser Ser Leu Gln Glu Asp Thr Gly Asp
                500                 505                 510

Lys Leu Thr Arg Phe Ala Tyr Gln Thr Ser Phe Ala Ser Asp Lys Asn
            515                 520                 525

Trp Ala Gly Asp Leu Thr Arg Tyr Ser Leu Thr Thr Gln Asp Lys Ala
            530                 535                 540

Thr Val Gln Thr Lys Leu Trp Ser Ala Gln Ser Ile Leu Asp Ala Met
545                 550                 555                 560

Pro Asn Gly Gly Ala Gly Arg Lys Ile Met Met Ala Gly Ser Gly Thr
                565                 570                 575

Ser Gly Leu Lys Glu Phe Thr Trp Gly Ser Leu Ser Ala Asp Gln Gln
            580                 585                 590

Arg Gln Leu Asn Arg Asp Pro Asp Arg Asn Asp Val Ala Asp Thr Lys
            595                 600                 605

Gly Gln Asp Arg Val Ala Phe Leu Arg Gly Asp Arg Arg Lys Glu Asn
            610                 615                 620

Ser Asp Asn Phe Arg Thr Arg Asn Ser Ile Leu Gly Asp Ile Ile Asn
625                 630                 635                 640

Ser Ser Pro Ala Thr Val Gly Lys Ala Gln Tyr Leu Thr Tyr Leu Ala
                645                 650                 655

Gln Pro Ile Glu Pro Ser Gly Asn Tyr Ser Thr Phe Ala Glu Ala Gln
            660                 665                 670

Lys Thr Arg Ala Pro Arg Val Tyr Val Gly Ala Asn Asp Gly Met Leu
            675                 680                 685

His Gly Phe Asp Thr Asp Gly Asn Glu Thr Phe Ala Phe Ile Pro Ser
            690                 695                 700

Ala Val Phe Glu Lys Leu His Lys Leu Thr Ala Arg Gly Tyr Gln Gly
705                 710                 715                 720

Gly Ala His Gln Phe Tyr Val Asp Gly Ser Pro Val Val Ala Asp Ala
                725                 730                 735

Phe Phe Gly Gly Ala Trp His Thr Val Leu Ile Gly Ser Leu Arg Ala
                740                 745                 750

Gly Gly Lys Gly Leu Phe Ala Leu Asp Val Thr Asp Pro Ala Asn Ile
            755                 760                 765

Lys Leu Leu Trp Glu Ile Gly Val Asp Gln Glu Pro Asp Leu Gly Tyr
            770                 775                 780

Ser Phe Pro Lys Pro Thr Val Ala Arg Leu His Asn Gly Lys Trp Ala
785                 790                 795                 800

Val Val Thr Gly Asn Gly Tyr Ser Ser Leu Asn Asp Lys Ala Ala Leu
                805                 810                 815

Leu Ile Ile Asp Leu Glu Thr Gly Ala Ile Thr Arg Lys Leu Glu Val
                820                 825                 830

Thr Gly Arg Thr Gly Val Pro Asn Gly Leu Ser Ser Pro Arg Leu Ala
            835                 840                 845
```

```
Asp Asn Asn Ser Asp Gly Val Ala Asp Tyr Ala Tyr Ala Gly Asp Leu
            850                 855                 860

Gln Gly Asn Leu Trp Arg Phe Asp Leu Ile Ala Gly Lys Val Asn Gln
865                 870                 875                 880

Asp Asp Pro Phe Ser Arg Ala Asn Asp Gly Pro Ala Val Ala Ser Ser
                885                 890                 895

Phe Arg Val Ser Phe Gly Gly Gln Pro Leu Tyr Ser Ala Val Asp Ser
                900                 905                 910

Ala Gly Ala Ala Gln Ala Ile Thr Ala Ala Pro Ser Leu Val Arg His
                915                 920                 925

Pro Thr Arg Lys Gly Tyr Ile Val Ile Phe Gly Thr Gly Lys Tyr Phe
    930                 935                 940

Glu Asn Ala Asp Ala Arg Ala Asp Thr Ser Arg Ala Gln Thr Leu Tyr
945                 950                 955                 960

Gly Ile Trp Asp Gln Gln Thr Lys Gly Glu Ala Ala Gly Ser Thr Pro
                965                 970                 975

Arg Leu Thr Arg Gly Asn Leu Gln Gln Gln Thr Leu Asp Leu Gln Ala
                980                 985                 990

Asp Ser Thr Phe Ala Ser Thr Ala Arg Thr Ile Arg Ile Ala Ser Gln
                995                 1000                1005

Asn Pro Val Asn Trp Leu Asn Asn Asp Gly Ser Thr Lys Gln Ser
    1010                1015                1020

Gly Trp Tyr Leu Asp Phe Met Val Asn Gly Thr Leu Lys Gly Glu
    1025                1030                1035

Met Leu Ile Glu Asp Met Ile Ala Ile Gly Gln Val Val Leu Leu
    1040                1045                1050

Gln Thr Ile Thr Pro Asn Asp Pro Cys Ala Asp Gly Ala Ser
    1055                1060                1065

Asn Trp Thr Tyr Gly Leu Asp Pro Tyr Thr Gly Arg Thr Ser
    1070                1075                1080

Phe Thr Val Phe Asp Leu Ala Arg Gln Gly Val Val Asp Ser Lys
    1085                1090                1095

Ser Asp Tyr Ser Tyr Asn Lys Gln Asn Val Ala Val Ser Gly Thr
    1100                1105                1110

Glu Gln Lys Gly Leu Gly Gly Leu Thr Leu Ser Thr Asn Glu Gln
    1115                1120                1125

Gly Asn Pro Glu Val Cys Ser Ser Gly Glu Cys Leu Thr Val Asn
    1130                1135                1140

Pro Gly Pro Asn Thr Arg Gly Arg Gln Asn Trp Arg Pro Ile Glu
    1145                1150                1155

Gly Lys Asn
    1160

<210> SEQ ID NO 27
<211> LENGTH: 1211
<212> TYPE: PRT
<213> ORGANISM: Pseudomonas aeruginosa

<400> SEQUENCE: 27

Met Lys Ile Leu Ala Ile Arg Leu Lys Asn Leu Ala Ser Leu Ala Gly
1               5                   10                  15

Glu Gln Glu Ile Asp Phe Thr Arg Glu Pro Leu Ser Ser Ala Gly Leu
                20                  25                  30

Phe Ala Ile Thr Gly Pro Thr Gly Ala Gly Lys Ser Thr Val Leu Asp
            35                  40                  45
```

```
Ala Leu Cys Leu Ala Leu Phe Gly Ser Thr Pro Arg Leu Glu Ser Thr
 50                  55                  60
Ser Ala Ser Ser Lys Val Pro Asp Gly Arg Asn Glu Leu Ser Ser Asn
 65                  70                  75                  80
Asp Glu Arg Asn Leu Leu Arg Arg Gly Cys Ala Ser Gly Tyr Ala Glu
                 85                  90                  95
Val Asp Phe Val Gly Ile Asp Gly His Arg Tyr Arg Ala Arg Trp Glu
            100                 105                 110
Thr Arg Arg Ser Arg Asp Lys Ala Asp Gly Ala Leu Gln Lys Ser Gln
            115                 120                 125
Gln Ser Leu Gln Asp Leu Glu Thr Gln Gln Met Leu Ala Ala Asn Lys
            130                 135                 140
Lys Ser Glu Phe Arg Glu Gln Leu Glu Gln Lys Leu Gly Leu Asn Phe
145                 150                 155                 160
Ala Gln Phe Thr Arg Ala Val Leu Leu Ala Gln Ser Glu Phe Ser Ala
                165                 170                 175
Phe Leu Lys Ala Ser Asp Asn Asp Arg Gly Ala Leu Leu Glu Lys Leu
            180                 185                 190
Thr Asp Thr Gly Leu Tyr Ser Gln Leu Ser Lys Ala Ala Tyr Gln Arg
            195                 200                 205
Ala Ser Gln Ala Asp Glu Gln Arg Lys Gln Leu Glu Gln Arg Leu Glu
            210                 215                 220
Gly Ser Leu Pro Leu Ala Glu Gln Ala Arg Ala Gly Leu Glu Ala Ala
225                 230                 235                 240
Leu Glu Ser His Ala Gln Ala Arg Leu Gln Glu Gln Ala Leu Gln
                245                 250                 255
Arg Leu Glu Gly Gln Gln Gln Trp Phe Thr Glu Glu Arg Leu Leu
            260                 265                 270
Gln Ser Cys Glu His Ala Gln Gly Gln Leu Ala Glu Ala Arg Gln Ala
            275                 280                 285
Trp Asp Ala Leu Ala Thr Glu Arg Glu Thr Leu Gln Trp Leu Glu Arg
            290                 295                 300
Leu Ala Pro Val Arg Gly Leu Ile Glu Arg Leu Lys Gln Leu Glu Gln
305                 310                 315                 320
Glu Leu Arg His Ser Glu Gln Gln Arg Gln Arg Thr Glu Gln
                325                 330                 335
Ala Ala Gly Thr Glu Arg Leu Gln Gly Leu Gln Ala Arg Leu Gln Glu
            340                 345                 350
Ala Arg Glu Arg Gln Ala Gln Ala Asp Asn His Leu Arg Gln Ala Gln
            355                 360                 365
Ala Pro Leu Arg Glu Ala Phe Gln Leu Glu Ser Glu Ala Arg Arg Leu
370                 375                 380
Glu Arg Thr Leu Ala Glu Arg Gln Glu Leu His Arg Gln Ser Asn Gln
385                 390                 395                 400
Arg His Ala Gln Gln Ser Asp Ala Ala Arg Gln Leu Asp Met Glu Gln
                405                 410                 415
Gln Arg His Val Ala Glu Gln Ala Gln Leu Gln Ala Ala Leu Arg Asp
            420                 425                 430
Ser Gln Ala Leu Ala Ala Leu Gly Asp Ala Trp Val Thr His Gln Gly
            435                 440                 445
Gln Leu Ala Thr Phe Val Gln Arg Arg Gln Arg Ala Leu Glu Ser Gln
            450                 455                 460
```

```
Ala Gln Leu Pro Glu Leu Glu Lys Ser Leu Ala His Ala Gly Glu Pro
465                 470                 475                 480

Leu Glu Arg Leu Gln Ala Gln Trp Thr Ala Leu His Gly Ser Glu Pro
            485                 490                 495

Asp Asp Leu Ala Ala Arg Leu Val Glu Leu Arg Arg Gln Thr Asp Ser
        500                 505                 510

Leu Glu Arg Gln Gln Ala Leu His Lys Glu Trp Gln Gln Val Leu Asp
    515                 520                 525

Gln Arg Ala Gly Leu Ala Arg Arg Leu Gly Glu Leu Asp Gln Arg Met
530                 535                 540

Val Glu Gln Glu Gln Ala Leu Leu Asp Leu Lys Arg Gln Gly Ser Gln
545                 550                 555                 560

Cys Ala Glu Glu Val Lys Ala Ala Glu Gln Ala Leu Gln Val Thr Arg
                565                 570                 575

Glu Leu Leu Gln Arg Gln Arg Leu Ala Arg Ser Ala Ser Val Glu Gln
            580                 585                 590

Leu Arg Ala Gly Leu Val Asp Gly Glu Ala Cys Pro Val Cys Gly Ser
    595                 600                 605

Gln Glu His Pro Tyr His His Ser Glu Gln Leu Leu Ala Ala Leu Gly
610                 615                 620

Glu His Asp Asp Gln Glu Gln Val Arg Ala Glu Gln Ser Leu Glu Arg
625                 630                 635                 640

Leu Arg Gln Thr Leu Val Gly Leu Arg Glu Gly Tyr Ser Ser Gln Arg
                645                 650                 655

Glu Arg Leu Asn Gln Ser Arg Gln Glu Gln Glu Leu Thr Gly Gln
            660                 665                 670

Leu Ala Ala Leu Asp Arg Gln Leu Asp Gln Trp Thr Leu Pro Glu Glu
    675                 680                 685

Leu Arg Leu Leu Gln Pro Ser Ala Gln Leu Glu Trp Leu Ala Gln Arg
690                 695                 700

Leu Asp Asp Leu Ala Gly Gln Arg Gln Gln Cys Gln Arg Asp Phe Asp
705                 710                 715                 720

Arg Leu Ile Ala Arg Gln Arg Gln Thr Gln Gln Leu Gln Gln Glu Leu
                725                 730                 735

Arg Ala Ala Glu Thr Ile Leu Gln Gln Arg Gln Gln Ala Leu Thr Glu
            740                 745                 750

Gln Arg Gln Arg Tyr Glu His Leu Gln Gln Val Glu Glu Asp Ser
    755                 760                 765

Gln Gln Leu Arg Pro Leu Leu Ser Asp Glu His Trp Gln Arg Trp Gln
770                 775                 780

Ala Asp Pro Leu Arg Thr Phe Gln Ala Leu Gly Glu Ser Ile Glu Gln
785                 790                 795                 800

Arg Arg Gln Gln Gln Ala Arg Leu Gln Gln Ile Glu Gln Arg Leu Gln
                805                 810                 815

Glu Leu Lys Gln Arg Cys Asp Glu Ser Ser Trp Gln Leu Lys Gln Ser
            820                 825                 830

Asp Glu Gln Arg Asn Glu Ala Arg Gln Ala Glu Glu Arg Ala Gln Ala
    835                 840                 845

Glu Leu Ala Glu Leu Asn Gly Arg Leu Gly Ala His Leu Gly Gln His
850                 855                 860

Ala Cys Ala Gln Asp Trp Gln Leu Ser Leu Glu His Ala Ala Gln Ala
865                 870                 875                 880

Ala Gln Ser Ala Val Glu Thr Leu Gln Ala Pro Leu Asp Ser Leu Arg
```

```
                        885                 890                 895
Glu Glu Gln Leu Arg Leu Ala Glu Ala Leu Glu His Leu Gln Gln Gln
                    900                 905                 910

Arg Gln Arg Gln Gln Asp Glu Phe Gln Arg Leu Gln Ala Asp Trp Gln
                915                 920                 925

Ala Trp Arg Glu Arg Gln Asp Asn Leu Asp Asp Ser Arg Leu Asp Ala
            930                 935                 940

Leu Leu Gly Leu Ser Glu Glu Gln Ala Thr Gln Trp Arg Glu Gln Leu
945                 950                 955                 960

Gln Arg Leu Gln Glu Glu Ile Thr Arg Gln Gly Thr Leu Glu Ala Glu
                965                 970                 975

Arg Gln Ala Gln Leu Leu Gln His Arg Arg Gln Arg Pro Glu Thr Asp
            980                 985                 990

Arg Glu Ala Leu Glu Asp Asn Leu Arg Gln Gln Arg Glu Arg Leu Ala
        995                 1000                1005

Ala Ser Glu Gln Ala Tyr Leu Glu Thr Tyr Ser Gln Leu Gln Ala
    1010                1015                1020

Asp Asn Gln Arg Arg Glu Gln Ser Gln Ala Leu Leu Ala Glu Leu
    1025                1030                1035

Glu Arg Ala Arg Ala Glu Phe Arg Arg Trp Gly Arg Leu Asn Glu
    1040                1045                1050

Leu Ile Gly Ser Ser Ser Gly Asp Lys Phe Arg Arg Ile Ala Gln
    1055                1060                1065

Gly Tyr Asn Leu Asp Leu Leu Val Gln His Ser Asn Val Gln Leu
    1070                1075                1080

Arg Gln Leu Ala Arg Arg Tyr Arg Leu Gln Arg Gly Gly Ser Glu
    1085                1090                1095

Leu Gly Leu Leu Val Val Asp Thr Glu Met Gly Asp Glu Leu Arg
    1100                1105                1110

Ser Val Tyr Ser Leu Ser Gly Gly Glu Thr Phe Leu Ile Ser Leu
    1115                1120                1125

Ala Leu Ala Leu Gly Leu Ala Ser Met Ala Ser Ser Lys Leu Arg
    1130                1135                1140

Ile Glu Ser Leu Phe Ile Asp Glu Gly Phe Gly Ser Leu Asp Pro
    1145                1150                1155

Glu Ser Leu Gln Leu Ala Met Asp Ala Leu Asp Asn Leu Gln Ala
    1160                1165                1170

Gln Gly Arg Lys Val Ala Val Ile Ser His Val Gln Glu Met His
    1175                1180                1185

Glu Arg Ile Pro Val Gln Val Arg Val Gln Arg Glu Gly Asn Gly
    1190                1195                1200

Met Ser Ser Leu Lys Val Val Gly
    1205                1210

<210> SEQ ID NO 28
<211> LENGTH: 2468
<212> TYPE: PRT
<213> ORGANISM: Pseudomonas aeruginosa

<400> SEQUENCE: 28

Met Ser Ile Gln Ala Lys Val Thr Pro Ile Asp Gln Ser Ile Ser Ser
1               5                   10                  15

Ala Ala Val Glu Val Pro Gly Asn Gly Ile Leu Lys Leu Ser Gln
            20                  25                  30
```

-continued

```
Ser Ser Asn Val Ala Leu Asp Val Ala Pro Glu Ser Val Ala Gly Tyr
        35                  40                  45
Ser Lys Ser Gly Ser Asp Leu Ile Val Gln Leu Lys Thr Gly Glu Ser
 50                  55                  60
Val Arg Ile Ala Asn Phe Tyr Ala Glu Gly Gln Pro Ser Ser Gln Leu
 65                  70                  75                  80
Phe Leu Ala Asp Lys Asp Lys Leu Val Ala Val Asp Leu Pro Pro Val
                 85                  90                  95
Ala Ala Asp Gly Pro Leu Met Ala Gly Tyr Ile Pro Gln Glu Ser Leu
            100                 105                 110
Ala Gly Phe Glu Ser Leu Thr Gly Ala Gly Val Leu Gly Gly Met Ser
        115                 120                 125
Ala Gly Thr Ala Leu Leu Val Gly Ala Ala Ile Gly Ala Gly Val
    130                 135                 140
Ala Ile Ser Asn Ser Ser Gly Gly Gly Gly Gly Ser Ser Val
145                 150                 155                 160
Pro Pro Asp Thr Thr Pro Pro Lys Ala Ala Ser Gly Leu Lys Ile Ala
                165                 170                 175
Pro Asp Gly Ser Ser Ile Ser Gly Gln Ala Glu Ala Gly Ala Ser Val
            180                 185                 190
Gly Ile Asp Thr Asn Gly Asp Gly Lys Pro Asp Leu Thr Val Ile Ala
        195                 200                 205
Asp Ala Asn Gly Asn Phe Thr Ala Pro Leu Asn Pro Pro Leu Thr Asn
    210                 215                 220
Gly Gln Thr Val Thr Val Val Thr Asp Pro Ala Gly Asn Ala Ser
225                 230                 235                 240
Pro Pro Ala Gln Val Thr Ala Pro Asp Thr Thr Ala Pro Ala
                245                 250                 255
Thr Asp Val Gln Val Ala Pro Asp Gly Ser Ser Val Thr Gly Lys Ala
            260                 265                 270
Glu Pro Gly Ser Thr Val Gly Val Asp Thr Asp Gly Asp Gly Gln Pro
        275                 280                 285
Asp Thr Thr Val Val Val Gly Pro Gly Gly Ser Phe Glu Val Pro Leu
    290                 295                 300
Asn Pro Pro Leu Thr Asn Gly Glu Thr Val Thr Val Ile Val Thr Asp
305                 310                 315                 320
Pro Ala Gly Asn Asn Ser Thr Pro Val Thr Val Glu Ala Pro Asp Thr
                325                 330                 335
Thr Ala Pro Ala Pro Ala Thr Asp Val Gln Val Ala Pro Asp Gly Ser
            340                 345                 350
Ser Val Thr Gly Asn Ala Glu Pro Gly Ala Thr Val Gly Val Asp Thr
        355                 360                 365
Asp Gly Asp Gly Gln Pro Asp Thr Thr Val Val Gly Pro Gly Gly
    370                 375                 380
Ser Phe Glu Val Pro Leu Asn Pro Pro Leu Thr Asn Gly Glu Thr Val
385                 390                 395                 400
Thr Val Ile Val Thr Asp Pro Ala Gly Asn Ser Ser Thr Pro Val Thr
                405                 410                 415
Ala Glu Ala Pro Asp Phe Pro Asp Ala Pro Gln Val Asn Ala Ser Asn
            420                 425                 430
Gly Ser Val Leu Ser Gly Thr Ala Glu Ala Gly Val Thr Ile Val Ile
        435                 440                 445
Thr Asp Gly Asn Gly Asn Pro Ile Gly Gln Thr Ser Ala Asp Ala Asn
```

```
                    450                 455                 460
Gly Asn Trp Ser Phe Thr Pro Gly Ser Gln Leu Pro Asp Gly Thr Val
465                 470                 475                 480

Val Asn Val Val Ala Arg Asp Ala Ala Gly Asn Ser Ser Pro Ala Thr
                    485                 490                 495

Ser Ile Thr Val Asp Gly Val Ala Pro Asn Ala Pro Val Val Glu Pro
                500                 505                 510

Ser Asn Gly Ser Glu Leu Ser Gly Thr Ala Glu Pro Gly Ser Ser Val
                515                 520                 525

Thr Leu Thr Asp Gly Asn Gly Asn Pro Ile Gly Gln Thr Thr Ala Asp
530                 535                 540

Ala Asn Gly Asn Trp Ser Phe Thr Pro Ser Thr Pro Leu Pro Asp Gly
545                 550                 555                 560

Thr Val Val Asn Val Val Ala Arg Asp Ala Ala Gly Asn Ser Ser Pro
                565                 570                 575

Pro Ala Ser Val Thr Val Asp Ala Val Ala Pro Ala Thr Pro Thr Val
                580                 585                 590

Asp Pro Ser Asn Gly Thr Thr Leu Ser Gly Thr Ala Glu Pro Gly Ser
                595                 600                 605

Ser Val Thr Leu Thr Asp Gly Asn Gly Asn Pro Ile Gly Gln Val Thr
                610                 615                 620

Ala Asp Gly Ser Gly Asn Trp Thr Phe Thr Pro Ser Thr Pro Leu Pro
625                 630                 635                 640

Asn Gly Thr Val Val Asn Ala Thr Ala Thr Asp Pro Ser Gly Asn Ala
                    645                 650                 655

Ser Ser Pro Ala Ser Val Thr Val Asp Ala Val Ala Pro Ala Thr Pro
                660                 665                 670

Val Val Asn Pro Ser Asn Gly Thr Thr Leu Ser Gly Thr Ala Glu Pro
                675                 680                 685

Gly Ala Thr Val Thr Leu Thr Asp Gly Asn Gly Asn Pro Ile Gly Gln
            690                 695                 700

Val Thr Ala Asp Gly Ser Gly Asn Trp Ser Phe Thr Pro Thr Thr Pro
705                 710                 715                 720

Leu Pro Asn Gly Thr Val Asn Ala Thr Ala Thr Asp Ala Ser Gly
                    725                 730                 735

Asn Thr Ser Ala Gly Ser Ser Val Thr Val Asp Ser Val Ala Pro Ala
                740                 745                 750

Thr Pro Val Ile Asn Pro Ser Asn Gly Thr Thr Leu Ser Gly Thr Ala
                755                 760                 765

Glu Pro Gly Ser Ser Val Thr Leu Thr Asp Gly Asn Gly Asn Pro Ile
770                 775                 780

Gly Gln Val Thr Ala Asp Gly Ser Gly Asn Trp Ser Phe Thr Pro Ser
785                 790                 795                 800

Thr Pro Leu Ala Asp Gly Thr Val Val Asn Ala Thr Ala Thr Asp Pro
                805                 810                 815

Ala Gly Asn Thr Ser Gly Gln Gly Ser Thr Val Asp Gly Val Ala
                820                 825                 830

Pro Thr Thr Pro Thr Val Asn Leu Ser Asn Gly Ser Ser Leu Ser Gly
                835                 840                 845

Thr Ala Glu Pro Gly Ser Thr Val Ile Leu Thr Asp Gly Asn Gly Asn
                850                 855                 860

Pro Ile Ala Glu Val Thr Ala Asp Gly Ser Gly Asn Trp Thr Tyr Thr
865                 870                 875                 880
```

```
Pro Ser Thr Pro Ile Ala Asn Gly Thr Val Val Asn Val Ala Gln
            885                 890                 895

Asp Ala Ala Gly Asn Ser Ser Pro Gly Ala Ser Val Thr Val Asp Ser
            900                 905                 910

Gln Ala Pro Ala Ala Pro Val Val Asn Pro Ser Asn Gly Thr Thr Leu
            915                 920                 925

Ser Gly Thr Ala Glu Pro Gly Ala Thr Val Thr Leu Thr Asp Gly Asn
            930                 935                 940

Gly Asn Pro Ile Gly Gln Val Thr Ala Asp Gly Ser Gly Asn Trp Ser
945                 950                 955                 960

Phe Thr Pro Gly Thr Pro Leu Ala Asn Gly Thr Val Val Asn Ala Thr
            965                 970                 975

Ala Ser Asp Pro Thr Gly Asn Thr Ser Ala Pro Ala Ser Thr Thr Val
            980                 985                 990

Asp Ser Val Ala Pro Ala Ala Pro  Val Val Asn Pro Ser  Asn Gly Ala
            995                1000                1005

Glu Ile  Ser Gly Thr Ala Glu  Pro Gly Ala Thr Val  Thr Leu Thr
            1010               1015               1020

Asp Gly  Ser Gly Asn Pro Ile  Gly Gln Val Thr Ala  Asp Gly Ser
            1025               1030               1035

Gly Asn  Trp Ser Phe Thr Pro  Ser Thr Pro Leu Ala  Asp Gly Thr
            1040               1045               1050

Val Val  Asn Ala Thr Ala Thr  Asp Pro Ala Gly Asn  Thr Gly Gly
            1055               1060               1065

Gln Gly  Ser Thr Thr Val Asp  Ala Ile Ala Pro Ala  Thr Pro Thr
            1070               1075               1080

Val Asn  Leu Ser Asn Gly Ser  Ser Leu Ser Gly Thr  Ala Glu Pro
            1085               1090               1095

Gly Ser  Thr Val Ile Leu Thr  Asp Gly Asn Gly Asn  Pro Ile Ala
            1100               1105               1110

Glu Val  Thr Ala Asp Gly Ser  Gly Asn Trp Thr Tyr  Thr Pro Ser
            1115               1120               1125

Thr Pro  Ile Ala Asn Gly Thr  Val Val Asn Val Val  Ala Gln Asp
            1130               1135               1140

Ala Ser  Gly Asn Ser Ser Pro  Pro Ala Thr Val Thr  Val Asp Ser
            1145               1150               1155

Ser Ala  Pro Pro Ala Pro Val  Ile Asn Pro Ser Asn  Gly Val Val
            1160               1165               1170

Ile Ser  Gly Thr Ala Glu Ala  Gly Ala Thr Val Thr  Leu Thr Asp
            1175               1180               1185

Ala Gly  Gly Asn Pro Ile Gly  Gln Val Thr Ala Asp  Gly Ser Gly
            1190               1195               1200

Asn Trp  Ser Phe Thr Pro Gly  Thr Pro Leu Ala Asn  Gly Thr Val
            1205               1210               1215

Ile Val  Ala Thr Ala Thr Asp  Pro Thr Gly Asn Thr  Gly Pro Gln
            1220               1225               1230

Ala Ala  Thr Thr Val Asp Ala  Val Ala Pro Pro Ala  Pro Val Ile
            1235               1240               1245

Asp Pro  Ser Asn Gly Thr Thr  Ile Ser Gly Thr Ala  Glu Ala Gly
            1250               1255               1260

Ala Lys  Val Ile Leu Thr Asp  Gly Asn Gly Asn Pro  Ile Gly Glu
            1265               1270               1275
```

```
Thr Thr Ala Asp Gly Ser Gly Asn Trp Ser Phe Thr Pro Gly Thr
1280                1285                1290

Pro Leu Ala Asn Gly Thr Val Val Asn Ala Val Ala Gln Asp Pro
1295                1300                1305

Ala Gly Asn Thr Gly Pro Gln Gly Ser Thr Thr Val Asp Ala Val
1310                1315                1320

Ala Pro Asn Thr Pro Val Val Asn Pro Ser Asn Gly Asn Leu Leu
1325                1330                1335

Asn Gly Thr Ala Glu Pro Gly Ser Thr Val Thr Leu Thr Asp Gly
1340                1345                1350

Asn Gly Asn Pro Ile Gly Gln Thr Thr Ala Asp Gly Ser Gly Asn
1355                1360                1365

Trp Ser Phe Thr Pro Gly Ser Gln Leu Pro Asn Gly Thr Val Val
1370                1375                1380

Asn Val Thr Ala Ser Asp Ala Ala Gly Asn Thr Ser Leu Pro Ala
1385                1390                1395

Thr Thr Thr Val Asp Ser Ser Leu Pro Ser Ile Pro Gln Val Asp
1400                1405                1410

Pro Ser Asn Gly Ser Val Ile Ser Gly Thr Ala Asp Ala Gly Asn
1415                1420                1425

Thr Ile Ile Ile Thr Asp Gly Asn Gly Asn Pro Ile Gly Gln Val
1430                1435                1440

Thr Ala Asp Gly Ser Gly Asn Trp Ser Phe Thr Pro Gly Ile Pro
1445                1450                1455

Leu Pro Asp Gly Thr Val Val Asn Val Val Ala Arg Ser Pro Ser
1460                1465                1470

Asn Val Asp Ser Ala Pro Ala Val Ile Thr Val Asp Gly Val Ala
1475                1480                1485

Pro Ala Ala Pro Val Ile Asp Pro Ser Asn Gly Thr Glu Ile Ser
1490                1495                1500

Gly Thr Ala Glu Ala Gly Ala Thr Val Ile Leu Thr Asp Gly Gly
1505                1510                1515

Gly Asn Pro Ile Gly Gln Ala Thr Ala Asp Gly Ser Gly Asn Trp
1520                1525                1530

Thr Phe Thr Pro Ser Thr Pro Leu Ala Asn Gly Thr Val Ile Asn
1535                1540                1545

Ala Val Ala Gln Asp Pro Ala Gly Asn Thr Ser Gly Pro Ala Ser
1550                1555                1560

Val Thr Val Asp Ala Ile Ala Pro Pro Ala Pro Val Ile Asn Pro
1565                1570                1575

Ser Asn Gly Val Val Ile Ser Gly Thr Ala Glu Ala Gly Ala Thr
1580                1585                1590

Val Ile Leu Thr Asp Gly Asn Gly Asn Pro Ile Gly Gln Val Thr
1595                1600                1605

Ala Asp Gly Ser Gly Asn Trp Ser Phe Thr Pro Gly Thr Pro Leu
1610                1615                1620

Ala Asn Gly Ser Val Ile Asn Ala Leu Ala Gln Asp Ala Ala Gly
1625                1630                1635

Asn Asn Ser Ser Pro Thr Ser Ala Thr Val Asp Ser Leu Ala Pro
1640                1645                1650

Ala Ala Pro Val Ile Asp Pro Ser Asn Gly Ser Val Ile Ala Gly
1655                1660                1665

Thr Ala Glu Ala Gly Ala Thr Val Ile Leu Thr Asp Gly Asn Gly
```

-continued

```
            1670                1675                1680

Asn Pro Ile Gly Gln Val Thr Ala Asp Gly Ser Gly Asn Trp Ser
            1685                1690                1695

Phe Thr Pro Gly Thr Pro Leu Ser Asn Gly Thr Val Val Asn Ala
            1700                1705                1710

Val Ala Gln Asp Ala Ala Gly Asn Thr Ser Gly Pro Val Ser Thr
            1715                1720                1725

Thr Val Asp Ala Val Ala Pro Ala Thr Pro Val Ile Asp Pro Ser
            1730                1735                1740

Asn Gly Val Glu Leu Ser Gly Thr Ala Glu Pro Gly Val Arg Val
            1745                1750                1755

Ile Leu Thr Asp Gly Asn Gly Asn Pro Ile Gly Gln Thr Leu Ala
            1760                1765                1770

Asp Gly Ser Gly Asn Trp Ser Phe Thr Pro Gly Thr Pro Leu Ala
            1775                1780                1785

Asn Gly Thr Val Val Asn Ala Val Ala Gln Asp Pro Ala Gly Asn
            1790                1795                1800

Thr Ser Gly Pro Ala Ser Thr Thr Val Asp Thr Val Ala Pro Ala
            1805                1810                1815

Thr Pro Val Ile Asn Pro Ser Asn Gly Ser Val Ile Thr Gly Thr
            1820                1825                1830

Ala Glu Val Gly Ala Lys Val Ile Leu Thr Asp Gly Asn Gly Asn
            1835                1840                1845

Pro Ile Gly Glu Thr Thr Ala Asp Gly Ser Gly Asn Trp Thr Phe
            1850                1855                1860

Thr Pro Gly Thr Pro Leu Ala Asn Gly Thr Val Ile Asn Ala Val
            1865                1870                1875

Ala Glu Asp Ala Ala Gly Asn Ala Ser Gly Pro Ala Ser Thr Thr
            1880                1885                1890

Val Asp Ser Val Ala Pro Ser Ala Pro Leu Leu Ser Ile Ser Ala
            1895                1900                1905

Asp Gly Ala Leu Leu Thr Gly Thr Ala Glu Pro Asn Ser Gln Val
            1910                1915                1920

Arg Ile Val Val Asn Gly Asp Thr Ala Asn Pro Ile Thr Val Thr
            1925                1930                1935

Val Asp Gly Ala Gly Asn Phe Ser Leu Pro Phe Ala Pro Pro Leu
            1940                1945                1950

Ile Thr Gly Glu Leu Ile Ala Gly Val Ala Val Asp Ala Ala Gly
            1955                1960                1965

Asn Val Ser Gly Pro Ala Thr Ile Asn Ala Pro Asp Leu Ala Pro
            1970                1975                1980

Pro Thr Ile Ser Val Pro Glu Ala Ala Asp Thr Trp Ile Asn Ala
            1985                1990                1995

Ala Glu Ile Gly Asp Gly Ile Gln Val Asp Val Thr Val Arg Pro
            2000                2005                2010

Thr Met Gln Val Gly Gln Val Val Thr Val Lys Phe Ala Gly Gln
            2015                2020                2025

Asn Gly Tyr Glu Ala Glu Val Ser His Thr Leu Thr Ala Gly Asp
            2030                2035                2040

Ile Ala Ala Gly Asn Leu Thr Leu Thr Leu Thr Pro Pro Gly Gly
            2045                2050                2055

Met Gly Pro Phe Pro Glu Gly Ala Ser Thr Val Thr Ala Asp Ile
            2060                2065                2070
```

```
Asn Gly Gly Thr Ala Ser Thr Pro Val Pro Phe Thr Ile Asp Thr
    2075            2080                    2085

Ile Pro Pro Ala Thr Pro Val Leu Ser Leu Val Gly Asn Ile Leu
    2090            2095                    2100

Thr Ile Ser Ala Glu Pro Gly Thr Glu Leu Thr Val Thr Val Asp
    2105            2110                    2115

Val Gly Gly Val Thr Ala Thr Ala Thr Val Thr Ala Asp Asn Ser
    2120            2125                    2130

Gly Leu Ala Ser Leu Asn Leu Leu Thr Asp Leu Asp Ile Asp Phe
    2135            2140                    2145

Ser Trp Asp Gln Leu Leu Asn Ala Gln Val Ser Val Val Gly Arg
    2150            2155                    2160

Asp Pro Ala Gly Asn Pro Ser Asn Thr Ala Ser Ile Gly Val Gly
    2165            2170                    2175

Thr Ser Ile Glu Gln Pro Val Thr Ile Gly Asn Phe Gly Leu Asp
    2180            2185                    2190

Val Ser Leu Asn Pro Leu Asn Pro Arg Phe Gly Phe Ser Gly Thr
    2195            2200                    2205

Thr Glu Pro Asp Ser Ser Val Val Ile Arg Val Ile Thr Pro Ala
    2210            2215                    2220

Leu Asn Val Glu Leu Leu Pro Ile Gln Ala Asp Ser Ser Gly Asn
    2225            2230                    2235

Phe Ser Leu Asn Leu Leu Ser Pro Thr Ile Leu Thr Gln Leu Gly
    2240            2245                    2250

Leu Asn Ile Thr Asp Ile Leu Asn Leu Gly Ser Gln Ile Ser Phe
    2255            2260                    2265

Asn Leu Val Ser Thr Asp Ser Asn Gly Asn Asp Ser Ala Ala Tyr
    2270            2275                    2280

Gly Ile Thr Leu Thr Pro Asn Gly Leu Ser Leu Asn Ile Gly Gln
    2285            2290                    2295

Ile Asp Val Asn Gly Thr Ser Gly Asp Asp Val Leu Ser Gly Ala
    2300            2305                    2310

Asn Gly Ser Ser Glu His Ile Asn Gly Gly Asp Gly Ser Asp Leu
    2315            2320                    2325

Ile Phe Asn Val Gly Thr Gly Asp His Val Val Ala Gly Asn Gly
    2330            2335                    2340

Asn Asp Thr Ile Gln Ile Thr Ala Thr Asp Phe Val Ser Ile Asp
    2345            2350                    2355

Gly Gly Ala Gly Phe Asp Thr Leu Val Leu Ala Asn Gly Ile Asp
    2360            2365                    2370

Leu Asp Tyr Asn Ala Val Gly Val Gly Thr Leu Ser Asn Leu Glu
    2375            2380                    2385

Arg Ile Asp Leu Gly Lys Gly Asp Ser Gly Ser Val Leu Thr Leu
    2390            2395                    2400

Thr Ala Ala Glu Val Asp Ala Ile Thr Asp Ala Asn Asn Thr Leu
    2405            2410                    2415

Gln Ile Thr Gly Glu Asn Asn Asp Thr Leu Asn Val Val Gly Ala
    2420            2425                    2430

Val Asn Thr Gly Thr Thr Gln Leu Ile Asn Gly Ile Thr Tyr Asp
    2435            2440                    2445

Val Tyr Thr Phe Gly Ser Thr Thr Leu Leu Ile Glu Asp Asn Thr
    2450            2455                    2460
```

Val Gln Val Val Val
    2465

<210> SEQ ID NO 29
<211> LENGTH: 3535
<212> TYPE: PRT
<213> ORGANISM: Pseudomonas aeruginosa

<400> SEQUENCE: 29

Met Asp Ile Arg Ser Pro Leu Asn Gln Cys Ile Ala Leu Ser Leu Ala
1               5                   10                  15

Gly Ile Leu Phe Leu Asn Pro Ile Val Ala Ala Ala Gly Leu Ala
            20                  25                  30

Leu Asp Lys Ala Ala Gly Gly Asn Thr Gly Leu Gly Gln Ala Gly Asn
        35                  40                  45

Gly Val Pro Ile Val Asn Ile Ala Thr Pro Asn Asp Ala Gly Leu Ser
    50                  55                  60

Asn Asn His Phe Arg Asp Tyr Asn Val Gly Ala Asn Gly Leu Ile Leu
65                  70                  75                  80

Asn Asn Ala Thr Gly Lys Thr Gln Gly Thr Gln Leu Gly Gly Ile Ile
                85                  90                  95

Leu Gly Asn Pro Asn Leu Lys Gly Gln Ala Ala Gln Val Ile Leu Asn
            100                 105                 110

Gln Val Thr Gly Gly Asn Arg Ser Thr Leu Ala Gly Tyr Thr Glu Val
        115                 120                 125

Ala Gly Gln Ser Ala Arg Val Ile Val Ala Asn Pro His Gly Ile Thr
    130                 135                 140

Cys Gln Gly Cys Gly Phe Ile Asn Thr Pro Arg Ala Thr Leu Thr Thr
145                 150                 155                 160

Gly Lys Pro Ile Met Asp Gly Gln Arg Leu Glu Arg Phe Gln Val Asp
                165                 170                 175

Gly Gly Asp Ile Val Val Glu Gly Ala Glu Leu Asn Val Gly Asn Leu
            180                 185                 190

Glu Gln Phe Asp Leu Ile Thr Arg Ser Ala Lys Leu Asn Ala Lys Leu
        195                 200                 205

Tyr Ala Lys Asn Leu Asn Ile Val Thr Gly Arg Asn Asp Val Gln Ala
    210                 215                 220

Asp Ser Leu Gln Ala Thr Pro Arg Ala Ala Asp Gly Ser Glu Lys Pro
225                 230                 235                 240

Gln Leu Ala Ile Asp Ser Ser Ala Leu Gly Gly Met Tyr Ala Gly Ala
                245                 250                 255

Ile Arg Leu Val Gly Thr Glu Gln Gly Val Gly Val Arg Leu Ala Gly
            260                 265                 270

Asp Met Ala Ala Ser Gly Gly Asp Ile Arg Ile Asp Ala Ser Gly Lys
        275                 280                 285

Leu Ser Leu Ala Gln Ala Ser Ser Gln Gly Asp Leu Lys Ile Ala Ala
    290                 295                 300

Gln Ala Val Glu Leu Asn Gly Lys Thr Tyr Ala Gly Gly Ser Ala Glu
305                 310                 315                 320

Ile Arg Ser Ala Glu Glu Leu Val Asn Arg Gln Ser Leu Ala Ala Arg
                325                 330                 335

Glu Arg Ile Val Leu Glu Ala Ala His Ile Asp Asn Ala Gly Val Ile
            340                 345                 350

Glu Ala Gly Val Glu Pro Asp Glu Arg Arg Asn Ala Arg Gly Asp Leu
        355                 360                 365

```
Glu Leu Arg Ser Gly Thr Leu Arg Asn Ala Gly Ser Leu Val Ala Ser
    370                 375                 380

Arg Ala Leu Glu Ala Lys Ala Ser Gln Ala Leu Asp Asn Gln Gly Gly
385                 390                 395                 400

Ser Leu Lys Gly Ala Thr Val Arg Val Asp Ala Gly His Leu Asp Asn
                405                 410                 415

Arg Gly Gly Lys Leu Leu Ala Glu Gly Glu Leu Arg Val Glu Ala Ser
            420                 425                 430

Ser Leu Asp Asn Arg Gln Asp Gly Leu Leu Gln Ser Arg Asp Arg Ala
        435                 440                 445

Val Val Lys Thr Arg Gly Asp Leu Asp Asn Arg Gly Gly Gln Val Ile
450                 455                 460

Gly Leu Asn Asp Leu Glu Val Gly Ala Ala Thr Leu Asp Asn Gly Gln
465                 470                 475                 480

Gln Gly Leu Leu Gly Ser Gln Gln Ser Thr Arg Val Ser Ala Gln Ala
                485                 490                 495

Leu Val Asn Arg Gly Asp Gly Glu Val Ser Gly Lys Arg Val Glu Ala
                500                 505                 510

Arg Val Gly Ser Leu Asp Asn Arg Gly Gly Lys Leu Ile Gly Asp Asp
            515                 520                 525

Leu Leu Val Val Ala Ser Gly Ala Ile Asp Asn Arg Leu Gly Leu Phe
        530                 535                 540

Ser Ala Ala Asn Arg Leu Asp Leu Arg Ala Arg Ser Leu Asp Asn Ser
545                 550                 555                 560

Gly Lys Gly Thr Leu Ser Ser Arg Gly Gly Leu Glu Val Ser Leu Gly
                565                 570                 575

Gly Leu Leu Asp Asn Arg Asp Glu Gly Asn Leu Leu Ser Gln Gly Ala
            580                 585                 590

Gln Arg Val Thr Val Gly Gln Leu Asp Asn Arg Ala Gly Gly Leu Leu
        595                 600                 605

Ser Ser Arg Ser Glu Leu Asn Val His Gly Ala Ser Leu Asp Asn Arg
610                 615                 620

Gly Gly Val Leu Val Ala Asp Ala Gly Leu Ser Ala Thr Gly Gly Ala
625                 630                 635                 640

Phe Asp Asn Arg Asp Gly Gly Ser Ala Ser Gly Lys Ala Gly Val Arg
                645                 650                 655

Val Glu Val Ala Ser Leu Arg Asn Asp Gln Gly Gly Lys Leu Leu Ser
                660                 665                 670

Asp Gly Arg Leu Asp Leu Ala Ala Asn Ala Val Gly Asn Ala Gly Gly
            675                 680                 685

Arg Ile Ala Ala Lys Gly Asp Leu Gln Ala Thr Leu Gly Ser Leu Ala
        690                 695                 700

Gln Gln Gly Gly Glu Leu Val Ser Glu Lys Thr Leu Lys Val Ala Ala
705                 710                 715                 720

Asp Thr Leu Asp Asn Ser Gln Ser Gly Leu Ile Ala Asn Gly Gly
                725                 730                 735

Ile Ala Ile Glu Ala Arg Gln Val Asp Asn Arg Ala Gly Glu Ile Ser
            740                 745                 750

Ser Thr Ser Lys Val Ala Val Asn Ala Arg Glu Gln Leu Asp Asn Arg
        755                 760                 765

Gly Gly Lys Val Ile Gly Asp Ser Gly Leu Arg Leu Thr Val Gln Arg
770                 775                 780
```

```
Leu Leu Asn Gln Ala Lys Gly Val Leu Ala Gly Arg Asp Gly Leu Ser
785                 790                 795                 800

Leu Asp Gly Gly Glu Leu Phe Asn Gly Asp Gly Arg Leu Asp Ser
                805                 810                 815

Gln Asn Ser Leu Ser Val Ser Leu Gly Gly Val Leu Asp Asn Gln Gly
                820                 825                 830

Gly Ala Leu Val Ser Glu Gly Ser Leu Thr Ala Arg Ala Ala Arg Leu
                835                 840                 845

Asp Asn Arg Gly Gly Thr Phe Ser Ser Ala Gly Ala Leu Ala Leu Thr
850                 855                 860

Ser Gln Ala Ala Leu Asp Asn Gln Gly Gly Arg Leu Leu Ser Asp Ala
865                 870                 875                 880

Gly Val Thr Leu Gln Gly Ala Ser Leu Asp Asn Ser Arg Ser Gly Val
                885                 890                 895

Ile Ser Ala Lys Gly Ala Val Asp Ile Arg Thr Gly Val Leu Asp Asn
                900                 905                 910

Ser Arg Asn Gly Gly Ile Gly Ser Asn Ala Gly Ile Thr Leu Val Ala
                915                 920                 925

Ala Arg Leu Asp Asn Gly Gln Gln Gly Arg Val Ser Ala Lys Gly Leu
                930                 935                 940

Leu Asp Ala Asn Leu Lys Gly Leu Asp Gln Arg Gly Gly Val Leu
945                 950                 955                 960

Ile Ser Glu Thr Gly Val Thr Leu Asp Leu Asn Gly Gly Thr Leu Val
                965                 970                 975

Asn Arg Asp Gly Gly Leu Ile Ala Thr Pro Gly Ala Leu Leu Leu Arg
                980                 985                 990

Gln Leu Gly Ala Val Asp Asn Gly Ala Gly Gly Glu Ile Ser Ser Asp
                995                 1000                1005

Arg Ala Phe Thr Leu Ala Ala Ala Ser Leu Asp Asn Arg Gly Gly
                1010                1015                1020

Arg Leu Ile Gly Ala Ala Asn Leu Thr Leu Arg Ile Ala Gln Ala
                1025                1030                1035

Leu Asp Asn Ser Leu Ala Gly Val Ile Ser Gly Ala Ala Gly Leu
                1040                1045                1050

Asp Ile Ala Ala Ala Arg Leu Asp Asn Ser Ala Lys Gly Thr Leu
                1055                1060                1065

Ala Ser Arg Ala Gly Ile Asp Leu Arg Val Asp Gly Ala Leu Asp
                1070                1075                1080

Asn His Ala Glu Gly Thr Val Ser Gly Ala Arg Leu Thr Leu Ala
                1085                1090                1095

Ser Ala Ser Leu Asp Asn Ser Gly Lys Gly Leu Leu Ser Gly Asn
                1100                1105                1110

Ala Gly Leu Ser Val Ala Thr Gly Ala Leu Asp Asn Ala Glu Gly
                1115                1120                1125

Gly Gln Leu Ile Ser Gln Gly Val Leu Asp Val Ser Ser Ala Asp
                1130                1135                1140

Leu Asp Asn Arg Gly Gly Ala Leu Ser Gly Lys Gln Ser Leu Arg
                1145                1150                1155

Leu Ser Ala Ala Asn Leu Asp Asn Arg Gly Gly Leu Leu Thr Ser
                1160                1165                1170

Asp Gly Glu Leu Glu Leu Thr Ala Gly Arg Val Asp Ser Ala Asp
                1175                1180                1185

Gly Gly Glu Ile Ser Ala Arg Gly Asp Leu Arg Leu Thr Val Glu
```

```
            1190                1195                1200

Arg Leu Val Gln Arg Gln Gly Arg Leu Val Gly Glu Arg Gly Val
    1205                1210                1215

Ser Leu Asp Leu Arg Gly Gly Asp Leu Asp Asn Gln Gly Gly Leu
    1220                1225                1230

Ile Ser Ala Arg Gly Pro Leu Ser Ile Glu Arg Leu Ser Val Leu
    1235                1240                1245

Asp Asn Arg Gln Gly Gly Glu Ile Ser Ser Gln Gln Gly Phe Glu
    1250                1255                1260

Leu Leu Ala Arg Arg Ile Asp Asn Gly Gln Gln Gly Arg Ile Ile
    1265                1270                1275

Ser Ala Gly Lys Leu Arg Leu Asp Ala Asp Ala Leu Gly Asn Ala
    1280                1285                1290

Gly Ala Gly Leu Leu Ser Gly Trp Gln Gly Leu Thr Val Thr Gly
    1295                1300                1305

Gly Ser Leu Asp Asn Ser Ala Gly Gly Thr Leu Ser Ser Lys Asp
    1310                1315                1320

Gly Glu Leu Ala Ile Ser Leu Gly Gly Ala Leu Asp Asn His Gly
    1325                1330                1335

Gln Gly Ala Leu Val Ser Lys Gly Ala Gln Arg Ile Asp Ala Ala
    1340                1345                1350

Ser Leu Asp Asn Ala Gln Gly Ile Val Ser Gly Glu Ser Asp Val
    1355                1360                1365

Thr Leu Ser Ile Ala Gly Lys Leu Asp Asn Gly Gln Gly Gly Leu
    1370                1375                1380

Val Ser Ala Gln Arg Ala Leu Ser Phe Glu Arg Asp Asp Thr Leu
    1385                1390                1395

Leu Asn Asn Ala Gly Gly Arg Ile Asn Gly Gly Ser Leu Leu Leu
    1400                1405                1410

Lys Gly Ala Ser Leu Asp Asn Ser Asp Gly Gln Leu Ile Ser Gln
    1415                1420                1425

Gly Arg Leu Asp Ala Ile Leu Gly Gly Ala Leu Val Asn Thr Gly
    1430                1435                1440

Ala Ala Arg Leu Ala Ser Gly Gly Asp Leu Leu Leu Arg Ser Ala
    1445                1450                1455

Ser Val Asp Asn Arg Gly Gly Lys Leu Val Ser Gln Gly Leu Leu
    1460                1465                1470

Glu Ile Ser Ala Gly Ser Leu Asp Asn Ser Ala Ser Gly Thr Leu
    1475                1480                1485

Ala Ser Gln Ala Gly Met Ser Leu Arg Leu Gly Gly Ala Leu
    1490                1495                1500

Arg Asn Gln Gln Asp Gly Leu Ile Phe Ser Gln Ala Gly Ala Leu
    1505                1510                1515

Asp Val Gln Ala Gly Ser Leu Asp Asn Arg Gln Gly Thr Leu Gln
    1520                1525                1530

Ala Gln Gly Asp Asn Arg Leu Arg Ile Gly Gly Ala Leu Asp Asn
    1535                1540                1545

Gln Gly Gly Arg Leu Asp Ser Arg Ala Gly Asn Leu Asp Leu Gln
    1550                1555                1560

Ser Gly Ser Leu Asp Asn Gly Ala Gly Gly Val Leu Asn Ser Ala
    1565                1570                1575

Lys Gly Trp Leu Lys Leu Val Thr Gly Leu Phe Asp Asn Ser Ala
    1580                1585                1590
```

```
Gly Val Thr Gln Ala Gln Ser Leu Glu Ile Arg Ala Gly Gln Gly
1595                1600                1605

Val Arg Asn Gln Gln Gly His Leu Ser Ala Leu Gly Gly Asp Asn
1610                1615                1620

Arg Ile Val Thr Ala Asp Phe Asp Asn Gln Gly Gly Gly Leu Tyr
1625                1630                1635

Ala Ser Gly Leu Leu Ser Leu Asp Gly Gln Arg Phe Leu Asn Gln
1640                1645                1650

Gly Ala Ala Ala Gly Gln Gly Gly Lys Val Gly Ala Gly Arg Ile
1655                1660                1665

Asp Phe Ser Leu Ala Gly Ala Leu Ala Asn Arg Phe Gly Gln Leu
1670                1675                1680

Glu Ser Glu Ser Glu Leu His Leu Arg Ala Ala Ala Ile Asp Asn
1685                1690                1695

Ser Gly Gly Ser Leu Arg Ala Leu Gly Arg Ser Gly Ser Thr Arg
1700                1705                1710

Leu Val Ala Gly Gly Leu Asn Asn Ala Tyr Gly Val Leu Glu Ser
1715                1720                1725

Ala Asn Gln Asp Leu Asp Leu Gln Leu Gly Ser Leu Ala Asn Ala
1730                1735                1740

Gly Gly Arg Ile Leu His Thr Gly Asn Gly Thr Phe Gly Leu Asp
1745                1750                1755

Ser Gly Gln Val Ile Arg Ala Gly Gly Glu Leu Thr Thr Asn Gly
1760                1765                1770

Leu Leu Asp Ile Arg Ala Ser Glu Trp Thr Asn Ser Ser Val Leu
1775                1780                1785

Gln Ala Gly Arg Leu Asn Leu Asp Ile Gly Thr Phe Arg Gln Thr
1790                1795                1800

Ala Glu Gly Lys Leu Leu Ala Val Gln Ser Phe Thr Gly Arg Gly
1805                1810                1815

Gly Asp Trp Ser Asn Asp Gly Leu Leu Ala Ser Asp Gly Ser Phe
1820                1825                1830

Arg Leu Asp Leu Ser Gly Gly Tyr Arg Gly Asn Gly Arg Ala Thr
1835                1840                1845

Ser Leu Gly Asp Phe Ala Leu Asn Ala Ala Ser Leu Asp Leu Gly
1850                1855                1860

Asn Ala Ala Ser Leu Ala Gly Gly Ala Asn Val Thr Leu Gly Ala
1865                1870                1875

Gly Asn Leu Leu Val Asn Arg Gly Arg Ile Thr Ala Ala Gly Asp
1880                1885                1890

Leu Val Ala Ser Ala Ala Ser Leu Asn Asn Tyr Gly Thr Leu Gly
1895                1900                1905

Gly Gly Gly Asn Leu Arg Leu Asn Ala Pro Ala Leu Leu Asn Glu
1910                1915                1920

Arg Gly Leu Leu Phe Ser Gly Ala Asp Met Thr Leu Arg Ala Gly
1925                1930                1935

Asp Ile Thr Asn Leu Tyr Gly Asp Val Tyr Ser Leu Gly Arg Leu
1940                1945                1950

Asp Ile Ala Arg Asp Asp Ala Gly Asn Arg Ala Ala Ser Leu Arg
1955                1960                1965

Asn Leu Ser Gly Val Ile Glu Ser Gly Lys Asp Phe Ser Leu Arg
1970                1975                1980
```

```
Ala Ser Leu Ile Glu Asn Arg Arg Ala Val Leu Glu Ser Lys Ser
1985                1990                1995

Gly Leu Tyr Thr Ala Lys Met Glu Gln Thr Ala Cys Ile Glu Gly
2000                2005                2010

Val Asn Ala Gly Asp Cys Ser Gly Lys Arg Asn Ala Ile Trp Thr
2015                2020                2025

Ile Thr Gln Arg Asp Lys Thr Glu Val Thr Ala Ser Ser Ala Met
2030                2035                2040

Gly Gln Leu Leu Ala Gly Gly Asp Phe Ala Ile Asp Gly Gly Thr
2045                2050                2055

Leu Asn Asn Leu Ser Ser Leu Ile Gly Ser Gly Gly Asn Leu Thr
2060                2065                2070

Ala Asn Leu Glu Val Leu Asp Asn Gln Gly Leu Glu Thr Gly Glu
2075                2080                2085

Leu Glu Thr Ile Arg Val Leu Arg Thr Ala Arg Gly Gly Asp Ile
2090                2095                2100

Gly Gly Ile Asp Gln Lys Ser Arg Asn Phe Thr Asn Leu Tyr Trp
2105                2110                2115

Tyr Gln Ser Ala Asn Phe Asp Pro Ala Arg Ala Gly Glu Ile Pro
2120                2125                2130

Ala Ala Leu Asn Ala Ile Leu Ser Asp Trp Ser Phe Glu Tyr Glu
2135                2140                2145

Phe Pro Ser Lys Gly Pro Thr Pro Ile Ser Ser Gly Asp Gln Ser
2150                2155                2160

Tyr Ala Ala Val Ile Gln Ala Ala Gly Asp Val Thr Val Asn Ala
2165                2170                2175

Ser Thr Arg Ile Asp Asn Gly Val Thr Arg Pro Gly Tyr Thr Phe
2180                2185                2190

Val Gly Ser Gly Arg Gln Val Gly Asp Ser Ala Val Gly Gly Ser
2195                2200                2205

Gly Val Ser Val Val Pro Leu Thr Ser Gln Leu Pro Pro Asp
2210                2215                2220

Leu Ala Arg Arg Gln Val Asn Pro Val Thr Leu Pro Gly Phe Ser
2225                2230                2235

Leu Pro Gln Gly Asp Asn Gly Leu Phe Arg Leu Ser Ser Arg Phe
2240                2245                2250

Ala Glu Asp Gly Asn Gly Ser Ala Ala Leu Gly Ala Gly Ala Asp
2255                2260                2265

Arg Thr Gln Gly Gly Ser Gly Val Ser Val Gly Gln Gln Gly Ala
2270                2275                2280

Gly Asn Ala Ala Gly Thr Trp Gln Gly Gln Gly Val Arg Val Asp
2285                2290                2295

Gly Leu Ala Gly Ala Ala Asn Val Gln Gly Gln Gly Gly Ser Thr
2300                2305                2310

Leu Gly Gly Ser Leu Pro Gly Val Ala Arg Val Gln Gly Val Pro
2315                2320                2325

Gly Asn Ala Thr Pro Ser Ala Ser His Lys Tyr Leu Ile Glu Thr
2330                2335                2340

Asn Pro Ala Leu Thr Glu Leu Lys Gln Phe Leu Asn Ser Asp Tyr
2345                2350                2355

Leu Leu Ser Gly Leu Gly Met Asn Pro Asp Asp Ser Lys Lys Arg
2360                2365                2370

Leu Gly Asp Gly Leu Tyr Glu Gln Arg Leu Ile Arg Asp Ala Val
```

```
              2375                2380                2385
Val Ala Arg Thr Gly Gln Arg Tyr Ile Asp Gly Leu Ser Ser Asp
    2390                2395                2400
Glu Ala Leu Phe Arg Tyr Leu Met Asp Asn Ala Ile Ala Tyr Lys
    2405                2410                2415
Asp Gln Leu His Leu Gln Leu Gly Val Gly Leu Ser Ala Glu Gln
    2420                2425                2430
Met Ala Ala Leu Thr His Asp Ile Val Trp Leu Glu Glu Val Glu
    2435                2440                2445
Val Asn Gly Glu Lys Val Leu Ala Pro Val Val Tyr Leu Ala Gln
    2450                2455                2460
Ala Glu Gly Arg Leu Ala Pro Asn Gly Ala Leu Ile Gln Gly Arg
    2465                2470                2475
Asp Val Lys Leu Val Ser Gly Gly Asp Leu His Asn Val Gly Thr
    2480                2485                2490
Leu Arg Ala Arg Asn Asp Leu Ser Ala Thr Ala Asp Asn Leu Asp
    2495                2500                2505
Asn Ser Gly Leu Ile Glu Ala Gly Lys Arg Leu Asp Leu Leu Ala
    2510                2515                2520
Gly Asp Ser Ile Arg Asn Arg Gln Gly Gly Val Ile Ala Gly Arg
    2525                2530                2535
Asp Val Ser Leu Thr Ala Leu Thr Gly Asp Val Ile Asn Glu Arg
    2540                2545                2550
Ser Val Thr Arg Tyr Asp Ser Ala Leu Asp Gly Arg Thr Trp Glu
    2555                2560                2565
Arg Ser Phe Ala Asp Ser Ala Arg Val Glu Ala Ala Asn Ser
    2570                2575                2580
Leu Asn Val Gln Ala Gly Arg Asp Ile Ala Asn Leu Gly Gly Val
    2585                2590                2595
Leu Gln Ser Arg Gly Asp Leu Ser Leu Asp Ala Gly Arg Asp Val
    2600                2605                2610
Thr Val Ala Ala Val Glu Asp Arg Gln Gly Gln Thr Arg Trp Ser
    2615                2620                2625
Thr Ser Arg Leu Gln Ser Val Thr Gln Leu Gly Ala Glu Val Ser
    2630                2635                2640
Ala Gly Arg Asp Leu Asn Val Ser Ala Gly Arg Asp Leu Thr Ala
    2645                2650                2655
Val Ala Ser Thr Leu Glu Ala Arg Arg Asp Ile Ala Leu Ser Ala
    2660                2665                2670
Gly Arg Asp Val Thr Leu Ala Ala Ala Asn Glu Glu His Ala
    2675                2680                2685
Tyr Ser Lys Thr Arg Lys Val Thr Tyr Gln Glu Asp Lys Val Ala
    2690                2695                2700
Gln Gln Gly Thr Arg Val Asp Ala Gly Gly Asp Leu Ala Ile Asn
    2705                2710                2715
Ala Gly Gln Asp Leu Arg Leu Ile Ala Ser Gln Ala Ser Ala Gly
    2720                2725                2730
Asp Glu Ala Tyr Leu Val Ala Gly Asp Lys Leu Glu Leu Leu Ala
    2735                2740                2745
Ala Asn Asp Ser Asn Tyr Tyr Leu Tyr Asp Lys Lys Lys Lys Gly
    2750                2755                2760
Asp Phe Gly Arg Lys Glu Thr Arg Arg Asp Glu Val Thr Asp Val
    2765                2770                2775
```

```
Lys Ala Val Gly Ser Gln Ile Ser Ser Gly Gly Asp Leu Thr Leu
        2780                2785            2790

Leu Ser Gly Gly Asp Gln Thr Tyr Gln Gly Ala Lys Leu Glu Ser
        2795                2800            2805

Gly Asn Asp Leu Ala Ile Val Ser Gly Gly Ala Val Thr Phe Glu
        2810                2815            2820

Ala Val Lys Asp Leu His Gln Glu Ser His Glu Lys Ser Lys Gly
        2825                2830            2835

Asp Leu Ala Trp Asn Ser Ala Lys Gly Lys Gly Gln Thr Asp Glu
        2840                2845            2850

Thr Leu Arg Gln Thr Gln Ile Val Ala Gln Gly Asn Leu Ala Ile
        2855                2860            2865

Lys Ala Val Glu Gly Leu Lys Ile Asp Leu Lys His Ile Asp Gln
        2870                2875            2880

Lys Thr Val Ser Gln Thr Ile Asp Ala Met Val Gln Ala Asp Pro
        2885                2890            2895

Gln Leu Ala Trp Leu Lys Glu Ala Glu Gln Arg Gly Asp Val Asp
        2900                2905            2910

Trp Arg Met Val Gln Glu Val His Asp Ser Trp Lys Tyr Ser Asn
        2915                2920            2925

Ser Gly Met Gly Pro Ala Thr Gln Ile Ala Val Ala Ile Ala Ala
        2930                2935            2940

Ala Ala Ile Gly Gly Met Ala Ala Gly Ala Leu Ser Gly Ala
        2945                2950            2955

Gly Val Gly Ala Ser Ser Phe Ala Met Gly Ala Gly Val Gly Ala
        2960                2965            2970

Ala Gly Ser Leu Ser Gly Thr Ala Ala Val Ser Leu Ile Asn Asn
        2975                2980            2985

Lys Gly Asp Leu Gly Lys Val Leu Lys Asp Ser Phe Ser Ser Asp
        2990                2995            3000

Ser Leu Lys Gln Ile Ala Ile Ala Ser Leu Thr Gly Gly Leu Thr
        3005                3010            3015

Ala Glu Tyr Phe Asp Gly Ile Leu Gln Thr Lys Thr Asp Pro Leu
        3020                3025            3030

Thr Gly Lys Val Thr Val Asp Leu Ser Ser Leu Ser Gly Val Gly
        3035                3040            3045

Arg Phe Ala Ala Asn Gln Ala Met Gln Asn Ala Thr Ser Thr Val
        3050                3055            3060

Leu Ser Gln Ala Leu Gly Gln Gly Gly Ser Leu Asn Glu Ala Leu
        3065                3070            3075

Lys Ser Ala Leu Tyr Asn Ser Phe Ala Ala Ala Gly Phe Asn Phe
        3080                3085            3090

Val Gly Asp Ile Gly Gln Glu Tyr Ser Leu Lys Pro Gly Asp Pro
        3095                3100            3105

Ser Met Val Thr Met His Ala Leu Met Gly Gly Leu Ala Ala Gln
        3110                3115            3120

Val Ser Gly Gly Asp Phe Ala Thr Gly Ala Ala Ala Gly Ala
        3125                3130            3135

Asn Glu Ala Leu Val Ala Lys Leu Asp Gln Ala Phe Lys Ser Leu
        3140                3145            3150

Ser Pro Glu Asn Arg Glu Ala Met Val Thr Met Gly Ser Gln Leu
        3155                3160            3165
```

Val Gly Val Leu Ala Ala Ala Val Arg Asp Pro Asp Val Thr Gly
3170            3175                3180

Lys Ala Leu Glu Ser Ala Ala Trp Val Ala Lys Asn Ser Thr Gln
3185            3190                3195

Tyr Asn Phe Leu Asn His Gln Asp Val Ala Asp Leu Asp Asn Ala
3200            3205                3210

Leu Gln Lys Cys Lys Ser Gln Gly Asn Cys Arg Gln Val Glu Glu
3215            3220                3225

Glu Phe Lys Ala Arg Ser Asp Glu Asn Arg Arg Leu Asn Gly
3230            3235                3240

Cys Val Ala Val Gly Asn Cys Ala Glu Ile Arg Ala Glu Ile Asp
3245            3250                3255

Ala Gly Ser Thr Ala Leu Asn Glu Leu Val Ala Arg Gln Glu Thr
3260            3265                3270

Ala Asn Pro Gly Gly Ser Asp Ser Asp Ile Ala Tyr Gly Phe Leu
3275            3280                3285

Met Gly Arg Asn Val Val Asp Trp Thr Thr Ala Gly Gln Leu His
3290            3295                3300

Leu Glu Gln Thr Ala Asn Leu Trp Trp Asn Gly Asn Pro Gln Trp
3305            3310                3315

Gln Lys Glu Val Gly Ala Tyr Leu Asp Gln Thr Gly Phe Asn Pro
3320            3325                3330

Phe Gly Ile Gly Val Pro Ala Met Gly Gly Ala Ala Gly Lys Val
3335            3340                3345

Thr Ala Lys Ala Leu Met Asn Ala Leu Lys Ala Gly Glu Leu Pro
3350            3355                3360

Lys Gly Glu Val Ala Pro Gly Lys Ala Asn Leu Pro Thr Ile Gly
3365            3370                3375

Ala Leu Ala Asp Ala Glu Ala Gly Met Pro Tyr Thr His Pro Val
3380            3385                3390

Lys Leu Ala Ala Lys Ala Thr Gly Thr Ala Gly Lys Ile Lys Ile
3395            3400                3405

Glu Ala Gly Ala Ile Pro Asp Ala Asn Glu Val Arg Ala Gly Gln
3410            3415                3420

Gly Leu Ser Gly Leu Gly Tyr Asp Val Thr His Gln Thr Thr Ala
3425            3430                3435

Ser Ala Lys Gly Ile Gln Gly Gln Arg Thr Ala Asp Leu His Val
3440            3445                3450

Asp Gly Leu Gly Ser Ile Asp Val Tyr Thr Pro Lys Asn Leu Asp
3455            3460                3465

Pro Thr Lys Ile Val Arg Ala Ile Glu Lys Lys Ser Asn Gln Ala
3470            3475                3480

Gly Gly Val Leu Val Gln Ala Asp Leu Pro Ser Thr Asp Met Ser
3485            3490                3495

Ser Ile Ala Ala Arg Met Trp Gly Lys Thr Asn Ala Gln Ser Ile
3500            3505                3510

Lys Thr Ile Phe Phe Gln Lys Pro Asp Gly Ser Leu Val Arg Phe
3515            3520                3525

Asp Arg Pro Ala Gly Gly Gly
3530            3535

<210> SEQ ID NO 30
<211> LENGTH: 5627
<212> TYPE: PRT

<213> ORGANISM: Pseudomonas aeruginosa

<400> SEQUENCE: 30

```
Met Asp Ile Arg Ser Pro Leu Asn Gln Cys Ile Ala Leu Ser Leu Ala
1               5                   10                  15
Gly Ile Leu Phe Leu Asn Pro Ile Val Ala Ala Ala Gly Leu Ala
            20                  25                  30
Leu Asp Lys Ala Ala Gly Gly Asn Thr Gly Leu Gly Gln Ala Gly Asn
        35                  40                  45
Gly Val Pro Ile Val Asn Ile Ala Thr Pro Asn Gly Ala Gly Leu Ser
    50                  55                  60
Asn Asn His Phe Arg Asp Tyr Asn Val Gly Ala Asn Gly Leu Ile Leu
65                  70                  75                  80
Asn Asn Ala Thr Gly Lys Thr Gln Gly Thr Gln Leu Gly Gly Ile Ile
                85                  90                  95
Leu Gly Asn Pro Asn Leu Lys Gly Gln Ala Ala Gln Val Ile Leu Asn
            100                 105                 110
Gln Val Thr Gly Gly Asn Arg Ser Thr Leu Ala Gly Tyr Thr Glu Val
        115                 120                 125
Ala Gly Gln Ser Ala Arg Val Ile Val Ala Asn Pro His Gly Ile Thr
    130                 135                 140
Cys Gln Gly Cys Gly Phe Ile Asn Thr Pro Arg Ala Thr Leu Thr Thr
145                 150                 155                 160
Gly Lys Pro Ile Met Asp Gly Gln Arg Leu Glu Arg Phe Gln Val Asp
                165                 170                 175
Gly Gly Asp Ile Val Val Glu Gly Ala Glu Leu Asn Val Gly Asn Leu
            180                 185                 190
Glu Gln Phe Asp Leu Ile Thr Arg Ser Ala Lys Leu Asn Ala Lys Leu
        195                 200                 205
Tyr Ala Lys Asn Leu Asn Ile Val Thr Gly Arg Asn Asp Val Gln Ala
    210                 215                 220
Asp Ser Leu Gln Ala Thr Pro Arg Ala Ala Asp Gly Ser Glu Lys Pro
225                 230                 235                 240
Gln Leu Ala Ile Asp Ser Ser Ala Leu Gly Gly Met Tyr Ala Gly Ala
                245                 250                 255
Ile Arg Leu Val Gly Thr Glu Gln Gly Val Gly Val Lys Leu Ala Gly
            260                 265                 270
Asp Met Ala Ala Ser Gly Gly Asp Ile Arg Ile Asp Ala Ser Gly Lys
        275                 280                 285
Leu Ser Leu Ala Gln Ala Ser Ser Gln Gly Asp Leu Lys Ile Ala Ala
    290                 295                 300
Gln Ala Val Glu Leu Asn Gly Lys Thr Tyr Ala Gly Gly Ser Ala Glu
305                 310                 315                 320
Ile Arg Ser Ala Glu Glu Leu Val Asn Arg Gln Ser Leu Ala Ala Arg
                325                 330                 335
Glu Arg Ile Ala Leu Glu Ala Ala His Ile Asp Asn Ala Gly Val Ile
            340                 345                 350
Glu Ala Gly Val Glu Pro Asp Glu Arg Arg Asn Ala Arg Gly Asp Leu
        355                 360                 365
Glu Leu Arg Ser Gly Thr Leu Arg Asn Ala Gly Ser Leu Val Ala Ser
    370                 375                 380
Arg Ala Leu Glu Ala Lys Ala Ser Gln Ala Leu Asp Asn Gln Gly Gly
385                 390                 395                 400
```

-continued

```
Ser Leu Lys Gly Ala Thr Val Arg Val Asp Gly His Leu Asp Asn
                405                 410                 415

Arg Gly Gly Lys Leu Leu Ala Glu Gly Glu Leu Arg Val Glu Ala Ser
            420                 425                 430

Ser Leu Asp Asn Arg Gln Asp Gly Leu Leu Gln Ser Arg Asp Arg Ala
            435                 440                 445

Val Val Lys Thr Arg Gly Asp Leu Asp Asn Arg Gly Gly Gln Val Val
    450                 455                 460

Gly Leu Asn Glu Leu Gln Val Gln Ala Ala Leu Asp Asn Arg Ser
465                 470                 475                 480

Ala Gly Leu Leu Ser Ser Lys Gly Asp Met Asp Ile Glu Phe Ala Arg
            485                 490                 495

Leu Asp Asn Ser Ala Gly Gly Lys Leu Val Ser Glu Arg Arg Thr Leu
            500                 505                 510

Leu Lys Ala Asp Arg Leu Asp Asn Arg Ser Gly Arg Ile Val Ala Gly
            515                 520                 525

Gln Asp Leu Asp Leu Ser Ser Arg Leu Ile Asp Asn Arg Ala Gly Asp
            530                 535                 540

Ile Ser Ser Thr Ser Arg Val Val Ala Ser Ala Arg Glu Gln Leu Asp
545                 550                 555                 560

Asn Arg Gly Gly Lys Ile Val Gly Asp Ser Gly Leu Asp Ile Thr Thr
                565                 570                 575

Pro Arg Met Leu Asn Gln Asp Lys Gly Val Leu Ala Ser Arg Asp Gly
            580                 585                 590

Leu Arg Leu Ser Ala Thr Glu Leu Phe Asn Gly Ala Gly Gly Leu Leu
            595                 600                 605

Ser Ser Gln Lys Gly Ile Asp Val Ser Leu Ala Gly Ala Phe Asp Asn
            610                 615                 620

Gln Ala Gly Ser Leu Asp Ser Arg Gly Phe Leu Thr Val Lys Ser Ala
625                 630                 635                 640

Trp Leu Asp Asn Gln Gly Gly Thr Leu Ser Ser Ala Gly Ala Leu Ala
                645                 650                 655

Val Thr Ser Gln Gly Ala Leu Asn Asn Gln Gly Gly Arg Leu Ala Ser
            660                 665                 670

Asp Ala Gly Leu Ser Leu Ser Ser Ala Ser Leu Asp Asn Ser Gln Ala
            675                 680                 685

Gly Ala Ile Ser Gly Lys Gly Ala Val Glu Ile Arg Thr Gly Asn Leu
            690                 695                 700

Asn Asn Ser Arg Lys Ala Ser Ile Gly Ser Asp Ala Gly Leu Thr Leu
705                 710                 715                 720

Val Ala Ala Arg Val Asp Asn Ser Gln Ala Gly Arg Ile Ala Ala Lys
                725                 730                 735

Gly Val Ile Asp Ala Asp Leu Gln Gly Leu Asp Gln His Asp Arg Gly
            740                 745                 750

Asn Leu Val Ser Asp Thr Gly Ile Thr Leu Asp Leu Asn Lys Gly Ser
            755                 760                 765

Leu Val Asn Arg Ala Gln Gly Leu Ile Ala Thr Pro Gly Thr Leu Leu
            770                 775                 780

Leu Arg Gln Leu Gly Val Asp Asn Ser Gly Glu Ile Ser Ser
785                 790                 795                 800

Asp Arg Ala Phe Thr Leu Ala Thr Ser Ala Leu Asn Asn Gln Gly Gly
            805                 810                 815

Arg Leu Leu Ser Gly Gly Ala Leu Thr Leu Arg Ile Ala Gln Ala Leu
```

-continued

```
                820                 825                 830
Asp Asn Ser Leu Glu Gly Ile Val Ser Gly Ala Gly Leu Asp Ile
                835                 840                 845

Gln Ala Phe Val Leu Asp Asn Arg Ser Gly Ser Ile Gly Ser Lys Gly
            850                 855                 860

Ala Ile Asp Ile Gly Val Thr Arg Leu Glu Asn Asp Ala Gly Thr Leu
865                 870                 875                 880

Ile Ala Glu Arg Gly Leu Lys Leu Val Ala Asp Glu Ala Asn Ser Ser
                885                 890                 895

Lys Gly Arg Ile Ala Ala Asn Gly Ser Leu His Ala Lys Val Gly Thr
            900                 905                 910

Leu Ser Gln Lys Gly Gly Glu Leu Thr Ser Gln Asp Ser Leu Thr Leu
            915                 920                 925

Asp Leu Gly Ile Leu Asn Asn Ala Gly Arg Ile Ala Gly Asn Gln
            930                 935                 940

Gly Val Asp Ile Thr Ala Arg Gln Val Asp Asn Ser Val Gly Glu Ile
945                 950                 955                 960

Ala Ser Gln Gly Val Val Ala Leu Asn Leu Thr Glu Gln Leu Asp Asn
                965                 970                 975

Arg Gly Gly Lys Ile Val Gly Asp Ser Gly Leu Gly Ile Thr Ala Pro
            980                 985                 990

His Val Leu Asn Gln Asp Lys Gly Val Leu Ala Ser Arg Asp Gly Leu
            995                1000                1005

Arg Leu Ser Ala Thr Glu Leu Phe Asn Gly Ala Gly Gly Leu Leu
        1010                1015                1020

Ser Ser Gln Lys Gly Ile Asp Val Ser Leu Ala Gly Ala Phe Asp
        1025                1030                1035

Asn Gln Ala Gly Ser Leu Asp Ser Arg Gly Phe Leu Thr Val Lys
        1040                1045                1050

Ser Ala Trp Leu Asp Asn Gln Gly Gly Thr Leu Ser Ser Ala Gly
        1055                1060                1065

Ala Leu Ala Val Thr Ser Gln Gly Ala Leu Asn Asn Gln Gly Gly
        1070                1075                1080

Arg Leu Ala Ser Asp Ala Gly Leu Ser Leu Ser Ser Ala Ser Leu
        1085                1090                1095

Asp Asn Ser Gln Ala Gly Ala Ile Ser Gly Lys Gly Ala Val Glu
        1100                1105                1110

Ile Arg Thr Gly Asn Leu Asn Asn Ser Arg Lys Ala Ser Ile Gly
        1115                1120                1125

Ser Asp Ala Gly Leu Thr Leu Val Ala Ala Arg Val Asp Asn Ser
        1130                1135                1140

Gln Ala Gly Arg Ile Ala Ala Lys Gly Ala Ile Asp Ala Ala Leu
        1145                1150                1155

Gln Gly Leu Asp Gln His Asp Arg Gly Ser Leu Val Ser Asp Thr
        1160                1165                1170

Gly Ile Thr Leu Asp Leu Asn Lys Gly Ser Leu Val Asn Arg Ala
        1175                1180                1185

Gln Gly Leu Ile Ala Thr Pro Gly Thr Leu Leu Leu Arg Gln Leu
        1190                1195                1200

Gly Val Val Asp Asn Ser Gly Gly Glu Ile Ser Ser Asp Arg Ala
        1205                1210                1215

Phe Thr Leu Ala Thr Ser Ala Leu Asn Asn Gln Gly Gly Arg Leu
        1220                1225                1230
```

```
Leu Ser Gly Gly Ala Leu Thr Leu Arg Ile Ala Gln Ala Leu Asp
    1235                1240                1245

Asn Ser Leu Glu Gly Ile Val Ser Gly Ala Gly Gly Leu Asp Ile
    1250                1255                1260

Gln Ala Phe Val Leu Asp Asn Arg Ser Gly Ser Ile Gly Ser Lys
    1265                1270                1275

Gly Ala Ile Asp Ile Gly Val Thr Arg Leu Glu Asn Asp Ala Gly
    1280                1285                1290

Thr Leu Ile Ala Glu Arg Gly Leu Lys Leu Ala Ala Asp Glu Ala
    1295                1300                1305

Asn Asn Ser Lys Gly Arg Ile Val Ala Lys Asp Glu Leu Arg Ala
    1310                1315                1320

Lys Leu Gly Ala Leu Val Gln Asn Gly Gly Glu Leu Thr Thr Gln
    1325                1330                1335

Gly Ala Leu Ala Leu Asp Ala Asp Lys Val Asp Asn Gly Ala Gly
    1340                1345                1350

Arg Ile Ala Gly Asn Arg Gly Val Val Ile Asp Ala Arg Gln Val
    1355                1360                1365

Asp Asn Arg Ala Gly Glu Ile Ala Ser Gln Gly Val Ala Thr Leu
    1370                1375                1380

Asn Leu Thr Glu Gln Leu Asp Asn Arg Gly Gly Lys Val Val Ala
    1385                1390                1395

Asp Ser Gly Leu Gly Ile Thr Ala Pro Arg Val Leu Asn Gln Asp
    1400                1405                1410

Lys Gly Val Ile Ala Ser Arg Asp Gly Leu Arg Leu Ser Gly Thr
    1415                1420                1425

Glu Leu Phe Asn Gly Asn Ala Gly Leu Leu Ser Ser Gln Arg His
    1430                1435                1440

Ile Glu Val Thr Leu Asp Gly Val Leu Asp Asn Gln Gly Lys Gly
    1445                1450                1455

Ala Leu Leu Ser Asp Gly Thr Leu Thr Val Ser Ala Gly Arg Ile
    1460                1465                1470

His Asn Gln Asp Ala Thr Leu Ser Ser Ala Gly Ala Leu Arg Leu
    1475                1480                1485

Ser Ser Gln Glu Ala Val Asp Asn Arg Gly Gly Lys Leu Val Thr
    1490                1495                1500

Asp Ser Ser Leu Arg Leu Thr Ser Ala Ser Leu Asp Asn Ser Arg
    1505                1510                1515

Ser Gly Ile Ile Ser Ala Asn Ala Ala Ala Glu Ile His Thr Gly
    1520                1525                1530

Val Leu Asn Asn Ser Gln Lys Gly Asn Leu Gly Ser Asn Asp Gly
    1535                1540                1545

Leu Gly Leu Ile Ala Thr Glu Val Asp Asn Ser Gln Glu Gly Arg
    1550                1555                1560

Ile Thr Ala Lys Gly Met Ile Asp Ala Asn Ile Lys Gly Leu Asp
    1565                1570                1575

Gln Gln Gly Lys Gly Arg Leu Val Ser Asn Ala Gly Ile Ile Leu
    1580                1585                1590

Asp Leu Asn Glu Gly Thr Leu Ala Asn Gly Ala Gln Gly Leu Ile
    1595                1600                1605

Ala Thr Pro Gly Thr Leu Leu Leu Arg Gln Leu Gly Met Val Asp
    1610                1615                1620
```

```
Asn Ser Gly Gly Glu Ile Ser  Ser Asp Arg Ala Phe  Thr Leu Thr
1625                1630                 1635

Thr Ser Ala Leu Thr Asn Gln  Gly Gly Arg Leu Arg  Ser Gly Gly
1640                1645                 1650

Val Leu Thr Leu Arg Ile Ala  Gln Ala Leu Asp Asn  Ser Leu Glu
1655                1660                 1665

Gly Val Leu Ser Gly Thr Gly  Gly Leu Asp Ile Arg  Ala Leu Ala
1670                1675                 1680

Leu Asp Asn Arg Ser Gly Ser  Ile Gly Ser Lys Gly  Ala Val Asp
1685                1690                 1695

Ile Asp Val Ser Arg Leu Glu  Asn Asp Asp Gly Asp  Leu Leu Ser
1700                1705                 1710

Glu Gly Arg Leu Lys Leu Thr  Ala Glu Arg Ala Asn  Ser Val Arg
1715                1720                 1725

Gly Arg Ile Ala Ala Arg Gly  Asp Leu His Ala Ser  Val Thr Ala
1730                1735                 1740

Phe Asn Gln Ala Gly Gly Glu  Leu Ser Ser Glu Gly  Ala Leu Met
1745                1750                 1755

Leu Glu Ala Asp Ser Leu Asp  Asn Arg Ser Gly Gly  Leu Val Ser
1760                1765                 1770

Ala Asp Gly Asn Leu Thr Val  Ser Ala Arg Arg Ile  Asp Asn Arg
1775                1780                 1785

Ala Gly Glu Ile Ala Ser Pro  Gly Gln Val Thr Leu  Asp Val Ala
1790                1795                 1800

Glu Gln Leu Asp Asn Arg Gly  Gly Lys Ala Ile Gly  Asp Ser Gly
1805                1810                 1815

Leu Arg Leu Ala Ala Pro Arg  Val Leu Asn Gln Asp  Gly Gly Val
1820                1825                 1830

Leu Ala Ser Arg Asp Gly Leu  Arg Leu Asn Gly Ala  Glu Leu Phe
1835                1840                 1845

Asn Gly Asn Gly Gly Leu Leu  Ser Ser Gln Gln Ser  Ile Asp Val
1850                1855                 1860

Ile Leu Asp Gly Val Leu Gly  Asn Gln Ala Gly Ser  Leu Ser Ser
1865                1870                 1875

Gln Gly Arg Leu Ser Val Lys  Ser Gly Arg Leu Asp  Asn Gln Gly
1880                1885                 1890

Gly Ala Val Ser Ser Ala Gly  Thr Leu Ser Leu Ser  Ser Gln Gly
1895                1900                 1905

Ala Leu Asn Asn Gln Gly Gly  Arg Val Val Thr Asp  Ala Gly Ala
1910                1915                 1920

Val Leu Arg Ser Ala Ser Leu  Asp Asn Ser Gln Gly  Gly Ile Val
1925                1930                 1935

Ser Ala Lys Gly Ala Ala Glu  Ile Arg Thr Gly Ser  Leu Asn Asn
1940                1945                 1950

Ser Gln Lys Gly Gly Ile Gly  Ser Gly Ala Gly Leu  Ala Leu Val
1955                1960                 1965

Ala Asp Leu Val Asp Asn Ser  Gln Asn Gly Arg Ile  Thr Ala Lys
1970                1975                 1980

Gly Ala Ile Asp Ala Asn Leu  Lys Gly Leu Asp Gln  Gln Gly Ser
1985                1990                 1995

Gly Arg Leu Val Ser Asp Thr  Ala Ile Ala Leu Asp  Leu Arg Gly
2000                2005                 2010

Gly Glu Leu Val Asn Arg Ala  Gln Gly Leu Ile Ala  Thr Pro Gly
```

-continued

```
            2015                2020                2025
Ala Leu Leu Leu Arg Gln Leu Gly Val Val Asp Asn Ser Gly Gly
            2030                2035                2040
Gly Glu Ile Ser Ser Asp Arg Ser Phe Thr Leu Ala Ala Thr Ala
            2045                2050                2055
Leu Ser Asn Arg Gly Gly Arg Val Ile Ser Gly Asp Ser Leu Thr
            2060                2065                2070
Leu Arg Ile Ala Gln Ala Leu Asp Asn Ser Leu Gln Gly Val Leu
            2075                2080                2085
Ser Ala Ser Gly Gly Leu Asp Val Ala Ala Leu Val Phe Asp Asn
            2090                2095                2100
His Ser Gly Ile Val Ala Ser Lys Gly Asp Thr His Ile Gly Val
            2105                2110                2115
Asn Arg Leu Glu Asn Glu Ala Gly Arg Val Val Ser Glu Gly Ala
            2120                2125                2130
Leu Asp Leu Thr Ala Lys Gln Val Ser Ser Ala Lys Gly Arg Ile
            2135                2140                2145
Ala Ala Lys Gly Asp Leu Gln Val Thr Val Gly Thr Leu Glu Gln
            2150                2155                2160
Gln Gly Gly Glu Leu Ala Ser Gln Gly Thr Leu Thr Leu Asp Ala
            2165                2170                2175
Asp Ser Leu Asp Asn Arg Asn Gly Gly Leu Val Ser Ala Asp Gly
            2180                2185                2190
Gly Val Thr Ala Glu Ala Arg Gln Ile Asp Asn Arg Gly Gly Glu
            2195                2200                2205
Ile Ser Ser Val Ala Lys Val Ala Leu Ala Val Arg Glu Gln Leu
            2210                2215                2220
Asp Asn Arg Gly Gly Lys Val Ile Gly Asp Ser Glu Leu Ser Leu
            2225                2230                2235
Thr Val Gln Arg Leu Leu Asn Gln Ala Lys Gly Val Leu Ala Ser
            2240                2245                2250
Arg Asp Gly Leu His Leu Asp Gly Ala Glu Leu Leu Asn Gly Asp
            2255                2260                2265
Gly Gly Leu Leu Ser Ser Gln Arg Leu Val Asp Val Thr Leu Ser
            2270                2275                2280
Gly Ala Leu Asp Asn Gln Gly Ser Gly Ala Leu Val Ser Glu Glu
            2285                2290                2295
Ser Leu Thr Val Lys Ala Asp Gln Val Asn Asn Gln Ala Gly Thr
            2300                2305                2310
Phe Ser Ser Ala Gly Ser Leu Leu Val Thr Ser Arg Gly Glu Leu
            2315                2320                2325
Asn Asn Gln Gly Gly Arg Leu Val Thr Asp Ala Gly Ala Thr Leu
            2330                2335                2340
Asn Ser Thr Gly Phe Asp Asn Ser Arg Ala Gly Leu Val Ser Ala
            2345                2350                2355
Lys Gly Ala Val Ala Ile Arg Thr Gly Ala Leu Asn Asn Ser Gln
            2360                2365                2370
Lys Gly Ser Ile Gly Gly Asn Thr Gly Val Thr Leu Val Ala Gly
            2375                2380                2385
Leu Val Asp Asn Gly Arg Glu Gly Arg Ile Ser Thr Lys Gly Thr
            2390                2395                2400
Leu Asp Ala Asn Leu Lys Gly Leu Leu Gln Gln Gly Gly Gly Ser
            2405                2410                2415
```

```
Leu Val Gly Glu Arg Gly Val Thr Leu Asp Leu Asn Gly Gly Thr
    2420            2425            2430

Leu Asp Asn His Asp Leu Gly Leu Val Ser Thr Pro Gly Ala Leu
    2435            2440            2445

Leu Leu Arg Gln Leu Gly Met Val Asp Asn Ser Val Gly Gly Glu
    2450            2455            2460

Ile Ser Ser Asp Arg Ala Phe Thr Leu Ala Ala Asn Thr Leu Asn
    2465            2470            2475

Asn Gln Gly Gly Arg Leu Ile Ser Ser Glu Ala Leu Thr Leu Arg
    2480            2485            2490

Ile Ala Lys Thr Leu Asp Asn Ser Leu Lys Gly Gln Val Leu Ala
    2495            2500            2505

Thr Asp Gly Leu Ala Ile Glu Ser Gln Val Leu Asp Asn Arg Ala
    2510            2515            2520

Gly Thr Ile Gly Ser Lys Gly Asp Ala Arg Ile Ser Val Thr Ser
    2525            2530            2535

Leu Asp Asn Ala Glu Gln Gly Ser Leu Val Ser Glu Gly Arg Leu
    2540            2545            2550

Glu Leu Val Ala Asp Gln Val Ser Asn Gly Asn Gln Gly Arg Ile
    2555            2560            2565

Ala Ala Arg Gly Val Leu Glu Ala Ala Val Gly Thr Leu Leu Gln
    2570            2575            2580

Gln Gly Gly Glu Leu Val Ser Gln Gly Ser Leu Asp Leu Arg Ala
    2585            2590            2595

Asp Thr Leu Asp Asn Ser Gln Ser Gly Leu Ile Ala Ala Asn Gly
    2600            2605            2610

Gly Ile Ala Ile Glu Ala Arg Gln Val Asp Asn Arg Ala Gly Glu
    2615            2620            2625

Ile Ser Ser Thr Ser Lys Val Ala Val Asn Ala Arg Glu Gln Leu
    2630            2635            2640

Asp Asn Arg Gly Gly Lys Val Ile Gly Asp Ser Gly Leu Arg Leu
    2645            2650            2655

Thr Val Gln Arg Leu Leu Asn Gln Ala Lys Gly Val Leu Ala Gly
    2660            2665            2670

Arg Asp Gly Leu Ser Leu Asp Gly Gly Glu Leu Phe Asn Gly Asp
    2675            2680            2685

Gly Gly Arg Leu Asp Ser Gln Asn Ser Leu Ser Val Ser Leu Gly
    2690            2695            2700

Gly Val Leu Asp Asn Gln Gly Gly Ala Leu Val Ser Glu Gly Ser
    2705            2710            2715

Leu Thr Ala Arg Ala Ala Arg Leu Asp Asn Arg Gly Gly Thr Phe
    2720            2725            2730

Ser Ser Ala Gly Ala Leu Ala Leu Thr Ser Gln Ala Val Leu Asp
    2735            2740            2745

Asn Gln Gly Gly Arg Leu Leu Ser Asp Ala Gly Val Thr Leu Lys
    2750            2755            2760

Gly Ala Ser Leu Asp Asn Ser Arg Ser Gly Val Ile Ser Ala Lys
    2765            2770            2775

Gly Ala Val Asp Ile Arg Thr Gly Val Leu Asp Asn Ser Arg Asn
    2780            2785            2790

Gly Gly Ile Gly Ser Asn Ala Gly Ile Thr Leu Val Ala Ala Arg
    2795            2800            2805
```

| Leu | Asp | Asn | Gly | Gln | Gln | Gly | Arg | Val | Ser | Ala | Lys | Gly | Leu | Leu |
| 2810 | | | | | 2815 | | | | | 2820 | | | | |

| Asp | Ala | Asn | Leu | Lys | Gly | Leu | Asp | Gln | Arg | Gly | Gly | Val | Leu |
| 2825 | | | | | 2830 | | | | | 2835 | | | | |

| Val | Ser | Glu | Thr | Gly | Val | Thr | Leu | Asp | Leu | Asn | Gly | Gly | Thr | Leu |
| 2840 | | | | | 2845 | | | | | 2850 | | | | |

| Val | Asn | Arg | Asp | Gly | Gly | Leu | Ile | Ala | Thr | Pro | Gly | Ala | Leu | Leu |
| 2855 | | | | | 2860 | | | | | 2865 | | | | |

| Leu | Arg | Gln | Leu | Gly | Ala | Val | Asp | Asn | Gly | Ala | Gly | Gly | Glu | Ile |
| 2870 | | | | | 2875 | | | | | 2880 | | | | |

| Ser | Ser | Asp | Arg | Ala | Phe | Thr | Leu | Ala | Ala | Ala | Ser | Leu | Asp | Asn |
| 2885 | | | | | 2890 | | | | | 2895 | | | | |

| Arg | Gly | Gly | Arg | Leu | Ile | Gly | Ala | Asp | Ser | Leu | Thr | Leu | Arg | Ile |
| 2900 | | | | | 2905 | | | | | 2910 | | | | |

| Ala | Gln | Ala | Leu | Asp | Asn | Ser | Leu | Ala | Gly | Val | Ile | Ser | Gly | Ala |
| 2915 | | | | | 2920 | | | | | 2925 | | | | |

| Ala | Gly | Leu | Asp | Ile | Ala | Ala | Ala | Arg | Leu | Asp | Asn | Ser | Ala | Lys |
| 2930 | | | | | 2935 | | | | | 2940 | | | | |

| Gly | Thr | Leu | Ala | Ser | Arg | Ala | Gly | Ile | Asp | Leu | Arg | Val | Asp | Gly |
| 2945 | | | | | 2950 | | | | | 2955 | | | | |

| Ala | Leu | Asp | Asn | His | Ala | Glu | Gly | Thr | Val | Ser | Gly | Ala | Arg | Leu |
| 2960 | | | | | 2965 | | | | | 2970 | | | | |

| Thr | Leu | Ala | Ser | Ala | Ser | Leu | Asp | Asn | Ser | Gly | Lys | Gly | Leu | Leu |
| 2975 | | | | | 2980 | | | | | 2985 | | | | |

| Ser | Gly | Asn | Ala | Gly | Leu | Ser | Val | Ala | Thr | Gly | Ala | Leu | Asp | Asn |
| 2990 | | | | | 2995 | | | | | 3000 | | | | |

| Ala | Glu | Gly | Gly | Gln | Leu | Ile | Ser | Gln | Gly | Val | Leu | Asp | Val | Ser |
| 3005 | | | | | 3010 | | | | | 3015 | | | | |

| Ser | Ala | Asp | Leu | Asp | Asn | Arg | Gly | Gly | Ala | Leu | Ser | Gly | Lys | Gln |
| 3020 | | | | | 3025 | | | | | 3030 | | | | |

| Ser | Leu | Arg | Leu | Ser | Ala | Ala | Asn | Leu | Asp | Asn | Arg | Gly | Gly | Leu |
| 3035 | | | | | 3040 | | | | | 3045 | | | | |

| Leu | Thr | Ser | Asp | Gly | Glu | Leu | Glu | Leu | Thr | Ala | Gly | Arg | Val | Asp |
| 3050 | | | | | 3055 | | | | | 3060 | | | | |

| Ser | Ala | Asp | Gly | Gly | Glu | Ile | Ser | Ala | Arg | Gly | Asp | Leu | Arg | Leu |
| 3065 | | | | | 3070 | | | | | 3075 | | | | |

| Thr | Val | Glu | Arg | Leu | Val | Gln | Arg | Gln | Gly | Arg | Leu | Ile | Gly | Glu |
| 3080 | | | | | 3085 | | | | | 3090 | | | | |

| Arg | Gly | Val | Ser | Leu | Asp | Leu | Arg | Gly | Gly | Asp | Leu | Asp | Asn | Gln |
| 3095 | | | | | 3100 | | | | | 3105 | | | | |

| Gly | Gly | Leu | Ile | Ser | Ala | Arg | Gly | Pro | Leu | Ser | Ile | Glu | Arg | Leu |
| 3110 | | | | | 3115 | | | | | 3120 | | | | |

| Asn | Val | Leu | Asp | Asn | Arg | Gln | Gly | Gly | Glu | Ile | Tyr | Ser | Gln | Gln |
| 3125 | | | | | 3130 | | | | | 3135 | | | | |

| Gly | Phe | Glu | Leu | Leu | Ala | Arg | Arg | Ile | Asp | Asn | Gly | Gln | Gln | Gly |
| 3140 | | | | | 3145 | | | | | 3150 | | | | |

| Arg | Ile | Ile | Ser | Ala | Gly | Lys | Leu | Arg | Leu | Asp | Ala | Asp | Ala | Leu |
| 3155 | | | | | 3160 | | | | | 3165 | | | | |

| Gly | Asn | Ala | Gly | Ala | Gly | Leu | Leu | Ser | Gly | Trp | Gln | Gly | Leu | Thr |
| 3170 | | | | | 3175 | | | | | 3180 | | | | |

| Val | Thr | Gly | Gly | Ser | Leu | Asp | Asn | Ser | Ala | Gly | Gly | Thr | Leu | Ser |
| 3185 | | | | | 3190 | | | | | 3195 | | | | |

Ser Lys Asp Gly Glu Leu Ala Ile Ser Leu Gly Gly Ala Leu Asp

-continued

```
                3200                3205                3210

Asn His Gly Gln Gly Ala Leu Val Ser Lys Gly Ala Gln Arg Ile
    3215                3220                3225

Asp Ala Ala Ser Leu Asp Asn Ala Gln Gly Ile Val Ser Gly Glu
    3230                3235                3240

Ser Asp Val Thr Leu Ser Ile Ala Gly Lys Leu Asp Asn Gly Gln
    3245                3250                3255

Gly Gly Leu Val Ser Ala Gln Arg Ala Leu Ser Phe Glu Arg Asp
    3260                3265                3270

Asp Thr Leu Leu Asn Asn Ala Gly Gly Arg Ile Asn Gly Gly Ser
    3275                3280                3285

Leu Leu Leu Lys Gly Ala Ser Leu Asp Asn Ser Asp Gly Gln Leu
    3290                3295                3300

Ile Ser Gln Gly Arg Leu Asp Ala Ile Leu Gly Gly Ala Leu Val
    3305                3310                3315

Asn Ala Gly Ala Ala Arg Leu Ala Ser Gly Gly Asp Leu Leu Leu
    3320                3325                3330

Arg Ser Ala Ser Val Asp Asn Arg Gly Gly Lys Leu Val Ser Gln
    3335                3340                3345

Gly Leu Leu Glu Ile Ser Ala Gly Ser Leu Asp Asn Ser Ala Ser
    3350                3355                3360

Gly Thr Leu Ala Ser Gln Ala Asp Met Ser Leu Arg Leu Gly Gly
    3365                3370                3375

Gly Ala Leu Arg Asn Gln Gln Asp Gly Leu Ile Phe Ser Gln Ala
    3380                3385                3390

Gly Ala Leu Glu Val Gln Ala Gly Ser Leu Asp Asn Arg Gln Gly
    3395                3400                3405

Thr Leu Gln Ala Gln Gly Asp Asn Arg Leu Arg Ile Gly Gly Ala
    3410                3415                3420

Leu Asp Asn Gln Ala Gly Arg Leu Asp Ser Arg Ala Gly Asn Leu
    3425                3430                3435

Asp Leu Gln Ser Gly Ser Leu Asp Asn Gly Ala Gly Gly Val Leu
    3440                3445                3450

Asn Ser Ala Lys Gly Trp Leu Lys Leu Val Thr Gly Leu Phe Asp
    3455                3460                3465

Asn Ser Ala Gly Val Thr Gln Ala Gln Ser Leu Glu Ile Arg Ala
    3470                3475                3480

Gly Gln Gly Val Arg Asn Gln Gly His Leu Ser Ala Leu Gly
    3485                3490                3495

Gly Asp Asn Arg Ile Val Thr Ala Asp Phe Asp Asn Gln Gly Gly
    3500                3505                3510

Gly Leu Tyr Ala Ser Gly Leu Leu Ser Leu Asp Gly Gln Arg Phe
    3515                3520                3525

Leu Asn Gln Gly Ala Ala Ala Gly Gln Gly Gly Lys Val Gly Ala
    3530                3535                3540

Gly Arg Ile Asp Phe Ser Leu Ala Gly Ala Leu Ala Asn Arg Phe
    3545                3550                3555

Gly Gln Leu Glu Ser Glu Ser Glu Leu His Leu Arg Ala Ala Ala
    3560                3565                3570

Ile Asp Asn Ser Gly Gly Ser Leu Arg Ala Leu Gly Arg Ser Gly
    3575                3580                3585

Ser Thr Arg Leu Val Ala Gly Asp Leu Asn Asn Ala Tyr Gly Val
    3590                3595                3600
```

-continued

```
Leu Glu Ser Ala Asn Gln Asp Leu Asp Leu Gln Leu Gly Ser Leu
    3605                3610                3615

Ala Asn Ala Gly Gly Arg Ile Leu His Thr Gly Asn Gly Thr Phe
    3620                3625                3630

Gly Leu Asp Ser Gly Gln Val Ile Arg Ala Gly Glu Leu Thr
    3635                3640                3645

Thr Asn Gly Leu Leu Asp Ile Arg Ala Ser Glu Trp Thr Asn Ser
    3650                3655                3660

Ser Val Leu Gln Ala Gly Arg Leu Asn Leu Asp Ile Gly Thr Phe
    3665                3670                3675

Arg Gln Thr Ala Glu Gly Lys Leu Leu Ala Val Gln Ser Phe Thr
    3680                3685                3690

Gly Arg Gly Gly Asp Trp Ser Asn Asp Gly Leu Leu Ala Ser Asn
    3695                3700                3705

Gly Ser Leu Arg Leu Glu Leu Ser Gly Gly Tyr Arg Gly Asn Gly
    3710                3715                3720

Arg Ala Thr Ser Leu Gly Asp Phe Ala Leu Asn Ala Ala Ser Leu
    3725                3730                3735

Asp Leu Gly Asn Ala Ala Ser Leu Ala Gly Gly Ala Asn Val Thr
    3740                3745                3750

Leu Gly Ala Gly Asn Leu Leu Val Asn Arg Gly Arg Ile Thr Ala
    3755                3760                3765

Ala Gly Asp Leu Val Ala Ser Ala Ala Ser Leu Asn Asn Tyr Gly
    3770                3775                3780

Thr Leu Gly Gly Gly Gly Asn Leu Arg Leu Asn Ala Pro Ala Leu
    3785                3790                3795

Leu Asn Glu Arg Gly Leu Leu Phe Ser Gly Ala Asp Met Thr Leu
    3800                3805                3810

Arg Ala Gly Asp Ile Thr Asn Leu Tyr Gly Asp Val Tyr Ser Leu
    3815                3820                3825

Gly Arg Leu Asp Ile Ala Arg Asp Asp Ala Gly Gly Trp Ala Asn
    3830                3835                3840

Arg Leu Glu Asn Ile Ser Gly Asn Leu Glu Ser Thr Gly Asp Met
    3845                3850                3855

Arg Phe Ser Val Ser Ser Leu Leu Asn Arg Arg Glu Thr Leu Glu
    3860                3865                3870

Ile Glu Gly Asp Leu Gln Asn Ser Ala Ile Gly Val Arg Cys Thr
    3875                3880                3885

Gly Cys Gln Leu Ser Glu Arg Trp Gly Lys Thr Arg Ser Ser Ser
    3890                3895                3900

Glu Leu Val Trp Ile Arg Glu Tyr Lys Ser Thr Leu Gly Asp Ser
    3905                3910                3915

Ser Ala Ala Ala Ser Ile Thr Ala Gly Arg Asp Leu Leu Val Val
    3920                3925                3930

Gly Ala Ser Leu Gln Asn Ile Ala Ser Asn Ile Ser Ala Val Arg
    3935                3940                3945

Asp Ala Thr Leu Ser Leu Ser Asn Phe Glu Asn Lys Gly Tyr Ala
    3950                3955                3960

Leu Gly Glu Tyr Ala Val Arg Gly Val Tyr Ser Pro Pro Ser Lys
    3965                3970                3975

Phe Gly Glu Glu Leu Leu Met Arg Ile Leu Ala Tyr Asn Ala Val
    3980                3985                3990
```

```
Asn Asp Pro Ser Tyr Gly Glu Gly Tyr Ala Ser Thr Gly Gly Arg
    3995            4000                4005

Leu Pro Asn Ile His Tyr Phe Asp Lys Asn Phe Asn Glu Lys Val
    4010            4015                4020

Ser Pro Leu Glu Val Ile His Gly Asn Gly Lys Asn Gly Gly Pro
    4025            4030                4035

Gly Trp His Leu Tyr Phe Gly Thr Leu Asp Val Glu Tyr Pro Asp
    4040            4045                4050

Thr Asp Arg Trp Asn Lys Ala Ile Gly Arg Ile Pro Ala Pro Asn
    4055            4060                4065

Tyr Ser Ser Lys Lys Thr Asp Ala Ile Pro Asp Leu Leu Lys Gly
    4070            4075                4080

Leu Ala Pro Leu Asp Glu Leu Thr Ile Asn Lys Gly Ala Asn Ser
    4085            4090                4095

Thr Val Gly Ala Val Val Gln Ala Gly Gly Arg Val Thr Val Asn
    4100            4105                4110

Ala Ala Glu Ser Phe Asn Asn Ser Val Leu Gln Gly Phe Gln Ala
    4115            4120                4125

Val Gln Glu Thr Gln Leu Pro His Gln Asp Ile Ala Val Ser Ser
    4130            4135                4140

Thr Thr Ser Ala Val Val Thr Leu Lys Ser Gln Leu Pro Ala Asp
    4145            4150                4155

Leu Ala Arg Gln Gln Ile Asn Pro Leu Thr Leu Pro Gly Phe Ser
    4160            4165                4170

Leu Pro Gln Gly Gln Asn Gly Leu Phe Arg Leu Ala Ser Gln Gly
    4175            4180                4185

Ala Gln Val Asn Gln Ala Ser Gly Ala Leu Lys Ser Ala Ser Asp
    4190            4195                4200

Leu Thr Gln Ser Gly His Gly Val Ser Val Ser Ala Gln Thr Gly
    4205            4210                4215

Ser Gly Ala Ser Gly Trp Ser Thr Gln Ala Arg Arg Val Gly Asp
    4220            4225                4230

Asp Arg Val Thr Ser Leu Ala Gly Ser Ala Tyr Gln Gly Arg Val
    4235            4240                4245

Ala Glu Ala Ile Asp Ala Leu Arg Ala Ser Ala Pro Ile Ser Gly
    4250            4255                4260

Asp Gly Gly Asn Thr Gly Arg Phe Gln Ala Gly Glu His Gln Ala
    4265            4270                4275

Thr Thr Gly Leu Gly Gly Leu Val Glu Gly Asn Ala Ser Gly His
    4280            4285                4290

Ser Gly Asn Gly Val Ile Leu Ala Asp Leu Arg Gly Gly Leu Pro
    4295            4300                4305

Ser Phe Ser Ser Leu Pro Ala Ser Asp His Val Gln Gly Thr Val
    4310            4315                4320

Pro Gly His Asp Gly Asn Gly Thr Ile Leu Ala Asn Trp Gln Gly
    4325            4330                4335

Ala Gln Ala Thr Val Gln Ala Ser Pro Ser Thr Val Arg Val Glu
    4340            4345                4350

Gly Val Val Ser Ser Pro Gly Gly Asn Gly Ser Ile Leu Ala Asp
    4355            4360                4365

Leu Pro Ala Glu Gln Ser Ser Val Gln Ala Leu Pro Ser Ala Val
    4370            4375                4380

Arg Ala Gln Gly Ser Leu Pro Arg Leu Glu Glu Arg Ser Ala Leu
```

```
                4385                4390                4395

Leu Ala Glu Pro Pro Val Gly Gln Pro Ala Leu Gln Thr Leu Pro
    4400                4405                4410

Ser Val Ala Arg Val Glu Gly Val Pro Ser Asn Ala Thr Pro Ser
    4415                4420                4425

Asn Ser His Lys Tyr Leu Ile Glu Thr Asn Pro Ala Leu Thr Glu
    4430                4435                4440

Leu Lys Gln Phe Leu Asn Ser Asp Tyr Leu Leu Gly Gly Leu Gly
    4445                4450                4455

Ile Asn Pro Asp Asp Ser Lys Lys Arg Leu Gly Asp Gly Leu Tyr
    4460                4465                4470

Glu Gln Arg Leu Val Arg Glu Ala Ile Val Gln Arg Thr Gly Gln
    4475                4480                4485

Arg Phe Ile Ala Gly Leu Asn Ser Asp Glu Ala Met Phe Arg Tyr
    4490                4495                4500

Leu Met Asp Asn Ala Ile Ala Ser Lys Asp Val Leu Gly Leu Thr
    4505                4510                4515

Pro Gly Val Thr Leu Ser Ala Ala Gln Val Ala Ala Leu Thr His
    4520                4525                4530

Asp Ile Val Trp Leu Glu Glu Val Glu Val Asn Gly Glu Lys Val
    4535                4540                4545

Leu Ala Pro Val Val Tyr Leu Ala Gln Ala Glu Gly Arg Leu Gly
    4550                4555                4560

Pro Asn Gly Ala Leu Ile Gln Gly Arg Asp Val Asn Leu Ile Thr
    4565                4570                4575

Gly Gly Asp Leu Arg Asn Ala Gly Thr Leu Arg Ala Gln Asn Asp
    4580                4585                4590

Leu Ser Ala Thr Ala Gly Asn Ile Asp Asn Ser Gly Leu Ile Glu
    4595                4600                4605

Ala Gly Asn Arg Leu Asp Leu Leu Ala Ser Gly Ser Ile Arg Asn
    4610                4615                4620

Asp Gln Gly Gly Ile Ile Ala Gly Arg Glu Val Ser Leu Ser Ala
    4625                4630                4635

Leu Thr Gly Asp Val Ile Asn Glu Arg Thr Val Thr Gln His Gln
    4640                4645                4650

Ser Ser Tyr Arg Gly Thr Gly Thr Thr Glu Ala Phe Ala Asp Ser
    4655                4660                4665

Ala Ala Arg Ile Glu Ala Ala Gln Lys Leu Thr Val Ser Ala Gly
    4670                4675                4680

Arg Asp Val Ala Asn Ile Gly Gly Val Ile Asp Ser Lys Gly Asp
    4685                4690                4695

Leu Ala Leu Gln Gly Gly Arg Asp Val Leu Val Ser Ala Ala Val
    4700                4705                4710

Ala Glu Arg Gly Trp Thr Ala Gly Ser Gln Ala Tyr Gln Thr Gln
    4715                4720                4725

Thr Thr Gln Met Gly Ala Glu Val Val Ala Gly Arg Asp Ile Ser
    4730                4735                4740

Val Ser Ala Gly Arg Asp Ile Ser Val Val Gly Ser Arg Ile Asp
    4745                4750                4755

Ala Arg Arg Asp Val Thr Phe Glu Ala Gly Arg Asp Val Gly Leu
    4760                4765                4770

Val Ala Ala Ala Asn Glu Glu His Ala Tyr Gly Lys Thr Lys Lys
    4775                4780                4785
```

```
Val Thr Phe Gln Asp Asp Lys Ile Thr Gln Gln Ala Thr Arg Val
    4790            4795            4800

Asp Ala Gly Gly Asp Leu Ala Ile Asn Ala Gly Gln Asp Leu Arg
    4805            4810            4815

Leu Val Ala Ser Gln Ala Ser Ala Gly Asp Glu Ala Tyr Leu Val
    4820            4825            4830

Ala Gly Asp Lys Leu Glu Leu Leu Ala Ala Asn Asp Ser Ser Tyr
    4835            4840            4845

Tyr Leu Tyr Asp Lys Lys Ser Lys Gly Ser Phe Gly Ser Lys Lys
    4850            4855            4860

Thr Arg Arg Asp Glu Ile Thr Asp Val Thr Ala Val Gly Ser Gln
    4865            4870            4875

Ile Ser Ser Gly Gly Asp Leu Thr Leu Leu Ser Gly Gly Asp Gln
    4880            4885            4890

Thr Tyr Gln Gly Ala Lys Leu Glu Ser Gly Asn Asp Leu Ala Ile
    4895            4900            4905

Val Ser Gly Gly Ala Val Thr Phe Glu Ala Val Lys Asp Leu His
    4910            4915            4920

Gln Glu Ser His Glu Lys Ser Lys Gly Asp Leu Ala Trp Gln Ser
    4925            4930            4935

Ser Lys Gly Lys Gly Gln Thr Asp Glu Thr Val Arg Gln Ser Gln
    4940            4945            4950

Ile Val Ala Gln Gly Asn Leu Ala Ile Lys Ala Val Glu Gly Leu
    4955            4960            4965

Lys Ile Asp Leu Lys His Ile Asp Gln Lys Thr Val Ser Gln Thr
    4970            4975            4980

Ile Asp Ala Met Val Gln Ala Asp Pro Gln Leu Ala Trp Leu Lys
    4985            4990            4995

Gln Met Glu Gln Arg Gly Asp Val Asp Trp Arg Arg Val Gln Glu
    5000            5005            5010

Leu His Asp Ser Trp Lys Tyr Ser Asn Ser Gly Leu Gly Val Gly
    5015            5020            5025

Ala Gln Leu Ala Ile Ala Ile Val Val Ala Tyr Phe Thr Ala Gly
    5030            5035            5040

Ala Ala Ser Ala Ala Leu Gly Ser Met Ala Gly Val Gly Ala Gly
    5045            5050            5055

Ser Gly Ser Met Met Ala Ala Gly Ser Thr Ala Met Val Gln
    5060            5065            5070

Ala Gly Thr Ala Val Gly Thr Ala Ala Ala Gly Trp Ala Asn Ala
    5075            5080            5085

Ala Gly Thr Ala Val Ala Met Gly Met Ala Ser Asn Gly Ala Ile
    5090            5095            5100

Ser Thr Ile Asn Asn Arg Gly Asn Leu Gly Asp Val Val Lys Asp
    5105            5110            5115

Val Thr Ser Ser Asp Ala Leu Arg Gly Tyr Val Val Ala Gly Thr
    5120            5125            5130

Thr Ala Gly Leu Thr Ala Gly Val Tyr Asp Lys Trp Thr Ser Thr
    5135            5140            5145

Gln Thr Gly Thr Ser Thr Ala Leu Pro Asn Thr Gly Ala Val Ala
    5150            5155            5160

Pro Ala Ala Gly Leu Gly Thr Trp Gln Gly Val Gly Gln Phe Thr
    5165            5170            5175
```

```
Ser Asn  Gln Leu Leu Gln Asn  Gly Thr Ser Val Leu  Leu Asp Arg
    5180             5185                 5190

Ala Leu  Gly Gly Lys Gly Ser  Leu Gly Asp Ala Leu  Gln Asn Ser
    5195             5200                 5205

Leu Ala  Asn Ala Phe Ala Ala  Tyr Gly Phe Lys Leu  Ile Gly Asp
    5210             5215                 5220

Thr Thr  His Gly Val Leu Asp  Asp Gly Ser Leu Gly  Lys Ile Gly
    5225             5230                 5235

Leu His  Ala Leu Met Gly Gly  Leu Ala Ala Glu Ala  Val Gly Gly
    5240             5245                 5250

Asp Phe  Arg Thr Gly Ala Leu  Ala Ala Gly Val Asn  Glu Ala Leu
    5255             5260                 5265

Val Asp  Ser Leu Ala Lys Gln  Tyr Ala Ser Leu Pro  Ile Asp Asp
    5270             5275                 5280

Lys Lys  Gly Leu Leu Ile Met  Ser Ser Gln Leu Ile  Gly Val Leu
    5285             5290                 5295

Ala Ala  Ser Thr Gln Gly Asp  Ala Asp Ala Lys Ser  Leu Gln Thr
    5300             5305                 5310

Gly Ala  Trp Val Ala Gly Asn  Ala Thr Gln His Asn  Tyr Leu Ser
    5315             5320                 5325

His Trp  Gln Glu Glu Lys Lys  Arg Gln Glu Val Asp  Gly Cys Lys
    5330             5335                 5340

Asp Lys  Gln Leu Cys Lys Thr  Gly Ile Glu Ala Lys  Trp Ala Ile
    5345             5350                 5355

Ile Ser  Ala Gln Gln Asp Val  Gly Ile Val Val Gly  Val Gly Gly
    5360             5365                 5370

Gly Ile  Gly Leu Ser Thr Ala  Glu Thr Ala Val Gly  Val Tyr Glu
    5375             5380                 5385

Leu Val  Lys Asn Trp Arg Glu  Thr Tyr Ala Ala Leu  Glu Gln Leu
    5390             5395                 5400

Ala Thr  Ser Pro Glu Phe Arg  Gln Gln Phe Gly Asp  Asn Tyr Leu
    5405             5410                 5415

Lys Gly  Leu Glu Glu Arg Ala  Ala Phe Leu Thr Gln  Ala Tyr Glu
    5420             5425                 5430

Asp Ala  Gly Trp Gln Gly Ser  Val Thr Ala Gly Val  Glu Gly Gly
    5435             5440                 5445

Arg Phe  Ala Ala Glu Leu Val  Gly Val Leu Thr Ala  Val Lys Gly
    5450             5455                 5460

Gly Ala  Gln Ile Thr Ala Lys  Leu Pro Thr Ala Ala  Lys Asn Leu
    5465             5470                 5475

Val Asn  Ala Ile Ala Glu Ser  Pro Val Ser Gly Ser  Met Ser Ser
    5480             5485                 5490

Gln Leu  Gly Ala Val Gly Asp  Leu Gly Arg Leu Gly  Gly Gly Gly
    5495             5500                 5505

Lys Gly  Tyr Val Asp Ile Leu  Ser His Glu Ala Lys  Gln His Ile
    5510             5515                 5520

Leu Tyr  Gly Asp Lys Pro Gly  Ser Gly Gly His Leu  Trp Pro Gly
    5525             5530                 5535

Gln Ala  Gly Lys Thr Val Phe  Pro Gln Asn Trp Ser  Ala Asp Lys
    5540             5545                 5550

Ile Val  His Glu Val Gly Asp  Ile Ala Thr Ser Pro  Ser Thr Lys
    5555             5560                 5565

Trp Tyr  Ala Gln Thr Gly Thr  Gly Gly Val Tyr Thr  Ser Lys Gly
```

```
                     5570                5575                5580
Asp Pro Ala Lys Trp Val Ala Tyr Glu Val Arg Asp Gly Val Arg
        5585                5590                5595

Met Arg Val Val Tyr Gln Pro Ala Thr Gly Lys Val Ile Thr Ala
    5600                5605                5610

Phe Pro Asp Asn Ala Pro Ile Pro Pro Tyr Lys Pro Ile Lys
    5615                5620                5625

<210> SEQ ID NO 31
<211> LENGTH: 201
<212> TYPE: DNA
<213> ORGANISM: Pseudomonas aeruginosa

<400> SEQUENCE: 31
atgagtcagg aacccacgt acacggcccg aactgcaacc acgaccacga tcatcatcac      60
gatcatggcc atggtcatgt ccatggtccg cactgcaacc acagccacga gccggtgcgc     120
aatccgctca aggccgtagg ccgcaacgat ccctgcccct gcggcagcga aagaaattc      180 aagaagtgcc acggcgcctg a                                               201

<210> SEQ ID NO 32
<211> LENGTH: 237
<212> TYPE: DNA
<213> ORGANISM: Pseudomonas aeruginosa

<400> SEQUENCE: 32 atgaaaaga ccgtaactct tgccctgctg ctcgctgcca gccttggcct ggccgcttgc       60
gacaagaaag aggaagacaa ggcagcggcc ccggcagctc cggctaccga gacccagccg     120
agcgctccgg ctactccccc tgccgagccc agcgccccgg cgccgtcgag cgacactccg     180
gcaaccccgc agactccggc accgactccg gagcaaccgc aacagaacca gcaataa        237

<210> SEQ ID NO 33
<211> LENGTH: 315
<212> TYPE: DNA
<213> ORGANISM: Pseudomonas aeruginosa

<400> SEQUENCE: 33
atgaaaaaga tttccctcgc ttcttccgtc gtcggcgctg ctctgctcgg cgtagccagt      60
gtcggcgcgc atgccgcgca gaatcccttc gccgtgcagg agctgagcag cggctacagc     120
gtggctgccg ccgagaaagc caaggaaggt tcctgcggcg aggccaagtg cggtgccgac     180
aagggcaagc gcgaagcctc caaggccggt catgaaggca gctgcggtgc ggatcgcaag     240
gccaaggaag gttcctgcgg tggcgagaag aaggccggcg aaggcaactg cggcgccgac     300
aagaagaagt cgtaa                                                      315

<210> SEQ ID NO 34
<211> LENGTH: 468
<212> TYPE: DNA
<213> ORGANISM: Pseudomonas aeruginosa

<400> SEQUENCE: 34
atgtccgttt tcgattcgcg tcaaaagact tccgccagcc tgctcggtgc cgtactggtg      60
gggggaatgc tgctcggcgg ttcggcgttc gccgtcgagc cgctgggcca ggggctgcaa     120
gtggcggcgg cgagcgccgg cgaaggcaag tgccgagaag gcaagtgtgg tagcggcggc     180
tccgcgaaga ccccggccaa ggccggcgcc gagggcaagt gcggggaggg caagtgcggc     240
```

```
gacgcctcct ttgcccgaac cgacaccgat cacgatggca aggtctcgcg cgccgagttc      300
ctcgcggtgg ccaaggaccg tgccggtgag ttcgacagca tcgatagcga ccatgacggc      360
ttcatttccg aagccgaggc ctacgaacac ctgcgcaaga cctacgaggc caacggcaag      420
ccgatgcccg ccgggctgtt cagcaagctg gagcaaggcc agcactga                  468
```

<210> SEQ ID NO 35
<211> LENGTH: 540
<212> TYPE: DNA
<213> ORGANISM: Pseudomonas aeruginosa

<400> SEQUENCE: 35

```
atgcgttccc tgtccctcct tctcctcctc tcgctggcgt ccacctgcga ggccgctgcg       60
gtattccgct gcgaagacgc cagcggccat gtcagcttca cccaactcgg ttgccccgcc      120
gggcaggccg gcgagaccgt cgtggcggac aacccgccgc cgggaggcag gagcgtcacg      180
ccgatggccg agacgaagac gaaaaaggcg tccatcggcc ggaaaagcgt gccgctcgcg      240
gtgatcggag aaagagaaga tcgctgcggc agacgcctgg acgagaagga acgccgcaag      300
gcgatcgtgg agcagcggat aatggcggga atgacccgct ccgatgtgga gcgggcgctg      360
ggcaagccgg accgggtcag cgggaacaat gcggaggtgc gttatcagta caaggccgac      420
aagcgacggg gagcgagaag cgtgagcttc gatcaggagg gatgtgtgaa gggaagagaa      480
ggtaccgggt ggagcgagtc gatcccggga gctaaggccg gccgtcctc ataccgatga      540
```

<210> SEQ ID NO 36
<211> LENGTH: 915
<212> TYPE: DNA
<213> ORGANISM: Pseudomonas aeruginosa

<400> SEQUENCE: 36

```
atgagccaac ccagcgaaaa ccgtttgatc acctcggcgc gctacgcgct ctgcctgttg       60
accgccagcg gcgtgctgct cagcggctgc gccagcagcg cgtcggctc ggtcgcccag      120 accacccgcg cggaatacta cccgtcctgc tacgagccgg tgtcgcacct gcgcagcacc      180
gataacgcag tgcgcaattc ggccatcacc ggcgccatta ccggcggcct cctgggcggc      240
ctggccggcg gcctggccag cgacgagaac cgcggccgca tgccgccct cgctgccgca      300 ggcggcgccc tggccggcgg cgcggcgggc tactacatgg agaagcagaa gcagatcagc      360
gatgaccgcg cgcgcatcgg ctcctacggt accgacgtcg accgcagcac cgtcgagatc      420
aaccgtagcg tggcctacgc caagtcggcg caaagctgct accagagcca gttcaaggct      480
ctgctcgacg gtcgcaagaa caagtcgatc aacgaagccg aagggcgcaa cgcctggcc      540 gagatcgtca gcggcctgca ggagaccaac gccttgctgg tcgccgccaa cggccgtgcc      600
ggcgagaaca tcagcaacta cacccaggcc tacgagaaag acctgcagca ggtcggcgta      660
ccgcgcgccg aggtgaccaa ggtcgccgag gccgagaacc gcgccagcac tacgaaaggc      720
ggcagcaagc ccaagaccgg cagcaatccc aaggtgccga aggaagcggt cgccaccgag      780
cagaccatcc gcaaggccca ggacgcgcaa agcgaaggca acaaggtggc ctcccagggc      840
cagggcatga tccggggaagt ctgcaacagc ccggacatgg cgactgggc gccgccgagc      900 tgcgccaagg cctga                                                      915
```

<210> SEQ ID NO 37
<211> LENGTH: 930
<212> TYPE: DNA
<213> ORGANISM: Pseudomonas aeruginosa

<400> SEQUENCE: 37

```
atggctggca agaagaagag cgaaaaagag tccagttgga tcggcgagat cgagaaatac      60
tcgcggcaga tctggctggc tggtctgggg gcctactcga aggtcagcaa ggacggcagc     120
aagctgttcg agaccttggt gaaagacggc gagaaggctg aaaaagaagc gaagtccgat     180
gtggacgcgc aggtcggtgc ggcgaaggct tccgcccgct ctgcgaagag caaggtcgac     240
gaggttcggg accgtgcgct cggcaagtgg agcgagctcg aggaagcttt cgacaagcgc     300
ctgaacagcg ccatctcgcg tctcggcgtg ccagccgca acgaggtgaa ggagctgcac      360
agcaaggtcg atacgctgac caagcagatc gagaaactca ccggcgtcag cgtcaagccg     420
gcggcgaagg cagcggccaa gcctgcggcg aaaccggctg ccaagcccgc ggcgaaaacc     480
gcagcggcca agccggcagc taaaccggca gccaaggccg ccgccaagcc tgcggcgaaa     540
cccgcggcga aaaaaccgc ggcgaaaacc gcggccgcca agccggcagc caagcccgcc      600
gccaaaccga ctgcgaaggc cgcagcgaaa ccggcgacca gccggcagc caaggccgcg      660
gcgaagcctg ctgcgaaacc tgccgcagcc aagcctgccg cgaagccggc agccaagccg     720
gccgctgcga ccgccgccaa gcccgcgcg aaacctgccg ccaagccggc tgcgaaaaag      780
cctgcggcga agaagccggc agccaagccc gccgcggcga accggccgc tcccgccgcg      840
tcttcgagcg cgcccgctgc cccgccgcc acaccggctg ccagcgctcc ggcagcgaac      900
gctccggcga cgccgagcag ccagggctga                                      930
```

<210> SEQ ID NO 38
<211> LENGTH: 1023
<212> TYPE: DNA
<213> ORGANISM: Pseudomonas aeruginosa

<400> SEQUENCE: 38

```
atgaaagcga ctatggtcct gaccccgctg ccctggcaa tggctgcagt gctgtcggta      60
tcggcctacg ccggaaacga aggtggctgg cacccgccga acccaacccc gcagtcgaac     120
aacaagggcg gagccacggc cctggtggtg gatacgcagc agaactacaa caacaaggtc     180
agcaacttcg gcacgctgaa caatgcctcg gtgagcggct cgatcaagga tgcctcgggc     240
aacgtcgggg tcaacgtcgc cgccggcgac aacaaccagc aggccaacgc cgccgcgctg     300
gccagcgccg acgccagctt cgtgttcggc accgcgaccg ccagcaccag cgtgctgcag     360
agcggctacg gcaatacgct gaacaactac tccaaccca acaccgcatc gctgagcaac      420
tcggccaaca acgtctcggg caacctgggc gtgaacgtcg ccgccggcaa cttcaaccag     480
cagaagaacg acctggccgc cgccgtctcc aacgccagt acagcactgc cggtagcgcc     540
gcgtcgcaga cctccaccgg caacaccacc gtcaacagcg ccaactacgc ctatggcggc     600
acctacgtgt cgctgaagct gaacgccgac ggcagctaca agggcacctc gaccagatc      660
ggcgacgtct acctcgacac ctgggaaggc cagacccatc cggcggcag caataccggc     720
cacatcgacg tggacagcca ggcccagggc gccaaggacc tgaaccacga cggcggcgcg     780
ttcgccttca aggaaaaggg cgacgtcgac ctgaaaggca cggtgtccgg cttcatcccg     840
gcgatcgtcg gcttcaagac cccggtcacc aacaacgcca gcctgagcaa ctcgttgcag     900
aacgtctcgg gcaacgtcgg ggtgaacatc gccgccggtg gcgcaaacca gcagagcaac     960
tccctgtcca tcgccgccgg ttgcagcagc tgcccggccg gtggcgagag ccttggcttc    1020
tga                                                                   1023
```

<210> SEQ ID NO 39
<211> LENGTH: 1044
<212> TYPE: DNA
<213> ORGANISM: Pseudomonas aeruginosa

<400> SEQUENCE: 39

```
atgaagcaac agttcgaacg ctcgccttcc gagagttatt tctggcccgt cgtcctggcg      60
gtggtcctgc acgttctgat cttcgccatg ctgttcgtca gctgggcgtt tgctccggag     120
cttcctcccct ccaagccgat cgtgcaggcc acgctctacc agctcaagtc gaagagccag    180
gcgacgacac agaccaacca gaagatcgct ggcgaggcga agaagaccgc ctccaagcaa     240
tacgaagtcg agcagctcga acagaagaag ctcgagcagc agaaactcga gcaacaaaag    300
ctggaacagc agcaggtcgc tgctgcgaaa gcggcggaac aaaagaaggc tgacgaggct    360
cgaaaggccg aggcccagaa agccgccgag gcgaaaaagg ccgatgaagc caagaaagct    420
gccgaggcca aggccgccga acagaagaag caggctgaca tagccaagaa gcgcgccgag    480
gacgaggcca agaaaaaggc cgctgaggac gccaagaaaa aggcagccga ggacgcgaag    540
aagaaagcgg ccgaggaggc caagaagaag gctgctgcgg aagcggcgaa gaagaaagcc    600
gccgtcgagg ccgccaagaa aaaggccgcc gccgctgccg cggcagcccg caaggctgcc    660
gaggacaaga aggcgcgggc attggccgag ttgctttcgg atacgaccga gcgccagcag    720
gccctggccg acgaggtggg cagcgaggtc accggcagtc tcgacgacct gatcgtcaac    780
ctggtgagcc agcagtggcg gcgtcctcca tcggcgcgta atggaatgag cgtagaagta    840
ctgatcgaaa tgctgccgga cggtaccatc accaatgcca cgtcagccg ttcgagtggc     900
gacaagcctt tcgacagttc ggcggtggcg gcggtgcgca acgtcggccg tattcccgag    960
atgcagcaat tgccgcgggc taccttcgac agcctgtatc gtcagcgccg catcatcttt   1020
aaaccggagg atttgagtct gtga                                          1044
```

<210> SEQ ID NO 40
<211> LENGTH: 1059
<212> TYPE: DNA
<213> ORGANISM: Pseudomonas aeruginosa

<400> SEQUENCE: 40

```
atgtcggcca acaagaagcc cgtcaccacc cccttgcacc tgttgcagca actttcccac      60
agccttgtcg agcacctgga aggtgcgtgc aaacaagcgc tggtcgattc ggaaaagctc     120
ctggccaaac ttgaaaagca acgtggcaaa gcccaggaaa agctgcacaa ggctcgcacc     180
aagctgcagg atgctgccaa ggccggcaag accaaggcac aggccaaggc gcgcgagacc    240
atcagcgacc tggaagaggc gttggatacc ctgaaggccc ggcaggcgga cacccgtacc    300
tacatcgtcg gcctcaagcg tgacgtacag gaaagcctca gctggcgca gggtgtcggc    360
aaggtgaagg aagctgctgg caaggctctg gagagccgca aggcgaaacc cgcgaccaaa    420
cctgctgcga aggcggcagc caagcctgcg gtgaaaaccg tagcggcgaa gcctgcggcc    480
aagccggctg cgaagcctgc tgcgaaaccg gcggccaagc ctgcggcgaa accgcggca    540
gcgaagcccg cagccaagcc gacggcgaag cctgctgcga accggcggc caagcccgcg    600
gcgaaaaccg cagccgcgaa gcccgcagcc aagccggcgg cgaagcctgt ggcgaaaccg    660
gcggccaagc ctgcggcgaa aaccgcagcc gcgaagcccg ccaagcc ggcagcgaag       720
cctgtcgcga aaccgacggc caagcccgcg gcgaaaaccg cagccgcgaa gcccgcagcc    780
aagccagctg cgaagcctgc ggcgaaaccg gcggccaagc ctgtggcgaa atccgcggcc    840
```

```
gcgaagcctg cagccaagcc ggctgcgaag cctgcggcga aaccggcggc caagcctgcg    900
gcgaaacccg tagccgcgaa acctgccgca accaagcccg ccaccgctcc tgctgcgaag    960
cctgcggcga ctcccagcgc cccggcagcc gcctccagcg ctgcttcggc aacgcctgcc   1020
gcgggcagca acggcgccgc cccgaccagc gcctcctaa                          1059
```

<210> SEQ ID NO 41
<211> LENGTH: 1263
<212> TYPE: DNA
<213> ORGANISM: Pseudomonas aeruginosa

<400> SEQUENCE: 41

```
atgtggggtc ttacgatgaa gtttgcgagc ctgattctga tgcttctctt tgccacggtg     60
gcgagggctg aggattacta ctggaaaatt cagtcactgc ctgaacgctt ttcttcgccc    120
tcggcagctt gcgcggcgtg ggccaaagcc acgggacgcc ctggggagtt caccttcacc    180
gggtctatga aagcccgtga ccagacctcg ttttggtgcg agttcacgaa caacgaaacc    240
ggcaagactg ctgccgggta tggtcctgcc ggacgctatg gcgatagctg tcccgagggg    300
acggaatacg ataaggcgac cggggttttgt aagtcgcctc cgcaagaatg caaggaaggc    360
gaactgttcc cggccaaagg cccggactct cccgtggtta cctcgggagg ccgtaactat    420
gtcggtgacg gcgcgcccc gaccgcctgc tatcaaagct gtgagtatgg cggcaatccc    480
agcccggcca gttgctatct ggtcaaaggc tccaccacga ccggcttctg caattacatc    540
ctcaagggca ccggacagaa ttgcggtgcc gattcctaca ccttctccca gaccggcgat    600
tcgctgaacc cgcccgacac tccgaacacc gatccttccg acccgaacga ccccggctgc    660
ccgcccggct ggtcgtggtc gggaactacc tgcgtcaagg ccccgaccga tcccacggat    720
ccaaccgacc cgaccacgcc gggcagtgac ggcggcggcg atggcaatgg cggtggaaac    780
aataacggcg gcggcaatga cggcggcacc ggcaatggcg gcgacggcag cggggggaggg    840 gacggcaacg gcggggggcga tggtagcggc gacggtgacg gcagcggcac gggcggcgat    900
ggcaacggca cctgcgaccc ggcgaaagag aactgctcca ccggcccccga aggccccggc    960 ggcgaactca aggagcccac gcccggcacc tgggatgacg ccatcgccac ctgggaaaag   1020
aaggtcgagg acgccaagca agaactcaag accaaggtga aggccaacgt cgatcagatg   1080
aagggcgcct tcgacctcaa cctggcgaa ggcggcgggc aactgccctg cgagtccatg   1140
accatttggg gcaagtccta ctccctctgt atctccgact acgccggcca actctccagc   1200
ctgcgcgtgg cgctgctgct gatggccgcg ctgatcgccg ccctcattct gctgaaggac   1260
tga                                                                1263
```

<210> SEQ ID NO 42
<211> LENGTH: 1284
<212> TYPE: DNA
<213> ORGANISM: Pseudomonas aeruginosa

<400> SEQUENCE: 42

```
atggccgtcg cccctggtgt gttgttgccg ccgacgcctg atgtaaagcc caaggccgct     60
gcgccgaaga gccagcagaa aacgcctgag cccagtaacg acaagacttc cagcttctcc    120
gacatgtatg ccaaggagac cgcgaagaag cccgccgagc gcgccgacgg tcccgcgaag    180
ggttcgcggg acaagccacg ggacgccggc aaggacgccg ccgaagcgca gccgacggat    240
gccgtcaggc agccggccgt tgccgaagac ggcaagcctt gccggccgga cggccaggcc    300
```

```
aaggccgacg gcgaagataa agtcgaaacg ccggtcgatc cgctgcaatt gctcggcctc      360
ggcggtgccg taccgttgct cgacgagaat acccaggcga cttgctgcc accggccgtg      420 ccgacggcca gcagtgctcc ggccagcctt accgaagcca gcagcgaccc gaccctggtc      480
aagctcaacg gcgtgccggc ggtgaacatg gccctggagc agggcgccca ggacgccgcg      540
cagacggcga aaggcgggcc ggcgaagagc gccgatcccc gccaggcgaa cctcggcgat      600
gcccttgccg gcctgacctc ggattccttg accaaggccg tcgacggcaa ggcgctcgag      660
gcccagttgc agcagaccgc cgagccggcc gtcgccagcg ccgcctccga gagcctgctg      720
gagagcaagg cggaaccccg cggtgaacct ttcgcggcca agctcaacgg gctgacccag      780
gccatggcgc aacaggccct gaccaaccgt ccggtgaacg gcacggtgcc cggccagccg      840
gtggcgatgc agcagaacgg ctggagcgag gcggtggtgg accgggtgat gtggatgtcc      900
agccagaacc tgaagtcggc ggagatccag ctcgaccccg ccgagctggg acgcctggac      960
gtgcgcatcc acatgaccgc cgaccagacc caggtgacct tcgccagtcc caacgccggc     1020
gttcgcgacg ccctggaaag ccagatgcac cggctgcgcg acatgttcag ccagcagggc     1080
atgaaccagc tcgacgtgaa cgtctccgac cagtcgctgg cgcggggctg cagggccag      1140 cagcagggcg agggcggatc ggcgcgcgga cgcggcttgg ccggcgaggc ctcgggcgat     1200
gaggaaaccc tcgccggagt cagcgagatc cgcagccggc cgggtgcgtc ggcggcgcgc     1260
ggtctggtcg actactacgc ctga                                            1284

<210> SEQ ID NO 43
<211> LENGTH: 1287
<212> TYPE: DNA
<213> ORGANISM: Pseudomonas aeruginosa

<400> SEQUENCE: 43
atgctccgcc tccttcctct cctgctatcc ctcgcctgtc tcgctccggc cttcgccgac       60
gagcgcgccg acacccaacg ccagctggaa cagacgcaga aggacatcgg cgagctgaag      120
aagctgctgg acggcatcca gcaggaaaag agcggcgtgc agaagcagct gaagtccacc      180
gagaccgaga tgggcgacct ggaaaaacag atcaaggccc tgcaggacga gctggacaag      240
agcgaagccg agctgaaacg gctggatggg gagaaaaaaa aactccagga cgcgcgcatt      300
gagcagcagc gcctcctcgc catccaggcc cgcgcggcct accagagtgg acgcgaggaa      360
tacctgaagc tgctgctgaa ccaggaacac ccggaaaaat tcagccgcac cctcacctac      420
tacgactaca tcaacaaagc ccgtctcgaa cagctcgcca gcttcaacga acccctccgc      480
cagctggcca acgtcgagca ggacatctct gcgcagaaag ccgaacaact gagcaagcaa      540
ggcgagctgg acagccgccg cgaggcgctg cagcgacccc gcaaggagcg ccagcaagcc      600
ctggccaagc tgaacagcga ctaccgcgaa cgcgaccaga agctcaagtc cgccaacag       660 gaccaggccg agctggccaa ggtactgcgg accatcgagg aaaccctggc ccgccaggcc      720
cgcgaagccg ccgccgcggc ggagcgcgag cgccagcgcg cgctggccgc cgaacgcgag      780
cgtgcgcgcc agcagcaggc cgcccccgga cgagtcacca gcccgccgcg cgaacctgcg      840
ccgggccccg tggtctcaag cactggcgcg gtctacggcg gcgcgttcgg ctcggcccgc      900
ggcaagctgc cgtggccggt gaatggccgc gtcgtggcgc gcttcggcag ccagcgcggc      960
gacgatccgc gggcgaaatg ggacggcgta ctgatttcgg cgagcgcggg cagcaccgtc     1020
cgcgcggtgc acggcggacg cgtggtattc gccgactggt tgcgcggagc cggcctgttg     1080
gtcatcctcg accacggtgg cggctacctc agcctttatg gccataatca aagcctgctg     1140
```

```
aaagacgccg gcgacaccgt gaaggccgga gacccgatcg ccaccgttgg aaccagcggc    1200
ggccagagta gcccggccgt gtacttcgcc attcgccatc agggccgccc ggcggaccct    1260
actacctggt gccgcgcaca gggatag                                        1287

<210> SEQ ID NO 44
<211> LENGTH: 1707
<212> TYPE: DNA
<213> ORGANISM: Pseudomonas aeruginosa

<400> SEQUENCE: 44
atgcaaagac tgtcgcgtat cggccgcaac accctcgccg tctccgtttc caccttgctc      60
ctcagcgcct gcaaccaggg cgacgatgcg ccgaagcctg cggcagtcgc gccgcaaccg     120
gccgcaccga gcatggctgc actgagcatc ccgctatgcc tcaacggcca gtgcgcggtg     180
atcgaccagg acgccaagct gctcgtgccg ttcgacaacg actacgacaa tatcgtcgcc     240
agcgcctacc agggcaccct gatggcggcg cgcgaggagc gctggaacct gatccaggcg     300
aaggacggca aggtgttgcg cgacgatatc ggcgaagccc tgtcgctgct caccccaac      360 ctctatggct tcgtccgcga tggcaagtac ggcgtggtcg acggccaggg caaggaagtc     420
caggcgccgc gtttcgacga catctacccc aacagtgcca acgaattcat catctacgag     480
atcgatggca gcgcggcat cctcgatgcc aagggcaagc agctcaccga ggcgctctac      540
gacaccaccc tggtcaacgg cagcgtcgcc gaacacggtg gcttgatcag cgccgagcgt     600
ggcgaggaga gtggatcat caacctcgct accggcgaac agaaggccgt ggcctacgag      660
agcctgggcg acctccacga cggcgtgatg agcgccagcg tcatcggcaa gggctcccaa     720
ctggtggatg ccaagggcga cgtggtcggt gacggcaaga gctacgatta cctgggcacc     780
ccggccaacg gcctggtcgc gttccgcgag aagtacgaca gccctgtgg ctacctcgac       840 taccagggca aggtggcgat cgccgcccag ttcgccggtt gcggcgcctt cggcaagcag     900
ggcgggctgg cccagcagcg catggaagat ggctcgtcgg gcaagtacgg cctgatcgat     960
cgcagcggcg cctggaaggt gcagccgcag tacgattcgg ccgacagcgc cggcctcacc    1020
gcgcttggct acaccgtcga cgtgcccggc ctggctgccg tcggcgtgag caccggcctg    1080
ttcagcgccg acttcggcat cttcaacctc gacgaaggca gcgagtgggt gaagccgggt    1140
tatgcgcaga tcggcgcgct gggcaacgac ctgttcgtcg tggcgaagaa gggcgggccg    1200
cagaagaccg tcagcttcat gggttcggaa agccaggtgc cggtggtggg cctgatggac    1260
cgcagcggca agatgctgct ggagccggac gaactgatca gcatccagtc tgcttatgac    1320
ggtcgtttcc tggaaggtct cgacggtatg gacaacgctg cccacaccgt gttgctcgat    1380
cgccagggac gcacgctggt tccagcgctc tggcagaagc tggaggtgaa tccgcagcag    1440
ggttacatcc tgggctacga agtcagcggc actggcgacg aggcgacgga aaccttgcgc    1500
gcactgtacg acctgaacgg caagccgcgc ttcaccgtgg ccaccaccga ttgcggcgcc    1560
gaacagttgc tcgacggcaa tgcaaggcg atctggccgc aggacccgac cccgtattgc      1620
cagtcggacg acgagcagga cgacgaaggc gagccggagc aggagccggc gcccgtcgaa    1680
gagagcgagg aaaccagcga gagctga                                        1707

<210> SEQ ID NO 45
<211> LENGTH: 1740
<212> TYPE: DNA
<213> ORGANISM: Pseudomonas aeruginosa
```

<400> SEQUENCE: 45

```
atgcttcgcc ccgccaggtc tctctcgctc tgctccgccc tggtcatcct gctcgccgcc        60
tgtggcgagg gcgaaccgct gctcccggcc gatgcgcgcc tgcctgacgg cgcgcgctat       120
cgcggcgagc tggtggacgg cgcgcctgaa ggccagggcc ggctggacta cgacaacggc       180
gcctggtacg ccgccgcttc gagcatggc ctgctgcacg ccatggcac ctggcagggc         240
gccgacggca ccgctacag cggtggcttc gcggccggcc tgttcgacgg tcagggacgc        300
ctggcgatgg ccgatggcag cgtctaccag ggcggtttcc gccagggcct gttcgatggc       360
gaaggcagcc tggaacaaca gggcactcgc taccgcggcg gtttccgcaa gggcctgtac       420
agcggccagg gcacgctgga cggcagcgat ggcagccgct accagggcag cttccgccag       480
ggccgcctgg aaggcgaagg cagcttcagc gacagccagg gcaaccagta cgccggtacc       540
ttccgcgacg ggcaactgaa cggcaagggg cgctggagcg ggcccgatgg cgaccgctac       600
gtcggccagt tcaaggacaa ccagttccat ggccaggggc gctacgaaag cgccagcggc       660
gatgtctgga tcggccgctt cagcgaaggc gcgctgaacg ccccggcga gcttctcggc        720
gccgacggca ccgctaccg cggcggtttc cagttctggc gcttccatgg ccagggcctg        780
ctcgaacaac tggacggcac ccgctacgaa ggcggcttcg ccgccggcgc ctatgccggc       840
caaggcaccc tggaccgcgc cgacggcagc cgtgagcagg gactctgggc cgacggcaag       900
cgcatccgcg acgccgccgg caaggccctg cccgacactc tggaagtcgg cctgttggcc       960
cagggtcgcc tgctcgacga agaactgcgc aagatcccgg cctcgacgcc ggccagcgaa      1020
ctctatgccc tgagcctggg cggcgatggc cgccagggcc tgttcctgcg cgaggccgat      1080
tacgccggcg acctgctcgg ccagcgtttc gccgctcgtg gcgtgattcg cctggtcaac      1140
caccgcgacc acttcggcga ccgccgctg gctacccggg aaagcctgtc ccgcgccgtg       1200
cgcaccctgg ccgaacgcag cgggccggaa gacctggtct tcatctacct gaccagccac      1260
ggctccagcg accaccagtt ggccctggac atgcccggcc tgaacctcgg cgacctgccg      1320
gccgcggaac tggccgaact gctcgcgccg ctgcgccagc gcgacaaggt gctggtggta      1380
tcggcctgct acagcggggg cttcatcccg ccgctgaaag acgaacgtac cctgatcctg      1440
accgccgcgc gtgccgaccg ggtctcgttc ggctgttccg acgacgccga cttcacctat      1500
ttcgccgcg ccttgctggc caatgcgctg aaccgcaccg acgatctgtc caaagcgttc       1560
gaactggcga agaggaagt gcgtcaaagg gagaaggagg aaggtttcga agcttcggaa       1620
ccgcaagcct ggttaccgga acgcgtgctc cgcgcactgg cgacgctgcg ggggcagcaa      1680
gccgagcgcg cgctcgcgtc ccgggaagga aaaaccggcg agggcgcggc gggcaaatag      1740
```

<210> SEQ ID NO 46
<211> LENGTH: 1866
<212> TYPE: DNA
<213> ORGANISM: Pseudomonas aeruginosa

<400> SEQUENCE: 46

```
atgctgcaga acatcaggga taattcccag ggctggatcg ccaagaccat cattggcgtg        60
atcatcgttc tcctgtcgct gaccggcttc gacgcgatca tccgggccac cgaccactcc       120
aacgtggccg ccaaggtcaa cggcgacgat atcagtctca atgaagtcca acaggccgtg       180
gacatgcagc gtcgccagct gctgcaacgc ctgggcaagg atttcgatcc atccatgctg       240
gatgacaagc tgctcaagga agcggccctg aaggggctga tcgagcgtac cctgctgctc       300
caggccgcca aggacgacaa gttcgccttc tccgaccagg cgctggacca gttgatcctg       360
```

-continued

```
caaactcccg agttccaggt cgacggcaag ttcaacgcgg atcgcttcga ccaggtcatc      420
cgccagatga actacagccg catgcagttc cgccagatgc tcggccagga aatgctcatc      480
ggccagcttc gcgccggcct ggcgggcacc ggtttcgtca ccgacaacga attgcagtcc      540
ttcgctcgcc tcgagaagca gacccgcgac ttcgccaccc tggcgatcaa ggccgacgcc      600
tccaagagca gcgtgagcga cgacgaggtg aaggccttct acgaaggcca agagcgag      660 ttcatgactc ccgagcaggt ggtcgtcgaa tacgtggagc tgaagaagtc ctccttcttc      720
gaccaggtca aggtgaagca ggaagacctc gaggcgctgt accagaagga aatcgccaac      780
ctttccgagc agcgcgatgc cgcccacatc ctgatcgagg tgaacgacaa ggtcggcgac      840
gagcaggcca aggcgaagat cgacgagatc aaggctcgcc tggccaaggg cgaggatttc      900
gccgcgctgg ccaaggagtt ctcccaggat atcggctcgg ccgccaccgg cggcgacctg      960
ggctacgccg tcgcggcgt gtacgacccc gcgttcgagg aggcgctgta tgcgctgaag     1020
caaggtgagt atccgccccc ggtgaagact ccgtacggct accacctgat caagctgctg     1080
ggcgtgcagg cgccggaagt accgagcctg gaaagcctca gccgaagct cgaggacgaa     1140 ctgaagaaac agatggtcga gcagcgcttc gtcgaggcta ccaaggacct ggaaagctcc     1200
gcctacgaag ccgccgacct gagccagccg cgcaggaaa tgggcctgaa ggtccagacc     1260
agccagccgt tcggacgttc ggggggcgac ggcatcgctg ccaaccgcca gatcgtgcag     1320
accgcgttca gcgccgaggt gctggaagaa gccgccaaca gtggcgccat cgagctggat     1380
ccggacaccg tggtggtgct gcgggtcaag gaacacaaca agccgaagga gcaaccgctg     1440
gagcaggtcg cggcgaacat ccgcgagcgc ctggccgccg aaaaggccgc cgaggaggcg     1500
cagaagcgtg gcgaggccct gatcgcagag ctgcgtgaag gccgtacctc ttccgcagcg     1560
ggtgagtcgt ggaaagtggt cgaggcggcc tcccgcggcc acgaaggcgt cgatccgaaa     1620
ctgctccagg cggtgttccg catgcagcgt ccggaggcca aggacaagcc ttcgttctct     1680
ggcgtgaccc tggccaatgg cgattacgtg gtgatccgcc tgaatggcgt cagcgagccg     1740
gaggaggcta tctccgacga cgagaaggcc atgtaccgcc gcttcctggc ttcgcgcagc     1800
ggacaggcag acttcgccgc cttccgccgt cagttgcagg acaaggcgga agtcgagaaa     1860
tactga                                                                  1866
```

<210> SEQ ID NO 47
<211> LENGTH: 2067
<212> TYPE: DNA
<213> ORGANISM: Pseudomonas aeruginosa

<400> SEQUENCE: 47

```
atggatatga cgtcgctgat gcccctcctg ctgggagtgg gcctggtcgt tctgctggtc       60
gtgggcctgc tggccctgtt caaggccttc tacatcaagg tcccgcaagg caccgcgctg      120
atcgtcaacg acatgtcgtc gacgcccaag gtgcatttca ccggtgcgct ggtctatccg      180
gtgatccacc tgaaggagtt catgcgcatc tcgctgatca ccctggaggt cgaccggcgc      240
ggcaaggacg gcctgatctg ccgcgacaac atgcgcgcgg acatcaccgt tgccttctac      300
ctgcgggtca acgagaccca ggacgacgtg ctcaaggtgg ccaaggccat cggcgtcgac      360
cgtgcttccg accgttcggc ggtgaacgag ctgttcaatg ccaagttctc cgaggcgctg      420
aagaccgtcg gcaagcagtt cgacttcgtc cagctgttcg agaatcgcca ggacttccgt      480
gaccgcatca tcgaggtgat cggcaacgac ctgaacggct acgtcctgga agacgtcgcc      540
```

| | |
|---|---|
| atcgactacc tggagcagac cgcgaagaac tcgctggacc cgagcaacat ccttgatgcc | 600 |
| gagggcatcc gcaagatcac cgagctgacc gccacccaga acgtcatcac caacgaactg | 660 |
| gagcgcaacg aagagctggc gatcaagaag aagaacgtcg agacccgcga ggcggccctg | 720 |
| gccctggagc gccagcaggc tgacgccgag gcccggcaga agcgcgagat cgagaccatc | 780 |
| cgtgcccgcg aggaagcgga aaccgcgcgg gtcaaggaag aggagcggct gaaggccgag | 840 |
| caggcgcgga tccaggcgca gcaggaaatc gacgtgcgca ccgagaacca ccagcgcgag | 900 |
| gtcgaggtgg cgcagcagaa ccgccagcgc gcggtggtca tcgaggtgga aaggtcacc | 960 |
| cgcgccaagg acctggagat cgtcgcccgc gagcgtgagg tggagctgca aagatcgag | 1020 |
| aaggaaaagg cgctggaaga gcagcgcaag aacattgcca atgtgattcg cgagcgcgtc | 1080 |
| gcggtggaaa agaccgtggc caagaggag gagcggatca aggaggtgcg cgaggtttcc | 1140 |
| gaggccgagc gggtcaagca ggtgatactg ctgcaggccc aggcggaagc cgagcaggag | 1200 |
| ctggtacgcc aggtcaagca ggcggaagcc gacgaggccc gctccaagca caggcggtg | 1260 |
| gaaatcaaca ccatggcgca ggccgagctg gaggcggcgt cgaagcaggc cgaggcgaag | 1320 |
| aagcgtctgg ccgagggcat cgaggccgag cgcgcagcgc cgggcctggc cgatgcgcgg | 1380 |
| gtgctggaag tcaccgccgc ggcgaaggaa aaggatggct tggcagcggc gcgggtacgt | 1440 |
| gccgaacaac tgatcgccga agccaggggc gacgaagagc gcggcctggc cgacgcccgg | 1500 |
| gtgctcgagg cgcaggccgc ggccaaggag aaggacggcc tggccgaagc caaggtgctg | 1560 |
| gccgagaagc tcggcgccca ggcgcgcggc gaggagcagc tcggcgcggc caaggccaag | 1620 |
| gccaccaagg accagggcag cgcggaagcg gaagtactgc tgcagcgcct gaatgccgag | 1680 |
| gccgaggggc ttggcaagaa gttcggcgcc ctggatgccc tcagcgacag cgctcgccag | 1740 |
| cacgaagagt tccgcatgca gctggagaag agcttcgagg aggccatggc ggccatcgcc | 1800 |
| gcgaacaagg acatcgccaa ggaccaggcc gaggtgctcg ccaccgcgct gggcaaggcg | 1860 |
| aacatcgaga tcgtcggcgg cgagggcgac ttcttcaact ccttcgccaa gtcgctgtcg | 1920 |
| gtgggcaagg ccatcgaagg tgtggtcggc aagagcccgg tggtgcagga cgtcctcgcc | 1980 |
| cgcctgctca acggccgtgg cgcagccgct gcggtgatgc cggaacgcaa gagcggccac | 2040 |
| gagaacgagc cggcggcgga agtctga | 2067 |

<210> SEQ ID NO 48
<211> LENGTH: 2229
<212> TYPE: DNA
<213> ORGANISM: Pseudomonas aeruginosa

<400> SEQUENCE: 48

| | |
|---|---|
| atgtaccccc aattccgtcg cggccatctc gccgctgccg tccttttcgc ttcatcgagc | 60 |
| ctgctgggcg ggcaggccct ggccgaggac gagcgcctgg aagaactgga cgaacgcgcc | 120 |
| gaatcggtgg tccagctggg tgacgaggtg gtgctgggca ccgccgaaca ggagctcaag | 180 |
| caggcaccgg gggtatccat catcaccgcc gaggacatca ggaagcgccc gccggtgaac | 240 |
| gatctctccg agatcatccg caccatgccc ggggtcaacc tcaccggcaa cagttccagc | 300 |
| ggccagcgcg gcaacaaccg gcagatcgac atccgcggca tggggccgga aacaccctg | 360 |
| atcctggtcg acggcaaacc ggtcagctcg cgcaactcgg tgcgctacgg ctggcgcggc | 420 |
| gaacgcgaca cccgcggcga cagcaactgg gtgccgccgg aggaggtcga gcgcatcgag | 480 |
| gtcctccgtg ggcccgcggc ggcacgctac ggttccggcg cggcgggcgg ggtagtcaac | 540 |
| atcatcacca agcgcccgac cgatcgtttg cgtggttcca tgacggtgtt caccaacatt | 600 |

```
ccggaaagct ccaaggatgg cgccacgcgc cgcgccaact tcagccttag cgggccgctg      660
accgaagcct tgagcttccg cgcgtacggc agcgcgaaca agaccgattc ggacgatacc      720
gacatcaacc tcggacatac cgtcaacccg agccgtaccg tggccggacg cgaagggta       780 cgcaatcgcg atctcagcgg gatgctgtcg tggcaggtga cccccgacca ggtcgtcgat      840
ttcgaagcgg gcttcagccg acagggcaat atctatgccg gcgataccca gaacaacaac      900
ggcaccgcca atacccaggg actcgccgac gacggtgcgg agaccaaccg catgtatcgc      960
gagaactacg ccatcaccca acgggaccc tggtcgttcg gtacttccag gttcgtcgcc      1020
cagtacgact ccacccgcaa caaccgtctg gaggaggggc tggccggttc cgtcgagggg      1080
cagatcggcg ccgaccgttc gttcagcgcc agcaagctgg agaactatcg cctcagcggc      1140
gaactcaacc ttccgttgca tgcgttgttc gagcaggtgc tgacggtggg cgcggagtgg      1200
aacaaggaaa ccctcaacga cccgtcctcg ctcaagcagg gcttcgtggg aagcgatagc      1260
ttgccgggga ccccgcggc cggctcgcga agcccgaaaa gcaaggcgga gatccgcgcg      1320
ctgtacgtgg aagacaatat cgaactgcgc cccggcacca tgctcacccc cgggctgcgc      1380
ctggacgatc acagcgactt cggcctgaac tggagcccga gcctgaacgc ttcccaaacg      1440
ctcggcgaat acttcacggt caaggccggt atcgcacggg ccttcaaggc gcccaacctg      1500
taccagagca acccgaacta cctgctctat accgtggca acggttgccc gatccagact       1560
agcagcggcg gctgctacct ggtcggcaac gagaacctgg acgccgagac cagcgtaaac      1620
aaggaactgg gcatcgagtt ccggcgcgat ggctgggtcg ccgggctcac ctacttccgc      1680
aacgactaca gaacaagat cgtcgcgccg ctggatgtca tgggacagac cgggaccggc       1740
aacaacatcc tgcaatggag caacgcgaag aaagcagtgg tcgagggcct ggaaggcaac      1800
ctgctggtcc cctgcacga ggacctgagc tggagcacca acctgaccta tatgctgcaa       1860
tccaaggaca aggacaccgg caacccgctt tcggtgatcc ccgagtacac cctgaactcg      1920
accctggact ggcaggccag cgagcgtctt tccacccaac tgaccagcac catctacggc      1980
cgccaggagc cgccgaagca tggcaccagc cgcaacacgc cggtggtctc gcgaaaagag      2040
gtgggtacct atggcatctg gggcgtcagc gccggctaca ccttcagcga gaacctgagc      2100
gtacggggcg gggtaagcaa cctcttcgac aagcgcctgt accgccaggg caactccttc      2160
gacgccggcg cggcaaccta caacgagccg ggtcgcgcct actacgtttc gatgaccacc      2220
tcgttctga                                                              2229
```

<210> SEQ ID NO 49
<211> LENGTH: 2241
<212> TYPE: DNA
<213> ORGANISM: Pseudomonas aeruginosa

<400> SEQUENCE: 49

```
atgtcctcac gcgcccttcc cgccgttccc ttcctgctgc tgtccagttg cctgctcgcc       60
aacgccgtac acgccgccgg ccagggcgac ggctccgtca tcgagctggg cgagcagacc      120
gtggtcgcca ccgcccagga ggaaaccaag caggcgccgg gggtttccat catcaccgcc      180
gaggacatcg ccaagcgacc gccgagcaac gacctgtcgc agatcatccg gaccatgccg      240
ggggtcaacc tgaccggcaa cagctccagc ggccagcgtg aaacaaccg gcagatcgac       300 atccgcggca tgggcccgga gaacaccctg atcctggtcg acggcaagcc ggtcagctcg      360
cgcaactcgg tgcgctacgg ctggcgcggc gagcgcgaca gccgcggcga caccaactgg      420
```

```
gtgccggccg accaggtcga gcgcatcgaa gtgatccgcg gcccggcggc ggcgcgctac      480
ggcaacggcg cggcgggcgg cgtggtgaac atcatcacca agcaggccgg cgcggaaacc      540
cacggtaatc tcagcgtcta cagcaatttc ccgcaacaca aggccgaagg cgccagcgaa      600
cggatgagct tcggtctcaa cgggccgctc acggaaaacc tcagctaccg cgtctacggc      660
aacatcgcca agaccgactc ggacgactgg gacatcaacg ccggccacga atccaaccgt      720
accggcaagc aggccggcac cctccccgcc ggtcgcgaag gcgtgcgcaa caaggacatc      780
gacgggctgc tcagctggcg cctgacgccc gagcagaccc tcgagttcga ggccggcttc      840
agccgccagg gcaacatcta caccggcgac acgcagaaca ccaacagcaa caactacgtg      900
aagcagatgc tcggccacga gaccaaccgc atgtaccgcg agacctactc ggtcacccat      960
cgcggcgaat gggacttcgg cagctcgctg gcctacctgc agtacgagaa gacccgcaac     1020
agccggatca acgaaggcct ggccggcggc accgaaggta tcttcgaccc caacaacgcc     1080
ggcttctaca ccgccaccct gcgcgacctg accgcccacg gcgaggtcaa cctgccgctg     1140
cacctgggct acgagcagac cctgaccctc ggcagcgagt ggaccgagca gaagctcgac     1200
gaccccagct ccaacaccca gaacaccgag gaaggcggct cgatccccgg tctcgccgga     1260
aagaaccgca gcagcagttc ctcggcgcgg atcttctcgc tgttcgccga ggacaacatc     1320
gagctgatgc ccggcaccat gctcacccca ggcctgcgct gggaccacca cgacatcgtc     1380
ggcgacaact ggagcccatc gctgaacctg tcccacgcgc tcaccgagcg ggtcaccctg     1440
aaggccggta tcgcccgcgc ctacaaggcc cccaacctgt accagctgaa ccccgactac     1500
ctgctctaca gccgtggcca gggttgctac gggcaaagca ccagttgcta cctgcgcggc     1560
aacgacggcc tcaaggccga gaccagcgtg aacaaggaac tgggcatcga gtacagccac     1620
gacggcctgg tagcggggct gacctacttc cgcaacgact acaagaacaa gatcgaatcc     1680
ggcctgtcac cggtcgacca cgccagcggc ggcaagggcg actacgccaa cgcggcgatc     1740
taccagtggg agaacgtgcc caaggcgtgt gtcgagggcc tcgaaggcac cctgaccctg     1800
cccctggccg acggcctgaa gtggagcaac aacctcacct acatgctgca atcgaagaac     1860
aaggaaaccg gcgacgtgct ctcggtgacg ccgcgctaca ccctcaactc gatgctcgac     1920
tggcaggcca ccgacgacct ctcgctgcaa gccacggtca cctggtacgg caagcagaag     1980
ccgaagaaat acgactatca cggcgaccgt gtcaccggca cgccaacga ccagctctcg     2040
ccctacgcca tcgccggcct cggcggcacc tatcggttga gcaagaacct gagcctcggc     2100
gccgcgtcg acaacctgtt cgacaagcgc ctgttccgcg ccggcaatgc ccagggcgtg     2160
gtcggcatcg acggggccgg cgcggcgacc tacaacgagc ccggacggac cttctatacc     2220
agcctgaccg cgtcgttctg a                                               2241
```

<210> SEQ ID NO 50
<211> LENGTH: 2355
<212> TYPE: DNA
<213> ORGANISM: Pseudomonas aeruginosa

<400> SEQUENCE: 50

```
atgtccccgt cacgcgccct gtcgccgctc agccgcgccc tgctcctcgc ctgcctcggc       60
ggtcccgtcc tggtttccgc cggcagcgcc tgcgccgccg agatccgcac cgatgcccgc      120
cagtactacc gcctgcctgc cgagccgctg gagcaggcgc tgaaccacct aggccgccag      180
gccggcgtgc tgatcgcctt cagcccggaa cagaccgccg cgcgacgcag ccaggcgctg      240
gacggcgagt acaccctgga ggaagccctg gccgccctgc tcgtcggctc cggcctggag      300
```

```
gcgcgcgccc gcggcgacgg cgcctacacc ctggaagcgc tgccggtgga agacccggcc    360
aacctgcagg cgctcaccgt ggtcggcgac tggctggccg acgccagcgc cgccgacgtc    420
ttcgagcatc ccggtgcgcg cgacgtggtc cgccgcgagc agttccaggc ccaaggcgcg    480
gccagcaccc gcgaagtgct ggagcgcatt cccggggtca gcgcgccgct caacaacggc    540
accggcagcc acgacctggc attgaacttc ggcattcgcg gcctcaaccc gcgcctggcg    600
tcgcgctcga cggtgctgat ggacggcatc ccggtgccct cgcccccta cggccagcca    660 cagttgtcgc tggcgccggt gtccatcggc aacatggacg cggtggacgt ggtccgcggc    720
ggcggcgcgg tgcgctacgg gccgcagaac gtcggcggca tcgtcaactt cgtgacccgg    780
gcgatccccg aggacttcgc caccaagctc gacgtgcaca gcgaactcag ccccagctcc    840
agccaggacg gcctgaagac cacccacaac gtgctgatcg gcggcaccgg cgccaacggc    900
ctcggcggcg ccctgctcta ctccggcacc cgcggcggcg attggcgcga gcacagcgat    960
acgcggatcg acgacctgat cctcaagggc cgcttccagc ccagcgacga acacgttt     1020 tcggcgatga cccagtacta cgacggcgag gccgacatgc ccggcggcct cggcaccgcg    1080
gcctaccacg acgacccgta ccagtcgacc cgtccctacg acaagttctg gggccgccgt    1140
accctggcca gcgccagcta cgaatacacc cccaacgcca gccagaagct caacgtcacc    1200
ggcttcttca ccaagaccct gcgcagcggc tacctcgacc agggccgcaa cctcaccctg    1260
tcgccgcgcg aatactgggt gcgaggcctg gaaacccgct tcagccaggg cttcgagctg    1320
ggcgaaagtc gccacgaagt gggcatcggc caccgctacg tcaacgaagc cagccacgag    1380
ctgcgctact ggacccgcgc cgacagcggc cagctaccca gcaccggcag ccgcaacgac    1440
cgcgacaccc gcggcagcac cgaagccaac gcgttctaca tcgacgatcg catcgacatc    1500
ggcaactgga ccatcacccc cggcatccgc tacgagaaga tcgattccga acagaagaac    1560
ctgctgaaga acagcaagga cagcggccgc tacaacgcct cgctgccggc gctcaacgtg    1620
atctaccacc tcacgccgag ctggaacctc tacgccaaca ccgagggctc gttcggcacc    1680
gtgcagtaca gccagatggg caaggcggtg cgcagcggcg acatcgagcc ggagaaggcc    1740
cgcacctggg aactcggcag ccgctacgac gacggcatcc tgcgcgccga actgggcgcc    1800
ttcctgatca acttcgacaa ccagtacgag agcaaccagc agaccgacag cgtgaccgcc    1860
cgcggcaaga cccggcacaa gggcatcgag gcggcgatcg cctacgacct ggccgatctc    1920
gacccgctgc tctccggctt cgacgtctat gccagctacg cctacgtcga cgcgagcatt    1980
cgcgaagacg ggccgaacaa gggcaaccag gtgccgttct cctcgaagca caagggcacc    2040
cttggcgcca actaccgcac cggcgcctgg agctacaacc tcgacggcag cttccagacc    2100
agccagtacg ccgacaacgc caacaccgag agcgaaagcg ccgacggcag caccgggcgg    2160
atcgccggct ggatggtctg gagcgcgcgc ggcacctacg acttcggccc gcaactgaac    2220
gacctcaagc tcggcctggg ggtgaagaac ctgttcgatc gccgctacta cacccgctcg    2280
ttcgacgaca acaacaaggg cctctacgtc ggccagccgc gcaccctgta cgtacaggcc    2340
tcggtcggtt tctga                                                     2355
```

<210> SEQ ID NO 51
<211> LENGTH: 2556
<212> TYPE: DNA
<213> ORGANISM: Pseudomonas aeruginosa

<400> SEQUENCE: 51

```
atgaccttgc ctttcacccg cgccgcctgg cgcccgctgt gttccgccgc cgtgctcggc    60
gccgcgttgt gggccgccgg cgccagcgct gccgaacgac gcttcgacct gccggcgcag   120
ccgctggccg cctcgctgtc gcgcctggcg cagcaggcgc aggtccaggt gctgttcgac   180
gagtcgctcc tgcggggcct gcgcgctccg gcgctgagcg gcagctacgg ggtgcgcgag   240
gcgctggagc ggttgctggt cggttccgag ctggagctgg tggaggcggg cggcggctac   300
gtggtgcgcc ggcgccaggt cgacgcctac agcgacaacg cgctgcaact ggacgcgcag   360
accatcgtcg gcaacggtcg cgaagtggac gccagcaacg tcggccgttc gaccctgacc   420
cggcgggata tcgaacgcca gcaggcggac aacatcccca gcctgctgca gaccctgccc   480
ggagtgacca tgggcggctc gcccaagccg ggcggacaga ccaccaacat ctggggcctg   540
ggcgacgccg aggacgtgcc ctataccctg gacggcgcgc agaagagcgg cttcgagcgc   600
taccagcagg gcaccgtgtt catcgaaccg gaaatgatca gcgcatcga ggtggagaag    660
ggaccgcact cggtgttcac cggcaatggc ggcttcggcg caccgtgca catggagacc    720
aaggacgcgc cggacctgct gcgcgaaggc gcgacgtcg cgccatgct caagtacggc    780
tatcactcca acgaccagca gaagatctac tccggcgccg tgttcggtcg cagcgaagac   840
cgccgcgtcg atgccctgct ctatctcaac ggtcgcgacg gccgcgacat gaagctggcc   900
gacaacctgc cgctgtcgcc caccgactac ccgatcaacc ccaagcgcct gcccaacagc   960
gcccaggacg agaagaccgg cctgttcaag ctcaacctgc accccaccga ggagcacgac  1020
ctgggtttca cctacctgcg ctcgaaaagc tcgcgctgga cgccgttctc cgccagcagc  1080
tacccgaccc cgccgagcca gtggaccatc gaccgctacg gctacgagct gggcctgacc  1140
cgcctgctgg cccaccgcga taccaccgac accacctgga ccggcaagta caactaccat  1200
ccgctggaca cccctggat cgacctgcaa ctgagctatt ccgacgcccg caccgagcaa  1260
ctcgaccgtc gcgaggacac cgccttctac cagctcgcca ccggtggcaa gcggatgcgt  1320
accgagtacc aggacaaggt cctggaactg cgcaacacca gccgtttcga taccggagcg  1380
ctacagcacg agctgaccct gggcgcggcg ctgcacaagc acaagcgcga catcctcatg  1440
cacatgccgg gcaagaccta cgagacccccg cgctacaatt acggctggct gcaaccggca  1500
ttcatgccgg ccggcaagca ggacacgcag agcttctaca tccaggacgc gatcacctac  1560
ggcagcctga ccgtcacccc atcgatgcgc ttcgacagcg tgcgcaacga cggccaggcc  1620
aacctggcgc cgatctacga caatcccaag ctcggccatg actatcgcgc ccagacctac  1680
tccggctggt caccgcggct gtcggtgttc tggaccgcga cgccgaacct ggcgttcttc  1740
gccgactaca ccgagacctg gcgagcgccg gtgatcgacg agcagtacga agtgcagaac  1800
agttcgacca tcggtggcag cagccgcgac ctggacgccg agcgcatcca tgcgatccgt  1860
ggcggcagcg tgatcaacct gccggacctg ctggtcgccg gcgacagcct gcagatccgc  1920
accacgttgt tccagaaccg catcaaggac gagatattcc gcaccgcag cgtcggctgc  1980
cgccagcagt cgatcgacaa cggcagtatc ggtggtagct cggcgacat gctgccgctg  2040
agcaactacc gcaacttgcc gggcctgacc atcaagggct cgagatcga gcttctac    2100
gacagccagc ggctgttcgg cagcctgtcc tactcgtgga tgaccggcaa gcacgatggg  2160
gcctacagca atccctgggg accgaacgtg tgggcgcgcg catcccgcc gccgaagtgg  2220
gtggccatgc tcggcctgaa ggttccggaa tgggatgcca agctcggctg gcagggcgag  2280
ttcgtgcgca agaccgaccg cctgcccagc gatcgctaca cgccgggat gggtaccggt  2340
tccggcgata tctactggga tcacgcggcc aacgacagct acgacactca tcggctgttc  2400
```

```
gccgagtggg tcccggccaa gctgggcctg aaggacaccc gcatcgactt caccgtggac    2460
aacctgttca accgctccta tcgccagccg ctgggcggcg acctggtcta cagccaggga    2520
cgcaacgcca agatcagcgt cacccagttc ttctga                              2556
```

<210> SEQ ID NO 52
<211> LENGTH: 2643
<212> TYPE: DNA
<213> ORGANISM: Pseudomonas aeruginosa

<400> SEQUENCE: 52

```
atgcaccgat cgctccacac cgacgcgccg ctgggcgccg ccctgctgct ggccctgcag      60
ctcgctcccg gcagcgccgc cgcggcggag aacaggcgc ctgtcgaccc gcccacggtc     120
cagttgcaac gaatcgaggt gaccggcagc gcgatccgcc gggtcgatgc ggaaaccgcg    180
gtgccgatca gcgtcctgcg cgccgaggag ctgcgccaac agggcgtgac cagcaccgag    240
gaactgatcg gccggctttc cggcaaccag ggcgtataca actccagtcg ctcggtcggc    300
agcgccaccg gcggcgcctc gttcgccgac ctgcgcggaa tcggcgcgaa caagaccctg    360
gtgctgctca acgccggcg cctggcgaac aatgccatcg acggctccgc ggtggatctc    420
aacaccattc ccttcgccgc catcgaccgg gtcgaggtgc tgcgcgacgg cgcctccgcg    480
ctgtacggca ccgatgccat cggcggggtg atcaacttca tcacccgcaa gagcctgaac    540
gaaggccgct tcgacagcgg ctacgcctcc cccacccacg acggcggcgg caaccagcgc    600
aacgtcagcg ctagctgggg cttcggcgag ctggaggagg atcgcttcaa tgtcttcgcg    660
gtggccaact acgacaagca ggagcgcctc ggcgccaagg accgcggcta cacctacaac    720
taccagccgg gacgcggcct cgactacagc tccggcaccg ccttccccgg caactggagc    780
cagggcgcca acgccagcaa tccgctggcc gccggcggtt gcaagggcgc cgacctgatt    840
ccgcgcaacg gcatctgccg gcagagcctg tggcgctacc tcgacctggt gccggaaacc    900
gagaagacct cggtgttcag ccgcgccacc ggcaagctgg ccgacgagca aacgtcagc    960 ctggagtact tctggtcgcg cagcgacaac gctacccagg tcggcccagg accctcacc   1020 ggcctgcaga tcgatcccgg caccgccttc tatcccggca acggcatcac tcccggaccc   1080
ggcggcttcg tcctcgaccc gagccggccg gtggaggtca actggcgaca gagcgtgctc   1140
gggccgcgcc tgcaatcctc gcagaacacc ggccagcgcc tgctgctcgg cttcgacggc   1200
cagttcgccg gctgggacta cgatatcggc gcctcgtaca accagaacaa ggtggtcgac   1260
catatccaca gcggctacgt cgatgatcgc gccgccgccc tcggcatcgc caacgggacg   1320 ctgaaccgt tcgggccgca gaccgacgcc ggcctcgcct acctcggcag ccatgccctg    1380
agcggcgact ccgtacctc ggtcggccgc gtcaagggcc tggacgcccg cgccagccgg    1440
gagatcggcg actggttcgg cgccgggccg gcggccctgg cgctgggcgg cgagttccgc   1500
aaggaagcgt tccaccagga catccaggac ttcgccggca acgtgcagag cctcggcgtc   1560
gatcccgccg ccacggtcag cggcgagcgc aacctgaagg cgcagtacgc cgaactcaac   1620
gtgccggtgc tggacagcct ggaactcagc gcggcgatcc gccacgacaa gtacagcgac   1680
ttcggcagca ccagcaaccc gaaatattcg ttccgcttcc agccgttccg ccagttggtc   1740
ctgcgcggcg cctacagcga aggtttccgt gcgccgtcgc tgtacgaact gtacaacccg   1800
accttcacca cctataccag cgccaactac gacgacccgc gcctgtgcgc cggcggccag   1860
ccgagccagg gcggcatcgc caaccgcgac tgcgcccagc agttctacaa cgccaccggc   1920
```

| | |
|---|---:|
| ggcaataccg acctgcgacc ggaaaccgcg cgcaacgtta ccctgggcct ggtctaccag | 1980 |
| ccgctgcgcg acctttccgt cggcctggac ttctggtgga tcaggatcgc caaccagatc | 2040 |
| gccgagtttc ccgaagcggc gatcttcgcc gacccgcagg cctacgccgg acgcatcgtg | 2100 |
| cgcaaggccg acggctcgat cgatcacgtc gtcaccggac tggccaacct cggcaaagtg | 2160 |
| aagaccagcg gcgtcgacct gagcctcgat tatcgtttcc cggccagccg ctacgggcag | 2220 |
| ttcgggctcg acctgcaagg cacctacgtg tcccgctacg acttccagca gcagatcggc | 2280 |
| ggccagtacc tggacaacgt cggcgacttc cagggcgtcg gcgtgatcgc ccgctggaag | 2340 |
| cacgtcgcca cgccacctg gagccgcgac gcctggcagg ccaccctgag caaccgctac | 2400 |
| accagcggct acaacgacta cgaccgcgcc agccacggca aggtcggctc gtggaacctc | 2460 |
| tgggacctgg ccggcagcta ccgcctcagc cacgcgctgg ggctgaccct cggggtgaag | 2520 |
| aacctgttcg accgcgaacc gccgttcagc aaccagacct acaccttcca gagcggctac | 2580 |
| gacccgcgct acaccgatcc ctacgggcgc atcctgttcg gccgcctcag ctacagcttc | 2640 |
| tga | 2643 |

<210> SEQ ID NO 53
<211> LENGTH: 2760
<212> TYPE: DNA
<213> ORGANISM: Pseudomonas aeruginosa

<400> SEQUENCE: 53

| | |
|---|---:|
| atggttcggc ttcgtacact ggttcgggca atcgcggcgg cctcggtcct gacttccggc | 60 |
| atggcgcatg gattgggact gggggaaatc accctgaagt cggcgttgaa ccaaccgttg | 120 |
| gatgccgaga tcgagctgct cgaagttcgt gacctgggtt cgggcgaggt gatcccgagc | 180 |
| ctggcgtcgc cggaagagtt cagcaaggcg ggcgtcgatc gcctgtacta cctcaccgac | 240 |
| ctgaagttca cgccggtggt gaagcccaac ggcaagagcg tcattcgcgt gacctcgtcg | 300 |
| aagccggtgc aggagcccta cctgaacttc ctggtccagg tgctctggcc gaacggccgc | 360 |
| ctgctgcgcg agtacaccgt cctgctggat ccgccgctgt actccccgca ggccgcggca | 420 |
| agcgctccgc aagcgccggt cagcgcgccg cgcgcgaccg cgccccgcg agccccgcag | 480 |
| gctccggctc cggtgcgtac caccgcgccg gcaggcagcg acacctatcg caccgtttcc | 540 |
| aacgacacgc tctgggagat cgcccagcgc aaccgtaccg atcgcgtttc cgtaccccag | 600 |
| gcgatgctcg cgttccagga gctgaatccg ggcgccttcg tcgatggcaa catcaaccgg | 660 |
| ctgaagagcg gccaggtcct cgcattccc accgaacagc agatgctgga gcgctcgccg | 720 |
| cgcgaggcgc tgtcccaggt gcaggcgcag aaccagagct ggcgcggcag ccgcaatccg | 780 |
| gccgcgggca cgctggcgc caggcagttg gatgcgaccc agcgcaatgc cgccgggtcg | 840 |
| gcgccatcca aggtcgacgc cacggacaat ctgcgcctgg tgtctggcga gggcaaggcc | 900 |
| agcaagggtg ccgacaaggg cggaaagggc gacagcaagg cgatcgccga taccctggcg | 960 |
| gtgaccaagg aaagcctcga cagcactcgc gcgagaacg aagaactgca gagtcgcatg | 1020 |
| caggatctgc agagccagtt ggacaagctg cagaagttga tccagctgaa ggacgcccag | 1080 |
| ttggccaagc tgcaagggca gttgggcgcc gaaggccagg cgcagcccca gccgaacgca | 1140 |
| gccctgccgg atgcgtccca gcccaatgcg gccgcgcagg gcggctca gccgggact | 1200 |
| cctgctgcgc cagcgccgac tcctgctcca gccggagaag cacccgccgc tccggcgcag | 1260 |
| cctcggtgg cgccgccgcc cgcgccagct gccgagaagc tccggcacc tgccgttccg | 1320 |
| gcgcccgctc cggtacaggc ggcagagcag ccggcaccga gcttcctcga cgaactgctg | 1380 |

```
gccaacccgc tgtggttggc ggtgatcggc ggtagcgcac tgctggcgtt gctggtgctg    1440
ctgatgatcc tgtcgcggcg caatgcgcag aaagagaagg aagaagccca ggctttcgcc    1500
gcggataccg gcgaggaaca ggaggatgcg ctggacctgg aaaggacgg cttcgacgac     1560 ctgaccctcg acgagcctga ccgcaggtc gcagccgtcg ctccgcaggt cgagaagacc     1620
accgcgcaga cttccgatgc gctgggcgag gccgacatct atatcgccta cgggcgtttc    1680
aaccaggccg ccgaactgtt gcagaacgcc atctacgacg agccgcagcg caccgacctg    1740
cgcctcaagc tgatggaagt ctatgccgag atgggcgatc gcgaaggttt cgctcgccag    1800
gaaaacgagc tgcgcgaaat cggcggcgca cagccgcagg tcgagcagct caagtcgcgc    1860
tatccggcaa tggtcgcggt cgccgcggtt gccggcctgg ccggcgccaa gctggcgcag    1920
gacgagctgg atagcttcag ccttgacgac ctgtcgctcg acgacagcgg tcacgcggcc    1980
aagccggatg cggcaggaca ggatctcgac gacgccttcg acctgagcct ggacgacctg    2040
ggcggcgacg acgtgcaggc cgacctcaag tccgacagcg gggcgctgga cgacctgacc    2100
ctggacagcg atctggacct ggcggcctcg accccggcgg acaagcctgt cgacgatctc    2160
gacttcggcc tggatttcgc ggagttggca gagactccga ccaacccaa gcatgacgac    2220 ctgggcgatt tctccctgga tctcgacgcg ccggaagaca agctttcgga cgacgacttc    2280
ctgctttcgc tgaacgacga agtgcccgcc gcggcgcctg ccgacaacga attcaccctc    2340
gataccgagg ctgccgaaga gccggcgttg tccctgccgg acgacttcga cctgtcgctg    2400
gccgacgagc cgacggagcc ggccgctccg gagaagggcg aggacagttt cgccgcccag    2460
ttggacgagg tgagtgcgca gttggacgag ttggccagca accttgacga gccgaagagc    2520
gcgacgccga gtttctccgc cgaagatgca gcggtcgcct ccgccctgga cggagacgcc    2580
gacgatgact tcgacttcct ctccggtgcc gacgaagcgg cgaccaagct ggatctggct    2640
cgcgcctaca tcgacatggg cgatagcgaa ggcgcgcgcg atatcctcga cgaagtcctg    2700
gccgaaggta atgacagcca gcaggcggaa gcccgcgagt tgctggagcg cctggcctga    2760
```

<210> SEQ ID NO 54
<211> LENGTH: 2988
<212> TYPE: DNA
<213> ORGANISM: Pseudomonas aeruginosa

<400> SEQUENCE: 54

```
atgaccgacg accactcctt ccgccctcgc cccacctcgt tgtcagccgc cctgctgctg      60
ggcgcctgga tcgcacagcc ggccacggcc gcctatgtcg aagccggtcg gcccggcgat     120
ccggccagtt ggcgctccgc cgaataccag caggactggg gcctggaacg gatgcgggcc     180
gaccaggcct atgccgccgg catcgacggc cagggcgtga agatcggcga gatggactcc     240
ggtttcgacc cgagccatcc ggatactccc gcctcgcgct accagccggt gacggccagc     300
ggcacctatg tcgacggcac gccgttcagc gtcagcggcg cgatgaacgg caacaacgac     360
tcccacggta cccacgtcgg cggcacccte ggcgcctcgc gcgacggcgt cggcatgcac    420
ggggtggcct acgcggcaca ggtgtatgtc gccaacacca accagaacga cagcttcctg    480
ttcggcccga cgcccgaccc gaactatttc aaggccgcct accaggcgct ggccgacgcc    540
ggggtgcggg cgatcaacaa cagttgggc agccagccca aggacgtcag ctacgagacc    600
ctcgacggcc tgcacgccgc ctatgccag cactacgggc gctccaccig gctgacgcc      660 gccgccggcg tctcccgcca gggcgtgatc aacgtcttca gcgccggcaa cagcggctac    720
```

```
gccaacgcca gcgtgcgctc cgccctgccc tacttccagc cggacctgga aggccactgg      780
ctggccgtgt ccggcctcga ccagcagaac ggccagcgct acaaccgctg cggcatcgcc      840
aagtactggt gcatcaccac gcccggccgc ctgatcaaca gcaccatgcc cggcggcggc      900
tacgccaaca agtccggtac ctcgatggcc gcgccccacg ccaccggcgc gctggccctg      960
gtcatgcagc gctatccgta cctgaacaac gagcaggcgc tgcaggttct gctgaccacc     1020
gccacccagc tcgacggcac gccgaccggc gcccccaccg acaccgtcgg ctggggcgtg     1080
ccggatctcg gtcgggcgat gcatgggcct ggacaattgc tcggccgctt cgaggccaac     1140
ctcccggccg gcctgcgcga cgaatggagc aacccgattt ccgatagcgc cctgctccag     1200
cgccaggccg aggacgccgc cgagcacgcg gcctggcagc ggacgctgaa ggacaagggc     1260
tgggaaaacg gcttgccggc cggtgccagc cagcaggaac gcaccgacta tgccatcggc     1320
atggcccgcg accaggccgc cgcccagcgc cagtaccagg gcagcctggt caaggccggt     1380
gccggcagcc tggtcctgag cggcgacagc acctatcgcg ggccgaccct ggtcgatggc     1440
gggctgctca gcgtcgacgg ttcgctgctg tccgccgtcg aagtcaatgc cggcggcacc     1500
ctcggcggca gcggcaggat cggcggcctg ctggcgcgct ccggcggcac ggtggccgcg     1560
ggcaactcca tcggcaccct ggaggtcgcc ggggacctgc gcttcgaatc cggctcgacc     1620
tacgcggtgg agctttcgga aagcgccagc gaccggatcg tcgccagcgg caaggcgagc     1680
atcgcgggcg gcaacgtcac cctggccatg gaaaacagcc ccgacctgct cagccagtcc     1740
caggtcgaga gcctggtcgg ccgccgctac gacatcctcg acgccgccgg cggcatcgac     1800
gggcgcttcg acgcggtatt gccgaactac ctgttcctcg gcggcaccct ggactacgcg     1860
gccaacgcca tccgcctgga tatcggacgc aacggcacga ccctcgccag cgtcgcgcag     1920
acgcccaacc aggcggcggt cgctggggcc gtggaaacgc tcggcgccgg caacccggtc     1980
tacgaaagcc tgctcctgtc ggaaaacgcc gcaaccgccc aacgggcctt ccagcaattg     2040
tccggggaaa tctacccggc gctcgccggc ctgttgctca cgacagccg ctatctgcgc     2100 gacagcgtcg gcgaacgcct gcgccagacc agcgacggcg aggccggcgg ggaggctccc     2160
gaaggctggt tcaaggcgct cggctcctgg ggcaagagcg ccgatggcag ccacggtagc     2220
gaaggctacc ggcattcggt cggcggcttc ctgctcggcg tcgacagcca ggtcgccagc     2280
gacacgcgcc tcggcctggt ggccggctac agcaacagct cgctgaacat ggacagcagc     2340
ctgcaatcct ccgccagcat cgacagctac cacctcggcg cctacctcgg ccggcaattg     2400
cagcaatggc gcctgagcct cggcgcagcg cacgcctggc accgcgccga ggtcaagcgc     2460
gacctgcaat acggcgccgt ggccggcaag cagaaggcca agctcgacgc acagagcagc     2520
cagttgttcg ccgaggccgc ctacgcgctg ggttggcgca gcctggagct ggaacccttc     2580
gccgggctgg cctacgtgca cgtcgccagc gatgacttcc gcgaacgcgg tagcgccgcg     2640
gccctggagg gtggcgacga caacctggac gccgccttca ccaccctggg cctgcgcgcg     2700
aaacggcatt tcgagctgga tgccggacgc cgcctggcgc tctccggcac cctcggctgg     2760
cgccacaacc tgagcgacac cacccccgca acgccacctgg cgttcgccag cggcagccag     2820
ccattcagcg tggaaagcgt ggccctgtcc cgcgacgccg cgctgctcgg cgtcgacgcc     2880
agcctcgcgg tgaatcgcga agtgagcgtg cggctgggct acaacggcct gctgggcagc     2940
cgcgagaagg accatggcgt cggactggcc gtcgactggc gtttctga                 2988
```

<210> SEQ ID NO 55
<211> LENGTH: 3174

<212> TYPE: DNA
<213> ORGANISM: Pseudomonas aeruginosa

<400> SEQUENCE: 55

```
atgaaaagaa tgctgatcaa cgcgactcaa cccgaggagt tgcgtgttgc actggtcgac      60
ggccaacgcc tgttcgacct cgacatcgag tcgggcgccc gcgagcagaa gaaggccaac     120
atctacaaag gccgcatcac tcgcgtcgaa cccagcctcg aagccgcctt cgtcgacttc     180
ggcgccgaac gccacggctt cctcccctc aaagaaatct cccgcgaata cttcaagaaa      240
tcccccgaag gccggatcaa catcaaggaa gtcctgagcg aaggccagga agtcatcgtc     300
caggtcgaga aggaagagcg cggcaacaag gcgccgccc tgaccacctt catcagcctg      360
gccggccgtt acctggtgct gatgccgaac aacccgcgcg ccggcggcat ctcccgccgt     420
atcgaaggcg aagagcgcaa cgagctgcgc gaggccctga cggcctcaa cgcaccggcc      480
gacatgggcc tgatcgtgcg caccgccggc ctcggccgca gcaccgagga actgcagtgg     540
gacctcgact acctgctgca actgtggagc gcgatcaagg aagcgtccgg cgaacgtggc     600
gcgcccttcc tgatctacca ggaaagcaac gtcatcatcc gcgccatccg cgactacctg     660
cgccaggaca tcggcgaagt gctgatcgac agcatcgacg cccaggaaga agccctgaac     720
ttcatccgcc aggtgatgcc gcagtacgcc agcaaggtga agctgtacca ggacagcgtt     780
ccgctgttca atcgcttcca gatcgagagc cagatcgaga ccgctttcca gcgcgaagtg     840
aagctgccgt ccggcggctc catcgtcatc gacccgaccg aggccctggt ttccatcgac     900
atcaactcgg cgcgcgccac caagggcggc gacatcgagg aaaccgccct gcagaccaac     960
ctggaagcgg ccgaggaaat cgcccgccag ctgcgcctgc gtgacatcgg cggcctgatc    1020
gtcatcgact tcatcgacat gaccccggca aagaaccagc gcgccgtgga agagcgtgtc    1080
cgcgaagccc tcgaggccga ccgcgcgcgc gtccaggtcg gtcgcatctc gcgcttcggc    1140
ctgctggaaa tgtcccgcca gcgcctgcgt ccgtccctcg gcgagaccag cggcatcgtc    1200
tgcccgcgct gcaacggcca gggcatcatc gcgcgacgtcg agtcgctgtc gctggccatc    1260
ctgcgcctga tcgaggaaga agccctgaag gaccgcaccg cggaagtccg cgcccgcgtg    1320
cccttccagg tcgccgcctt cctgctcaac gagaagcgca acgccatcac caagatcgaa    1380
ctgcgtaccc gcgcgcgcat cttcatcctg ccggacgatc atctggaaac cccgcatttc    1440
gaagtccagc gtctgcgcga tgacagcccc gaactggttg ccggcagac cagctacgaa     1500
atggccaccg tcgagcacga agaagcccag ccggtcagct cgacccgcac cctggtccgc    1560
caggaagcag cagtcaagac cgtcgctccc cagcagcccg caccgcaaca caccgaagca    1620
ccggtcgagc cggccaagcc gatgcccgag ccgagcctgt tccagggcct ggtgaagtcc    1680
ctggtcggcc tgttcgcagg caaggatcaa cctgccgcca agcctgctga aaccagcaag    1740
ccggctgccg agcgccaaac ccgccaggac gagcgtcgca acggccgcca gcagaaccgc    1800
cgccgcgatg gccgcgatgg caatcgccgc gacgaagagc gcaaaccgcg cgaggagcgt    1860
gcagagcgtc aaccgcgcga agagcgcgcc gaacgcccga accgcgaaga gcgcagcgaa    1920
cgtcgccgcg aagagcgcgc cgagcgcccg gctcgcgagg agcgccagcc gcgcgaaggc    1980
cgtgaagagc gcgccgagcg gacacccgcg gaagagcgcg agccgcgcga aggccgcgaa    2040
ggtcgcgagg aacgcagcga acgccgccgc gaagagcgcg ccgaacgccc ggccccgcgaa   2100
gagcgccaac cccgcgaagg ccgtgaagaa cgcgccgagc gccggcccg cgaagagcgc    2160
cagccgcgcg aggatcgcca ggctcgcgac gccgcggccc tggaagccga ggcattgccg    2220
```

| | |
|---|---:|
| aacgacgaga gcctggagca ggacgagcag gacgataccg atggcgagcg cccgcgccgc | 2280 |
| cgctcccgcg gccagcgtcg tcgcagcaac cgccgcgaac gccagcgcga ggtcagcggc | 2340 |
| gagctggaag gcagcgaggc gaccgataac gccgccgcgc cgctgaacac cgtcgcagcc | 2400 |
| gccgccgctg ccggtatcgc tgtcgccagc gaagccgtag aagcaaacgt ggagcaagcc | 2460 |
| ccggccacta ccagcgaggc tgccagcgaa accacggcaa gcgatgagac cgacgcgtcg | 2520 |
| accagcgaag ccgtcgaaac ccagggcgcg gacagcgagg ccaataccgg cgaaaccgcc | 2580 |
| gacatcgaag cgccggtgac cgtcagcgtg gtccgggacg aagccgacca gagcaccctg | 2640 |
| ctggtcgcgc aagccactga agaagctccc ttcgccagcg aaagcgtgga aagccgcgaa | 2700 |
| gacgccgaga gcgccgtgca accggcaacg gaagcggccg aagaagttgc cgctccggtg | 2760 |
| cccgtcgaag tagcagcccc tagcgagccc gcagccaccg aggagccgac cccgccatc | 2820 |
| gcggcggtgc cggccaacgc gactggccgt gccctcaacg acccacggga aaaacgtcgc | 2880 |
| ctgcaacgcg aagccgagcg tctggcacgc gaagccgcag cagcagccga agcggcagct | 2940 |
| caggccgctc ccgccgtcga ggagatcccg gctgtagcga gcgaggaagc gtcggcccag | 3000 |
| gaggaacctg ctgcacccca ggctgaagaa atcacccagg ccgacgttcc gtcccaggcg | 3060 |
| gacgaagccc aggaagcggt acaggccgag cctgaagctt ccggcgaagg cgccgccgac | 3120 |
| acggagcacg cgaaaaagac cgaggaaagc gaaacctcgc gcccgcatgc ctga | 3174 |

<210> SEQ ID NO 56
<211> LENGTH: 3486
<212> TYPE: DNA
<213> ORGANISM: Pseudomonas aeruginosa

<400> SEQUENCE: 56

| | |
|---|---:|
| atgaaatcgg tactccacca gatcggcaag acctcgctgg cagccgcgct cagcggcgcc | 60 |
| gtcctgctct ccgcccagac cacccacgcc gccgccctgt cggtcagcca gcagccgctg | 120 |
| atgctgatcc agggcgtcgc cccgaacatg ctggtgactc tcgacgactc gggcagtatg | 180 |
| gcgttcgcct atgcgccaga cagcatttcc ggctatggaa actatacgtt cttcgcgtcg | 240 |
| aacagcttca acccgatgta cttcgatccg aacacgcaat acaagcttcc gaagaaactc | 300 |
| acactggtga acggacaggt acagatccag gattatccgg cccccaactt ctcctctgcc | 360 |
| tggcgcaatg gcttcactcg cagcgggagt atcaatctgt cgaacagcta caaggtcacc | 420 |
| atcgagtacg gcaggggata tgataaggag tcgacgataa aagccgacgc tgcctactac | 480 |
| tatgacttca cgggctcatc cagttgcaac cgcaccaatc aggcatgcta cacccgccgt | 540 |
| tatgtgagca cagagcaaag gcagaacttc gccaactggt attcgttcta ccgcacccgc | 600 |
| gcccttgcca ctcagaccgc cgccaacctg gcgttctaca gctgcctga aaacgctcgg | 660 |
| gtgagctggc aattgctgaa cgactcgaac tgcaaccaga tgggcagcgg ctccagctcc | 720 |
| ggcaactgtt tcagcaacta tctacgggac ttcaccggtc aacaccgggt gaacttcttc | 780 |
| aattggctgg aaaaactttc ggtcaatggt ggtacgccac tgcgccaggc gatgacccgg | 840 |
| gcaggcgagt ttctcaagaa gaccggcgtc aacggtccct atgcctatcg cccagggacc | 900 |
| cagaccgcgc ccgagtacag ttgccggggc agctatcata tcctgatgac cgacggtctc | 960 |
| tggaacaacg actcggccaa cgtaggcaat gccgacagca ccgctcgtaa cctccccgac | 1020 |
| gggaagagct atagcagcca gacaccctac agggacggta cgttcgatac cctggccgac | 1080 |
| caggccttcc attactgggc caccgatgcc cggccggata tcgacgacaa tatcaaaccg | 1140 |
| tacattccct acccggacca ggccaatccc tcggcggaat actggaatcc ccgcaacgat | 1200 |

```
ccggcaacct ggcaacacat ggtgacctac accctgggcc tgggcctgac caccagcctc   1260
accagtccga gatgggaagg ctccacctt tccggtggct acaacgatat cgtggctggc   1320
aacctgagct ggccccgcgc gtcgaacaac gactccaaca acgtctacga tctgtggcac   1380
gccgcagtga actcccgggg cgagttcttc agcgccgact cgccggacca actggtcgcg   1440
gccttccagg acatcctcaa ccgaatttcg ggcaaggacc tgccggcatc ccgccccgcc   1500
atcagctcgt ccctgcagga agacgacact ggcgacaagc tgacccgctt cgcctaccag   1560
accagcttcg ccagcgacaa gaactgggct ggcgacctga cccgctacag cctgaccacc   1620
caggacaagg ccaccgtgca gaccaagctg tggagcgcgc agagcatcct cgacgcgatg   1680
cccaacggtg gagctggccg caagatcatg atggccggat ccggtacctc gggcctcaag   1740
gagttcacct ggggcagcct cagcgccgac cagcagcggc agttgaaccg cgatccggac   1800
cgcaacgatg tcgccgacac caagggccag gaccgcgtgg ccttcctgcg cggcgatcgc   1860
cgcaaggaga acagcgacaa cttccgcacc cgcaactcga tcctcggcga tatcatcaac   1920
tcctcgccgg cgacggtcgg caaggcccag tacctgacct acctggccca gccgatcgag   1980
cccagcggta actactccac gttcgcagaa gcacagaaaa cccgtgcccc gcgggtatac   2040
gtcggcgcca acgacggcat gctgcacggt ttcgataccg acggtaacga gaccttcgcc   2100
ttcatcccaa gcgcggtctt cgagaagctc cacaagttga ccgcccgcgg ctaccagggc   2160
ggcgcccacc agttctacgt cgacggttcg ccggtggtcg ccgacgcctt cttcggcggc   2220
gcctggcata ccgtgctgat cggcagcctg cgcgccggcg gcaagggcct gttcgccctc   2280
gacgtgaccg atcccgccaa catcaagctg ctctgggaaa tcggcgtgga ccaggagccc   2340
gaccttggct acagcttccc caaacccacg gtcgcccggc tgcacaacgg caagtgggcc   2400
gtggtcaccg gaaacggtta ttccagcctg aacgacaagg ccgcgctgct gatcatcgac   2460
ctggagaccg gggccatcac ccgcaaactg gaagtcaccg gcaggaccgg cgtacccaac   2520
ggcctatcca gccctcgcct ggcagacaac aacagcgacg gcgtagccga ctacgcctac   2580
gccggcgacc tgcaaggcaa cctctggcgc ttcgacctga tcgccggcaa ggtcaaccag   2640
gacgatccgt tcagccgagc caacgacggc ccggcggtgg cctcgagctt cagggtgtct   2700
ttcggtggcc agccgctcta ttcggcagtc gactccgccg gcgcggcgca agcgatcacc   2760
gccgcgccct cgctggttcg ccatccgaca cgcaagggct acatcgtgat cttcggtacc   2820
ggcaagtatt tcgagaacgc cgacgcccgg gccgatacca ccgcgcccca gacgctctac   2880
ggcatctggg accagcaaac caagggcgaa ccgcgggca gcacacccg actgacgcgc   2940
ggcaacctgc agcagcagac cctggacctc caggccgact cgaccttcgc ctcgaccgct   3000
cgcaccattc gcatcgccag tcagaacccg gtcaactggc tgaacaatga cggcagcacc   3060
aagcagtccg gctggtatct ggacttcatg gtcaacggca ccctgaaggg cgagatgctg   3120
atcgaggaca tgatcgccat cggccaggtg gtgctgctgc aaaccatcac cccgaacgat   3180
gaccccctgtg ccgacggcgc cagcaactgg acctatggcc tcgatcccta taccggcggt   3240
cgcaccagct tcaccgtgtt cgacctggca cgccagggcg tcgtggactc gaaatccgac   3300
tacagctaca caagcagaa cgtcgcgta tccggtaccg agcagaaagg cctgggaggc   3360
ttgacgctga gcaccaacga acagggcaat ccggaagtct gctcctcggg cgaatgcctg   3420
accgtgaacc ccggtccgaa cacccgtggc cgccagaact ggcgccccat cgaaggaaag   3480
aactga                                                              3486
```

<210> SEQ ID NO 57
<211> LENGTH: 3636
<212> TYPE: DNA
<213> ORGANISM: Pseudomonas aeruginosa

<400> SEQUENCE: 57

| | | | | | |
|---|---|---|---|---|---|
| atgaagattc | tcgccatccg | cctgaagaac | ctcgcctccc | tcgctggcga | gcaggaaatc | 60 |
| gacttcaccc | gcgaaccgct | gtccagcgcc | ggcctgttcg | ccatcaccgg | tccgaccggc | 120 |
| gccggcaaga | gcaccgtgct | ggacgccctg | tgcctggccc | tgttcggcag | cacgccgcgg | 180 |
| ctggaaagca | cttcggccag | cagcaaggtt | cccgatggcc | ggaacgagct | gtccagcaac | 240 |
| gacgaacgca | acctgctgcg | ccgcggttgc | gccagcggct | acgccgaagt | ggatttcgtc | 300 |
| ggcatcgacg | gccaccgcta | tcgcccccgc | tgggaaaccc | ggcgctcccg | ggacaaggcg | 360 |
| gacggcgcct | tgcaaaagag | ccagcagagc | ctccaggacc | tggagaccca | gcaaatgctg | 420 |
| gcagcgaaca | gaaaagcga | gttccgcgaa | cagctggagc | agaagctcgg | cctcaatttc | 480 |
| gcccagttca | ctcgcgccgt | gctgctggcc | cagagcgaat | tcagcgcctt | cctcaaggcc | 540 |
| agcgacaacg | accgcggcgc | attgctggag | aaactcaccg | caccggcct | gtacagccaa | 600 |
| ttgagcaaag | ccgcctatca | gcgcgccagc | caggccgacag | agcagcgcaa | gcaactcgag | 660 |
| caacgcctgg | aaggcagcct | gcccctggcc | gagcaggccc | gggccgggct | cgaggcggcg | 720 |
| ctggaatccc | acgccaggc | gcgtctccag | gagcaacagg | cactgcaacg | tctggaaggc | 780 |
| cagcaacaat | ggttcaccga | ggagcagcgg | ctgctgcaat | cctgcgagca | cgcacaaggc | 840 |
| caactggccg | aggccaggca | ggcctgggac | gccctggcga | cggagcggga | aaccctgcaa | 900 |
| tggctggagc | gcctggctcc | ggttcgcgga | ctgatcgaac | gcctgaagca | actcgagcag | 960 |
| gaactccggc | actccgagca | gcagcagcgg | cagcgcaccg | agcagcaagc | cgcgggcacc | 1020 |
| gagcgcttgc | aaggattgca | ggcccgcttg | caggaggcgc | gcgagcgcca | ggcccaggcc | 1080 |
| gacaaccatc | tgcgtcaggc | ccaggcgccg | ttgcgcgagg | cttcagct | ggagagcgag | 1140 |
| gccaggcgcc | tggagcgaac | gctggccgag | cgacaggaac | tccatcggca | atcgaaccag | 1200 |
| cgccacgccc | agcaaagcga | cgccgctcgg | caactggata | tggagcagca | cgccatgtc | 1260 |
| gcggaacagg | cgcaactgca | ggcggcattg | cgcgacagcc | aggctctcgc | cgcgctcggc | 1320 |
| gacgcctggg | tgacccacca | gggccagctc | gccaccttcg | tgcaacgtcg | ccagcgcgcg | 1380 |
| ctcgaaagcc | aggcgcagct | ccccgagctg | aaaaatccc | tggcccacgc | cggggaaccg | 1440 |
| ctcgaacgct | tgcaggcgca | atggaccgcc | ctccatggca | gcgagccgga | cgacctggcg | 1500 |
| gcacgcctgg | tcgaattgcg | ccggcagacc | gatagcctgg | aacgacaaca | agcgctccac | 1560 |
| aaggaatggc | aacaggtcct | cgaccaacgc | gccggtctgg | ctcgacgcct | gggcgaactc | 1620 |
| gaccagcgta | tggtcgagca | ggagcaggca | ttgctcgacc | tgaaacgaca | aggcagccaa | 1680 |
| tgcgccgagg | aggtgaaggc | ggcggagcag | gccctgcagg | tcaccgcga | gttgctccag | 1740 |
| cgccaacgtc | tggcccgcag | cgccagcgtc | gagcaactgc | gcgccggcct | ggtggacggc | 1800 |
| gaggcctgcc | cggtctgcgg | cagccaggag | catccctatc | accattccga | gcaactgctc | 1860 |
| gccgccctcg | gtgaacacga | cgaccaggag | caggtccgcg | ccgagcagtc | cctcgagcgg | 1920 |
| ctgcgacaga | ccctggtcgg | tctgcgcgag | ggctattcca | gccagcggga | aagactcaac | 1980 |
| cagagtcgcc | aggagcagca | ggaactgact | ggccaactgg | ccgcgctcga | tcggcaactg | 2040 |
| gaccaatgga | cgctgccgga | agaactgcga | ctcctgcagc | cgtccgcgca | gttggagtgg | 2100 |
| ctggcacaac | gcctggacga | cctggcaggg | cagcgccagc | agtgccaacg | agacttcgac | 2160 |

```
cggctgatcg cccgccagcg ccagacccag caattgcagc aggaactgcg ggccgccgag      2220
acgatcctgc aacagcgcca gcaggcgctg acggaacaac ggcagcgcta cgaacatttg      2280
cagcagcagg tcgaggagga cagccagcaa ttgcgtccat tgctctccga cgagcactgg      2340
cagcgctggg aggcagatcc gctgcggact ttccaggcac tcggcgagtc catcgagcaa      2400
cgccggcagc aacaggcgcg gcttcagcag atcgaacagc gtctgcagga gctcaagcag      2460
cgctgcgatg aatcgagctg gcaactgaag caaagcgacg agcaacgcaa cgaagcccgt      2520
caggcagagg aaagggccca ggcggaactc gccgaactga acggacgcct cggcgctcac      2580
ctgggccagc acgcctgcgc ccaggactgg cagctatcgc tggagcacgc cgcgcaagcg      2640
gcgcagagcg ccgtcgagac gctccaggcg cccctggatt cgctgcgcga ggaacaactg      2700
cgactcgccg aagccctgga cacctgcag cagcaacggc agcgccaaca ggatgagttc      2760
cagcgccttc aggccgactg caggcctgg cgcgaacgcc aggacaacct cgacgacagc      2820
cgcctcgacg ccctgctcgg cctttccgag gaacaggcga cgcaatggcg ggagcaattg      2880
cagcgactgc aagaggagat cacccgccag cagacactgg aagcagagcg ccaggcgcaa      2940
ctgctccagc atcgccggca gcggccgaa accgaccgcg aggcgctgga agacaacctg      3000
cggcaacagc gcgaacgcct ggccgccagc gaacaggcct acctggagac ctacagccag      3060
ttgcaggccg acaaccagcg ccgcgagcag agccaggcgc tgcttgccga actggagcga      3120
gcccgcgccg agttccgcag atgggccgc ctgaacgaac tgatcggttc gtccagcggc      3180
gacaagttcc gccgcatcgc ccagggctac aacctcgacc tgctggtgca gcacagcaac      3240
gtgcagttgc gccagttggc gcggcgctac cgcctgcagc gcggcggcag cgaactgggc      3300
ctgctggtgg tggacaccga gatgggcgac gaactgcgct cggtgtattc gctctccggc      3360
ggcgagacct tcctgatttc cctggccctg gcgctcggcc tggcctcgat ggcatcgagc      3420
aagctgcgca tcgagtcgct gttcatcgac gaaggcttcg gcagcctcga cccggaatcc      3480
ctgcaactgg cgatggatgc cctggacaac ctgcaggccc agggacgcaa ggtggcggtg      3540
atttcccacg tccaggaaat gcacgaacgg atcccggtcc aggtgcgggt ccagcgcgag      3600
ggcaacggca tgagcagcct gaaggtggtc ggctga                              3636

<210> SEQ ID NO 58
<211> LENGTH: 7407
<212> TYPE: DNA
<213> ORGANISM: Pseudomonas aeruginosa

<400> SEQUENCE: 58
atgtcgatcc aggcgaaagt taccctatc gatcagagta tttcttctgc ggctgccgtc      60
gaggttccgg aaaacgggat actcaaactc tccagagca gtaatgtcgc gctcgatgtc      120
gcaccggagt cggtggcggg atactcgaag agcggttcgg acctgatcgt ccagctgaag      180
accggggaaa gcgtccggat cgccaacttc tatgcggaag ccagccttc agccaactg       240 ttcctggccg acaaggacaa gctggtggcg gtagatctgc cgccggtcgc tgccgacggg      300
ccgctgatgg ccggctacat cccgcaggaa agcctggccg gtttcgagtc gctgaccggc      360
gccggtgtgc tcggtggcat gagcgcaggg actgcgctgt ggtcggtgc ggcggccatc      420 ggcgccgggg tggcgatttc aacagcagc ggcggcggtg gcggcggcgg ttcttcggtg      480
cccccggaca ccactccgcc gaaggcgcc agcggcctga gatagcgcc tgacggcagc       540 agcatcagcg gccaggccga ggccggcgcg agcgtcggca tcgataccaa tggcgacggc      600
```

```
aagccggacc tcaccgtgat cgccgatgcc aacggcaatt tcaccgctcc gctgaacccg    660
ccgctgacca atggccagac ggtcaccgtg gtggtcaccg acccggctgg caacgccagc    720
ccgccggccc aggtcaccgc tccggacact accgccccgg cgccggctac cgacgtgcag    780
gtggcgccgg acggcagcag cgtcaccggc aaggccgaac ccggctcgac ggtgggcgtc    840
gataccgacg gcgacggcca gccggacacc accgtggtgg tcggccccgg cggcagcttc    900
gaggttccgc tgaacccgcc gctgaccaat ggcgagacgg tgacggtgat cgttaccgac    960
ccggccggca acaacagcac cccggtgacc gtcgaggcgc cggacaccac cgccccggcg   1020
ccggccaccg acgtgcaggt ggcgccggac ggcagcagcg tcaccggcaa cgcagagccg   1080
ggcgccaccg tcggtgtcga caccgatggc gacggccagc cggacaccac cgtggtggtc   1140
ggtcccggcg gcagcttcga ggttccgctg aacccgccgc tgaccaatgg cgagacggtg   1200
acggtgatcg ttaccgaccc ggccggcaac agcagccacc cggtcaccgc cgaagccccc   1260
gacttccccg acgcgcccca ggtcaatgcc agcaacggca cgtcctcag tggtacggcg   1320 gaagcgggcg tgaccatcgt gatcaccgac ggcaacggca atccgatcgg ccagaccagc   1380
gccgatgcca acggcaactg gagcttcacc cccggtagcc aactgccgga tggcaccgtg   1440
gtcaatgtgg tggccaggga cgccgccggc aacagcagcc cggcgacctc catcaccgtc   1500
gacggcgtgg cgccgaacgc gccggtggtc gagccgagca cggcagcga actcagcggg   1560 actgccgaac cgggcagcag cgtgaccctg accgacggca atggcaatcc gatcggccag   1620
accaccgccg atgccaacgg caactggtct ttcacgccgt ccaccccgtt gccggacggt   1680
accgtggtca acgtggtggc cagggatgcc gccggcaaca gcagtccgcc ggccagcgtt   1740
accgtggatg ccgtcgcgcc ggccacgccc accgtcgatc cgagcaacgg tacgaccctc   1800
agcggcaccg ccgagccggg cagtagcgtg accctgaccg acggcaacgg taacccgata   1860
gggcaggtca ccgccgacgg cagcggcaac tggaccttca ccccgagcac gccgttgccc   1920
aacggcacgg tggtcaacgc cacggctacc gacccgtccg gcaacgccag ttcgccggcc   1980
agcgtcaccg tggacgccgt ggcaccggcc acgccagtgg tcaacccgag caacggcacc   2040
acgctcagcg gcaccgccga gccgggcgcc accgtgaccc tgaccgatgg caacggcaat   2100
cccatcgggc aggtcaccgc cgatggcagc ggcaactgga gcttcactcc gaccacgccg   2160
ttgcccaacg gcaccgtggt caacgccacg gccaccgacg cctccggcaa caccagtgcg   2220
ggcagcagtg tcaccgtgga ctcggtagcc ccggccacgc cagtgatcaa ccccagcaac   2280
ggcaccacgc tcagcggcac cgccgagccg ggcagcagcg tgactctgac cgatggcaac   2340
ggcaacccga ttggccaggt caccgccgac ggcagcggca actggagctt caccccgtcc   2400
acgccgctgg cggatggaac cgtggtcaac gccacggcca ccgatccggc gggcaacacc   2460
agcggccagg gcagcaccac cgtcgatggc gtggcgccga ccacgccgac cgtcaacctg   2520
agcaacggca gcagcctcag cggcactgcg gaacccgggca gcggtgat cctcaccgac   2580 ggcaacggca atccgatcgc cgaggtcacc gccgacggca cgcaactg gacctacacc   2640 ccgtccacgc cgatcgccaa cggcaccgtg gtcaacgtgg tggcccagga cgccgccggc   2700
aatagcagcc cggcgccag cgtcaccgtg gactcgcagg ccccgcggc tccggtggtc   2760 aacccgagca acggcactac gctcagcggc accgccgagc cgggcgctac cgtgaccctg   2820
accgacggca acggcaaccc gattggccag gtcaccgccg acggcagcgg caactggagc   2880
ttcacaccgg gcacgccgct ggccaacggc accgtggtca acgccacggc cagcgacccg   2940
accggcaata ccagcgctcc ggccagcacc accgtggact cggtggcgcc ggccgcgccg   3000
```

```
gtggtcaatc cgagcaacgg cgcggagatc agcggcaccg ccgaaccggg cgccaccgtg    3060
accctgaccg atggcagcgg caatccgatc gggcaggtca ccgccgacgg cagcggcaac    3120
tggagcttca ccccgtccac gccgctggcg gatggaaccg tggtcaacgc caccgctacc    3180
gacccggccg gcaataccgg cggccagggc agcaccaccg tggacgccat cgcgccggcc    3240
acgccgaccg tcaacctgag caatggcagc agcctcagcg gcaccgccga gccgggcagc    3300
acggtgattc tcaccgacgg caacggcaat ccgatcgccg aggtcaccgc cgacggcagc    3360
ggcaactgga cctacacccc gtccacgccg atcgccaacg gtactgtggt caacgtggtg    3420
gcccaggacg cctccggtaa cagcagcccg ccggcgacgg tgaccgtcga ttccagcgcg    3480
ccgccggcgc cggtgatcaa cccgagcaac ggcgtcgtca tcagcggcac cgccgaggcc    3540
ggtgccacgg tgaccctcac cgatgccggc ggcaacccga tagggcaggt caccgccgac    3600
ggcagcggca actggagctt cacgccgggc accccgctgg ccaacggcac ggtgatcgtc    3660
gccacggcca ccgacccgac cggcaatacc ggcccgcagg ccgccaccac ggtggacgcg    3720
gtggcgccgc cggcgccggt gatcgatccg agcaacggca cgaccatcag cggcaccgcg    3780
gaggccgggc ccaaggtgat cctcaccgac ggcaacggca cccgatcgg cgaaaccacc    3840 gccgacggca gcggcaactg gagcttcacg cccggcacgc cgctggccaa cggcacggtg    3900
gtcaacgccg tggcccagga ccctgcgggc aataccggcc gcagggcag cactaccgtg    3960 gacgcggtgg cgccgaacac gcctgtggtc aatccgagca cggcaacct gctcaacggt    4020 accgccgagc cgggcagcac cgtgaccttg accgacggca acggcaaccc gatcggccag    4080
accaccgccg atggcagcgg caactggagc ttcacgcccg gctcgcaact gcccaacggc    4140
accgtggtca acgtgaccgc gagcgacgcc gccggcaata ccagccttcc cgctaccacg    4200
acggtggatt cctcgctgcc gtcgatcccg caggtggatc cgagcaacgg ttcggtgatc    4260
agcggcaccg cggacgccgg caacaccatc atcatcaccg atggcaacgg caacccgatt    4320
ggccaggtca ccgccgacgg cagcggcaac tggtccttca ctccaggcat cccgctgccg    4380
gatggcacgg tggtcaacgt ggtggcgcgc agcccaagca atgtcgacag tgcgccggcg    4440
gtgatcactg tggatggcgt ggccccggcg gcgccggtga tcgatccgag caacggcacc    4500
gagataagcg gtaccgcgga ggccggcgcg acggtgatcc tcaccgatgg cggcggcaac    4560
ccgatcggcc aggccaccgc cgacggcagc ggcaactgga cgttcacccc gagcaccccg    4620
ctggccaacg gcaccgtgat caacgccgtg gcccaggacc cggccggcaa taccagcggt    4680
ccggccagcg tcaccgtcga tgccatcgcc ccgccggcgc cggtgatcaa tccgagcaat    4740
ggagtcgtca tcagcggtac ggcggaagcc ggggccacgg tgatcctcac cgacggcaac    4800
ggcaacccga tcgccaggt caccgccgac ggcagcggca actggagctt cacgccggc    4860 acgccgctgg ccaacggctc ggtgatcaat gcgctggccc aggacgccgc cggcaacaac    4920
agcagtccca ccagcgccac cgtcgactcg ctggcgccag cagccccggt gatcgatccg    4980
agcaacggta gcgtgatcgc cggtaccgcc gaggctggtg ccacggtgat cctcaccgac    5040
ggcaacggca accgatcgg ccaggtcacc gccgatggca gcggcaactg gagcttcacg    5100
cccggcacgc cgctgtccaa tggcacggtg gtcaatgcgg tgcccagga cgctgccggc    5160 aacaccagcg gcccggtcag caccacggtg gacgcggtgg ccccggccac cccggtgatc    5220
gacccgagca cggtgtcga actcagcggc accgccgaac ccggcgtccg ggtgatcctc    5280
accgatggca atggcaatcc gatcggccag acccttgccg acggcagcgg caactggagc    5340
```

| | |
|---|---|
| ttcacgccgg gcacgccgct ggccaacggc acggtggtca atgccgtggc ccaggacccg | 5400 |
| gccggcaata ccagcggccc ggccagcacc acggtggaca cggtggctcc ggccacgccg | 5460 |
| gtgatcaatc ccagcaacgg cagcgtgatc accggcaccg ccgaggtcgg cgccaaggtg | 5520 |
| atcctcaccg atggcaacgg caacccgatc ggcgagacca ccgccgacgg cagtggtaac | 5580 |
| tggaccttca cccccggcac gccgctggcc aacggtacgg tgatcaacgc cgtcgccgag | 5640 |
| gacgccgcgg gcaacgccag cggtccggcc agcaccacgg tggactcggt ggcgccgtcc | 5700 |
| gctccgctgc tgagcatcag cgccgacggc gcgctgctga ccggcaccgc cgagccgaac | 5760 |
| agccaggtgc gcatcgtggt caacggcgac accgccaacc cgatcacggt caccgtcgac | 5820 |
| ggcgccggca acttcagcct gccgttcgcg ccgccgctga tcaccggcga gctgatcgcc | 5880 |
| ggggtcgccg tcgacgccgc cggcaacgtc agcgggccgg ccaccatcaa cgccccggac | 5940 |
| ctggcgccgc cgaccatcag cgtgccggaa gccgccgata cctggatcaa tgccgcggag | 6000 |
| atcggcgacg gtatccaggt cgatgtgacg gtccgtccga ccatgcaggt cggccaggtg | 6060 |
| gtcacggtca agttcgccgg gcagaacggc tacgaggccg aggtcagcca tccctcacc | 6120 |
| gccggcgaca tcgccgccgg caacctgacc ctgaccctga cgcctcccgg cggcatgggc | 6180 |
| ccgttcccgg agggtgcctc gaccgtcacc gccgacatca acggcggcac cgcgtcgacc | 6240 |
| ccggtgccgt tcaccatcga caccattccg ccggcgaccc cggtgctgtc cctggtcggc | 6300 |
| aacatcctga ccatctcggc ggagccaggg accgagttga cggtgaccgt cgacgtcggc | 6360 |
| ggggtgaccg ccaccgccac ggtgaccgcc gacaacagcg ggctggcgtc gctgaacctg | 6420 |
| ctcaccgacc tggacatcga cttcagttgg gaccagttgc tcaatgccca ggtgtcggtg | 6480 |
| gtcggacgcg acccggccgg caacccgagc aacacggcga gcatcggcgt cggcaccagc | 6540 |
| atcgagcaac cggtgaccat cggcaacttc ggcctcgacg tcagcctcaa cccgctgaac | 6600 |
| ccgcgtttcg gtttcagcgg aaccaccgag cctgactcca gcgtggtgat ccgggtcatc | 6660 |
| accccggcgt tgaacgtcga attgctgccg atccaggcgg attcgtccgg aaacttctcg | 6720 |
| ctgaacctgc tgagcccgac catcctcacc cagttggggc tgaacatcac cgacatcctc | 6780 |
| aacctcggct cgcagatctc gttcaacctg gtgtccaccg actccaatgg caacgacagc | 6840 |
| gccgcctacg ggatcaccct gaccccaac ggactgtcgc tcaatatcgg ccagatcgat | 6900 |
| gtcaacggta cttccggcga cgacgtgctg tccggcgcca acggcagttc ggagcacatc | 6960 |
| aacggcggcg acgcagcga cctgatcttc aacgtgggca ccggcgatca cgtggtggcc | 7020 |
| ggcaacggca cgacaccat ccagatcacc gcgaccgatt tcgtcagcat cgatggcggc | 7080 |
| gccgggttcg acaccctggt cctggccaac ggcatcgacc tcgactacaa cgccgtcggc | 7140 |
| gtcggcacgc tcagcaacct cgagcgcatc gacctcggca agggcgattc gggtagcgtg | 7200 |
| ctgaccctga ccgcggcgga ggtggatgcc atcaccgatg ccaacaacac gttgcagatc | 7260 |
| accggcgaga caacgacac cctgaacgtg gtgggcgcgg tgaataccgg taccacgcaa | 7320 |
| ctgatcaacg gcattaccta cgacgtctac accttcggca gtaccaccct gctgatcgag | 7380 |
| gacaacacgg tacaggtcgt ggtctga | 7407 |

<210> SEQ ID NO 59
<211> LENGTH: 10608
<212> TYPE: DNA
<213> ORGANISM: Pseudomonas aeruginosa

<400> SEQUENCE: 59

| | |
|---|---|
| atggacatcc gcagcccgct gaaccagtgc atcgccctgt ccctggccgg catcttgttc | 60 |

```
ctcaacccga tcgtcgccgc ggcggcgggg ctggcgctgg acaaggccgc cggcggcaac      120
accggcctgg gccaggcggg caacggcgtg cccatcgtca atatcgccac gcccaacgac      180
gccgggctgt cgaacaacca tttccgcgac tacaacgtcg gcgccaacgg gctgatcctc      240
aacaacgcta ccggcaagac ccagggtacc cagctcggcg ggatcatcct cggcaacccc      300
aacctcaagg gccaggcggc gcaggtgatc ctcaaccagg tcaccggcgg caaccgcagc      360
accctggccg gctacaccga ggtggccggg cagtcggcgc gggtgatcgt cgccaacccg      420
cacggcatca cctgccaggg ctgcggcttc atcaacacgc cgcgcgcgac cctcaccacc      480
ggcaagccga tcatggacgg ccagcgcctg gagcgcttcc aggtggacgg cggcgacatc      540
gtcgtcgaag gcgccgaact gaacgtcggc aacctcgaac agttcgacct gatcacccgc      600
agcgccaagc tcaacgccaa gctctacgcg aagaacctca acatcgtcac cggccgcaac      660
gacgtccagg ccgacagcct gcaggccacg ccgcgcgccg ccgatggcag cgagaagccg      720
cagctggcga tcgacagctc ggcgctgggc gggatgtacg ccggggcgat ccgcctggtc      780
ggcaccgagc agggcgtggg ggtgcggctg gccggcgaca tggccgccag cggcggcgac      840
atccgcatcg acgccagcgg caagctgagt ctggcccagg cctccagcca gggcgacctg      900
aagatcgcgg cccaggccgt ggagctgaat ggcaagacct acgccggcgg cagcgccgag      960
atccgcagcg cggaggaact ggtcaaccgg cagagcctgg cggcgcgcga acgcatcgtg     1020
ctggaggcgg cgcatatcga caacgccggg gtgatcgaag ccggcgtcga gccagacgag     1080
cgacgcaacg cgcgcggcga cctcgagctg cgcagcggca ccctgcgcaa cgccggcagc     1140
ctggtggcca gccgcgcgct ggaagcgaag gcgagccagg cgctggacaa ccagggcggc     1200
agcctgaagg gggcgaccgt ccgggtcgac gccgggcacc tggacaaccg tggcggcaag     1260
ctgctcgccg agggcgaact gcgggtcgag gcgagcagcc tggacaaccg ccaggacggc     1320
ctgttgcaga gccgggaccg cgccgtggtc aagacccgtg gcgatctcga caaccgtggc     1380
ggccaggtga tcggcctgaa cgatctggag gtcggcgcgg cgacgctcga caacggccag     1440
caaggcctgc tcggcagcca gcagtccacc cgcgtcagcg cccaggcgct ggtcaaccgg     1500
ggggacggcg aagtctccgg caagcgcgtc gaggctcgcg tcggtagcct cgacaatcgc     1560
ggcggcaagc tgatcggcga cgacctgctg gtggtcgcca gcggtgccat cgacaaccgc     1620
ctcggcttgt tctccgcagc caaccgcctc gacctgcggg cgcgcagcct ggacaacagc     1680
ggcaagggca cgctgagcag ccggggcggc ctggaggtca gcctcggcgg cctgctggac     1740
aaccgcgatg aaggcaacct gctcagccag ggcgcgcagc gcgtgacggt ggggcaactg     1800
gacaaccgcg ccggcggcct gctgtcgagc cgcagcgagt tgaacgtcca cggcgccagc     1860
ctggacaacc gtggcggcgt gctggtggcc gacgccggcc tgagcgccac gggaggcgcc     1920
ttcgacaacc gcgacggcgg cagcgccagc ggcaaggctg gcgtgcgcgt ggaggtcgcc     1980
agcctgcgca cgaccagggg tggcaagctg ctcagcgatg gccgcctgga cctcgcagcg     2040
aacgccgtcg gcaacgccgg agggcgtatc gccgccaagg gcgacctgca ggcgacgctt     2100
ggcagcctgg cccagcaagg tggcgaactg gtcagcgaaa agaccctgaa ggtcgcggcc     2160
gacacgctcg acaacagcca gtccgggctg atcgccgcga atggcggcat cgctatcgag     2220
gcgcggcagg tcgacaaccg cgccggcgag atttccagca cctcgaaggt cgccgtgaac     2280
gcccgcgagc aactggacaa ccgcggcggc aaggtcatcg cgacagcgg cctgcgcctc     2340 accgtgcagc gcctgctgaa ccaggccaag ggggtgctgg ccgggcgcga cggcctgagc     2400
```

```
ctggacggcg gcgaactgtt caacggcgac ggcggtcggc tcgacagcca gaacagcctg    2460
agcgtgagcc tcggcggcgt gctggacaac cagggcggcg cgctggtcag cgaaggcagc    2520
ctgacggcgc gcgccgcgcg cctggacaac cgtggcggga ccttctccag cgccggtgcg    2580
ctggcgctga ccagccaggc cgcgctggac aaccagggcg gcaggctgct cagcgatgcc    2640
ggcgtgacgc tgcagggcgc cagcctcgac aacagccgtt ccggcgtgat cagcgccaag    2700
ggcgcggtgg atatccgcac cggcgtactg acaacagcc gcaacggcgg catcggcagc    2760
aacgccggca tcaccctggt ggccgcccgg ctggacaacg ccagcaggg ccgggtcagc    2820 gccaagggcc tgctcgacgc caacctgaaa ggcctcgacc agcgcggagg cggcgtcctg    2880
atcagcgaaa ccggcgtcac cctcgacctc aatggcggca cgctggtcaa ccgcgacggc    2940
ggcctgatcg ccacgcccgg cgcgctgctg ctgcgccagc tcggcgcggt ggacaacggc    3000
gccggcgggg aaatctccag cgaccgcgcc ttcaccctcg ccgccgccag cctggacaac    3060
cgcggcgggc gcctgatcgg cgccgccaac ctgaccctgc gatcgcccca ggccctggac    3120
aacagcctgg ccggggtgat ctccggcgcc gccggcctgg acatcgcggc cgctcgcctg    3180
gacaacagcg ccaagggcac cctggccagc cgcgccggca tcgacctgcg cgtcgatggc    3240
gcgctggaca ccacgccga aggcaccgtc tccggcgccc gcctgacgct cgccagcgcc    3300
tcgctggaca cagcggcaa gggcctgctc tccggcaacg ccggcctgag cgtcgccact    3360
ggcgcgctga caacgccga gggtggccag ttgatcagcc agggcgtcct ggacgtcagc    3420
agcgccgacc tcgacaaccg tggcggcgcc ctcagtggca gcagtcgct gcgcctgagc    3480 gccgccaacc tggacaaccg tggcggcctg ctcaccagcg acggcgaact ggaactgacg    3540
gcagggcgcg tcgattccgc cgacggcggc gaaatctccg cccggggcga cctgcgcctg    3600
acggtcgagc gcctggtgca acgccagggc cggctggtcg gcgagcgcgg cgtcagtctc    3660
gacctgcggg gcggcgacct ggacaaccag ggcggcctga tcagtgcccg cggccgctg    3720 agcatcgagc ggctgagcgt cctcgacaac cgccagggcg gcgagatttc cagccagcag    3780
ggcttcgagc tgctggccag gcgcatcgac aacggccagc aggggcgcat catcagcgcc    3840
gggaaactgc gcctagacgc cgacgcgctg gcaacgccg gcgccggcct gctctccgga    3900
tggcagggcc tgacggtgac aggcgggagc ctggacaaca gcgccggcgg caccctttcg    3960
agcaaggacg gcgagctggc catcagcctc ggcggcgcgc tggacaacca ggccagggc    4020 gcgctggtca gcaagggcgc gcaacggatc gacgccgcca gcctggataa cgcccagggc    4080
attgtctccg gcgaaagcga cgtgaccctg agcatcgccg ggaagctgga caacggccag    4140
ggcggcctgg tctcggcgca gcgcgcgctg agcttcgagc gcgacgatac gctgctgaac    4200
aacgccggcg gccggatcaa cggcggcagc ctgctgctca gggcgccag cctggataac    4260 agcgacggcc agttgatcag ccagggccgg ctcgacgcca tcctcggcgg cgccctggtc    4320
aacaccggcg cggcgcgcct ggccagcggc ggcgacctgc tgctgcgcag cgccagcgtc    4380
gacaaccgcg gcggcaagct ggtcagccag gggctgctgg agatcagcgc cggcagcctc    4440
gacaacagcg cctccggcac cctcgccagc caggccggca tgagcctgcg cctgggcggc    4500
ggcgccctgc gcaaccagca ggacggcctg atcttcagcc aggccggcgc cctcgatgtg    4560
caggccggca gcctggacaa ccgccagggc acgctccagg cccagggcga caaccggctg    4620
cgtatcggcg gcgcgctgga caaccagggc ggccgcctgg acagccggc cggcaacctc    4680 gacctgcaga gcgcagcct cgacaacggc gccggcggc tgctcaacag cgccaagggt    4740
tggctgaagc tggtcaccgg gctgttcgac aacagcgccg gcgtcaccca ggcgcagtcg    4800
```

```
ctggagattc gcgccgggca aggcgtgcgc aaccagcagg gccacctctc ggcgctgggc    4860
ggcgacaacc gcatcgtcac cgccgacttc gacaaccagg gcggcggcct ctacgccagc    4920
ggcctgctca gcctcgacgg ccagcgcttc ctcaaccagg gcgcggcggc gggccagggc    4980
ggcaaggtcg gcgccgggcg catcgacttc agcctggccg gcgcgctggc caaccgcttc    5040
ggccagttgg aaagcgaaag cgagctgcac ctgcgcgccg ccgcgatcga caacagcggc    5100
ggcagcctgc gcgccctcgg ccgcagcggc agcacgcgt tggtcgctgg cggcctgaac     5160
aacgcctacg gcgtgctgga aagcgccaac caggacctcg acctgcaact gggcagcctg    5220
gccaacgccg gtgggcgcat cctccacacc ggcaatggca ccttcggcct ggattccggg    5280
caggtgatcc gcgccggcgg cgaactgacc accaatggcc tgctggacat ccgcgccagc    5340
gaatggacca acagcagcgt gctgcaagcc ggacgcctga acctggacat cggcaccttc    5400
cgccagacgg ccgagggcaa gctgttggcg gtgcagtcct tcactggccg cggcggcgac    5460
tggagcaacg acgcctgct ggccagcgac ggcagcttcc gcctcgacct gagcggcggc     5520
taccgtggca acggccgcgc caccagcctc ggcgacttcg ccctgaacgc cgccagcctc    5580
gacctcggca acgccgccag cctcgccggc ggtgccaatg tcacgctcgg cgccggcaac    5640
ctgctggtca accgtgggcg gatcaccgcc gccggcgacc tcgtggccag cgccgcgagc    5700
ctgaacaact acggcaccct gggcggcggc ggcaacctgc gattgaacgc gcccgccctg    5760
ctcaacgagc gcgggttgct gttcagtggc gccgacatga ccctgcgcgc cggcgacatc    5820
accaacctct acggggatgt gtacagcctc ggcaggctgg atatcgcccg cgacgatgcg    5880
ggcaaccgtg ccgccagcct gcgcaacctt ccggggtga tcgagagcgg caaggacttc      5940
agcctgcgtg ccagcctgat cgagaaccgt cgcgccgtgc tggaaagcaa gtcgggcctg    6000
tacaccgcga agatggagca gaccgcctgc atcgaaggcg tcaacgcggg cgactgcagc    6060
ggcaagcgca acgccatctg gaccatcacc cagcgcgaca agaccgaggt caccgccagc    6120
agcgccatgg ggcaactgct ggccggaggc gacttcgcca tcgacggcgg cacccctgaac    6180 aacctttcca gtctgatcgg cagcggcggc aacctcaccg ccaacctcga agtcctcgac    6240
aaccagggcc tggaaaccgg cgagctggaa accatccgcg tgctgcgtac cgctcgcggc    6300
ggcgatatcg gcggcatcga ccagaagtcg cgcaacttca ccaacctcta ctggtaccag    6360
agcgccaatt cgacccggc gcgcgcgggc gagatccccg ccgcgctcaa cgcgatcctc      6420
agcgactggt ccttcgagta cgaattcccg agcaaggggc cgaccccgat cagcagtggc    6480
gaccagtcct acgcagcggt gatccaggcc gccggcgacg tcacggtcaa tgccagcacg    6540
cgcatcgaca acggcgtcac ccgccccggc tacaccttcg tcggcagcgg ccgccaggtg    6600
ggcgacagcg cggtgggcgg cagcgggtt tcggtggtcg tgccgctgac ctcgcaactg     6660
ccgcccgacc tggcgcggcg ccaggtcaac ccggttaccc tgcccggctt cagcctgccc    6720
cagggtgaca acgcctgtt ccgtctcagc tcgcgctttg ccgaggacgg caatggcagc     6780
gccgcgctcg gtgccggcgc cgaccgcacc cagggcggta gcggcgtctc ggtcggccag    6840
caaggcgccg gcaacgccgc cggtacctgg cagggccagg gcgtgcgagt cgacggcctg    6900
gctggcgcgc ccaacgtcca gggtcagggc ggcagcacgc tcggcggtag cctgccgggc    6960
gtcgcccggg tccagggcgt gcccggcaac gccacgccga cgccagcca caagtacctg     7020 atcgagacca cccggcgct caccgaactg aagcagttcc tcaactcgga ctacctgctc      7080
agcggcctgg gcatgaaccc ggacgatagc aagaagcgtc tcggcgacgg tctctacgag    7140
```

```
cagcggctga tccgcgacgc ggtggtggcg cgcaccggcc agcgctacat cgacgggctg    7200
agcagcgacg aggcgctgtt ccgctacctg atggacaacg ccatcgctta caaggaccaa    7260
ctgcacctgc aactgggtgt gggcctgagc gcggagcaga tggcggcgct gacccacgac    7320
atcgtctggc tggaagaggt cgaggtgaac ggcgagaagg tcctcgcgcc ggtggtctac    7380
ctggcccagg cggagggtcg gctggcaccc aacggtgcgc tgatccaggg ccgcgacgtg    7440
aagctggtga gcgcggcgga cctgcataac gtcggcaccc tgcgcgcgcg gaacgacctc    7500
tcggcgacgg ccgacaacct cgacaacagc ggcctgatcg aggccggcaa gcgcctcgac    7560
ctgctcgccg cgcgactcga tccgcaaccg cagggcgggg tcatcgccgg gcgtgacgtg    7620
agcctcaccg cgctgaccgg cgacgtaatc aacgaacgca gcgtgacccg ctacgacagc    7680
gcgctcgacg gccgcacctg ggaacgcagc ttcgccgaca gcgccgcgcg ggtggaggcg    7740
gcgaacagcc tgaacgtcca ggccggacgc gacatcgcca acctcggcgg ggtgctgcag    7800
agccgcggcg acctcagcct cgacgccgga cgcgacgtca ccgtcgccgc cgtcgaggac    7860
cgccagggcc agacccgctg gagcacgtcg cggctccaga gcgtgaccca gctcggcgcc    7920
gaagtcagcg ccgggcggga cctgaacgtc agcgccggcc gcgacttgac ggcggtggcc    7980
agcaccctcg aagcgcgccg cgacatcgcc ctctccgccg ggcgcgacgt gaccctggcc    8040
gcggcggcga acgaggagca tgcctacagc aagaccagga aggtcaccta ccaggaagac    8100
aaggtcgccc agcaaggcac ccgcgtggac gccggcggcg acctggcgat caatgccgga    8160
caggacctgc gcctgatcgc gagccaggcc agcgccggcg acgaggccta cctggtggcc    8220
ggcgacaagc tggaactgct ggccgccaac gacagcaact actacctgta cgacaagaag    8280
aagaaaggcg acttcggccg caaggaaacc cggcgcgacg aagtcaccga cgtcaaggcg    8340
gtgggcagcc agatcagcag cggcggcgac ctcaccctgc tcagcggcgg cgaccagacc    8400
taccagggcg cgaagctgga atcgggcaac gacctggcca tcgtcagcgg cggcgcggtg    8460
accttcgagg cggtgaagga cctgcaccag gaaagccacg agaagagcaa gggcgacctg    8520
gcgtggaaca gcgccaaggg gaaagggcag accgatgaaa cgcttcggca gacccagatc    8580
gtggcccagg ggaatctggc gatcaaggcc gtggaagggc tgaagatcga cctcaagcat    8640
atcgaccaga agaccgtaag ccagaccatc gacgcgatgg tgcaggcgga tccgcaactg    8700
gcgtggctga aggaggccga gcagcgcggg gatgtggact ggcgcatggt gcaggaggtg    8760
cacgatagct ggaagtacag caactcgggc atggggccgg cgacgcagat cgctgtcgcc    8820
atcgcggcgg cagccatcgg tggcatggcg gcagcgggag cgctcagtgg tgcaggagtg    8880
ggtgccagta gcttcgccat gggcgcagga gttggtgcgg caggaagcct gtcgggcacg    8940
gcagcggtca gcctgatcaa caacaagggc gatctcggga aggtgctgaa agacagcttc    9000
agtagtgaca gtctgaagca gattgctatt gcgagcctga ccgggggggct gacggctgag    9060 tacttcgacg ggattcttca gaccaagact gatccgctta ctggaaaggt cacggtagac    9120
ctcagcagcc tatctggtgt tggtcgcttc gctgccaatc aggcgatgca gaacgctaca    9180
tccactgtac tgagccaggc cttgggccag ggcgggagcc tgaacgaggc gctgaagagc    9240
gcgctctaca cagtttcgc ggcggcaggt ttcaacttcg tcggcgatat cggccaggaa    9300
tacagcctga agcaggcga tccttcgatg gtgaccatgc acgccctgat gggtggcctg    9360
gcggcgcagg tcagcggtgg cgatttcgcc acgggcgccg cggcggctgg cgccaatgaa    9420
gcgctggtgg ccaagctaga ccaggccttc aagagcttga gccctgagaa ccgtgaagcc    9480
atggtcacta tggggtcgca attggttggt gttctggctg cggcggtacg cgatcctgat    9540
```

-continued

```
gtgacaggca aagctctgga aagcgctgct tgggtagcga agaactcgac gcaatacaac    9600
ttcctcaacc atcaggatgt ggccgatctg gataatgcct tgcagaaatg caagtcccag    9660
ggaaattgcc gtcaggtaga ggaagagttc aaggcgcgta gcgacgagaa ccggcggagg    9720
ttgaatggct gcgtggctgt gggtaattgc gcggagattc gtgcggagat cgatgcgggg    9780
tctacggctc tcaacgagct ggtggcccgg caggaaacag ctaatccggg aggaagtgac    9840
agcgatatag cctacggttt cctgatgggc cgaaatgttg tcgactggac gacggctggt    9900
cagttgcacc tggagcagac cgccaacctc tggtggaacg gtaatccaca gtggcagaag    9960
gaagtcggtg catacctaga ccagacgggg ttcaatccgt tcggaatcgg cgttccggca   10020
atgggcggtg ccgctggcaa ggtaacggcc aaggcgctca tgaatgcgct gaaggcggga   10080
gagttgccca aggagaggt ggccccagga aaggctaatc tgcctaccat tggggcgttg    10140
gcggatgctg aggcgggaat gccttatacc catccagtta agctcgccgc aaaagcgact   10200
gggacagcag ggaagattaa gattgaagcc ggcgcaatac ctgacgcaaa tgaagtacgt   10260
gcaggacaag ggttatctgg tcttgggtac gatgttacgc accaaaccac tgcgtcagct   10320
aaaggtattc aagggcagcg aactgcggac ttgcatgttg atggactcgg ttccattgat   10380
gtgtatacgc cgaagaatct tgatccgaca agatagttc gagcgataga aagaagtcg    10440
aatcaagccg gcggagtctt ggtgcaggcg gacttgccaa gcactgacat gtcgtccatt   10500
gctgctcgta tgtggggaa gactaacgcg cagagtataa aaactatatt tttccagaaa   10560
ccagacggat cattggtccg atttgatcga cctgctggag gaggctga               10608
```

<210> SEQ ID NO 60
<211> LENGTH: 16884
<212> TYPE: DNA
<213> ORGANISM: Pseudomonas aeruginosa

<400> SEQUENCE: 60

```
atggacatcc gcagcccgct gaaccagtgc atcgccctgt ccctggccgg catcctgttc      60
ctcaacccga tcgtcgccgc ggcggcgggg ctggcgctgg acaaggccgc cggcggcaac    120
accggcctgg gccaggcggg caacggcgtg cccatcgtca atatcgccac gcccaacggc    180
gccgggctgt cgaacaacca tttccgcgac tacaacgtcg cgccaacgg gctgatcctc     240
aacaacgcca ccggcaagac ccagggtacc cagctcggcg ggatcatcct cggcaacccc    300
aacctcaagg ccaggcggc gcaggtgatc ctcaaccagg tcaccggcgg caaccgcagc    360
accctggccg gctacaccga ggtggccggg cagtcggcgc gggtgatcgt cgccaacccg    420
cacggcatca cctgccaggg ctgcggcttc atcaacacgc cgcgcgcgac cctcaccacc    480
ggcaagccga tcatggacgg ccagcgcctg gagcgcttcc aggtggacgg cggcgacatc    540
gtcgtcgaag cgccgaact gaacgtcggc aacctcgaac agttcgacct gatcacccgc     600
agcgccaagc tcaacgccaa gctctacgcg aagaacctca acatcgtcac cggccgcaac    660
gacgtccagg ccgacagcct gcaggccacg ccgcgcgccg ccgatggcag cgagaagcca    720
caactggcga tcgacagctc ggcgctgggc gggatgtacg ccggggcgat ccgcctggtc    780
ggcaccgagc agggcgtggg ggtgaagctg ccggcgaca tggccgccag cggcggcgac    840
atccgcatcg acgccagcgg caagctgagc ctggcccagg cctccagcca gggcgaccta    900
aagatcgcgg cccaggccgt ggagctgaac ggcaagacct acgccggcgg cagcgccgag    960
attcgcagcg cggaggaact ggtcaaccgg cagagcctgg cggcgcgcga acgcatcgcg   1020
```

-continued

```
ctggaggcgg cgcatatcga caacgccggg gtgatcgaag ccggcgtcga gccagacgag    1080
cgacgcaacg cgcgtggcga cctcgagctg cgcagcggca ccctgcgcaa cgccggcagc    1140
ctggtggcca gccgcgcgct ggaagcgaag gcgagccagg cgctggacaa ccagggcggc    1200
agcctgaagg gggcgaccgt ccgggtcgac ggcggacacc tggacaaccg tggcggcaag    1260
ctgctcgccg agggcgaact gcgggtcgag gcgagcagcc tggacaaccg ccaggacggc    1320
ctgttgcaga gccgggaccg cgccgtggtc aagacccgtg gcgatctcga caaccgtggc    1380
ggccaggtcg tcggtctgaa cgaactgcag gtccaggctg ccgcactgga caatcgcagt    1440
gccggtctcc tttccagcaa gggagacatg gacatcgagt tcgctcgtct ggacaacagt    1500
gcgggcggca agctggtcag cgagcgccgt acgctcctga aggcggatcg gctcgataat    1560
cgcagcggtc gcattgtcgc cggccaggat ctcgacttga gctctcggtt gatcgacaac    1620
cgagcgggcg atatctccag cacgtcgagg gtggtggcga gcgctcgcga acagttggac    1680
aaccgcggtg gcaagatcgt cggtgacagt ggcctggaca tcacaacgcc acgcatgctc    1740
aaccaggaca agggggtact cgccagccgc gatgggctgc cctgagtgc tacgagttg     1800 ttcaacggcg cggggggcct gctgtccagc cagaagggta tcgacgtctc cctggccggt    1860
gcgttcgata accaggccgg cagcctggac agccggggct tcctgacggt gaagtcagcc    1920
tggctcgaca accagggcgg tacgctatcc agcgcagggg cattggcagt gaccagccag    1980
ggcgccctga caatcaggg cggcagactg gcgagcgacg ccggacttag cttgagcagc    2040
gccagcctcg acaacagcca ggccggtgcg atcagtggca agggggccgt ggagattcgt    2100
accggcaacc tgaacaacag ccggaaagcc agtatcggca gcgatgcggg actcaccctg    2160
gtcgccgctc gggtagacaa cagccaggcg ggccggatcg ccgccaaggg tgtgatcgat    2220
gcggatctcc aagggctgga ccagcatgac agggcaacc tggtcagcga taccggcatc    2280
acgctcgatc tgaacaaggg aagcctggtc aatcgcgctc aaggcctgat cgccacgcct    2340
ggcaccttgc tcctgcgcca actcggcgtg tggacaaca gcgtgggga aatctccagc     2400 gaccgcgcgt tcactcttgc cacctccgcg ttgaacaacc agggggacg cctgctcagc    2460 ggcggagccc tgaccttgcg tatcgcgcag gccctggaca acagcctcga ggggattgtc    2520
tccggtgctg gaggtctgga tatccaggca ttcgtcctgg acaaccgtag tggctccatc    2580
ggcagcaagg gcgccatcga tatcggtgtg acccgcctgg aaaacgacgc tggcacactg    2640
atcgctgaac gcggcctgaa gctggtagcc gatgaggcga acagttccaa ggggcgtatc    2700
gccgccaatg gtagcctgca tgccaaggtt ggcacgctga gccagaaggg aggagaactg    2760
accagtcagg actcgctgac tctcgacctg gcatcctaa caataacgc tggccgtatc     2820 gctggcaacc agggcgtgga catcacgcc cggcaggtgg acaacagcgt cggcgagatt    2880
gccagccagg gcgtggtggc gctgaacctc actgagcagc tggacaaccg tggcggcaag    2940
atcgtcggtg acagtggtct gggcatcacc gcgccgcacg tgctcaacca ggacaagggg    3000
gtactcgcca gccgcgatgg gctgcgcctg agtgctacgg agttgttcaa cggcgcgggg    3060
ggcctgctgt ccagccagaa gggtatcgac gtctccctgg ccggtgcgtt cgataaccag    3120 gccgcagcc tggacagccg gggcttcctg acggtgaagt cagcctggct cgacaaccag     3180
ggcggtacgc tatccagcgc aggggcattg gcagtgacca gccagggcgc cctgaacaat    3240
cagggcggca gactggcgag cgacgccgga cttagcttga gcagcgccag cctcgacaac    3300
agccaggccg gtgcgatcag tggcaagggg gccgtggaga ttcgtaccgg caacctgaac    3360
aacagccgga aagccagtat cggcagcgat gcgggactca ccctggtcgc cgctcgggta    3420
```

```
gacaacagcc aggcgggccg gatcgctgcc aagggtgcga tcgatgcggc tctccaaggg    3480
ttggaccagc atgacagggg cagcctggtc agcgataccg gcatcacgct cgatctgaac    3540
aagggaagcc tggtcaatcg cgctcaaggc ctgatcgcca cgcctggcac cttgcttctg    3600
cgccaactcg gcgtggtgga caacagcggt ggggaaatct ccagcgaccg cgcgttcact    3660
cttgccacct ccgcgttgaa caaccagggt ggacgcctgc tcagcggtgg agccctgacc    3720
ttgcgtatcg cgcaggccct ggacaacagc ctcgagggga ttgtctccgg cgccggaggt    3780
ctggatatcc aggcattcgt cctggacaac cgtagtggct ccatcggcag caagggcgcc    3840
atcgatatcg gtgtgacccg cctggaaaac gacgctggca cgctgatcgc cgaacgcggc    3900
ctgaagctgg cggccgatga ggcgaacaac tccaaggggc gtatcgtcgc caaggatgaa    3960
ctgcgtgcca aactcggtgc gctggtgcag aacggggggag agctgacgac tcagggcgcg    4020
ctggccctcg acgccgacaa agtcgacaac ggcgctggtc gcatcgccgg caaccgaggt    4080
gtggtcatcg atgcccggca ggtggacaac cgtgccggcg agattgccag ccagggcgtg    4140
gcgacgctga atctcactga gcaactggac aaccgtggcg gcaaagtcgt tgctgacagt    4200
ggtctgggca tcaccgcgcc acgcgtgctc aaccaggaca agggagtaat cgccagccgc    4260
gatgggctgc gcctgagtgg taccgaattg ttcaatggca atgccggact gctcagcagt    4320
cagagacata tagaggtcac tctggacggc gtgctggaca tcagggcaa gggcgcgctg    4380
ctcagcgacg gtaccctgac ggtgagcgcc gggcgcatac acaaccagga cgccactctg    4440
tccagcgccg gtgcgctgag actgagcagc caggaggcgg tggacaaccg tggcggcaag    4500
ttggtgacgg actccagcct gcgcctgacc agcgccagcc tggacaacag ccgatcaggg    4560
atcatcagtg ccaacgctgc ggcggagatc cataccgggg ttctgaacaa cagccagaaa    4620
ggcaatcttg gcagtaatga cgggctcggc ctgattgcta ctgaggtgga taacagccag    4680
gaaggtcgga tcactgccaa aggcatgatc gacgcaaata tcaagggact cgatcagcag    4740
ggcaaagggc ggctggtcag taatgccggc atcatactcg acctgaacga gggaaccctg    4800
gccaatggcg ctcagggcct gatcgccacg cctggaacct tgctcctgcg ccaactcggc    4860
atggtggaca acagcggcgg ggaaatttcc agcgaccgag ccttcacact caccacctcc    4920
gcgctgacca accagggtgg ccgcctgcgc agcggcggtg tactgacgtt gcgcatcgcc    4980
caggctctgg acaacagcct cgaaggtgtt ctctccggca ccggaggcct ggatatccgg    5040
gcgcttgccc tggacaaccg cagtggctcc atcggcagca agggcgccgt cgatatcgac    5100
gtgtcccgtt tggaaaacga tgacggcgac ctgcttagcg aaggtcgtct gaaactgact    5160
gccgagcgag cgaacagtgt caggggacgg atcgcggcca gggtgacct gcacgccagc    5220
gtgacagcct ttaaccaggc gggtggcgaa ttgagcagcg agggtgcgct gatgctcgag    5280
gccgatagcc tcgacaaccg cagcggcggt ctggtcagtg ctgatggcaa cctgaccgtt    5340
tccgcccgga ggatcgacaa ccgtgcgggc gaaatcgcca gcccgggcca ggtgacactg    5400
gacgtcgccg agcagttgga caaccgaggc ggcaaggcca tcggcgatag cggacttcgc    5460
ctcgccgcgc cacgggtact caaccaggac ggcggggtac tcgccagtcg tgatgggctg    5520
cgcctgaatg gcgccgaact gttcaatggc aacggcggc tgctcagcag ccagcaaagc    5580
atcgacgtca ttctggacgg cgtattgggc aatcaggcag gcagcttgag cagccaggga    5640
cgcctgagcg tgaagagcgg tcggctggac aaccagggcg gtgcagtctc cagcgccggg    5700
accttgtcgc tttccagcca gggtgcgttg aacaaccagg ggggcagggt ggtcaccgac    5760
```

```
gccggtgccg tcctgcgcag cgccagcctc gacaatagcc agggcggcat cgtcagcgcc    5820
aaggggcccg cggagatccg tactggcagc ctcaacaata gccagaaggg cggcataggc    5880
agcggtgccg ggctcgcgct ggtcgcggac ctggtggaca acagccagaa cggccggatc    5940
actgccaagg gtgcgatcga tgccaacctg aaggggctgg atcagcaggg cagcggcagg    6000
ctggtcagcg atacggccat cgcgctcgat ctgcgcgggg agaactggt caaccgtgct    6060
cagggcctga tcgccacgcc tggagccttg ctgctgcggc aactgggtgt cgtggacaac    6120
agtggcggtg gcgagatctc cagcgatcga agctttaccc tcgccgcgac cgcgctgagc    6180
aaccggggtg gccgcgtgat cagcggcgac tccctgaccc tgcgcatcgc ccaggcactg    6240
gacaacagcc tccaaggcgt tctttccgca gcggagggc tggatgtcgc tgcactcgtc    6300
ttcgacaacc atagcggcat cgttgctagc aagggcgata cacacatcgg ggtgaaccgc    6360
ctggagaacg aggcaggccg cgtggtcagc gaaggcgccc tggatctgac cgccaagcag    6420
gtgagcagcg ccaaggggcg cattgccgcg aagggcgatc tgcaggtcac ggttggcacc    6480
ctggagcagc agggtggaga actggccagt caggggacgt gactctcga cgccgatagc    6540
ctggataacc gcaatggcgg cctggtgagc gccgatggcg gggtcaccgc cgaggcacgc    6600
cagatcgata accgcggtgg ggaaatatcc agcgtggcca aggtggctct ggctgtccgg    6660
gaacaactgg acaaccgggg gggcaaggtg atcggcgaca gtgagctgag cctaaccgtg    6720
cagcgcctgc tgaaccaggc caagggtgtg ctcgccagtc gcgatggatt gcacctggac    6780
ggcgcggaac tgctcaatgg cgatggcggc ctgctcagca gccaacgcct ggtggatgta    6840
acgctcagtg gtgcattgga caaccagggg agcggtgcac tggtcagcga agagtcgctg    6900
acagtgaagg ccgaccaggt caataaccag gcggggactt tctccagtgc gggtagcctg    6960
ctcgttacca gccggggcga gttgaacaac caggtggcag ggttggtgac cgatgctgga    7020
gccaccctga acagcactgg cttcgacaac agccgtgcgg gcctggtcag tgcgaaaggg    7080
gctgtggcca ttcgtaccgg agccctgaac aacagtcaga agggatccat ggcggcaat    7140
acgggcgtca ccctggtcgc cgggttggtc gacaacggcc gggaaggacg gatcagcacc    7200
aagggtacgc tcgacgccaa cctgaaaggg ttgcttcagc agggggagg ctcgctggtc    7260
ggcgagcgcg gtgtcaccct cgacctcaac ggtggcaccc tggacaacca cgacctcggt    7320
ctggtttcaa cgcctggcgc gctcctgctg cgccaactcg gcatggtgga caacagcgtc    7380
ggcggagaga tatccagcga ccgtgctttt accctcgccg ccaacacact gaacaatcag    7440
ggcgggcggc tgatcagcag cgaagctttg accctgcgca tcgccaagac actggacaac    7500
agtctcaagg gcaggtcct ggcgaccgac ggactggcca tcgagtctca ggtcttggac    7560
aaccgtgcgg gaaccatcgg cagcaagggt gatgcccgta tcagcgtgac cagcctggac    7620
aacgccgaac aaggcagcct ggtgagtgaa ggccgcctgg agcttgtagc cgaccaggtg    7680
agcaacggca accaaggccg tatcgccgcc agaggcgtgc tggaggcggc ggtcggtacg    7740
ctgctccagc aaggcggcga actggtcagc caggggagcc tggaccttcg cgccgacacg    7800
ctcgacaaca gccagtccgg gctgatcgcc gcgaatggcg gcatcgctat cgaggcgcgg    7860
caggtcgaca accgcgccgg cgagatttcc agcacctcga aggtcgccgt gaacgcccgc    7920
gagcaactgg acaaccgcgg cggcaaggtc atcggcgaca gcggcctgcg cctcaccgtg    7980
cagcgcctgc tgaaccaggc caagggggtg ctggccgggc gcgacggcct gagcctggac    8040
ggcgcgaac tgttcaacgg cgacggcggt cggctcgaca gccagaacag cctgagcgtg    8100
agcctcggcg gcgtgctgga caaccagggc ggcgcgctgg tcagcgaagg cagcctgacg    8160
```

```
gcgcgcgccg cgcgcctgga caaccgtggc gggaccttct ccagcgccgg tgcgctggcg   8220
ctgaccagcc aggccgtgct ggacaaccag ggcggcaggc tgctcagcga tgccggtgtg   8280
acgctgaagg cgccagcct cgacaacagc cgttccggcg tgatcagcgc caagggagcg   8340
gtggatatcc gcaccggcgt actgacaac agccgcaacg gcggcatcgg cagcaacgcc   8400
ggcatcaccc tggtggccgc ccggctggac aacggccagc agggccgggt cagcgccaag   8460
ggcctgctcg acgccaacct gaaaggcctc gaccagcgcg gaggcggcgt tctggtcagc   8520
gaaaccggcg tcaccctcga cctcaatggc ggcacgctgg tcaaccgcga cggcggcttg   8580
atcgccacgc ccggcgcgct gctgctgcgc cagctcggcg cggtggacaa cggcgccggc   8640
ggggaaatct ccagcgaccg cgccttcacc ctcgccgccg ccagcctgga caaccgcggc   8700
gggcgcctga tcgcgccga cagcctgacc ctgcgcatcg cccaggccct ggacaacagc   8760
ctggccgggg tgatctccgg cgccgccggc ctggacatcg cggccgctcg cctggacaac   8820
agcgccaagg gcaccctggc cagtcgcgcc ggcatcgacc tgcgcgtcga cggcgcgctg   8880
gacaaccacg ccgaaggcac cgtctccggc gcccgcctga cgctcgccag cgcctcgctg   8940
gacaacagcg gcaagggcct gctctccggc aacgccggcc tgagcgtcgc cactggcgcg   9000
ctggacaacg ccgagggtgg ccagttgatc agccagggcg tcctggacgt cagcagcgcc   9060
gacctcgaca ccgtggcgg cgccctcagt ggcaagcagt cgctgcgcct gagcgccgcc   9120
aacctggaca ccgtggcgg cctgctcacc agcgacggcg aactggaact gacggcaggg   9180
cgcgtcgatt ccgccgacgg cggcgaaatc tccgcccggg gcgacctgcg cctgacggtc   9240
gagcgcctgg tgcaacgcca gggccggctg attggcgagc gcggcgtcag tctcgacctg   9300
cggggcggcg acctggacaa ccagggcggc ctgatcagtg cccgcggccc gctgagcatc   9360
gagcggctga acgtcctcga caaccgccag ggcggcgaga tttacagcca gcagggcttc   9420
gagctgctgg ccaggcgcat cgacaacggc cagcaggggc gcatcatcag cgccgggaaa   9480
ctgcgcctgg acgccgacgc gctgggcaac gccggcgccg gcctgctctc cggatggcag   9540
ggcctgacgg tgacaggcgg gagcctggac aacagcgccg gcggcaccct ttcgagcaag   9600
gacggcgagc tggccatcag cctcggcggc gcgctggaca accacggcca gggcgcgctg   9660
gtcagcaagg gcgcgcaacg gatcgacgcc gccagcctgg ataacgccca gggcatcgtc   9720
tccggcgaaa gcgacgtgac cctgagcatc gccgggaagc tggacaacgg ccagggcggc   9780
ctggtctcgg cgcagcgcgc gctgagcttc gagcgcgacg atacgctgct gaacaacgcc   9840
ggcggccgga tcaacggcgg cagcctgctg ctcaagggcg ccagcctgga taacagcgac   9900
ggccagttga tcagccaggg ccggctcgac gccatcctcg gcggcgccct ggtcaacgcc   9960
ggcgcggcgc gcctggccag cggcggcgac ctgctgctgc gcagcgccag cgtcgacaac  10020
cgcggcggca agctggtcag ccaggggctg ctggagatca gcgccggcag cctcgacaac  10080
agcgcctccg gcaccctcgc cagccaggcc gacatgagcc tgcgcctggg cggcggcgcc  10140
ctgcgcaacc agcaggacgg cctgatcttc agccaggccg gcgccctcga ggtgcaggcc  10200
ggcagcctgg acaaccgcca gggcacgctc caggcccagg gcgacaaccg gctgcgtatc  10260
ggtggcgcgc tggacaacca ggccggccgc ctggacagcc gggccggcaa cctcgacctg  10320
cagagcggca gcctcgacaa cggcgccggc ggcgtgctca acagcgccaa gggttggctg  10380
aagctggtca ccgggctgtt cgacaacagc gccggcgtca cccaggcgca gtcgctggag  10440
attcgcgccg ggcaaggcgt gcgcaaccag cagggccatc tctcggcgct gggcggcgac  10500
```

```
aaccgcatcg tcaccgccga cttcgacaac cagggcggcg gcctctacgc cagcggcctg    10560
ctcagcctcg acggccagcg cttcctcaac cagggcgcgg cggcgggcca gggcggcaag    10620
gtcggcgccg ggcgcatcga cttcagcctg gccggcgcgc tggccaaccg cttcggccag    10680
ttggaaagcg agagcgagct gcacctgcgc gccgccgcga tcgacaacag cggcggcagc    10740
ctgcgcgccc tcggccgcag cggcagcacg cggctggtcg ctggcgacct gaacaacgcc    10800
tacgccgtgc tggaaagcgc caaccaggac ctcgacctgc aactgggcag cctgccaaac    10860
gccggcgggc gcatcctcca cactggcaac ggcaccttcg gcctggattc cgggcaggtg    10920
atccgcgccg gcggcgaact gaccaccaat ggcctgctgg acatccgtgc cagcgaatgg    10980
accaacagca gcgtgctgca agccggacgc ctgaacctgg acatcggcac cttccgccag    11040
acggccgagg gcaagctgct ggcggtgcag tccttcactg gccgcggcgg cgactggagc    11100
aacgacggcc tgctggccag caacggcagc ttgcgactcg agctgagcgg cggctaccgt    11160
ggcaacggcc gcgccaccag cctcggcgac ttcgccctga cgccgccag cctcgacctc    11220 ggcaatgccg ccagcctcgc cggcggcgcc aatgtcacgc ttggcgccgg caacctgctg    11280
gtcaaccgtg ggcggatcac cgctgccggc gacctcgtgg ccagcgccgc gagcctgaac    11340
aactacggca ccctgggcgg cggcggcaac ctgcgattga acgcgcccgc cctgctcaac    11400
gagcgcgggt tgctgttcag tggcgccgac atgacccctgc gcgccggcga catcaccaac    11460
ctctacgggg atgtgtacag cctcggcagg ctggatatcg cccgcgacga tgcgggggc    11520 tgggcaaatc gcttggagaa catttccggg aatttagaga gcacaggtga tatgcgtttc    11580
tccgtgagtt cacttctcaa tagaagggaa actctagaga ttgaaggtga cttgcagaat    11640
agcgctattg gcgtccgctg tacggggtgt cagctttctg agaggtgggg aaaaactagg    11700
tcttcgagcg agcttgtctg gatcaggaaa tataagtcta cattgggaga ttcttctgcc    11760
gctgcttcaa ttacggctgg tcgagatctg cttgttgtag gtgcaagcct gcagaatatt    11820
gcttctaata taagtgctgt aagagacgcc acgctatctc tgagtaattt cgaaaacaaa    11880
ggttatgcgt tagggaata tgcggtcagg ggcgtttatt cgccgccgag taaatttggc    11940
gaagaattgc ttatgcgcat attggcgtat aacgctgtca acgatcccag ttatgggag    12000 ggatatgcga gcacaggggg gagacttccg aatattcatt atttcgacaa gaattttaat    12060
gaaaaagtct ctccgctgga ggtcattcat ggaaacggga aaatggtgg gccgggttgg    12120 cacctgtact tcggtaccttt agatgttgag tatccggaca cagatcgctg gaataaggct    12180
attggacgaa taccggcgcc gaattattca tcgaaaaaaa cggatgctat tccagatcta    12240
cttaagggat tggctcctct cgatgagttg acgattaaca aaggggcgaa ctcaacggtt    12300
ggtgctgtcg tgcaagctgg cggtcgtgta acggtgaatg ctgcggagag tttcaataat    12360
tctgtcctac agggatttca ggccgttcag gaaacccagt tacctcatca ggacatagct    12420
gtttcaagca cgacgagcgc cgtagtgact ctgaagagtc aactgccagc ggatttggca    12480
aggcaacaga tcaatcctct cacctgccg ggcttcagcc tgcctcaagg ccagaatggg    12540
ctcttccgcc tggcgtccca aggagcccag gtgaaccagg caagtggtgc tctgaaatcc    12600
gccagcgatc tcacccagag cggccatggc gtatctgtat ccgcacagac aggcagtggc    12660
gcaagtggct ggagtaccca ggcgcgtcgt gtcggcgatg atcgggtcac ctcgcttgcc    12720
ggttccgcct atcaaggccg ggtagctgag gctatcgatg cgctacgggc ttccgcgcca    12780
atctcgggcg acggggggaaa cactggccgt ttccaggccg gtgagcacca ggcgaccacg    12840
ggactgggtg gactcgtcga gggcaatgca tcgggtcaca gcggcaatgg cgtcatcctc    12900
```

```
gccgatctgc gcggtggtct accctcgttc tcaagccttc ccgcgtctga tcatgttcaa   12960
ggcacagtgc ccggtcacga tgggaatgga actattctcg ccaattggca gggtgcgcag   13020
gcgacggtcc aggcctcgcc ttcgacagtg cgtgtagagg gggtagtctc cagtccaggt   13080
ggcaatggca gcatccttgc cgatctgccg gctgaacagt cgtcggtgca ggcactgcct   13140
tcggccgtta gggctcaggg cagcctgcct cgcctcgaag agcggagcgc ccttcttgcc   13200
gagcctccgg ttgggcagcc ggcgttgcaa acctgccgt cggttgcgcg cgttgagggc    13260
gtgcccagca atgccacacc gagcaacagc cacaagtatc tgatcgagac caacccggcg   13320
ctcaccgagc tgaagcagtt cctcaactcg gactacctgc tcggtggtct gggtatcaat   13380
ccggacgata gcaagaagcg cctgggtgac ggtctatacg agcagcgcct ggtacgcgaa   13440
gcgatcgtcc agcgtacggg gcagcgcttc atcgccggat tgaacagcga cgaagcgatg   13500
ttccgctatc tgatggacaa cgccatcgcc agcaaggacg tattgggact gaccccctggc  13560 gtcaccctca gcgccgccca ggtggcgcg ctgacccacg atatcgtttg ctggaagaa     13620 gtcgaggtga atggcgaaaa ggtcctcgcc cccgtggtct acctggccca ggccgagggg   13680
cggttgggcc cgaacggcgc gctgatccag gggcgcgacg tgaacctgat caccggcggg   13740
gacctgagga acgccggtac cctgcgcgcg cagaacgacc tcagcgcgac agccggcaac   13800
atcgacaaca gcggcctgat cgaggccggc aaccgcctcg acctgctggc cagcggctcc   13860
atccgcaatg accagggcgg catcattgcc gggcgcgagg taagcctctc tgcccttacc   13920
ggagacgtca tcaatgaacg gacggtgacc cagcaccagt cctcctacag gggaaccggt   13980
accactgagg catttgccga tagcgccgcg cgtatcgagg ctgcgcagaa gctgaccgtt   14040
tcggcaggac gcgatgtagc caatattggc ggtgtcatcg acagcaaggg cgacctcgcc   14100
ttgcaaggcg gcagggatgt cctggtttcg gctgcgtag cggagcgggg ctggacggca    14160
ggaagccagg cataccagac ccagacgacc cagatgggcg ccgaggtcgt ggcgggcgc    14220 gatatcagcg tcagcgccgg acgcgatatc agcgtcgtgg gcagccgcat cgacgctcgt   14280
cgcgacgtga cattcgaggc gggtcgcgat gtgggcctgg tcgcggctgc caacgaagag   14340
catgcctatg gcaagaccaa gaaggtcact ttccaggacg acaagatcac ccagcaggcc   14400
actcgcgtgg acgctggcgg cgacctggcg atcaatgccg gacaggacct gcggctggtc   14460
gcgagccagg ccagcgccgg cgacgaagcc tacctggtgg ccggcgacaa gctggagctg   14520
ctggccgcga acgacagcag ttactacctc tacgacaaga gagcaaaagg cagcttcggt   14580
agcaagaaga cccggcgcga cgaaatcacc gatgtgacgg cagtgggcag ccaaatatcc   14640
agcggcggcg acctcaccct gctcagtggc ggcgaccaga cttaccaggg cgcgaagctg   14700
gaatcgggca acgacctggc catcgtcagc ggcggcgcg tgaccttcga ggcggtaaag    14760
gacctgcacc aggaaagcca cgagaagagc aagggcgacc tggcgtggca gtcgtcgaag   14820
ggcaagggcc agaccgacga aaccgtgcgc cagagccaga tcgtggccca ggggaatctg   14880
gcgatcaagg ccgtggaagg gctgaagatc gacctcaagc acatcgacca gaagaccgtg   14940
agccagacca tcgacgcgat ggtgcaggcg gatccgcaac tggcctggct gaagcagatg   15000
gagcagcgcg gcgatgtgga ttggcggcgc gtgcaggaac tgcatgacag ctggaagtac   15060
agcaactccg ggctgggcgt cggcgcgcag ttggcgatag cgatcgttgt ggcctacttc   15120
acggcgggtg cggcgagtgc ggcattggga tcgatggcgg gagtgggggc gggctcagga   15180
agcatgatgg ctgctgccgg tagcactgca atggtccagg ccggtacagc agtaggaaca   15240
```

```
gctgccgccg gctgggcgaa tgcagctgga actgccgtgg ctatgggcat ggccagcaat    15300
ggagcgatca gcaccatcaa caaccgggga aacctggggg atgtcgtcaa ggacgtgacc    15360
tccagcgatg cgctgagggg ctatgtagtc gctggcacga ctgcgggct  gactgccggc    15420 gtctacgaca aatggacctc gacccagacc ggcacctcga ccgctctacc gaacaccggg    15480
gccgtggcgc cgccgcagg  gttgggcacc tggcaaggcg tgggccagtt cacctcgaac    15540
cagttgctgc agaatggtac ttcggtgctg ttggaccggg cgctgggcgg caagggcagc    15600
ctgggcgatg cgttgcaaaa cagcctggca aatgcctttg cggcctacgg cttcaagctg    15660
attggcgaca ccacccatgg cgtgctggac gacggcagcc tcggcaagat cggcttgcac    15720
gccctgatgg gaggtctggc cgccgaagcg gtcggtggcg atttccgtac cggagccctg    15780
gctgcgggag tcaacgaggc gctggtggat agcctcgcca gcaatacgc  cagcctgccc    15840 atcgatgaca agaagggcct gctgatcatg agttcgcagt tgatcggcgt gctggcggct    15900
tcgacgcagg gcgatgcgga cgccaagagc ttgcagacgg gggcctgggt ggcggggaat    15960
gccacccaac acaactacct cagtcattgg caggaggaga agaagcggca ggaggtcgat    16020
ggctgcaaag acaaacagct ctgcaaaacc ggaatagaag ccaaatgggc aattatttcg    16080
gcccagcagg atgtcggtat cgtcgtaggt gttggaggag gcatcggtct ttcgacagct    16140
gaaaccgcag tgggtgttta tgagctggtc aagaactgga gggaaaccta tgcagctctg    16200
gagcagttgg ccacttcgcc agagttccgg cagcaatttg cgataacta  cctgaagggg    16260 ctggaggagc gcgccgcatt cttgacccag gcatacgagg atgccggctg caaggttcg    16320 gtcacagctg tgtcgagggg cggtaggttc gctgcggaac ttgttggcgt tctgacggca    16380
gtgaaaggtg gcgcgcagat aaccgccaag ctgccaacag cagccaagaa cctggtcaac    16440
gcgattgcga gtcacctgt  ttccggtagt atgagttcgc agcttgggc  agtggggat     16500 ttgggtcggc tgggtggggg aggtaaaggt tatgtcgata ttctttccca cgaagctaaa    16560
cagcatattt tgtatggcga caaacctggg agtggtggcc atttgtgcc  ggggcaggca    16620 gggaagacag ttttcccctca aaactggtcg gcagataaga tagttcacga ggttggtgat    16680
attgcgacgt cccctagtac caaatggtat gcccaaacag gaactggtgg ggtttataca    16740
agcaagggtg atcccgctaa atgggttgct tatgaggttc gtgatggagt tcgtatgcgc    16800
gttgtttatc agcccgctac aggaaaggtg atcacagcct tccccgacaa cgcacctatc    16860
ccaccttata agcccattaa atag                                           16884
```

```
<210> SEQ ID NO 61
<211> LENGTH: 201
<212> TYPE: RNA
<213> ORGANISM: Pseudomonas aeruginosa

<400> SEQUENCE: 61
augagucagg aaccccacgu acacggcccg aacugcaacc acgaccacga ucaucaucac     60
gaucauggcc auggucaugu ccauggucccg cacugcaacc acagccacga gccggugcgc    120
aauccgcuca aggccguagg ccgcaacgau cccugcccccu gcggcagcga aagaaauuc     180 aagaagugcc acggcgccug a                                                201

<210> SEQ ID NO 62
<211> LENGTH: 237
<212> TYPE: RNA
<213> ORGANISM: Pseudomonas aeruginosa

<400> SEQUENCE: 62
```

```
augaaaaaga ccguaacucu ugcccugcug cucgcugcca gccuuggccu ggccgcuugc    60
gacaagaaag aggaagacaa ggcagcggcc ccggcagcuc cggcuaccga acccagccg    120 agcgcuccgg cuacucccc ugccgagccc agcgccccgg cgccgucgag cgacacuccg    180
gcaaccccgc agacuccggc accgacuccg gagcaaccgc aacagaaacca gcaauaa    237
```

```
<210> SEQ ID NO 63
<211> LENGTH: 315
<212> TYPE: RNA
<213> ORGANISM: Pseudomonas aeruginosa

<400> SEQUENCE: 63
augaaaaaga uuucccucgc uucuuccguc gucggcgcug cucugcucgg cguagccagu    60
gucggcgcgc augccgcgca gaaucccuuc gccgugcagg agcugagcag cggcuacagc    120
guggcugccg ccgagaaagc caaggaaggu uccugcggcg aggccaagug cggugccgac    180
aagggcaagc gcgaagccuc caaggccggu caugaaggca gcugcggugc ggaucgcaag    240
gccaaggaag guuccugcgg uggcgagaag aaggccggcg aaggcaacug cggcgccgac    300
aagaagaagu cguaa                                                      315
```

```
<210> SEQ ID NO 64
<211> LENGTH: 468
<212> TYPE: RNA
<213> ORGANISM: Pseudomonas aeruginosa

<400> SEQUENCE: 64
auguccguuu ucgauucgcg ucaaaagacu uccgccagcc ugcucggugc cguacuggug    60
gggggaaugc ugcucggcgg uucggcguuc gccgucgagc cgcugggcca ggggcugcaa    120
guggcggcgg cgagcgccgg cgaaggcaag ugcgagaag caagugugg uagcggcggc    180 uccgcgaaga cccggccaa ggccggcgcc gagggcaagu gcggggaggg caagugcggc    240
gacgccuccu uugcccgaac cgacaccgau cacgauggca aggucgcgcg cgccgaguuc    300
cucgcggugg ccaaggaccg ugccggugag uucgacagca ucgauagcga ccaugacggc    360
uucauuuccg aagccgaggc cuacgaacac cugcgcaaga ccuacgaggc caacggcaag    420
ccgaugcccg ccgggcuguu cagcaagcug gagcaaggcc agcacuga                468
```

```
<210> SEQ ID NO 65
<211> LENGTH: 540
<212> TYPE: RNA
<213> ORGANISM: Pseudomonas aeruginosa

<400> SEQUENCE: 65
augcguuccc uguccuccuc ucuccuccuc ucgcuggcgu ccaccugcga ggccgcugcg    60
guauuccgcu gcgaagacgc cagcggccau gucagcuuca cccaacucgg uugccccgcc    120
gggcaggccg gcgagaccgu cguggcggac aacccgccgc cggagggcag gagcgucacg    180
ccgauggccg agacgaagac gaaaaaggcg uccaucggcc ggaaaagcgu gccgcucgcg    240
gugaucggag aaagagaaga ucgcucgggc agacgccugg acgagaagga acgccgcaag    300
gcgaucgugg agcagcggau aauggcggga augacccgcu ccgaugugga gcgggcgcug    360
ggcaagccgg accggggucag cgggaacaau gcggagggugc guuaucagua caaggccgac    420
aagcgacggg gagcgagaag cgugagcuuc gaucaggagg gaugugugaa gggaagagaa    480
gguaccgggu ggagcgaguc gaucccggga gcuaaggccg ggccgvccuc auaccgauga    540
```

<210> SEQ ID NO 66
<211> LENGTH: 915
<212> TYPE: RNA
<213> ORGANISM: Pseudomonas aeruginosa

<400> SEQUENCE: 66

| | | | | | |
|---|---|---|---|---|---|
| augagccaac | ccagcgaaaa | ccguuugauc | accucggcgc | gcuacgcgcu | cugccuguug | 60 |
| accgccagcg | gcgugcugcu | cagcggcugc | gccagcagcg | gcgucggcuc | ggucgcccag | 120 |
| accacccgcg | cggaauacua | cccguccugc | uacgagccgg | ugucgcaccu | gcgcagcacc | 180 |
| gauaacgcag | ugcgcaauuc | ggccaucacc | ggcgccauua | ccggcggccu | ccugggcggc | 240 |
| cuggccggcg | gccuggccag | cgacgagaac | cgcgccgca | augccgcccu | cgcugccgca | 300 |
| ggcggcgccc | uggccggcgg | cgcggcgggc | uacuacaugg | agaagcagaa | gcagaucagc | 360 |
| gaugaccgcg | cgcgcaucgg | cuccuacggu | accgacgucg | accgcagcac | cgucgagauc | 420 |
| aaccguagcg | uggccuacgc | caagucggcg | caaagcugcu | accagagcca | guucaaggcu | 480 |
| cugcucgacg | gucgcaagaa | caagucgauc | aacgaagccg | aagggcgcaa | gccuggcc | 540 |
| gagaucguca | gcggccugca | ggagaccaac | gccuugcugg | ucgccgccaa | cggccgugcc | 600 |
| ggcgagaaca | ucagcaacua | cacccaggcc | uacgagaaag | accugcagca | ggucggcgua | 660 |
| ccgcgcgccg | aggugaccaa | ggucgccgag | gccgagaacc | gccagcac | uacgaaaggc | 720 |
| ggcagcaagc | ccaagaccgg | cagcaauccc | aaggugccga | aggaagcggu | cgccaccgag | 780 |
| cagaccaucc | gcaaggccca | ggacgcgcaa | agcgaaggca | caaggugcc | cucccagggc | 840 |
| cagggcauga | uccgggaagu | cugcaacagc | ccggacaugg | gcgacugggc | gccgccgagc | 900 |
| ugcgccaagg | ccuga | | | | | 915 |

<210> SEQ ID NO 67
<211> LENGTH: 930
<212> TYPE: RNA
<213> ORGANISM: Pseudomonas aeruginosa

<400> SEQUENCE: 67

| | | | | | |
|---|---|---|---|---|---|
| auggcuggca | agaagaagag | cgaaaaagag | uccaguugga | ucggcgagau | cgagaaauac | 60 |
| ucgcggcaga | ucuggcuggc | uggucggggg | gccuacucga | aggucagcaa | ggacggcagc | 120 |
| aagcuguucg | agaccuuggu | gaagacggg | gagaaggcug | aaaaagaagc | gaaguccgau | 180 |
| guggacgcgc | aggucggugc | ggcgaaggcu | uccgcccgcu | cugcgaagag | caaggucgac | 240 |
| gagguucggg | accgugcgcu | cggcaagugg | agcgagcucg | aggaagcuuu | cgacaagcgc | 300 |
| cugaacagcg | ccaucucgcg | ucucggcgug | ccgagccgca | acgaggugaa | ggagcugcac | 360 |
| agcaaggucg | auacgcugac | caagcagauc | gagaaacuca | ccggcgucag | cgucaagccg | 420 |
| gcggcgaagg | cagcggccaa | gccugcggcg | aaaccggcug | ccaagcccgc | ggcgaaaacc | 480 |
| gcagcggcca | agccggcagc | uaaaccggca | gccaaggccg | ccgccaagcc | ugcggcgaaa | 540 |
| cccgcggcga | aaaaaccgc | ggcgaaaacc | gcggccgcca | agccggcagc | caagcccgcc | 600 |
| gccaaaccga | cugcgaaggc | cgcagcgaaa | ccgcggacca | agccggcagc | caaggccgcg | 660 |
| gcgaagccug | cugcgaaacc | ugccgcagcc | aagccugccg | cgaagccggc | agccaagccg | 720 |
| gccgcugcga | ccgccgccaa | gcccgcggcg | aaaccugccg | caagccggc | ugcgaaaaag | 780 |
| ccugcggcga | agaagccggc | agccaagccc | gccgcggcga | aaccggccgc | ucccgccgcg | 840 |
| ucuucgagcg | cgcccgcugc | ccccgccgcc | acaccggcug | ccagcgcucc | ggcagcgaac | 900 |
| gcuccggcga | cgccgagcag | ccagggcuga | | | | 930 |

<210> SEQ ID NO 68
<211> LENGTH: 1023
<212> TYPE: RNA
<213> ORGANISM: Pseudomonas aeruginosa

<400> SEQUENCE: 68

| | | | | | |
|---|---|---|---|---|---|
| augaaagcga | cuaugguccu | gaccccgcug | gcccuggcaa | uggcugcagu | gcugucggua | 60 |
| ucggccuacg | ccggaaacga | agguggcugg | cacccgccga | aacccaaccc | gcagucgaac | 120 |
| aacaagggcg | gagccacggc | ccugguggug | gauacgcagc | agaacuacaa | caacaagguc | 180 |
| agcaacuucg | gcacgcugaa | caaugccucg | gugagcggcu | cgaucaagga | ugccucgggc | 240 |
| aacgucgggg | ucaacgucgc | cgccggcgac | aacaaccagc | aggccaacgc | cgccgcgcug | 300 |
| gccagcgccg | acgccagcuu | cguguucggc | ccgcgaccg | ccagcaccag | cgucugcag | 360 |
| agcggcuacg | gcaauacgcu | gaacaacuac | uccaacccca | caccgcauc | gcugagcaac | 420 |
| ucggccaaca | cgucucggg | caaccuggc | gugaacgucg | ccgccggcaa | cuucaaccag | 480 |
| cagaagaacg | accuggccgc | cgccgucucc | aacggccagu | acagcacugc | cgguagcgcc | 540 |
| gcgucgcaga | ccuccaccgg | caacaccacc | gucaacagcg | ccaacuacgc | cuauggcggc | 600 |
| accuacgugu | cgcugaagcu | gaacgccgac | ggcagcuaca | agggcaccuc | cgaccagauc | 660 |
| ggcgacgucu | accucgacac | cugggaaggc | cagacccauc | cgggcggcag | caauaccggc | 720 |
| cacaucgacg | uggacagcca | ggcccagggc | gccaaggacc | ugaaccacga | cggcggcgcg | 780 |
| uucgccuuca | ggaaaaggg | cgacgucgac | cugaaaggca | cggugccggg | cuucaucccg | 840 |
| gcgaucgucg | gcuucaagac | cccggucacc | aacaacgcca | gccugagcaa | cucguugcag | 900 |
| aacgucucgg | gcaacgucgg | ggugaacauc | ccgccggug | gcggcaacca | gcagagcaac | 960 |
| ucccugucca | ucgccgccgg | uugcagcagc | ugcccggccg | guggcgagag | ccuuggcuuc | 1020 |
| uga | | | | | | 1023 |

<210> SEQ ID NO 69
<211> LENGTH: 1044
<212> TYPE: RNA
<213> ORGANISM: Pseudomonas aeruginosa

<400> SEQUENCE: 69

| | | | | | |
|---|---|---|---|---|---|
| augaagcaac | aguucgaacg | cucgccuucc | gagaguuauu | ucuggcccgu | cguccuggcg | 60 |
| gugguccugc | acguucugau | cuucgccaug | cuguucguca | gcugggcguu | ugcuccggag | 120 |
| cuuccucccu | ccaagccgau | cgugcaggcc | acgcucuacc | agcucaaguc | gaagagccag | 180 |
| gcgacgacac | agaccaacca | gaagaucgcu | ggcgaggcga | agaagaccgc | cuccaagcaa | 240 |
| uacgaagucg | agcagcucga | acagaagaag | cucgagcagc | agaaacucga | gcaacaaaag | 300 |
| cuggaacagc | agcaggucgc | ugcugcgaaa | gcggcggaac | aaaagaaggc | ugacgaggcu | 360 |
| cgaaaggccg | aggcccagaa | agccgccgag | gcgaaaaagg | ccgaugaagc | caagaaagcu | 420 |
| gccgaggcca | aggccgccga | acagaagaag | caggcugaca | uagccaagaa | gcgcgccgag | 480 |
| gacgaggcca | agaaaaaggc | cgcugaggac | gccaagaaaa | aggcagccga | ggacgcgaag | 540 |
| aagaaagcgg | ccgaggaggc | caagaagaag | gcugcugcgg | aagcggcgaa | gaagaaagcc | 600 |
| gccgucgagg | ccgccaagaa | aaaggccgcc | gccgcugccg | cggcagcccg | caaggcugcc | 660 |
| gaggacaaga | aggcgcgggc | auuggccgag | uugcuuucgg | auacgaccga | gcgcagcag | 720 |
| gcccuggccg | acgagguggg | cagcgagguc | accggcaguc | ucgacgaccu | gaucgucaac | 780 |

| | |
|---|---|
| cuggugagcc agcaguggcg gcguccucca ucggcgcgua auggaaugag cguagaagua | 840 |
| cugaucgaaa ugcugccgga cgguaccauc accaaugcca gcgucagccg uucgagugge | 900 |
| gacaagccuu ucgacaguuc ggcgguggcg gcggugcgca acgucggccg uauucccgag | 960 |
| augcagcaau ugccgcgggc uaccuucgac agccuguauc gucagcgccg caucaucuuu | 1020 |
| aaaccggagg auuugagucu guga | 1044 |

<210> SEQ ID NO 70
<211> LENGTH: 1059
<212> TYPE: RNA
<213> ORGANISM: Pseudomonas aeruginosa

<400> SEQUENCE: 70

| | |
|---|---|
| augucggcca acaagaagcc cgucaccacc cccuugcacc uguugcagca acuuucccac | 60 |
| agccuugucg agcaccugga aggugcgugc aaacaagcgc uggucgauuc ggaaaagcuc | 120 |
| cuggccaaac uugaaaagca acguggcaaa gcccaggaaa agcugcacaa ggcucgcacc | 180 |
| aagcugcagg augcugccaa ggccggcaag accaaggcac aggccaaggc gcgcgagacc | 240 |
| aucagcgacc uggaagaggc guuggauacc cugaaggccc ggcaggcgga cacccguacc | 300 |
| uacaucgucg gccucaagcg ugacguacag gaaagccuca agcuggcgca ggguguccggc | 360 |
| aaggugaagg aagcugcugg caaggcucug gagagccgca aggcgaaacc cgcgaccaaa | 420 |
| ccugcugcga aggcggcagc caagcccgcg gugaaaaccg uagcggcgaa gccugcggcc | 480 |
| aagccggcug cgaagccugc ugcgaaaccg gcggccaagc cugcggcgaa accgcggca | 540 |
| gcgaagcccg cagccaagcc gacggcgaag ccugcugcga aaccggcggc caagcccgcg | 600 |
| gcgaaaaccg cagccgcgaa gcccgcagcc aagccggcgg cgaagccugu ggcgaaaccg | 660 |
| gcggccaagc cugcggcgaa aaccgcagcc gcgaagcccg ccgccaagcc ggcagcgaag | 720 |
| ccugucgcga aaccgacggc caagcccgcg gcgaaaaccg cagccgcgaa gcccgcagcc | 780 |
| aagccagcug cgaagccugc ggcgaaaccg gcggccaagc cuguggcgaa auccgcggcc | 840 |
| gcgaagccug cagccaagcc ggcugcgaag ccugcggcga aacggcggc caagccugcg | 900 |
| gcgaaacccg uagccgcgaa accugccgca accaagcccg ccaccgcucc ugcugcgaag | 960 |
| ccugcggcga cucccagcgc cccggcagcc gccuccagcg cugcuucggc aacgccugcc | 1020 |
| gcgggcagca acggcgccgc cccgaccagc gccuccuaa | 1059 |

<210> SEQ ID NO 71
<211> LENGTH: 1263
<212> TYPE: RNA
<213> ORGANISM: Pseudomonas aeruginosa

<400> SEQUENCE: 71

| | |
|---|---|
| auguggggguc uuacgaugaa guuugcgagc cugauucuga ugcuucucuu ugccacgggug | 60 |
| gcgagggcug aggauuacua cuggaaaauu cagucacugc cugaacgcuu uucuucgccc | 120 |
| ucggcagcuu gcgcggcgug ggccaaagcc acggacgcc cuggggaguu caccuucacc | 180 |
| gggucuauga agcccguga ccagaccucg uuuuggugcg aguucacgaa caacgaaacc | 240 |
| ggcaagacug cugccgggua uggccugccg ggacgcuaug gcgauagcug ucccgaggggg | 300 |
| acggaauacg auaaggcgac cggggguugu aagucgccuc cgcaagaaug caaggaaggc | 360 |
| gaacuguucc cggccaaagg cccggacucu cccguggguua ccucgggagg ccguaacuau | 420 |
| gucggugacg gcgcgccccc gaccgccugc uacaaagcu ugagguaugg cggcaauccc | 480 |
| agcccggcca guugcuaucu ggucaaaggc uccaccacga ccggcuucug caauuacauc | 540 |

```
cucaagggca ccggacagaa uugcggugcc gauuccuaca ccuucuccca gaccggcgau    600
ucgcugaacc cgcccgacac uccgaacacc gauccuuccg acccgaacga ccccggcugc    660
ccgcccggcu ggucgugguc gggaacuacc ugcgucaagg ccccgaccga ucccacggau    720
ccaaccgacc cgaccacgcc gggcagugac ggcggcggcg auggcaaugg cgguggaaac    780
aauaacggcg gcggcaauga cggcggcacc ggcaauggcg gcgacggcag cggggagggg    840
gacggcaacg gcggggcga ugguagcggc gacggugacg gcagcggcac gggcggcgau    900
ggcaacggca ccugcgaccc ggcgaaagag aacugcucca ccggccccga aggccccggc    960
ggcgaacuca aggagcccac gcccggcacc ugggaugacg ccaucgccac cuggaaaaag   1020
aaggucgagg acgccaagca agaacucaag accaagguga aggccaacgu cgaucagaug   1080
aagggcgccu ucgaccucaa ccuggcggaa ggcggcgggc aacugcccug cgaguccaug   1140
accauuuggg gcaaguccua ucccucugu aucuccgacu acgccggcca acucuccagc   1200
cugcgcgugg cgcugcugcu gauggccgcg cugaucgccg cccucauucu gcugaaggac   1260
uga                                                                 1263

<210> SEQ ID NO 72
<211> LENGTH: 1284
<212> TYPE: RNA
<213> ORGANISM: Pseudomonas aeruginosa

<400> SEQUENCE: 72
auggccgucg cccugguguu guuguugccg ccgacgccug auguaaagcc caaggccgcu     60
gcgccgaaga gccagcagaa aacgccugag cccaguaacg acaagacuuc cagcuucucc    120
gacauguaug ccaaggagac cgcgaaggaag cccgccgagc gcgccgacgg ucccgcgaag   180
gguucgcggg acaagccacg ggacgccggc aaggacgccg ccgaagcgca gccgacggau    240
gccgucaggc agccggccgu ugccgaagac ggcaagccuu gccggccgga cggccaggcc    300
aaggccgacg gcgaagauaa agucgaaacg ccggucgauc cgcugcaauu gcucggccuc    360
ggcggugccg uaccguugcu cgacgagaau acccaggcga cuuugcugcc accggccgug    420
ccgacggcca gcagugcucc ggccagccuu accgaagcca gcagcgaccc gacccugguc    480
aagcucaacg gcgugccggc ggugaacaug gcccuggagc agggcgccca ggacgccgcg    540
cagacggcga aaggcgggcc ggcgaagagc gccgaucccc gccaggcgaa ccucggcgau    600
gcccuugccg gccugaccuc ggauuccuug accaaggccg ucgacggcaa ggcgcucgag    660
gcccaguugc agcagaccgc cgagccggcc gucgccagcg ccgccuccga gagccugcug    720
gagagcaagg cggaaccccg cggugaaccu uucgcggcca agcucaacgg gcugacccag    780
gccauggcgc aacagcccu gaccaaccgu ccggugaacg gcacggugcc cggccagccg    840
guggcgaugc agcagaacgg cuggagcgag gcgguggugg accgggugau guggauguc    900 agccagaaac ugaagucggc ggagauccag cucgaccccg ccgagcuggg acgccuggac    960
gugcgcaucc acaugaccgc cgaccagacc caggugaccu ucgccagucc caaccgcggc   1020
guucgcgacg cccuggaaag ccagaugcac cggcugcgcg acauguucag ccagcagggc   1080
augaaccagc ucgacgugaa cgucccgac cagucgcugg cgcggggcug gcagggccag   1140
cagcagggcg agggcggauc ggcgcgcgga cgcggcuugg ccggcgaggc cucgggcgau   1200
gaggaaaccc ucgccggagu cagcgagauc cgcagccggc cgggugcguc ggcggcgcgc   1260
ggucugguca cuacuacgc cuga                                           1284
```

```
<210> SEQ ID NO 73
<211> LENGTH: 1287
<212> TYPE: RNA
<213> ORGANISM: Pseudomonas aeruginosa

<400> SEQUENCE: 73
augcuccgcc uccuuccucu ccugcuaucc cucgccuguc ucgcuccggc cuucgccgac      60
gagcgcgccg acacccaacg ccagcuggaa cagacgcaga aggacaucgg cgagcugaag     120
aagcugcugg acggcaucca gcaggaaaag agcggcgugc agaagcagcu gaaguccacc     180
gagaccgaga ugggcgaccu ggaaaaacga aucaaggccc ugcaggacga gcuggacaag     240
agcgaagccg agcugaaacg gcuggauggg gagaaaaaaa aacuccagga cgcgcgcauu     300
gagcagcagc gccuccucgc cauccaggcc cgcgcggccu accagagugg acgcgaggaa     360
uaccugaagc ugcugcugaa ccaggaacac ccggaaaaau ucagccgcac ccucaccuac     420
uacgacuaca ucaacaaagc ccgucucgaa cagcucgcca gcuucaacga aacccuccgc     480
cagcuggcca cgucgagca ggacaucucu gcgcagaaag ccgaacaacu gagcaagcaa     540
ggcgagcugg acagccgccg cgaggcgcug gcagcgaccc gcaaggagcg ccagcaagcc     600
cuggccaagc ugaacagcga cuaccgcgaa cgcgaccaga gcucaaguc ccgccaacag     660
gaccaggccg agcuggccaa gguacugcgg accaucgagg aaacccuggc ccgccaggcc     720
cgcgaagccg ccgccgcggc ggagcgcgag cgccagcgcg cgcuggccgc cgaacgcgag     780
cgugcgcgcc agcagcaggc cgccccggga cgagucacca gcccgccgcg cgaaccugcg     840
ccgggcccgc uggucucaag cacuggcgcg gucuacggcg gcgcguucgg cucggcccgc     900
ggcaagcugc cguggccggu gaauggccgc gucguggcgc gcuucggcag ccagcgcggc     960
gacgauccgc gggcgaaaug ggacggcgua cugauuucgg cgagcgccgg cagcaccguc    1020
cgcgcggugc acggcggacg cguguauuc gccgacuggu ugcgcggagc cggccuguug    1080
gucauccucg accacggugg cggcuaccuc agccuuuaug ccauaauca aagccugcug    1140
aaagacgccg gcgacaccgu gaaggccgga gacccgaucg ccaccguugg aaccagcggc    1200
ggccagagua gccggccgu guacuucgcc auucgccauc agggccgccc ggcggacccu    1260
acuaccuggu gccgcgcaca gggauag                                       1287

<210> SEQ ID NO 74
<211> LENGTH: 1707
<212> TYPE: RNA
<213> ORGANISM: Pseudomonas aeruginosa

<400> SEQUENCE: 74
augcaaagac ugucgcguau cggccgcaac acccucgccg ucccguuuc caccuugcuc      60
cucagcgccu gcaaccaggg cgacgaugcg ccgaagccug cggcagucgc gccgcaaccg     120
gccgcaccga gcauggcugc acugagcauc ccgcuaugcc ucaacggcca gugcgcggug     180
aucgaccagg acgccaagcu gcucgugccg uucgacaacg acuacgacaa uaucgucgcc     240
agcgccuacc agggcacccu gaugcggcg cgcgaggagc gcuggaaccu gauccaggcg     300
aaggacggca aggugucgcg cgacgauauc ggcgaagccc ugcgcugcu caccccaac     360
cucuauggcu ucgucgcga uggcaaguac ggcguggucg acggccaggg caaggaaguc     420
caggcgccgc guuucgacga cauucacccc aacagugcca acgaauucau caucuacgag     480
aucgauggca agcgcggcau cucgaugcc aaggcaaga gcucaccga ggcgcucuac     540
gacaccaccc uggucaacgg cagcgucgcc gaacacggug gcuugaucag cgccgagcgu     600
```

-continued

| | |
|---|---|
| ggcgaggaga aguggaucau caaccucgcu accggcgaac agaaggccgu ggccuacgag | 660 |
| agccugggcg accuccacga cggcgugaug agcgccagcg ucaucggcaa gggcucccaa | 720 |
| cugguggaug ccaagggcga cguggucggu gacggcaaga gcuacgauua ccugggcacc | 780 |
| ccggccaacg gccuggucgc guuccgcgag aaguacgaca gccccugugg cuaccucgac | 840 |
| uaccagggca aggugccgau cgccgcccag uucgccgguu gcggcgcccu cggcaagcag | 900 |
| ggcgggcugg cccagcagcg cauggaagau ggcucgucgg gcaaguacgg ccugaucgau | 960 |
| cgcagcggcg ccuggaaggu gcagccgcag uacgauucgg ccgacagcgc cggccucacc | 1020 |
| gcgcuuggcu acaccgucga cgugcccggc cuggcugccg ucggcgugag caccggccug | 1080 |
| uucagcgccg acuucggcau cuucaaccuc gacgaaggca gcgaguggu gaagccgggu | 1140 |
| uaugcgcaga ucgcgcgcu gggcaacgac cuguucgucg uggcgaagaa gggcgggccg | 1200 |
| cagaagaccg ucagcuucau ggguucggaa agccaggugc cgguggugg ccugauggac | 1260 |
| cgcagcggca agaugcugcu ggagccggac gaacugauca gcauccaguc ugcuuaugac | 1320 |
| ggucguuucc uggaaggucu cgacgguaug gacaacgcug cccacaccgu guugcucgau | 1380 |
| cgccagggac gcacgcuggu uccagcgcuc uggcagaagc uggaggugaa uccgcagcag | 1440 |
| gguuacaucc ugggcuacga agucagcggc acuggcgacg aggcgacgga aaccuugcgc | 1500 |
| gcacuguacg accugaacgg caagccgcgc uucaccgugg ccaccaccga uugcggcgcc | 1560 |
| gaacaguugc ucgacggcaa uggcaaggcg aucuggccgc aggacccgac cccguauugc | 1620 |
| cagucgacg acgagcagga cgacgaaggc gagccggagc aggagccggc gcccgucgaa | 1680 |
| gagagcgagg aaaccagcga gagcuga | 1707 |

<210> SEQ ID NO 75
<211> LENGTH: 1740
<212> TYPE: RNA
<213> ORGANISM: Pseudomonas aeruginosa

<400> SEQUENCE: 75

| | |
|---|---|
| augcuucgcc ccgccagguc ucucucgcuc ugcuccgccc uggucauccu gcucgccgcc | 60 |
| uguggcgagg gcgaaccgcu gcucccggcc gaugcgcgcu gccugacgg cgcgcgcuau | 120 |
| cgcggcgagc ugguggacgg gcgccuggaa ggccagggcc ggcuggacua cgacaacggc | 180 |
| gccugguacg ccggccgcuu cgagcauggc cugcugcacg gccauggcac cuggcagggc | 240 |
| gccgacggca ccgcgcuacag cggguggcuuc gcggccggcc uguucgacgg ucaggacgc | 300 |
| cuggcgaugg ccgauggcag cgucuaccag ggcgguuucc gccagggccu guucgauggc | 360 |
| gaaggcagcc uggaacaaca gggcacucgc uaccgcggcg guuccgcaa gggccuguac | 420 |
| agcggccagg gcacgcugga cggcagcgau ggcagccgcu accagggcag cuuccgccag | 480 |
| ggccgccugg aaggcgaagg cagcuucagc gacagccagg gcaaccagua cgccgguacc | 540 |
| uuccgcgacg gcaacugaa cggcaagggg cgcuggagcg ggcccgaugg cgaccgcuac | 600 |
| gucggccagu ucaaggacaa ccaguuccau ggccaggggc gcuacgaaag cgccagcggc | 660 |
| gaugucugga ucggccgcuu cagcgaaggc gcgcugaacg gccccggcga gcuucucggc | 720 |
| gccgacggca gccgcuaccg cggcgguuuc caguucuggc gcuuccauggcc cagggccug | 780 |
| cucgaacaac uggacggcac ccgcuacgaa ggcggcuucg ccgccggcgc cuaugccggc | 840 |
| caaggcaccc uggaccgcgc cgacggcagc cgugagcagg gacucuggc cgacggcaag | 900 |
| cgcauccgcg acgccgccgg caaggccuug ccgacacuc uggaagucgg ccuguuggcc | 960 |

| | |
|---|---|
| cagggucgcc ugcucgacga agaacugcgc aagaucccgg ccucgacgcc ggccagcgaa | 1020 |
| cucuaugccc ugagccuggg cggcgauggc cgccagggcg uguuccgcg cgaggccgau | 1080 |
| uacgccggcg accugcucgg ccagcguuuc gccgcucgug gcgugauucg ccggucaac | 1140 |
| caccgcgacc acuucggcga ccgcccgcug gcuacccggg aaagccuguc ccgcgccgug | 1200 |
| cgcacccugg ccgaacgcag cgggccggaa gaccuggucu ucaucuaccu gaccagccac | 1260 |
| ggcuccagcg accaccaguu ggcccuggac augcccggcc ugaaccucgg cgaccugccg | 1320 |
| gccgcggaac uggccgaacu gcucgcgccg cugcgccagc gcgacaaggu gcuggugua | 1380 |
| ucggccugcu acagcggggg cuucaucccg ccgcugaaag acgaacguac ccugauccug | 1440 |
| accgccgcgc gugccgaccg ggucucguuc ggcuguuccg acgacgccga cuucaccuau | 1500 |
| uucggccgcg ccuugcuggc caaugcgcug aaccgcaccg acgaucuguc caaagcguuc | 1560 |
| gaacuggcga agaggaagu gcgucaaagg gagaaggagg aagguuucga agcuucggaa | 1620 |
| ccgcaagccu gguuaccgga acgcgugcuc gcgcacuggc ggacgcugcg ggggcagcaa | 1680 |
| gccgagcgcg cgcucgcguc ccgggaagga aaaaccggcg agggcgcggc gggcaaauag | 1740 |

<210> SEQ ID NO 76
<211> LENGTH: 1866
<212> TYPE: RNA
<213> ORGANISM: Pseudomonas aeruginosa

<400> SEQUENCE: 76

| | |
|---|---|
| augcugcaga acaucaggga uaauucccag ggcuggaucg ccaagaccau cauuggcgug | 60 |
| aucaucguuc uccugucgcu gaccggcuuc gacgcgauca uccgggccac cgaccacucc | 120 |
| aacguggccg ccaaggucaa cggcgacgau acagcucua augaaguccaa acaggccgug | 180 |
| gacaugcagc gucgccagcu gcugcaacgc cugggcaagg auuucgaucc auccaugcug | 240 |
| gaugacaagc ugcucaagga agcggcccug aaggggcuga ucgagcguac ccugcugcuc | 300 |
| caggccgcca aggacgacaa guucgccuuc uccgaccagg cgcuggacca guugauccug | 360 |
| caaacucccg aguccaggu cgacggcaag uucaacgcgg aucgcuucga ccaggucauc | 420 |
| cgccagauga acuacagccg caugcaguuc cgccagaugc ucggccagga aaugcucauc | 480 |
| ggccagcuuc gcgccggccu ggcgggcacc gguuucguca ccgacaacga auugcagucc | 540 |
| uucgcucgcc ucgagaagca gaccccgcgac uucgccaccc uggcgaucaa ggccgacgcc | 600 |
| uccaagagca gcgugagcga cgacgaggug aaggccuucu acgaaggcca caagagcgag | 660 |
| uucaugacuc ccgagcaggu ggucgucgaa uacguggagc ugaagaaguc cuccuucuuc | 720 |
| gaccagguca aggugaagca ggaagaccuc gaggcgcugu accagaagga aaucgccaac | 780 |
| cuuuccgagc agcgcgaugc cgcccacauc cugaucgagg ugaacgacaa ggucggcgac | 840 |
| gagcaggcca aggcgaagau cgacgagauc aaggcucgcc uggccaaggg cgaggauuuc | 900 |
| gccgcgcugg ccaaggaguu ucccaggau aucggcucgg ccgccaccgg cggcgaccug | 960 |
| ggcuacgccg gucgcggcgu guacgacccc gcguucgagg aggcgcugua ugcgcugaag | 1020 |
| caaggugagg uauccgcccc ggugaagacu ccguacggcu accaccugau caagcugcug | 1080 |
| ggcgugcagg cgccggaagu accgagccug gaaagccuca gccgaagcu cgaggacgaa | 1140 |
| cugaagaaac agauggucga gcagcgcuuc gucgaggcua ccaaggaccu ggaaagcucc | 1200 |
| gccuacgaag ccgccgaccu gagccagccg cgcaggaaa ugggccugaa gguccagacc | 1260 |
| agccagccgu cgacgacuuc gggggcgac ggcaucgcug ccaaccgcca gaucgugcag | 1320 |
| accgcguuca cgccgaggu gcuggaagaa gccgccaaca guggcgccau cgagcuggau | 1380 |

-continued

```
ccggacaccg uggugguqcu gcgggucaag gaacacaaca agccgaagga gcaaccgcug    1440
gagcaggucg cggcgaacau ccgcgagcgc cuggccgccg aaaaggccgc cgaggaggcg    1500
cagaagcgug gcgaggcccu gaucgcagag cugcgugaag gccguaccuc uuccgcagcg    1560
ggugagucgu ggaaaguggu cgaggcggcc ucccgcggcc acgaaggcgu cgauccgaaa    1620
cugcuccagg cggucguuccg caugcagcgu ccggaggcca aggacaagcc uucguucucu    1680
ggcgugaccc uggccaaugg cgauuacgug gugauccgcc ugaauggcgu cagcgagccg    1740
gaggaggcua ucuccgacga cgagaaggcc auguaccgcc gcuuccuggc uucgcgcagc    1800
ggacaggcag acuucgccgc cuuccgccgu caguugcagg acaaggcgga agucgagaaa    1860
uacuga                                                              1866
```

<210> SEQ ID NO 77
<211> LENGTH: 2067
<212> TYPE: RNA
<213> ORGANISM: Pseudomonas aeruginosa

<400> SEQUENCE: 77

```
auggauauga cgucgcugau gccccuccug cugggagugg gccuggucgu ucugcugguc      60
gugggccugc uggcccuguu caaggccuuc uacaucaagg ucccgcaagg caccgcgcug     120
aucgucaacg acaugucguc gacgccaag gugcauuuca ccggugcgcu ggucuauccg      180
gugauccacc ugaaggaguu caugcgcauc ucgcugauca cccuggaggu cgaccggcgc     240
ggcaaggacg gccugaucug ccgcgacaac augcgcgcgg acaucaccgu ugccuucuac     300 cugcgggguca acgagaccca ggacgacgug cucaaggugg ccaaggccau cggcgucgac     360
cgugcuuccg accguucggc ggugaacgag cuguucaaug ccaaguucuc cgaggcgcug     420
aagaccgucg gcaagcaguu cgacuucguc cagcuguucg agaaucgcca ggacuuccgu     480
gaccgcauca ucgaggugau cggcaacgac cugaacggcu acguccugga agacgucgcc     540
aucgacuacc uggagcagac cgcgaagaac ucgcuggacc cgagcaacau ccuugaugcc     600
gagggcaucc gcaagaucac cgagcugacc gccaccccaga acgucaucac caacgaacug     660
gagcgcaacg aagagcuggc gaucaagaag aagaacgucg agaccgcga ggcggcccug     720 gcccuggagc gccagcaggc ugacgccgag gcccggcaga agcgcgagau cgagaccauc     780
cgugcccgcg aggaagcgga aaccgcgcgg gucaaggaag aggagcggcu gaaggccgag     840
caggcgcgga uccaggcgca gcaggaaauc gacgugcgca ccgagaacca ccagcgcgag     900
gucgaggugg cgcagcagaa ccgccagcgc cggguggucu cgagguggga aaggucaccc    960
cgcgccaagg accuggagau cgucgcccgc gagcgugagg uggagcugca aaagaucgag    1020
aaggaaaagg cgcuggaaga gcagcgcaag aacauugcca auguqauucg cgagcgcguc    1080 gcgguggaaa agaccguggc ccaagaggag gagcggauca aggaggugcg caggguuucc    1140
gaggccgagc gggucaagca gguqauacqu cuqcaggccc aggcggaaqc cqagcaqgaq    1200 cugguacqcc aggucaagca ggcggaagcc gacgaggccc gcuccaagca caaggcggug    1260
gaaaucaaca ccauggcgca ggccgagcug gaggcggcgu cgaagcaggc cgaggcgaag    1320 aaqcqucuqg ccqaqqqcau cqaqqccqaq cqcqcaqcqc cqqqccuqqc cqauqcqcqq    1380 gugcuggaag ucaccgccgc ggcgaaggaa aaggauqqcu uggcagcqgc gcgqguacgu    1440 gccgaacaac ugaucgccga agccaqqqqc gacgaagagc gcggccuggc cgacgcccgg    1500
gugcucgagg cgcaggccgc ggccaaggag aaggacggcc uggccgaagc caaggugcug    1560
```

-continued

| | |
|---|---|
| gccgagaagc ucggcgccca ggcgcgcggc gaggagcagc ucggcgcggc caaggccaag | 1620 |
| gccaccaagg accagggcag cgcggaagcg gaaguacgc ugcagcgccu gaaugccgag | 1680 |
| gccgaggggc uuggcaagaa guucggcgcc cuggaugccc ucagcgacag cgcucgccag | 1740 |
| cacgaagagu uccgcaugca gcuggagaag agcuucgagg aggccauggc ggccaucgcc | 1800 |
| gcgaacaagg acaucgccaa ggaccaggcc gaggugcucg ccaccgcgcu gggcaaggcg | 1860 |
| aacaucgaga ucgucggcgg cgagggcgac uucuucaacu ccuucgccaa gucgcugucg | 1920 |
| gugggcaagg ccaucgaagg uguggucggc aagagcccgg uggugcagga cguccucgcc | 1980 |
| cgccugcuca acggccgugg cgcagccgcu gcggugaugc cggaacgcaa gagcggccac | 2040 |
| gagaacgagc cggcggcgga agucuga | 2067 |

<210> SEQ ID NO 78
<211> LENGTH: 2229
<212> TYPE: RNA
<213> ORGANISM: Pseudomonas aeruginosa

<400> SEQUENCE: 78

| | |
|---|---|
| auguaccccc aauuccgucg cggccaucuc gccgcugccg uccuuuucgc uucaucgagc | 60 |
| cugcugggcg ggcaggcccu ggccgaggac gagcgccugg aagaacugga cgaacgcgcc | 120 |
| gaaucggugg uccagcuggg ugacgaggug gugcugggca ccgccgaaca ggagcucaag | 180 |
| caggcaccgg ggguauccau caucaccgcc gaggacauca ggaagcgccc gccggugaac | 240 |
| gaucucuccg agaucauccg caccaugccc ggggucaacc ucaccggcaa caguuccagc | 300 |
| ggccagcgcg gcaacaaccg gcagaucgac auccgcggca uggggccgga gaacacccug | 360 |
| auccuggucg acggcaaacc ggucagcucg cgcaacucgg ugcgcuacgg cuggcgcggc | 420 |
| gaacgcgaca cccgcggcga cagcaacugg gugccgccgg aggaggucga gcgcaucgag | 480 |
| guccuccgug ggcccgcggc ggcacgcuac gguuccggcg cggcgggcgg gguagucaac | 540 |
| aucaucacca agcgcccgac cgaucguuug cguggwucca ugacgguguu caccaacauu | 600 |
| ccggaaagcu ccaaggaugg cgccacgcgc cgcgccaacu ucagccuuag cgggccgcug | 660 |
| accgaagccu ugagcuuccg cgcguacggc agcgcgaaca agaccgauuc ggacgauacc | 720 |
| gacaucaacc ucggacauac cgucaacccg agccguaccg uggccggacg cgaaggggua | 780 |
| cgcaaucgcg aucucagcgg gaugcugucg uggcaggluga cccccgacca ggucgucgau | 840 |
| uucgaagcgg gcuucagccg acagggcaau acuaugccg gcgauaccca gaacaacaac | 900 |
| ggcaccgcca auacccaggg acucgccgac gacggugcgg agaccaaccg cauguaucgc | 960 |
| gagaacuacg ccaucaccca caacgggacc ugglucguucg guacuuccag guucgucgcc | 1020 |
| caguacgacu ccaccgcaa caaccgucug gaggagggcc uggccgguuc cgucgagggg | 1080 |
| cagaucggcg ccgaccguuc guucagcgcc agcaagcugg agaacuaucg ccucagcggc | 1140 |
| gaacucaacc uucgguugca ugcguuguuc gagcaggugc ugacgguggg cgcggagugg | 1200 |
| aacaaggaaa cccucaacga cccguccucg cucaagcagg gcuucguggg aagcgauagc | 1260 |
| uugccgggga ccccgcggc cggcucgcga agcccgaaaa gcaaggcgga gauccgcgcg | 1320 |
| cguguacgug aagacaauau cgaacugcgc cccggcacca ugcucacccc cgggcugcgc | 1380 |
| cuggacgauc acagcgacuu cggccugaac uggagcccga gccugaacgc uucccaaacg | 1440 |
| cucggcgaau acuucacggu caaggccggu aucgcacggg ccuucaaggc gcccaaccug | 1500 |
| uaccagagca cccgaacua ccugcucuau acccgguggca acgguugccc gauccagacu | 1560 |
| agcagcggcg gcugcuaccu ggucggcaac gagaaccugg acgccgagac cagcguaaac | 1620 |

```
aaggaacugg gcaucgaguu ccggcgcgau ggcugggucg ccgggcucac cuacuuccgc    1680
aacgacuaca agaacaagau cgucgcgccg cuggauguca uggacagac cgggaccggc     1740 aacaacaucc ugcaauggag caacgcgaag aaagcagugg ucgagggccu ggaaggcaac    1800
cugcuggucc cccugcacga ggaccugagc uggagcacca accugaccua uaugcugcaa    1860
uccaaggaca aggacaccgg caacccgcuu ucggugaucc ccgaguacac ccugaacucg    1920
acccuggacu gcaggccag cgagcgucuu uccacccaac ugaccagcac caucuacggc     1980
cgccaggagc cgccgaagca uggcaccagc cgcaacacgc cggugguguc gcgaaaagag    2040 gugggucuaccu auggcaucug ggcgucagc gccggcuaca ccuucagcga gaaccugagc   2100
guacggggcg ggguaagcaa ccucuucgac aagcgccugu accgccaggg caacuccuuc    2160
gacgccggcg cggcaaccua caacgagccg ggucgcgccu acuacguuuc gaugaccacc    2220
ucguucuga                                                           2229

<210> SEQ ID NO 79
<211> LENGTH: 2241
<212> TYPE: RNA
<213> ORGANISM: Pseudomonas aeruginosa

<400> SEQUENCE: 79
auguccucac gcgcccuucc cgccguuccc uuccugcugc uguccaguug ccugcucgcc     60
aacgccguac acgccgccgg ccagggcgac ggcuccguca ucgagcuggg cgagcagacc    120
guggucgcca ccgcccagga ggaaaccaag caggcgccgg ggguuuccau caucaccgcc    180
gaggacaucg ccaagcgacc gccgagcaac gaccugucgc agaucauccg gaccaugccg    240
ggggucaacc ugaccggcaa cagcuccagc ggccagcgug aaacaaccg gcagaucgac    300 auccgcggca ugggcccgga gaacacccug auccuggucg acggcaagcc ggucagcucg    360
cgcaacucgg ugcgcuacgg cuggcgcggc gagcgcgaca ccgcggcgga caccaacugg    420
gugccggccg accaggucga gcgcaucgaa gugauccgcg gccggcggc ggcgcgcuac     480 ggcaacggcg cggcgggcgg cguggugaac aucaucacca gcaggccgg cgcggaaacc    540 cacggcuaauc ucagcgucua cagcaauuuc ccgcaacaca aggccgaagg cgccagcgaa    600
cggaugagcu ucggucucaa cgggccgcuc acggaaaacc ucagcuaccg cgucuacggc    660
aacaucgcca agaccgacuc ggacgacugg gacaucaacg ccggccacga auccaaccgu    720
accggcaagc aggccggcac ccucccgcc ggucgcgaag gcgugcgcaa caaggacauc     780
gacgggcugc ucagcuggcg ccugacgccc gagcagaccc ucgaguucga ggccggcuuc    840
agccgccagg gcaacaucua caccggcgac acgcagaaca ccaacagcaa caacuacgug    900
aagcagaugc ucggccacga gaccaaccgc auguaccgcg agaccuacuc ggucacccau    960
cgcggcgaau gggacuucgg cagcucgcug gccuaccugc aguacgagaa gacccgcaac   1020
agccggauca acgaaggccu ggccggcggc accgaaggua ucuucgaccc caacaacgcc   1080
ggcuucuaca ccgccacccu gcgcgaccug accgccacg gcgaggucaa ccugccgcug   1140
caccugggcu acgagcagac ccugaccccu ggcagcgagu ggaccgagca aagcucgac    1200 gaccccagcu ccaacaccca gaacaccgag gaaggcggcu cgauccccgg ucucgccgga   1260
aagaaccgca gcagcaguuc cucggcgcgg aucuucgcgc uguucgccga ggacaacauc   1320
gagcugaugc ccggcaccau gcucaccccca ggcugcgcu gggaccacca cgacaucguc   1380
ggcgacaacu ggagcccauc gcugaaccug ucccacgcgc ucaccgagcg ggucacccug   1440
```

| | |
|---|---|
| aaggccggua ucgcccgcgc cuacaaggcc cccaaccugu accagcugaa ccccgacuac | 1500 |
| cugcucuaca gccguggcca ggguugcuac gggcaaagca ccaguugcua ccugcgcggc | 1560 |
| aacgacggcc ucaaggccga gaccagcgug aacaaggaac ugggcaucga guacagccac | 1620 |
| gacggccugg uagcggggcu gaccuacuuc cgcaacgacu acaagaacaa gaucgaaucc | 1680 |
| ggccugucac cggucgacca cgccagcggc ggcaagggcg acuacgccaa cgcggcgauc | 1740 |
| uaccaguggg agaacgugcc caaggcggug gucgagggcc ucgaaggcac ccugacccug | 1800 |
| ccccuggccg acgccugaa guggagcaac aaccucaccu acaugcugca aucgaagaac | 1860 |
| aaggaaaccg cgacgugcu cucgugacg ccgcgcuaca cccucaacuc gaugcucgac | 1920 |
| uggcaggcca ccgacgaccu cucgcugcaa gccacggguca ccugguacgg caagcagaag | 1980 |
| ccgaagaaau acgacuauca cggcgaccgu gucaccggca cgccaacga ccagcucucg | 2040 |
| cccuacgcca ucgccggccu cggcggcacc uaucgguuga gcaagaaccu gagccucggc | 2100 |
| gccggcgucg acaaccuguu cgacaagcgc cuguuccgcg ccggcaaugc ccagggcgug | 2160 |
| gucggcaucg acggggccgg cgcggcgacc uacaacgagc ccggacggac cuucuauacc | 2220 |
| agccugaccg cgucguucug a | 2241 |

<210> SEQ ID NO 80
<211> LENGTH: 2355
<212> TYPE: RNA
<213> ORGANISM: Pseudomonas aeruginosa

<400> SEQUENCE: 80

| | |
|---|---|
| auguccccgu cacgcgcccu gucgccgcuc agccgcgccc ugcuccucgc cugccucggc | 60 |
| ggucccgucc ugguuuccgc cggcagcgcc ugcgccgccg agauccgcac cgaugcccgc | 120 |
| caguacuacc gccugccugc cgagccgcug gagcaggcgc ugaaccaccu aggccgccag | 180 |
| gccggcgugc ugaucgccuu cagcccggaa cagaccgccg cgcgacgcag ccaggcgcug | 240 |
| gacggcgagu acaccccugga ggaagcccug gccgcccugc ucgucggcuc cggccuggag | 300 |
| gcgcgcgccc gcggcgacgg cgccuacacc cuggaagcgc ugccggugga agacccggcc | 360 |
| aaccugcagg cgcucaccgu ggucggcgac uggcuggccg acgccagcgc cgccgacguc | 420 |
| uucgagcauc ccggugcgcg cgacuggguc cgccgcgagc aguuccaggc ccaaggcgcg | 480 |
| gccagcaccc gcgaagugcu ggagcgcauu cccgggguca gcgcgccgcu caacaacggc | 540 |
| accggcagcc acgaccuggc auugaacuuc ggcauucgcg ccucaacccc gcgccuggcg | 600 |
| ucgcgcucga cggugcugau ggacggcauc ccggugcccu ucgcccccua cggcagcca | 660 |
| cagcgucgc uggcgccggu guccaucggc aacauggacg cgguggacgu ggccgcggc | 720 |
| ggcggcgcgg ugcgcuacgg gccgcagaac gucggcggca cgucaacuu cgugacccgg | 780 |
| gcgaucccg aggacuucgc caccaagcuc gacgugcaca gcgaacucag ccccagcucc | 840 |
| agccaggacg gccugaagac cacccacaac gugcugaucg gcggcaccgg cgccaacggc | 900 |
| cucggcggcg cccugcucua ucccggcacc cgcggcggcg auuggcgcga gcacagcgau | 960 |
| acgcggaucg acgaccugau ccucaagggc cgcuccagc ccagcgacga acacacguuu | 1020 |
| ucggcgauga cccaguacua cgacggcgag gcgacaugc ccggcggccu cggcaccgcg | 1080 |
| gccuaccacg acgacccgua ccagucgacc cgucccuacg acaaguucug gggccgccgu | 1140 |
| acccuggcca gcgccagcua cgaauacacc cccaacgcca gcagaagcu caacgucacc | 1200 |
| ggcuucuuca ccaagacccu gcgcagcggc uaccucgacc agggccgcaa ccucacccug | 1260 |
| ucgccgcgcg aauacugggu gcgaggccug gaaacccgcu ucagccaggg cuucgagcug | 1320 |

| | |
|---|---:|
| ggcgaaaguc gccacgaagu gggcaucggc caccgcuacg ucaacgaagc cagccacgag | 1380 |
| cugcgcuacu ggacccgcgc cgacagcggc cagcuaccca gcaccggcag ccgcaacgac | 1440 |
| cgcgacaccc gcggcagcac cgaagccaac gcguucuaca ucgacgaucg caucgacauc | 1500 |
| ggcaacugga ccaucacccc cggcauccgc uacgagaaga ucgauuccga acagaagaac | 1560 |
| cugcugaaga acagcaagga cagcggccgc uacaacgccu cgcugccggc gcucaacgug | 1620 |
| aucuaccacc ucacgccgag cuggaaccuc uacgccaaca ccgagggcuc guucggcacc | 1680 |
| gugcaguaca gccagauggg caaggcggug cgcagcggcg acaucgagcc ggagaaggcc | 1740 |
| cgcaccuggg aacucggcag ccgcuacgac gacggcaucc ugcgcgccga acugggcgcc | 1800 |
| uuccugauca acuucgacaa ccaguacgag agcaaccagc agaccgacag cgugaccgcc | 1860 |
| cgcggcaaga cccggcacaa gggcaucgag gcggcgaucg ccuacgaccu ggccgaucuc | 1920 |
| gacccgcugc ucuccggcuu cgacgucuau gccagcuacg ccuacgucga cgcgagcauu | 1980 |
| cgcgaagacg ggcgaacaa gggcaaccag gugccguucu ccucgaagca caagggcacc | 2040 |
| cuuggcgcca acuaccgcac cggcgccugg agcuacaacc ucgacggcag cuuccagacc | 2100 |
| agccaguacg ccgacaacgc caacaccgag agcgaaagcg ccgacggcag caccgggcgg | 2160 |
| aucgccggcu ggauggucug gagcgcgcgc ggcaccuacg acuucggccc gcaacugaac | 2220 |
| gaccucaagc ucggccuggg ggugaagaac cuguucgauc gccgcuacua cacccgcucg | 2280 |
| uucgacgaca caacaaggg ccucuacguc ggccagccgc gcacccugua cguacaggcc | 2340 |
| ucggucgguu ucuga | 2355 |

<210> SEQ ID NO 81
<211> LENGTH: 2556
<212> TYPE: RNA
<213> ORGANISM: Pseudomonas aeruginosa

<400> SEQUENCE: 81

| | |
|---|---:|
| augaccuugc cuuucacccg cgccgccugg cgcccgcugu guuccgccgc cgugcucggc | 60 |
| gccgcguugu gggccgccgg cgccagcgcu gccgaacgac gcuucgaccu gccggcgcag | 120 |
| ccgcuggccg ccucgcuguc gcgccuggcg cagcaggcgc agguccaggu gcuguucgac | 180 |
| gagucgcucc ugcggggccu gcgcgcuccg gcgcugagcg gcagcuacgg ggugcgcgag | 240 |
| gcgcuggagc gguugcuggu cgguuccgag cuggagcugg uggaggcggg cggcggcuac | 300 |
| guggugcgcc ggcgccaggu cgacgccuac agcgacaacg cgcugcaacu ggacgcgcag | 360 |
| accaucgucg gcaacggucg cgaaguggac gccagcaacg ucggccguuc gacccugacc | 420 |
| cggcgggaua ucgaacgcca gcaggcggac aacaucccca gccugcugca gacccugccc | 480 |
| ggagugacca ugggcggcuc gcccaagccg ggcggacaga ccaccaacau cuggggccug | 540 |
| ggcgacgccg aggacgugcc cuauacccug gacggcgcgc agaagagcgg cuucgagcgc | 600 |
| uaccagcagg gcaccguguu caucgaaccg gaaaugauca agcgcaucga gguggagaag | 660 |
| ggaccgcacu cggugaucac cggcaauggc ggcuucggcg gcaccgugca cauggagacc | 720 |
| aaggacgcgc cggaccugcu gcgcgaaggc cgcgacgucg cgccaugcu caaguacggc | 780 |
| uaucacucca cgaccagca gaagaucuac uccggcgccg uguucggucg cagcgaagac | 840 |
| cgccgcgucg augcccugcu cuaucucaac ggucgcgacg gccgcgacau gaagcuggcc | 900 |
| gacaaccugc cgcugucgcc caccgacuac ccgaucaacc caagcgccu gcccaacagc | 960 |
| gcccaggacg agaagaccgg ccuguucaag cucaaccugc accccaccga ggagcacgac | 1020 |

```
cuggguuuca ccuaccugcg cucgaaaagc ucgcgcugga cgccguucuc cgccagcagc    1080
uacccgaccc cgccgagcca guggaccauc gaccgcuacg gcuacgagcu gggccugacc    1140
cgccugcugg cccaccgcga uaccaccgac accaccugga ccggcaagua caacuaccau    1200
ccgcuggaca accccuggau cgaccugcaa cugagcuauu ccgacgcccg caccgagcaa    1260
cucgaccguc gcgaggacac cgccuucuac cagcucgcca ccgguggcaa gcggaugcgu    1320
accgaguacc aggacaaggu ccuggaacug cgcaacacca gccguuucga uaccggagcg    1380
cuacagcacg agcugacccu gggcgcggcg cugcacaagc acaagcgcga cauccucaug    1440
cacaugccgg gcaagaccua cgagaccccg cgcuacaauu acggcuggcu gcaaccggca    1500
uucaugccgg ccggcaagca ggacacgcag agcuucuaca uccaggacgc gaucaccuac    1560
ggcagccuga ccgucacccc aucgaugcgc uucgacagcg ugcgcaacga cggccaggcc    1620
aaccuggcgc cgaucuacga caaucccaag cucggccaug acuaucgcgc ccagaccuac    1680
uccggcuggu caccgcggcu gucgguguuc uggaccgcga cgccgaaccu ggcguucuuc    1740
gccgacuaca ccgagaccug gcgagcgccg gugaucgacg agcaguacga agugcagaac    1800
aguucgacca ucgguggcag cagccgcgac cuggacgccg agcgcaucca ugcgauccgu    1860
ggcggcagcg ugaucaaccu gccggaccug cuggucgccg gcgacagccu gcagauccgc    1920
accacguugu uccagaaccg caucaaggac gagauauucc gcacccgcag cgucggcugc    1980
cgccagcagu cgaucgacaa cggcaguauc ggugguagcu gcggcgacau gcugccgcug    2040
agcaacuacc gcaacuugcc gggccugacc aucaagggcu ucgagaucga gagcuucuac    2100
gacagccagc ggcuguucgg cagccuguuc uacucgugga ugaccggcaa gcacgauggg    2160
gccuacagca aucccugggg accgaacgug ugggcgcgcg caucccgcc gccgaagugg    2220 guggccaugc ucggccugaa gguuccggaa ugggaugcca agcucggcug gcagggcgag    2280
uucgugcgca agaccgaccg ccugcccagc gaucgcuaca gcggcgggau gggguaccggu    2340 uccggcgaua ucuacuggga ucacgcgcc aacgacagcu acgacacuca ucggcuguuc    2400 gccgagugggu ucccggccaa gcugggccug aaggacacccc gcaucgacuu caccgguggac    2460 aaccuguuca accgcuccua ucgccagccg cugggcggcg accugucua cagccaggga    2520 cgcaacgcca agaucagcgu cacccaguuc uucuga    2556
```

<210> SEQ ID NO 82
<211> LENGTH: 2643
<212> TYPE: RNA
<213> ORGANISM: Pseudomonas aeruginosa

<400> SEQUENCE: 82

```
augcaccgau cgcuccacac cgacgcgccg cugggcgccg cccugcugcu ggcccugcag      60
cucgcucccg gcagcgccgc cgcggcggag gaacaggcgc cugucgaccc gcccacgguc     120
caguugcaac gaaucgaggu gaccggcagc gcgaucgcc gggucgaugc ggaaaccgcg     180
gugccgauca gcguccugcg cgccgaggag cugcgccaac agggcgugac cagcaccgag     240
gaacugaucg gccggcuuuc cggcaaccag ggcguauaca acuccagucg cucggucggc     300
agcgccaccg gcgcgccauc guucgccgac cugcgcggaa ucggcgcgaa caagacccug     360
gugcugcuca acggccggcg ccuggcgaac aaugccaucg acggcuccgc gguggaucuc     420
aacaccauuc ccuucgccgc caucgaccgg gucgagguugc ugcgcgacgg cgccuccgcg     480
cuguacggca ccgaugccau cggcggggug aucaacuuca ucacccgcaa gagccugaac     540
gaaggccgcu ucgacagcgg cuacgccucc cccacccacg acgcggcgg caaccagcgc     600
```

```
aacgucagcg cuagcuggggg cuucggcgag cuggaggagg aucgcuucaa ugucuucgcg    660
guggccaacu acgacaagca ggagcgccuc ggcgccaagg accgcggcua caccuacaac    720
uaccagccgg gacgcggccu cgacuacagc uccggcaccg ccuucccgg caacuggagc     780
cagggcgcca acgccagcaa uccgcuggcc gccggcgguu gcaagggcgc cgaccugauu    840
ccgcgcaacg gcaucugccg gcagagccug uggcgcuacc ucgaccuggu gccggaaacc    900
gagaagaccu cggguguucag ccgcgccacc ggcaagcugg ccgacgagca acgucagc     960
cuggaguacu ucuggucgcg cagcgacaac gcuacccagg ucggcccagg gaccucacc   1020
ggccugcaga ucgaucccgg caccgccuuc uaucccggca acggcaucac ucccggaccc  1080
ggcggcuucg uccucgaccc gagccggccg guggagguca acuggcgaca gagcgugcuc  1140
gggccgcgcc ugcaauccuc gcagaacacc ggccagcgcc ugcugcucgg cuucgacggc  1200
caguucgccg gcugggacua cgauaucggc gccucguaca accagaacaa gguggucgac  1260
cauauccaca gcggcuacgu cgaugaucgc cgccgcccc ucggcaucgc caacgggacg   1320
cugaacccgu ucgggccgca gaccgacgcc ggccucgccu accucggcag ccaugcccug  1380
agcggcgacu uccguaccuc ggucggccgc gucaagggcc uggacgcccg cgccagccgg  1440
gagaucggcg acugguucgg cgccgggccg gcggcccugg cgcugggcgg cgaguccgc   1500
aaggaagcgu uccaccagga cauccaggac uucgccggca acgugcagag ccucggcguc  1560
gaucccgccg ccacggucag cggcgagcgc aaccugaagg cgcaguacgc cgaacucaac  1620
gugccggugc uggacagccu ggaacucagc gcggcgaucc gccacgacaa guacagcgac  1680
uucggcagca ccagcaaccc gaaauauucg uuccgcuucc agccguuccg ccaguugguc  1740
cugcgcggcg ccuacagcga agguuuccgu gcgccgucgc uguacgaacu guacaacccg  1800
accuucacca ccuauaccag cgccaacuac gacgacccgc gccugugcgc cggcggccag  1860
ccgagccagg gcggcaucgc caaccgcgac ugcgcccagc aguucuacaa cgccaccggc  1920
ggcaauaccg accugcgacc ggaaaccgcg cgcaacguua cccugggccu ggucuaccag  1980
ccgcugcgcg accuuccgu cggccuggac uucggguggaa ucaggaucgc caaccagauc  2040
gccgaguuuc ccgaagcggc gaucuucgcc gacccgcagg ccuacgccgg acgcaucgug  2100
cgcaaggccg acggcucgau cgaucacguc gucaccggac uggccaaccu cggcaaagug  2160
aagaccagcg gcgucgaccu gagccucgau uaucguuucc cggccagccg cuacgggcag  2220
uucgggcucg accugcaagg caccuacgug ucccgcuacg acuuccagca gcagaucggc  2280
ggccaguacc uggacaacgu cggcgacuuc cagggcgucg gcgugaucgc ccgcuggaag  2340
cacgucgcca acgccaccug gagccgcgac gccuggcagg ccacccugag caaccgcuac  2400
accagcggcu acaacgacua cgaccgcgcc agcacggca aggucggcuc guggaaccuc   2460
ugggaccugg ccggcagcua ccgccucagc cacgcgcugg ggcugacccu cggggugaag  2520
aaccuguucg accgcgaacc gccguucagc aaccagaccu acaccuucca gagcggcuac  2580
gacccgcgcu acaccgaucc cuacgggcgc auccuguucg gccgccucag cuacagcuuc  2640
uga                                                               2643
```

<210> SEQ ID NO 83
<211> LENGTH: 2760
<212> TYPE: RNA
<213> ORGANISM: Pseudomonas aeruginosa

<400> SEQUENCE: 83

```
augguucggc uucguacacu gguucgggca aucgcggcgg ccucgguccu gacuuccggc      60
auggcgcaug gauugggacu gggggaaauc acccugaagu cggcguugaa ccaaccguug     120
gaugccgaga ucgagcugcu cgaaguucgu gaccugggu  cgggcgaggu gaucccgagc    180
cuggcgucgc cggaagaguu cagcaaggcg ggcgucgauc gccuguacua ccucaccgac    240
cugaaguuca cgccgguggu gaagcccaac ggcaagagcg ucauucgcgu gaccucgucg    300
aagccggugc aggagcccua ccugaacuuc cugguccagg ugcucuggcc gaacggccgc    360
cugcugcgcg aguacaccgu ccugcuggau ccgccgcugu acuccccgca ggccgcggca    420
agcgcuccgc aagcgccggu cagcgcgccg cgcgcgaccg cgccccgcg  agccccgcag    480
gcuccggcuc cggugcguac caccgcgccg gcaggcagcg acaccuaucg caccguuucc    540
aacgacacgc ucugggagau cgcccagcgc aaccguaccg aucgcguuuc cguaccccag    600
gcgaugcucg cguuccagga gcugaauccg ggcgccuucg ucgauggcaa caucaaccgg    660
cugaagagcg gccaggyccu ugcgcauccc accgaacagc agaugcugga gcgcucgccg    720
cgcgaggcgc ugucccaggu gcaggcgcag aaccagagcu ggcgcggcag ccgcaauccg    780
gccgcgggca gcgcuggcgc caggcaguug gaucgcgaccc agcgcaaugc cgccgggucg    840
gcgccauccu aggucgacgc cacgacaauu cugcgccugg ugucuggcga gggcaaggcc    900
agcaagggug ccgacaaggg cggaaagggc gacagcaagg cgaucgccga uacccuggcg    960
gugaccaagg aaagccucga cagcacucgc gcgagaacg  aagaacugca gagucgcaug   1020
caggaucugc agagccaguu ggacaagcug cagaaguuga ccagcugaa  ggacgcccag   1080
uuggccaagc ugcaagggca guugggcgcc gaaggccagg gcgcagccca gccgaacgca   1140
gcccugccgg augcgucccga gcccaaugcg gccgcgcagg gccgggcuca gcccgggacu   1200
ccugcugcgg cagcgccgac uccugcucca gccgagaaag caccgccgc  uccggcgcag   1260
ccuccggugg cgccgccgcc cgcgccagcu gccgagaagc cuccggcacc ugccguuccg   1320
gcgcccgcuc ggguacaggc ggcagagcag ccggcaccga gcuuccucga cgaacugcug   1380
gccaacccgc uguggyuggc ggugaucggc gguagcgcac ugcuggcguu gcuggugcug   1440
cugaugaucc ugucgcgg  caaugcgcag aaagagaagg aagaagccca ggcuuucgcc   1500
gcggauaccg gcgaggaaca ggaggaugcg cuggaccugg gaaaggacgg cuucgacgac   1560
cugacccucg acgagccuga ccgcaggguc gcagccgucg cuccgcaggu cgagaagacc   1620
accgcgcaga cuuccgaugc gcugggcgag gccgacaucu auaucgccua cgggcguuuc   1680
aaccaggccg ccgaacuguu gcagaacgcc aucuacgacg agccgcagcg caccgaccug   1740
cgccucaagc ugaugagu  cuaugccgag auggcgauc  gcgaagguuu cgcucgccag   1800
gaaaacgagc ugcgcgaaau cggcggcgca cagccgcagg ucgagcagcu caagucgcgc   1860
uauccggcaa uggucgcggu cgccgcgguu gccggccugg ccggcgccaa gcuggcgcag   1920
gacgagcugg auagcuucag ccuugacgac cugucgcucg acgacagcgg ucacgcggcc   1980
aagccggaug cggcaggaca ggaucucgac gacgccuucg accugagccu ggacgaccug   2040
ggcggcgacg acgugcaggc cgaccucaag uccgacagcg gggcgcugga cgaccugacc   2100
cuggacagcg aucuggaccu ggcgccucg  accccgcgg  acaagccugu cgacgaucuc   2160
gacuucggcc uggauuucgc ggaguggca  gagacuccga gccaacccaa gcaugacgac   2220
cugggcgauu ucucccugga ucucgacgcg ccggaagaca agcuuucgga cgacgacuuc   2280
cugcuuucgc ugaacgacga agugcccgcc gggcgccgc  ccgacaacga auucacccuc   2340
gauaccgagg cugccgaaga gccggcguug ucccugccgg acgacuucga ccugucgcug   2400
```

```
gccgacgagc cgacggagcc ggccgcuccg gagaagggcg aggacaguuu cgccgcccag   2460
uuggacgagg ugagugcgca guuggacgag uuggccagca accuugacga gccgaagagc   2520
gcgacgccga guuucuccgc cgaagaugca gcggucgccu ccgcccugga cggagacgcc   2580
gacgaugacu cgacuuccu cuccggugcc gacgaagcgg cgaccaagcu ggaucuggcu    2640
cgcgccuaca ucgacauggg cgauagcgaa ggcgcgcgcg auauccucga cgaaguccug   2700
gccgaaggua augacagcca gcaggcggaa gcccgcgagu ugcuggagcg ccuggccuga   2760
```

<210> SEQ ID NO 84
<211> LENGTH: 2988
<212> TYPE: RNA
<213> ORGANISM: Pseudomonas aeruginosa

<400> SEQUENCE: 84

```
augaccgacg accacuccuu ccgcccucgc cccaccucgu ugucagccgc ccugcugcug     60
ggcgccugga ucgcacagcc ggccacggcc gccuaugucg aagccggucg gcccggcgau    120
ccggccaguu ggcgcuccgc cgaauaccag caggacuggg gccuggaacg gaugcgggcc    180
gaccaggccu augccgccgg caucgacggc cagggcguga agaucggcga gauggacucc    240
gguuucgacc cgagccaucc ggauacuccc gccucgcgcu accagccggu gacggccagc    300
ggcaccuaug ucgacggcac gccguucagc gucagcggcg cgaugaacgg caacaacgac    360
ucccacggua cccacgucgg cggcacccuc ggcgccucgc gcgacggcgu cggcaugcac    420 ggggugccu acgcggcaca ggugauaugc gccaacacca accagaacga cagcuuccug    480
uucggcccga cgcccgaccc gaacuauuuc aaggccgccu accaggcgcu ggccgacgcc    540
ggggugcggg cgaucaacaa caguuggggc agccagccca aggacgucag cuacgagacc    600
cucgacggcc ugcacgccgc cuaugccagc cacuacgggc gcuccaccug gcuggacgcc    660
gccgccggcg ucucccgcca gggcgugauc aacgucuuca cgccggcaa cagcggcuac    720 gccaacgcca gcgugcgcuc cgcccugccc uacuuccagc cggaccugga aggccacugg    780
cuggccgugu ccggccucga ccagcagaac ggccagcgcu acaaccgcug cggcaucgcc    840
aaguacuggu gcaucaccac gcccggccgc cugaucaaca gcaccaugcc cggcggcggc    900
uacgccaaca gguccgguac ucgcgauggcc gcgccccacg ccaccggcgc gcuggcccug    960
gucaugcagc gcuauccgua ccugaacaac gagcaggcgc ugcagguucu gcugaccacc   1020
gccacccagc ucgacggcac gccgaccggc gccccaccg acaccgucgg cuggggcgug   1080
ccggaucucg gucgggcgau gcaugggccu ggacaauugc ucggccgcuu cgaggccaac   1140
cucccggccg gccugcgcga cgaauggagc aacccgauuu ccgauagcgc ccugcuccag   1200
cgccaggcca aggacgccgc cgagcacgcg gccuggcagc ggacgcugaa ggacaagggc   1260
ugggaaaacg gcuugccggc cggugccagc cagcaggaac gcaccgacua ugccaucggc   1320
auggcccgcg accaggccgc cgcccagcgc caguaccagg gcagccuggu caaggccggu   1380
gccggcagcc uggccugag cggcgacagc accaucgcg ggccgacccu ggucgauggc    1440
gggcugcuca gcgucgacgg uucgcugcug uccgccgucg aagucaaugc cggcggcacc   1500
cucggcggca gcgcaggau cggcggccug cuggcgcgcu ccggcggcac gguggccgcg   1560
ggcaacucca ucggcacccu ggaggucgcc ggggaccugc gcuucgaauc cggcucgacc   1620
uacgcggugg agcuuucgga aagccagc gaccggaucg ucgccagcgg caaggcgagc     1680
aucgcgggcg gcaacgucac ccuggccaug gaaaacagcc ccgaccugcu cagccagucc   1740
```

| | |
|---|---|
| caggucgaga gccuggucgg ccgccgcuac gacauccucg acgccgccgg cggcaucgac | 1800 |
| gggcgcuucg acgcgguauu gccgaacuac cuguuccucg gcggcacccu ggacuacgcg | 1860 |
| gccaacgcca uccgccugga uaucggacgc aacggcacga cccucgccag cgucgcgcag | 1920 |
| acgcccaacc aggcggcggu cgcuggggcc guggaaacgc ucggcgccgg caacccgguc | 1980 |
| uacgaaagcc ugcuccuguc ggaaaacgcc gcaaccgccc aacgggccuu ccagcaauug | 2040 |
| uccggggaaa cuacccggc gcucgccggc cguuugcuca acgacagccg cuaucugcgc | 2100 |
| gacagcgucg gcgaacgccu cgccagacc agcgacggcg aggccggcgg ggaggcuccc | 2160 |
| gaaggcuggu ucaaggcgcu cggcuccugg ggcaagagcg ccgauggcag ccacggguagc | 2220 |
| gaaggcuacc ggcauucggu cggcggcuuc cugcucggcg ucgacagcca ggucgccagc | 2280 |
| gacacgcgcc ucggccuggu ggccggcuac agcaacagcu cgcugaacau ggacagcagc | 2340 |
| cugcaauccu ccgccagcau cgacagcuac caccucgggc cuaccucgg ccggcaauug | 2400 |
| cagcaauggc gccugagccu cggcgcagcg cacgccuggc accgcgccga ggucaagcgc | 2460 |
| gaccugcaau acgcgccgu ggccggcaag cagaaggcca agcucgacgc acagagcagc | 2520 |
| caguuguucg ccgaggccgc cuacgcgcug gguuggcgca gccuggagcu ggaacccuuc | 2580 |
| gccgggcugg ccuacgugca cgucgccagc gaugacuucc cgaacgcggg uagcgccgcg | 2640 |
| gcccuggagg uggcgacga caaccuggac gccgccuuca ccacccuggg ccugcgcgcg | 2700 |
| aaacggcauu ucgagcugga ugccggacgc cgccuggcgc ucccggcac ccucggcugg | 2760 |
| cgccacaacc ugagcgacac caccccgcaa cgccaccugg cguucgccag cggcagccag | 2820 |
| ccauucagcg uggaaagcgu ggcccugucc ccgcgacgccg cgcugcucgg cgucgacgcc | 2880 |
| agccucgcgg ugaaucgcga agugagcgug cggcugggcu acaacggccu gcugggcagc | 2940 |
| cgcgagaagg accauggcgu cggacuggcc gucgacuggc guuucuga | 2988 |

<210> SEQ ID NO 85
<211> LENGTH: 3174
<212> TYPE: RNA
<213> ORGANISM: Pseudomonas aeruginosa

<400> SEQUENCE: 85

| | |
|---|---|
| augaaaagaa ugcugaucaa cgcgacucaa cccgaggagu ugcguguugc acuggucgac | 60 |
| ggccaacgcc uguucgaccu cgacaucgag ucgggcgccc gcgagcagaa gaaggccaac | 120 |
| aucuacaaag gccgcaucac ucgcgucgaa cccagccucg aagccgccuu cgucgacuuc | 180 |
| ggcgccgaac gccacggcuu ccucccccuc aaagaaaucu cccgcgaaua cuucaagaaa | 240 |
| uccccccgaag gccggaucaa caucaaggaa guccugagcg aaggccagga agucaucguc | 300 |
| caggucgaga ggaagagcg cggcaacaag gcgccgcccc ugaccaccuu caucagccug | 360 |
| gccggccguu accggugcu gaugccgaac aacccgcgcg ccggcggcau cucccgccgu | 420 |
| aucgaaggcg aagagcgcaa cgagcugcgc gaggccugag acggccucaa cgcaccggcc | 480 |
| gacaugggcc ugaucgugcg caccgccggc cucgccgcca gcaccgagga acugcagugg | 540 |
| gaccucgacu accugcugca cugguggagc gcgaucaagg aagcguccgg cgaacguggc | 600 |
| gcgcccuucc ugaucuacca ggaaagcaac gucaucaucc cgccauccg cgacuaccug | 660 |
| cgccaggaca ucggcgaagu gcugaucgac agcaucgacg cccaggaaga agcccugaac | 720 |
| uucauccgcc aggugaugcc gcaguacgcc agcaagguga agcuguacca ggacagcguu | 780 |
| ccgcuguuca aucgcuucca gaucgagagc cagaucgaga ccgcuuucca gcgcgaagug | 840 |
| aagcugccgu ccggcggcuc caucgucauc gacccgaccg aggcccuggu uccaucgac | 900 |

```
aucaacucgg cgcgcgccac caagggcggc gacaucgagg aaaccgcccu gcagaccaac    960
cuggaagcgg ccgaggaaau cgcccgccag cugcgccugc gugacaucgg cggccugauc   1020
gucaucgacu ucaucgacau gaccccggcg aagaaccagc gcgccgugga agagcgaguc   1080
cgcgaagccc ucgaggccga ccgcgcgcgc guccaggucg gucgcaucuc gcgcuucggc   1140
cugcuggaaa uguccogcca gcgccugcgu ccgucccucg gcgagaccag cggcaucguc   1200
ugcccgcgcu gcaacggcca gggcaucauc cgcgacgucg agucgcuguc gcuggccauc   1260
cugcgccuga ucgaggaaga agcccugaag gaccgcaccg cggaaguccg cgcccgcgug   1320
cccuuccagg ucgccgccuu ccugcucaac gagaagcgca acgccaucac caagaucgaa   1380
cugcguaccc gcgcgcgcau cuucauccug ccggacgauc aucuggaaac cccgcauuuc   1440
gaaguccagc gucugcgcga ugacagcccc gaacugguug ccggccagac cagcuacgaa   1500
auggccaccg ucgagcacga agaagcccag ccggucagcu cgacccgcac ccuggucogc   1560
caggaagcag cagucaagac cgucgcuccc cagcagcccg caccgcaaca caccgaagca   1620
ccggucgagc cggccaagcc gaugcccgag ccgagccugu ccagggccu ggugaagucc   1680
cuggucggc uguucgcagg caaggaucaa ccugccgcca agccugcuga aaccagcaag   1740
ccggcugccg agcgccaaac ccgccaggac gagcgucgca acggccgcca gcagaaccgc   1800
cgccgcgaug gccgcgaugg caaucgccgc gacgaagagc gcaaaccgcg cgaggagcgu   1860
gcagagcguc aaccgcgcga agagcgcgcc gaacgcccga accgcgaaga gcgcagcgaa   1920
cgucgccgcg aagagcgcgc cgagcgcccg gcucgcgagg agcgcagcc gcgcgaaggc   1980
cgugaagagc gcgccgagcg gacacccogc gaagagcgcc agccgcgcga aggccgcgaa   2040
ggucgcgagg aacgcagcga acgccgcgc gaagagcgcg ccgaacgccc ggcccgcgaa   2100
gagcgccaac cccgcgaagg ccgugaagaa cgcgccgagc gccoggcccg cgaagagcgc   2160
cagccgcgcg aggaucgcca ggcucgcgac ccgcggccc uggaagccga ggcauugccg   2220
aacgacgaga gccuggagca ggacgagcag gacgauaccg auggcgagcg cccgcgccgc   2280
cgcucccgcg gccagcgucg ucgcagcaac cgccgcgaac gccagcgcga ggucagcggc   2340
gagcuggaag gcagcgaggc gaccgauaac gccgccgcgc cgcugaacac cgucgcagcc   2400
gccgccgcug ccgguaucgc ugucgccagc gaagccguag aagcaaacgu ggagcaagcc   2460
ccggccacua ccagcgaggc ugccagcgaa accacggcaa gcgaugagac cgacgcgucg   2520
accagcgaag ccgucgaaac ccagggcgcg gacagcgagg ccaauaccgg cgaaaccgcc   2580
gacaucgaag cgccggugac cgucagcgug guccgggacg aagccgacca gagcacccug   2640
cuggucgcgc aagccacuga agaagcuccc uucgccagcg aaagcgugga aagccgcgaa   2700
gacgccgaga gcgccgugca accggcaacg gaagcggccg aagaaguugc cgcuccggug   2760
cccgucgaag uagcagcccc uagcgagccc gcagccaccg aggagccgac cccggccauc   2820
gcggcggugc cggccaacgc gacuggccgu gcccucaacg acccacggga aaaacgucgc   2880
cugcaacgcg aagccgagcg ucuggcacgc gaagccgcag cagcagccga agcggcagcu   2940
caggccgcuc ccgccgucga ggagaucccg gcuguagcga gcgaggaagc gucggcccag   3000
gaggaaccug cugcacccca ggcugaagaa aucacccagg ccgacguucc gucccaggcg   3060
gacgaagccc aggaagcggu acaggccgag ccugaagcuu ccggcgaagg cgccgccgac   3120
acggagcacg cgaaaaagac cgaggaaagc gaaaccucgc gcccgcaugc cuga         3174
```

<210> SEQ ID NO 86

<211> LENGTH: 3486
<212> TYPE: RNA
<213> ORGANISM: Pseudomonas aeruginosa

<400> SEQUENCE: 86

| | | | | | |
|---|---|---|---|---|---|
| augaaaucgg | uacuccacca | gaucggcaag | accucgcugg | cagccgcgcu | cagcggcgcc | 60 |
| guccugcucu | ccgcccagac | cacccacgcc | gccgcccugu | cggucagcca | gcagccgcug | 120 |
| augcugaucc | agggcgucgc | cccgaacaug | cuggugacuc | ucgacgacuc | gggcaguaug | 180 |
| gcguucgccu | augcgccaga | cagcauuucc | ggcuauggaa | acuauacguu | cuucgcgucg | 240 |
| aacagcuuca | acccgaugua | cuucgauccg | aacacgcaau | acaagcuucc | gaagaaacuc | 300 |
| acacgguga | acggacaggu | acagauccag | gauuauccgg | ccccaacuu | ucccucugcc | 360 |
| uggcgcaaug | gcuucacucg | cagcgggagu | aucaaucugu | cgaacagcua | caaggucacc | 420 |
| aucgaguacg | gcaggggaua | ugauaaggag | ucgacgauaa | aagccgacgc | ugccuacuac | 480 |
| uaugacuuca | cgggcucauc | caguugcaac | cgcaccaauc | aggcaugcua | cacccgccgu | 540 |
| uaugugagca | cagagcaaag | gcagaacuuc | gccaacuggu | auucguucua | ccgcacccgc | 600 |
| gcccuugcca | cucagaccgc | cgccaaccug | gcguucuaca | gccgccuga | aaacgcucgg | 660 |
| gugagcuggc | aauugcugaa | cgacucgaac | ugcaaccaga | ugggcagcgg | cuccagcucc | 720 |
| ggcaacuguu | ucagcaacua | ucuacgggac | uucaccgguc | aacaccgggu | gaacuucuuc | 780 |
| aauuggcugg | aaaaacuuuc | ggucaauggu | gguacgccac | ugcgccaggc | gaugacccgg | 840 |
| gcaggcgagu | uucucaagaa | gaccggcguc | aacggucccu | augccuaucg | cccagggacc | 900 |
| cagaccgcgc | ccgaguacag | uugccggggc | agcuaucaua | uccugaugac | cgacggucuc | 960 |
| uggaacaacg | acucggccaa | cguaggcaau | gccgacagca | ccgcucguaa | ccucccccgac | 1020 |
| gggaagagcu | auagcagcca | gacacccuac | agggacggua | cguucgauac | ccuggccgac | 1080 |
| caggccuucc | auuacugggc | caccgaugcc | cggccggaua | ucgacgacaa | uaucaaaccg | 1140 |
| uacauucccu | acccgaccca | ggccaauccc | ucggcggaau | acuggaauuc | ccgcaacgau | 1200 |
| ccggcaaccu | ggcaacacau | ggugaccuac | acccugggcc | ugggccugac | caccagccuc | 1260 |
| accagccga | gaugggaagg | cuccaccuuu | uccggguggcu | acaacgauau | cguggcuggc | 1320 |
| aaccugagcu | ggccccgcgc | gucgaacaac | gacuccaaca | acgucuacga | ucuguggcac | 1380 |
| gccgcaguga | acucccgggg | cgaguucuuc | agcgccgacu | cgccggacca | acuggucgcg | 1440 |
| gccuuccagg | acauccucaa | ccgaauuucg | ggcaaggacc | ugccggcauc | ccgccccgcc | 1500 |
| aucagcucgu | cccugcagga | agacgacacu | ggcgacaagc | ugaccgcuu | cgccuaccag | 1560 |
| accagcuucg | ccagcgacaa | gaacugggcu | ggcgaccuga | cccgcuacag | ccugaccacc | 1620 |
| caggacaagg | ccaccgugca | gaccaagcug | uggagcgcgc | agagcauccu | cgacgcgaug | 1680 |
| cccaacggug | gagcuggccg | caagaucaug | auggccggau | ccgguaccuc | gggccucaag | 1740 |
| gaguucaccu | ggggcagccu | cagcgccgac | cagcagcggc | aguugaaccg | cgauccggac | 1800 |
| cgcaacgaug | ucgccgacac | caagggccag | gaccgcgugg | ccuuccugcg | cggcgaucgc | 1860 |
| cgcaaggaga | acagcgacaa | cuuccgcacc | cgcaacucga | uccucggcga | uaucaucaac | 1920 |
| uccucgccgg | cgacgucgg | caaggcccag | uaccugaccu | accuggccca | gccgaucgag | 1980 |
| cccagcggua | acuacuccac | guucgcagaa | gcacagaaaa | cccgugcccc | gcggguauac | 2040 |
| gucggcgcca | acgacggcau | gcugcacggu | uucgauaccg | acgguaacga | gaccuucgcg | 2100 |
| uucauccccaa | gcgcggucuu | cgagaagcuc | cacaaguuga | ccgcccgcgg | cuaccagggc | 2160 |
| ggcgcccacc | aguucuacgu | cgacgguucg | ccgguggucg | ccgacgccuu | cuucggcggc | 2220 |

```
gccuggcaua ccgugcugau cggcagccug cgcgccggcg gcaagggccu guucgcccuc    2280
gacgugaccg aucccgccaa caucaagcug cucuggaaaa ucggcgugga ccaggagccc    2340
gaccuuggcu acagcuuccc caaacccacg gucgcccggc ugcacaacgg caagugggcc    2400
guggucaccg gaaacgguua uuccagccug aacgacaagg ccgcgcugcu gaucaucgac    2460
cuggagaccg ggccaucac ccgcaaacug gaagucaccg gcaggaccgg cguacccaac    2520
ggccuaucca gcccucgccu ggcagacaac aacagcgacg cguagccga cuacgccuac    2580
gccggcgacc ugcaaggcaa ccucuggcgc uucgaccuga ucgccggcaa ggucaaccag    2640
gacgauccgu ucagccgagc caacgacggc ccggcgugg ccucgagcuu caggugucu     2700
uucgguggcc agccgcucua uucggcaguc gacuccgccg gcgggcgca agcgaucacc     2760
gccgcgcccu cgcugguucg ccauccgaca cgcaagggcu acaucgugau cuucggguacc   2820
ggcaaguauu ucgagaacgc cgacgcccgg gccgauacca gccgcgccca gacgcucuac    2880
ggcaucuggg accagcaaac caagggcgaa gccgcgggca gcacacccg acugacgcgc     2940
ggcaaccugc agcagcagac ccuggaccuc caggccgacu cgaccuucgc cucgaccgcu    3000
cgcaccauuc gcaucgccag ucagaacccg gucaacuggc ugaacaauga cggcagcacc    3060
aagcaguccg gcugguaucu ggacuucaug gucaacggca cccugaaggg cgagaugcug    3120
aucgaggaca ugaucgccau cggccaggug gugcugcugc aaaccaucac cccgaacgau    3180
gaccccugug ccgacggcgc cagcaacugg accauggcc ucgaucccua uaccggcggu     3240
cgcaccagcu ucaccguguu cgaccuggca cgccagggcg ucguggacuc gaaauccgac    3300
uacagcuaca caagcagaa cgucgcggua uccgguaccg agcagaaagg ccugggaggc    3360
uugacgcuga gcaccaacga acagggcaau ccggaagucu gcuccucggg cgaaugccug   3420
accgugaacc ccgguccgaa cacccgugc cgccagaacu ggcgcccau cgaaggaaag    3480
aacuga                                                                3486
```

<210> SEQ ID NO 87
<211> LENGTH: 3636
<212> TYPE: RNA
<213> ORGANISM: Pseudomonas aeruginosa

<400> SEQUENCE: 87

```
augaagauuc ucgccauccg ccugaagaac cucgccuccc ucgcuggcga gcaggaaauc      60
gacuucaccc gcgaaccgcu guccagcgcc ggccuguucg ccaucaccgg uccgaccggc     120
gccggcaaga gcaccgugcu ggacgcccug ugccuggccc uguucggcag cacgccgcgg     180
cuggaaagca cuucggccag cagcaagguu cccgauggcc ggaacgagcu guccagcaac     240
gacgaacgca accugcugcg ccgcgguugc gccagcggcu acgccgaagu ggauuucguc    300
ggcaucgacg gccaccgcua ucgcccccgc ugggaaaccc ggcgcucccg ggacaaggcg    360
gacggcgccu ugcaaaagag ccagcagagc cuccaggacc uggagaccca gcaaaugcug    420
gcagcgaaca agaaaagcga guuccgcgaa cagcuggagc agaagcucgg ccucaauuuc    480
gcccaguuca cucgcgccgu gcugcuggcc cagagcgaau ucagcgccuu ccucaaggcc    540
agcgacaacg accgcggcgc auugcuggag aaacucaccg acaccggccu guacagccaa    600
uugagcaaag ccgccuauca gcgcgccagc caggccgacg agcagcgcaa gcaacucgag    660
caacgccugg aaggcagccu gccccuggcc gagcaggccc gggccgggcu cgaggcggcg    720
cuggaauccc acgccaggc gcgucuccag gagcaacagg cacugcaacg ucuggaaggc    780
```

| | |
|---|---|
| cagcaacaau gguucaccga ggagcagcgg cugcugcaau ccugcgagca cgcacaaggc | 840 |
| caacuggccg aggccaggca ggccugggac gcccugggcga cggagcggga aacccugcaa | 900 |
| uggcuggagc gccuggcucc gguucgcgga cugaucgaac gccugaagca acucgagcag | 960 |
| gaacuccggc acuccgagca gcagcagcgg cagcgcaccg agcagcaagc cgcgggcacc | 1020 |
| gagcgcuugc aaggauugca ggcccgcuug caggaggcgc gcgagcgcca ggcccaggcc | 1080 |
| gacaaccauc ugcgucaggc ccaggcgccg uugcgcgagg cuuccagcu ggagagcgag | 1140 |
| gccaggcgcc uggagcgaac gcuggccgag cgacaggaac uccaucggca aucgaaccag | 1200 |
| cgccacgccc agcaaagcga cgccgcucgg caacuggaua uggagcagca gcgccauguc | 1260 |
| gcggaacagg cgcaacugca ggcggcauug cgcgacagcc aggcucucgc cgcgcucggc | 1320 |
| gacgccuggg ugacccacca gggccagcuc gccaccuucg ugcaacgucg ccagcgcgcg | 1380 |
| cucgaaagcc aggcgcagcu ccccgagcug gaaaaauccc uggcccacgc cggggaaccg | 1440 |
| cucgaacgcu ugcaggcgca auggaccgcc uccauggca gcgagccgga cgaccuggcg | 1500 |
| gcacgccugg ucgaauugcg ccggcagacc gauagccugg aacgacaaca agcgcuccac | 1560 |
| aaggaauggc aacagguccu cgaccaacgc gccggucugg cucgacgccu gggcgaacuc | 1620 |
| gaccagcgua uggucgagca ggagcaggca uugcucgacc ugaaacgaca aggcagccaa | 1680 |
| ugcgccgagg aggugaaggc ggcggagcag gcccugcagg ucacccgcga guugcuccag | 1740 |
| cgccaacguc uggcccgcag cgccagcguc gagcaacugc gcgccggccu gguggacggc | 1800 |
| gaggccugcc cggucugcgg cagccaggag caucccuauc accauuccga gcaacugcuc | 1860 |
| gccgcccucg ugaacacga cgaccaggag caggucgcg ccgagcaguc ccucgagcgg | 1920 |
| cugcgacaga cccggucgg ucugcgcgag ggcuauucca gccagcggga aagacucaac | 1980 |
| cagagucgcc aggagcagca ggaacugacu ggccaacugg ccgcgcucga ucggcaacug | 2040 |
| gaccaaugga cgcugccgga agaacugcga cuccugcagc cguccgcgca guuggagugg | 2100 |
| cuggcacaac gccuggacga ccuggcaggg cagcgccagc agugccaacg agacuucgac | 2160 |
| cggcugaucg cccgccagcg ccagacccag caauugcagc aggaacugcg ggccgccgag | 2220 |
| acgauccugc aacagcgcca gcaggcgcug acggaacaac ggcagcgcua cgaacauuug | 2280 |
| cagcagcagg ucgaggagga cagccagcaa uugcguccau ugcucuccga cgagcacugg | 2340 |
| cagcgcuggc aggcagaucc gcugcggacu uuccaggcac ucggcgaguc caucgagcaa | 2400 |
| cgccggcagc aacaggcgcg gcuucagcag aucgaacagc gucugcagga gcucaagcag | 2460 |
| cgcugcgaug aaucgagcug gcaacugaag caaagcgacg agcaacgcaa cgaagcccgu | 2520 |
| caggcagagg aaagggccca ggcggaacuc gccgaacuga acggacgccu cggcgcucac | 2580 |
| cugggccagc acgccugcgc ccaggacugg cagcuaucgc uggagcacgc cgcgcaagcg | 2640 |
| gcgcagagcg ccgucgagac gcuccaggcg ccccuggauu cgcugcgcga ggaacaacug | 2700 |
| cgacucgccg aagcccugga acaccugcag cagcaacggc agcgccaaca ggaugaguuc | 2760 |
| cagcgccuuc aggccgacug gcaggccugg cgcgaacgcc aggacaaccu cgacgacagc | 2820 |
| cgccucgacg cccugcucgg ccuuccgag gaacaggcga cgcaauggcg ggagcaauug | 2880 |
| cagcgacugc aagaggagau cacccgccag cagacacugg aagcagagcg ccaggcgcaa | 2940 |
| cugcuccagc aucgccggca gcggccggaa accgaccgcg aggcgcugga agacaaccug | 3000 |
| cggcaacagc gcgaacgccu ggccgccagc gaacaggccu accuggagac cuacagccag | 3060 |
| uugcaggcca acaaccagcg ccgcgagcag agccaggcgc ugccuugccga acuggagcga | 3120 |
| gcccgcgccg aguuccgcag augggggccgc cugaacgaac ugaucgguuc guccagcggc | 3180 |

| | | | | |
|---|---|---|---|---|
| gacaaguucc | gccgcaucgc | ccagggcuac | aaccucgacc | ugcuggugca | gcacagcaac | 3240 |
| gugcaguugc | gccaguuggc | gcggcgcuac | cgccugcagc | gcggcggcag | cgaacugggc | 3300 |
| cugcuggugg | uggacaccga | gaugggcgac | gaacugcgcu | cgguguauuc | gcucuccggc | 3360 |
| ggcgagaccu | uccugauuuc | ccuggcccug | gcgcucggcc | uggccucgau | ggcaucgagc | 3420 |
| aagcugcgca | ucgagucgcu | guucaucgac | gaaggcuucg | gcagccucga | cccggaauuc | 3480 |
| cugcaacugg | cgauggaugc | ccuggacaac | cugcaggccc | agggacgcaa | gguggcggug | 3540 |
| auuucccacg | uccaggaaau | gcacgaacgg | aucccggucc | aggugcgggu | ccagcgcgag | 3600 |
| ggcaacggca | ugagcagccu | gaaggugguc | ggcuga | | | 3636 |

<210> SEQ ID NO 88
<211> LENGTH: 7407
<212> TYPE: RNA
<213> ORGANISM: Pseudomonas aeruginosa

<400> SEQUENCE: 88

| | | | | | | |
|---|---|---|---|---|---|---|
| augucgaucc | aggcgaaagu | uaccccuauc | gaucagagua | uucuucugc | ggcugccguc | 60 |
| gagguuccgg | aaaacgggau | acucaaacuc | ucccagagca | guaaugucgc | gcucgaugue | 120 |
| gcaccggagu | cgguggcggg | auacucgaag | agcgguucgg | accugaucgu | ccagcugaag | 180 |
| accggggaaa | cguccggau | cgccaacuuc | uaugcgaag | gccagccuuc | cagccaacug | 240 |
| uuccuggccg | acaaggacaa | gcugguggcg | guagaucugc | cgccggucgc | ugccgacggg | 300 |
| ccgcugaugg | ccggcuacau | cccgcaggaa | agccuggccg | guucgaguc | gcugaccggc | 360 |
| gccgugugc | ucgguggcau | gagcgcaggg | acugcgcugc | uggucggugc | ggcggccauc | 420 |
| ggcgccgggg | uggcgauuuc | caacagcagc | ggcggcggug | gcggcggcgg | uucuucggug | 480 |
| cccccggaca | ccacuccgcc | gaaggcggcc | agcggccuga | agauagcgcc | ugacggcagc | 540 |
| agcaucagcg | gccaggccga | ggccggcgcg | agcgucggca | ucgauaccaa | uggcgacggc | 600 |
| aagccggacc | ucaccgugau | cgccgaugcc | aacggcaauu | ucaccgcucc | gcugaacccg | 660 |
| ccgcugacca | auggccagac | ggucaccgug | guggucaccg | acccggcugg | caacgccagc | 720 |
| ccgccggccc | aggucaccgc | uccggacacu | accgccccgg | cgccgcuac | cgacgugcag | 780 |
| guggcgccgg | acggcagcag | cgucaccggc | aaggccgaac | ccggcucgac | ggugggcguc | 840 |
| gauaccgacg | gcgacggcca | gccggacacc | accgugguug | ucggcccegg | cggcagcuuc | 900 |
| gagguuccgc | ugaacccgcc | gcugaccaau | ggcgagacgg | ugacggugau | cguuaccgac | 960 |
| ccggccggca | caacagcac | cccggugacc | gucgaggcgc | cggacaccac | cgccccggcg | 1020 |
| ccggccaccg | acgugcaggu | ggcgccggac | ggcagcagcg | ucaccggcaa | cgcagagccg | 1080 |
| ggcgccaccg | ucgugucga | caccgauggc | gacggccagc | cggacaccac | cgugguugguc | 1140 |
| ggucccggcg | gcagcuucga | gguccgcug | aacccgccgc | ugaccaaugg | cgagacgguu | 1200 |
| acggugaucg | uuaccgaccc | ggccggcaac | agcagcaccc | cggucaccgc | cgaagccccc | 1260 |
| gacuucccg | acgcgcccca | ggucaaugcc | agcaacggca | gcguccucag | gguacggcg | 1320 |
| gaagcgggcg | ugaccaucgu | gaucaccgac | ggcaacggca | auccgaucgg | ccagaccagc | 1380 |
| gccgaugcca | acgcaacug | gagcuucacc | cccguuagcc | aacugccgga | ugcaccgug | 1440 |
| gucaaugugg | uggccaggga | cgccgccggc | aacagcagcc | ggcgaccuc | caucaccguc | 1500 |
| gacggcgugg | cgccgaacgc | gccgguggc | gagccgagca | cggcagcga | acucagcggg | 1560 |
| acugccgaac | cgggcagcag | cgugacccug | accgacggca | auggcaaucc | gaucggccag | 1620 |

```
accaccgccg augccaacgg caacuggucu uucacgccgu ccaccccguu gccggacggu    1680
accgguguca acguggaggc cagggaugcc gccggcaaca gcaguccgcc ggccagcguu    1740
accguggaug ccgucgcgcc ggccacgccc accgucgauc cgagcaacgg uacgacccuc    1800
agcggcaccg ccgagccggg caguagcgug acccugaccg acggcaacgg uaacccgaua    1860
gggcagguca ccgccgacgg cagcggcaac uggaccuuca ccccgagcac gccguugccc    1920
aacggcacgg uggucaacgc cacggcuacc gacccguccg gcaacgccag uucgccggcc    1980
agcgucaccg uggacgccgu ggcaccggcc acgccagugg ucaacccgag caacggcacc    2040
acgcucagcg gcaccgccga ccgggcgccc accgugaccc ugaccgaugg caacggcaau    2100
cccaucgggc aggucaccgc cgauggcagc ggcaacugga gcuucacucc gaccacgccg    2160
uugcccaacg gcaccguggu caacgccacg gccaccgacg ccuccggcaa caccagugcg    2220
ggcagcagug ucaccgugga cucgguagcc ccggccacgc cagugaucaa ccccagcaac    2280
ggcaccacgc ucagcggcac cgccgagccg ggcagcagcg ugacucugac cgauggcaac    2340
ggcaacccga uuggccaggu caccgccgac ggcagcggca acuggagcuu caccccgucc    2400
acgccgcugg cggauggaac cguggucaac gccacggcca ccgauccggc gggcaacacc    2460
agcggccagg gcagcaccac cgucgauggc guggcgccga ccacgccgac cgucaaccug    2520
agcaacggca gcagccucag cggcacugcg gaaccgggca gcacggugau ccucaccgac    2580
ggcaacggca auccgaucgc cgaggucacc gccgacggca cggcaacug gaccuacacc    2640 ccguccacgc cgaucgccaa cggcaccgug gucaacgugg uggcccagga cgccgccggc    2700
aauagcagcc cggcgccag cgucaccgug gacucgcagg ccccggcggc uccgguggug    2760 aaccgagca acggcacuac gcucagcggc accgccgagc cgggcgcuac cgugacccug    2820
accgacggca acggcaaccc gauuggccag gucaccgccg acggcagcgg caacuggagc    2880
uucacaccgg gcacgccgcu ggccaacggc accgguguca cgccacggc cagcgacccg    2940 accggcaaua ccagcgcucc ggccagcacc accguggacu cggugggcgcc ggccgcgccg    3000 guggucaauc cgagcaacgg cgcggagauc agcggcaccg ccgaaccggg cgccaccgug    3060
acccugaccg auggcagcgg caauccgauc gggcagguca ccgccgacgg cagcggcaac    3120
uggagcuuca ccccguccac gccgcuggcg gauggaaccg uggucaacgc caccgcuacc    3180
gacccggccg gcaauaccgg cggcagggc agcaccaccg uggacgccau cgcgccggcc    3240
acgccgaccg ucaaccugag caauggcagc agccucagcg gcaccgccga gcgggcagc    3300 acggugauuc ucaccgacgg caacggcaau ccgaucgccg aggucaccgc cgacggcagc    3360
ggcaacugga ccuacacccc guccacgccg aucgccaacg guacugguggu caacguggug    3420 gcccaggacg ccuccgguaa cagcagcccg ccggcgacgg ugaccgucga uuccagcgcg    3480
ccgccggcgc cggugaucaa cccgagcaac ggcgucguca ucagcggcac cgccgaggcc    3540
ggugccacgg ugacccucac cgaugccggc ggcaacccga uagggcaggu caccgccgac    3600
ggcagcggca acuggagcuu cacgccgggc accccgcugg ccaacggcac ggugaucguc    3660
gccacggcca ccgacccgac cggcaauacc ggcccgcagg ccgccaccac gguggacgcg    3720
guggcgccgc cggcgccggu gaucgauccg agcaacggca cgaccaucag cggcaccgcg    3780
gaggccgggg ccaaggugau ccucaccgac ggcaacggca acccgaucgg cgaaccaccc    3840
gccgacggca gcggcaacug gagcuucacg cccggcacgc cgcuggccaa cggcacggug    3900
gucaacgccc uggcccagga cccugcgggc aauaccggcc gcagggcag cacuaccgug    3960 gacgcggugg cgccgaacac gccuguggu caauccgagca acggcaaccu gcucaacggu    4020
```

```
accgccgagc cgggcagcac cgugaccuug accgacggca acggcaaccc gaucggccag   4080
accaccgccg auggcagcgg caacuggagc uucacgcccg gcucgcaacu gcccaacggc   4140
accgguguca acgugaccgc gagcgacgcc gccggcaaua ccagccuucc cgcuaccacg   4200
acgguggauu ccucgcugcc gucgaucccg cagguggauc cgagcaacgg uucggugauc   4260
agcggcaccg cggacgccgg caacaccauc aucaucaccg auggcaacgg caacccgauu   4320
ggccagguca ccgccgacgg cagcggcaac ugguccuuca cuccaggcau cccgcugccg   4380
gauggcacgg uggucaacgu ggugcgcgc agcccaagca augucgacag ugcgccggcg   4440
gugaucacug uggauggcgu ggccccggcg gcgccgguga ucgauccgag caacggcacc   4500
gagauaagcg guaccgcgga ggccggcgcg acggugaucc ucaccgaugg cggcggcaac   4560
ccgaucggcc aggccaccgc cgacggcagc ggcaacugga cguucacccc gagcaccccg   4620
cuggccaacg gcaccgugau caacgccgug gcccaggacc cggccggcaa uaccagcggu   4680
ccggccagcg ucaccgucga ugccaucgcc ccgccggcgc cggugaucaa uccgagcaau   4740
ggagucguca ucagcgguac ggcggaagcc ggggccacgg ugauccucac cgacggcaac   4800
ggcaacccga ucgccaggu caccgccgac ggcagcggca acuggagcuu cacgcccggc   4860
acgccgcugg ccaacggcuc ggugaucaau gcgcuggccc aggacgccgc cggcaacaac   4920
agcagcccca ccagcgccac cgucgacucg cuggcgccag cagccccggu gaucgauccg   4980
agcaacggua gcgugaucgc cgguaccgcc gaggcuggug ccacggugau ccucaccgac   5040
ggcaacggca acccgaucgg ccaggucacc gccgauggca gcggcaacug gagcuucacg   5100
cccggcacgc cgcuguccaa uggcacggug ucaaugcgg uggcccagga cgcugccggc   5160
aacaccagcg gcccggucag caccacggug gacgcggugg ccccggccac cccggugauc   5220
gacccgagca acgguguga acucagcggc accgccgaac ccggcguccg ggugauccuc   5280
accgauggca auggcaaucc gaucggccag acccuugccg acggcagcgg caacuggagc   5340
uucacgccgg gcacgccgcu ggccaacggc acgguggca augccguggc ccaggacccg   5400
gccggcaaua ccagcggccc ggccagcacc acgguggaca cgguggcucc ggccacgccg   5460
gugaucaauc ccagcaacgg cagcgugauc accggcaccg ccgaggucgg cgccaaggug   5520
auccucaccg auggcaacgg caacccgauc ggcgagacca ccgccgacgg caguggcaac   5580
uggaccuuca cccccggcac gccgcuggcc aacgguacgc ugaucaacgc cgucgccgag   5640
gacgccgcgg gcaacgccag cgguccggcc agcaccacgg uggacucggu ggcgccgucc   5700
gcuccgcugc ugagcaucag cgccgacggc gcgcugcuga ccggcaccgc cgagccgaac   5760
agccaggugc gcaucguggu caacggcgac accgccaacc gaucacggu caccgucgac   5820 ggcgccggca acuucagccu gccguucgcg ccgccgcuga ucaccggcga gcugaucgcc   5880
ggggucgccg ucgacgccgc cggcaacguc agcgggccgg ccaccaucaa cgccccggac   5940
cuggcgccgc cgaccaucag cgugccggaa gccgccgaua ccuggaucaa ugccgcggag   6000
aucggcgacg guaccagu cgaugugacg guccgucccga ccaugcaggu cggccaggug   6060
gucacgguca aguucgccgg gcagaacggc uacgaggccg aggucagcca uaccccucacc   6120 gccgcgaca ucgccgccgg caaccugacc cugacccuga cgccucccgg cggcaugggc   6180
ccguucccgg agggugccuc gaccgucacc gccgacauca acggcggcac cgcgucgacc   6240
ccggugccgu ucaccaucga caccauuccg ccggcgaccc cggugcuguc ccuggucggc   6300
aacauccuga ccaucucggc ggagccaggg accgaguuga cggugaccgu cgacgucggc   6360
```

```
gggguugaccg ccaccgccac ggugaccgcc gacaacagcg ggcuggcguc gcugaaccug      6420
cucaccgacc uggacaucga cuucaguugg gaccaguugc ucaaugccca ggugucgguc      6480
gucggacgcg acccggccgg caacccgagc aacacggcga gcaucggcgu cggcaccagc      6540
aucgagcaac cggugaccau cggcaacuuc ggccucgacg ucagcccaa  cccgcugaac      6600 ccgcguuucg guuucagcgg aaccaccgag ccugacucca gcguggugau ccggoucauc      6660 accccggcgu ugaacgucga auugcugccg auccaggcgg auucguccgg aaacuucucg      6720
cugaaccugc ugagcccgac caucucacc  caguuggggc ugaacaucac cgacauccuc      6780
aaccucggcu cgcagaucuc guucaaccug guguccaccg acuccaaugg caacgacagc      6840
gccgccuacg ggaucacccu gaccccaac  ggacugucgc ucaauaucgg ccagaucgau      6900
gucaacggua cuuccggcga cgacgugcug uccggcgcca acggcaguuc ggagcacauc      6960
aacggcggcg acggcagcga ccugaucuuc aacgugggca ccggcgauca cguggugcc       7020 ggcaacggca acgacaccau ccagaucacc gcgaccgauu ucgucagcau cgauggcggc      7080
gccgggcucg acaccuugguc cuggccaac  ggcaucgacc ucgacuacaa cgccgucggc      7140
gucggcacgc ucagcaaccu cgagcgcauc gaccucggca agggcgauuc gggucgcgug      7200
cugaccucga ccgcggcgga gguggaugcc aucaccgaug ccaacaacac guugcagauc      7260
accggcgaga caacgacac  ccugaacgug gugggcgcgg ugaauaccgg uaccacgcaa      7320
cugaucaacg gcauuaccua cgacgucuac accuucggca guaccacccu gcugaucgag      7380
gacaacacgg uacaggucgu ggucuga                                          7407

<210> SEQ ID NO 89
<211> LENGTH: 10608
<212> TYPE: RNA
<213> ORGANISM: Pseudomonas aeruginosa

<400> SEQUENCE: 89
auggacaucc gcagcccgcu gaaccagugc aucgcccugu cccuggccgg caucuuguuc         60
cucaacccga ucgucgccgc ggcggcgggg cuggcgcugg acaaggccgc cggcggcaac        120
accggccugg gccaggcggg caacggccug cccaucguca auaucgccac gcccaacgac        180
gccgggcugu cgaacaacca uuuccgcgac uacaacgucg gcgccaacgg gcugauccuc        240
aacaacgcua ccggcaagac ccagggcuacc cagcucggcg ggaucauccu cggcaacccc        300
aaccucaagg gccaggcggc gcaggugauc ucuaaccagg ucaccggcgg caaccgcagc        360
acccugggcg gcuacaccga ggguggccggg cagucggcgc gggugaucgu cgccaacccg        420
cacggcauca ccugccaggg cugcggcuuc aucaacacgc gcgcgcgcac ccucaccacc        480
ggcaagccga ucauggacgg ccagcgccug gagcgcuucc aggaggacgg cggcgacauc        540
gucgucgaag gcgccgaacu gaacgucggc aaccucgaac aguucgaccu gaucacccgc        600
agcgccaagc ucaacgccaa gcucuacgcg aagaaccuca acaucgucac cggccgcaac        660
gacguccagg ccgacagccu gcaggccacg ccgcgcgccg ccgauggcag cgagaagccg        720
cagcuggcga ucgacagcuc ggcgcugggc gggauguacg ccggggcgau ccgccugguc        780
ggcaccgagc agggcguggg ggucggcucg ccggcgaca  uggccgccag cggcggcgac        840
auccgcaucg acgccagcgg caagcugagu cuggcccagg ccuccagcca gggcgaccug        900 aagaucgcg  cccaggccgu ggagcugaau ggcaagaccu acgccggcgg cagcgccgag        960
auccgcagcg cggaggaacu ggucaaccgg cagagccugg cggcgcgcga acgcaucgug       1020
cuggaggcgg cgcauaucga caacgccggg gugaucgaag ccggcgucga gccagacgag       1080
```

```
cgacgcaacg cgcgcggcga ccucgagcug cgcagcggca cccugcgcaa cgccggcagc    1140
cugguggcca gccgcgcgcu ggaagcgaag gcgagccagg cgcuggacaa ccagggcggc    1200
agccugaagg gggcgaccgu ccggucgacg gccgggcacc uggacaaccg uggcggcaag    1260
cugcucgccg agggcgaacu gcgggucgag gcgagcagcc uggacaaccg ccaggacggc    1320
cuguugcaga gccgggaccg cgccgugguc aagacccgug gcgaucucga caaccguggc    1380
ggccagguga ucggccugaa cgaucuggag gucggcgcgg cgacgcucga caacggccag    1440
caaggccugc ucggcagcca gcaguccacc cgcgucagcg cccaggcgcu ggucaaccgg    1500
ggggacggca aagucuccgg caagcgcguc gaggcucgcg ucgguagccu cgacaaucgc    1560
ggcggcaagc ugaucggcga cgaccugcug gugguccgcca gcggugccau cgacaaccgc    1620
cucggcuugu ucuccgcagc caaccgccuc gaccugcggg cgcgcagccu ggacaacagc    1680
ggcaagggca cgcugagcag ccggggcggc cuggaggucca gcccggccgc ccugcuggac    1740
aaccgcgaug aaggcaaccu gcucagcagg gcgcgcagc gcgugacggu ggggcaacug    1800
gacaaccgcg ccggcggccu gcugucgagc cgcagcgagu ugaacgucca cggcgccagc    1860 cuggacaaccc guggcggcgu gcuggugcc gacgccggcc ugagcgccac gggaggcgcc    1920 uucgacaaccc gcgacggcgg cagcgccagc ggcaaggcug gcgugcgcgu ggaggucgcc    1980
agccugcgca cgaccagggg uggcaagcug cucagcgaug gccgccugga ccucgcagcg    2040
aacgccgucg gcaacgccgg agggcguauc gccgccaagg gcgaccugca ggcgacgcuu    2100
ggcagccugg cccagcaagg uggcgaacug gucagcgaaa agaccuugaa ggucgcggcc    2160
gacacgcucg acaacagcca guccgggcug aucgccgcga auggcggcau cgcuaucgag    2220
gcgcggcagg ucgacaaccg cgccggcgag auuuccagca ccucgaaggu cgccgugaac    2280
gcccgcgagc aacuggacaa ccgcggcggc aaggucaucg cgacagcgg ccugcgccuc    2340 accgugcagc gccugcugaa ccaggccaag ggggucuggg ccgggcgcga cggccugagc    2400
cuggacggcg gcgaacuguu caacggcgac ggcggucggc ucgacagcca gaacagccug    2460
agcgugagcc ucggcggcgu gcuggacaac cagggcggcg cgcuggucag cgaaggcagc    2520
cugacggcgc gcgccgcgcg ccuggacaac cguggcggga ccuucuccag cgccggugcg    2580
cuggcgcuga ccagccaggc cgcgcuggac aaccagggcg gcaggcugcu cagcgaugcc    2640
ggcgugacgc ugcagggcgc cagccucgac aacagccguu ccggcgugau cagcgccaag    2700
ggcgcggugg auauccgcac cggcguacug gacaacagcc gcaacggcgg caucggcagc    2760
aacgccggca ucacccuggu ggccgccgcg cuggacaacg ccagcagggg ccggucagc    2820 gccaagggcc ugcucgacgc caaccugaaa ggccucgacc agcgcggagg cggcguccug    2880
aucagcgaaa ccggcgucac ccucgaccuc aauggcggca cgcuggucaa ccgcgacggc    2940
ggccugaucg ccacgcccgg cgcgcugcug cugcgccagc ucgcgcgcgu ggacaacggc    3000
gccgcggggg aaaucuccag cgaccgcgcc uucaccccuucg ccgccccag ccuggacaac    3060 cgcggcgggc gccugaucgg cgccgccaac cugacccugc gcaucgccca ggccuggac    3120 aacagccugg ccgggugau cuccggcgcc gccggccugg acaucgcggc cgcucgcccug    3180 gacaacagcg ccaagggcac ccuggccagc cgcgccggca ucgaccugcg cgucgauggc    3240
gcgcuggaca accacgccga aggcaccguc uccggcgcccc gccgacgcu cgccagcgcc    3300 ucgcuggaca acagcggcaa gggcugcuc uccggcaacg ccggccugag cgucgccacu    3360
ggcgcgcugg acaacgccga ggguggccag uugaucagcc agggcguccu ggacgucagc    3420
```

-continued

```
agcgccgacc ucgacaaccg uggcggcgcc cucaguggca agcagucgcu gcgccugagc   3480
gccgccaacc uggacaaccg uggcggccug cucaccagcg acggcgaacu ggaacugacg   3540
gcagggcgcg ucgauuccgc cgacggcggc gaaaucuccg cccggggcga ccugcgccug   3600
acggucgagc gccuggugca acgccagggc cggcuggugc gcgagcgcgg cgucagucuc   3660
gaccugcggg gcggcgaccu ggacaaccag ggcggccuga ucagugcccg cggcccgcug   3720
agcaucgagc ggcugagcgu ccucgacaac cgccagggcg gcgagauuuc cagcagcag    3780 ggcuucgagc ugcuggccag gcgcaucgac aacggccagc aggggcgcau caucagcgcc   3840
gggaaacugc gccuagacgc cgacgcgcug ggcaacgccg cgccggccu gcucuccgga    3900 uggcagggcc ugacggugac aggcgggagc cuggacaaca gcgccggcgg cacccuuucg   3960
agcaaggacg gcgagcuggc caucagccuc ggcggcgcgc uggacaacca cggccagggc   4020
gcgcugguca gcaagggcgc gcaacggauc gacgccgcca gccuggauaa cgcccagggc   4080
auugucuccg gcgaaagcga cgugacccug agcaucgccg ggaagcugga caacggccag   4140
ggcggccugg ucucggcgca gcgcgcgcug agcuucgagc gcgacauac gcugcugaac    4200 aacgccggcg gccggaucaa cggcggcagc cugcugcuca agggcgccag ccuggauaac   4260
agcgacggca aguugaucag ccagggccgg cucgacgcca uccucggcgg cgcccugguc   4320
aacaccggcg cggcgcgccu ggccagcggc ggcgaccugc ugcugcgcag cgccagcguc   4380
gacaaccgcg cggcaagcu ggucagccag gggcugcugg agaucagcgc cggcagccuc    4440
gacaacagcg ccuccggcac ccucgccagc caggccggca ugagccugcg ccugggcggc   4500 ggcgccugc gcaaccagca ggacggccug aucuucagcc aggccggcgc ccucgaugug   4560
caggccggca gccuggacaa ccgccagggc acgcuccagg cccagggcga caaccggcug   4620
cguaucggcg gcgcgcugga caaccagggc ggccgccugg acagccgggc cggcaaccuc   4680
gaccugcaga gcggcagccu cgacaacggc gccggcggcg ugcucaacag cgccaagggu   4740
uggcugaagc uggucaccgg gcuguucgac aacagcgccg cgucaccca ggcgcagucg    4800 cuggagauuc gcgccgggca aggcgugcgc aaccagcagg gccaccucuc ggcgcugggc   4860
ggcgacaacc gcaucgucac cgccgacuuc gacaaccagg gcggcggccu cuacgccagc   4920
ggccugcuca gccucgacgg ccagcgcuuc cucaaccagg gcggcggc gggccagggc    4980 ggcaaggucg gcgccgggcg caucgacuuc agccuggccg gcgcgcuggc caaccgcuuc   5040
ggccaguugg aaagcgaaag cgagcugcac cugcgcgccg ccgcgaucga caacagcggc   5100
ggcagccugc gcgccucgg ccgcagcggc agcacgcggu uggucgcugg cggccugaac    5160
aacgccuacg gcgugcugga aagcgccaac caggaccucg accugcaacu gggcagccug   5220
gccaacgccg gugggcgcau ccuccacacc ggcaauggca ccuucggccu ggauuccggg   5280 cagguagaucc gcgccggcgg cgaacugacc accaauggcu gcuggacau ccgcgccagc    5340 gaauggacca acagcagcgu gcugcaagcc ggacgccuga accuggacau cggcaccuuc   5400
cgccagacgg ccgagggcaa gcuguuggcg gugcaguccu ucacuggccg cggcggcgac   5460
uggagcaacg acggccugcu ggccagcgac ggcagcuucc gccucgaccu gagcggcggc   5520
uaccguggca acgccgcgc caccagccuc ggcgacuucg cccugaacgc cgccagccuc    5580
gaccucggca acgccgccag cccucgccggc ggugccaaug ucacgcucgg cgccggcaac   5640
cugcugguca accgugggcg gaucaccgcc gccggcgacc ucguggcag cgccgcgagc   5700 cugaacaacu acggcacccu ggggcggcggc ggcaaccugc gauugaacgc gcccgcccug   5760
cucaacgagc gcgggutugcu guucagguggc gccgacauga cccugcgcgc cggcgacauc   5820
```

-continued

```
accaaccucu acggggaugu guacagccuc ggcaggcugg auaucgcccg cgacgaugcg    5880
ggcaaccgug ccgccagccu gcgcaaccuu uccgggguga ucgagagcgg caaggacuuc    5940
agccugcgug ccagccugau cgagaaccgu cgcgccgugc uggaaagcaa gucgggccug    6000
uacaccgcga agauggagca gaccgccugc aucgaaggcg ucaacgcggg cgacugcagc    6060
ggcaagcgca acgccaucug gaccaucacc cagcgcgaca agaccgaggu caccgccagc    6120
agcgccaugg ggcaacugcu ggccggaggc gacuucgcca ucgacggcgg cacccugaac    6180
aaccuuucca gucugaucgg cagcggcggc aaccucaccg ccaaccucga aguccucgac    6240
aaccagggcc uggaaaccgg cgagcuggaa accauccgcg ugcugcguac cgcucgcggc    6300
ggcgauaucg gcggcaucga ccagaagucg cgcaacuuca ccaaccucua cugguaccag    6360
agcgccaauu ucgacccggc gcgcgcgggc gagaucccgc ccgcgcucaa cgcgauccuc    6420
agcgacuggu ccuucgagua cgaauucccg agcaaggggc cgaccccgau cagcaguggc    6480
gaccaguccu acgcagcggu gauccaggcc gccggcgacg ucacgucaa ugccagcacg    6540 cgcaucgaca acggcgucac ccgcccccggc uacaccuucg ucggcagcgg ccgccaggug    6600
ggcgacagcg cggugggcgg cagcggggguu ucgguggucg ugccgcugac cucgcaacug    6660
ccgcccgacc uggcgcggcg ccaggucaac ccgguuaccc ugcccggcuu cagccugccc    6720
cagggugaca acggccuguu ccgucucagc ucgcgcuuug ccgaggacgg caauggcagc    6780
gccgcgcucg gugccggcgc cgaccgcacc cagggcggua gcggcgucuc ggucggccag    6840
caaggcgccg gcaacgccgc cgguaccugg cagggccagg gcgugcgagu cgacggccug    6900
gcuggcgcgg ccaacgucca gggucagggc ggcagcacgc ucggcgguag ccugccgggc    6960
gucgcccggg uccagggcgu gccggcaac gccacgccga gcgccagcca caaguaccug    7020
aucgagacca cccggcgcu caccgaacug aagcaguucc ucaacucgga cuaccugcuc    7080
agcggccugg gcaugaaccc ggacgauagc aagaagcguc ucggcgacgg ucucuacgag    7140
cagcggcuga uccgcgacgc gguggugcg cgcaccggcc agcgcuacau cgacgggcug    7200
agcagcgacg aggcgcuguu ccgcuaccug auggacaacg ccaucgcuua caaggaccaa    7260
cugcaccugc aacuggugu gggccugagc gcggagcaga uggcggcgcu gacccacgac    7320
aucgucuggc uggaagaggu cgaggugaac ggcgagaagg uccucgcgcc ggugguguac    7380
cuggcccagg cggagggucg gcuggcaccc aacggugcgc ugauccaggg ccgcgacgug    7440
aagcugguga gcggcggcga ccugcauaac gucggcaccc ugcgcgcgcg aacgaccuc    7500 ucggcgacgg ccgacaaccu cgacaacagc ggccugaucg aggccggcaa gcgccucgac    7560
cugcucgccg gcgacucgau ccgcaaccgc cagggcgggg ucaucgccgg gcgugacgug    7620
agccucaccg cgcugaccgg cgacguaauc aacgaacgca gcgugacccg cuacgacagc    7680
gcgcucgacg gccgcaccug ggaacgcagc uucgccgaca gcgccgcgcg ggcggaggcg    7740
gcgaacagcu ugaacgucca ggccggacgc gacaucgcca accucggcgg ggugcugcag    7800
agccgcggcg accucagccu cgacgccgga gcgacgucca ccgucgccgc cgucgaggac    7860
cgccagggcc agacccgcug gagcacgucg cggcuccaga gcugacccca gcucggcgcc    7920
gaagucagcc ccgggcggga ccugaacguc agcgccggcc gcgacuugac ggcgguggcc    7980
agcacccucg aagcgcgccg cgacaucgcc cucuccgccg ggcgcgacgu gacccuggcg    8040
gcggcggcga acgaggagca ugccuacagc aagaccagga aggucaccua ccaggaagac    8100
aaggucgccc agcaaggcac ccgcguggac gccggcggcg accuggcgau caaugccgga    8160
```

```
caggaccugc gccugaucgc gagccaggcc agcgccggcg acgaggccua ccuggnggcc    8220
ggcgacaagc uggaacugcu ggccgccaac gacagcaacu acuaccugua cgacaagaag    8280
aagaaaggcg acuucggccg caaggaaacc cggcgcgacg aagucaccga cgucaaggcg    8340
gugggcagca agaucagcag cggcggcgac cucacccugc ucagcggcgg cgaccagacc    8400
uaccagggcg cgaagcugga aucgggcaac gaccuggcca ucgucagcgg cggcgcggug    8460
accuucgagg cggugaagga ccugcaccag gaaagccacg agaagagcaa gggcgaccug    8520
gcguggaaca gcgccaaggg gaaagggcag accgaugaaa cgcuucggca gacccagauc    8580 gugggcccagg ggaaucuggc gaucaaggcc guggaagggc ugaagaucga ccucaagcau    8640
aucgaccaga agaccguaag ccagaccauc gacgcgaugg ugcaggcgga uccgcaacug    8700
gcguggcuga aggaggccga gcagcgcggg gaugggacu ggcgcauggu gcaggaggug    8760
cacgauagcu ggaaguacag caacucgggc augggccgg cgacgcagau cgcugucgcc    8820
aucgcggcgg cagccaucgg uggcauggcg cagcgggag cgcucagugg ucaggagug    8880 ggugccagua gcuucgccau gggcgcagga guugugcgg caggaagccu gucgggcacg    8940
gcagcgguca gccugaucaa caacaagggc gaucucggga aggugcugaa agacagcuuc    9000
aguagugaca gucugaagca gauugcuauu gcgagccuga ccgggggggu gacggcugag    9060
uacuucgacg ggauucuuca gaccaagacu gauccgcuua cuggaaaggu cacgguagac    9120
cucagcagcc uaucuggugu uggucgcuuc gcugccaauc aggcgaugca gaacgcuaca    9180
uccacuguac ugagccaggc cuugggccag ggcgggagcc ugaacgaggc gcugaagagc    9240
gcgcucuaca acaguuucgc ggcggcaggu uucaacuucg ucggcgauau cggccaggaa    9300
uacagccuga agccaggcga uccuucgaug gugaccaugc acgcccgau ggguggccug    9360 gcggcgcagg ucagcgguggg cgauuucgcc acgggcgccg cggcggcugg cgccaaugaa    9420
gcgcuggugg ccaagcuaga ccaggccuuc aagagcuuga gcccugagaa ccgugaagcc    9480
auggucacua uggggucgca auugguggu guucuggcug cggcguacg cgauccugau    9540 gugacaggca aagcucugga aagcgcugcu ugggauagcga agaacucgac gcaauacaac    9600
uuccucaacc aucaggaugu ggccgaucug gauaugccu ugcagaaaug caagucccag    9660
ggaaauugcc gucagguaga ggaagaguuc aaggcgcgua gcgacgagaa ccggcggagg    9720
uugaauggcu gcguggcugu ggguaauugc gcggagauuc gucggagau cgaucgcggg    9780 ucuacggcuc ucaacgagcu gguggcccgg caggaaacag cuaauccggg aggaagugac    9840
agcgauauag ccuacgguuu ccugauggc cgaaauguug ucgacuggac gacgcuggu    9900 caguugcacc uggagcagac cgccaaccuc uggaggaacg guauccaca guggcagaag    9960 gaagucggug cauaccuaga ccagacgggg uucaauccgu ucggaaucgg cguuccggca   10020
augggcggug ccgcuggcaa gguaacggcc aaggcgcuca ugaaugcgcu gaaggcggga   10080
gaguugccca aggagaggu ggccccagga aaggcuaauc ugccuaccau uggggcguug   10140
gcggaugcug aggcggaau gccuuauacc cauccaguua agcucgccgc aaaagcgacu   10200
gggacagcag ggaagauuaa gauugaagcc ggcgcaauac cugacgcaaa ugaaguacgu   10260
gcaggacaag gguaucugg ucuugggguac gauguuacgc accaaccac ugcgucagcu   10320 aaagguauuc aagggcagcg aacugcggac uugcauguug auggacucgg uuccauugau   10380
guguaucgcg aagaaucu ugauccgaca aagauaguuc gagcgauaga gaagagucg   10440 aaucaagccg gcgagucuuu ggugcaggcg gacuugccaa gcacgacau gucgccauu   10500 gcugcucgua ugugggggaa gacuaacgcg cagaguauaa aaacuauauu uuccagaaa   10560
```
ccagacggau cauugguccg auuugaucga ccugcuggag gaggcuga   10608

<210> SEQ ID NO 90
<211> LENGTH: 16884
<212> TYPE: RNA
<213> ORGANISM: Pseudomonas aeruginosa

<400> SEQUENCE: 90

| | | | | | |
|---|---|---|---|---|---|
| auggacaucc | gcagcccgcu | gaaccagugc | aucgcccugu | ccuggccgg | cauccuguuc | 60 |
| cucaacccga | ucgucgccgc | ggcggcgggg | cuggcgcugg | acaaggccgc | cggcggcaac | 120 |
| accggccugg | gccaggcggg | caacggcgug | cccaucguca | auaucgccac | gcccaacggc | 180 |
| gccgggcugu | cgaacaacca | uuuccgcgac | uacaacgucg | gcgccaacgg | gcugauccuc | 240 |
| aacaacgcca | ccggcaagac | ccaggguacc | cagcucggcg | ggaucauccu | cggcaaccc | 300 |
| aaccucaagg | gccaggcggc | gcaggugauc | cucaaccagg | ucaccggcgg | caaccgcagc | 360 |
| acccuggccg | gcuacaccga | gguggccggg | cagucggcgc | gggugaucgu | cgccaacccg | 420 |
| cacggcauca | ccugccaggg | cugcggcuuc | aucaacacgc | cgcgcgcgac | ccucaccacc | 480 |
| ggcaagccga | ucauggacgg | ccagcgccug | gagcgcuucc | aggugaacgg | cggcgacauc | 540 |
| gucgucgaag | gcgccgaacu | gaacgucggc | aaccucgaac | aguucgaccu | gaucacccgc | 600 |
| agcgccaagc | ucaacgccaa | gcucuacgcg | aagaaccuca | acaucgucac | cggccgcaac | 660 |
| gacguccagg | ccgacagccu | gcaggccacg | ccgcgcgccg | ccgauggcag | cgagaagcca | 720 |
| caacuggcga | ucgacagcuc | ggcgcugggc | gggauguacg | ccggggcgau | ccgccugguc | 780 |
| ggcaccgagc | agggcgugg | ggugaagcug | gccggcgaca | uggccgccag | cggcggcgac | 840 |
| auccgcaucg | acgccagcgg | caagcugagc | cuggcccagg | ccuccagcca | gggcgaccug | 900 |
| aagaucgcgg | cccaggccgu | ggagcugaac | ggcaagaccu | acgccggcgg | cagcgccgag | 960 |
| auucgcagcg | cggaggaacu | ggucaaccgg | cagagccugg | cggcgcgcga | acgcaucgcg | 1020 |
| cuggaggcgg | cgcauaucga | caacgccggg | gugaucgaag | ccggcgucga | gccagacgag | 1080 |
| cgacgcaacg | cgcguggcga | ccucgagcug | cgcagcggca | cccugcgcaa | cgccggcagc | 1140 |
| cugguggcca | gccgcgcgcu | ggaagcgaag | gcgaccagg | cgcuggacaa | ccagggcggc | 1200 |
| agccugaagg | gggcgaccgu | ccgggucgac | ggcggacacc | uggacaaccg | uggcggcaag | 1260 |
| cugcucgccg | agggcgaacu | gcgggucgag | gcgagcagcc | uggacaaccg | ccaggacggc | 1320 |
| cuguugcaga | gccgggaccg | cgccgugguc | aagacccgug | gcgaucucga | caaccguggc | 1380 |
| ggccaggucg | ucggucugaa | cgaacugcag | guccaggcug | ccgcacugga | caaucgcagu | 1440 |
| gccggucucc | uuccagcaa | gggagacaug | gacaucgagu | cgcucgucu | ggacaacagu | 1500 |
| gcgggcggca | agcuggucag | cgagcgccgu | acgcuccuga | aggcggaucg | gcucgauaau | 1560 |
| cgcagcgguc | gcauugucgc | cggccaggau | cucgacuuga | gcucucgguu | gaucgacaac | 1620 |
| cgagcgggcg | auaucuccag | cacgucgagg | gugguggcga | gcgcucgcga | acaguuggac | 1680 |
| aaccgcggug | gcaagaucgu | cggugacagu | ggccuggaca | ucacaacgcc | acgcaugcuc | 1740 |
| aaccaggaca | aggggguacu | cgccagccgc | gaugggcugc | gccugagugc | uacggaguug | 1800 |
| uucaacggcg | cgggggggccu | gcugccagc | cagaagggua | ucgacgucuc | ccuggccggu | 1860 |
| gcguucgaua | accaggccgg | cagccuggac | agccggggcu | uccugacggu | gaagucagcc | 1920 |
| uggcucgaca | accagggcgg | uacgcuaucc | agcgcagggg | cauuggcagu | gaccagccag | 1980 |
| ggcgcccuga | acaaucaggg | cggcagacug | gcgagcgacg | ccggacuuag | cuugagcagc | 2040 |

```
gccagccucg acaacagcca ggccggugcg aucaguggca aggggggccgu ggagauucgu    2100 accggcaacc ugaacaacag ccggaaagcc aguaucggca gcgaugcggg acucacccug    2160
gucgccgcuc ggguagacaa cagccaggcg ggccggaucg ccgccaaggg ugugaucgau    2220
gcggaucucc aagggcugga ccagcaugac aggggcaacc uggucagcga uaccggcauc    2280
acgcucgauc ugaacaaggg aagccugguc aaucgcgcuc aaggccugau cgccacgccu    2340
ggcaccuugc uccugcgcca acucggcgug uggacaacaa gcgguggga aaucuccagc    2400 gaccgcgcgu ucacucuugc caccuccgcg uugaacaacc agggggacg ccugcucagc     2460 ggcggagccc ugaccuugcg uaucgcgcag gcccuggaca acagccucga ggggauugu c   2520 uccggugcug gaggucugga uauccaggca uucguccugg caaccguag uggcuccauc     2580 ggcagcaagg gcgccaucga uaucggugug acccgccugg aaaacgacgc uggcacacug    2640
aucgcugaac gcggccugaa gcugguagcc gaugaggcga acaguccaa ggggcguauc     2700 gccgccaaug uagccugca ugccaagguu ggcacgcuga gccagaaggg aggagaacug     2760
accagucagg acucgcugac ucucgaccug gcauccuaa acaauaacgc uggccguauc     2820
gcuggcaacc agggcgugga caucacggcc cggcaggug acaacagcgu cggcgagauu     2880
gccagccagg gcguggugge gcugaaccuc acugagcagc uggacaaccg uggcggcaag    2940
aucgucggug acaguggucu gggcaucacc gcgccgcacg ugcucaacca ggacaagggg    3000
guacucgcca gccgcgaugg gcugcgccug agugcuacgg aguuguucaa cggcgcgggg    3060
ggccugcugu ccagccagaa ggguaucgac gucucccugg ccggugcguu cgauaaccag    3120
gccggcagcc uggacagccg ggcuccug acgugaagu cagccuggcu cgacaaccag      3180
ggcgguacgc uauccagcgc aggggcauug gcagugacca gccagggcgc ccugaacaau    3240
cagggcggca gacuggcgag cgacgccgga cuuagcuuga gcagcgccag ccucgacaac    3300
agccaggccg gugcgaucag uggcaagggg gccguggaga uucguaccgg caaccugaac    3360
aacagccgga aagccaguau cggcagcgau gcgggacuca cccugucgc cgcucgggua    3420 gacaacagcc aggcgggccg gaucgcugcc aagggugcga ucgaugcggc ucuccagggg   3480
uuggaccagc augacagggg cagccugguc agcgauaccg gcaucacgcu cgaucugaac    3540
aagggaagcc uggucaaucg cgcucaaggc cugaucgcca cgccuggcac cuugcuucug    3600
cgccaacucg gcguggugga acagcggu ggggaaaucu ccagcgaccg cgcguucacu     3660
cuugccaccu ccgcguugaa caaccagggu ggacgccugc ucagcggugg agcccugacc    3720
uugcguaucg cgcaggcccu ggacaacagc cucgagggga uugucuccgg cgccggaggu    3780
cuggauaucc aggcauucgu ccuggacaac cguaguggcu ccaucggcag caagggcgcc    3840
aucgauaucg ugugacccg ccuggaaaac gacgcuggca cgcugaucgc cgaacgcggc    3900
cugaagcugg cggccgauga ggcgaacaac uccaagggc guaucgucgc caaggaugaa    3960 cugccgugccaa acucggugc gcuggugcag aacgggggag agcugacgac ucagggcgcg   4020
cuggcccucg acgccgacaa agucgacaac ggccuggcu caucgccgg caaccgaggu    4080 gugucaucg augcccggca ggugacaac cgugccggcg agauugccag ccagggcgug    4140
gcgacgcuga aucucacuga gcaacuggac aaccgugggc gcaaagucgu ugcugacagu    4200
ggucugggca ucaccgcgcc acgcgugcuc aaccaggaca agggaguaau cgccagccgc    4260
gaugggcugc gccugagugg uaccgaauug uucaauggca augccggacu gcucagcagu    4320
cagagacaua uagaggucac ucuggacggc gucggaca ucagggcaa gggcgcgcug      4380 cucagcgacg guacccugac ggugagcgcc gggcgcauac acaaccagga cgccacucug    4440
```

```
uccagcgccg gugcgcugag acugagcagc caggaggcgg uggacaaccg uggcggcaag    4500 uugguigacgg acuccagccu gcgccugacc agcgccagcc uggacaacag ccgaucaggg    4560
aucaucagug ccaacgcugc ggcggagauc cauaccgggg uucugaacaa cagccagaaa    4620
ggcaaucuug gcaguaauga cgggcucggc cugauugcua cugaggugga uaacagccag    4680
gaaggucgga ucacugccaa aggcaugauc gacgcaaaua ucaagggacu cgaucagcag    4740
ggcaaagggc ggcuggucag uaaugccggc aucauacucg accugaacga gggaacccug    4800
gccaauggcg cucagggccu gaucgccacg ccuggaaccu ugcccugcg ccaacucggc     4860 augguggaca cagcggcgg ggaaauuucc agcgaccgag ccuucacacu caccaccucc     4920
gcgcugacca accaggguigg ccgccugcgc agcggcggug uacugacguu gcgcaucgcc    4980
caggcucugg acaacagccu cgaaggliguu cucuccggca ccggaggccu ggauauccgg    5040
gcgcuugccc uggacaaccg caguiggcucc aucggcagca agggcgccgu cgauaucgac    5100 guglucccguu uggaaaacga ugacggcgac cugculuagcg aaggucgucu gaaacugacu    5160
gccgagcgag cgaacagugu caggggacgg aucgcggcca ggggugaccu gcacgccagc    5220
gugacagccu uuaaccaggc ggglguggcgaa uugagcagcg agggugcgcu gaugcucgag    5280
gccgauagcc ucgacaaccg cagcggcggu cugglucagug cugauggcaa ccugaccgluu    5340 uccgcccgga ggaucgacaa ccgugcgggc gaaaucgcca gcccgggcca ggugacacug    5400
gacgucgccg agcaguugga caaccgaggc ggcaaggcca ucggcgauag cggacuucgc    5460
cucgccgcgc cacggguiacu caaccaggac ggcgggguac ucgccagucg ugaluggggcug    5520 cgccugaaug gcgccgaacu guucaauggc aacggcggcc ugcucagcag ccagcaaagc    5580
aucgacguca uucuggacgg cgualuiggggc aaucaggcag gcagcuugag cagccaggga    5640
cgccugagcg ugaagagcgg ucggcuggac aaccagggcg gugcagucuc cagcgccggg    5700
accuugucgc uuuccagcca ggguigcguug aacaaccagg ggggcagggu ggucaccgac    5760
gccggugccg uccugcgcag cgccagcccluc gacaauagcc agggcggcau cgucagcgcc    5820 aaggggggccg cggagaluccg uacuggcagc cucaacaaua gccagaaggg cggcauaggc    5880 agcggulgccg ggcucgcgcu ggucgcggac cugguggaca cagccagaa cggccggaluc    5940 acugccaagg gugcgaucga ugccaaccug aaggggcugg aucagcaggg cagcggcagg    6000 cugglucagcg auacgccau cgcgcucgau cugcgcgggg gagaacuggu caaccgugcu    6060 cagggccuga lucgccacgcc uggagccuug cugcugcggc aacggggigu cguggacaac    6120 agluggcggug gcgagaucuc cagcgaucga agcuuuaccc ucgccgcgac cgcgcugagc    6180
aaccggggug gccgcgugau cagcggcgac ucccugaccc ugcgcaucgc ccaggcacug    6240
gacaacagcc uccaaggcgu ucuuccgcaa agcggagggc uggaluigucgc ugcacucguc    6300 uucgacaacc auagcggcau cgluugcuagc aagggcgaua cacacaucgg ggugaaccgc    6360 cuggagaacaa aggcaggccg cguggucagc gaaggccccc uggaucugac cgccaagcag    6420
gugagcagcg ccaaggggcg cauugccgcg aagggcgauc ugcaggucac gguuggcacc    6480
cuggagcagc aggguggaga acuggccagu caggggacgc ugacucucga cgccgauagc    6540 cuggaluaacc gcaauggcgg ccuggugagc gccgauggcg ggucaccgc cgaggcacgc     6600 cagaucgaua accgcgglugg ggaaauaucc agcguggcca agguggcucu ggclugluccgg    6660 gaacaacugg acaaccgggg gggcaagglug aucggcgaca gugagcugag ccuaaccgug    6720
cagcgccugc ugaaccaggc caagggglgug cucgccagluc gcgauggauu gcaccluggac    6780
```

```
ggcgcggaac ugcucaaugg cgauggcggc cugcucagca gccaacgccu gguggaugua   6840
acgcucagug gugcauugga caaccagggg agcggugcac uggucagcga agagucgcug   6900
acagugaagg ccgaccaggu caauaaccag gcggggacuu ucccagugc ggguagccug   6960 cucguuacca gccggggcga guugaacaac cagguggca gguuggugac cgaugcugga    7020
gccacccuga acagcacugg cuucgacaac agccgugcgg gccggucag ugcgaaaggg    7080 gcuguggcca uucguaccgg agcccugaac aacagucaga agggauccau uggcggcaau   7140
acgggcguca cccuggucgc cggguugguc gacaacggcc gggaaggacg gaucagcacc   7200
aaggguacgc ucgacgccaa ccugaaaggg uugcuucagc agggggagg cucgcuggcc    7260 ggcgagcgcg gugucacccu cgaccucaac gguggcaccc uggacaacca cgaccucggu   7320
cugguuucaa cgccggcgc gcuccugcug cgccaacucg gcauggugga caacagcguc    7380
ggcggagaga uaccagcga ccgugcuuuu acccucgccg ccaacacacu gaacaaucag    7440
ggcgggcggc ugaucagcag cgaagcuuug acccugcgca ucgccaagac acuggacaac   7500
agucucaagg ggcagguccu ggcgaccgac ggacuggcca ucgagucuca ggucuuggac   7560
aaccgugcgg gaaccaucgg cagcaagggu gaugcccgua ucagcgugac cagcccggac   7620
aacgccgaac aaggcagccu ggugagugaa ggccgccugg agcuuguagc cgaccaggug   7680
agcaacggca accaaggccg uaucgccgcc agaggcgugc uggaggcggc ggucgguacg   7740
cugcuccagc aaggcggcga acuggucagc caggggagcc uggaccuucg cgccgacacg   7800
cucgacaaca gccagucogg gcugaucgcc gcgaauggcg gcaucgcuau cgaggcgcgg   7860
caggucgaca accgcgccgg cgagauuucc agcaccucga aggucgccgu gaacgccgc   7920 gagcaacugg acaaccgcgg cggcaaagguc aucggcgaca gcggccugcg ccucaccgug  7980
cagccccugc ugaaccaggc caagggggug cuggccgggc gcgacggccu gagccuggac   8040
ggcggcgaac uguucaacgg cgacggcggu cggcucgaca gccagaacag ccugagcgug   8100
agccucggcg gcgugcugga caaccagggc ggcgcgcugg ucagcgaagg cagccugacg   8160
gcgcgcgccg cgcgccugga caaccgugge gggaccuucu ccagcgccgg ugcgcuggcg   8220
cugaccagcc aggccgugcu ggacaaccag ggcggcaggc ugcucagcga ugccggugug   8280
acgcugaagg gcgccagccu cgacaacagc cguuccggcg ugaucagcgc caagggagcg   8340
guggauaucc gcaccggcgu acuggacaac agccgcaacg gcggcaucgg cagcaacgcc   8400
ggcaucaccc ugguggccgc ccggcuggac aacggccagc agggccgggu cagcgccaag   8460
ggccugcucg acgccaaccu gaaaggccuc gaccagcgcg gaggcggcgu ucggucagc    8520 gaaaccggcg ucacccucga ccucaauggc ggcacgcugg ucaaccgcga cggcggcuug   8580
aucgccacgc ccggcgcgcu gcugcugcgc cagcucggcg cgguggacaa cggcgccggc   8640
ggggaaaucu ccagcgaccg cgccuucacc cucgccgccg ccagccugga caaccgcggc   8700
gggcgccuga ucgcgccga cagccugacc cugcgcaucg cccaggcccu ggacaacagc   8760
cugggccggg ugaucuccgg cgccgccggc cuggacaucg cggccgcucg ccuggacaac   8820
agcgccaagg gcacccuggc cagucgcgcc ggcaucgacc ugcgcgucga cggcgcgcug   8880
gacaaccacg ccgaaggcac cgucuccggc gcccgccuga cgcucgccag cgccucgcug   8940
gacaacagcg gcaagggccu gcucuccggc aacgccggcc ugagcgucgc cacuggcgcg   9000
cuggacaacg ccgaggguhg ccaguugauc agccaggcg uccuggacgu cagcagcgcc   9060
gaccucgaca accgugggcgg cgcccucagu ggcaagcagu cgcucgccu gagcgccgcc   9120 aaccuggaca accguggcgg ccugcucacc agcgacggcg aacuggaacu gacggcaggg   9180
```

-continued

```
cgcgucgauu ccgccgacgg cggcgaaauc uccgcccggg gcgaccgcg ccugacgguc      9240 gagcgccugg ugcaacgcca gggccggcug auuggcgagc gcggcgucag ucucgaccug      9300
cggggcggcg accuggacaa ccagggcggc cugaucagug cccgcggccc gcugagcauc      9360
gagcggcuga acguccucga caaccgccag ggcggcgaga uuuacagcca gcagggcuuc      9420
gagcugcugg ccaggcgcau cgacaacggc cagcagggcc gcaucaucag cgccgggaaa      9480
cugcgccugg acgccgacgc gcugggcaac gccggcgccg gccugcucuc cggauggcag      9540
ggccugacgg ugacaggcgg gagccuggac aacagcgccg gcggcacccu uucgagcaag      9600
gacggcgagc uggccaucag ccucggcggc gcgcuggaca accacggcca gggcgcgcug      9660
gucagcaagg gcgcgcaacg gaucgacgcc gccagccugg auaacgccca gggcaucguc      9720
uccggcgaaa gcgacgugac ccugagcauc gccgggaagc uggacaacgg ccagggcggc      9780
cuggucucgg cgcagcgcgc gcugagcuuc gagcgcgacg auacgcugcu gaacaacgcc      9840
ggcggccgga ucaacggcgg cagccugcug cucaagggcg ccagccugga uaacagcgac      9900
ggccaguuga ucagccaggg ccggcucgac gccauccucg gcggcgcccu ggucaacgcc      9960
ggcgcggcgc gccuggccag cggcggcgac cugcugcugc gcagcgccag cgucgacaac     10020
cgcggcggca agcuggucag ccaggggcug cuggagauca gcgccggcag ccucgacaac     10080
agcgccuccg gcacccucgc cagccaggcc gacaugagcc ugcgccuggg cggcggcgcc     10140
cugcgcaacc agcaggacgg ccugaucuuc agccaggccg gcgcccucga ggugcaggcc     10200
ggcagccugg acaaccgcca gggcacgcuc caggcccagg gcgacaaccg gcugcguauc     10260
gguggcgcgc uggacaacca ggccggccgc cuggacagcc gggccggcaa ccucgaccug     10320
cagagcggca gccucgacaa cggcgccggc ggcgugcuca acagcgccaa ggguuggcug     10380
aagcuggcua ccgggcuguu cgacaacagc gccggcguca cccaggcgca gucgcuggag     10440
auucgcgccg gcaaggcgu gcgcaaccag cagggccauc ucucggcgcu gggcggcgac     10500
aaccgcaucg ucaccgccga cuucgacaac cagggcggcg ccucuacgc cagcggccug     10560 cucagccucg acggcagcg cuuccucaac cagggcgcgg cggcgggcca gggcggcaag     10620
gucggcgccg ggcgcaucga cuucagccug gccggcgcgc uggccaaccg cuucggccag     10680
uuggaaagcg agagcgagcu gcaccugcgc gccgccgcga ucgacaacag cggcggcagc     10740
cugcgcgccc ucgccgcag cggcagcacg cggcugguucg cuggcgaccu gaacaacgcc     10800
uacggcgugc uggaaagcgc caaccaggac cucgaccugc aacugggcag ccuggccaac     10860
gccggcgggc gcauccucca cacuggcaac ggcaccuucg gccuggauuc cgggcaggug     10920
auccgcgccg gcggcgaacu gaccaccaau ggccugcugg acauccgugc cagcgaaugg     10980
accaacagca gcgugcugca agccggacgc cugaaccugc acaucggcac cuccgccag     11040 acggccgagg gcaagcugcu ggcggugcag uccuucacug gccgcggcgg cgacuggagc     11100
aacgacggcc ugcuggccag caacggcagc uugcgacucg agcugagcgg cggcuacgu      11160 ggcaacggcc gcgccaccag ccucggcgac uucgcccuga cgccgccag ccucgaccuc     11220 ggcaaugccg ccagccucgc cggcggcgcc aaugucacgc uuggcgcgg caaccugcug     11280 gucaaccgug ggcggaucac cgcugccggc gaccucgugg ccagccgcgc gagccugaac     11340
aacuacggca cccugggcgg cggcggcaac cugcgauuga acgcgcccgc ccugcucaac     11400
gagcgcgggu ugcuguucag uggcgccgac augacccugc gcgccggcga caucaccaac     11460
cucuacgggg augugacag ccucggcagg cuggauaucg cccgcgacga ugcgggggggc     11520
```

-continued

```
ugggcaaauc gcuuggagaa cauuuccggg aauuuagaga gcacagguga uaugcguuuc    11580
uccgugaguu cacuucucaa uagaagggaa acucuagaga uugaagguga cuugcagaau    11640
agcgcuauug gcguccgcug uacggggugu cagcuuucug agaggugggg aaaaacuagg    11700
ucuucgagcg agcuugucug gaucaggaaa uauaagucua cauugggaga uucuucugcc    11760
gcugcuucaa uuacggcugg ucgagaucug cuuguuguag gugcaagccu gcagaauauu    11820
gcuucuaaua uaagucugu aagagacgcc acgcuaucuc ugaguaauuu cgaaaacaaa     11880
gguuaugcgu uaggggaaua ugcggucagg ggcguuuauu cgccgccgag uaaauuuggc    11940
gaagaauugc uuaugcgcau auuggcguau aacgcuguca acgaucccag uuauggggag    12000
ggauaugcga gcacaggggg gagacuuccg aauauucauu auuucgacaa gaauuuuaau    12060
gaaaagucu cuccgcugga ggucauucau ggaaacggga aaauggugg gccgggguugg    12120
caccuguacu ucgguaccuu agauguugag uauccggaca cagaucgcug gaauaaggcu    12180
auuggacgaa uaccggcgcc gaauuauuca ucgaaaaaaa cggaugcuau uccagaucua    12240
cuuaagggau uggcuccucu cgaugaguug acgauuaaca aaggggcgaa cucaacgguu    12300
ggugcugucg ugcaagcugg cggucgugua acgugaaug cugcggagag uuucaauaau     12360
ucugccuac agggauuuca ggccguucag gaaacccagu uaccaucau ggacauagcu      12420
guuucaagca cgacgagcgc cguagugacu cugaagaguc aacugccagc ggauuuggca    12480
aggcaacaga ucaauccucu cacccugccg ggcuucagcc ugcccaagg ccagaauggg     12540
cucuuccgcc uggcguccca aggagcccag gugaaccagg caaguggugc ucugaaaucc    12600
gccagcgauc ucacccagag cggccauggc guaucuguau ccgcacagac aggcaguggc    12660
gcaagugcu ggaguaccca ggcgcgucgu ucggcgaug aucgggucac cucgcuugcc      12720
gguuccgccu aucaaggccg gguagcgag gcuaucgaug cgcuacgggc uuccgcgcca     12780
aucucgggcg acgggggaaa cacuggccgu uccaggccg gugagcacca ggcgaccacg     12840
ggacugggug gacucgucga gggcaaugca ucgggucaca gcggcaaugg cgucauccuc    12900
gccgaucugc gcggugucu acccucguuc ucaagccuuc ccgcgucuga ucauguucaa     12960
ggcacagugc ccggucacga ugggaaugga acuauucucg ccaauuggca gggugcgcag    13020
gcgacggucc aggccucgcc uucgacagug cguagagg gguuagucuc cagccaggu      13080
ggcaauggca gcauccuugc cgaucugccg gcugaacagu cgccggugca ggcacugccu    13140
ucggccguua gggcucaggg cagccugccu cgccucgaag agcggagcgc ccuucuugcc    13200
gagccuccgg uugggcagcc ggcguugcaa acccugccgu cgguucgcg cguugagggc    13260
gugcccagca augccacacc gagcaacagc cacaaguauc ugaucgagac caacccggcg    13320
cucaccgagc ugaagcaguu ccucaacucg gacuaccugc ucgguggucu ggguaucaau    13380
ccggacgaua gcaagaagcg ccugggugac ggucuauacg agcagcgccu gguacgcgaa    13440
gcgaucgucc agcguacggg gcagcgcuuc aucgccggau ugaacagcga cgaagcgaug    13500
uuccgcuauc ugaugggaaa cgccaucgcc agcaaggacg uauugggacu gaccccuggc    13560
gucacccuca gcgccgccca ggugcggcg cugacccacg auaucguuug gcuggaagaa    13620
gucgagguga auggcgaaaa ggccucgcc cccgugguucu accuggccca ggccgagggg    13680
cgguuggggcc cgaacggcgc gcugauccag gggcgcgacg ugaaccugau caccggcggg    13740
gaccugagga acgccgguac ccugcgcgcg cagaacgacc ucagcgcgac agccggcaac    13800
aucgacaaca gcgccugau cgaggccggc aaccgcucg accugcuggc cagcggcucc     13860
auccgcaaug accagggcgg caucauugcc gggcgcgagg uaagccucuc ugcccuuacc    13920
```

```
ggagacguca ucaaugaacg gacggugacc cagcaccagu ccuccuacag gggaaccggu    13980
accacugagg cauuugccga uagcgccgcg cguaucgagg cugcgcagaa gcugaccguu    14040
ucggcaggac gcgauguagc caauauuggc ggugucaucg acagcaaggg cgaccucgcc    14100
uugcaaggcg gcagggaugu ccugguuucg gcugcgguag cggagcgggg cuggacggca    14160
ggaagccagg cauaccagac ccagacgacc cagaugggcg ccgaggucgu ggcggggcgc    14220
gauaucagcg ucagcgccgg acgcgauauc agcgucgugg gcagccgcau cgacgcucgu    14280
cgcgacguga cauucgaggc gggucgcgau gugggccugg ucgcggcugc caacgaagag    14340
caugccuaug gcaagaccaa gaaggucacu uccaggacg acaagaucac ccagcaggcc    14400
acucgcgugg acgcuggcgg cgaccuggcg aucaaugccg acaggaccu gcggcugguc    14460 gcgagccagg ccagcgccgg cgacgaagcc uaccuggugg ccggcgacaa gcuggagcug    14520
cuggccgcga acgacagcag uuacuaccuc uacgacaaga gagcaaagg cagcuucggu    14580 agcaagaaga cccggcgcga cgaaaucacc gaugugacgg caguggcag ccaaauaucc    14640 agcggcggcg accucacccu gcucagugcc ggcgaccaga cuuaccaggg cgcgaagcug    14700
gaaucgggca acgaccuggc caucgucagc ggcggcgcgg ugaccuucga ggcgguaaag    14760
gaccugcacc aggaaagcca cgagaagagc aagggcgacc uggcgugcca gucgucgaag    14820
ggcaagggcc agaccgacga aaccgugcgc cagagccaga ucguggccca ggggaaucug    14880
gcgaucaagg ccguggaagg gcugaagauc gaccucaagc acaucgacca gaagaccgug    14940
agccagacca ucgacgcgau ggugcaggcg gauccgcaac uggccuggcu gaagcagaug    15000
gagcagcgcg gcgaugugga uuggcggcgc gugcaggaac ugcaugacag cuggaaguac    15060
agcaacuccg gcugggcgu cggcgcgcag uuggcgauag cgaucguugu ggccuacuuc    15120 acggcggug cggcgagugc ggcauuggga ucgauggcgg gagugggc gggcucagga    15180 agcaugaugg cugcugccgg uagcacugca augguccagg ccgguacagc aguaggaaca    15240
gcugccgccg gcuggggcgaa ugcagcugga acugccgugg cuauggggcau ggccagcaau    15300 ggagcgauca gcaccaucaa caaccgggga aaccuggggg augucgucaa ggacgugacc    15360
uccagcgaug cgcugagggg cuauguaguc gcuggcacga cugcggggcu gacugccggc    15420
gucuacgaca aauggaccuc gacccagacc ggcaccucga ccgcucuacc gaacaccggg    15480
gccguggcgc ccgccgcagg guugggcacc uggcaaggcg ugggccaguu caccucgaac    15540
caguugcugc agaaugguac uucggugcug uuggaccggg cgcugggcgg caagggcagc    15600
cugggcgaug cguugcaaaa cagccuggca aaugccuuug cggccuacgg cuucaagcug    15660
auuggcgaca ccacccaugg cgugcuggac gacggcagcc ucggcaagau cggcuugcac    15720
gcccugaugg gaggucugc cgccgaagcg ucgguggcg auuuccguac cggagcccug    15780
gcugcgggag ucaacgaggc gcuggugau ag c c c ucgcca agcaauacgc cagccugccc    15840
aucgaugaca agaagggccu gcugaucaug aguucgcagu ugaucggcgu gcuggcggcu    15900
ucgacgcagg gcgaugcgga cgccaagagc uugcagacgg gggccugggu ggcggggaau    15960
gccacccaac acaacuaccu cagucauugg caggaggaga agaagcggca ggaggucgau    16020
ggcugcaaag acaaacagcu cugcaaaacc ggaauagaag ccaaugggc aauuauuucg    16080 gcccagcagg augucgguau cgucguaggu guuggaggag gcaucggucu uucgacagcu    16140
gaaaccgcag uggguguuua ugagcugguc aagaacugga gggaaaccua ugcagcucug    16200
gagcaguugg ccacuucgcc agaguuccgg cagcaauuug gcgauaacua ccugaagggg    16260
```

```
cuggaggagc gcgccgcauu cuugacccag gcauacgagg augccggcug gcaagguucg    16320
gucacagcug gugucgaggg cgguagguuc gcugcggaac uuguuggcgu ucugacggca    16380
gugaaaggug gcgcgcagau aaccgccaag cugccaacag cagccaagaa ccuggucaac    16440
gcgauugcgg agucaccugu uuccgguagu augaguucgc agcuuggggc agugggggau    16500 uuggucggc uggguggggg agguaaaggu uaugucgaua uucuuuccca cgaagcuaaa     16560
cagcauauuu uguauggcga caaaccuggg aguggugcc auuuguggcc ggggcaggca     16620
gggaagacag uuuucccuca aaacuggucg gcagauaaga uaguucacga gguuggugau    16680
auugcgacgu ccccuaguac caaaugguau gcccaaacag gaacuggugg gguuuauaca    16740
agcaagggug aucccgcuaa auggguugcu uaugagguuc gugauggagu ucguaugcgc    16800
guuguuuauc agcccgcuac aggaaaggug aucacagccu ucccgacaa cgcaccuauc     16860 ccaccuuaua agcccauuaa auag                                           16884
```

PROTEINS AND NUCLEIC ACIDS USEFUL IN VACCINES TARGETING *PSEUDOMONAS AERUGINOSA*

CROSS REFERENCE TO RELATED APPLICATIONS

In accordance with 37 C.F.R. § 1.76, a claim of priority is included in an Application Data Sheet filed concurrently herewith. Accordingly, the present invention claims priority as a divisional of U.S. patent application Ser. No. 15/741,881, filed Jan. 4, 2018, which is a § 371 of PCT/EP2016/065647, filed Jul. 4, 2016, which claims the benefit of the priority of European Patent Application No. 15175365.4, filed Jul. 4, 2015, the contents of each are incorporated herein by reference.

FIELD OF THE INVENTION

The present invention relates to the field of antimicrobial prophylaxis and therapy. In particular the present invention relates to novel proteins and polynucleotides derived from *Pseudomonas aeruginosa*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

*Pseudomonas aeruginosa* is an opportunistic gram-negative pathogen. It represents a major course of hospital-acquired infections, especially in burnt and other immuno-compromised patients, including transplant or cancer patients. Therefore, it is regarded as a "problem microbe" in human medicine.

Many efforts have been made so far in order to develop a vaccine against *Pseudomonas aeruginosa*. For example, in the EP-0 297 291 the complete amino acid-sequence of the outer membrane protein F, as well as the nucleotide sequence coding for OprF is disclosed. In the EP-0 357 024 the complete amino acid sequence of the outer membrane protein I and, additionally, the nucleotide sequence coding for OprI is shown. Furthermore, with both proteins it was shown that they may be useful for conferring immunoprotection against *Pseudomonas aeruginosa* to an animal or human proband. However, improvement of procedures of vaccination against and treatment of a lethal *Pseudomonas aeruginosa* infection is still an object.

Vaccination is considered to be a very effective method of preventing infectious diseases in human and veterinary health care. Vaccination is the administration of immunogenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *Pseudomonas aeruginosa* derived antigenic polypeptides that may serve as constituents in vaccines against *Pseudomonas aeruginosa* infections and in diagnosis of *Pseudomonas aeruginosa* infections. It is also an object to provide nucleic acids, vectors, transformed cells, vaccine compositions, and other useful means for molecular cloning as well as for therapy and diagnosis with relevance for *Pseudomonas* aeruginosa.

SUMMARY OF THE INVENTION

It has been found by the present inventor(s) that *Pseudomonas aeruginosa* expresses a number of hitherto unknown putatively surface exposed proteins which are candidates as vaccine targets as well as candidates as immunizing agents for preparation of antibodies that target *Pseudomonas* aeruginosa.

So, in a first aspect the present invention relates to a polypeptide comprising
 a) an amino acid sequence selected from the group consisting of any one of SEQ ID NOs: 1-30, or
 b) an amino acid sequence consisting of at least 5 contiguous amino acid residues from any one of SEQ ID NOs: 1-30, or
 c) an amino acid sequence having a sequence identity of at least 60% with the amino acid sequence of a),
 d) an amino acid sequence having a sequence identity of at least 60% with the amino acid sequence of b), or
 e) an assembly of amino acids derived from any one of SEQ ID NOs: 1-30 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or
ii) a nucleotide sequence consisting of any one of SEQ ID NOs: 31-90.
iii) a nucleotide sequence consisting of at least 10 consecutive nucleotides in any one of SEQ ID NOs: 31-90,
iv) a nucleotide sequence having a sequence identity of at least 60% with the nucleotide sequence in i) or ii),
v) a nucleotide sequence having a sequence identity of at least 60% with the nucleotide sequence in iii),
vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *Pseudomonas aeruginosa* in the animal.

In a seventh and eighth aspect, the invention relates to 1) a polyclonal antibody in which the antibodies specifically bind to at least one polypeptide of the invention, and which is essentially free from antibodies binding specifically to other *Pseudomonas aeruginosa* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *Pseudomonas aeruginosa*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *Pseudomonas aeruginosa*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *Pseudomonas aeruginosa* in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *Pseudomonas aeruginosa*, in particular the presence of a nucleic acid characteristic of *Pseudomonas aeruginosa*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with *Pseudomonas aeruginosa*, the method comprising contacting the polypeptide of the invention with the substance and subsequently establishing whether the substance has at least one of the following characteristics:
1) the ability to bind specifically to said polypeptide,
2) the ability to compeed with said polypeptide for specific binding to a ligand/receptor, and
3) the ability to specifically inactivate said polypeptide.

Finally, in a $16^{th}$ aspect, the invention relates to a method for determining whether a substance, such as a nucleic acid, is potentially useful for treating infection with *Pseudomonas aeruginosa*, the method comprising contacting the substance with the nucleic acid fragment of claim of the invention and subsequently establishing whether the substance has either the ability to
1) bind specifically to the nucleic acid fragment, or
2) bind specifically to a nucleic acid that hybridizes specifically with the nucleic acid fragment.

LEGENDS TO THE FIGURE

FIG. 1. Graph of clinical score four days post-infection, Example 1.

Mice immunized with the 7-valent combination vaccine had a significantly lower clinical score 96 hours post-infection compared to the control group immunized with adjuvant. The data were analysed using Student's t-test, P=0.0109.

Figure 2:
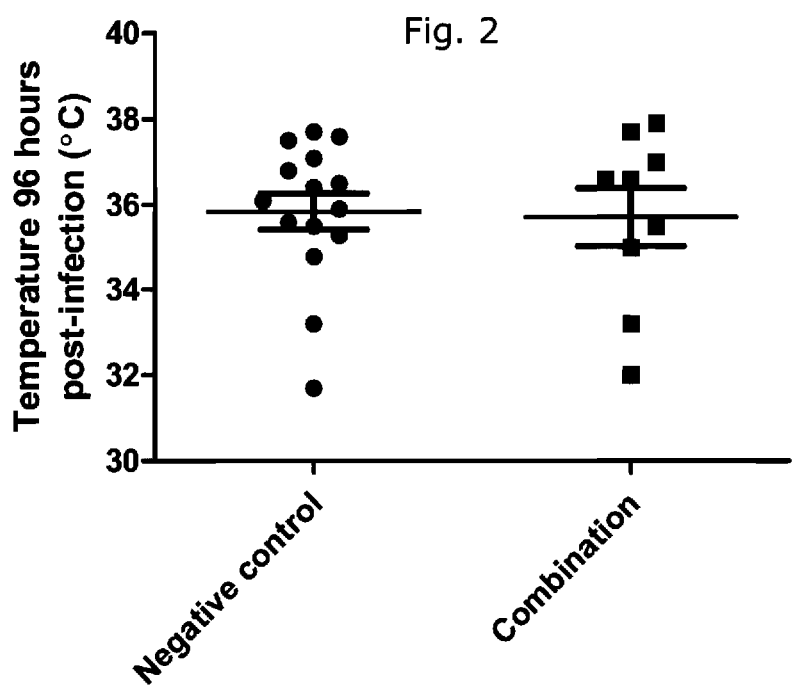

FIG. 2. Graph of body temperature four days post-infection, Example 1.

Comparison of body temperature, measured in the two groups of mice four days post-infection, showed that there was no significant difference in body temperature. The data were analyzed using the Mann Whitney test, P=0.8814.

Figure 3:
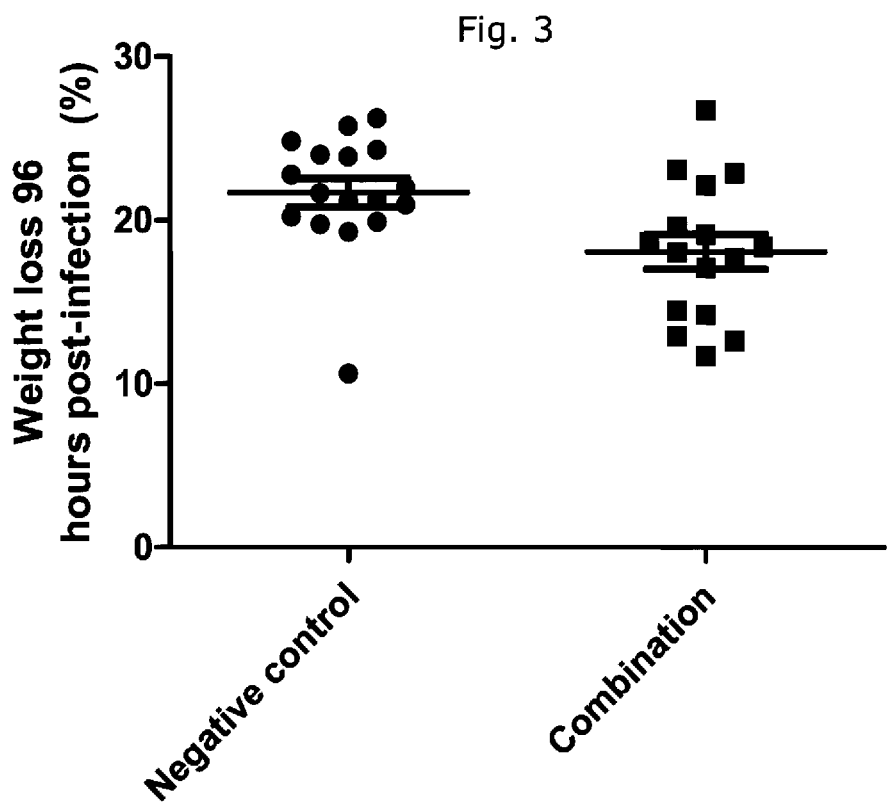

FIG. 3. Weight loss 96 hours post-infection, Example 1.

The group of mice immunized with the 7-valent combination vaccine had a significantly smaller weight loss than the control group. The data were analyzed using the Mann Whitney test, P=0.0081.

Figure 4:
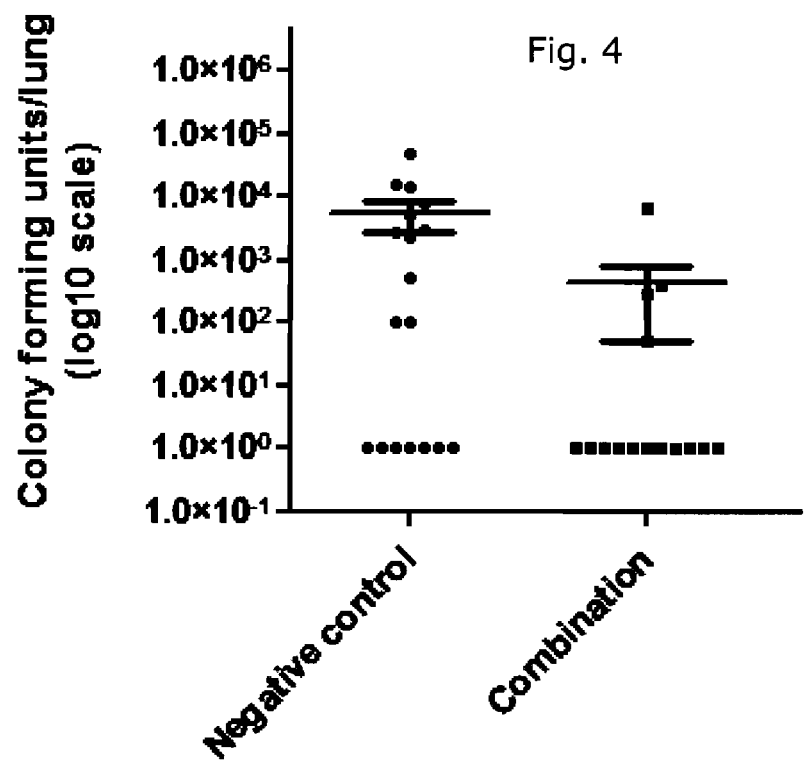

FIG. 4. Lung bacteriology, Example 1.

The number of colony forming units was significantly smaller in lung homogenates from mice immunized with the 7-valent combination vaccine compared to the control group. Note that in this figure the CFU values equaled 0 are altered to 1, this is purely for illustrative purposes as a value of 0 cannot be shown on a logarithmic scale. The CFU data are given in appendix 4. The data were analyzed using the Mann Whitney test, P=0.0176.

Figure 5:
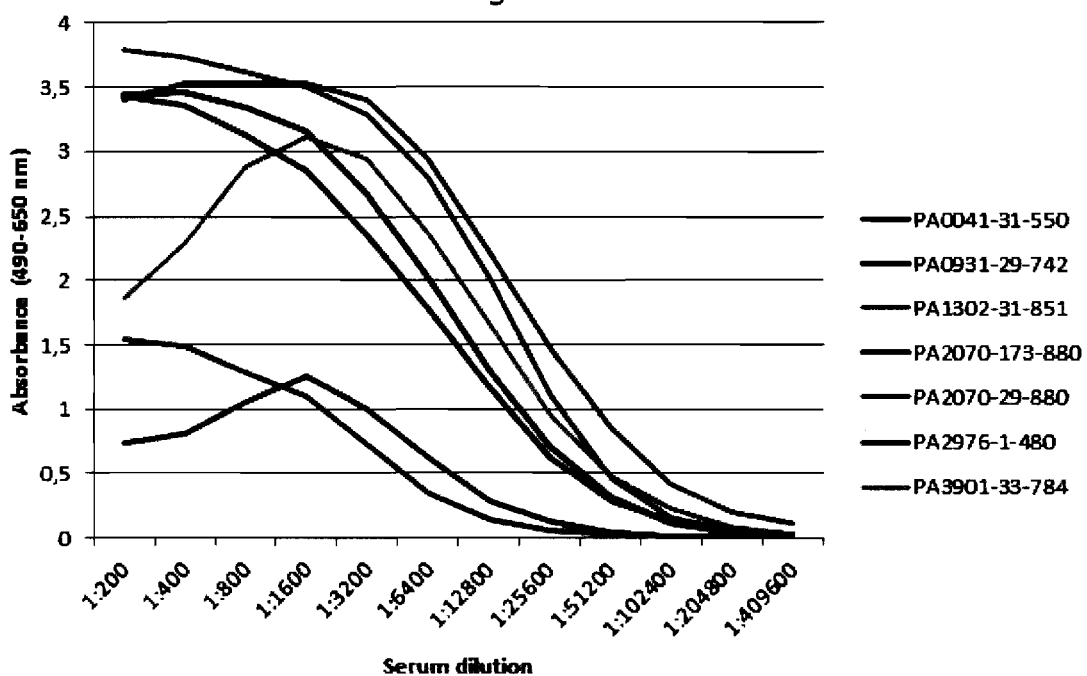

FIG. 5. Mean antibody responses to the seven antigens tested in Example 1.

The Y-axis represents the absorbance measured at 490 nm-650 nm (reference), and the X-axis shows the serum dilution. In general, the antibody response to five of the seven antigens was high, while the antibody response to PA2976-1-480 and PA0041-34-550 was quite low.

Figure 6:
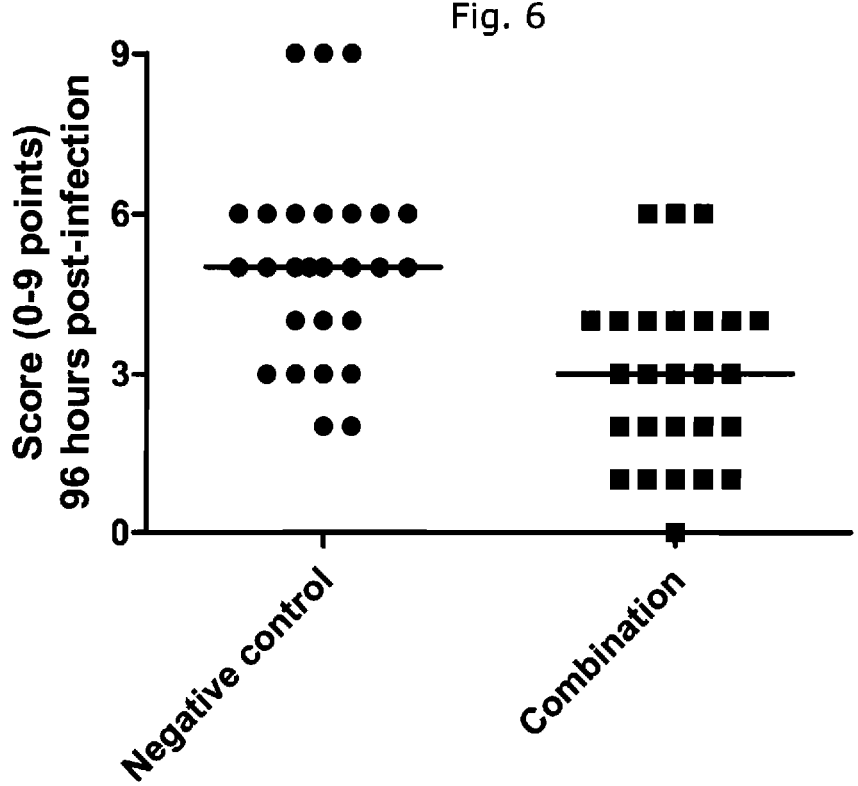

FIG. 6. Clinical score four days post-infection, Example 2.

The mice immunized with the 7-valent combination vaccine had a significantly lower clinical score 96 hours post-infection compared to the control group immunized with adjuvant. The data were analysed using a two-tailed t-test, P<0.0001.

Figure 7:
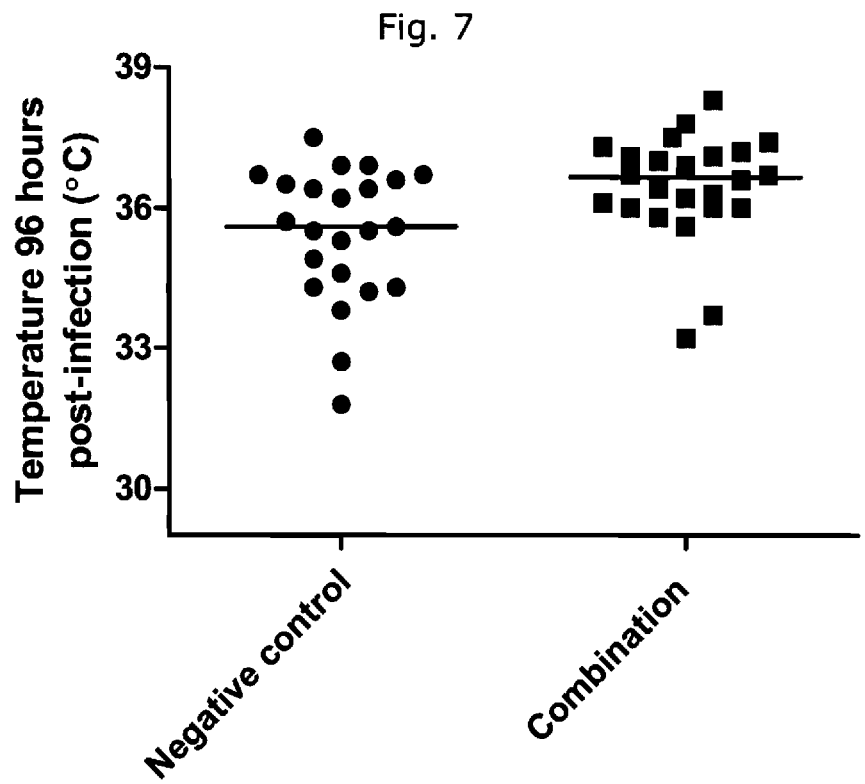

FIG. 7. Body temperature four days post-infection, Example 2.

Comparison of body temperature, measured in the two groups of mice four days post-infection, showed that mice immunized with the 7-valent combination vaccine had a significantly higher body temperature compared to controls. The data were analyzed using the Mann Whitney test, P=0.0085.

Figure 8:
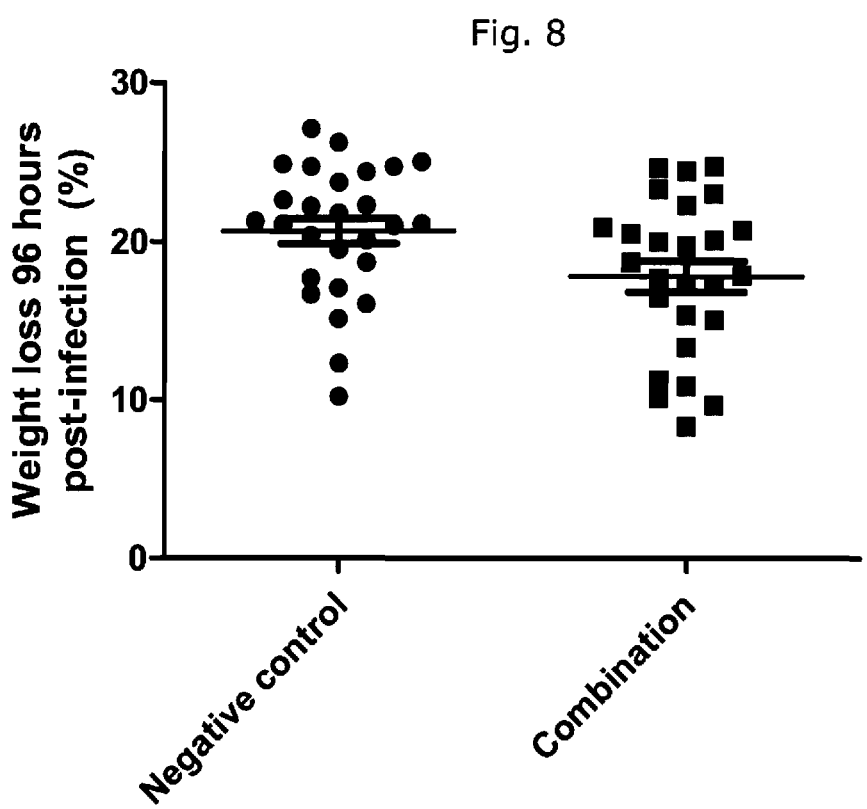

FIG. 8. Weight loss 96 hours post-infection, Example 2.

The group of mice immunized with the 7-valent combination vaccine had a significantly smaller weight loss than the control group. The data were analyzed using a two-tailed t-test, P=0.0262.

FIG. 4. Lung bacteriology, Example 2.

There was no significant difference when comparing CFU in lung homogenates from mice immunized with the 7-valent combination vaccine and the control group. Note that in this figure the CFU values equaled 0 are altered to 1, this is purely for illustrative purposes as a value of 0 cannot be shown on a logarithmic scale. The CFU data are given in appendix 4. The data were analyzed using the Mann Whitney test, P=0.0888. In relation to this note that the high number of animals having complete clearance complicates statistical test of bacterial load, hence no significant p-value <0.05. However, a higher number of animals in the vaccinated group (11/26) experienced total clearance of bacteria in the kidneys compared to control (6/27).

Figure 10:
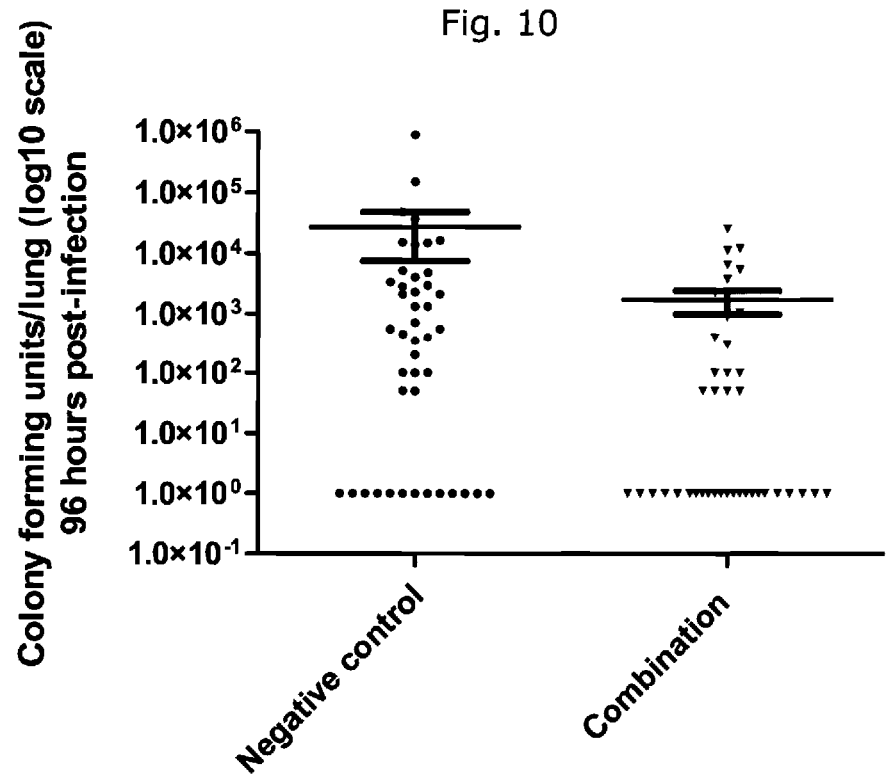

FIG. 10. Lung bacteriology—combined results from Examples 1 and 2.

When pooling the CFU results obtained in ER_0039 and ER_0040, two completely identical experiments, the mice immunized with the 7-valent vaccine exhibit a significantly lower lung CFU compared to controls. Note that in this figure, the CFU values equaled 0 are altered to 1, this is purely for illustrative purposes as a value of 0 cannot be shown on a logarithmic scale. The data were analyzed using the Mann Whitney test, P=0.0044.

Figure 11:
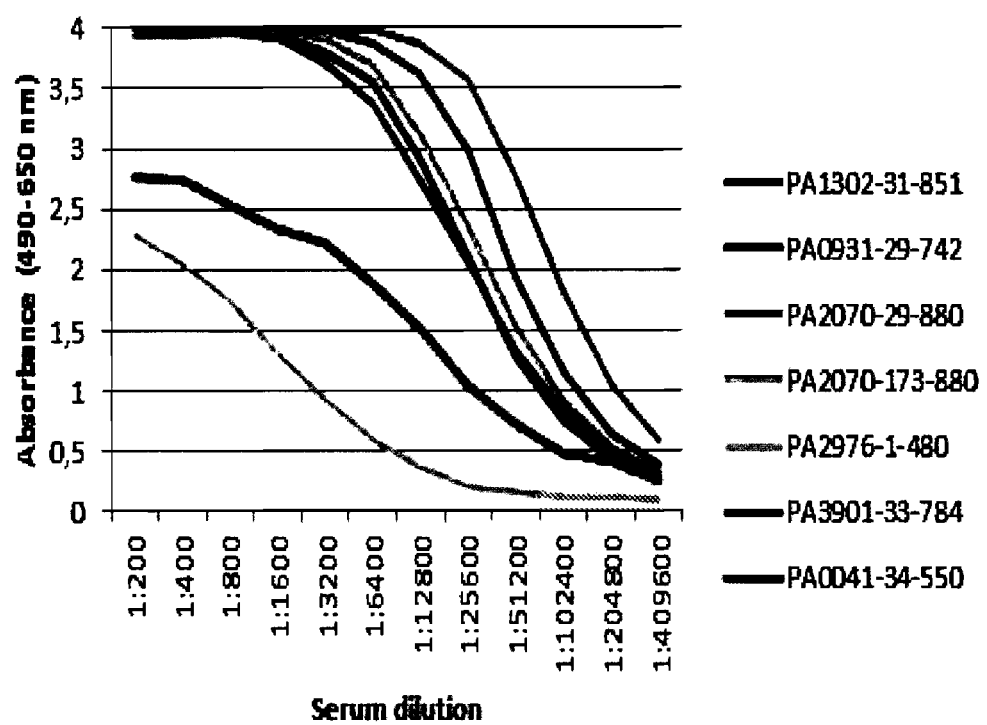

FIG. 11. Mean antibody responses to the seven antigens. The Y-axis represents the absorbance measured at 490 nm-650 nm (reference), and the X-axis shows the serum dilution. In general, the antibody responses to five of the seven antigens were high, while the antibody responses to PA2976-1-480 and PA0041-34-550 were quite low.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" s the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAAC-3' and 5'-ATACGGGAC-3' will provide the sequence identity 77.8% ($N_{ref}$=9 and $N_{dif}$=2). It will be understood that such a sequence identity determination requires that the two aligned sequences are aligned so that there are no overhangs between the two sequences: each amino acid in each sequence will have to be matched with a counterpart in the other sequence.

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule prese An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigen determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen.

"Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

Specific Embodiments of the Invention

The Polypeptides of the Invention

In some embodiments the at least 5 contiguous amino acids referred to in option b) in the definition of the first aspect of the invention constitute at least or exactly or at most 6, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64 and at least or exactly or at most 65 contiguous amino acid residues.

The number of contiguous amino acids in option b) can be higher, for all of SEQ ID NOs. 2-30. Another way to phrase this is that for each of SEQ ID NOs: 1-30, the number of the contiguous amino acid residues is at least or exactly or at most N−n, where N is the length of the sequence ID in question and n is any integer between 1 and N−5; that is, the at least or exactly 5 contiguous amino acids can be at least any number between 5 and the length of the reference sequence minus one, in increments of one.

Insofar as embodiment b relates to SEQ ID NOs: 2-30, the at least 5 contiguous amino acids referred to in option b) in the definition of the first aspect of the invention may also constitute at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, or at least or exactly or at most 77 contiguous amino acid residues.

Insofar as embodiment b relates to SEQ ID NOs: 3-30, the at least 5 contiguous amino acids referred to in option b) in the definition of the first aspect of the invention may also constitute at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, or at least or exactly or at most 103 contiguous amino acid residues.

Insofar as embodiment b relates to SEQ ID NOs: 4-30, the at least 5 contiguous amino acids referred to in option b) in the definition of the first aspect of the invention may also constitute at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, or at least or exactly or at most 154 contiguous amino acid residues.

Insofar as embodiment b relates to SEQ ID NOs: 5-30, the at least 5 contiguous amino acids referred to in option b) in the definition of the first aspect of the invention may also constitute at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, or at least or exactly or at most 178 contiguous amino acid residues.

Insofar as embodiment b relates to SEQ ID NOs: 6-30, the at least 5 contiguous amino acids referred to in option b) in the definition of the first aspect of the invention may also constitute at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, or at least or exactly or at most 303 contiguous amino acid residues.

Insofar as embodiment b relates to SEQ ID NOs: 7-30, the at least 5 contiguous amino acids referred to in option b) in the definition of the first aspect of the invention may also constitute at least or exactly or at most 304, at least or exactly or at most 305, at least or exactly or at most 306, at least or exactly or at most 307, or at least or exactly or at most 308 contiguous amino acid residues.

Insofar as embodiment b relates to SEQ ID NOs: 8-30, the at least 5 contiguous amino acids referred to in option b) in the definition of the first aspect of the invention may also constitute at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, or at least or exactly or at most 339 contiguous amino acid residues.

Insofar as embodiment b relates to SEQ ID NOs: 9-30, the at least 5 contiguous amino acids referred to in option b) in the definition of the first aspect of the invention may also constitute at least or exactly or at most 340, at least or exactly or at most 341, at least or exactly or at most 342, at least or exactly or at most 343, at least or exactly or at most 344, at least or exactly or at most 345, or at least or exactly or at most 346 contiguous amino acid residues.

Insofar as embodiment b relates to SEQ ID NOs: 10-30, the at least 5 contiguous amino acids referred to in option b) in the definition of the first aspect of the invention may also constitute at least or exactly or at most 347, at least or exactly or at most 348, at least or exactly or at most 349, at least or exactly or at most 350, or at least or exactly or at most 351 contiguous amino acid residues.

Insofar as embodiment b relates to SEQ ID NOs: 11-30, the at least 5 contiguous amino acids referred to in option b) in the definition of the first aspect of the invention may also constitute at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, or at least or exactly or at most 419 contiguous amino acid residues.

Insofar as embodiment b relates to SEQ ID NOs: 12-30, the at least 5 contiguous amino acids referred to in option b) in the definition of the first aspect of the invention may also constitute at least or exactly or at most 420, at least or exactly or at most 421, at least or exactly or at most 422, at least or exactly or at most 423, at least or exactly or at most 424, at least or exactly or at most 425, or at least or exactly or at most 426 contiguous amino acid residues.

Insofar as embodiment b relates to SEQ ID NOs: 13-30, the at least 5 contiguous amino acids referred to in option b) in the definition of the first aspect of the invention may also constitute at least or exactly or at most 427 contiguous amino acid residues.

Insofar as embodiment b relates to SEQ ID NOs: 14-30, the at least 5 contiguous amino acids referred to in option b) in the definition of the first aspect of the invention may also constitute at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, or at least or exactly or at most 567 contiguous amino acid residues.

Insofar as embodiment b relates to SEQ ID NOs: 15-30, the at least 5 contiguous amino acids referred to in option b) in the definition of the first aspect of the invention may also constitute at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, or at least or exactly or at most 578 contiguous amino acid residues.

Insofar as embodiment b relates to SEQ ID NOs: 16-30, the at least 5 contiguous amino acids referred to in option b) in the definition of the first aspect of the invention may also constitute at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, or at least or exactly or at most 620 contiguous amino acid residues.

Insofar as embodiment b relates to SEQ ID NOs: 17-30, the at least 5 contiguous amino acids referred to in option b) in the definition of the first aspect of the invention may also constitute at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, or at least or exactly or at most 687 contiguous amino acid residues.

Insofar as embodiment b relates to SEQ ID NOs: 18-30, the at least 5 contiguous amino acids referred to in option b) in the definition of the first aspect of the invention may also constitute at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, or at least or exactly or at most 741 contiguous amino acid residues.

Insofar as embodiment b relates to SEQ ID NOs: 19-30, the at least 5 contiguous amino acids referred to in option b) in the definition of the first aspect of the invention may also constitute at least or exactly or at most 742, at least or exactly or at most 743, at least or exactly or at most 744, or at least or exactly or at most 745 contiguous amino acid residues.

Insofar as embodiment b relates to SEQ ID NOs: 20-30, the at least 5 contiguous amino acids referred to in option b) in the definition of the first aspect of the invention may also constitute at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, or at least or exactly or at most 783 contiguous amino acid residues.

Insofar as embodiment b relates to SEQ ID NOs: 21-30, the at least 5 contiguous amino acids referred to in option b) in the definition of the first aspect of the invention may also constitute at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, or at least or exactly or at most 850 contiguous amino acid residues.

Insofar as embodiment b relates to SEQ ID NOs: 22-30, the at least 5 contiguous amino acids referred to in option b) in the definition of the first aspect of the invention may also constitute at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, or at least or exactly or at most 879 contiguous amino acid residues.

Insofar as embodiment b relates to SEQ ID NOs: 23-30, the at least 5 contiguous amino acids referred to in option b) in the definition of the first aspect of the invention may also constitute at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, or at least or exactly or at most 918 contiguous amino acid residues.

Insofar as embodiment b relates to SEQ ID NOs: 24-30, the at least 5 contiguous amino acids referred to in option b) in the definition of the first aspect of the invention may also constitute at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, or at least or exactly or at most 994 contiguous amino acid residues.

Insofar as embodiment b relates to SEQ ID NOs: 25-30, the at least 5 contiguous amino acids referred to in option b) in the definition of the first aspect of the invention may also constitute at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, or at least or exactly or at most 1056 contiguous amino acid residues.

Insofar as embodiment b relates to SEQ ID NOs: 26-30, the at least 5 contiguous amino acids referred to in option b) in the definition of the first aspect of the invention may also constitute at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, or at least or exactly or at most 1160 contiguous amino acid residues.

Insofar as embodiment b relates to SEQ ID NOs: 27-30, the at least 5 contiguous amino acids referred to in option b) in the definition of the first aspect of the invention may also constitute at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, or at least or exactly or at most 1210 contiguous amino acid residues.

Insofar as embodiment b relates to SEQ ID NOs: 28-30, the at least 5 contiguous amino acids referred to in option b) in the definition of the first aspect of the invention may also constitute at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, at least or exactly or at most 1559, at least or exactly or at most 1560, at least or exactly or at most 1561, at least or exactly or at most 1562, at least or exactly or at most 1563, at least or exactly or at most 1564, at least or exactly or at most 1565, at least or exactly or at most 1566, at least or exactly or at most 1567, at least or exactly or at most 1568, at least or exactly or at most 1569, at least or exactly or at most 1570, at least or exactly or at most 1571, at least or exactly or at most 1572, at least or exactly or at most 1573, at least or exactly or at most 1574, at least or exactly or at most 1575, at least or exactly or at most 1576, at least or exactly or at most 1577, at least or exactly or at most 1578, at least or exactly or at most 1579, at least or exactly or at most 1580, at least or exactly or at most 1581, at least or exactly or at most 1582, at least or exactly or at most 1583, at least or exactly or at most 1584, at least or exactly or at most 1585, at least or exactly or at most 1586, at least or exactly or at most 1587, at least or exactly or at most 1588, at least or exactly or at most 1589, at least or exactly or at most 1590, at least or exactly or at most 1591, at least or exactly or at most 1592, at least or exactly or at most 1593, at least or exactly or at most 1594, at least or exactly or at most 1595, at least or exactly or at most 1596, at least or exactly or at most 1597, at least or exactly or at most 1598, at least or exactly or at most 1599, at least or exactly or at most 1600, at least or exactly or at most 1601, at least or exactly or at most 1602, at least or exactly or at most 1603, at least or exactly or at most 1604, at least or exactly or at most 1605, at least or exactly or at most 1606, at least or exactly or at most 1607, at least or exactly or at most 1608, at least or exactly or at most 1609, at least or exactly or at most 1610, at least or exactly or at most 1611, at least or exactly or at most 1612, at least or exactly or at most 1613, at least or exactly or at most 1614, at least or exactly or at most 1615, at least or exactly or at most 1616, at least or exactly or at most 1617, at least or exactly or at most 1618, at least or exactly or at most 1619, at least or exactly or at most 1620, at least or exactly or at most 1621, at least or exactly or at most 1622, at least or exactly or at most 1623, at least or exactly or at most 1624, at least or exactly or at most 1625, at least or exactly or at most 1626, at least or exactly or at most 1627, at least or exactly or at most 1628, at least or exactly or at most 1629, at least or exactly or at most 1630, at least or exactly or at most 1631, at least or exactly or at most 1632, at least or exactly or at most 1633, at least or exactly or at most 1634, at least or exactly or at most 1635, at least or exactly or at most 1636, at least or exactly or at most 1637, at least or exactly or at most 1638, at least or exactly or at most 1639, at least or exactly or at most 1640, at least or exactly or at most 1641, at least or exactly or at most 1642, at least or exactly or at most 1643, at least or exactly or at most 1644, at least or exactly or at most 1645, at least or exactly or at most 1646, at least or exactly or at most 1647, at least or exactly or at most 1648, at least or exactly or at most 1649, at least or exactly or at most 1650, at least or exactly or at most 1651, at least or exactly or at most 1652, at least or exactly or at most 1653, at least or exactly or at most 1654, at least or exactly or at most 1655, at least or exactly or at most 1656, at least or exactly or at most 1657, at least or exactly or at most 1658, at least or exactly or at most 1659, at least or exactly or at most 1660, at least or exactly or at most 1661, at least or exactly or at most 1662, at least or exactly or at most 1663, at least or exactly or at most 1664, at least or exactly or at most 1665, at least or exactly or at most 1666, at least or exactly or at most 1667, at least or exactly or at most 1668, at least or exactly or at most 1669, at least or exactly or at most 1670, at least or exactly or at most 1671, at least or exactly or at most 1672, at least or exactly or at most 1673, at least or exactly or at most 1674, at least or exactly or at most 1675, at least or exactly or at most 1676, at least or exactly or at most 1677, at least or exactly or at most 1678, at least or exactly or at most 1679, at least or exactly or at most 1680, at least or exactly or at most 1681, at least or exactly or at most 1682, at least or exactly or at most 1683, at least or exactly or at most 1684, at least or exactly or at most 1685, at least or exactly or at most 1686, at least or exactly or at most 1687, at least or exactly or at most 1688, at least or exactly or at most 1689, at least or exactly or at most 1690, at least or exactly or at most 1691, at least or exactly or at most 1692, at least or exactly or at most 1693, at least or exactly or at most 1694, at least or exactly or at most 1695, at least or exactly or at most 1696, at least or exactly or at most 1697, at least or exactly or at most 1698, at least or exactly or at most 1699, at least or exactly or at most 1700, at least or exactly or at most 1701, at least or exactly or at most 1702, at least or exactly or at most 1703, at least or exactly or at most 1704, at least or exactly or at most 1705, at least or exactly or at most 1706, at least or exactly or at most 1707, at least or exactly or at most 1708, at least or exactly or at most 1709, at least or exactly or at most 1710, at least or exactly or at most 1711, at least or exactly or at most 1712, at least or exactly or at most 1713, at least or exactly or at most 1714, at least or exactly or at most 1715, at least or exactly or at most 1716, at least or exactly or at most 1717, at least or exactly or at most 1718, at least or exactly or at most 1719, at least or exactly or at most 1720, at least or exactly or at most 1721, at least or exactly or at most 1722, at least or exactly or at most 1723, at least or exactly or at most 1724, at least or exactly or at most 1725, at least or exactly or at most 1726, at least or exactly or at most 1727, at least or exactly or at most 1728, at least or exactly or at most 1729, at least or exactly or at most 1730, at least or exactly or at most 1731, at least or exactly or at most 1732, at least or exactly or at most 1733, at least or exactly or at most 1734, at least or exactly or at most 1735, at least or exactly or at most 1736, at least or exactly or at most 1737, at least or exactly or at most 1738, at least or exactly or at most 1739, at least or exactly or at most 1740, at least or exactly or at most 1741, at least or exactly or at most 1742, at least or exactly or at most 1743, at least or exactly or at most 1744, at least or exactly or at most 1745, at least or exactly or at most 1746, at least or exactly or at most 1747, at least or exactly or at most 1748, at least or exactly or at most 1749, at least or exactly or at most 1750, at least or exactly or at most 1751, at least or exactly or at most 1752, at least or exactly or at most 1753, at least or exactly or at most 1754, at least or exactly or at most 1755, at least or exactly or at most 1756, at least or exactly or at most 1757, at least or exactly or at most 1758, at least or exactly or at most 1759, at least or exactly or at most 1760, at least or exactly or at most 1761, at least or exactly or at most 1762, at least or exactly or at most 1763, at least or exactly or at most 1764, at least or exactly or at most 1765, at least or exactly or at most 1766, at least or exactly or at most 1767, at least or exactly or at most 1768, at least or exactly or at most 1769, at least or exactly or at most 1770, at least or exactly or at most 1771, at least or exactly or at most 1772, at least or exactly or at most 1773, at least or exactly or at most 1774, at least or exactly or at most 1775, at least or exactly or at most 1776, at least or exactly or at most 1777, at least or exactly or at most 1778, at least or exactly or at most 1779, at least or exactly or at most 1780, at least or exactly or at most 1781, at least or exactly or at most 1782, at least or exactly or at most 1783, at least or exactly or at most 1784, at least or exactly or at most 1785, at least or exactly or at most 1786, at least or exactly or at most 1787, at least or exactly or at most 1788, at least or exactly or at most 1789, at least or exactly or at most 1790, at least or exactly or at most 1791, at least or exactly or at most 1792, at least or exactly or at most 1793, at least or exactly or at most 1794, at least or exactly or at most 1795, at least or exactly or at most 1796, at least or exactly or at most 1797, at least or exactly or at most 1798, at least or exactly or at most 1799, at least or exactly or at most 1800, at least or exactly or at most 1801, at least or exactly or at most 1802, at least or exactly or at most 1803, at least or exactly or at most 1804, at least or exactly or at most 1805, at least or exactly or at most 1806, at least or exactly or at most 1807, at least or exactly or at most 1808, at least or exactly or at most 1809, at least or exactly or at most 1810, at least or exactly or at most 1811, at least or exactly or at most 1812, at least or exactly or at most 1813, at least or exactly or at most 1814, at least or exactly or at most 1815, at least or exactly or at most 1816, at least or exactly or at most 1817, at least or exactly or at most 1818, at least or exactly or at most 1819, at least or exactly or at most 1820, at least or exactly or at most 1821, at least or exactly or at most 1822, at least or exactly or at most 1823, at least or exactly or at most 1824, at least or exactly or at most 1825, at least or exactly or at most 1826, at least or exactly or at most 1827, at least or exactly or at most 1828, at least or exactly or at most 1829, at least or exactly or at most 1830, at least or exactly or at most 1831, at least or exactly or at most 1832, at least or exactly or at most 1833, at least or exactly or at most 1834, at least or exactly or at most 1835, at least or exactly or at most 1836, at least or exactly or at most 1837, at least or exactly or at most 1838, at least or exactly or at most 1839, at least or exactly or at most 1840, at least or exactly or at most 1841, at least or exactly or at most 1842, at least or exactly or at most 1843, at least or exactly or at most 1844, at least or exactly or at most 1845, at least or exactly or at most 1846, at least or exactly or at most 1847, at least or exactly or at most 1848, at least or exactly or at most 1849, at least or exactly or at most 1850, at least or exactly or at most 1851, at least or exactly or at most 1852, at least or exactly or at most 1853, at least or exactly or at most 1854, at least or exactly or at most 1855, at least or exactly or at most 1856, at least or exactly or at most 1857, at least or exactly or at most 1858, at least or exactly or at most 1859, at least or exactly or at most 1860, at least or exactly or at most 1861, at least or exactly or at most 1862, at least or exactly or at most 1863, at least or exactly or at most 1864, at least or exactly or at most 1865, at least or exactly or at most 1866, at least or exactly or at most 1867, at least or exactly or at most 1868, at least or exactly or at most 1869, at least or exactly or at most 1870, at least or exactly or at most 1871, at least or exactly or at most 1872, at least or exactly or at most 1873, at least or exactly or at most 1874, at least or exactly or at most 1875, at least or exactly or at most 1876, at least or exactly or at most 1877, at least or exactly or at most 1878, at least or exactly or at most 1879, at least or exactly or at most 1880, at least or exactly or at most 1881, at least or exactly or at most 1882, at least or exactly or at most 1883, at least or exactly or at most 1884, at least or exactly or at most 1885, at least or exactly or at most 1886, at least or exactly or at most 1887, at least or exactly or at most 1888, at least or exactly or at most 1889, at least or exactly or at most 1890, at least or exactly or at most 1891, at least or exactly or at most 1892, at least or exactly or at most 1893, at least or exactly or at most 1894, at least or exactly or at most 1895, at least or exactly or at most 1896, at least or exactly or at most 1897, at least or exactly or at most 1898, at least or exactly or at most 1899, at least or exactly or at most 1900, at least or exactly or at most 1901, at least or exactly or at most 1902, at least or exactly or at most 1903, at least or exactly or at most 1904, at least or exactly or at most 1905, at least or exactly or at most 1906, at least or exactly or at most 1907, at least or exactly or at most 1908, at least or exactly or at most 1909, at least or exactly or at most 1910, at least or exactly or at most 1911, at least or exactly or at most 1912, at least or exactly or at most 1913, at least or exactly or at most 1914, at least or exactly or at most 1915, at least or exactly or at most 1916, at least or exactly or at most 1917, at least or exactly or at most 1918, at least or exactly or at most 1919, at least or exactly or at most 1920, at least or exactly or at most 1921, at least or exactly or at most 1922, at least or exactly or at most 1923, at least or exactly or at most 1924, at least or exactly or at most 1925, at least or exactly or at most 1926, at least or exactly or at most 1927, at least or exactly or at most 1928, at least or exactly or at most 1929, at least or exactly or at most 1930, at least or exactly or at most 1931, at least or exactly or at most 1932, at least or exactly or at most 1933, at least or exactly or at most 1934, at least or exactly or at most 1935, at least or exactly or at most 1936, at least or exactly or at most 1937, at least or exactly or at most 1938, at least or exactly or at most 1939, at least or exactly or at most 1940, at least or exactly or at most 1941, at least or exactly or at most 1942, at least or exactly or at most 1943, at least or exactly or at most 1944, at least or exactly or at most 1945, at least or exactly or at most 1946, at least or exactly or at most 1947, at least or exactly or at most 1948, at least or exactly or at most 1949, at least or exactly or at most 1950, at least or exactly or at most 1951, at least or exactly or at most 1952, at least or exactly or at most 1953, at least or exactly or at most 1954, at least or exactly or at most 1955, at least or exactly or at most 1956, at least or exactly or at most 1957, at least or exactly or at most 1958, at least or exactly or at most 1959, at least or exactly or at most 1960, at least or exactly or at most 1961, at least or exactly or at most 1962, at least or exactly or at most 1963, at least or exactly or at most 1964, at least or exactly or at most 1965, at least or exactly or at most 1966, at least or exactly or at most 1967, at least or exactly or at most 1968, at least or exactly or at most 1969, at least or exactly or at most 1970, at least or exactly or at most 1971, at least or exactly or at most 1972, at least or exactly or at most 1973, at least or exactly or at most 1974, at least or exactly or at most 1975, at least or exactly or at most 1976, at least or exactly or at most 1977, at least or exactly or at most 1978, at least or exactly or at most 1979, at least or exactly or at most 1980, at least or exactly or at most 1981, at least or exactly or at most 1982, at least or exactly or at most 1983, at least or exactly or at most 1984, at least or exactly or at most 1985, at least or exactly or at most 1986, at least or exactly or at most 1987, at least or exactly or at most 1988, at least or exactly or at most 1989, at least or exactly or at most 1990, at least or exactly or at most 1991, at least or exactly or at most 1992, at least or exactly or at most 1993, at least or exactly or at most 1994, at least or exactly or at most 1995, at least or exactly or at most 1996, at least or exactly or at most 1997, at least or exactly or at most 1998, at least or exactly or at most 1999, at least or exactly or at most 2000, at least or exactly or at most 2001, at least or exactly or at most 2002, at least or exactly or at most 2003, at least or exactly or at most 2004, at least or exactly or at most 2005, at least or exactly or at most 2006, at least or exactly or at most 2007, at least or exactly or at most 2008, at least or exactly or at most 2009, at least or exactly or at most 2010, at least or exactly or at most 2011, at least or exactly or at most 2012, at least or exactly or at most 2013, at least or exactly or at most 2014, at least or exactly or at most 2015, at least or exactly or at most 2016, at least or exactly or at most 2017, at least or exactly or at most 2018, at least or exactly or at most 2019, at least or exactly or at most 2020, at least or exactly or at most 2021, at least or exactly or at most 2022, at least or exactly or at most 2023, at least or exactly or at most 2024, at least or exactly or at most 2025, at least or exactly or at most 2026, at least or exactly or at most 2027, at least or exactly or at most 2028, at least or exactly or at most 2029, at least or exactly or at most 2030, at least or exactly or at most 2031, at least or exactly or at most 2032, at least or exactly or at most 2033, at least or exactly or at most 2034, at least or exactly or at most 2035, at least or exactly or at most 2036, at least or exactly or at most 2037, at least or exactly or at most 2038, at least or exactly or at most 2039, at least or exactly or at most 2040, at least or exactly or at most 2041, at least or exactly or at most 2042, at least or exactly or at most 2043, at least or exactly or at most 2044, at least or exactly or at most 2045, at least or exactly or at most 2046, at least or exactly or at most 2047, at least or exactly or at most 2048, at least or exactly or at most 2049, at least or exactly or at most 2050, at least or exactly or at most 2051, at least or exactly or at most 2052, at least or exactly or at most 2053, at least or exactly or at most 2054, at least or exactly or at most 2055, at least or exactly or at most 2056, at least or exactly or at most 2057, at least or exactly or at most 2058, at least or exactly or at most 2059, at least or exactly or at most 2060, at least or exactly or at most 2061, at least or exactly or at most 2062, at least or exactly or at most 2063, at least or exactly or at most 2064, at least or exactly or at most 2065, at least or exactly or at most 2066, at least or exactly or at most 2067, at least or exactly or at most 2068, at least or exactly or at most 2069, at least or exactly or at most 2070, at least or exactly or at most 2071, at least or exactly or at most 2072, at least or exactly or at most 2073, at least or exactly or at most 2074, at least or exactly or at most 2075, at least or exactly or at most 2076, at least or exactly or at most 2077, at least or exactly or at most 2078, at least or exactly or at most 2079, at least or exactly or at most 2080, at least or exactly or at most 2081, at least or exactly or at most 2082, at least or exactly or at most 2083, at least or exactly or at most 2084, at least or exactly or at most 2085, at least or exactly or at most 2086, at least or exactly or at most 2087, at least or exactly or at most 2088, at least or exactly or at most 2089, at least or exactly or at most 2090, at least or exactly or at most 2091, at least or exactly or at most 2092, at least or exactly or at most 2093, at least or exactly or at most 2094, at least or exactly or at most 2095, at least or exactly or at most 2096, at least or exactly or at most 2097, at least or exactly or at most 2098, at least or exactly or at most 2099, at least or exactly or at most 2100, at least or exactly or at most 2101, at least or exactly or at most 2102, at least or exactly or at most 2103, at least or exactly or at most 2104, at least or exactly or at most 2105, at least or exactly or at most 2106, at least or exactly or at most 2107, at least or exactly or at most 2108, at least or exactly or at most 2109, at least or exactly or at most 2110, at least or exactly or at most 2111, at least or exactly or at most 2112, at least or exactly or at most 2113, at least or exactly or at most 2114, at least or exactly or at most 2115, at least or exactly or at most 2116, at least or exactly or at most 2117, at least or exactly or at most 2118, at least or exactly or at most 2119, at least or exactly or at most 2120, at least or exactly or at most 2121, at least or exactly or at most 2122, at least or exactly or at most 2123, at least or exactly or at most 2124, at least or exactly or at most 2125, at least or exactly or at most 2126, at least or exactly or at most 2127, at least or exactly or at most 2128, at least or exactly or at most 2129, at least or exactly or at most 2130, at least or exactly or at most 2131, at least or exactly or at most 2132, at least or exactly or at most 2133, at least or exactly or at most 2134, at least or exactly or at most 2135, at least or exactly or at most 2136, at least or exactly or at most 2137, at least or exactly or at most 2138, at least or exactly or at most 2139, at least or exactly or at most 2140, at least or exactly or at most 2141, at least or exactly or at most 2142, at least or exactly or at most 2143, at least or exactly or at most 2144, at least or exactly or at most 2145, at least or exactly or at most 2146, at least or exactly or at most 2147, at least or exactly or at most 2148, at least or exactly or at most 2149, at least or exactly or at most 2150, at least or exactly or at most 2151, at least or exactly or at most 2152, at least or exactly or at most 2153, at least or exactly or at most 2154, at least or exactly or at most 2155, at least or exactly or at most 2156, at least or exactly or at most 2157, at least or exactly or at most 2158, at least or exactly or at most 2159, at least or exactly or at most 2160, at least or exactly or at most 2161, at least or exactly or at most 2162, at least or exactly or at most 2163, at least or exactly or at most 2164, at least or exactly or at most 2165, at least or exactly or at most 2166, at least or exactly or at most 2167, at least or exactly or at most 2168, at least or exactly or at most 2169, at least or exactly or at most 2170, at least or exactly or at most 2171, at least or exactly or at most 2172, at least or exactly or at most 2173, at least or exactly or at most 2174, at least or exactly or at most 2175, at least or exactly or at most 2176, at least or exactly or at most 2177, at least or exactly or at most 2178, at least or exactly or at most 2179, at least or exactly or at most 2180, at least or exactly or at most 2181, at least or exactly or at most 2182, at least or exactly or at most 2183, at least or exactly or at most 2184, at least or exactly or at most 2185, at least or exactly or at most 2186, at least or exactly or at most 2187, at least or exactly or at most 2188, at least or exactly or at most 2189, at least or exactly or at most 2190, at least or exactly or at most 2191, at least or exactly or at most 2192, at least or exactly or at most 2193, at least or exactly or at most 2194, at least or exactly or at most 2195, at least or exactly or at most 2196, at least or exactly or at most 2197, at least or exactly or at most 2198, at least or exactly or at most 2199, at least or exactly or at most 2200, at least or exactly or at most 2201, at least or exactly or at most 2202, at least or exactly or at most 2203, at least or exactly or at most 2204, at least or exactly or at most 2205, at least or exactly or at most 2206, at least or exactly or at most 2207, at least or exactly or at most 2208, at least or exactly or at most 2209, at least or exactly or at most 2210, at least or exactly or at most 2211, at least or exactly or at most 2212, at least or exactly or at most 2213, at least or exactly or at most 2214, at least or exactly or at most 2215, at least or exactly or at most 2216, at least or exactly or at most 2217, at least or exactly or at most 2218, at least or exactly or at most 2219, at least or exactly or at most 2220, at least or exactly or at most 2221, at least or exactly or at most 2222, at least or exactly or at most 2223, at least or exactly or at most 2224, at least or exactly or at most 2225, at least or exactly or at most 2226, at least or exactly or at most 2227, at least or exactly or at most 2228, at least or exactly or at most 2229, at least or exactly or at most 2230, at least or exactly or at most 2231, at least or exactly or at most 2232, at least or exactly or at most 2233, at least or exactly or at most 2234, at least or exactly or at most 2235, at least or exactly or at most 2236, at least or exactly or at most 2237, at least or exactly or at most 2238, at least or exactly or at most 2239, at least or exactly or at most 2240, at least or exactly or at most 2241, at least or exactly or at most 2242, at least or exactly or at most 2243, at least or exactly or at most 2244, at least or exactly or at most 2245, at least or exactly or at most 2246, at least or exactly or at most 2247, at least or exactly or at most 2248, at least or exactly or at most 2249, at least or exactly or at most 2250, at least or exactly or at most 2251, at least or exactly or at most 2252, at least or exactly or at most 2253, at least or exactly or at most 2254, at least or exactly or at most 2255, at least or exactly or at most 2256, at least or exactly or at most 2257, at least or exactly or at most 2258, at least or exactly or at most 2259, at least or exactly or at most 2260, at least or exactly or at most 2261, at least or exactly or at most 2262, at least or exactly or at most 2263, at least or exactly or at most 2264, at least or exactly or at most 2265, at least or exactly or at most 2266, at least or exactly or at most 2267, at least or exactly or at most 2268, at least or exactly or at most 2269, at least or exactly or at most 2270, at least or exactly or at most 2271, at least or exactly or at most 2272, at least or exactly or at most 2273, at least or exactly or at most 2274, at least or exactly or at most 2275, at least or exactly or at most 2276, at least or exactly or at most 2277, at least or exactly or at most 2278, at least or exactly or at most 2279, at least or exactly or at most 2280, at least or exactly or at most 2281, at least or exactly or at most 2282, at least or exactly or at most 2283, at least or exactly or at most 2284, at least or exactly or at most 2285, at least or exactly or at most 2286, at least or exactly or at most 2287, at least or exactly or at most 2288, at least or exactly or at most 2289, at least or exactly or at most 2290, at least or exactly or at most 2291, at least or exactly or at most 2292, at least or exactly or at most 2293, at least or exactly or at most 2294, at least or exactly or at most 2295, at least or exactly or at most 2296, at least or exactly or at most 2297, at least or exactly or at most 2298, at least or exactly or at most 2299, at least or exactly or at most 2300, at least or exactly or at most 2301, at least or exactly or at most 2302, at least or exactly or at most 2303, at least or exactly or at most 2304, at least or exactly or at most 2305, at least or exactly or at most 2306, at least or exactly or at most 2307, at least or exactly or at most 2308, at least or exactly or at most 2309, at least or exactly or at most 2310, at least or exactly or at most 2311, at least or exactly or at most 2312, at least or exactly or at most 2313, at least or exactly or at most 2314, at least or exactly or at most 2315, at least or exactly or at most 2316, at least or exactly or at most 2317, at least or exactly or at most 2318, at least or exactly or at most 2319, at least or exactly or at most 2320, at least or exactly or at most 2321, at least or exactly or at most 2322, at least or exactly or at most 2323, at least or exactly or at most 2324, at least or exactly or at most 2325, at least or exactly or at most 2326, at least or exactly or at most 2327, at least or exactly or at most 2328, at least or exactly or at most 2329, at least or exactly or at most 2330, at least or exactly or at most 2331, at least or exactly or at most 2332, at least or exactly or at most 2333, at least or exactly or at most 2334, at least or exactly or at most 2335, at least or exactly or at most 2336, at least or exactly or at most 2337, at least or exactly or at most 2338, at least or exactly or at most 2339, at least or exactly or at most 2340, at least or exactly or at most 2341, at least or exactly or at most 2342, at least or exactly or at most 2343, at least or exactly or at most 2344, at least or exactly or at most 2345, at least or exactly or at most 2346, at least or exactly or at most 2347, at least or exactly or at most 2348, at least or exactly or at most 2349, at least or exactly or at most 2350, at least or exactly or at most 2351, at least or exactly or at most 2352, at least or exactly or at most 2353, at least or exactly or at most 2354, at least or exactly or at most 2355, at least or exactly or at most 2356, at least or exactly or at most 2357, at least or exactly or at most 2358, at least or exactly or at most 2359, at least or exactly or at most 2360, at least or exactly or at most 2361, at least or exactly or at most 2362, at least or exactly or at most 2363, at least or exactly or at most 2364, at least or exactly or at most 2365, at least or exactly or at most 2366, at least or exactly or at most 2367, at least or exactly or at most 2368, at least or exactly or at most 2369, at least or exactly or at most 2370, at least or exactly or at most 2371, at least or exactly or at most 2372, at least or exactly or at most 2373, at least or exactly or at most 2374, at least or exactly or at most 2375, at least or exactly or at most 2376, at least or exactly or at most 2377, at least or exactly or at most 2378, at least or exactly or at most 2379, at least or exactly or at most 2380, at least or exactly or at most 2381, at least or exactly or at most 2382, at least or exactly or at most 2383, at least or exactly or at most 2384, at least or exactly or at most 2385, at least or exactly or at most 2386, at least or exactly or at most 2387, at least or exactly or at most 2388, at least or exactly or at most 2389, at least or exactly or at most 2390, at least or exactly or at most 2391, at least or exactly or at most 2392, at least or exactly or at most 2393, at least or exactly or at most 2394, at least or exactly or at most 2395, at least or exactly or at most 2396, at least or exactly or at most 2397, at least or exactly or at most 2398, at least or exactly or at most 2399, at least or exactly or at most 2400, at least or exactly or at most 2401, at least or exactly or at most 2402, at least or exactly or at most 2403, at least or exactly or at most 2404, at least or exactly or at most 2405, at least or exactly or at most 2406, at least or exactly or at most 2407, at least or exactly or at most 2408, at least or exactly or at most 2409, at least or exactly or at most 2410, at least or exactly or at most 2411, at least or exactly or at most 2412, at least or exactly or at most 2413, at least or exactly or at most 2414, at least or exactly or at most 2415, at least or exactly or at most 2416, at least or exactly or at most 2417, at least or exactly or at most 2418, at least or exactly or at most 2419, at least or exactly or at most 2420, at least or exactly or at most 2421, at least or exactly or at most 2422, at least or exactly or at most 2423, at least or exactly or at most 2424, at least or exactly or at most 2425, at least or exactly or at most 2426, at least or exactly or at most 2427, at least or exactly or at most 2428, at least or exactly or at most 2429, at least or exactly or at most 2430, at least or exactly or at most 2431, at least or exactly or at most 2432, at least or exactly or at most 2433, at least or exactly or at most 2434, at least or exactly or at most 2435, at least or exactly or at most 2436, at least or exactly or at most 2437, at least or exactly or at most 2438, at least or exactly or at most 2439, at least or exactly or at most 2440, at least or exactly or at most 2441, at least or exactly or at most 2442, at least or exactly or at most 2443, at least or exactly or at most 2444, at least or exactly or at most 2445, at least or exactly or at most 2446, at least or exactly or at most 2447, at least or exactly or at most 2448, at least or exactly or at most 2449, at least or exactly or at most 2450, at least or exactly or at most 2451, at least or exactly or at most 2452, at least or exactly or at most 2453, at least or exactly or at most 2454, at least or exactly or at most 2455, at least or exactly or at most 2456, at least or exactly or at most 2457, at least or exactly or at most 2458, at least or exactly or at most 2459, at least or exactly or at most 2460, at least or exactly or at most 2461, at least or exactly or at most 2462, at least or exactly or at most 2463, at least or exactly or at most 2464, at least or exactly or at most 2465, at least or exactly or at most 2466, or at least or exactly or at most 2467 contiguous amino acid residues.

Insofar as embodiment b relates to SEQ ID NOs: 29-30, the at least 5 contiguous amino acids referred to in option b) in the definition of the first aspect of the invention may also constitute at least or exactly or at most 2468, at least or exactly or at most 2469, at least or exactly or at most 2470, at least or exactly or at most 2471, at least or exactly or at most 2472, at least or exactly or at most 2473, at least or exactly or at most 2474, at least or exactly or at most 2475, at least or exactly or at most 2476, at least or exactly or at most 2477, at least or exactly or at most 2478, at least or exactly or at most 2479, at least or exactly or at most 2480, at least or exactly or at most 2481, at least or exactly or at most 2482, at least or exactly or at most 2483, at least or exactly or at most 2484, at least or exactly or at most 2485, at least or exactly or at most 2486, at least or exactly or at most 2487, at least or exactly or at most 2488, at least or exactly or at most 2489, at least or exactly or at most 2490, at least or exactly or at most 2491, at least or exactly or at most 2492, at least or exactly or at most 2493, at least or exactly or at most 2494, at least or exactly or at most 2495, at least or exactly or at most 2496, at least or exactly or at most 2497, at least or exactly or at most 2498, at least or exactly or at most 2499, at least or exactly or at most 2500, at least or exactly or at most 2501, at least or exactly or at most 2502, at least or exactly or at most 2503, at least or exactly or at most 2504, at least or exactly or at most 2505, at least or exactly or at most 2506, at least or exactly or at most 2507, at least or exactly or at most 2508, at least or exactly or at most 2509, at least or exactly or at most 2510, at least or exactly or at most 2511, at least or exactly or at most 2512, at least or exactly or at most 2513, at least or exactly or at most 2514, at least or exactly or at most 2515, at least or exactly or at most 2516, at least or exactly or at most 2517, at least or exactly or at most 2518, at least or exactly or at most 2519, at least or exactly or at most 2520, at least or exactly or at most 2521, at least or exactly or at most 2522, at least or exactly or at most 2523, at least or exactly or at most 2524, at least or exactly or at most 2525, at least or exactly or at most 2526, at least or exactly or at most 2527, at least or exactly or at most 2528, at least or exactly or at most 2529, at least or exactly or at most 2530, at least or exactly or at most 2531, at least or exactly or at most 2532, at least or exactly or at most 2533, at least or exactly or at most 2534, at least or exactly or at most 2535, at least or exactly or at most 2536, at least or exactly or at most 2537, at least or exactly or at most 2538, at least or exactly or at most 2539, at least or exactly or at most 2540, at least or exactly or at most 2541, at least or exactly or at most 2542, at least or exactly or at most 2543, at least or exactly or at most 2544, at least or exactly or at most 2545, at least or exactly or at most 2546, at least or exactly or at most 2547, at least or exactly or at most 2548, at least or exactly or at most 2549, at least or exactly or at most 2550, at least or exactly or at most 2551, at least or exactly or at most 2552, at least or exactly or at most 2553, at least or exactly or at most 2554, at least or exactly or at most 2555, at least or exactly or at most 2556, at least or exactly or at most 2557, at least or exactly or at most 2558, at least or exactly or at most 2559, at least or exactly or at most 2560, at least or exactly or at most 2561, at least or exactly or at most 2562, at least or exactly or at most 2563, at least or exactly or at most 2564, at least or exactly or at most 2565, at least or exactly or at most 2566, at least or exactly or at most 2567, at least or exactly or at most 2568, at least or exactly or at most 2569, at least or exactly or at most 2570, at least or exactly or at most 2571, at least or exactly or at most 2572, at least or exactly or at most 2573, at least or exactly or at most 2574, at least or exactly or at most 2575, at least or exactly or at most 2576, at least or exactly or at most 2577, at least or exactly or at most 2578, at least or exactly or at most 2579, at least or exactly or at most 2580, at least or exactly or at most 2581, at least or exactly or at most 2582, at least or exactly or at most 2583, at least or exactly or at most 2584, at least or exactly or at most 2585, at least or exactly or at most 2586, at least or exactly or at most 2587, at least or exactly or at most 2588, at least or exactly or at most 2589, at least or exactly or at most 2590, at least or exactly or at most 2591, at least or exactly or at most 2592, at least or exactly or at most 2593, at least or exactly or at most 2594, at least or exactly or at most 2595, at least or exactly or at most 2596, at least or exactly or at most 2597, at least or exactly or at most 2598, at least or exactly or at most 2599, at least or exactly or at most 2600, at least or exactly or at most 2601, at least or exactly or at most 2602, at least or exactly or at most 2603, at least or exactly or at most 2604, at least or exactly or at most 2605, at least or exactly or at most 2606, at least or exactly or at most 2607, at least or exactly or at most 2608, at least or exactly or at most 2609, at least or exactly or at most 2610, at least or exactly or at most 2611, at least or exactly or at most 2612, at least or exactly or at most 2613, at least or exactly or at most 2614, at least or exactly or at most 2615, at least or exactly or at most 2616, at least or exactly or at most 2617, at least or exactly or at most 2618, at least or exactly or at most 2619, at least or exactly or at most 2620, at least or exactly or at most 2621, at least or exactly or at most 2622, at least or exactly or at most 2623, at least or exactly or at most 2624, at least or exactly or at most 2625, at least or exactly or at most 2626, at least or exactly or at most 2627, at least or exactly or at most 2628, at least or exactly or at most 2629, at least or exactly or at most 2630, at least or exactly or at most 2631, at least or exactly or at most 2632, at least or exactly or at most 2633, at least or exactly or at most 2634, at least or exactly or at most 2635, at least or exactly or at most 2636, at least or exactly or at most 2637, at least or exactly or at most 2638, at least or exactly or at most 2639, at least or exactly or at most 2640, at least or exactly or at most 2641, at least or exactly or at most 2642, at least or exactly or at most 2643, at least or exactly or at most 2644, at least or exactly or at most 2645, at least or exactly or at most 2646, at least or exactly or at most 2647, at least or exactly or at most 2648, at least or exactly or at most 2649, at least or exactly or at most 2650, at least or exactly or at most 2651, at least or exactly or at most 2652, at least or exactly or at most 2653, at least or exactly or at most 2654, at least or exactly or at most 2655, at least or exactly or at most 2656, at least or exactly or at most 2657, at least or exactly or at most 2658, at least or exactly or at most 2659, at least or exactly or at most 2660, at least or exactly or at most 2661, at least or exactly or at most 2662, at least or exactly or at most 2663, at least or exactly or at most 2664, at least or exactly or at most 2665, at least or exactly or at most 2666, at least or exactly or at most 2667, at least or exactly or at most 2668, at least or exactly or at most 2669, at least or exactly or at most 2670, at least or exactly or at most 2671, at least or exactly or at most 2672, at least or exactly or at most 2673, at least or exactly or at most 2674, at least or exactly or at most 2675, at least or exactly or at most 2676, at least or exactly or at most 2677, at least or exactly or at most 2678, at least or exactly or at most 2679, at least or exactly or at most 2680, at least or exactly or at most 2681, at least or exactly or at most 2682, at least or exactly or at most 2683, at least or exactly or at most 2684, at least or exactly or at most 2685, at least or exactly or at most 2686, at least or exactly or at most 2687, at least or exactly or at most 2688, at least or exactly or at most 2689, at least or exactly or at most 2690, at least or exactly or at most 2691, at least or exactly or at most 2692, at least or exactly or at most 2693, at least or exactly or at most 2694, at least or exactly or at most 2695, at least or exactly or at most 2696, at least or exactly or at most 2697, at least or exactly or at most 2698, at least or exactly or at most 2699, at least or exactly or at most 2700, at least or exactly or at most 2701, at least or exactly or at most 2702, at least or exactly or at most 2703, at least or exactly or at most 2704, at least or exactly or at most 2705, at least or exactly or at most 2706, at least or exactly or at most 2707, at least or exactly or at most 2708, at least or exactly or at most 2709, at least or exactly or at most 2710, at least or exactly or at most 2711, at least or exactly or at most 2712, at least or exactly or at most 2713, at least or exactly or at most 2714, at least or exactly or at most 2715, at least or exactly or at most 2716, at least or exactly or at most 2717, at least or exactly or at most 2718, at least or exactly or at most 2719, at least or exactly or at most 2720, at least or exactly or at most 2721, at least or exactly or at most 2722, at least or exactly or at most 2723, at least or exactly or at most 2724, at least or exactly or at most 2725, at least or exactly or at most 2726, at least or exactly or at most 2727, at least or exactly or at most 2728, at least or exactly or at most 2729, at least or exactly or at most 2730, at least or exactly or at most 2731, at least or exactly or at most 2732, at least or exactly or at most 2733, at least or exactly or at most 2734, at least or exactly or at most 2735, at least or exactly or at most 2736, at least or exactly or at most 2737, at least or exactly or at most 2738, at least or exactly or at most 2739, at least or exactly or at most 2740, at least or exactly or at most 2741, at least or exactly or at most 2742, at least or exactly or at most 2743, at least or exactly or at most 2744, at least or exactly or at most 2745, at least or exactly or at most 2746, at least or exactly or at most 2747, at least or exactly or at most 2748, at least or exactly or at most 2749, at least or exactly or at most 2750, at least or exactly or at most 2751, at least or exactly or at most 2752, at least or exactly or at most 2753, at least or exactly or at most 2754, at least or exactly or at most 2755, at least or exactly or at most 2756, at least or exactly or at most 2757, at least or exactly or at most 2758, at least or exactly or at most 2759, at least or exactly or at most 2760, at least or exactly or at most 2761, at least or exactly or at most 2762, at least or exactly or at most 2763, at least or exactly or at most 2764, at least or exactly or at most 2765, at least or exactly or at most 2766, at least or exactly or at most 2767, at least or exactly or at most 2768, at least or exactly or at most 2769, at least or exactly or at most 2770, at least or exactly or at most 2771, at least or exactly or at most 2772, at least or exactly or at most 2773, at least or exactly or at most 2774, at least or exactly or at most 2775, at least or exactly or at most 2776, at least or exactly or at most 2777, at least or exactly or at most 2778, at least or exactly or at most 2779, at least or exactly or at most 2780, at least or exactly or at most 2781, at least or exactly or at most 2782, at least or exactly or at most 2783, at least or exactly or at most 2784, at least or exactly or at most 2785, at least or exactly or at most 2786, at least or exactly or at most 2787, at least or exactly or at most 2788, at least or exactly or at most 2789, at least or exactly or at most 2790, at least or exactly or at most 2791, at least or exactly or at most 2792, at least or exactly or at most 2793, at least or exactly or at most 2794, at least or exactly or at most 2795, at least or exactly or at most 2796, at least or exactly or at most 2797, at least or exactly or at most 2798, at least or exactly or at most 2799, at least or exactly or at most 2800, at least or exactly or at most 2801, at least or exactly or at most 2802, at least or exactly or at most 2803, at least or exactly or at most 2804, at least or exactly or at most 2805, at least or exactly or at most 2806, at least or exactly or at most 2807, at least or exactly or at most 2808, at least or exactly or at most 2809, at least or exactly or at most 2810, at least or exactly or at most 2811, at least or exactly or at most 2812, at least or exactly or at most 2813, at least or exactly or at most 2814, at least or exactly or at most 2815, at least or exactly or at most 2816, at least or exactly or at most 2817, at least or exactly or at most 2818, at least or exactly or at most 2819, at least or exactly or at most 2820, at least or exactly or at most 2821, at least or exactly or at most 2822, at least or exactly or at most 2823, at least or exactly or at most 2824, at least or exactly or at most 2825, at least or exactly or at most 2826, at least or exactly or at most 2827, at least or exactly or at most 2828, at least or exactly or at most 2829, at least or exactly or at most 2830, at least or exactly or at most 2831, at least or exactly or at most 2832, at least or exactly or at most 2833, at least or exactly or at most 2834, at least or exactly or at most 2835, at least or exactly or at most 2836, at least or exactly or at most 2837, at least or exactly or at most 2838, at least or exactly or at most 2839, at least or exactly or at most 2840, at least or exactly or at most 2841, at least or exactly or at most 2842, at least or exactly or at most 2843, at least or exactly or at most 2844, at least or exactly or at most 2845, at least or exactly or at most 2846, at least or exactly or at most 2847, at least or exactly or at most 2848, at least or exactly or at most 2849, at least or exactly or at most 2850, at least or exactly or at most 2851, at least or exactly or at most 2852, at least or exactly or at most 2853, at least or exactly or at most 2854, at least or exactly or at most 2855, at least or exactly or at most 2856, at least or exactly or at most 2857, at least or exactly or at most 2858, at least or exactly or at most 2859, at least or exactly or at most 2860, at least or exactly or at most 2861, at least or exactly or at most 2862, at least or exactly or at most 2863, at least or exactly or at most 2864, at least or exactly or at most 2865, at least or exactly or at most 2866, at least or exactly or at most 2867, at least or exactly or at most 2868, at least or exactly or at most 2869, at least or exactly or at most 2870, at least or exactly or at most 2871, at least or exactly or at most 2872, at least or exactly or at most 2873, at least or exactly or at most 2874, at least or exactly or at most 2875, at least or exactly or at most 2876, at least or exactly or at most 2877, at least or exactly or at most 2878, at least or exactly or at most 2879, at least or exactly or at most 2880, at least or exactly or at most 2881, at least or exactly or at most 2882, at least or exactly or at most 2883, at least or exactly or at most 2884, at least or exactly or at most 2885, at least or exactly or at most 2886, at least or exactly or at most 2887, at least or exactly or at most 2888, at least or exactly or at most 2889, at least or exactly or at most 2890, at least or exactly or at most 2891, at least or exactly or at most 2892, at least or exactly or at most 2893, at least or exactly or at most 2894, at least or exactly or at most 2895, at least or exactly or at most 2896, at least or exactly or at most 2897, at least or exactly or at most 2898, at least or exactly or at most 2899, at least or exactly or at most 2900, at least or exactly or at most 2901, at least or exactly or at most 2902, at least or exactly or at most 2903, at least or exactly or at most 2904, at least or exactly or at most 2905, at least or exactly or at most 2906, at least or exactly or at most 2907, at least or exactly or at most 2908, at least or exactly or at most 2909, at least or exactly or at most 2910, at least or exactly or at most 2911, at least or exactly or at most 2912, at least or exactly or at most 2913, at least or exactly or at most 2914, at least or exactly or at most 2915, at least or exactly or at most 2916, at least or exactly or at most 2917, at least or exactly or at most 2918, at least or exactly or at most 2919, at least or exactly or at most 2920, at least or exactly or at most 2921, at least or exactly or at most 2922, at least or exactly or at most 2923, at least or exactly or at most 2924, at least or exactly or at most 2925, at least or exactly or at most 2926, at least or exactly or at most 2927, at least or exactly or at most 2928, at least or exactly or at most 2929, at least or exactly or at most 2930, at least or exactly or at most 2931, at least or exactly or at most 2932, at least or exactly or at most 2933, at least or exactly or at most 2934, at least or exactly or at most 2935, at least or exactly or at most 2936, at least or exactly or at most 2937, at least or exactly or at most 2938, at least or exactly or at most 2939, at least or exactly or at most 2940, at least or exactly or at most 2941, at least or exactly or at most 2942, at least or exactly or at most 2943, at least or exactly or at most 2944, at least or exactly or at most 2945, at least or exactly or at most 2946, at least or exactly or at most 2947, at least or exactly or at most 2948, at least or exactly or at most 2949, at least or exactly or at most 2950, at least or exactly or at most 2951, at least or exactly or at most 2952, at least or exactly or at most 2953, at least or exactly or at most 2954, at least or exactly or at most 2955, at least or exactly or at most 2956, at least or exactly or at most 2957, at least or exactly or at most 2958, at least or exactly or at most 2959, at least or exactly or at most 2960, at least or exactly or at most 2961, at least or exactly or at most 2962, at least or exactly or at most 2963, at least or exactly or at most 2964, at least or exactly or at most 2965, at least or exactly or at most 2966, at least or exactly or at most 2967, at least or exactly or at most 2968, at least or exactly or at most 2969, at least or exactly or at most 2970, at least or exactly or at most 2971, at least or exactly or at most 2972, at least or exactly or at most 2973, at least or exactly or at most 2974, at least or exactly or at most 2975, at least or exactly or at most 2976, at least or exactly or at most 2977, at least or exactly or at most 2978, at least or exactly or at most 2979, at least or exactly or at most 2980, at least or exactly or at most 2981, at least or exactly or at most 2982, at least or exactly or at most 2983, at least or exactly or at most 2984, at least or exactly or at most 2985, at least or exactly or at most 2986, at least or exactly or at most 2987, at least or exactly or at most 2988, at least or exactly or at most 2989, at least or exactly or at most 2990, at least or exactly or at most 2991, at least or exactly or at most 2992, at least or exactly or at most 2993, at least or exactly or at most 2994, at least or exactly or at most 2995, at least or exactly or at most 2996, at least or exactly or at most 2997, at least or exactly or at most 2998, at least or exactly or at most 2999, at least or exactly or at most 3000, at least or exactly or at most 3001, at least or exactly or at most 3002, at least or exactly or at most 3003, at least or exactly or at most 3004, at least or exactly or at most 3005, at least or exactly or at most 3006, at least or exactly or at most 3007, at least or exactly or at most 3008, at least or exactly or at most 3009, at least or exactly or at most 3010, at least or exactly or at most 3011, at least or exactly or at most 3012, at least or exactly or at most 3013, at least or exactly or at most 3014, at least or exactly or at most 3015, at least or exactly or at most 3016, at least or exactly or at most 3017, at least or exactly or at most 3018, at least or exactly or at most 3019, at least or exactly or at most 3020, at least or exactly or at most 3021, at least or exactly or at most 3022, at least or exactly or at most 3023, at least or exactly or at most 3024, at least or exactly or at most 3025, at least or exactly or at most 3026, at least or exactly or at most 3027, at least or exactly or at most 3028, at least or exactly or at most 3029, at least or exactly or at most 3030, at least or exactly or at most 3031, at least or exactly or at most 3032, at least or exactly or at most 3033, at least or exactly or at most 3034, at least or exactly or at most 3035, at least or exactly or at most 3036, at least or exactly or at most 3037, at least or exactly or at most 3038, at least or exactly or at most 3039, at least or exactly or at most 3040, at least or exactly or at most 3041, at least or exactly or at most 3042, at least or exactly or at most 3043, at least or exactly or at most 3044, at least or exactly or at most 3045, at least or exactly or at most 3046, at least or exactly or at most 3047, at least or exactly or at most 3048, at least or exactly or at most 3049, at least or exactly or at most 3050, at least or exactly or at most 3051, at least or exactly or at most 3052, at least or exactly or at most 3053, at least or exactly or at most 3054, at least or exactly or at most 3055, at least or exactly or at most 3056, at least or exactly or at most 3057, at least or exactly or at most 3058, at least or exactly or at most 3059, at least or exactly or at most 3060, at least or exactly or at most 3061, at least or exactly or at most 3062, at least or exactly or at most 3063, at least or exactly or at most 3064, at least or exactly or at most 3065, at least or exactly or at most 3066, at least or exactly or at most 3067, at least or exactly or at most 3068, at least or exactly or at most 3069, at least or exactly or at most 3070, at least or exactly or at most 3071, at least or exactly or at most 3072, at least or exactly or at most 3073, at least or exactly or at most 3074, at least or exactly or at most 3075, at least or exactly or at most 3076, at least or exactly or at most 3077, at least or exactly or at most 3078, at least or exactly or at most 3079, at least or exactly or at most 3080, at least or exactly or at most 3081, at least or exactly or at most 3082, at least or exactly or at most 3083, at least or exactly or at most 3084, at least or exactly or at most 3085, at least or exactly or at most 3086, at least or exactly or at most 3087, at least or exactly or at most 3088, at least or exactly or at most 3089, at least or exactly or at most 3090, at least or exactly or at most 3091, at least or exactly or at most 3092, at least or exactly or at most 3093, at least or exactly or at most 3094, at least or exactly or at most 3095, at least or exactly or at most 3096, at least or exactly or at most 3097, at least or exactly or at most 3098, at least or exactly or at most 3099, at least or exactly or at most 3100, at least or exactly or at most 3101, at least or exactly or at most 3102, at least or exactly or at most 3103, at least or exactly or at most 3104, at least or exactly or at most 3105, at least or exactly or at most 3106, at least or exactly or at most 3107, at least or exactly or at most 3108, at least or exactly or at most 3109, at least or exactly or at most 3110, at least or exactly or at most 3111, at least or exactly or at most 3112, at least or exactly or at most 3113, at least or exactly or at most 3114, at least or exactly or at most 3115, at least or exactly or at most 3116, at least or exactly or at most 3117, at least or exactly or at most 3118, at least or exactly or at most 3119, at least or exactly or at most 3120, at least or exactly or at most 3121, at least or exactly or at most 3122, at least or exactly or at most 3123, at least or exactly or at most 3124, at least or exactly or at most 3125, at least or exactly or at most 3126, at least or exactly or at most 3127, at least or exactly or at most 3128, at least or exactly or at most 3129, at least or exactly or at most 3130, at least or exactly or at most 3131, at least or exactly or at most 3132, at least or exactly or at most 3133, at least or exactly or at most 3134, at least or exactly or at most 3135, at least or exactly or at most 3136, at least or exactly or at most 3137, at least or exactly or at most 3138, at least or exactly or at most 3139, at least or exactly or at most 3140, at least or exactly or at most 3141, at least or exactly or at most 3142, at least or exactly or at most 3143, at least or exactly or at most 3144, at least or exactly or at most 3145, at least or exactly or at most 3146, at least or exactly or at most 3147, at least or exactly or at most 3148, at least or exactly or at most 3149, at least or exactly or at most 3150, at least or exactly or at most 3151, at least or exactly or at most 3152, at least or exactly or at most 3153, at least or exactly or at most 3154, at least or exactly or at most 3155, at least or exactly or at most 3156, at least or exactly or at most 3157, at least or exactly or at most 3158, at least or exactly or at most 3159, at least or exactly or at most 3160, at least or exactly or at most 3161, at least or exactly or at most 3162, at least or exactly or at most 3163, at least or exactly or at most 3164, at least or exactly or at most 3165, at least or exactly or at most 3166, at least or exactly or at most 3167, at least or exactly or at most 3168, at least or exactly or at most 3169, at least or exactly or at most 3170, at least or exactly or at most 3171, at least or exactly or at most 3172, at least or exactly or at most 3173, at least or exactly or at most 3174, at least or exactly or at most 3175, at least or exactly or at most 3176, at least or exactly or at most 3177, at least or exactly or at most 3178, at least or exactly or at most 3179, at least or exactly or at most 3180, at least or exactly or at most 3181, at least or exactly or at most 3182, at least or exactly or at most 3183, at least or exactly or at most 3184, at least or exactly or at most 3185, at least or exactly or at most 3186, at least or exactly or at most 3187, at least or exactly or at most 3188, at least or exactly or at most 3189, at least or exactly or at most 3190, at least or exactly or at most 3191, at least or exactly or at most 3192, at least or exactly or at most 3193, at least or exactly or at most 3194, at least or exactly or at most 3195, at least or exactly or at most 3196, at least or exactly or at most 3197, at least or exactly or at most 3198, at least or exactly or at most 3199, at least or exactly or at most 3200, at least or exactly or at most 3201, at least or exactly or at most 3202, at least or exactly or at most 3203, at least or exactly or at most 3204, at least or exactly or at most 3205, at least or exactly or at most 3206, at least or exactly or at most 3207, at least or exactly or at most 3208, at least or exactly or at most 3209, at least or exactly or at most 3210, at least or exactly or at most 3211, at least or exactly or at most 3212, at least or exactly or at most 3213, at least or exactly or at most 3214, at least or exactly or at most 3215, at least or exactly or at most 3216, at least or exactly or at most 3217, at least or exactly or at most 3218, at least or exactly or at most 3219, at least or exactly or at most 3220, at least or exactly or at most 3221, at least or exactly or at most 3222, at least or exactly or at most 3223, at least or exactly or at most 3224, at least or exactly or at most 3225, at least or exactly or at most 3226, at least or exactly or at most 3227, at least or exactly or at most 3228, at least or exactly or at most 3229, at least or exactly or at most 3230, at least or exactly or at most 3231, at least or exactly or at most 3232, at least or exactly or at most 3233, at least or exactly or at most 3234, at least or exactly or at most 3235, at least or exactly or at most 3236, at least or exactly or at most 3237, at least or exactly or at most 3238, at least or exactly or at most 3239, at least or exactly or at most 3240, at least or exactly or at most 3241, at least or exactly or at most 3242, at least or exactly or at most 3243, at least or exactly or at most 3244, at least or exactly or at most 3245, at least or exactly or at most 3246, at least or exactly or at most 3247, at least or exactly or at most 3248, at least or exactly or at most 3249, at least or exactly or at most 3250, at least or exactly or at most 3251, at least or exactly or at most 3252, at least or exactly or at most 3253, at least or exactly or at most 3254, at least or exactly or at most 3255, at least or exactly or at most 3256, at least or exactly or at most 3257, at least or exactly or at most 3258, at least or exactly or at most 3259, at least or exactly or at most 3260, at least or exactly or at most 3261, at least or exactly or at most 3262, at least or exactly or at most 3263, at least or exactly or at most 3264, at least or exactly or at most 3265, at least or exactly or at most 3266, at least or exactly or at most 3267, at least or exactly or at most 3268, at least or exactly or at most 3269, at least or exactly or at most 3270, at least or exactly or at most 3271, at least or exactly or at most 3272, at least or exactly or at most 3273, at least or exactly or at most 3274, at least or exactly or at most 3275, at least or exactly or at most 3276, at least or exactly or at most 3277, at least or exactly or at most 3278, at least or exactly or at most 3279, at least or exactly or at most 3280, at least or exactly or at most 3281, at least or exactly or at most 3282, at least or exactly or at most 3283, at least or exactly or at most 3284, at least or exactly or at most 3285, at least or exactly or at most 3286, at least or exactly or at most 3287, at least or exactly or at most 3288, at least or exactly or at most 3289, at least or exactly or at most 3290, at least or exactly or at most 3291, at least or exactly or at most 3292, at least or exactly or at most 3293, at least or exactly or at most 3294, at least or exactly or at most 3295, at least or exactly or at most 3296, at least or exactly or at most 3297, at least or exactly or at most 3298, at least or exactly or at most 3299, at least or exactly or at most 3300, at least or exactly or at most 3301, at least or exactly or at most 3302, at least or exactly or at most 3303, at least or exactly or at most 3304, at least or exactly or at most 3305, at least or exactly or at most 3306, at least or exactly or at most 3307, at least or exactly or at most 3308, at least or exactly or at most 3309, at least or exactly or at most 3310, at least or exactly or at most 3311, at least or exactly or at most 3312, at least or exactly or at most 3313, at least or exactly or at most 3314, at least or exactly or at most 3315, at least or exactly or at most 3316, at least or exactly or at most 3317, at least or exactly or at most 3318, at least or exactly or at most 3319, at least or exactly or at most 3320, at least or exactly or at most 3321, at least or exactly or at most 3322, at least or exactly or at most 3323, at least or exactly or at most 3324, at least or exactly or at most 3325, at least or exactly or at most 3326, at least or exactly or at most 3327, at least or exactly or at most 3328, at least or exactly or at most 3329, at least or exactly or at most 3330, at least or exactly or at most 3331, at least or exactly or at most 3332, at least or exactly or at most 3333, or at least or exactly or at most 3334 contiguous amino acid residues.

Insofar as embodiment b relates to SEQ ID NO: 30, the at least 5 contiguous amino acids referred to in option b) in the definition of the first aspect of the invention may also constitute at least or exactly or at most 3535, at least or exactly or at most 3536, at least or exactly or at most 3537, at least or exactly or at most 3538, at least or exactly or at most 3539, at least or exactly or at most 3540, at least or exactly or at most 3541, at least or exactly or at most 3542, at least or exactly or at most 3543, at least or exactly or at most 3544, at least or exactly or at most 3545, at least or exactly or at most 3546, at least or exactly or at most 3547, at least or exactly or at most 3548, at least or exactly or at most 3549, at least or exactly or at most 3550, at least or exactly or at most 3551, at least or exactly or at most 3552, at least or exactly or at most 3553, at least or exactly or at most 3554, at least or exactly or at most 3555, at least or exactly or at most 3556, at least or exactly or at most 3557, at least or exactly or at most 3558, at least or exactly or at most 3559, at least or exactly or at most 3560, at least or exactly or at most 3561, at least or exactly or at most 3562, at least or exactly or at most 3563, at least or exactly or at most 3564, at least or exactly or at most 3565, at least or exactly or at most 3566, at least or exactly or at most 3567, at least or exactly or at most 3568, at least or exactly or at most 3569, at least or exactly or at most 3570, at least or exactly or at most 3571, at least or exactly or at most 3572, at least or exactly or at most 3573, at least or exactly or at most 3574, at least or exactly or at most 3575, at least or exactly or at most 3576, at least or exactly or at most 3577, at least or exactly or at most 3578, at least or exactly or at most 3579, at least or exactly or at most 3580, at least or exactly or at most 3581, at least or exactly or at most 3582, at least or exactly or at most 3583, at least or exactly or at most 3584, at least or exactly or at most 3585, at least or exactly or at most 3586, at least or exactly or at most 3587, at least or exactly or at most 3588, at least or exactly or at most 3589, at least or exactly or at most 3590, at least or exactly or at most 3591, at least or exactly or at most 3592, at least or exactly or at most 3593, at least or exactly or at most 3594, at least or exactly or at most 3595, at least or exactly or at most 3596, at least or exactly or at most 3597, at least or exactly or at most 3598, at least or exactly or at most 3599, at least or exactly or at most 3600, at least or exactly or at most 3601, at least or exactly or at most 3602, at least or exactly or at most 3603, at least or exactly or at most 3604, at least or exactly or at most 3605, at least or exactly or at most 3606, at least or exactly or at most 3607, at least or exactly or at most 3608, at least or exactly or at most 3609, at least or exactly or at most 3610, at least or exactly or at most 3611, at least or exactly or at most 3612, at least or exactly or at most 3613, at least or exactly or at most 3614, at least or exactly or at most 3615, at least or exactly or at most 3616, at least or exactly or at most 3617, at least or exactly or at most 3618, at least or exactly or at most 3619, at least or exactly or at most 3620, at least or exactly or at most 3621, at least or exactly or at most 3622, at least or exactly or at most 3623, at least or exactly or at most 3624, at least or exactly or at most 3625, at least or exactly or at most 3626, at least or exactly or at most 3627, at least or exactly or at most 3628, at least or exactly or at most 3629, at least or exactly or at most 3630, at least or exactly or at most 3631, at least or exactly or at most 3632, at least or exactly or at most 3633, at least or exactly or at most 3634, at least or exactly or at most 3635, at least or exactly or at most 3636, at least or exactly or at most 3637, at least or exactly or at most 3638, at least or exactly or at most 3639, at least or exactly or at most 3640, at least or exactly or at most 3641, at least or exactly or at most 3642, at least or exactly or at most 3643, at least or exactly or at most 3644, at least or exactly or at most 3645, at least or exactly or at most 3646, at least or exactly or at most 3647, at least or exactly or at most 3648, at least or exactly or at most 3649, at least or exactly or at most 3650, at least or exactly or at most 3651, at least or exactly or at most 3652, at least or exactly or at most 3653, at least or exactly or at most 3654, at least or exactly or at most 3655, at least or exactly or at most 3656, at least or exactly or at most 3657, at least or exactly or at most 3658, at least or exactly or at most 3659, at least or exactly or at most 3660, at least or exactly or at most 3661, at least or exactly or at most 3662, at least or exactly or at most 3663, at least or exactly or at most 3664, at least or exactly or at most 3665, at least or exactly or at most 3666, at least or exactly or at most 3667, at least or exactly or at most 3668, at least or exactly or at most 3669, at least or exactly or at most 3670, at least or exactly or at most 3671, at least or exactly or at most 3672, at least or exactly or at most 3673, at least or exactly or at most 3674, at least or exactly or at most 3675, at least or exactly or at most 3676, at least or exactly or at most 3677, at least or exactly or at most 3678, at least or exactly or at most 3679, at least or exactly or at most 3680, at least or exactly or at most 3681, at least or exactly or at most 3682, at least or exactly or at most 3683, at least or exactly or at most 3684, at least or exactly or at most 3685, at least or exactly or at most 3686, at least or exactly or at most 3687, at least or exactly or at most 3688, at least or exactly or at most 3689, at least or exactly or at most 3690, at least or exactly or at most 3691, at least or exactly or at most 3692, at least or exactly or at most 3693, at least or exactly or at most 3694, at least or exactly or at most 3695, at least or exactly or at most 3696, at least or exactly or at most 3697, at least or exactly or at most 3698, at least or exactly or at most 3699, at least or exactly or at most 3700, at least or exactly or at most 3701, at least or exactly or at most 3702, at least or exactly or at most 3703, at least or exactly or at most 3704, at least or exactly or at most 3705, at least or exactly or at most 3706, at least or exactly or at most 3707, at least or exactly or at most 3708, at least or exactly or at most 3709, at least or exactly or at most 3710, at least or exactly or at most 3711, at least or exactly or at most 3712, at least or exactly or at most 3713, at least or exactly or at most 3714, at least or exactly or at most 3715, at least or exactly or at most 3716, at least or exactly or at most 3717, at least or exactly or at most 3718, at least or exactly or at most 3719, at least or exactly or at most 3720, at least or exactly or at most 3721, at least or exactly or at most 3722, at least or exactly or at most 3723, at least or exactly or at most 3724, at least or exactly or at most 3725, at least or exactly or at most 3726, at least or exactly or at most 3727, at least or exactly or at most 3728, at least or exactly or at most 3729, at least or exactly or at most 3730, at least or exactly or at most 3731, at least or exactly or at most 3732, at least or exactly or at most 3733, at least or exactly or at most 3734, at least or exactly or at most 3735, at least or exactly or at most 3736, at least or exactly or at most 3737, at least or exactly or at most 3738, at least or exactly or at most 3739, at least or exactly or at most 3740, at least or exactly or at most 3741, at least or exactly or at most 3742, at least or exactly or at most 3743, at least or exactly or at most 3744, at least or exactly or at most 3745, at least or exactly or at most 3746, at least or exactly or at most 3747, at least or exactly or at most 3748, at least or exactly or at most 3749, at least or exactly or at most 3750, at least or exactly or at most 3751, at least or exactly or at most 3752, at least or exactly or at most 3753, at least or exactly or at most 3754, at least or exactly or at most 3755, at least or exactly or at most 3756, at least or exactly or at most 3757, at least or exactly or at most 3758, at least or exactly or at most 3759, at least or exactly or at most 3760, at least or exactly or at most 3761, at least or exactly or at most 3762, at least or exactly or at most 3763, at least or exactly or at most 3764, at least or exactly or at most 3765, at least or exactly or at most 3766, at least or exactly or at most 3767, at least or exactly or at most 3768, at least or exactly or at most 3769, at least or exactly or at most 3770, at least or exactly or at most 3771, at least or exactly or at most 3772, at least or exactly or at most 3773, at least or exactly or at most 3774, at least or exactly or at most 3775, at least or exactly or at most 3776, at least or exactly or at most 3777, at least or exactly or at most 3778, at least or exactly or at most 3779, at least or exactly or at most 3780, at least or exactly or at most 3781, at least or exactly or at most 3782, at least or exactly or at most 3783, at least or exactly or at most 3784, at least or exactly or at most 3785, at least or exactly or at most 3786, at least or exactly or at most 3787, at least or exactly or at most 3788, at least or exactly or at most 3789, at least or exactly or at most 3790, at least or exactly or at most 3791, at least or exactly or at most 3792, at least or exactly or at most 3793, at least or exactly or at most 3794, at least or exactly or at most 3795, at least or exactly or at most 3796, at least or exactly or at most 3797, at least or exactly or at most 3798, at least or exactly or at most 3799, at least or exactly or at most 3800, at least or exactly or at most 3801, at least or exactly or at most 3802, at least or exactly or at most 3803, at least or exactly or at most 3804, at least or exactly or at most 3805, at least or exactly or at most 3806, at least or exactly or at most 3807, at least or exactly or at most 3808, at least or exactly or at most 3809, at least or exactly or at most 3810, at least or exactly or at most 3811, at least or exactly or at most 3812, at least or exactly or at most 3813, at least or exactly or at most 3814, at least or exactly or at most 3815, at least or exactly or at most 3816, at least or exactly or at most 3817, at least or exactly or at most 3818, at least or exactly or at most 3819, at least or exactly or at most 3820, at least or exactly or at most 3821, at least or exactly or at most 3822, at least or exactly or at most 3823, at least or exactly or at most 3824, at least or exactly or at most 3825, at least or exactly or at most 3826, at least or exactly or at most 3827, at least or exactly or at most 3828, at least or exactly or at most 3829, at least or exactly or at most 3830, at least or exactly or at most 3831, at least or exactly or at most 3832, at least or exactly or at most 3833, at least or exactly or at most 3834, at least or exactly or at most 3835, at least or exactly or at most 3836, at least or exactly or at most 3837, at least or exactly or at most 3838, at least or exactly or at most 3839, at least or exactly or at most 3840, at least or exactly or at most 3841, at least or exactly or at most 3842, at least or exactly or at most 3843, at least or exactly or at most 3844, at least or exactly or at most 3845, at least or exactly or at most 3846, at least or exactly or at most 3847, at least or exactly or at most 3848, at least or exactly or at most 3849, at least or exactly or at most 3850, at least or exactly or at most 3851, at least or exactly or at most 3852, at least or exactly or at most 3853, at least or exactly or at most 3854, at least or exactly or at most 3855, at least or exactly or at most 3856, at least or exactly or at most 3857, at least or exactly or at most 3858, at least or exactly or at most 3859, at least or exactly or at most 3860, at least or exactly or at most 3861, at least or exactly or at most 3862, at least or exactly or at most 3863, at least or exactly or at most 3864, at least or exactly or at most 3865, at least or exactly or at most 3866, at least or exactly or at most 3867, at least or exactly or at most 3868, at least or exactly or at most 3869, at least or exactly or at most 3870, at least or exactly or at most 3871, at least or exactly or at most 3872, at least or exactly or at most 3873, at least or exactly or at most 3874, at least or exactly or at most 3875, at least or exactly or at most 3876, at least or exactly or at most 3877, at least or exactly or at most 3878, at least or exactly or at most 3879, at least or exactly or at most 3880, at least or exactly or at most 3881, at least or exactly or at most 3882, at least or exactly or at most 3883, at least or exactly or at most 3884, at least or exactly or at most 3885, at least or exactly or at most 3886, at least or exactly or at most 3887, at least or exactly or at most 3888, at least or exactly or at most 3889, at least or exactly or at most 3890, at least or exactly or at most 3891, at least or exactly or at most 3892, at least or exactly or at most 3893, at least or exactly or at most 3894, at least or exactly or at most 3895, at least or exactly or at most 3896, at least or exactly or at most 3897, at least or exactly or at most 3898, at least or exactly or at most 3899, at least or exactly or at most 3900, at least or exactly or at most 3901, at least or exactly or at most 3902, at least or exactly or at most 3903, at least or exactly or at most 3904, at least or exactly or at most 3905, at least or exactly or at most 3906, at least or exactly or at most 3907, at least or exactly or at most 3908, at least or exactly or at most 3909, at least or exactly or at most 3910, at least or exactly or at most 3911, at least or exactly or at most 3912, at least or exactly or at most 3913, at least or exactly or at most 3914, at least or exactly or at most 3915, at least or exactly or at most 3916, at least or exactly or at most 3917, at least or exactly or at most 3918, at least or exactly or at most 3919, at least or exactly or at most 3920, at least or exactly or at most 3921, at least or exactly or at most 3922, at least or exactly or at most 3923, at least or exactly or at most 3924, at least or exactly or at most 3925, at least or exactly or at most 3926, at least or exactly or at most 3927, at least or exactly or at most 3928, at least or exactly or at most 3929, at least or exactly or at most 3930, at least or exactly or at most 3931, at least or exactly or at most 3932, at least or exactly or at most 3933, at least or exactly or at most 3934, at least or exactly or at most 3935, at least or exactly or at most 3936, at least or exactly or at most 3937, at least or exactly or at most 3938, at least or exactly or at most 3939, at least or exactly or at most 3940, at least or exactly or at most 3941, at least or exactly or at most 3942, at least or exactly or at most 3943, at least or exactly or at most 3944, at least or exactly or at most 3945, at least or exactly or at most 3946, at least or exactly or at most 3947, at least or exactly or at most 3948, at least or exactly or at most 3949, at least or exactly or at most 3950, at least or exactly or at most 3951, at least or exactly or at most 3952, at least or exactly or at most 3953, at least or exactly or at most 3954, at least or exactly or at most 3955, at least or exactly or at most 3956, at least or exactly or at most 3957, at least or exactly or at most 3958, at least or exactly or at most 3959, at least or exactly or at most 3960, at least or exactly or at most 3961, at least or exactly or at most 3962, at least or exactly or at most 3963, at least or exactly or at most 3964, at least or exactly or at most 3965, at least or exactly or at most 3966, at least or exactly or at most 3967, at least or exactly or at most 3968, at least or exactly or at most 3969, at least or exactly or at most 3970, at least or exactly or at most 3971, at least or exactly or at most 3972, at least or exactly or at most 3973, at least or exactly or at most 3974, at least or exactly or at most 3975, at least or exactly or at most 3976, at least or exactly or at most 3977, at least or exactly or at most 3978, at least or exactly or at most 3979, at least or exactly or at most 3980, at least or exactly or at most 3981, at least or exactly or at most 3982, at least or exactly or at most 3983, at least or exactly or at most 3984, at least or exactly or at most 3985, at least or exactly or at most 3986, at least or exactly or at most 3987, at least or exactly or at most 3988, at least or exactly or at most 3989, at least or exactly or at most 3990, at least or exactly or at most 3991, at least or exactly or at most 3992, at least or exactly or at most 3993, at least or exactly or at most 3994, at least or exactly or at most 3995, at least or exactly or at most 3996, at least or exactly or at most 3997, at least or exactly or at most 3998, at least or exactly or at most 3999, at least or exactly or at most 4000, at least or exactly or at most 4001, at least or exactly or at most 4002, at least or exactly or at most 4003, at least or exactly or at most 4004, at least or exactly or at most 4005, at least or exactly or at most 4006, at least or exactly or at most 4007, at least or exactly or at most 4008, at least or exactly or at most 4009, at least or exactly or at most 4010, at least or exactly or at most 4011, at least or exactly or at most 4012, at least or exactly or at most 4013, at least or exactly or at most 4014, at least or exactly or at most 4015, at least or exactly or at most 4016, at least or exactly or at most 4017, at least or exactly or at most 4018, at least or exactly or at most 4019, at least or exactly or at most 4020, at least or exactly or at most 4021, at least or exactly or at most 4022, at least or exactly or at most 4023, at least or exactly or at most 4024, at least or exactly or at most 4025, at least or exactly or at most 4026, at least or exactly or at most 4027, at least or exactly or at most 4028, at least or exactly or at most 4029, at least or exactly or at most 4030, at least or exactly or at most 4031, at least or exactly or at most 4032, at least or exactly or at most 4033, at least or exactly or at most 4034, at least or exactly or at most 4035, at least or exactly or at most 4036, at least or exactly or at most 4037, at least or exactly or at most 4038, at least or exactly or at most 4039, at least or exactly or at most 4040, at least or exactly or at most 4041, at least or exactly or at most 4042, at least or exactly or at most 4043, at least or exactly or at most 4044, at least or exactly or at most 4045, at least or exactly or at most 4046, at least or exactly or at most 4047, at least or exactly or at most 4048, at least or exactly or at most 4049, at least or exactly or at most 4050, at least or exactly or at most 4051, at least or exactly or at most 4052, at least or exactly or at most 4053, at least or exactly or at most 4054, at least or exactly or at most 4055, at least or exactly or at most 4056, at least or exactly or at most 4057, at least or exactly or at most 4058, at least or exactly or at most 4059, at least or exactly or at most 4060, at least or exactly or at most 4061, at least or exactly or at most 4062, at least or exactly or at most 4063, at least or exactly or at most 4064, at least or exactly or at most 4065, at least or exactly or at most 4066, at least or exactly or at most 4067, at least or exactly or at most 4068, at least or exactly or at most 4069, at least or exactly or at most 4070, at least or exactly or at most 4071, at least or exactly or at most 4072, at least or exactly or at most 4073, at least or exactly or at most 4074, at least or exactly or at most 4075, at least or exactly or at most 4076, at least or exactly or at most 4077, at least or exactly or at most 4078, at least or exactly or at most 4079, at least or exactly or at most 4080, at least or exactly or at most 4081, at least or exactly or at most 4082, at least or exactly or at most 4083, at least or exactly or at most 4084, at least or exactly or at most 4085, at least or exactly or at most 4086, at least or exactly or at most 4087, at least or exactly or at most 4088, at least or exactly or at most 4089, at least or exactly or at most 4090, at least or exactly or at most 4091, at least or exactly or at most 4092, at least or exactly or at most 4093, at least or exactly or at most 4094, at least or exactly or at most 4095, at least or exactly or at most 4096, at least or exactly or at most 4097, at least or exactly or at most 4098, at least or exactly or at most 4099, at least or exactly or at most 4100, at least or exactly or at most 4101, at least or exactly or at most 4102, at least or exactly or at most 4103, at least or exactly or at most 4104, at least or exactly or at most 4105, at least or exactly or at most 4106, at least or exactly or at most 4107, at least or exactly or at most 4108, at least or exactly or at most 4109, at least or exactly or at most 4110, at least or exactly or at most 4111, at least or exactly or at most 4112, at least or exactly or at most 4113, at least or exactly or at most 4114, at least or exactly or at most 4115, at least or exactly or at most 4116, at least or exactly or at most 4117, at least or exactly or at most 4118, at least or exactly or at most 4119, at least or exactly or at most 4120, at least or exactly or at most 4121, at least or exactly or at most 4122, at least or exactly or at most 4123, at least or exactly or at most 4124, at least or exactly or at most 4125, at least or exactly or at most 4126, at least or exactly or at most 4127, at least or exactly or at most 4128, at least or exactly or at most 4129, at least or exactly or at most 4130, at least or exactly or at most 4131, at least or exactly or at most 4132, at least or exactly or at most 4133, at least or exactly or at most 4134, at least or exactly or at most 4135, at least or exactly or at most 4136, at least or exactly or at most 4137, at least or exactly or at most 4138, at least or exactly or at most 4139, at least or exactly or at most 4140, at least or exactly or at most 4141, at least or exactly or at most 4142, at least or exactly or at most 4143, at least or exactly or at most 4144, at least or exactly or at most 4145, at least or exactly or at most 4146, at least or exactly or at most 4147, at least or exactly or at most 4148, at least or exactly or at most 4149, at least or exactly or at most 4150, at least or exactly or at most 4151, at least or exactly or at most 4152, at least or exactly or at most 4153, at least or exactly or at most 4154, at least or exactly or at most 4155, at least or exactly or at most 4156, at least or exactly or at most 4157, at least or exactly or at most 4158, at least or exactly or at most 4159, at least or exactly or at most 4160, at least or exactly or at most 4161, at least or exactly or at most 4162, at least or exactly or at most 4163, at least or exactly or at most 4164, at least or exactly or at most 4165, at least or exactly or at most 4166, at least or exactly or at most 4167, at least or exactly or at most 4168, at least or exactly or at most 4169, at least or exactly or at most 4170, at least or exactly or at most 4171, at least or exactly or at most 4172, at least or exactly or at most 4173, at least or exactly or at most 4174, at least or exactly or at most 4175, at least or exactly or at most 4176, at least or exactly or at most 4177, at least or exactly or at most 4178, at least or exactly or at most 4179, at least or exactly or at most 4180, at least or exactly or at most 4181, at least or exactly or at most 4182, at least or exactly or at most 4183, at least or exactly or at most 4184, at least or exactly or at most 4185, at least or exactly or at most 4186, at least or exactly or at most 4187, at least or exactly or at most 4188, at least or exactly or at most 4189, at least or exactly or at most 4190, at least or exactly or at most 4191, at least or exactly or at most 4192, at least or exactly or at most 4193, at least or exactly or at most 4194, at least or exactly or at most 4195, at least or exactly or at most 4196, at least or exactly or at most 4197, at least or exactly or at most 4198, at least or exactly or at most 4199, at least or exactly or at most 4200, at least or exactly or at most 4201, at least or exactly or at most 4202, at least or exactly or at most 4203, at least or exactly or at most 4204, at least or exactly or at most 4205, at least or exactly or at most 4206, at least or exactly or at most 4207, at least or exactly or at most 4208, at least or exactly or at most 4209, at least or exactly or at most 4210, at least or exactly or at most 4211, at least or exactly or at most 4212, at least or exactly or at most 4213, at least or exactly or at most 4214, at least or exactly or at most 4215, at least or exactly or at most 4216, at least or exactly or at most 4217, at least or exactly or at most 4218, at least or exactly or at most 4219, at least or exactly or at most 4220, at least or exactly or at most 4221, at least or exactly or at most 4222, at least or exactly or at most 4223, at least or exactly or at most 4224, at least or exactly or at most 4225, at least or exactly or at most 4226, at least or exactly or at most 4227, at least or exactly or at most 4228, at least or exactly or at most 4229, at least or exactly or at most 4230, at least or exactly or at most 4231, at least or exactly or at most 4232, at least or exactly or at most 4233, at least or exactly or at most 4234, at least or exactly or at most 4235, at least or exactly or at most 4236, at least or exactly or at most 4237, at least or exactly or at most 4238, at least or exactly or at most 4239, at least or exactly or at most 4240, at least or exactly or at most 4241, at least or exactly or at most 4242, at least or exactly or at most 4243, at least or exactly or at most 4244, at least or exactly or at most 4245, at least or exactly or at most 4246, at least or exactly or at most 4247, at least or exactly or at most 4248, at least or exactly or at most 4249, at least or exactly or at most 4250, at least or exactly or at most 4251, at least or exactly or at most 4252, at least or exactly or at most 4253, at least or exactly or at most 4254, at least or exactly or at most 4255, at least or exactly or at most 4256, at least or exactly or at most 4257, at least or exactly or at most 4258, at least or exactly or at most 4259, at least or exactly or at most 4260, at least or exactly or at most 4261, at least or exactly or at most 4262, at least or exactly or at most 4263, at least or exactly or at most 4264, at least or exactly or at most 4265, at least or exactly or at most 4266, at least or exactly or at most 4267, at least or exactly or at most 4268, at least or exactly or at most 4269, at least or exactly or at most 4270, at least or exactly or at most 4271, at least or exactly or at most 4272, at least or exactly or at most 4273, at least or exactly or at most 4274, at least or exactly or at most 4275, at least or exactly or at most 4276, at least or exactly or at most 4277, at least or exactly or at most 4278, at least or exactly or at most 4279, at least or exactly or at most 4280, at least or exactly or at most 4281, at least or exactly or at most 4282, at least or exactly or at most 4283, at least or exactly or at most 4284, at least or exactly or at most 4285, at least or exactly or at most 4286, at least or exactly or at most 4287, at least or exactly or at most 4288, at least or exactly or at most 4289, at least or exactly or at most 4290, at least or exactly or at most 4291, at least or exactly or at most 4292, at least or exactly or at most 4293, at least or exactly or at most 4294, at least or exactly or at most 4295, at least or exactly or at most 4296, at least or exactly or at most 4297, at least or exactly or at most 4298, at least or exactly or at most 4299, at least or exactly or at most 4300, at least or exactly or at most 4301, at least or exactly or at most 4302, at least or exactly or at most 4303, at least or exactly or at most 4304, at least or exactly or at most 4305, at least or exactly or at most 4306, at least or exactly or at most 4307, at least or exactly or at most 4308, at least or exactly or at most 4309, at least or exactly or at most 4310, at least or exactly or at most 4311, at least or exactly or at most 4312, at least or exactly or at most 4313, at least or exactly or at most 4314, at least or exactly or at most 4315, at least or exactly or at most 4316, at least or exactly or at most 4317, at least or exactly or at most 4318, at least or exactly or at most 4319, at least or exactly or at most 4320, at least or exactly or at most 4321, at least or exactly or at most 4322, at least or exactly or at most 4323, at least or exactly or at most 4324, at least or exactly or at most 4325, at least or exactly or at most 4326, at least or exactly or at most 4327, at least or exactly or at most 4328, at least or exactly or at most 4329, at least or exactly or at most 4330, at least or exactly or at most 4331, at least or exactly or at most 4332, at least or exactly or at most 4333, at least or exactly or at most 4334, at least or exactly or at most 4335, at least or exactly or at most 4336, at least or exactly or at most 4337, at least or exactly or at most 4338, at least or exactly or at most 4339, at least or exactly or at most 4340, at least or exactly or at most 4341, at least or exactly or at most 4342, at least or exactly or at most 4343, at least or exactly or at most 4344, at least or exactly or at most 4345, at least or exactly or at most 4346, at least or exactly or at most 4347, at least or exactly or at most 4348, at least or exactly or at most 4349, at least or exactly or at most 4350, at least or exactly or at most 4351, at least or exactly or at most 4352, at least or exactly or at most 4353, at least or exactly or at most 4354, at least or exactly or at most 4355, at least or exactly or at most 4356, at least or exactly or at most 4357, at least or exactly or at most 4358, at least or exactly or at most 4359, at least or exactly or at most 4360, at least or exactly or at most 4361, at least or exactly or at most 4362, at least or exactly or at most 4363, at least or exactly or at most 4364, at least or exactly or at most 4365, at least or exactly or at most 4366, at least or exactly or at most 4367, at least or exactly or at most 4368, at least or exactly or at most 4369, at least or exactly or at most 4370, at least or exactly or at most 4371, at least or exactly or at most 4372, at least or exactly or at most 4373, at least or exactly or at most 4374, at least or exactly or at most 4375, at least or exactly or at most 4376, at least or exactly or at most 4377, at least or exactly or at most 4378, at least or exactly or at most 4379, at least or exactly or at most 4380, at least or exactly or at most 4381, at least or exactly or at most 4382, at least or exactly or at most 4383, at least or exactly or at most 4384, at least or exactly or at most 4385, at least or exactly or at most 4386, at least or exactly or at most 4387, at least or exactly or at most 4388, at least or exactly or at most 4389, at least or exactly or at most 4390, at least or exactly or at most 4391, at least or exactly or at most 4392, at least or exactly or at most 4393, at least or exactly or at most 4394, at least or exactly or at most 4395, at least or exactly or at most 4396, at least or exactly or at most 4397, at least or exactly or at most 4398, at least or exactly or at most 4399, at least or exactly or at most 4400, at least or exactly or at most 4401, at least or exactly or at most 4402, at least or exactly or at most 4403, at least or exactly or at most 4404, at least or exactly or at most 4405, at least or exactly or at most 4406, at least or exactly or at most 4407, at least or exactly or at most 4408, at least or exactly or at most 4409, at least or exactly or at most 4410, at least or exactly or at most 4411, at least or exactly or at most 4412, at least or exactly or at most 4413, at least or exactly or at most 4414, at least or exactly or at most 4415, at least or exactly or at most 4416, at least or exactly or at most 4417, at least or exactly or at most 4418, at least or exactly or at most 4419, at least or exactly or at most 4420, at least or exactly or at most 4421, at least or exactly or at most 4422, at least or exactly or at most 4423, at least or exactly or at most 4424, at least or exactly or at most 4425, at least or exactly or at most 4426, at least or exactly or at most 4427, at least or exactly or at most 4428, at least or exactly or at most 4429, at least or exactly or at most 4430, at least or exactly or at most 4431, at least or exactly or at most 4432, at least or exactly or at most 4433, at least or exactly or at most 4434, at least or exactly or at most 4435, at least or exactly or at most 4436, at least or exactly or at most 4437, at least or exactly or at most 4438, at least or exactly or at most 4439, at least or exactly or at most 4440, at least or exactly or at most 4441, at least or exactly or at most 4442, at least or exactly or at most 4443, at least or exactly or at most 4444, at least or exactly or at most 4445, at least or exactly or at most 4446, at least or exactly or at most 4447, at least or exactly or at most 4448, at least or exactly or at most 4449, at least or exactly or at most 4450, at least or exactly or at most 4451, at least or exactly or at most 4452, at least or exactly or at most 4453, at least or exactly or at most 4454, at least or exactly or at most 4455, at least or exactly or at most 4456, at least or exactly or at most 4457, at least or exactly or at most 4458, at least or exactly or at most 4459, at least or exactly or at most 4460, at least or exactly or at most 4461, at least or exactly or at most 4462, at least or exactly or at most 4463, at least or exactly or at most 4464, at least or exactly or at most 4465, at least or exactly or at most 4466, at least or exactly or at most 4467, at least or exactly or at most 4468, at least or exactly or at most 4469, at least or exactly or at most 4470, at least or exactly or at most 4471, at least or exactly or at most 4472, at least or exactly or at most 4473, at least or exactly or at most 4474, at least or exactly or at most 4475, at least or exactly or at most 4476, at least or exactly or at most 4477, at least or exactly or at most 4478, at least or exactly or at most 4479, at least or exactly or at most 4480, at least or exactly or at most 4481, at least or exactly or at most 4482, at least or exactly or at most 4483, at least or exactly or at most 4484, at least or exactly or at most 4485, at least or exactly or at most 4486, at least or exactly or at most 4487, at least or exactly or at most 4488, at least or exactly or at most 4489, at least or exactly or at most 4490, at least or exactly or at most 4491, at least or exactly or at most 4492, at least or exactly or at most 4493, at least or exactly or at most 4494, at least or exactly or at most 4495, at least or exactly or at most 4496, at least or exactly or at most 4497, at least or exactly or at most 4498, at least or exactly or at most 4499, at least or exactly or at most 4500, at least or exactly or at most 4501, at least or exactly or at most 4502, at least or exactly or at most 4503, at least or exactly or at most 4504, at least or exactly or at most 4505, at least or exactly or at most 4506, at least or exactly or at most 4507, at least or exactly or at most 4508, at least or exactly or at most 4509, at least or exactly or at most 4510, at least or exactly or at most 4511, at least or exactly or at most 4512, at least or exactly or at most 4513, at least or exactly or at most 4514, at least or exactly or at most 4515, at least or exactly or at most 4516, at least or exactly or at most 4517, at least or exactly or at most 4518, at least or exactly or at most 4519, at least or exactly or at most 4520, at least or exactly or at most 4521, at least or exactly or at most 4522, at least or exactly or at most 4523, at least or exactly or at most 4524, at least or exactly or at most 4525, at least or exactly or at most 4526, at least or exactly or at most 4527, at least or exactly or at most 4528, at least or exactly or at most 4529, at least or exactly or at most 4530, at least or exactly or at most 4531, at least or exactly or at most 4532, at least or exactly or at most 4533, at least or exactly or at most 4534, at least or exactly or at most 4535, at least or exactly or at most 4536, at least or exactly or at most 4537, at least or exactly or at most 4538, at least or exactly or at most 4539, at least or exactly or at most 4540, at least or exactly or at most 4541, at least or exactly or at most 4542, at least or exactly or at most 4543, at least or exactly or at most 4544, at least or exactly or at most 4545, at least or exactly or at most 4546, at least or exactly or at most 4547, at least or exactly or at most 4548, at least or exactly or at most 4549, at least or exactly or at most 4550, at least or exactly or at most 4551, at least or exactly or at most 4552, at least or exactly or at most 4553, at least or exactly or at most 4554, at least or exactly or at most 4555, at least or exactly or at most 4556, at least or exactly or at most 4557, at least or exactly or at most 4558, at least or exactly or at most 4559, at least or exactly or at most 4560, at least or exactly or at most 4561, at least or exactly or at most 4562, at least or exactly or at most 4563, at least or exactly or at most 4564, at least or exactly or at most 4565, at least or exactly or at most 4566, at least or exactly or at most 4567, at least or exactly or at most 4568, at least or exactly or at most 4569, at least or exactly or at most 4570, at least or exactly or at most 4571, at least or exactly or at most 4572, at least or exactly or at most 4573, at least or exactly or at most 4574, at least or exactly or at most 4575, at least or exactly or at most 4576, at least or exactly or at most 4577, at least or exactly or at most 4578, at least or exactly or at most 4579, at least or exactly or at most 4580, at least or exactly or at most 4581, at least or exactly or at most 4582, at least or exactly or at most 4583, at least or exactly or at most 4584, at least or exactly or at most 4585, at least or exactly or at most 4586, at least or exactly or at most 4587, at least or exactly or at most 4588, at least or exactly or at most 4589, at least or exactly or at most 4590, at least or exactly or at most 4591, at least or exactly or at most 4592, at least or exactly or at most 4593, at least or exactly or at most 4594, at least or exactly or at most 4595, at least or exactly or at most 4596, at least or exactly or at most 4597, at least or exactly or at most 4598, at least or exactly or at most 4599, at least or exactly or at most 4600, at least or exactly or at most 4601, at least or exactly or at most 4602, at least or exactly or at most 4603, at least or exactly or at most 4604, at least or exactly or at most 4605, at least or exactly or at most 4606, at least or exactly or at most 4607, at least or exactly or at most 4608, at least or exactly or at most 4609, at least or exactly or at most 4610, at least or exactly or at most 4611, at least or exactly or at most 4612, at least or exactly or at most 4613, at least or exactly or at most 4614, at least or exactly or at most 4615, at least or exactly or at most 4616, at least or exactly or at most 4617, at least or exactly or at most 4618, at least or exactly or at most 4619, at least or exactly or at most 4620, at least or exactly or at most 4621, at least or exactly or at most 4622, at least or exactly or at most 4623, at least or exactly or at most 4624, at least or exactly or at most 4625, at least or exactly or at most 4626, at least or exactly or at most 4627, at least or exactly or at most 4628, at least or exactly or at most 4629, at least or exactly or at most 4630, at least or exactly or at most 4631, at least or exactly or at most 4632, at least or exactly or at most 4633, at least or exactly or at most 4634, at least or exactly or at most 4635, at least or exactly or at most 4636, at least or exactly or at most 4637, at least or exactly or at most 4638, at least or exactly or at most 4639, at least or exactly or at most 4640, at least or exactly or at most 4641, at least or exactly or at most 4642, at least or exactly or at most 4643, at least or exactly or at most 4644, at least or exactly or at most 4645, at least or exactly or at most 4646, at least or exactly or at most 4647, at least or exactly or at most 4648, at least or exactly or at most 4649, at least or exactly or at most 4650, at least or exactly or at most 4651, at least or exactly or at most 4652, at least or exactly or at most 4653, at least or exactly or at most 4654, at least or exactly or at most 4655, at least or exactly or at most 4656, at least or exactly or at most 4657, at least or exactly or at most 4658, at least or exactly or at most 4659, at least or exactly or at most 4660, at least or exactly or at most 4661, at least or exactly or at most 4662, at least or exactly or at most 4663, at least or exactly or at most 4664, at least or exactly or at most 4665, at least or exactly or at most 4666, at least or exactly or at most 4667, at least or exactly or at most 4668, at least or exactly or at most 4669, at least or exactly or at most 4670, at least or exactly or at most 4671, at least or exactly or at most 4672, at least or exactly or at most 4673, at least or exactly or at most 4674, at least or exactly or at most 4675, at least or exactly or at most 4676, at least or exactly or at most 4677, at least or exactly or at most 4678, at least or exactly or at most 4679, at least or exactly or at most 4680, at least or exactly or at most 4681, at least or exactly or at most 4682, at least or exactly or at most 4683, at least or exactly or at most 4684, at least or exactly or at most 4685, at least or exactly or at most 4686, at least or exactly or at most 4687, at least or exactly or at most 4688, at least or exactly or at most 4689, at least or exactly or at most 4690, at least or exactly or at most 4691, at least or exactly or at most 4692, at least or exactly or at most 4693, at least or exactly or at most 4694, at least or exactly or at most 4695, at least or exactly or at most 4696, at least or exactly or at most 4697, at least or exactly or at most 4698, at least or exactly or at most 4699, at least or exactly or at most 4700, at least or exactly or at most 4701, at least or exactly or at most 4702, at least or exactly or at most 4703, at least or exactly or at most 4704, at least or exactly or at most 4705, at least or exactly or at most 4706, at least or exactly or at most 4707, at least or exactly or at most 4708, at least or exactly or at most 4709, at least or exactly or at most 4710, at least or exactly or at most 4711, at least or exactly or at most 4712, at least or exactly or at most 4713, at least or exactly or at most 4714, at least or exactly or at most 4715, at least or exactly or at most 4716, at least or exactly or at most 4717, at least or exactly or at most 4718, at least or exactly or at most 4719, at least or exactly or at most 4720, at least or exactly or at most 4721, at least or exactly or at most 4722, at least or exactly or at most 4723, at least or exactly or at most 4724, at least or exactly or at most 4725, at least or exactly or at most 4726, at least or exactly or at most 4727, at least or exactly or at most 4728, at least or exactly or at most 4729, at least or exactly or at most 4730, at least or exactly or at most 4731, at least or exactly or at most 4732, at least or exactly or at most 4733, at least or exactly or at most 4734, at least or exactly or at most 4735, at least or exactly or at most 4736, at least or exactly or at most 4737, at least or exactly or at most 4738, at least or exactly or at most 4739, at least or exactly or at most 4740, at least or exactly or at most 4741, at least or exactly or at most 4742, at least or exactly or at most 4743, at least or exactly or at most 4744, at least or exactly or at most 4745, at least or exactly or at most 4746, at least or exactly or at most 4747, at least or exactly or at most 4748, at least or exactly or at most 4749, at least or exactly or at most 4750, at least or exactly or at most 4751, at least or exactly or at most 4752, at least or exactly or at most 4753, at least or exactly or at most 4754, at least or exactly or at most 4755, at least or exactly or at most 4756, at least or exactly or at most 4757, at least or exactly or at most 4758, at least or exactly or at most 4759, at least or exactly or at most 4760, at least or exactly or at most 4761, at least or exactly or at most 4762, at least or exactly or at most 4763, at least or exactly or at most 4764, at least or exactly or at most 4765, at least or exactly or at most 4766, at least or exactly or at most 4767, at least or exactly or at most 4768, at least or exactly or at most 4769, at least or exactly or at most 4770, at least or exactly or at most 4771, at least or exactly or at most 4772, at least or exactly or at most 4773, at least or exactly or at most 4774, at least or exactly or at most 4775, at least or exactly or at most 4776, at least or exactly or at most 4777, at least or exactly or at most 4778, at least or exactly or at most 4779, at least or exactly or at most 4780, at least or exactly or at most 4781, at least or exactly or at most 4782, at least or exactly or at most 4783, at least or exactly or at most 4784, at least or exactly or at most 4785, at least or exactly or at most 4786, at least or exactly or at most 4787, at least or exactly or at most 4788, at least or exactly or at most 4789, at least or exactly or at most 4790, at least or exactly or at most 4791, at least or exactly or at most 4792, at least or exactly or at most 4793, at least or exactly or at most 4794, at least or exactly or at most 4795, at least or exactly or at most 4796, at least or exactly or at most 4797, at least or exactly or at most 4798, at least or exactly or at most 4799, at least or exactly or at most 4800, at least or exactly or at most 4801, at least or exactly or at most 4802, at least or exactly or at most 4803, at least or exactly or at most 4804, at least or exactly or at most 4805, at least or exactly or at most 4806, at least or exactly or at most 4807, at least or exactly or at most 4808, at least or exactly or at most 4809, at least or exactly or at most 4810, at least or exactly or at most 4811, at least or exactly or at most 4812, at least or exactly or at most 4813, at least or exactly or at most 4814, at least or exactly or at most 4815, at least or exactly or at most 4816, at least or exactly or at most 4817, at least or exactly or at most 4818, at least or exactly or at most 4819, at least or exactly or at most 4820, at least or exactly or at most 4821, at least or exactly or at most 4822, at least or exactly or at most 4823, at least or exactly or at most 4824, at least or exactly or at most 4825, at least or exactly or at most 4826, at least or exactly or at most 4827, at least or exactly or at most 4828, at least or exactly or at most 4829, at least or exactly or at most 4830, at least or exactly or at most 4831, at least or exactly or at most 4832, at least or exactly or at most 4833, at least or exactly or at most 4834, at least or exactly or at most 4835, at least or exactly or at most 4836, at least or exactly or at most 4837, at least or exactly or at most 4838, at least or exactly or at most 4839, at least or exactly or at most 4840, at least or exactly or at most 4841, at least or exactly or at most 4842, at least or exactly or at most 4843, at least or exactly or at most 4844, at least or exactly or at most 4845, at least or exactly or at most 4846, at least or exactly or at most 4847, at least or exactly or at most 4848, at least or exactly or at most 4849, at least or exactly or at most 4850, at least or exactly or at most 4851, at least or exactly or at most 4852, at least or exactly or at most 4853, at least or exactly or at most 4854, at least or exactly or at most 4855, at least or exactly or at most 4856, at least or exactly or at most 4857, at least or exactly or at most 4858, at least or exactly or at most 4859, at least or exactly or at most 4860, at least or exactly or at most 4861, at least or exactly or at most 4862, at least or exactly or at most 4863, at least or exactly or at most 4864, at least or exactly or at most 4865, at least or exactly or at most 4866, at least or exactly or at most 4867, at least or exactly or at most 4868, at least or exactly or at most 4869, at least or exactly or at most 4870, at least or exactly or at most 4871, at least or exactly or at most 4872, at least or exactly or at most 4873, at least or exactly or at most 4874, at least or exactly or at most 4875, at least or exactly or at most 4876, at least or exactly or at most 4877, at least or exactly or at most 4878, at least or exactly or at most 4879, at least or exactly or at most 4880, at least or exactly or at most 4881, at least or exactly or at most 4882, at least or exactly or at most 4883, at least or exactly or at most 4884, at least or exactly or at most 4885, at least or exactly or at most 4886, at least or exactly or at most 4887, at least or exactly or at most 4888, at least or exactly or at most 4889, at least or exactly or at most 4890, at least or exactly or at most 4891, at least or exactly or at most 4892, at least or exactly or at most 4893, at least or exactly or at most 4894, at least or exactly or at most 4895, at least or exactly or at most 4896, at least or exactly or at most 4897, at least or exactly or at most 4898, at least or exactly or at most 4899, at least or exactly or at most 4900, at least or exactly or at most 4901, at least or exactly or at most 4902, at least or exactly or at most 4903, at least or exactly or at most 4904, at least or exactly or at most 4905, at least or exactly or at most 4906, at least or exactly or at most 4907, at least or exactly or at most 4908, at least or exactly or at most 4909, at least or exactly or at most 4910, at least or exactly or at most 4911, at least or exactly or at most 4912, at least or exactly or at most 4913, at least or exactly or at most 4914, at least or exactly or at most 4915, at least or exactly or at most 4916, at least or exactly or at most 4917, at least or exactly or at most 4918, at least or exactly or at most 4919, at least or exactly or at most 4920, at least or exactly or at most 4921, at least or exactly or at most 4922, at least or exactly or at most 4923, at least or exactly or at most 4924, at least or exactly or at most 4925, at least or exactly or at most 4926, at least or exactly or at most 4927, at least or exactly or at most 4928, at least or exactly or at most 4929, at least or exactly or at most 4930, at least or exactly or at most 4931, at least or exactly or at most 4932, at least or exactly or at most 4933, at least or exactly or at most 4934, at least or exactly or at most 4935, at least or exactly or at most 4936, at least or exactly or at most 4937, at least or exactly or at most 4938, at least or exactly or at most 4939, at least or exactly or at most 4940, at least or exactly or at most 4941, at least or exactly or at most 4942, at least or exactly or at most 4943, at least or exactly or at most 4944, at least or exactly or at most 4945, at least or exactly or at most 4946, at least or exactly or at most 4947, at least or exactly or at most 4948, at least or exactly or at most 4949, at least or exactly or at most 4950, at least or exactly or at most 4951, at least or exactly or at most 4952, at least or exactly or at most 4953, at least or exactly or at most 4954, at least or exactly or at most 4955, at least or exactly or at most 4956, at least or exactly or at most 4957, at least or exactly or at most 4958, at least or exactly or at most 4959, at least or exactly or at most 4960, at least or exactly or at most 4961, at least or exactly or at most 4962, at least or exactly or at most 4963, at least or exactly or at most 4964, at least or exactly or at most 4965, at least or exactly or at most 4966, at least or exactly or at most 4967, at least or exactly or at most 4968, at least or exactly or at most 4969, at least or exactly or at most 4970, at least or exactly or at most 4971, at least or exactly or at most 4972, at least or exactly or at most 4973, at least or exactly or at most 4974, at least or exactly or at most 4975, at least or exactly or at most 4976, at least or exactly or at most 4977, at least or exactly or at most 4978, at least or exactly or at most 4979, at least or exactly or at most 4980, at least or exactly or at most 4981, at least or exactly or at most 4982, at least or exactly or at most 4983, at least or exactly or at most 4984, at least or exactly or at most 4985, at least or exactly or at most 4986, at least or exactly or at most 4987, at least or exactly or at most 4988, at least or exactly or at most 4989, at least or exactly or at most 4990, at least or exactly or at most 4991, at least or exactly or at most 4992, at least or exactly or at most 4993, at least or exactly or at most 4994, at least or exactly or at most 4995, at least or exactly or at most 4996, at least or exactly or at most 4997, at least or exactly or at most 4998, at least or exactly or at most 4999, at least or exactly or at most 5000, at least or exactly or at most 5001, at least or exactly or at most 5002, at least or exactly or at most 5003, at least or exactly or at most 5004, at least or exactly or at most 5005, at least or exactly or at most 5006, at least or exactly or at most 5007, at least or exactly or at most 5008, at least or exactly or at most 5009, at least or exactly or at most 5010, at least or exactly or at most 5011, at least or exactly or at most 5012, at least or exactly or at most 5013, at least or exactly or at most 5014, at least or exactly or at most 5015, at least or exactly or at most 5016, at least or exactly or at most 5017, at least or exactly or at most 5018, at least or exactly or at most 5019, at least or exactly or at most 5020, at least or exactly or at most 5021, at least or exactly or at most 5022, at least or exactly or at most 5023, at least or exactly or at most 5024, at least or exactly or at most 5025, at least or exactly or at most 5026, at least or exactly or at most 5027, at least or exactly or at most 5028, at least or exactly or at most 5029, at least or exactly or at most 5030, at least or exactly or at most 5031, at least or exactly or at most 5032, at least or exactly or at most 5033, at least or exactly or at most 5034, at least or exactly or at most 5035, at least or exactly or at most 5036, at least or exactly or at most 5037, at least or exactly or at most 5038, at least or exactly or at most 5039, at least or exactly or at most 5040, at least or exactly or at most 5041, at least or exactly or at most 5042, at least or exactly or at most 5043, at least or exactly or at most 5044, at least or exactly or at most 5045, at least or exactly or at most 5046, at least or exactly or at most 5047, at least or exactly or at most 5048, at least or exactly or at most 5049, at least or exactly or at most 5050, at least or exactly or at most 5051, at least or exactly or at most 5052, at least or exactly or at most 5053, at least or exactly or at most 5054, at least or exactly or at most 5055, at least or exactly or at most 5056, at least or exactly or at most 5057, at least or exactly or at most 5058, at least or exactly or at most 5059, at least or exactly or at most 5060, at least or exactly or at most 5061, at least or exactly or at most 5062, at least or exactly or at most 5063, at least or exactly or at most 5064, at least or exactly or at most 5065, at least or exactly or at most 5066, at least or exactly or at most 5067, at least or exactly or at most 5068, at least or exactly or at most 5069, at least or exactly or at most 5070, at least or exactly or at most 5071, at least or exactly or at most 5072, at least or exactly or at most 5073, at least or exactly or at most 5074, at least or exactly or at most 5075, at least or exactly or at most 5076, at least or exactly or at most 5077, at least or exactly or at most 5078, at least or exactly or at most 5079, at least or exactly or at most 5080, at least or exactly or at most 5081, at least or exactly or at most 5082, at least or exactly or at most 5083, at least or exactly or at most 5084, at least or exactly or at most 5085, at least or exactly or at most 5086, at least or exactly or at most 5087, at least or exactly or at most 5088, at least or exactly or at most 5089, at least or exactly or at most 5090, at least or exactly or at most 5091, at least or exactly or at most 5092, at least or exactly or at most 5093, at least or exactly or at most 5094, at least or exactly or at most 5095, at least or exactly or at most 5096, at least or exactly or at most 5097, at least or exactly or at most 5098, at least or exactly or at most 5099, at least or exactly or at most 5100, at least or exactly or at most 5101, at least or exactly or at most 5102, at least or exactly or at most 5103, at least or exactly or at most 5104, at least or exactly or at most 5105, at least or exactly or at most 5106, at least or exactly or at most 5107, at least or exactly or at most 5108, at least or exactly or at most 5109, at least or exactly or at most 5110, at least or exactly or at most 5111, at least or exactly or at most 5112, at least or exactly or at most 5113, at least or exactly or at most 5114, at least or exactly or at most 5115, at least or exactly or at most 5116, at least or exactly or at most 5117, at least or exactly or at most 5118, at least or exactly or at most 5119, at least or exactly or at most 5120, at least or exactly or at most 5121, at least or exactly or at most 5122, at least or exactly or at most 5123, at least or exactly or at most 5124, at least or exactly or at most 5125, at least or exactly or at most 5126, at least or exactly or at most 5127, at least or exactly or at most 5128, at least or exactly or at most 5129, at least or exactly or at most 5130, at least or exactly or at most 5131, at least or exactly or at most 5132, at least or exactly or at most 5133, at least or exactly or at most 5134, at least or exactly or at most 5135, at least or exactly or at most 5136, at least or exactly or at most 5137, at least or exactly or at most 5138, at least or exactly or at most 5139, at least or exactly or at most 5140, at least or exactly or at most 5141, at least or exactly or at most 5142, at least or exactly or at most 5143, at least or exactly or at most 5144, at least or exactly or at most 5145, at least or exactly or at most 5146, at least or exactly or at most 5147, at least or exactly or at most 5148, at least or exactly or at most 5149, at least or exactly or at most 5150, at least or exactly or at most 5151, at least or exactly or at most 5152, at least or exactly or at most 5153, at least or exactly or at most 5154, at least or exactly or at most 5155, at least or exactly or at most 5156, at least or exactly or at most 5157, at least or exactly or at most 5158, at least or exactly or at most 5159, at least or exactly or at most 5160, at least or exactly or at most 5161, at least or exactly or at most 5162, at least or exactly or at most 5163, at least or exactly or at most 5164, at least or exactly or at most 5165, at least or exactly or at most 5166, at least or exactly or at most 5167, at least or exactly or at most 5168, at least or exactly or at most 5169, at least or exactly or at most 5170, at least or exactly or at most 5171, at least or exactly or at most 5172, at least or exactly or at most 5173, at least or exactly or at most 5174, at least or exactly or at most 5175, at least or exactly or at most 5176, at least or exactly or at most 5177, at least or exactly or at most 5178, at least or exactly or at most 5179, at least or exactly or at most 5180, at least or exactly or at most 5181, at least or exactly or at most 5182, at least or exactly or at most 5183, at least or exactly or at most 5184, at least or exactly or at most 5185, at least or exactly or at most 5186, at least or exactly or at most 5187, at least or exactly or at most 5188, at least or exactly or at most 5189, at least or exactly or at most 5190, at least or exactly or at most 5191, at least or exactly or at most 5192, at least or exactly or at most 5193, at least or exactly or at most 5194, at least or exactly or at most 5195, at least or exactly or at most 5196, at least or exactly or at most 5197, at least or exactly or at most 5198, at least or exactly or at most 5199, at least or exactly or at most 5200, at least or exactly or at most 5201, at least or exactly or at most 5202, at least or exactly or at most 5203, at least or exactly or at most 5204, at least or exactly or at most 5205, at least or exactly or at most 5206, at least or exactly or at most 5207, at least or exactly or at most 5208, at least or exactly or at most 5209, at least or exactly or at most 5210, at least or exactly or at most 5211, at least or exactly or at most 5212, at least or exactly or at most 5213, at least or exactly or at most 5214, at least or exactly or at most 5215, at least or exactly or at most 5216, at least or exactly or at most 5217, at least or exactly or at most 5218, at least or exactly or at most 5219, at least or exactly or at most 5220, at least or exactly or at most 5221, at least or exactly or at most 5222, at least or exactly or at most 5223, at least or exactly or at most 5224, at least or exactly or at most 5225, at least or exactly or at most 5226, at least or exactly or at most 5227, at least or exactly or at most 5228, at least or exactly or at most 5229, at least or exactly or at most 5230, at least or exactly or at most 5231, at least or exactly or at most 5232, at least or exactly or at most 5233, at least or exactly or at most 5234, at least or exactly or at most 5235, at least or exactly or at most 5236, at least or exactly or at most 5237, at least or exactly or at most 5238, at least or exactly or at most 5239, at least or exactly or at most 5240, at least or exactly or at most 5241, at least or exactly or at most 5242, at least or exactly or at most 5243, at least or exactly or at most 5244, at least or exactly or at most 5245, at least or exactly or at most 5246, at least or exactly or at most 5247, at least or exactly or at most 5248, at least or exactly or at most 5249, at least or exactly or at most 5250, at least or exactly or at most 5251, at least or exactly or at most 5252, at least or exactly or at most 5253, at least or exactly or at most 5254, at least or exactly or at most 5255, at least or exactly or at most 5256, at least or exactly or at most 5257, at least or exactly or at most 5258, at least or exactly or at most 5259, at least or exactly or at most 5260, at least or exactly or at most 5261, at least or exactly or at most 5262, at least or exactly or at most 5263, at least or exactly or at most 5264, at least or exactly or at most 5265, at least or exactly or at most 5266, at least or exactly or at most 5267, at least or exactly or at most 5268, at least or exactly or at most 5269, at least or exactly or at most 5270, at least or exactly or at most 5271, at least or exactly or at most 5272, at least or exactly or at most 5273, at least or exactly or at most 5274, at least or exactly or at most 5275, at least or exactly or at most 5276, at least or exactly or at most 5277, at least or exactly or at most 5278, at least or exactly or at most 5279, at least or exactly or at most 5280, at least or exactly or at most 5281, at least or exactly or at most 5282, at least or exactly or at most 5283, at least or exactly or at most 5284, at least or exactly or at most 5285, at least or exactly or at most 5286, at least or exactly or at most 5287, at least or exactly or at most 5288, at least or exactly or at most 5289, at least or exactly or at most 5290, at least or exactly or at most 5291, at least or exactly or at most 5292, at least or exactly or at most 5293, at least or exactly or at most 5294, at least or exactly or at most 5295, at least or exactly or at most 5296, at least or exactly or at most 5297, at least or exactly or at most 5298, at least or exactly or at most 5299, at least or exactly or at most 5300, at least or exactly or at most 5301, at least or exactly or at most 5302, at least or exactly or at most 5303, at least or exactly or at most 5304, at least or exactly or at most 5305, at least or exactly or at most 5306, at least or exactly or at most 5307, at least or exactly or at most 5308, at least or exactly or at most 5309, at least or exactly or at most 5310, at least or exactly or at most 5311, at least or exactly or at most 5312, at least or exactly or at most 5313, at least or exactly or at most 5314, at least or exactly or at most 5315, at least or exactly or at most 5316, at least or exactly or at most 5317, at least or exactly or at most 5318, at least or exactly or at most 5319, at least or exactly or at most 5320, at least or exactly or at most 5321, at least or exactly or at most 5322, at least or exactly or at most 5323, at least or exactly or at most 5324, at least or exactly or at most 5325, at least or exactly or at most 5326, at least or exactly or at most 5327, at least or exactly or at most 5328, at least or exactly or at most 5329, at least or exactly or at most 5330, at least or exactly or at most 5331, at least or exactly or at most 5332, at least or exactly or at most 5333, at least or exactly or at most 5334, at least or exactly or at most 5335, at least or exactly or at most 5336, at least or exactly or at most 5337, at least or exactly or at most 5338, at least or exactly or at most 5339, at least or exactly or at most 5340, at least or exactly or at most 5341, at least or exactly or at most 5342, at least or exactly or at most 5343, at least or exactly or at most 5344, at least or exactly or at most 5345, at least or exactly or at most 5346, at least or exactly or at most 5347, at least or exactly or at most 5348, at least or exactly or at most 5349, at least or exactly or at most 5350, at least or exactly or at most 5351, at least or exactly or at most 5352, at least or exactly or at most 5353, at least or exactly or at most 5354, at least or exactly or at most 5355, at least or exactly or at most 5356, at least or exactly or at most 5357, at least or exactly or at most 5358, at least or exactly or at most 5359, at least or exactly or at most 5360, at least or exactly or at most 5361, at least or exactly or at most 5362, at least or exactly or at most 5363, at least or exactly or at most 5364, at least or exactly or at most 5365, at least or exactly or at most 5366, at least or exactly or at most 5367, at least or exactly or at most 5368, at least or exactly or at most 5369, at least or exactly or at most 5370, at least or exactly or at most 5371, at least or exactly or at most 5372, at least or exactly or at most 5373, at least or exactly or at most 5374, at least or exactly or at most 5375, at least or exactly or at most 5376, at least or exactly or at most 5377, at least or exactly or at most 5378, at least or exactly or at most 5379, at least or exactly or at most 5380, at least or exactly or at most 5381, at least or exactly or at most 5382, at least or exactly or at most 5383, at least or exactly or at most 5384, at least or exactly or at most 5385, at least or exactly or at most 5386, at least or exactly or at most 5387, at least or exactly or at most 5388, at least or exactly or at most 5389, at least or exactly or at most 5390, at least or exactly or at most 5391, at least or exactly or at most 5392, at least or exactly or at most 5393, at least or exactly or at most 5394, at least or exactly or at most 5395, at least or exactly or at most 5396, at least or exactly or at most 5397, at least or exactly or at most 5398, at least or exactly or at most 5399, at least or exactly or at most 5400, at least or exactly or at most 5401, at least or exactly or at most 5402, at least or exactly or at most 5403, at least or exactly or at most 5404, at least or exactly or at most 5405, at least or exactly or at most 5406, at least or exactly or at most 5407, at least or exactly or at most 5408, at least or exactly or at most 5409, at least or exactly or at most 5410, at least or exactly or at most 5411, at least or exactly or at most 5412, at least or exactly or at most 5413, at least or exactly or at most 5414, at least or exactly or at most 5415, at least or exactly or at most 5416, at least or exactly or at most 5417, at least or exactly or at most 5418, at least or exactly or at most 5419, at least or exactly or at most 5420, at least or exactly or at most 5421, at least or exactly or at most 5422, at least or exactly or at most 5423, at least or exactly or at most 5424, at least or exactly or at most 5425, at least or exactly or at most 5426, at least or exactly or at most 5427, at least or exactly or at most 5428, at least or exactly or at most 5429, at least or exactly or at most 5430, at least or exactly or at most 5431, at least or exactly or at most 5432, at least or exactly or at most 5433, at least or exactly or at most 5434, at least or exactly or at most 5435, at least or exactly or at most 5436, at least or exactly or at most 5437, at least or exactly or at most 5438, at least or exactly or at most 5439, at least or exactly or at most 5440, at least or exactly or at most 5441, at least or exactly or at most 5442, at least or exactly or at most 5443, at least or exactly or at most 5444, at least or exactly or at most 5445, at least or exactly or at most 5446, at least or exactly or at most 5447, at least or exactly or at most 5448, at least or exactly or at most 5449, at least or exactly or at most 5450, at least or exactly or at most 5451, at least or exactly or at most 5452, at least or exactly or at most 5453, at least or exactly or at most 5454, at least or exactly or at most 5455, at least or exactly or at most 5456, at least or exactly or at most 5457, at least or exactly or at most 5458, at least or exactly or at most 5459, at least or exactly or at most 5460, at least or exactly or at most 5461, at least or exactly or at most 5462, at least or exactly or at most 5463, at least or exactly or at most 5464, at least or exactly or at most 5465, at least or exactly or at most 5466, at least or exactly or at most 5467, at least or exactly or at most 5468, at least or exactly or at most 5469, at least or exactly or at most 5470, at least or exactly or at most 5471, at least or exactly or at most 5472, at least or exactly or at most 5473, at least or exactly or at most 5474, at least or exactly or at most 5475, at least or exactly or at most 5476, at least or exactly or at most 5477, at least or exactly or at most 5478, at least or exactly or at most 5479, at least or exactly or at most 5480, at least or exactly or at most 5481, at least or exactly or at most 5482, at least or exactly or at most 5483, at least or exactly or at most 5484, at least or exactly or at most 5485, at least or exactly or at most 5486, at least or exactly or at most 5487, at least or exactly or at most 5488, at least or exactly or at most 5489, at least or exactly or at most 5490, at least or exactly or at most 5491, at least or exactly or at most 5492, at least or exactly or at most 5493, at least or exactly or at most 5494, at least or exactly or at most 5495, at least or exactly or at most 5496, at least or exactly or at most 5497, at least or exactly or at most 5498, at least or exactly or at most 5499, at least or exactly or at most 5500, at least or exactly or at most 5501, at least or exactly or at most 5502, at least or exactly or at most 5503, at least or exactly or at most 5504, at least or exactly or at most 5505, at least or exactly or at most 5506, at least or exactly or at most 5507, at least or exactly or at most 5508, at least or exactly or at most 5509, at least or exactly or at most 5510, at least or exactly or at most 5511, at least or exactly or at most 5512, at least or exactly or at most 5513, at least or exactly or at most 5514, at least or exactly or at most 5515, at least or exactly or at most 5516, at least or exactly or at most 5517, at least or exactly or at most 5518, at least or exactly or at most 5519, at least or exactly or at most 5520, at least or exactly or at most 5521, at least or exactly or at most 5522, at least or exactly or at most 5523, at least or exactly or at most 5524, at least or exactly or at most 5525, at least or exactly or at most 5526, at least or exactly or at most 5527, at least or exactly or at most 5528, at least or exactly or at most 5529, at least or exactly or at most 5530, at least or exactly or at most 5531, at least or exactly or at most 5532, at least or exactly or at most 5533, at least or exactly or at most 5534, at least or exactly or at most 5535, at least or exactly or at most 5536, at least or exactly or at most 5537, at least or exactly or at most 5538, at least or exactly or at most 5539, at least or exactly or at most 5540, at least or exactly or at most 5541, at least or exactly or at most 5542, at least or exactly or at most 5543, at least or exactly or at most 5544, at least or exactly or at most 5545, at least or exactly or at most 5546, at least or exactly or at most 5547, at least or exactly or at most 5548, at least or exactly or at most 5549, at least or exactly or at most 5550, at least or exactly or at most 5551, at least or exactly or at most 5552, at least or exactly or at most 5553, at least or exactly or at most 5554, at least or exactly or at most 5555, at least or exactly or at most 5556, at least or exactly or at most 5557, at least or exactly or at most 5558, at least or exactly or at most 5559, at least or exactly or at most 5560, at least or exactly or at most 5561, at least or exactly or at most 5562, at least or exactly or at most 5563, at least or exactly or at most 5564, at least or exactly or at most 5565, at least or exactly or at most 5566, at least or exactly or at most 5567, at least or exactly or at most 5568, at least or exactly or at most 5569, at least or exactly or at most 5570, at least or exactly or at most 5571, at least or exactly or at most 5572, at least or exactly or at most 5573, at least or exactly or at most 5574, at least or exactly or at most 5575, at least or exactly or at most 5576, at least or exactly or at most 5577, at least or exactly or at most 5578, at least or exactly or at most 5579, at least or exactly or at most 5580, at least or exactly or at most 5581, at least or exactly or at most 5582, at least or exactly or at most 5583, at least or exactly or at most 5584, at least or exactly or at most 5585, at least or exactly or at most 5586, at least or exactly or at most 5587, at least or exactly or at most 5588, at least or exactly or at most 5589, at least or exactly or at most 5590, at least or exactly or at most 5591, at least or exactly or at most 5592, at least or exactly or at most 5593, at least or exactly or at most 5594, at least or exactly or at most 5595, at least or exactly or at most 5596, at least or exactly or at most 5597, at least or exactly or at most 5598, at least or exactly or at most 5599, at least or exactly or at most 5600, at least or exactly or at most 5601, at least or exactly or at most 5602, at least or exactly or at most 5603, at least or exactly or at most 5604, at least or exactly or at most 5605, at least or exactly or at most 5606, at least or exactly or at most 5607, at least or exactly or at most 5608, at least or exactly or at most 5609, at least or exactly or at most 5610, at least or exactly or at most 5611, at least or exactly or at most 5612, at least or exactly or at most 5613, at least or exactly or at most 5614, at least or exactly or at most 5615, at least or exactly or at most 5616, at least or exactly or at most 5617, at least or exactly or at most 5618, at least or exactly or at most 5619, at least or exactly or at most 5620, at least or exactly or at most 5621, at least or exactly or at most 5622, at least or exactly or at most 5623, at least or exactly or at most 5624, at least or exactly or at most 5625, or at least or exactly or at most 5626 contiguous amino acid residues.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60 and 62 in any one of SEQ ID NOs: 1-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 63, 64, 65, 66, 67, 68, 69, 70, 71, 72, 73 and 74 in any on of SEQ ID NOs: 2-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 75, 76, 77, 78, 79, 80, 81, 82, 83, 84, 85, 86, 87, 88, 89, 90, 91, 92, 93, 94, 95, 96, 97, 98, 99 and 100 in any one of SEQ ID NOs: 3-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 101, 102, 103, 104, 105, 106, 107, 108, 109, 110, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 and 151 in any one of SEQ ID NOs: 4-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 152, 153, 154, 155, 156, 157, 158, 159, 160, 171, 172, 173, 174 and 175 in any one of SEQ ID NOs: 5-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299 and 300 in any one of SEQ ID NOs: 6-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 301, 302, 303, 304 and 305 in any one of SEQ ID NOs: 7-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 306, 307, 308, 309, 310, 311, 312, 313, 314, 315, 316, 317, 318, 319, 320, 321, 322, 323, 324, 325, 326, 327, 328, 329, 330, 331, 332, 333, 334, 335 and 336 in any one of SEQ ID NOs: 8-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 337, 338, 339, 340, 341, 342 and 343 in any one of SEQ ID NOs: 9-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 344, 345, 346, 347 and 348 in any one of SEQ ID NOs: 10-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415 and 416 in any one of SEQ ID NOs: 11-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 417, 418, 419, 420, 421, 422 and 423 in any one of SEQ ID NOs: 12-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to amino acid residue 424 in any one of SEQ ID NOs: 13-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563 and 564 in SEQ ID NOs: 14-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 563, 564, 565, 566, 567, 568, 569, 570, 571, 572, 573, 574 and 575 in SEQ ID NOs: 15-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616 and 617 in SEQ ID NOs: 16-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683 and 684 in SEQ ID NOs: 17-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737 and 738 in SEQ ID NOs: 18-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 739, 740, 741, and 742 in SEQ ID NOs: 19-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779 and 780 in SEQ ID NOs: 20-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846 and 847 in SEQ ID NOs: 21-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 848, 849, 850, 851, 852, 853, 854, 855, 856, 857, 858, 859, 860, 861, 862, 863, 864, 865, 866, 867, 868, 869, 870, 871, 872, 873, 874, 875 and 876 in SEQ ID NOs: 22-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914 and 915 in SEQ ID NOs: 23-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990 and 991 in SEQ ID NOs: 24-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052 and 1053 in SEQ ID NOs: 25-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, and 1157 in SEQ ID NOs: 26-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, and 1207 in SEQ ID NOs: 27-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463 and 2464 in SEQ ID NOs: 28-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, 3250, 3251, 3252, 3253, 3254, 3255, 3256, 3257, 3258, 3259, 3260, 3271, 3272, 3273, 3274, 3275, 3276, 3277, 3278, 3279, 3280, 3281, 3282, 3283, 3284, 3285, 3286, 3287, 3288, 3289, 3290, 3291, 3292, 3293, 3294, 3295, 3296, 3297, 3298, 3299, 3300, 3301, 3302, 3303, 3304, 3305, 3306, 3307, 3308, 3309, 3310, 3311, 3312, 3313, 3314, 3315, 3316, 3317, 3318, 3319, 3320, 3321, 3322, 3323, 3324, 3325, 3326, 3327, 3328, 3329, 3330, 3331, 3332, 3333, 3334, 3335, 3336, 3337, 3338, 3339, 3340, 3341, 3342, 3343, 3344, 3345, 3346, 3347, 3348, 3349, 3350, 3351, 3352, 3353, 3354, 3355, 3356, 3357, 3358, 3359, 3360, 3361, 3362, 3363, 3364, 3365, 3366, 3367, 3368, 3369, 3370, 3371, 3372, 3373, 3374, 3375, 3376, 3377, 3378, 3379, 3380, 3381, 3382, 3383, 3384, 3385, 3386, 3387, 3388, 3389, 3390, 3391, 3392, 3393, 3394, 3395, 3396, 3397, 3398, 3399, 3400, 3401, 3402, 3403, 3404, 3405, 3406, 3407, 3408, 3409, 3410, 3411, 3412, 3413, 3414, 3415, 3416, 3417, 3418, 3419, 3420, 3421, 3422, 3423, 3424, 3425, 3426, 3427, 3428, 3429, 3430, 3431, 3432, 3433, 3434, 3435, 3436, 3437, 3438, 3439, 3440, 3441, 3442, 3443, 3444, 3445, 3446, 3447, 3448, 3449, 3450, 3451, 3452, 3453, 3454, 3455, 3456, 3457, 3458, 3459, 3460, 3461, 3462, 3463, 3464, 3465, 3466, 3467, 3468, 3469, 3470, 3471, 3472, 3473, 3474, 3475, 3476, 3477, 3478, 3479, 3480, 3481, 3482, 3483, 3484, 3485, 3486, 3487, 3488, 3489, 3490, 3491, 3492, 3493, 3494, 3495, 3496, 3497, 3498, 3499, 3500, 3501, 3502, 3503, 3504, 3505, 3506, 3507, 3508, 3509, 3510, 3511, 3512, 3513, 3514, 3515, 3516, 3517, 3518, 3519, 3520, 3521, 3522, 3523, 3524, 3525, 3526, 3527, 3528, 3529, 3530 and 3531 in SEQ ID NOs: 29-30, if the length of the at least 5 amino acid residues so permit—if the length of the at least 5 amino acids are higher than 5, the N-terminal first residue will not be higher numbered than N–L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 3532, 3533, 3534, 3535, 3536, 3537, 3538, 3539, 3540, 3541, 3542, 3543, 3544, 3545, 3546, 3547, 3548, 3549, 3550, 3551, 3552, 3553, 3554, 3555, 3556, 3557, 3558, 3559, 3560, 3561, 3562, 3563, 3564, 3565, 3566, 3567, 3568, 3569, 3570, 3571, 3572, 3573, 3574, 3575, 3576, 3577, 3578, 3579, 3580, 3581, 3582, 3583, 3584, 3585, 3586, 3587, 3588, 3589, 3590, 3591, 3592, 3593, 3594, 3595, 3596, 3597, 3598, 3599, 3600, 3601, 3602, 3603, 3604, 3605, 3606, 3607, 3608, 3609, 3610, 3611, 3612, 3613, 3614, 3615, 3616, 3617, 3618, 3619, 3620, 3621, 3622, 3623, 3624, 3625, 3626, 3627, 3628, 3629, 3630, 3631, 3632, 3633, 3634, 3635, 3636, 3637, 3638, 3639, 3640, 3641, 3642, 3643, 3644, 3645, 3646, 3647, 3648, 3649, 3650, 3651, 3652, 3653, 3654, 3655, 3656, 3657, 3658, 3659, 3660, 3661, 3662, 3663, 3664, 3665, 3666, 3667, 3668, 3669, 3670, 3671, 3672, 3673, 3674, 3675, 3676, 3677, 3678, 3679, 3680, 3681, 3682, 3683, 3684, 3685, 3686, 3687, 3688, 3689, 3690, 3691, 3692, 3693, 3694, 3695, 3696, 3697, 3698, 3699, 3700, 3701, 3702, 3703, 3704, 3705, 3706, 3707, 3708, 3709, 3710, 3711, 3712, 3713, 3714, 3715, 3716, 3717, 3718, 3719, 3720, 3721, 3722, 3723, 3724, 3725, 3726, 3727, 3728, 3729, 3730, 3731, 3732, 3733, 3734, 3735, 3736, 3737, 3738, 3739, 3740, 3741, 3742, 3743, 3744, 3745, 3746, 3747, 3748, 3749, 3750, 3751, 3752, 3753, 3754, 3755, 3756, 3757, 3758, 3759, 3760, 3761, 3762, 3763, 3764, 3765, 3766, 3767, 3768, 3769, 3770, 3771, 3772, 3773, 3774, 3775, 3776, 3777, 3778, 3779, 3780, 3781, 3782, 3783, 3784, 3785, 3786, 3787, 3788, 3789, 3790, 3791, 3792, 3793, 3794, 3795, 3796, 3797, 3798, 3799, 3800, 3801, 3802, 3803, 3804, 3805, 3806, 3807, 3808, 3809, 3810, 3811, 3812, 3813, 3814, 3815, 3816, 3817, 3818, 3819, 3820, 3821, 3822, 3823, 3824, 3825, 3826, 3827, 3828, 3829, 3830, 3831, 3832, 3833, 3834, 3835, 3836, 3837, 3838, 3839, 3840, 3841, 3842, 3843, 3844, 3845, 3846, 3847, 3848, 3849, 3850, 3851, 3852, 3853, 3854, 3855, 3856, 3857, 3858, 3859, 3860, 3861, 3862, 3863, 3864, 3865, 3866, 3867, 3868, 3869, 3870, 3871, 3872, 3873, 3874, 3875, 3876, 3877, 3878, 3879, 3880, 3881, 3882, 3883, 3884, 3885, 3886, 3887, 3888, 3889, 3890, 3891, 3892, 3893, 3894, 3895, 3896, 3897, 3898, 3899, 3900, 3901, 3902, 3903, 3904, 3905, 3906, 3907, 3908, 3909, 3910, 3911, 3912, 3913, 3914, 3915, 3916, 3917, 3918, 3919, 3920, 3921, 3922, 3923, 3924, 3925, 3926, 3927, 3928, 3929, 3930, 3931, 3932, 3933, 3934, 3935, 3936, 3937, 3938, 3939, 3940, 3941, 3942, 3943, 3944, 3945, 3946, 3947, 3948, 3949, 3950, 3951, 3952, 3953, 3954, 3955, 3956, 3957, 3958, 3959, 3960, 3961, 3962, 3963, 3964, 3965, 3966, 3967, 3968, 3969, 3970, 3971, 3972, 3973, 3974, 3975, 3976, 3977, 3978, 3979, 3980, 3981, 3982, 3983, 3984, 3985, 3986, 3987, 3988, 3989, 3990, 3991, 3992, 3993, 3994, 3995, 3996, 3997, 3998, 3999, 4000, 4001, 4002, 4003, 4004, 4005, 4006, 4007, 4008, 4009, 4010, 4011, 4012, 4013, 4014, 4015, 4016, 4017, 4018, 4019, 4020, 4021, 4022, 4023, 4024, 4025, 4026, 4027, 4028, 4029, 4030, 4031, 4032, 4033, 4034, 4035, 4036, 4037, 4038, 4039, 4040, 4042, 4043, 4044, 4045, 4046, 4047, 4048, 4049, 4050, 4051, 4052, 4053, 4054, 4055, 4056, 4057, 4058, 4059, 4060, 4061, 4062, 4063, 4064, 4065, 4066, 4067, 4068, 4069, 4070, 4071, 4072, 4073, 4074, 4075, 4076, 4077, 4078, 4079, 4080, 4081, 4082, 4083, 4084, 4085, 4086, 4087, 4088, 4089, 4090, 4091, 4092, 4093, 4094, 4095, 4096, 4097, 4098, 4099, 4100, 4101, 4102, 4103, 4104, 4105, 4106, 4107, 4108, 4109, 4110, 4110, 4111, 4112, 4113, 4114, 4115, 4116, 4117, 4118, 4119, 4120, 4121, 4122, 4123, 4124, 4125, 4126, 4127, 4128, 4129, 4130, 4131, 4132, 4133, 4134, 4135, 4136, 4137, 4138, 4139, 4140, 4141, 4142, 4143, 4144, 4145, 4146, 4147, 4148, 4149, 4150, 4151, 4152, 4153, 4154, 4155, 4156, 4157, 4158, 4159, 4160, 4171, 4172, 4173, 4174, 4175, 4176, 4177, 4178, 4179, 4180, 4181, 4182, 4183, 4184, 4185, 4186, 4187, 4188, 4189, 4190, 4191, 4192, 4193, 4194, 4195, 4196, 4197, 4198, 4199, 4200, 4201, 4202, 4203, 4204, 4205, 4206, 4207, 4208, 4209, 4210, 4211, 4212, 4213, 4214, 4215, 4216, 4217, 4218, 4219, 4220, 4221, 4222, 4223, 4224, 4225, 4226, 4227, 4228, 4229, 4230, 4231, 4232, 4233, 4234, 4235, 4236, 4237, 4238, 4239, 4240, 4241, 4242, 4243, 4244, 4245, 4246, 4247, 4248, 4249, 4250, 4251, 4252, 4253, 4254, 4255, 4256, 4257, 4258, 4259, 4260, 4271, 4272, 4273, 4274, 4275, 4276, 4277, 4278, 4279, 4280, 4281, 4282, 4283, 4284, 4285, 4286, 4287, 4288, 4289, 4290, 4291, 4292, 4293, 4294, 4295, 4296, 4297, 4298, 4299, 4300, 4301, 4302, 4303, 4304, 4305, 4306, 4307, 4308, 4309, 4310, 4311, 4312, 4313, 4314, 4315, 4316, 4317, 4318, 4319, 4320, 4321, 4322, 4323, 4324, 4325, 4326, 4327, 4328, 4329, 4330, 4331, 4332, 4333, 4334, 4335, 4336, 4337, 4338, 4339, 4340, 4341, 4342, 4343, 4344, 4345, 4346, 4347, 4348, 4349, 4350, 4351, 4352, 4353, 4354, 4355, 4356, 4357, 4358, 4359, 4360, 4361, 4362, 4363, 4364, 4365, 4366, 4367, 4368, 4369, 4370, 4371, 4372, 4373, 4374, 4375, 4376, 4377, 4378, 4379, 4380, 4381, 4382, 4383, 4384, 4385, 4386, 4387, 4388, 4389, 4390, 4391, 4392, 4393, 4394, 4395, 4396, 4397, 4398, 4399, 4400, 4401, 4402, 4403, 4404, 4405, 4406, 4407, 4408, 4409, 4410, 4411, 4412, 4413, 4414, 4415, 4416, 4417, 4418, 4419, 4420, 4421, 4422, 4423, 4424, 4425, 4426, 4427, 4428, 4429, 4430, 4431, 4432, 4433, 4434, 4435, 4436, 4437, 4438, 4439, 4440, 4441, 4442, 4443, 4444, 4445, 4446, 4447, 4448, 4449, 4450, 4451, 4452, 4453, 4454, 4455, 4456, 4457, 4458, 4459, 4460, 4461, 4462, 4463, 4464, 4465, 4466, 4467, 4468, 4469, 4470, 4471, 4472, 4473, 4474, 4475, 4476, 4477, 4478, 4479, 4480, 4481, 4482, 4483, 4484, 4485, 4486, 4487, 4488, 4489, 4490, 4491, 4492, 4493, 4494, 4495, 4496, 4497, 4498, 4499, 4500, 4501, 4502, 4503, 4504, 4505, 4506, 4507, 4508, 4509, 4510, 4511, 4512, 4513, 4514, 4515, 4516, 4517, 4518, 4519, 4520, 4521, 4522, 4523, 4524, 4525, 4526, 4527, 4528, 4529, 4530, 4531, 4532, 4533, 4534, 4535, 4536, 4537, 4538, 4539, 4540, 4541, 4542, 4543, 4544, 4545, 4546, 4547, 4548, 4549, 4550, 4551, 4552, 4553, 4554, 4555, 4556, 4557, 4558, 4559, 4560, 4561, 4562, 4563, 4564, 4565, 4566, 4567, 4568, 4569, 4570, 4571, 4572, 4573, 4574, 4575, 4576, 4577, 4578, 4579, 4580, 4581, 4582, 4583, 4584, 4585, 4586, 4587, 4588, 4589, 4590, 4591, 4592, 4593, 4594, 4595, 4596, 4597, 4598, 4599, 4600, 4601, 4602, 4603, 4604, 4605, 4606, 4607, 4608, 4609, 4610, 4611, 4612, 4613, 4614, 4615, 4616, 4617, 4618, 4619, 4620, 4621, 4622, 4623, 4624, 4625, 4626, 4627, 4628, 4629, 4630, 4631, 4632, 4633, 4634, 4635, 4636, 4637, 4638, 4639, 4640, 4641, 4642, 4643, 4644, 4645, 4646, 4647, 4648, 4649, 4650, 4651, 4652, 4653, 4654, 4655, 4656, 4657, 4658, 4659, 4660, 4661, 4662, 4663, 4664, 4665, 4666, 4667, 4668, 4669, 4670, 4671, 4672, 4673, 4674, 4675, 4676, 4677, 4678, 4679, 4680, 4681, 4682, 4683, 4684, 4685, 4686, 4687, 4688, 4689, 4690, 4691, 4692, 4693, 4694, 4695, 4696, 4697, 4698, 4699, 4700, 4701, 4702, 4703, 4704, 4705, 4706, 4707, 4708, 4709, 4710, 4711, 4712, 4713, 4714, 4715, 4716, 4717, 4718, 4719, 4720, 4721, 4722, 4723, 4724, 4725, 4726, 4727, 4728, 4729, 4730, 4731, 4732, 4733, 4734, 4735, 4736, 4737, 4738, 4739, 4740, 4741, 4742, 4743, 4744, 4745, 4746, 4747, 4748, 4749, 4750, 4751, 4752, 4753, 4754, 4755, 4756, 4757, 4758, 4759, 4760, 4761, 4762, 4763, 4764, 4765, 4766, 4767, 4768, 4769, 4770, 4771, 4772, 4773, 4774, 4775, 4776, 4777, 4778, 4779, 4780, 4781, 4782, 4783, 4784, 4785, 4786, 4787, 4788, 4789, 4790, 4791, 4792, 4793, 4794, 4795, 4796, 4797, 4798, 4799, 4800, 4801, 4802, 4803, 4804, 4805, 4806, 4807, 4808, 4809, 4810, 4811, 4812, 4813, 4814, 4815, 4816, 4817, 4818, 4819, 4820, 4821, 4822, 4823, 4824, 4825, 4826, 4827, 4828, 4829, 4830, 4831, 4832, 4833, 4834, 4835, 4836, 4837, 4838, 4839, 4840, 4841, 4842, 4843, 4844, 4845, 4846, 4847, 4848, 4849, 4850, 4851, 4852, 4853, 4854, 4855, 4856, 4857, 4858, 4859, 4860, 4861, 4862, 4863, 4864, 4865, 4866, 4867, 4868, 4869, 4870, 4871, 4872, 4873, 4874, 4875, 4876, 4877, 4878, 4879, 4880, 4881, 4882, 4883, 4884, 4885, 4886, 4887, 4888, 4889, 4890, 4891, 4892, 4893, 4894, 4895, 4896, 4897, 4898, 4899, 4900, 4901, 4902, 4903, 4904, 4905, 4906, 4907, 4908, 4909, 4910, 4911, 4912, 4913, 4914, 4915, 4916, 4917, 4918, 4919, 4920, 4921, 4922, 4923, 4924, 4925, 4926, 4927, 4928, 4929, 4930, 4931, 4932, 4933, 4934, 4935, 4936, 4937, 4938, 4939, 4940, 4941, 4942, 4943, 4944, 4945, 4946, 4947, 4948, 4949, 4950, 4951, 4952, 4953, 4954, 4955, 4956, 4957, 4958, 4959, 4960, 4961, 4962, 4963, 4964, 4965, 4966, 4967, 4968, 4969, 4970, 4971, 4972, 4973, 4974, 4975, 4976, 4977, 4978, 4979, 4980, 4981, 4982, 4983, 4984, 4985, 4986, 4987, 4988, 4989, 4990, 4991, 4992, 4993, 4994, 4995, 4996, 4997, 4998, 4999, 5000, 5001, 5002, 5003, 5004, 5005, 5006, 5007, 5008, 5009, 5010, 5011, 5012, 5013, 5014, 5015, 5016, 5017, 5018, 5019, 5020, 5021, 5022, 5023, 5024, 5025, 5026, 5027, 5028, 5029, 5030, 5031, 5032, 5033, 5034, 5035, 5036, 5037, 5038, 5039, 5040, 5042, 5043, 5044, 5045, 5046, 5047, 5048, 5049, 5050, 5051, 5052, 5053, 5054, 5055, 5056, 5057, 5058, 5059, 5060, 5061, 5062, 5063, 5064, 5065, 5066, 5067, 5068, 5069, 5070, 5071, 5072, 5073, 5074, 5075, 5076, 5077, 5078, 5079, 5080, 5081, 5082, 5083, 5084, 5085, 5086, 5087, 5088, 5089, 5090, 5091, 5092, 5093, 5094, 5095, 5096, 5097, 5098, 5099, 5100, 5101, 5102, 5103, 5104, 5105, 5106, 5107, 5108, 5109, 5110, 5110, 5111, 5112, 5113, 5114, 5115, 5116, 5117, 5118, 5119, 5120, 5121, 5122, 5123, 5124, 5125, 5126, 5127, 5128, 5129, 5130, 5131, 5132, 5133, 5134, 5135, 5136, 5137, 5138, 5139, 5140, 5141, 5142, 5143, 5144, 5145, 5146, 5147, 5148, 5149, 5150, 5151, 5152, 5153, 5154, 5155, 5156, 5157, 5158, 5159, 5160, 5171, 5172, 5173, 5174, 5175, 5176, 5177, 5178, 5179, 5180, 5181, 5182, 5183, 5184, 5185, 5186, 5187, 5188, 5189, 5190, 5191, 5192, 5193, 5194, 5195, 5196, 5197, 5198, 5199, 5200, 5201, 5202, 5203, 5204, 5205, 5206, 5207, 5208, 5209, 5210, 5211, 5212, 5213, 5214, 5215, 5216, 5217, 5218, 5219, 5220, 5221, 5222, 5223, 5224, 5225, 5226, 5227, 5228, 5229, 5230, 5231, 5232, 5233, 5234, 5235, 5236, 5237, 5238, 5239, 5240, 5241, 5242, 5243, 5244, 5245, 5246, 5247, 5248, 5249, 5250, 5251, 5252, 5253, 5254, 5255, 5256, 5257, 5258, 5259, 5260, 5271, 5272, 5273, 5274, 5275, 5276, 5277, 5278, 5279, 5280, 5281, 5282, 5283, 5284, 5285, 5286, 5287, 5288, 5289, 5290, 5291, 5292, 5293, 5294, 5295, 5296, 5297, 5298, 5299, 5300, 5301, 5302, 5303, 5304, 5305, 5306, 5307, 5308, 5309, 5310, 5311, 5312, 5313, 5314, 5315, 5316, 5317, 5318, 5319, 5320, 5321, 5322, 5323, 5324, 5325, 5326, 5327, 5328, 5329, 5330, 5331, 5332, 5333, 5334, 5335, 5336, 5337, 5338, 5339, 5340, 5341, 5342, 5343, 5344, 5345, 5346, 5347, 5348, 5349, 5350, 5351, 5352, 5353, 5354, 5355, 5356, 5357, 5358, 5359, 5360, 5361, 5362, 5363, 5364, 5365, 5366, 5367, 5368, 5369, 5370, 5371, 5372, 5373, 5374, 5375, 5376, 5377, 5378, 5379, 5380, 5381, 5382, 5383, 5384, 5385, 5386, 5387, 5388, 5389, 5390, 5391, 5392, 5393, 5394, 5395, 5396, 5397, 5398, 5399, 5400, 5401, 5402, 5403, 5404, 5405, 5406, 5407, 5408, 5409, 5410, 5411, 5412, 5413, 5414, 5415, 5416, 5417, 5418, 5419, 5420, 5421, 5422, 5423, 5424, 5425, 5426, 5427, 5428, 5429, 5430, 5431, 5432, 5433, 5434, 5435, 5436, 5437, 5438, 5439, 5440, 5441, 5442, 5443, 5444, 5445, 5446, 5447, 5448, 5449, 5450, 5451, 5452, 5453, 5454, 5455, 5456, 5457, 5458, 5459, 5460, 5461, 5462, 5463, 5464, 5465, 5466, 5467, 5468, 5469, 5470, 5471, 5472, 5473, 5474, 5475, 5476, 5477, 5478, 5479, 5480, 5481, 5482, 5483, 5484, 5485, 5486, 5487, 5488, 5489, 5490, 5491, 5492, 5493, 5494, 5495, 5496, 5497, 5498, 5499, 5500, 5501, 5502, 5503, 5504, 5505, 5506, 5507, 5508, 5509, 5510, 5511, 5512, 5513, 5514, 5515, 5516, 5517, 5518, 5519, 5520, 5521, 5522, 5523, 5524, 5525, 5526, 5527, 5528, 5529, 5530, 5531, 5532, 5533, 5534, 5535, 5536, 5537, 5538, 5539, 5540, 5541, 5542, 5543, 5544, 5545, 5546, 5547, 5548, 5549, 5550, 5551, 5552, 5553, 5554, 5555, 5556, 5557, 5558, 5559, 5560, 5561, 5562, 5563, 5564, 5565, 5566, 5567, 5568, 5569, 5570, 5571, 5572, 5573, 5574, 5575, 5576, 5577, 5578, 5579, 5580, 5581, 5582, 5583, 5584, 5585, 5586, 5587, 5588, 5589, 5590, 5591, 5592, 5593, 5594, 5595, 5596, 5597, 5598, 5599, 5600, 5601, 5602, 5603, 5604, 5605, 5606, 5607, 5608, 5609, 5610, 5611, 5612, 5613, 5614, 5615, 5616, 5617, 5618, 5619, 5620, 5621, 5622 and 5623 in SEQ ID NO: 30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-30. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *Pseudomonas aeruginosa*. The polypeptide may in these cases induce a humeral and/or a cellular immune response.

A particularly preferred polypeptide of the invention is derived from SEQ ID NO: 17 and is otherwise as defined above.

Epitopes

SEQ ID NOs: 1-30 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised agains *Pseudomonas aeruginosa* or *Pseudomonas aeruginosa* derived proteins disclosed herein are tested for binding to overlapping oligomeric peptides derived from any one of SEQ ID NO: 1-30. Thereby, the regions of the *Pseudomonas aeruginosa* polypeptide which are responsible for or contribute to binding to the antibodies can be identified. Alternatively, or additionally, one can produce mutated versions of the polypeptides of the invention, e.g. version where each single non-alanine residue in SEQ ID NOs.: 1-30 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 31-60) or an RNA fragment (such as SEQ ID NOs 61-90).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 156, at least 157, at least 158, at least 159, at least 160, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200 and at least 201 consecutive nucleotides in any one of SEQ ID NOs: 31-90. Longer fragments are contemplated, i.e. fragments having at least 200, at least 300 at least 400, at least 500, at least 600, at least 700, at least 800, at least 900, at least 1000, at least 1500, at least 2000, at least 2500, at least 3000, at least 3500, and at least 4000 nucleotides from those of SEQ ID NOs: 31-90 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in *E coli*. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

A more detailed discussion of vectors of the invention is provided in the following: Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such Fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), αI-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/Heavy metals; MMTV (mouse mammary tumor virus)—Glucocorticoids; β-Interferon—poly(rl)x/poly(rc); Adenovirus 5 E2—EIA; Collagenase—Phorbol Ester (TPA); Stromelysin—Phorbol Ester (TPA); SV40—Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70—E1A/SV40 Large T Antigen; Proliferin—Phorbol Ester/TPA; Tumor Necrosis Factor—PMA; and Thyroid Stimulating Hormoneα Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

An interesting production system is the use of plants. For instance, proteins can be produced at low cost in plants using an *Agrobacterium* transfection system to genetically modify plants to express genes that encode the protein of interest. One commercially available platform are those provided by iBio CMO LLC (8800 HSC Pkwy, Bryan, Tex. 77807, USA) and iBio, Inc (9 Innovatoin Way, Suite 100, Newark, Del. 19711, USA) and disclosed in e.g. EP 2 853 599, EP 1 769 068, and EP 2 192 172. Hence, in such systems the vector is an *Agrobacterium* vector or other vector suitable for transfection of plants.

As noted above, stably transformed cells are preferred—these i.a. allows that cell lines comprised of transformed cells as defined herein may be established—such cell lines are particularly preferred aspects of the invention.

Further details on cells and cell lines are presented in the following: Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.orq) or from other depository institutions such as Deutsche Sammlung vor Micrroorganismen und Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JMI 09, and KC8, as well as a number of commercially available bacterial hosts such as SURE® Competent Cells and SOLOP ACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384,253); by calcium phosphate precipitation; by using DEAE dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563,055, 5,550,318, 5,538,877 and 5,538,880); by agitation with silicon carbide fibers (U.S. Pat. Nos. 5,302,523 and 5,464,765); by *Agrobacterium* mediated transformation (U.S. Pat. Nos. 5,591,616 and 5,563,055); or by PEG mediated transformation of protoplasts (U.S. Pat. Nos. 4,684,611 and 4,952,500); by desiccation/inhibition mediated DNA uptake. Through the application of techniques such as these, organelle(s), cell(s), tissue(s) or organism(s) may be stably or transiently transformed. See also "Fish Vaccination", 2014, edited by Gudding R., Lillehaug A, and Evensen Ø, published by Wiley Blackwell, ISBN 978-0-470-67455-0, chapter 5, which deals specifically with DNA vaccination of fish.

The Antibodies of the Invention—and their Production/Isolation

Antibodies directed against the proteins of the invention are useful for affinity chromatography, immunoassays, and for distinguishing/identifying *Pseudomonas* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 10-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and l25I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 115I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, l25I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

An embodiment of a pharmaceutical composition of the invention comprises exactly Y or at least Y distinct (i.e. having non-identical primary structure) polypeptides of the invention described above, where each of said Y or at least Y distinct polypeptides comprises an immunogenic amino acid sequence present in or derived from any one of SEQ ID NOs: 1-30 and wherein said Y or at least Y distinct polypeptides together comprise immunogenic amino acid sequences present in or derived from Y or at least Y of SEQ ID NOs. 1-30, wherein Y is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Another embodiment of a pharmaceutical composition of the invention comprises a peptide/polypeptide comprising or consisting of an immunogenic amino acid sequence present in or derived from SEQ ID NO: 1 in combination with at least one *P. aeruginosa* peptide/polypeptide, in particular with at least one peptide/polypeptide comprising or consisting of an immunogenic amino acid sequence present in or derived from any one of SEQ ID NOs: 2-30. Another embodiment of a pharmaceutical composition of the invention comprises a peptide/polypeptide comprising or consisting of an immunogenic amino acid sequence present in or derived from SEQ ID NO: 2 in combination with at least one *P. aeruginosa* peptide/polypeptide, in particular with at least one peptide/polypeptide comprising or consisting of an immunogenic amino acid sequence present in or derived from any one of SEQ ID NOs: 1, and 3-30. Another embodiment of a pharmaceutical composition of the invention comprises a peptide/polypeptide comprising or consisting of an immunogenic amino acid sequence present in or derived from SEQ ID NO: 3 in combination with at least one *P. aeruginosa* peptide/polypeptide, in particular with at least one peptide/polypeptide comprising or consisting of an immunogenic amino acid sequence present in or derived from any one of SEQ ID NOs: 1, 2, and 4-30. Another embodiment of a pharmaceutical composition of the invention comprises a peptide/polypeptide comprising or consisting of an immunogenic amino acid sequence present in or derived from SEQ ID NO: 4 in combination with at least one *P. aeruginosa* peptide/polypeptide, in particular with at least one peptide/polypeptide comprising or consisting of an immunogenic amino acid sequence present in or derived from any one of SEQ ID NOs: 1-3, and 5-30. Another embodiment of a pharmaceutical composition of the invention comprises a peptide/polypeptide comprising or consisting of an immunogenic amino acid sequence present in or derived from SEQ ID NO: 5 in combination with at least one *P. aeruginosa* peptide/polypeptide, in particular with at least one peptide/polypeptide comprising or consisting of an immunogenic amino acid sequence present in or derived from any one of SEQ ID NOs: 1-4, and 6-30. Another embodiment of a pharmaceutical composition of the invention comprises a peptide/polypeptide comprising or consisting of an immunogenic amino acid sequence present in or derived from SEQ ID NO: 6 in combination with at least one *P. aeruginosa* peptide/polypeptide, in particular with at least one peptide/polypeptide comprising or consisting of an immunogenic amino acid sequence present in or derived from any one of SEQ ID NOs: 1-5, and 7-30. Another embodiment of a pharmaceutical composition of the invention comprises a peptide/polypeptide comprising or consisting of an immunogenic amino acid sequence present in or derived from SEQ ID NO: 7 in combination with at least one *P. aeruginosa* peptide/polypeptide, in particular with at least one peptide/polypeptide comprising or consisting of an immunogenic amino acid sequence present in or derived from any one of SEQ ID NOs: 1-6, and 8-30. Another embodiment of a pharmaceutical composition of the invention comprises a peptide/polypeptide comprising or consisting of an immunogenic amino acid sequence present in or derived from SEQ ID NO: 8 in combination with at least one *P. aeruginosa* peptide/polypeptide, in particular with at least one peptide/polypeptide comprising or consisting of an immunogenic amino acid sequence present in or derived from any one of SEQ ID NOs: 1-7, and 9-30. Another embodiment of a pharmaceutical composition of the invention comprises a peptide/polypeptide comprising or consisting of an immunogenic amino acid sequence present in or derived from SEQ ID NO: 9 in combination with at least one *P. aeruginosa* peptide/polypeptide, in particular with at least one peptide/polypeptide comprising or consisting of an immunogenic amino acid sequence present in or derived from any one of SEQ ID NOs: 1-8, and 10-30. Another embodiment of a pharmaceutical composition of the invention comprises a peptide/polypeptide comprising or consisting of an immunogenic amino acid sequence present in or derived from SEQ ID NO: 10 in combination with at least one *P. aeruginosa* peptide/polypeptide, in particular with at least one peptide/polypeptide comprising or consisting of an immunogenic amino acid sequence present in or derived from any one of SEQ ID NOs: 1-9, and 11-30. Another embodiment of a pharmaceutical composition of the invention comprises a peptide/polypeptide comprising or consisting of an immunogenic amino acid sequence present in or derived from SEQ ID NO: 11 in combination with at least one *P. aeruginosa* peptide/polypeptide, in particular with at least one peptide/polypeptide comprising or consisting of an immunogenic amino acid sequence present in or derived from any one of SEQ ID NOs: 1-10, and 12-30. Another embodiment of a pharmaceutical composition of the invention comprises a peptide/polypeptide comprising or consisting of an immunogenic amino acid sequence present in or derived from SEQ ID NO: 12 in combination with at least one *P. aeruginosa* peptide/polypeptide, in particular with at least one peptide/polypeptide comprising or consisting of an immunogenic amino acid sequence present in or derived from any one of SEQ ID NOs: 1-11, and 13-30. Another embodiment of a pharmaceutical composition of the invention comprises a peptide/polypeptide comprising or consisting of an immunogenic amino acid sequence present in or derived from SEQ ID NO: 13 in combination with at least one *P. aeruginosa* peptide/polypeptide, in particular with at least one peptide/polypeptide comprising or consisting of an immunogenic amino acid sequence present in or derived from any one of SEQ ID NOs: 1-12, and 14-30. Another embodiment of a pharmaceutical composition of the invention comprises a peptide/polypeptide comprising or consisting of an immunogenic amino acid sequence present in or derived from SEQ ID NO: 14 in combination with at least one *P. aeruginosa* peptide/polypeptide, in particular with at least one peptide/polypeptide comprising or consisting of an immunogenic amino acid sequence present in or derived from any one of SEQ ID NOs: 1-13, and 15-30. Another embodiment of a pharmaceutical composition of the invention comprises a peptide/polypeptide comprising or consisting of an immunogenic amino acid sequence present in or derived from SEQ ID NO: 15 in combination with at least one *P. aeruginosa* peptide/polypeptide, in particular with at least one peptide/polypeptide comprising or consisting of an immunogenic amino acid sequence present in or derived from any one of SEQ ID NOs: 1-14, and 16-30. Another embodiment of a pharmaceutical composition of the invention comprises a peptide/polypeptide comprising or consisting of an immunogenic amino acid sequence present in or derived from SEQ ID NO: 16 in combination with at least one *P. aeruginosa* peptide/polypeptide, in particular with at least one peptide/polypeptide comprising or consisting of an immunogenic amino acid sequence present in or derived from any one of SEQ ID NOs: 1-15, and 17-30. Another embodiment of a pharmaceutical composition of the invention comprises a peptide/polypeptide comprising or consisting of an immunogenic amino acid sequence present in or derived from SEQ ID NO: 17 in combination with at least one *P. aeruginosa* peptide/polypeptide, in particular with at least one peptide/polypeptide comprising or consisting of an immunogenic amino acid sequence present in or derived from any one of SEQ ID NOs: 1-16, and 18-30. Another embodiment of a pharmaceutical composition of the invention comprises a peptide/polypeptide comprising or consisting of an immunogenic amino acid sequence present in or derived from SEQ ID NO: 18 in combination with at least one *P. aeruginosa* peptide/polypeptide, in particular with at least one peptide/polypeptide comprising or consisting of an immunogenic amino acid sequence present in or derived from any one of SEQ ID NOs: 1-17, and 19-30. Another embodiment of a pharmaceutical composition of the invention comprises a peptide/polypeptide comprising or consisting of an immunogenic amino acid sequence present in or derived from SEQ ID NO: 19 in combination with at least one *P. aeruginosa* peptide/polypeptide, in particular with at least one peptide/polypeptide comprising or consisting of an immunogenic amino acid sequence present in or derived from any one of SEQ ID NOs: 1-18, and 20-30. Another embodiment of a pharmaceutical composition of the invention comprises a peptide/polypeptide comprising or consisting of an immunogenic amino acid sequence present in or derived from SEQ ID NO: 20 in combination with at least one *P. aeruginosa* peptide/polypeptide, in particular with at least one peptide/polypeptide comprising or consisting of an immunogenic amino acid sequence present in or derived from any one of SEQ ID NOs: 1-19, and 21-30. Another embodiment of a pharmaceutical composition of the invention comprises a peptide/polypeptide comprising or consisting of an immunogenic amino acid sequence present in or derived from SEQ ID NO: 21 in combination with at least one *P. aeruginosa* peptide/polypeptide, in particular with at least one peptide/polypeptide comprising or consisting of an immunogenic amino acid sequence present in or derived from any one of SEQ ID NOs: 1-20, and 22-30. Another embodiment of a pharmaceutical composition of the invention comprises a peptide/polypeptide comprising or consisting of an immunogenic amino acid sequence present in or derived from SEQ ID NO: 22 in combination with at least one *P. aeruginosa* peptide/polypeptide, in particular with at least one peptide/polypeptide comprising or consisting of an immunogenic amino acid sequence present in or derived from any one of SEQ ID NOs: 1-21, and 23-30. Another embodiment of a pharmaceutical composition of the invention comprises a peptide/polypeptide comprising or consisting of an immunogenic amino acid sequence present in or derived from SEQ ID NO: 23 in combination with at least one *P. aeruginosa* peptide/polypeptide, in particular with at least one peptide/polypeptide comprising or consisting of an immunogenic amino acid sequence present in or derived from any one of SEQ ID NOs: 1-22, and 24-30. Another embodiment of a pharmaceutical composition of the invention comprises a peptide/polypeptide comprising or consisting of an immunogenic amino acid sequence present in or derived from SEQ ID NO: 24 in combination with at least one *P. aeruginosa* peptide/polypeptide, in particular with at least one peptide/polypeptide comprising or consisting of an immunogenic amino acid sequence present in or derived from any one of SEQ ID NOs: 1-23, and 25-30. Another embodiment of a pharmaceutical composition of the invention comprises a peptide/polypeptide comprising or consisting of an immunogenic amino acid sequence present in or derived from SEQ ID NO: 25 in combination with at least one *P. aeruginosa* peptide/polypeptide, in particular with at least one peptide/polypeptide comprising or consisting of an immunogenic amino acid sequence present in or derived from any one of SEQ ID NOs: 1-24, and 26-30. Another embodiment of a pharmaceutical composition of the invention comprises a peptide/polypeptide comprising or consisting of an immunogenic amino acid sequence present in or derived from SEQ ID NO: 26 in combination with at least one *P. aeruginosa* peptide/polypeptide, in particular with at least one peptide/polypeptide comprising or consisting of an immunogenic amino acid sequence present in or derived from any one of SEQ ID NOs: 1-25, and 27-30. Another embodiment of a pharmaceutical composition of the invention comprises a peptide/polypeptide comprising or consisting of an immunogenic amino acid sequence present in or derived from SEQ ID NO: 27 in combination with at least one *P. aeruginosa* peptide/polypeptide, in particular with at least one peptide/polypeptide comprising or consisting of an immunogenic amino acid sequence present in or derived from any one of SEQ ID NOs: 1-26, and 28-30. Another embodiment of a pharmaceutical composition of the invention comprises a peptide/polypeptide comprising or consisting of an immunogenic amino acid sequence present in or derived from SEQ ID NO: 28 in combination with at least one *P. aeruginosa* peptide/polypeptide, in particular with at least one peptide/polypeptide comprising or consisting of an immunogenic amino acid sequence present in or derived from any one of SEQ ID NOs: 1-27, 29, and 30. Another embodiment of a pharmaceutical composition of the invention comprises a peptide/polypeptide comprising or consisting of an immunogenic amino acid sequence present in or derived from SEQ ID NO: 29 in combination with at least one *P. aeruginosa* peptide/polypeptide, in particular with at least one peptide/polypeptide comprising or consisting of an immunogenic amino acid sequence present in or derived from any one of SEQ ID NOs: 1-28, and 30. Another embodiment of a pharmaceutical composition of the invention comprises a peptide/polypeptide comprising or consisting of an immunogenic amino acid sequence present in or derived from SEQ ID NO: 30 in combination with at least one *P. aeruginosa* peptide/polypeptide, in particular with at least one peptide/polypeptide comprising or consisting of an immunogenic amino acid sequence present in or derived from any one of SEQ ID NOs: 1-29.

These embodiments entail combinations of peptides/polypeptides which are admixed with each other. Alternatively, the same combinations of peptides/polypeptides can be constructed as fusion polypeptides. Another alternative entails compositions where the immunogens are nucleic acids encoding the peptide combinations or, preferably, encoding such fusion polypeptides.

Another embodiment of the pharmaceutical composition of the invention comprises Z or at least Z distinct nucleic acid molecules each encoding a polypeptide of the invention, where each of said Z or at least Z distinct nucleic acid molecules encodes an immunogenic amino acid sequence present in or derived from any one of SEQ ID NOs: 1-30 and wherein said at Z or least Z distinct nucleic acid molecules together encode immunogenic amino acid sequences present in or derived from at Z or least Z of SEQ ID NOs. 1-30, wherein Z is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30. Also, such a pharmaceutical composition may include nucleic acid that encode several immunogenic amino acid sequences disclosed herein, either as separate encoded species or as peptides fused to each other.

Vaccines of the invention typically comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition or targeting the protein/pathogen. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following: Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 µg and 500 mg (however, often not higher than 5,000 µg), and very often in the range between 10 and 200 µg.

The immunogenic compositions are conventionally administered parenterally, eg, by injection, either subcutaneously, intramuscularly, or transdermally/transcutaneously (eg. WO98/20734). Additional formulations suitable for other modes of administration include oral, pulmonary and nasal formulations, suppositories, and transdermal applications. In the case of nucleic acid vaccination and antibody treatment, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in ImIllunol 9: 271-283; Donnelly et al. (1997) Avnu Rev Innnunol 15: 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 µg of the polypeptide of the invention per administration.

In preferred embodiments of the sixth aspect, the immunization scheme includes that the animal (e.g. the human) receives a priming administration and one or more booster administrations.

Preferred embodiments of the 6$^{th}$ aspect of the invention comprise that the administration is for the purpose of inducing protective immunity against *Pseudomonas aeruginosa*. In this embodiment it is particularly preferred that the protective immunity is effective in reducing the risk of attracting infection with *Pseudomonas aeruginosa* or is effective in treating or ameliorating infection with *Pseudomonas* aeruginosa.

As mentioned herein, the preferred vaccines of the invention induce humoral immunity, so it is preferred that the administration is for the purpose of inducing antibodies specific for *Pseudomonas aeruginosa* and wherein said antibodies or B-lymphocytes producing said antibodies are subsequently recovered from the animal.

But, as also mentioned the method of the 6$^{th}$ aspect may also be useful in antibody production, so in other embodiments the administration is for the purpose of inducing antibodies specific for *Pseudomonas aeruginosa* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with *Pseudomonas* aeruginosa;

the nucleic acid fragment of the invention or the vector of the invention is for use as a pharmaceutical, in particular for use as a pharmaceutical in the treatment, prophylaxis or amelioration of infection with *Pseudomonas aeruginosa;* the transformed cell of the invention is for use as a pharmaceutical, in particular for use as a pharmaceutical in the treatment, prophylaxis or amelioration of infection with *Pseudomonas* aeruginosa.

the antibody, antibody fragment or antibody analogue of the invention is for use as a pharmaceutical, in particular for use as a pharmaceutical in the treatment, prophylaxis or amelioration of infection with *Pseudomonas* aeruginosa.

Example 1

The Protective Effect of PA1302-31-851, PA0931-29-742, PA2070-29-880, PA2070-173-880, PA2976-1-480, PA3901-33-784 and PA0041-34-550 in a Murine Model of Pneumonia The purpose of the experiment was to test the potentially protective effect of a combination of seven antigens of the invention in a well-characterized animal model of *Pseudomonas aeruginosa*-induced pneumonia. The primary parameter of comparison for this model is lung bacteriology, and secondly clinical symptoms, body temperature and weight loss.

Materials and Methods

Materials

NMRI mice, female (Janvier, France)
PA1302-31-851 (in 4 M urea; produced at University of Southern Denmark)
PA0931-29-742 (in 4 M urea; produced at University of Southern Denmark)
PA2070-29-880 (in 4 M urea; produced at University of Southern Denmark)
PA2070-173-880 (in 4 M urea; produced at University of Southern Denmark)
PA2976-1-480 (in 2 M urea; produced at University of Southern Denmark)
PA3901-33-784 (in 2 M urea; produced at University of Southern Denmark)
PA0041-34-550 (in 2 M urea; produced at University of Southern Denmark)
Aluminum hydroxide (Alhydrogel 2.0%; Brenntag, cat. no. 21645-51-2)
Freund's incomplete adjuvant (Sigma, cat. no. F5506-10X10ML)
Isoflurane
*Pseudomonas aeruginosa* PA01 Iglewski
Luria broth agar plates
Luria broth medium
Seaweed alginate (Pronatal LF 10/60 FT sample; FMC Biopolymer)
Ketamine (50 mg/ml)
Xylazine (20 mg/ml)
Pentobarbital
Microtainer tubes with serum separator additive (BD, #365967)
*Pseudomonas* isolation agar (Sigma-Aldrich, #17208-500G)

Immunization

A group of 21 female NMRI mice were immunized with seven recombinant proteins in combination with adjuvant. The 7-valent combination vaccine consisted of PA1302-31-851, PA0931-29-742, PA2070-29-880, PA2070-173-880, PA2976-1-480, PA3901-33-784 and PA0041-34-550. A second group made up the negative control group, which was immunized only with adjuvant. The amount of adjuvant used for immunization of the control group was the same as the amount used when immunizing the vaccine group. Each mouse was immunized subcutaneously three times at approximately two week intervals (Table 1). At all three immunizations the mice in the vaccine group received 15 µg of each protein. For the first immunization the proteins were mixed with aluminum hydroxide (Al(OH)$_3$) and Freund's incomplete adjuvant, whereas only Al(OH)$_3$ was used for the subsequent immunizations. Due to restrictions on injection volume in mice the seven protein antigens were split into two separate volumes; three proteins, in combination with adjuvant, were injected on the left side of the mouse and the other four proteins were injected on the right side. This immunization routine was the same in all three rounds of immunization.

TABLE 1

Time line of experiment. The two groups of mice were immunized simultaneously at approximately two week intervals. The length of the challenge was four days.

| | Immunization number | | | Challenge | |
|---|---|---|---|---|---|
| | 1 | 2 | 3 | Start | End |
| Date | Jun. 17, 2015 | Jun. 29, 2015 | Jul. 10, 2015 | Jul. 26, 2015 | Jul. 30, 2015 |
| Days before challenge start | 39 | 27 | 16 | 0 | +4 |

Temperature Transponders

Four days before inoculation temperature transponders (BMDS, cat. no. IPTT-300) were inserted into each mouse. The mice were briefly anaesthetised by inhalation of isoflurane, and a temperature transponder inserted underneath the skin on the lower back or side of the mouse.

Using a compatible wireless scanner (BMDS Smart Probe; BMDS, cat. no. DAS-7007s) body temperature could be registered when placing the scanner close to the transponders underneath the skin of the mouse.

Preparation of Bacterial Inoculum

A small amount of *Pseudomonas aeruginosa* PA01 Iglewski was extracted from a freeze stock (stored at –80° C.) and streaked out on a Luria broth agar plate. The plate was place at 37° C. over night. The following day a single colony was used to inoculate 100 ml sterile Luria broth medium. The culture was left to incubate at 37° C., with constant shaking, for 18 hours. After the 18 hours of incubation 50 ml of the bacterial culture was centrifuged at 5000×g for 10 minutes at 20° C. The pellet was resuspended in 5 ml Luria broth medium. The bacterial suspension was mixed with seaweed alginate in a ratio of 0.5 ml bacterial suspension to 12 ml seaweed alginate, and small alginate beads were created as described in Bjarnsholt et al. (2014). The number of colony forming units (CFU) per ml alginate bead solution was determined by dissolving the alginate beads in saline.

Challenge Setup

The mice were housed at the Biocenter at the University of Copenhagen. The animals were kept in an environment characterized by a 12 hours light-dark cycle and temperature and humidity control. They had access to food and water ad libitum. The experimental procedures were carried out in accordance with the guidelines of the Danish National Animal Ethics Committee (license number 2013-15-2934-00857).

Before inoculation the mice were anaesthetized with an intraperitoneal injection of ketamine (100 mg/kg) and xylazine (10 mg/kg). Once sedated each mouse was inoculated intranasally with 1.0×10$^7$ CFU of *Pseudomonas aeruginosa* PA01 Iglewski embedded in seaweed alginate beads. To ensure that the mice did not die from dehydration during the four day challenge, the mice received 1 ml of physiological saline subcutaneously once a day.

The mice were assessed daily to register symptoms and development of disease over the course of the four day challenge. To ensure a consistent evaluation of all animals each animal was scored individually following the scale of clinical symptoms given in table 2. Before the start of the challenge, the mouse cages were "blinded", leaving the scientist involved unaware of which treatment had been given to which animals. This ensured an unbiased scoring of the animals' clinical symptoms.

TABLE 2

Scale of clinical symptoms. The mice were individually assessed on their physical appearance and behavior, specifically registering details of fur, posture, movement, eyes and breathing for each animal. The sum of the scores was used in the overall evaluation of animal welfare, and in relation to humane endpoints.

| | |
|---|---|
| Fur | 0—well groomed |
| | 1—slightly ruffled |
| | 2—very ruffled |
| Posture | 0—normal |
| | 1—slightly hunched back |
| | 2—hunched back |
| Movement | 0—normal |
| | 1—decreased activity |
| | 2—completely immobile |
| Eyes | 0—normal |
| | 1—semi-closed |
| | 2—closed |
| Breathing | 0—normal |
| | 1—affected/forced breathing |

Humane Endpoints.

Animals were euthanized if the sum of clinical scores reached 9, using the scale given in table 2, or if the body temperature was below 30° C.

Organ Extraction and Bacteriology

Following registration of weight, temperature and clinical symptoms on day four after inoculation, the mice were euthanized by intraperitoneal injection of pentobarbital. Subsequently, the lungs were extracted aseptically, and placed in a tubes containing 4 ml sterile saline. Blood was collected after cardiac puncture and transferred to Microtainer tubes, in order to save serum for later ELISA analysis.

The lungs were homogenized, serially diluted and 100 µl of each dilution was plated on *Pseudomonas* Isolation agar-plates. The plates were incubated at 37° C. over night, and the number of colony forming units was quantified the following day.

Results
Clinical Symptoms

The animals were scored daily to register disease progression. The results of the clinical scoring are given in FIG. 1.

Temperature and Weight Loss

Body weight and body temperature were registered daily, as part of the overall assessment of animal welfare. The results of the registration of weight and temperature are given in FIGS. 2 and 3, respectively. Note that there was a general issue of malfunctioning temperature transponders, especially in the group immunized with the 7-valent combination vaccine, hence the low number of data points.

Bacteriology

Results are shown in FIG. 4.

Antibody Titer

After challenge completion blood was collected from the mice. The serum was used for subsequent analysis of antibody titer, using ELISA. The antibody titer to the seven antigens were analysed for eight of the vaccinated mice. FIG. 5 shows the mean antibody response to the seven protein antigens—each curve is the mean of eight separate ELISA curves.

Conclusions

The results indicate that the 7-valent combination vaccine protects mice from *Pseudomonas aeruginosa* PA01 Iglewski-induced pneumonia. The mice immunized with the combination vaccine had a significantly lower lung CFU compared to the negative controls. Similarly the clinical symptoms were significantly lower for mice immunized with the combination vaccine, hence these animals appeared less ill to an unbiased observer. Moreover, the animals immunized with the combination vaccine had a significantly smaller weight loss over the four days following inoculation, which is another indicator of a greater well-being. There was no significant difference in body temperature, when comparing the data from the two groups. It should, however, be noted that a great number of the animals in the vaccine group had been equipped with temperature transponders that were malfunctioning, hence the small number of data points. Analysis of the serum samples show that the mice immunized with the 7-valent combination vaccine had a relatively high antibody response to five of the seven protein antigens.

Example 2

Confirmation of the Protective Effect of PA1302-31-851, PA0931-29-742, PA2070-29-880, PA2070-173-880, PA2976-1-480, PA3901-33-784 and PA0041-34-550 in a Murine Model of Pneumonia ER_0040

The purpose of the experiment was to verify the results of claim 1, i.e. that a 7-valent combination vaccine protected mice against a *Pseudomonas aeruginosa*-induced pneumonia. The primary parameter of comparison for this model is lung bacteriology, and secondly clinical symptoms, body temperature and weight loss.

Materials and Methods

Materials

NMRI mice, female (Janvier, France)

PA1302-31-851 (in 4 M urea; produced at University of Southern Denmark)

PA0931-29-742 (in 4 M urea; produced at University of Southern Denmark)

PA2070-29-880 (in 4 M urea; produced at University of Southern Denmark)

PA2070-173-880 (in 4 M urea; produced at University of Southern Denmark)

PA2976-1-480 (in 2 M urea; produced at University of Southern Denmark)

PA3901-33-784 (in 2 M urea; produced at University of Southern Denmark)

PA0041-34-550 (in 2 M urea; produced at University of Southern Denmark)

Aluminum hydroxide (Alhydrogel 2.0%; Brenntag, cat. no. 21645-51-2)

Freund's incomplete adjuvant (Sigma, cat. no. F5506-10X10ML)

Isoflurane

*Pseudomonas aeruginosa* PA01 Iglewski

Luria broth agar plates

Luria broth medium

Seaweed alginate (Pronatal LF 10/60 FT sample; FMC Biopolymer)

Ketamine (50 mg/ml)

Xylazine (20 mg/ml)

Pentobarbital

Microtainer tubes with serum separator additive (BD, #365967)

*Pseudomonas* isolation agar (Sigma-Aldrich, #17208-500G)

Immunization

A group of 32 female NMRI mice were immunized with seven recombinant proteins in combination with adjuvant. The 7-valent combination vaccine consisted of PA1302-31-851, PA0931-29-742, PA2070-29-880, PA2070-173-880, PA2976-1-480, PA3901-33-784 and PA0041-34-550.

A second group made up the negative control group, which was immunized only with adjuvant. The amount of adjuvant used for immunization of the control group was the same as the amount used when immunizing the vaccine group. Each mouse was immunized subcutaneously three times at approximately two week intervals (Table 3). At all three immunizations the mice in the vaccine group received 15 µg of each protein. For the first immunization the proteins were mixed with aluminum hydroxide ($Al(OH)_3$) and Freund's incomplete adjuvant, whereas only $Al(OH)_3$ was used for the subsequent immunizations (see appendix 5). Due to restrictions on injection volume in mice the seven protein antigens were split into two separate volumes; three proteins, in combination with adjuvant, were injected on the left side of the mouse and the other four proteins were injected on the right side. This immunization routine was the same at all three rounds of immunization.

TABLE 3

Time line of experiment. The two groups of mice were immunized simultaneously at approximately two week intervals. The length of the challenge was four days.

| | Immunization number | | | Challenge | |
|---|---|---|---|---|---|
| | 1 | 2 | 3 | Start | End |
| Date | Nov. 26, 2015 | Dec. 11, 2015 | Dec. 26, 2015 | Jan. 9, 2016 | Jan. 14, 2016 |
| Days before challenge start | 44 | 29 | 14 | 0 | +4 |

Temperature Transponders

Four days before inoculation temperature transponders (BMDS, cat. no. IPTT-300) were inserted into each mouse. The mice were briefly anaesthetised by inhalation of isoflurane, and a temperature transponder inserted underneath the skin on the lower back or side of the mouse.

Using a compatible wireless scanner (BMDS Smart Probe; BMDS, cat. no. DAS-7007s) body temperature could be registered when placing the scanner close to the transponders underneath the skin of the mouse.

Preparation of Bacterial Inoculum

A small amount of *Pseudomonas aeruginosa* PA01 Iglewski was extracted from a freeze stock (stored at −80° C.) and streaked out on a Luria broth agar plate. The plate was place at 37° C. over night. The following day a single colony was used to inoculate 100 ml sterile Luria broth medium. The culture was left to incubate at 37° C., with constant shaking, for 18 hours. After the 18 hours of incubation 50 ml of the bacterial culture was centrifuged at 5000×g for 10 minutes at 20° C. The pellet was resuspended in 5 ml Luria broth medium. The bacterial suspension was mixed with seaweed alginate in a ratio of 0.5 ml bacterial suspension to 12 ml seaweed alginate, and small alginate beads were created as described in Bjarnsholt et al (2014). The number of colony forming units (CFU) per ml alginate bead solution was determined by dissolving the alginate beads in saline.

Challenge Setup

The mice were housed at the Biocenter at the University of Copenhagen. The animals were kept in an environment characterized by a 12 hours light-dark cycle and temperature and humidity control. They had access to food and water ad libitum. The experimental procedures were carried out in accordance with the guidelines of the Danish National Animal Ethics Committee (license number 2013-15-2934-00857).

Before inoculation the mice were anaesthetized with an intraperitoneal injection of ketamine (100 mg/kg) and xylazine (10 mg/kg). Once sedated each mouse was inoculated intranasally with $1.0 \times 10^7$ CFU of *Pseudomonas aeruginosa* PA01 Iglewski embedded in seaweed alginate beads. To ensure that the mice did not die from dehydration during the four day challenge, the mice received 1 ml of physiological saline subcutaneously once a day.

The mice were assessed daily to register symptoms and development of disease over the course of the four day challenge. To ensure a consistent evaluation of all animals each animal was scored individually following the scale of clinical symptoms given in table 2 in Example 1. Before the start of the challenge, the mouse cages were "blinded", leaving the scientist involved unaware of which treatment had been given to which animals. This ensured an unbiased scoring of the animals' clinical symptoms.

Humane Endpoints.

Animals were euthanized if the sum of clinical scores reached 9, using the scale given in table 2, or if the body temperature was below 30° C.

Organ Extraction and Bacteriology

Following registration of weight, temperature and clinical symptoms on day four after inoculation, the mice were euthanized by intraperitoneal injection of pentobarbital. Subsequently, the lungs were extracted aseptically, and placed in a tubes containing 4 ml sterile saline. Blood was collected after cardiac puncture and transferred to Microtainer tubes, in order to save serum for later ELISA analysis.

The lungs were homogenized, serially diluted and 100 µl of each dilution was plated on *Pseudomonas* Isolation agar-plates. The plates were incubated at 37° C. over night, and the number of colony forming units was quantified the following day.

Results

Clinical Symptoms

The animals were scored daily to register disease progression. The results of the clinical scoring are given in FIG. 6.

Temperature and Weight Loss

Body weight and body temperature were registered daily, as part of the overall assessment of animal welfare. The results of the registration of weight and temperature are given in FIGS. 7 and 8, respectively.

Bacteriology

Figure 9:
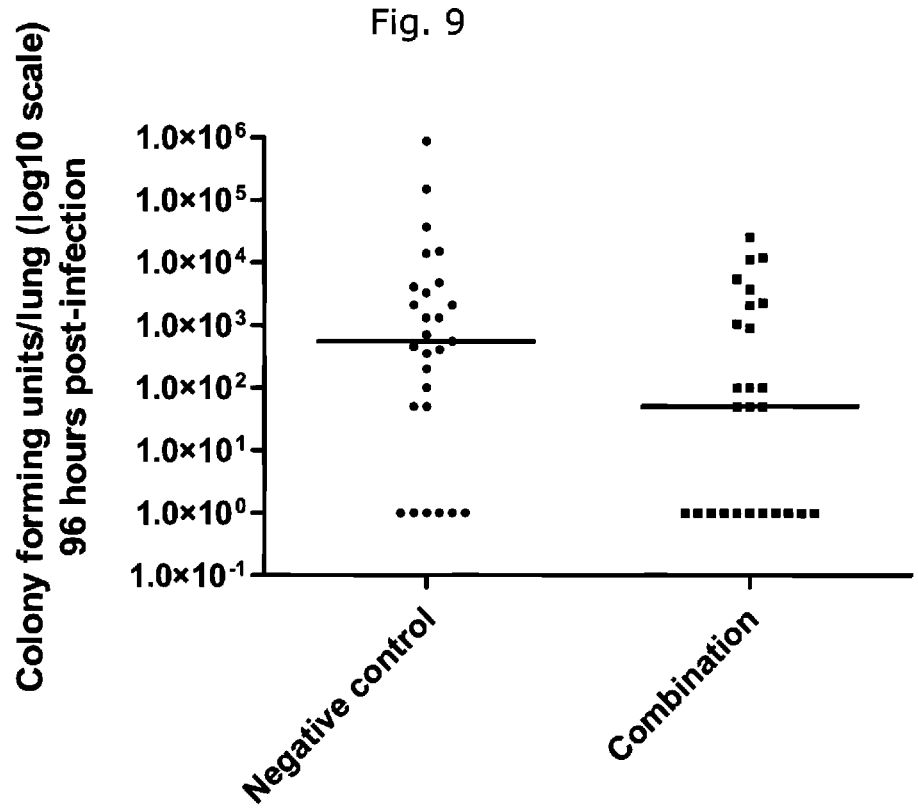

Results are shown in FIG. 9, and the pooled results with those of Example 1 are shown in FIG. 10.

Antibody Titer

After challenge completion blood was collected from the mice. The serum was used for subsequent analysis of antibody titer, using ELISA. The antibody titer to the seven antigens were analysed for all of the surviving vaccinated mice, i.e. 26 mice. FIG. 6 shows the mean antibody response to the seven protein antigens—each curve is the mean of 26 separate ELISA curves.

Conclusions

Generally the results indicate that the 7-valent combination vaccine protects mice from *Pseudomonas aeruginosa* PA01 Iglewski-induced pneumonia—results also found in Example 1. Analysis of the primary parameter of comparison—the lung bacteriology—did not suggest a protective effect of treatment with the 7-valent vaccine, as there was no significant difference in lung CFU when comparing the two groups. Only when the CFU results from both Examples 1 and 2 were analysed together, did a significant effect of the protein vaccine appear. The other parameters of interest collectively suggest that the protein-immunized mice had a better recovery from infection. The vaccinated group had significantly lower clinical scores in addition to a significantly higher body temperature and a significantly lower weight loss. Analysis of the serum samples show that the mice immunized with the 7-valent combination vaccine had a relatively high antibody response to five of the seven protein antigens.

Biologic Sequence Information

The full-length, native polypeptides of the invention have the following designations used herein:

| SEQ ID NO: | Polypeptide name |
|---|---|
| 1 | PA1034 |
| 2 | PA1592 |
| 3 | PA3284 |
| 4 | PA4107 |
| 5 | PA0912 |
| 6 | PA0070 |
| 7 | PA5060 |
| 8 | PA1954 |
| 9 | PA0971 |
| 10 | PA5253 |
| 11 | PA0724 |
| 12 | PA1441 |
| 13 | PA5133 |
| 14 | PA3716 |
| 15 | PA4016 |
| 16 | PA1805 |

-continued

| SEQ ID NO: | Polypeptide name |
|---|---|
| 17 | PA3729 |
| 18 | PA0931 |
| 19 | PA2688 |
| 20 | PA3901 |
| 21 | PA1302 |
| 22 | PA2070 |
| 23 | PA3115 |
| 24 | PA3535 |
| 25 | PA2976 |
| 26 | PA4554 |
| 27 | PA4282 |
| 28 | PA1874 |
| 29 | PA0041 |
| 30 | PA2462 |

A number of the polypeptides of the invention are fragments of the full-length, native polypepeptes. Such fragments as follows: PAXXXX-Y-Z, where XXXX is the number in the polypeptide name, X is the number of the N-terminal amino acid residue in the fragment and Z is the number of the C-terminal amino acid residue. For instance, PA2070-29-880 is the polypeptide having the amino acid sequence SEQ ID NO: 22, residues 29-880.

The polypeptides of the present invention have the following amino acid sequences:

SEQ ID NO: 1
MSQEPHVHGPNCNHDHDHHHDHGHGHVHGPHCNHSHEPVRNPLKAVGRNDPCPCGSEK
KFKKCHGA

SEQ ID NO: 2
MKKTVTLALLLAASLGLAACDKKEEDKAAAPAAPATETQPSAPATPPAEPSAPAPSSDTPATP
QTPAPTPEQPQQNQQ

SEQ ID NO: 3
MKKISLASSVVGAALLGVASVGAHAAQNPFAVQELSSGYSVAAAEKAKEGSCGEAKCGAD
KGKREASKAGHEGSCGADRKAKEGSCGGEKKAGEGNCGADKKKS

SEQ ID NO: 4
MSVFDSRQKTSASLLGAVLVGGMLLGGSAFAVEPLGQGLQVAAASAGEGKCGEGKCGSG
GSAKTPAKAGAEGKCGEGKCGDASFARTDTDHDGKVSRAEFLAVAKDRAGEFDSIDSDHD
GFISEAEAYEHLRKTYEANGKPMPAGLFSKLEQGQH

SEQ ID NO: 5
MRSLSLLLLLSLASTCEAAAVFRCEDASGHVSFTQLGCPAGQAGETVVADNPPPGGRSVTP
MAETKTKKASIGRKSVPLAVIGEREDRCGRRLDEKERRKAIVEQRIMAGMTRSDVERALGK
PDRVSGNNAEVRYQYKADKRRGARSVSFDQEGCVKGREGTGWSESIPGAKAGPSSYR

SEQ ID NO: 6
MSQPSENRLITSARYALCLLTASGVLLSGCASSGVGSVAQTTRAEYYPSCYEPVSHLRSTDN
AVRNSAITGAITGGLLGGLAGGLASDENRGRNAALAAAGGALAGGAAGYYMEKQKQISDDR

```
                                              -continued
ARIGSYGTDVDRSTVEINRSVAYAKSAQSCYQSQFKALLDGRKNKSINEAEGRKRLAEIVSGL

QETNALLVAANGRAGENISNYTQAYEKDLQQVGVPRAEVTKVAEAENRASTTKGGSKPKTG

SNPKVPKEAVATEQTIRKAQDAQSEGNKVASQGQGMIREVCNSPDMGDWAPPSCAKA

SEQ ID NO: 7
MAGKKKSEKESSWIGEIEKYSRQIWLAGLGAYSKVSKDGSKLFETLVKDGEKAEKEAKSDVD

AQVGAAKASARSAKSKVDEVRDRALGKWSELEEAFDKRLNSAISRLGVPSRNEVKELHSKV

DTLTKQIEKLTGVSVKPAAKAAAKPAAKPAAKPAAKTAAAKPAAKPAAKAAAKPAAKPAAKKT

AAKTAAAKPAAKPAAKPTAKAAAKPATKPAAKAAAKPAAKPAAAKPAAKPAAKPAAATAAKP

AAKPAAKPAAKKPAAKKPAAKPAAAKPAAPAASSSAPAAPAATPAASAPAANAPATPSSQG

SEQ ID NO: 8
MKATMVLTPLALAMAAVLSVSAYAGNEGGWHPPKPNPQSNNKGGATALVVDTQQNYNNKV

SNFGTLNNASVSGSIKDASGNVGVNVAAGDNNQQANAAALASADASFVFGTATASTSVLQS

GYGNTLNNYSNPNTASLSNSANNVSGNLGVNVAAGNFNQQKNDLAAAVSNGQYSTAGSAA

SQTSTGNTTVNSANYAYGGTYVSLKLNADGSYKGTSDQIGDVYLDTWEGQTHPGGSNTGHI

DVDSQAQGAKDLNHDGGAFAFKEKGDVDLKGTVSGFIPAIVGFKTPVTNNASLSNSLQNVS

GNVGVNIAAGGGNQQSNSLSIAAGCSSCPAGGESLGF

SEQ ID NO: 9
MKQQFERSPSESYFWPVVLAVVLHVLIFAMLFVSWAFAPELPPSKPIVQATLYQLKSKSQATT

QTNQKIAGEAKKTASKQYEVEQLEQKKLEQQKLEQQKLEQQQVAAAKAAEQKKADEARKAE

AQKAAEEAKKADEAKKAAEAKAAEQKKQADIAKKRAEDEAKKKAAEDAKKKAAEDAKKKAAE

EAKKKAAAEAAKKKAAVEAAKKKAAAAAAAARKAAEDKKARALAELLSDTTERQQALADEVG

SEVTGSLDDLIVNLVSQQWRRPPSARNGMSVEVLIEMLPDGTITNASVSRSSGDKPFDSSAV

AAVRNVGRIPEMQQLPRATFDSLYRQRRIIFKPEDLSL

SEQ ID NO: 10
MSANKKPVTTPLHLLQQLSHSLVEHLEGACKQALVDSEKLLAKLEKQRGKAQEKLHKARTKL

QDAAKAGKTKAQAKARETISDLEEALDTLKARQADTRTYIVGLKRDVQESLKLAQGVGKVKE

AAGKALESRKAKPATKPAAKAAAKPAVKTVAAKPAAKPAAKPAAKPAAKPAAKTAAAKPAAK

PTAKPAAKPAAKPAAKTAAAKPAAKPAAKPVAKPAAKPAAKTAAAKPAAKPAAKPVAKPTAK

PAAKTAAAKPAAKPAAKPAAKPAAKPVAKSAAAKPAAKPAAKPAAKPAAKPAAKPVAAKPAA

TKPATAPAAKPAATPSAPAAASSAASATPAAGSNGAAPTSAS

SEQ ID NO: 11
MWGLTMKFASLILMLLFATVARAEDYYWKIQSLPERFSSPSAACAAWAKATGRPGEFTFTGS

MKARDQTSFWCEFTNNETGKTAAGYGPAGRYGDSCPEGTEYDKATGVCKSPPQECKEGEL

FPAKGPDSPVVTSGGRNYVGDGGAPTACYQSCEYGGNPSPASCYLVKGSTTTGFCNYILKG

TGQNCGADSYTFSQTGDSLNPPDTPNTDPSDPNDPGCPPGWSWSGTTCVKAPTDPTDPTD

PTTPGSDGGGDGNGGGNNNGGGNDGGTGNGGDGSGGGDGNGGGDGSGDGDGSGTGG

DGNGTCDPAKENCSTGPEGPGGELKEPTPGTWDDAIATWEKKVEDAKQELKTKVKANVDQ

MKGAFDLNLAEGGGQLPCESMTIWGKSYSLCISDYAGQLSSLRVALLLMAALIAALILLKD

SEQ ID NO: 12
MAVAPGVLLPPTPDVKPKAAAPKSQQKTPEPSNDKTSSFSDMYAKETAKKPAERADGPAKG

SRDKPRDAGKDAAEAQPTDAVRQPAVAEDGKPLPADGQAKADGEDKVETPVDPLQLLGLG

GAVPLLDENTQATLLPPAVPTASSAPASLTEASSDPTLVKLNGVPAVNMALEQGAQDAAQTA

KGGPAKSADPRQANLGDALAGLTSDSLTKAVDGKALEAQLQQTAEPAVASAASESLLESKA

EPRGEPFAAKLNGLTQAMAQQALTNRPVNGTVPGQPVAMQQNGWSEAVVDRVMWMSSQ
```

```
NLKSAEIQLDPAELGRLDVRIHMTADQTQVTFASPNAGVRDALESQMHRLRDMFSQQGMNQ

LDVNVSDQSLARGWQGQQQGEGGSARGRGLAGEASGDEETLAGVSEIRSRPGASAARGL

VDYYA
                                                      SEQ ID NO: 13
MLRLLPLLLSLACLAPAFADERADTQRQLEQTQKDIGELKKLLDGIQQEKSGVQKQLKSTETE

MGDLEKQIKALQDELDKSEAELKRLDGEKKKLQDARIEQQRLLAIQARAAYQSGREEYLKLLL

NQEHPEKFSRTLTYYDYINKARLEQLASFNETLRQLANVEQDISAQKAEQLSKQGELDSRRE

ALAATRKERQQALAKLNSDYRERDQKLKSRQQDQAELAKVLRTIEETLARQAREAAAAAERE

RQRALAAERERARQQQAAPGRVTSPPREPAPGPLVSSTGAVYGGAFGSARGKLPWPVNG

RVVARFGSQRGDDPRAKWDGVLISASAGSTVRAVHGGRVVFADWLRGAGLLVILDHGGGY

LSLYGHNQSLLKDAGDTVKAGDPIATVGTSGGQSSPAVYFAIRHQGRPADPTTWCRAQG
                                                      SEQ ID NO: 14
MQRLSRIGRNTLAVSVSTLLLSACNQGDDAPKPAAVAPQPAAPSMAALSIPLCLNGQCAVID

QDAKLLVPFDNDYDNIVASAYQGTLMAAREERWNLIQAKDGKVLRDDIGEALSLLTPNLYGF

VRDGKYGVVDGQGKEVQAPRFDDIYPNSANEFIIYEIDGKRGILDAKGKQLTEALYDTTLVNG

SVAEHGGLISAERGEEKWIINLATGEQKAVAYESLGDLHDGVMSASVIGKGSQLVDAKGDVV

GDGKSYDYLGTPANGLVAFREKYDSPCGYLDYQGKVAIAAQFAGCGAFGKQGGLAQQRME

DGSSGKYGLIDRSGAWKVQPQYDSADSAGLTALGYTVDVPGLAAVGVSTGLFSADFGIFNL

DEGSEWVKPGYAQIGALGNDLFVVAKKGGPQKTVSFMGSESQVPVVGLMDRSGKMLLEPD

ELISIQSAYDGRFLEGLDGMDNAAHTVLLDRQGRTLVPALWQKLEVNPQQGYILGYEVSGTG

DEATETLRALYDLNGKPRFTVATTDCGAEQLLDGNGKAIWPQDPTPYCQSDDEQDDEGEPE

QEPAPVEESEETSES
                                                      SEQ ID NO: 15
MLRPARSLSLCSALVILLAACGEGEPLLPADARLPDGARYRGELVDGRLEGQGRLDYDNGA

WYAGRFEHGLLHGHGTWQGADGSRYSGGFAAGLFDGQGRLAMADGSVYQGGFRQGLFD

GEGSLEQQGTRYRGGFRKGLYSGQGTLDGSDGSRYQGSFRQGRLEGEGSFSDSQGNQY

AGTFRDGQLNGKGRWSGPDGDRYVGQFKDNQFHGQGRYESASGDVWIGRFSEGALNGP

GELLGADGSRYRGGFQFWRFHGQGLLEQLDGTRYEGGFAAGAYAGQGTLDRADGSREQG

LWADGKRIRDAAGKALPDTLEVGLLAQGRLLDEELRKIPASTPASELYALSLGGDGRQGVFL

READYAGDLLGQRFAARGVIRLVNHRDHFGDRPLATRESLSRAVRTLAERSGPEDLVFIYLT

SHGSSDHQLALDMPGLNLGDLPAAELAELLAPLRQRDKVLVVSACYSGGFIPPLKDERTLILT

AARADRVSFGCSDDADFTYFGRALLANALNRTDDLSKAFELAKEEVRQREKEEGFEASEPQ

AWLPERVLAHWRTLRGQQAERALASREGKTGEGAAGK
                                                      SEQ ID NO: 16
MLQNIRDNSQGWIAKTIIGVIIVLLSLTGFDAIIRATDHSNVAAKVNGDDISLNEVQQAVDMQRR

QLLQRLGKDFDPSMLDDKLLKEAALKGLIERTLLLQAAKDDKFAFSDQALDQLILQTPEFQVD

GKFNADRFDQVIRQMNYSRMQFRQMLGQEMLIGQLRAGLAGTGFVTDNELQSFARLEKQT

RDFATLAIKADASKSSVSDDEVKAFYEGHKSEFMTPEQVVVEYVELKKSSFFDQVKVKQEDL

EALYQKEIANLSEQRDAAHILIEVNDKVGDEQAKAKIDEIKARLAKGEDFAALAKEFSQDIGSA

ATGGDLGYAGRGVYDPAFEEALYALKQGEVSAPVKTPYGYHLIKLLGVQAPEVPSLESLKPK

LEDELKKQMVEQRFVEATKDLESSAYEAADLSQPAQEMGLKVQTSQPFGRSGGDGIAANR

QIVQTAFSAEVLEEAANSGAIELDPDTVVVLRVKEHNKPKEQPLEQVAANIRERLAAEKAAEE
```

AQKRGEALIAELREGRTSSAAGESWKVVEAASRGHEGVDPKLLQAVFRMQRPEAKDKPSFS

GVTLANGDYVVIRLNGVSEPEEAISDDEKAMYRRFLASRSGQADFAAFRRQLQDKAEVEKY

SEQ ID NO: 17
MDMTSLMPLLLGVGLVVLLVVGLLALFKAFYIKVPQGTALIVNDMSSTPKVHFTGALVYPVIHL

KEFMRISLITLEVDRRGKDGLICRDNMRADITVAFYLRVNETQDDVLKVAKAIGVDRASDRSA

VNELFNAKFSEALKTVGKQFDFVQLFENRQDFRDRIIEVIGNDLNGYVLEDVAIDYLEQTAKN

SLDPSNILDAEGIRKITELTATQNVITNELERNEELAIKKKNVETREAALALERQQADAEARQK

REIETIRAREEAETARVKEEERLKAEQARIQAQQEIDVRTENHQREVEVAQQNRQRAVVIEVE

KVTRAKDLEIVAREREVELQKIEKEKALEEQRKNIANVIRERVAVEKTVAQEEERIKEVREVSE

AERVKQVILLQAQAEAEQELVRQVKQAEADEARSKHKAVEINTMAQAELEAASKQAEAKKRL

AEGIEAERAAPGLADARVLEVTAAAKEKDGLAAARVRAEQLIAEARGDEERGLADARVLEAQ

AAAKEKDGLAEAKVLAEKLGAQARGEEQLGAAKAKATKDQGSAEAEVLLQRLNAEAEGLGK

KFGALDALSDSARQHEEFRMQLEKSFEEAMAAIAANKDIAKDQAEVLATALGKANIEIVGGEG

DFFNSFAKSLSVGKAIEGVVGKSPVVQDVLARLLNGRGAAAAVMPERKSGHENEPAAEV

SEQ ID NO: 18
MYPQFRRGHLAAAVLFASSSLLGGQALAEDERLEELDERAESVVQLGDEVVLGTAEQELKQ

APGVSIITAEDIRKRPPVNDLSEIIRTMPGVNLTGNSSSGQRGNNRQIDIRGMGPENTLILVDG

KPVSSRNSVRYGWRGERDTRGDSNWVPPEEVERIEVLRGPAAARYGSGAAGGVVNIITKRP

TDRLRGSMTVFTNIPESSKDGATRRANFSLSGPLTEALSFRAYGSANKTDSDDTDINLGHTV

NPSRTVAGREGVRNRDLSGMLSWQVTPDQVVDFEAGFSRQGNIYAGDTQNNNGTANTQG

LADDGAETNRMYRENYAITHNGTWSFGTSRFVAQYDSTRNNRLEEGLAGSVEGQIGADRSF

SASKLENYRLSGELNLPLHALFEQVLTVGAEWNKETLNDPSSLKQGFVGSDSLPGTPAAGS

RSPKSKAEIRALYVEDNIELRPGTMLTPGLRLDDHSDFGLNWSPSLNASQTLGEYFTVKAGIA

RAFKAPNLYQSNPNYLLYTRGNGCPIQTSSGGCYLVGNENLDAETSVNKELGIEFRRDGWV

AGLTYFRNDYKNKIVAPLDVMGQTGTGNNILQWSNAKKAVVEGLEGNLLVPLHEDLSWSTNL

TYMLQSKDKDTGNPLSVIPEYTLNSTLDWQASERLSTQLTSTIYGRQEPPKHGTSRNTPVVS

RKEVGTYGIWGVSAGYTFSENLSVRGGVSNLFDKRLYRQGNSFDAGAATYNEPGRAYYVS

MTTSF

SEQ ID NO: 19
MSSRALPAVPFLLLSSCLLANAVHAAGQGDGSVIELGEQTVVATAQEETKQAPGVSIITAEDIA

KRPPSNDLSQIIRTMPGVNLTGNSSSGQRGNNRQIDIRGMGPENTLILVDGKPVSSRNSVRY

GWRGERDSRGDTNWVPADQVERIEVIRGPAAARYGNGAAGGVVNIITKQAGAETHGNLSVY

SNFPQHKAEGASERMSFGLNGPLTENLSYRVYGNIAKTDSDDWDINAGHESNRTGKQAGTL

PAGREGVRNKDIDGLLSWRLTPEQTLEFEAGFSRQGNIYTGDTQNTNSNNYVKQMLGHETN

RMYRETYSVTHRGEWDFGSSLAYLQYEKTRNSRINEGLAGGTEGIFDPNNAGFYTATLRDLT

AHGEVNLPLHLGYEQTLTLGSEWTEQKLDDPSSNTQNTEEGGSIPGLAGKNRSSSSSARIFS

LFAEDNIELMPGTMLTPGLRWDHHDIVGDNWSPSLNLSHALTERVTLKAGIARAYKAPNLYQ

LNPDYLLYSRGQGCYGQSTSCYLRGNDGLKAETSVNKELGIEYSHDGLVAGLTYFRNDYKN

KIESGLSPVDHASGGKGDYANAAIYQWENVPKAVVEGLEGTLTLPLADGLKWSNNLTYMLQ

SKNKETGDVLSVTPRYTLNSMLDWQATDDLSLQATVTWYGKQKPKKYDYHGDRVTGSAND

QLSPYAIAGLGGTYRLSKNLSLGAGVDNLFDKRLFRAGNAQGVVGIDGAGAATYNEPGRTFY

TSLTASF

```
                                                    SEQ ID NO: 20
MSPSRALSPLSRALLLACLGGPVLVSAGSACAAEIRTDARQYYRLPAEPLEQALNHLGRQAG

VLIAFSPEQTAARRSQALDGEYTLEEALAALLVGSGLEARARGDGAYTLEALPVEDPANLQAL

TVVGDWLADASAADVFEHPGARDVVRREQFQAQGAASTREVLERIPGVSAPLNNGTGSHD

LALNFGIRGLNPRLASRSTVLMDGIPVPFAPYGQPQLSLAPVSIGNMDAVDVVRGGGAVRYG

PQNVGGIVNFVTRAIPEDFATKLDVHSELSPSSSQDGLKTTHNVLIGGTGANGLGGALLYSGT

RGGDWREHSDTRIDDLILKGRFQPSDEHTFSAMTQYYDGEADMPGGLGTAAYHDDPYQST

RPYDKFWGRRTLASASYEYTPNASQKLNVTGFFTKTLRSGYLDQGRNLTLSPREYWVRGLE

TRFSQGFELGESRHEVGIGHRYVNEASHELRYWTRADSGQLPSTGSRNDRDTRGSTEANA

FYIDDRIDIGNWTITPGIRYEKIDSEQKNLLKNSKDSGRYNASLPALNVIYHLTPSWNLYANTE

GSFGTVQYSQMGKAVRSGDIEPEKARTWELGSRYDDGILRAELGAFLINFDNQYESNQQTD

SVTARGKTRHKGIEAAIAYDLADLDPLLSGFDVYASYAYVDASIREDGPNKGNQVPFSSKHK

GTLGANYRTGAWSYNLDGSFQTSQYADNANTESESADGSTGRIAGWMVWSARGTYDFGP

QLNDLKLGLGVKNLFDRRYYTRSFDDNNKGLYVGQPRTLYVQASVGF
                                                    SEQ ID NO: 21
MTLPFTRAAWRPLCSAAVLGAALWAAGASAAERRFDLPAQPLAASLSRLAQQAQVQVLFDE

SLLRGLRAPALSGSYGVREALERLLVGSELELVEAGGGYVVRRRQVDAYSDNALQLDAQTIV

GNGREVDASNVGRSTLTRRDIERQQADNIPSLLQTLPGVTMGGSPKPGGQTTNIWGLGDAE

DVPYTLDGAQKSGFERYQQGTVFIEPEMIKRIEVEKGPHSVFTGNGGFGGTVHMETKDAPDL

LREGRDVGAMLKYGYHSNDQQKIYSGAVFGRSEDRRVDALLYLNGRDGRDMKLADNLPLS

PTDYPINPKRLPNSAQDEKTGLFKLNLHPTEEHDLGFTYLRSKSSRWTPFSASSYPTPPSQW

TIDRYGYELGLTRLLAHRDTTDTTWTGKYNYHPLDNPWIDLQLSYSDARTEQLDRREDTAFY

QLATGGKRMRTEYQDKVLELRNTSRFDTGALQHELTLGAALHKHKRDILMHMPGKTYETPR

YNYGWLQPAFMPAGKQDTQSFYIQDAITYGSLTVTPSMRFDSVRNDGQANLAPIYDNPKLG

HDYRAQTYSGWSPRLSVFWTATPNLAFFADYTETWRAPVIDEQYEVQNSSTIGGSSRDLDA

ERIHAIRGGSVINLPDLLVAGDSLQIRTTLFQNRIKDEIFRTRSVGCRQQSIDNGSIGGSCGDM

LPLSNYRNLPGLTIKGFEIESFYDSQRLFGSLSYSWMTGKHDGAYSNPWGPNVWARDIPPP

KWVAMLGLKVPEWDAKLGWQGEFVRKTDRLPSDRYSGGMGTGSGDIYWDHAANDSYDTH

RLFAEWVPAKLGLKDTRIDFTVDNLFNRSYRQPLGGDLVYSQGRNAKISVTQFF
                                                    SEQ ID NO: 22
MHRSLHTDAPLGAALLLALQLAPGSAAAAEEQAPVDPPTVQLQRIEVTGSAIRRVDAETAVPI

SVLRAEELRQQGVTSTEELIGRLSGNQGVYNSSRSVGSATGGASFADLRGIGANKTLVLLNG

RRLANNAIDGSAVDLNTIPFAAIDRVEVLRDGASALYGTDAIGGVINFITRKSLNEGRFDSGYA

SPTHDGGGNQRNVSASWGFGELEEDRFNVFAVANYDKQERLGAKDRGYTYNYQPGRGLD

YSSGTAFPGNWSQGANASNPLAAGGCKGADLIPRNGICRQSLWRYLDLVPETEKTSVFSRA

TGKLADEHNVSLEYFWSRSDNATQVGPGTLTGLQIDPGTAFYPGNGITPGPGGFVLDPSRP

VEVNWRQSVLGPRLQSSQNTGQRLLLGFDGQFAGWDYDIGASYNQNKVVDHIHSGYVDDR

AAALGIANGTLNPFGPQTDAGLAYLGSHALSGDFRTSVGRVKGLDARASREIGDWFGAGPA

ALALGGEFRKEAFHQDIQDFAGNVQSLGVDPAATVSGERNLKAQYAELNVPVLDSLELSAAI

RHDKYSDFGSTSNPKYSFRFQPFRQLVLRGAYSEGFRAPSLYELYNPTFTTYTSANYDDPRL

CAGGQPSQGGIANRDCAQQFYNATGGNTDLRPETARNVTLGLVYQPLRDLSVGLDFWWIRI

ANQIAEFPEAAIFADPQAYAGRIVRKADGSIDHVVTGLANLGKVKTSGVDLSLDYRFPASRYG
```

```
QFGLDLQGTYVSRYDFQQQIGGQYLDNVGDFQGVGVIARWKHVANATWSRDAWQATLSN

RYTSGYNDYDRASHGKVGSWNLWDLAGSYRLSHALGLTLGVKNLFDREPPFSNQTYTFQS

GYDPRYTDPYGRILFGRLSYSF
```

SEQ ID NO: 23
```
MVRLRTLVRAIAAASVLTSGMAHGLGLGEITLKSALNQPLDAEIELLEVRDLGSGEVIPSLASP

EEFSKAGVDRLYYLTDLKFTPVVKPNGKSVIRVTSSKPVQEPYLNFLVQVLWPNGRLLREYT

VLLDPPLYSPQAAASAPQAPVSAPRATGAPRAPQAPAPVRTTAPAGSDTYRTVSNDTLWEIA

QRNRTDRVSVPQAMLAFQELNPGAFVDGNINRLKSGQVLRIPTEQQMLERSPREALSQVQA

QNQSWRGSRNPAAGSAGARQLDATQRNAAGSAPSKVDATDNLRLVSGEGKASKGADKGG

KGDSKAIADTLAVTKESLDSTRRENEELQSRMQDLQSQLDKLQKLIQLKDAQLAKLQGQLGA

EGQGAAQPNAALPDASQPNAAAQAPAQPGTPAAAAPTPAPAGEAPAAPAQPPVAPPPAPA

AEKPPAPAVPAPAPVQAAEQPAPSFLDELLANPLWLAVIGGSALLALLVLLMILSRRNAQKEK

EEAQAFAADTGEEQEDALDLGKDGFDDLTLDEPEPQVAAVAPQVEKTTAQTSDALGEADIYI

AYGRFNQAAELLQNAIYDEPQRTDLRLKLMEVYAEMGDREGFARQENELREIGGAQPQVEQ

LKSRYPAMVAVAAVAGLAGAKLAQDELDSFSLDDLSLDDSGHAAKPDAAGQDLDDAFDLSL

DDLGGDDVQADLKSDSGALDDLTLDSDLDLAASTPADKPVDDLDFGLDFAELAETPSQPKH

DDLGDFSLDLDAPEDKLSDDDFLLSLNDEVPAAAPADNEFTLDTEAAEEPALSLPDDFDLSLA

DEPTEPAAPEKGEDSFAAQLDEVSAQLDELASNLDEPKSATPSFSAEDAAVASALDGDADD

DFDFLSGADEAATKLDLARAYIDMGDSEGARDILDEVLAEGNDSQQAEARELLERLA
```

SEQ ID NO: 24
```
MTDDHSFRPRPTSLSAALLLGAWIAQPATAAYVEAGRPGDPASWRSAEYQQDWGLERMRA

DQAYAAGIDGQGVKIGEMDSGFDPSHPDTPASRYQPVTASGTYVDGTPFSVSGAMNGNND

SHGTHVGGTLGASRDGVGMHGVAYAAQVYVANTNQNDSFLFGPTPDPNYFKAAYQALADA

GVRAINNSWGSQPKDVSYETLDGLHAAYAQHYGRSTWLDAAAGVSRQGVINVFSAGNSGY

ANASVRSALPYFQPDLEGHWLAVSGLDQQNGQRYNRCGIAKYWCITTPGRLINSTMPGGGY

ANKSGTSMAAPHATGALALVMQRYPYLNNEQALQVLLTTATQLDGTPTGAPTDTVGWGVPD

LGRAMHGPGQLLGRFEANLPAGLRDEWSNPISDSALLQRQAEDAAEHAAWQRTLKDKGWE

NGLPAGASQQERTDYAIGMARDQAAAQRQYQGSLVKAGAGSLVLSGDSTYRGPTLVDGGL

LSVDGSLLSAVEVNAGGTLGGSRIGGLLARSGGTVAAGNSIGTLEVAGDLRFESGSTYAVE

LSESASDRIVASGKASIAGGNVTLAMENSPDLLSQSQVESLVGRRYDILDAAGGIDGRFDAVL

PNYLFLGGTLDYAANAIRLDIGRNGTTLASVAQTPNQAAVAGAVETLGAGNPVYESLLLSENA

ATAQRAFQQLSGEIYPALAGLLLNDSRYLRDSVGERLRQTSDGEAGGEAPEGWFKALGSW

GKSADGSHGSEGYRHSVGGFLLGVDSQVASDTRLGLVAGYSNSSLNMDSSLQSSASIDSYH

LGAYLGRQLQQWRLSLGAAHAWHRAEVKRDLQYGAVAGKQKAKLDAQSSQLFAEAAYALG

WRSLELEPFAGLAYVHVASDDFRERGSAAALEGGDDNLDAAFTTLGLRAKRHFELDAGRRL

ALSGTLGWRHNLSDTTPQRHLAFASGSQPFSVESVALSRDAALLGVDASLAVNREVSVRLG

YNGLLGSREKDHGVGLAVDWRF
```

SEQ ID NO: 25
```
MKRMLINATQPEELRVALVDGQRLFDLDIESGAREQKKANIYKGRITRVEPSLEAAFVDFGAE

RHGFLPLKEISREYFKKSPEGRINIKEVLSEGQEVIVQVEKEERGNKGAALTTFISLAGRYLVL

MPNNPRAGGISRRIEGEERNELREALNGLNAPADMGLIVRTAGLGRSTEELQWDLDYLLQL

WSAIKEASGERGAPFLIYQESNVIIRAIRDYLRQDIGEVLIDSIDAQEEALNFIRQVMPQYASKV
```

-continued

KLYQDSVPLFNRFQIESQIETAFQREVKLPSGGSIVIDPTEALVSIDINSARATKGGDIEETALQ

TNLEAAEEIARQLRLRDIGGLIVIDFIDMTPAKNQRAVEERVREALEADRARVQVGRISRFGLL

EMSRQRLRPSLGETSGIVCPRCNGQGIIRDVESLSLAILRLIEEEALKDRTAEVRARVPFQVAA

FLLNEKRNAITKIELRTRARIFILPDDHLETPHFEVQRLRDDSPELVAGQTSYEMATVEHEEAQ

PVSSTRTLVRQEAAVKTVAPQQPAPQHTEAPVEPAKPMPEPSLFQGLVKSLVGLFAGKDQP

AAKPAETSKPAAERQTRQDERRNGRQQNRRRDGRDGNRRDEERKPREERAERQPREERA

ERPNREERSERRREERAERPAREERQPREGREERAERTPREERQPREGREGREERSERR

REERAERPAREERQPREGREERAERPAREERQPREDRQARDAAALEAEALPNDESLEQDE

QDDTDGERPRRRSRGQRRRSNRRERQREVSGELEGSEATDNAAAPLNTVAAAAAGIAVA

SEAVEANVEQAPATTSEAASETTASDETDASTSEAVETQGADSEANTGETADIEAPVTVSVV

RDEADQSTLLVAQATEEAPFASESVESREDAESAVQPATEAAEEVAAPVPVEVAAPSEPAAT

EEPTPAIAAVPANATGRALNDPREKRRLQREAERLAREAAAAAEAAAQAAPAVEEIPAVASE

EASAQEEPAAPQAEEITQADVPSQADEAQEAVQAEPEASGEGAADTEHAKKTEESETSRPH

A

SEQ ID NO: 26

MKSVLHQIGKTSLAAALSGAVLLSAQTTHAAALSVSQQPLMLIQGVAPNMLVTLDDSGSMAF

AYAPDSISGYGNYTFFASNSFNPMYFDPNTQYKLPKKLTLVNGQVQIQDYPAPNFSSAWRN

GFTRSGSINLSNSYKVTIEYGRGYDKESTIKADAAYYYDFTGSSSCNRTNQACYTRRYVSTE

QRQNFANWYSFYRTRALATQTAANLAFYSLPENARVSWQLLNDSNCNQMGSGSSSGNCFS

NYLRDFTGQHRVNFFNWLEKLSVNGGTPLRQAMTRAGEFLKKTGVNGPYAYRPGTQTAPE

YSCRGSYHILMTDGLWNNDSANVGNADSTARNLPDGKSYSSQTPYRDGTFDTLADQAFHY

WATDARPDIDDNIKPYIPYPDQANPSAEYWNPRNDPATWQHMVTYTLGLGLTTSLTSPRWE

GSTFSGGYNDIVAGNLSWPRASNNDSNNVYDLWHAAVNSRGEFFSADSPDQLVAAFQDILN

RISGKDLPASRPAISSSLQEDDTGDKLTRFAYQTSFASDKNWAGDLTRYSLTTQDKATVQTK

LWSAQSILDAMPNGGAGRKIMMAGSGTSGLKEFTWGSLSADQQRQLNRDPDRNDVADTKG

QDRVAFLRGDRRKENSDNFRTRNSILGDIINSSPATVGKAQYLTYLAQPIEPSGNYSTFAEAQ

KTRAPRVYVGANDGMLHGFDTDGNETFAFIPSAVFEKLHKLTARGYQGGAHQFYVDGSPVV

ADAFFGGAWHTVLIGSLRAGGKGLFALDVTDPANIKLLWEIGVDQEPDLGYSFPKPTVARLH

NGKWAVVTGNGYSSLNDKAALLIIDLETGAITRKLEVTGRTGVPNGLSSPRLADNNSDGVAD

YAYAGDLQGNLWRFDLIAGKVNQDDPFSRANDGPAVASSFRVSFGGQPLYSAVDSAGAAQ

AITAAPSLVRHPTRKGYIVIFGTGKYFENADARADTSRAQTLYGIWDQQTKGEAAGSTPRLTR

GNLQQQTLDLQADSTFASTARTIRIASQNPVNWLNNDGSTKQSGWYLDFMVNGTLKGEMLI

EDMIAIGQVVLLQTITPNDDPCADGASNWTYGLDPYTGGRTSFTVFDLARQGVVDSKSDYSY

NKQNVAVSGTEQKGLGGLTLSTNEQGNPEVCSSGECLTVNPGPNTRGRQNWRPIEGKN

SEQ ID NO: 27

MKILAIRLKNLASLAGEQEIDFTREPLSSAGLFAITGPTGAGKSTVLDALCLALFGSTPRLESTS

ASSKVPDGRNELSSNDERNLLRRGCASGYAEVDFVGIDGHRYRARWETRRSRDKADGALQ

KSQQSLQDLETQQMLAANKKSEFREQLEQKLGLNFAQFTRAVLLAQSEFSAFLKASDNDRG

ALLEKLTDTGLYSQLSKAAYQRASQADEQRKQLEQRLEGSLPLAEQARAGLEAALESHAQA

RLQEQQALQRLEGQQQWFTEEQRLLQSCEHAQGQLAEARQAWDALATERETLQWLERLA

PVRGLIERLKQLEQELRHSEQQQRQRTEQQAAGTERLQGLQARLQEARERQAQADNHLRQ

AQAPLREAFQLESEARRLERTLAERQELHRQSNQRHAQQSDAARQLDMEQQRHVAEQAQL

-continued

```
QAALRDSQALAALGDAWVTHQGQLATFVQRRQRALESQAQLPELEKSLAHAGEPLERLQA

QWTALHGSEPDDLAARLVELRRQTDSLERQQALHKEWQQVLDQRAGLARRLGELDQRMVE

QEQALLDLKRQGSQCAEEVKAAEQALQVTRELLQRQRLARSASVEQLRAGLVDGEACPVC

GSQEHPYHHSEQLLAALGEHDDQEQVRAEQSLERLRQTLVGLREGYSSQRERLNQSRQEQ

QELTGQLAALDRQLDQWTLPEELRLLQPSAQLEWLAQRLDDLAGQRQQCQRDFDRLIARQ

RQTQQLQQELRAAETILQQRQQALTEQRQRYEHLQQQVEEDSQQLRPLLSDEHWQRWQA

DPLRTFQALGESIEQRRQQQARLQQIEQRLQELKQRCDESSWQLKQSDEQRNEARQAEER

AQAELAELNGRLGAHLGQHACAQDWQLSLEHAAQAAQSAVETLQAPLDSLREEQLRLAEAL

EHLQQQRQRQQDEFQRLQADWQAWRERQDNLDDSRLDALLGLSEEQATQWREQLQRLQ

EEITRQQTLEAERQAQLLQHRRQRPETDREALEDNLRQQRERLAASEQAYLETYSQLQADN

QRREQSQALLAELERARAEFRRWGRLNELIGSSSGDKFRRIAQGYNLDLLVQHSNVQLRQL

ARRYRLQRGGSELGLLVVDTEMGDELRSVYSLSGGETFLISLALALGLASMASSKLRIESLFID

EGFGSLDPESLQLAMDALDNLQAQGRKVAVISHVQEMHERIPVQVRVQREGNGMSSLKVV

G

SEQ ID NO: 28
MSIQAKVTPIDQSISSAAAVEVPENGILKLSQSSNVALDVAPESVAGYSKSGSDLIVQLKTGES

VRIANFYAEGQPSSQLFLADKDKLVAVDLPPVAADGPLMAGYIPQESLAGFESLTGAGVLGG

MSAGTALLVGAAAIGAGVAISNSSGGGGGGGSSVPPDTTPPKAASGLKIAPDGSSISGQAEA

GASVGIDTNGDKPDLTVIADANGNFTAPLNPPLTNGQTVTVVVTDPAGNASPPAQVTAPDT

TAPAPATDVQVAPDGSSVTGKAEPGSTVGVDTDGDGQPDTTVVVGPGGSFEVPLNPPLTN

GETVTVIVTDPAGNNSTPVTVEAPDTTAPAPATDVQVAPDGSSVTGNAEPGATVGVDTDGD

GQPDTTVVVGPGGSFEVPLNPPLTNGETVTVIVTDPAGNSSTPVTAEAPDFPDAPQVNASN

GSVLSGTAEAGVTIVITDGNGNPIGQTSADANGNWSFTPGSQLPDGTVVNVVARDAAGNSS

PATSITVDGVAPNAPVVEPSNGSELSGTAEPGSSVTLTDGNGNPIGQTTADANGNWSFTPST

PLPDGTVVNVVARDAAGNSSPPASVTVDAVAPATPTVDPSNGTTLSGTAEPGSSVTLTDGN

GNPIGQVTADGSGNWTFTPSTPLPNGTVVNATATDPSGNASSPASVTVDAVAPATPVVNPS

NGTTLSGTAEPGATVTLTDGNGNPIGQVTADGSGNWSFTPTTPLPNGTVVNATATDASGNT

SAGSSVTVDSVAPATPVINPSNGTTLSGTAEPGSSVTLTDGNGNPIGQVTADGSGNWSFTP

STPLADGTVVNATATDPAGNTSGQGSTTVDGVAPTTPTVNLSNGSSLSGTAEPGSTVILTDG

NGNPIAEVTADGSGNWTYTPSTPIANGTVVNVVAQDAAGNSSPGASVTVDSQAPAAPVVNP

SNGTTLSGTAEPGATVTLTDGNGNPIGQVTADGSGNWSFTPGTPLANGTVVNATASDPTGN

TSAPASTTVDSVAPAAPVVNPSNGAEISGTAEPGATVTLTDGSGNPIGQVTADGSGNWSFTP

STPLADGTVVNATATDPAGNTGGQGSTTVDAIAPATPTVNLSNGSSLSGTAEPGSTVILTDG

NGNPIAEVTADGSGNWTYTPSTPIANGTVVNVVAQDASGNSSPPATVTVDSSAPPAPVINPS

NGVVISGTAEAGATVTLTDAGGNPIGQVTADGSGNWSFTPGTPLANGTVIVATATDPTGNTG

PQAATTVDAVAPPAPVIDPSNGTTISGTAEAGAKVILTDGNGNPIGETTADGSGNWSFTPGTP

LANGTVVNAVAQDPAGNTGPQGSTTVDAVAPNTPVVNPSNGNLLNGTAEPGSTVTLTDGN

GNPIGQTTADGSGNWSFTPGSQLPNGTVVNVTASDAAGNTSLPATTTVDSSLPSIPQVDPSN

GSVISGTADAGNTIIITDGNGNPIGQVTADGSGNWSFTPGIPLPDGTVVNVVARSPSNVDSAP

AVITVDGVAPAAPVIDPSNGTEISGTAEAGATVILTDGGGNPIGQATADGSGNWTFTPSTPLA

NGTVINAVAQDPAGNTSGPASVTVDAIAPPAPVINPSNGVVISGTAEAGATVILTDGNGNPIG
```

```
QVTADGSGNWSFTPGTPLANGSVINALAQDAAGNNSSPTSATVDSLAPAAPVIDPSNGSVIA

GTAEAGATVILTDGNGNPIGQVTADGSGNWSFTPGTPLSNGTVVNAVAQDAAGNTSGPVST

TVDAVAPATPVIDPSNGVELSGTAEPGVRVILTDGNGNPIGQTLADGSGNWSFTPGTPLANG

TVVNAVAQDPAGNTSGPASTTVDTVAPATPVINPSNGSVITGTAEVGAKVILTDGNGNPIGET

TADGSGNWTFTPGTPLANGTVINAVAEDAAGNASGPASTTVDSVAPSAPLLSISADGALLTG

TAEPNSQVRIVVNGDTANPITVTVDGAGNFSLPFAPPLITGELIAGVAVDAAGNVSGPATINAP

DLAPPTISVPEAADTWINAAEIGDIQVDVTVRPTMQVGQVVTVKFAGQNGYEAEVSHTLTA

GDIAAGNLTLTLTPPGGMGPFPEGASTVTADINGGTASTPVPFTIDTIPPATPVLSLVGNILTIS

AEPGTELTVTVDVGGVTATATVTADNSGLASLNLLTDLDIDFSWDQLLNAQVSVVGRDPAGN

PSNTASIGVGTSIEQPVTIGNFGLDVSLNPLNPRFGFSGTTEPDSSVVIRVITPALNVELLPIQA

DSSGNFSLNLLSPTILTQLGLNITDILNLGSQISFNLVSTDSNGNDSAAYGITLTPNGLSLNIGQI

DVNGTSGDDVLSGANGSSEHINGGDGSDLIFNVGTGDHVVAGNGNDTIQITATDFVSIDGGA

GFDTLVLANGIDLDYNAVGVGTLSNLERIDLGKGDSGSVLTLTAAEVDAITDANNTLQITGENN

DTLNVVGAVNTGTTQLINGITYDVYTFGSTTLLIEDNTVQVVV

SEQ ID NO: 29
MDIRSPLNQCIALSLAGILFLNPIVAAAAGLALDKAAGGNTGLGQAGNGVPIVNIATPNDAGLS

NNHFRDYNVGANGLILNNATGKTQGTQLGGIILGNPNLKGQAAQVILNQVTGGNRSTLAGYT

EVAGQSARVIVANPHGITCQGCGFINTPRATLTTGKPIMDGQRLERFQVDGGDIVVEGAELN

VGNLEQFDLITRSAKLNAKLYAKNLNIVTGRNDVQADSLQATPRAADGSEKPQLAIDSSALGG

MYAGAIRLVGTEQGVGVRLAGDMAASGGDIRIDASGKLSLAQASSQGDLKIAAQAVELNGKT

YAGGSAEIRSAEELVNRQSLAARERIVLEAAHIDNAGVIEAGVEPDERRNARGDLELRSGTLR

NAGSLVASRALEAKASQALDNQGGSLKGATVRVDAGHLDNRGGKLLAEGELRVEASSLDNR

QDGLLQSRDRAVVKTRGDLDNRGGQVIGLNDLEVGAATLDNGQQGLLGSQQSTRVSAQAL

VNRGDGEVSGKRVEARVGSLDNRGGKLIGDDLLVVASGAIDNRLGLFSAANRLDLRARSLD

NSGKGTLSSRGGLEVSLGGLLDNRDEGNLLSQGAQRVTVGQLDNRAGGLLSSRSELNVHG

ASLDNRGGVLVADAGLSATGGAFDNRDGGSASGKAGVRVEVASLRNDQGGKLLSDGRLDL

AANAVGNAGGRIAAKGDLQATLGSLAQQGGELVSEKTLKVAADTLDNSQSGLIAANGGIAIEA

RQVDNRAGEISSTSKVAVNAREQLDNRGGKVIGDSGLRLTVQRLLNQAKGVLAGRDGLSLD

GGELFNGDGGRLDSQNSLSVSLGGVLDNQGGALVSEGSLTARAARLDNRGGTFSSAGALA

LTSQAALDNQGGRLLSDAGVTLQGASLDNSRSGVISAKGAVDIRTGVLDNSRNGGIGSNAGI

TLVAARLDNGQQGRVSAKGLLDANLKGLDQRGGGVLISETGVTLDLNGGTLVNRDGGLIATP

GALLLRQLGAVDNGAGGEISSDRAFTLAAASLDNRGGRLIGAANLTLRIAQALDNSLAGVISG

AAGLDIAAARLDNSAKGTLASRAGIDLRVDGALDNHAEGTVSGARLTLASASLDNSGKGLLS

GNAGLSVATGALDNAEGGQLISQGVLDVSSADLDNRGGALSGKQSLRLSAANLDNRGGLLT

SDGELELTAGRVDSADGGEISARGDLRLTVERLVQRQGRLVGERGVSLDLRGGDLDNQGG

LISARGPLSIERLSVLDNRQGGEISSQQGFELLARRIDNGQQGRIISAGKLRLDADALGNAGA

GLLSGWQGLTVTGGSLDNSAGGTLSSKDGELAISLGGALDNHGQGALVSKGAQRIDAASLD

NAQGIVSGESDVTLSIAGKLDNGQGGLVSAQRALSFERDDTLLNNAGGRINGGSLLLKGASL

DNSDGQLISQGRLDAILGGALVNTGAARLASGGDLLLRSASVDNRGGKLVSQGLLEISAGSL

DNSASGTLASQAGMSLRLGGGALRNQQDGLIFSQAGALDVQAGSLDNRQGTLQAQGDNRL

RIGGALDNQGGRLDSRAGNLDLQSGSLDNGAGGVLNSAKGWLKLVTGLFDNSAGVTQAQS
```

```
LEIRAGQGVRNQQGHLSALGGDNRIVTADFDNQGGGLYASGLLSLDGQRFLNQGAAAGQG

GKVGAGRIDFSLAGALANRFGQLESESELHLRAAAIDNSGGSLRALGRSGSTRLVAGGLNNA

YGVLESANQDLDLQLGSLANAGGRILHTGNGTFGLDSGQVIRAGGELTTNGLLDIRASEWTN

SSVLQAGRLNLDIGTFRQTAEGKLLAVQSFTGRGGDWSNDGLLASDGSFRLDLSGGYRGN

GRATSLGDFALNAASLDLGNAASLAGGANVTLGAGNLLVNRGRITAAGDLVASAASLNNYGT

LGGGGNLRLNAPALLNERGLLFSGADMTLRAGDITNLYGDVYSLGRLDIARDDAGNRAASLR

NLSGVIESGKDFSLRASLIENRRAVLESKSGLYTAKMEQTACIEGVNAGDCSGKRNAIWTITQ

RDKTEVTASSAMGQLLAGGDFAIDGGTLNNLSSLIGSGGNLTANLEVLDNQGLETGELETIRV

LRTARGGDIGGIDQKSRNFTNLYWYQSANFDPARAGEIPAALNAILSDWSFEYEFPSKGPTPI

SSGDQSYAAVIQAAGDVTVNASTRIDNGVTRPGYTFVGSGRQVGDSAVGGSGVSVVVPLTS

QLPPDLARRQVNPVTLPGFSLPQGDNGLFRLSSRFAEDGNGSAALGAGADRTQGGSGVSV

GQQGAGNAAGTWQGQGVRVDGLAGAANVQGQGGSTLGGSLPGVARVQGVPGNATPSAS

HKYLIETNPALTELKQFLNSDYLLSGLGMNPDDSKKRLGDGLYEQRLIRDAVVARTGQRYIDG

LSSDEALFRYLMDNAIAYKDQLHLQLGVGLSAEQMAALTHDIVWLEEVEVNGEKVLAPVVYL

AQAEGRLAPNGALIQGRDVKLVSGGDLHNVGTLRARNDLSATADNLDNSGLIEAGKRLDLLA

GDSIRNRQGGVIAGRDVSLTALTGDVINERSVTRYDSALDGRTWERSFADSAARVEAANSLN

VQAGRDIANLGGVLQSRGDLSLDAGRDVTVAAVEDRQGQTRWSTSRLQSVTQLGAEVSAG

RDLNVSAGRDLTAVASTLEARRDIALSAGRDVTLAAAANEEHAYSKTRKVTYQEDKVAQQGT

RVDAGGDLAINAGQDLRLIASQASAGDEAYLVAGDKLELLAANDSNYYLYDKKKKGDFGRKE

TRRDEVTDVKAVGSQISSGGDLTLLSGGDQTYQGAKLESGNDLAIVSGGAVTFEAVKDLHQE

SHEKSKGDLAWNSAKGKGQTDETLRQTQIVAQGNLAIKAVEGLKIDLKHIDQKTVSQTIDAMV

QADPQLAWLKEAEQRGDVDWRMVQEVHDSWKYSNSGMGPATQIAVAIAAAAIGGMAAAGA

LSGAGVGASSFAMGAGVGAAGSLSGTAAVSLINNKGDLGKVLKDSFSSDSLKQIAIASLTGG

LTAEYFDGILQTKTDPLTGKVTVDLSSLSGVGRFAANQAMQNATSTVLSQALGQGGSLNEAL

KSALYNSFAAAGFNFVGDIGQEYSLKPGDPSMVTMHALMGGLAAQVSGGDFATGAAAAGA

NEALVAKLDQAFKSLSPENREAMVTMGSQLVGVLAAAVRDPDVTGKALESAAWVAKNSTQY

NFLNHQDVADLDNALQKCKSQGNCRQVEEEFKARSDENRRRLNGCVAVGNCAEIRAEIDAG

STALNELVARQETANPGGSDSDIAYGFLMGRNVVDWTTAGQLHLEQTANLWWNGNPQWQ

KEVGAYLDQTGFNPFGIGVPAMGGAAGKVTAKALMNALKAGELPKGEVAPGKANLPTIGALA

DAEAGMPYTHPVKLAAKATGTAGKIKIEAGAIPDANEVRAGQGLSGLGYDVTHQTTASAKGI

QGQRTADLHVDGLGSIDVYTPKNLDPTKIVRAIEKKSNQAGGVLVQADLPSTDMSSIAARMW

GKTNAQSIKTIFFQKPDGSLVRFDRPAGGG
                                                                    SEQ ID NO: 30
MDIRSPLNQCIALSLAGILFLNPIVAAAAGLALDKAAGGNTGLGQAGNGVPIVNIATPNGAG

LSNNHFRDYNVGANGLILNNATGKTQGTQLGGIILGNPNLKGQAAQVILNQVTGGNRSTLA

GYTEVAGQSARVIVANPHGITCQGCGFINTPRATLTTGKPIMDGQRLERFQVDGGDIVVEG

AELNVGNLEQFDLITRSAKLNAKLYAKNLNIVTGRNDVQADSLQATPRAADGSEKPQLAIDS

SALGGMYAGAIRLVGTEQGVGVKLAGDMAASGGDIRIDASGKLSLAQASSQGDLKIAAQA

VELNGKTYAGGSAEIRSAEELVNRQSLAARERIALEAAHIDNAGVIEAGVEPDERRNARGDL

ELRSGTLRNAGSLVASRALEAKASQALDNQGGSLKGATVRVDGGHLDNRGGKLLAEGELR

VEASSLDNRQDGLLQSRDRAVVKTRGDLDNRGGQVVGLNELQVQAAALDNRSAGLLSSK
```

-continued

GDMDIEFARLDNSAGGKLVSERRTLLKADRLDNRSGRIVAGQDLDLSSRLIDNRAGDISST

SRVVASAREQLDNRGGKIVGDSGLDITTPRMLNQDKGVLASRDGLRLSATELFNGAGGLLS

SQKGIDVSLAGAFDNQAGSLDSRGFLTVKSAWLDNQGGTLSSAGALAVTSQGALNNQGG

RLASDAGLSLSSASLDNSQAGAISGKGAVEIRTGNLNNSRKASIGSDAGLTLVAARVDNSQ

AGRIAAKGVIDADLQGLDQHDRGNLVSDTGITLDLNKGSLVNRAQGLIATPGTLLLRQLGV

VDNSGGEISSDRAFTLATSALNNQGGRLLSGGALTLRIAQALDNSLEGIVSGAGGLDIQAFV

LDNRSGSIGSKGAIDIGVTRLENDAGTLIAERGLKLVADEANSSKGRIAANGSLHAKVGTLS

QKGGELTSQDSLTLDLGILNNNAGRIAGNQGVDITARQVDNSVGEIASQGVVALNLTEQLD

NRGGKIVGDSGLGITAPHVLNQDKGVLASRDGLRLSATELFNGAGGLLSSQKGIDVSLAGA

FDNQAGSLDSRGFLTVKSAWLDNQGGTLSSAGALAVTSQGALNNQGGRLASDAGLSLSS

ASLDNSQAGAISGKGAVEIRTGNLNNSRKASIGSDAGLTLVAARVDNSQAGRIAAKGAIDA

ALQGLDQHDRGSLVSDTGITLDLNKGSLVNRAQGLIATPGTLLLRQLGVVDNSGGEISSDR

AFTLATSALNNQGGRLLSGGALTLRIAQALDNSLEGIVSGAGGLDIQAFVLDNRSGSIGSKG

AIDIGVTRLENDAGTLIAERGLKLAADEANNSKGRIVAKDELRAKLGALVQNGGELTTQGAL

ALDADKVDNGAGRIAGNRGVVIDARQVDNRAGEIASQGVATLNLTEQLDNRGGKVVADS

GLGITAPRVLNQDKGVIASRDGLRLSGTELFNGNAGLLSSQRHIEVTLDGVLDNQGKGALL

SDGTLTVSAGRIHNQDATLSSAGALRLSSQEAVDNRGGKLVTDSSLRLTSASLDNSRSGII

SANAAAEIHTGVLNNSQKGNLGSNDGLGLIATEVDNSQEGRITAKGMIDANIKGLDQQGK

GRLVSNAGIILDLNEGTLANGAQGLIATPGTLLLRQLGMVDNSGGEISSDRAFTLTTSALTN

QGGRLRSGGVLTLRIAQALDNSLEGVLSGTGGLDIRALALDNRSGSIGSKGAVDIDVSRLE

NDDGDLLSEGRLKLTAERANSVRGRIAARGDLHASVTAFNQAGGELSSEGALMLEADSLDN

RSGGLVSADGNLTVSARRIDNRAGEIASPGQVTLDVAEQLDNRGGKAIGDSGLRLAAPRVL

NQDGGVLASRDGLRLNGAELFNGNGGLLSSQQSIDVILDGVLGNQAGSLSSQGRLSVKSG

RLDNQGGAVSSAGTLSLSSQGALNNQGGRVVTDAGAVLRSASLDNSQGGIVSAKGAAEIR

TGSLNNSQKGGIGSGAGLALVADLVDNSQNGRITAKGAIDANLKGLDQQGSGRLVSDTAI

ALDLRGGELVNRAQGLIATPGALLLRQLGVVDNSGGGEISSDRSFTLAATALSNRGGRVISG

DSLTLRIAQALDNSLQGVLSASGGLDVAALVFDNHSGIVASKGDTHIGVNRLENEAGRVVS

EGALDLTAKQVSSAKGRIAAKGDLQVTVGTLEQQGGELASQGTLTLDADSLDNRNGGLVS

ADGGVTAEARQIDNRGGEISSVAKVALAVREQLDNRGGKVIGDSELSLTVQRLLNQAKGVL

ASRDGLHLDGAELLNGDGGLLSSQRLVDVTLSGALDNQGSGALVSEESLTVKADQVNNQA

GTFSSAGSLLVTSRGELNNQGGRLVTDAGATLNSTGFDNSRAGLVSAKGAVAIRTGALNNS

QKGSIGGNTGVTLVAGLVDNGREGRISTKGTLDANLKGLLQQGGGSLVGERGVTLDLNGG

TLDNHDLGLVSTPGALLLRQLGMVDNSVGGEISSDRAFTLAANTLNNQGGRLISSEALTLRI

AKTLDNSLKGQVLATDGLAIESQVLDNRAGTIGSKGDARISVTSLDNAEQGSLVSEGRLEL

VADQVSNGNQGRIAARGVLEAAVGTLLQQGGELVSQGSLDLRADTLDNSQSGLIAANGGI

AIEARQVDNRAGEISSTSKVAVNAREQLDNRGGKVIGDSGLRLTVQRLLNQAKGVLAGRD

GLSLDGGELFNGDGGRLDSQNSLSVSLGGVLDNQGGALVSEGSLTARAARLDNRGGTFSS

AGALALTSQAVLDNQGGRLLSDAGVTLKGASLDNSRSGVISAKGAVDIRTGVLDNSRNGGI

GSNAGITLVAARLDNGQQGRVSAKGLLDANLKGLDQRGGGVLVSETGVTLDLNGGTLVNR

DGGLIATPGALLLRQLGAVDNGAGGEISSDRAFTLAAASLDNRGGRLIGADSLTLRIAQALD

-continued

NSLAGVISGAAGLDIAAARLDNSAKGTLASRAGIDLRVDGALDNHAEGTVSGARLTLASAS

LDNSGKGLLSGNAGLSVATGALDNAEGGQLISQGVLDVSSADLDNRGGALSGKQSLRLSA

ANLDNRGGLLTSDGELELTAGRVDSADGGEISARGDLRLTVERLVQRQGRLIGERGVSLDL

RGGDLDNQGGLISARGPLSIERLNVLDNRQGGEIYSQQGFELLARRIDNGQQGRIISAGKL

RLDADALGNAGAGLLSGWQGLTVTGGSLDNSAGGTLSSKDGELAISLGGALDNHGQGALV

SKGAQRIDAASLDNAQGIVSGESDVTLSIAGKLDNGQGGLVSAQRALSFERDDTLLNNAG

GRINGGSLLLKGASLDNSDGQLISQGRLDAILGGALVNAGAARLASGGDLLLRSASVDNRG

GKLVSQGLLEISAGSLDNSASGTLASQADMSLRLGGGALRNQQDGLIFSQAGALEVQAGS

LDNRQGTLQAQGDNRLRIGGALDNQAGRLDSRAGNLDLQSGSLDNGAGGVLNSAKGWLK

LVTGLFDNSAGVTQAQSLEIRAGQGVRNQQGHLSALGGDNRIVTADFDNQGGGLYASGLL

SLDGQRFLNQGAAAGQGGKVGAGRIDFSLAGALANRFGQLESESELHLRAAAIDNSGGSL

RALGRSGSTRLVAGDLNNAYGVLESANQDLDLQLGSLANAGGRILHTGNGTFGLDSGQVIR

AGGELTTNGLLDIRASEWTNSSVLQAGRLNLDIGTFRQTAEGKLLAVQSFTGRGGDWSND

GLLASNGSLRLELSGGYRGNGRATSLGDFALNAASLDLGNAASLAGGANVTLGAGNLLVNR

GRITAAGDLVASAASLNNYGTLGGGGNLRLNAPALLNERGLLFSGADMTLRAGDITNLYGD

VYSLGRLDIARDDAGGWANRLENISGNLESTGDMRFSVSSLLNRRETLEIEGDLQNSAIGV

RCTGCQLSERWGKTRSSSELVWIREYKSTLGDSSAAASITAGRDLLVVGASLQNIASNISA

VRDATLSLSNFENKGYALGEYAVRGVYSPPSKFGEELLMRILAYNAVNDPSYGEGYASTGGR

LPNIHYFDKNFNEKVSPLEVIHGNGKNGGPGWHLYFGTLDVEYPDTDRWNKAIGRIPAPNY

SSKKTDAIPDLLKGLAPLDELTINKGANSTVGAVVQAGGRVTVNAAESFNNSVLQGFQAVQ

ETQLPHQDIAVSSTTSAVVTLKSQLPADLARQQINPLTLPGFSLPQGQNGLFRLASQGAQVN

QASGALKSASDLTQSGHGVSVSAQTGSGASGWSTQARRVGDDRVTSLAGSAYQGRVAEA

IDALRASAPISGDGGNTGRFQAGEHQATTGLGGLVEGNASGHSGNGVILADLRGGLPSFSS

LPASDHVQGTVPGHDGNGTILANWQGAQATVQASPSTVRVEGVVSSPGGNGSILADLPAE

QSSVQALPSAVRAQGSLPRLEERSALLAEPPVGQPALQTLPSVARVEGVPSNATPSNSHKYL

IETNPALTELKQFLNSDYLLGGLGINPDDSKKRLGDGLYEQRLVREAIVQRTGQRFIAGLNS

DEAMFRYLMDNAIASKDVLGLTPGVTLSAAQVAALTHDIVWLEEVEVNGEKVLAPVVYLAQ

AEGRLGPNGALIQGRDVNLITGGDLRNAGTLRAQNDLSATAGNIDNSGLIEAGNRLDLLAS

GSIRNDQGGIIAGREVSLSALTGDVINERTVTQHQSSYRGTGTTEAFADSAARIEAAQKLTV

SAGRDVANIGGVIDSKGDLALQGGRDVLVSAAVAERGWTAGSQAYQTQTTQMGAEVVAG

RDISVSAGRDISVVGSRIDARRDVTFEAGRDVGLVAAANEEHAYGKTKKVTFQDDKITQQA

TRVDAGGDLAINAGQDLRLVASQASAGDEAYLVAGDKLELLAANDSSYYLYDKKSKGSFGS

KKTRRDEITDVTAVGSQISSGGDLTLLSGGDQTYQGAKLESGNDLAIVSGGAVTFEAVKDL

HQESHEKSKGDLAWQSSKGKGQTDETVRQSQIVAQGNLAIKAVEGLKIDLKHIDQKTVSQ

TIDAMVQADPQLAWLKQMEQRGDVDWRRVQELHDSWKYSNSGLGVGAQLAIAIVVAYFT

AGAASAALGSMAGVGAGSGSMMAAAGSTAMVQAGTAVGTAAAGWANAAGTAVAMGMA

SNGAISTINNRGNLGDVVKDVTSSDALRGYVVAGTTAGLTAGVYDKWTSTQTGTSTALPNT

GAVAPAAGLGTWQGVGQFTSNQLLQNGTSVLLDRALGGKGSLGDALQNSLANAFAAYGFK

LIGDTTHGVLDDGSLGKIGLHALMGGLAAEAVGGDFRTGALAAGVNEALVDSLAKQYASLP

IDDKKGLLIMSSQLIGVLAASTQGDADAKSLQTGAWVAGNATQHNYLSHWQEEKKRQEV

DGCKDKQLCKTGIEAKWAIISAQQDVGIVVGVGGGIGLSTAETAVGVYELVKNWRETYAAL

-continued

EQLATSPEFRQQFGDNYLKGLEERAAFLTQAYEDAGWQGSVTAGVEGGRFAAELVGVLTAV

KGGAQITAKLPTAAKNLVNAIAESPVSGSMSSQLGAVGDLGRLGGGGKGYVDILSHEAKQ

HILYGDKPGSGGHLWPGQAGKTVFPQNWSADKIVHEVGDIATSPSTKWYAQTGTGGVYTS

KGDPAKWVAYEVRDGVRMRVVYQPATGKVITAFPDNAPIPPYKPIK

The corresponding nucleic acid sequences (DNA in SEQ ID NOs. 31-60 and RNA in SEQ ID NOs: 61-90) are set forth in the electronic sequence listing that forms part of the present application.

---

The invention claimed is:

1. A pharmaceutical composition comprising a polypeptide and a pharmaceutically acceptable carrier, vehicle or diluent, and an immunological adjuvant,
wherein the polypeptide comprises:
a) an amino acid sequence consisting of residues 29-742 of SEQ ID NO: 18, or
b) an amino acid sequence consisting of at least or exactly 100 contiguous amino acids from residues 29-742 of SEQ ID NO: 18, or
c) an amino acid sequence having a sequence identity of at least 90% with the amino acid sequence of a), or
d) an amino acid sequence having a sequence identity of at least 90% with the amino acid sequence of b),
wherein the polypeptide lacks amino acid residues 1-28 in SEQ ID NO: 18, and wherein the polypeptide is antigenic in a human being, to which the polypeptide has been administered.

2. The pharmaceutical composition according to claim 1, wherein the adjuvant is an aluminium based adjuvant.

3. The pharmaceutical composition according to claim 1, wherein the at least 100 contiguous amino acid residues have an N-terminal amino acid residue corresponding to any one of amino acid residues 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, and 643 in SEQ ID NO; 18 with the proviso that the selected amino acid residue satisfies the formula N≤743−n, where N is the number of the selected residue, and n is the number of consecutive amino acid residues.

4. The pharmaceutical composition according to claim 1, wherein the polypeptide comprises under c) or d) an amino acid sequence having a sequence identify of 95% with the amino acid sequence of a) or b), respectively.

5. The pharmaceutical composition according to claim 1, wherein the polypeptide is fused or conjugated to an immunogenic carrier molecule.

6. The pharmaceutical composition according to claim 5, wherein the immunogenic carrier molecule is a polypeptide that induces T-helper lymphocyte responses in a majority of humans, such as immunogenic carrier proteins selected from the group consisting of keyhole limpet hemocyanin or a fragment thereof, tetanus toxoid or a fragment thereof, diphtheria toxoid or a fragment thereof.

7. The pharmaceutical composition according to claim 1, wherein the polypeptide comprises an amino acid sequence consisting of at least or exactly 200 contiguous amino acid residues from residues 29-742 of SEQ ID NO: 18.

8. The pharmaceutical composition according to claim 1, wherein the polypeptide comprises an amino acid sequence consisting of at least or exactly 290 contiguous amino acid residues from residues 29-742 of SEQ ID NO: 18.

9. The pharmaceutical composition according to claim 1, wherein the polypeptide comprises an amino acid sequence consisting of at least or exactly 400 contiguous amino acid residues from residues 29-742 of SEQ ID NO: 18.

10. The pharmaceutical composition according to claim 1, wherein the polypeptide comprises an amino acid sequence consisting of at least or exactly 500 contiguous amino acid residues from residues 29-742 of SEQ ID NO: 18.

11. The pharmaceutical composition according to claim 1, wherein the polypeptide comprises an amino acid sequence consisting of at least or exactly 600 contiguous amino acid residues from residues 29-742 of SEQ ID NO: 18.

12. The pharmaceutical composition according to claim 1, wherein the polypeptide comprises an amino acid sequence consisting of at least or exactly 700 contiguous amino acid residues from residues 29-742 of SEQ ID NO: 18.

13. The pharmaceutical composition according to claim 1, where in the polypeptide comprises an amino acid sequence consisting of an amino acid sequence with at least 90% sequence identity with at least or exactly 200 contiguous amino acid residues from residues 29-742 of SEQ ID NO: 18.

14. The pharmaceutical composition according to claim 1, wherein the polypeptide comprises an amino acid sequence consisting of an amino acid sequence with at least 90% sequence identity with at least or exactly 290 contiguous amino acid residues from residues 29-742 of SEQ ID NO: 18.

15. The pharmaceutical composition according to claim 1, wherein the polypeptide comprises an amino acid sequence consisting of an amino acid sequence with at least 90% sequence identity with at least or exactly 400 contiguous amino acid residues from residues 29-742 of SEQ ID NO: 18.

16. The pharmaceutical composition according to claim 1, wherein the polypeptide comprises an amino acid sequence consisting of an amino acid sequence with at least 90% sequence identity with at least or exactly 500 contiguous amino acid residues from residues 29-742 of SEQ ID NO 18.

17. The pharmaceutical composition according to claim 1, wherein the polypeptide comprises an amino acid sequence consisting of an amino acid sequence with at least 90% sequence identity with at least or exactly 600 contiguous amino acid residues from residues 29-742 of SEQ ID NO 18.

18. The pharmaceutical composition according to claim 1, wherein the polypeptide comprises an amino acid sequence consisting of an amino acid sequence with at least 90% sequence identity with at least or exactly 700 contiguous amino acid residues from residues 29-742 of SEQ ID NO: 18.

* * * * *